United States Patent
Yang et al.

(10) Patent No.: US 11,771,709 B2
(45) Date of Patent: Oct. 3, 2023

(54) ALK PROTEIN DEGRADATION AGENT AND ANTI-TUMOR APPLICATION THEREOF

(71) Applicant: ShanghaiTech University, Shanghai (CN)

(72) Inventors: Xiaobao Yang, Shanghai (CN); Biao Jiang, Shanghai (CN); Xiaoling Song, Shanghai (CN); Haifan Lin, Shanghai (CN); Ning Sun, Shanghai (CN); Jinju Chen, Shanghai (CN); Xing Qiu, Shanghai (CN); Chaowei Ren, Shanghai (CN); Ying Kong, Shanghai (CN)

(73) Assignee: ShanghaiTech University, Shanghai (CN)

( * ) Notice: Subject to any disclaimer, the term of this patent is extended or adjusted under 35 U.S.C. 154(b) by 0 days.

(21) Appl. No.: 16/902,172

(22) Filed: Jun. 15, 2020

(65) Prior Publication Data

US 2020/0306273 A1    Oct. 1, 2020

Related U.S. Application Data

(63) Continuation of application No. PCT/CN2018/120745, filed on Dec. 12, 2018.

(30) Foreign Application Priority Data

Dec. 13, 2017 (CN) .................... 201711329773.4

(51) Int. Cl.
| | |
|---|---|
| *A61K 31/662* | (2006.01) |
| *A61P 35/00* | (2006.01) |
| *A61K 31/4439* | (2006.01) |
| *A61K 31/454* | (2006.01) |
| *A61K 31/496* | (2006.01) |
| *A61K 31/501* | (2006.01) |
| *A61K 31/506* | (2006.01) |
| *A61K 31/519* | (2006.01) |
| *A61K 45/06* | (2006.01) |

(52) U.S. Cl.
CPC ........ *A61K 31/662* (2013.01); *A61K 31/4439* (2013.01); *A61K 31/454* (2013.01); *A61K 31/496* (2013.01); *A61K 31/501* (2013.01); *A61K 31/506* (2013.01); *A61K 31/519* (2013.01); *A61P 35/00* (2018.01); *A61K 45/06* (2013.01)

(58) Field of Classification Search
CPC ... A61K 31/506; C07D 401/14; C07D 417/14
See application file for complete search history.

(56) References Cited

U.S. PATENT DOCUMENTS

| | | | |
|---|---|---|---|
| 10,813,933 B2 | 10/2020 | Katayama et al. | |
| 2017/0121321 A1* | 5/2017 | Crews | .................. A61K 47/55 |
| 2020/0306273 A1 | 10/2020 | Yang et al. | |
| 2021/0283261 A1* | 9/2021 | Jin | .................. G01N 33/5011 |

FOREIGN PATENT DOCUMENTS

| | | | | |
|---|---|---|---|---|
| CN | 106458993 A | 2/2017 | | |
| EP | 3725771 A1 | 10/2020 | | |
| JP | 2011-523646 A | 8/2011 | | |
| JP | 2017-513862 A | 6/2017 | | |
| WO | 2010/143664 A1 | 12/2010 | | |
| WO | WO-2013106643 A2 * | 7/2013 | .......... A61K 31/422 | |
| WO | 2017011371 A1 | 1/2017 | | |
| WO | 2017079267 A1 | 5/2017 | | |
| WO | 2017/200016 A1 | 11/2017 | | |
| WO | WO-2017204445 A2 * | 11/2017 | ......... A61K 31/4035 | |
| WO | 2017/204445 A3 | 9/2018 | | |
| WO | 2019114770 A1 | 6/2019 | | |

OTHER PUBLICATIONS

International Search Report issued in International Application No. PCT/CN2018/120745 dated Mar. 18, 2019 (7 pages).
Written Opinion issued in International Application No. PCT/CN2018/120745 dated Mar. 18, 2019 (9 pages).
Huang, Wei-Sheng et al., "Discovery of Brigatinib (AP26113), a Phosphine Oxide-Containing, Potent, Orally Active Inhibitor of Anaplastic Lymphoma Kinase", Journal of Medicinal Chemistry, 2016, 59(10), 4948-4964 (17 pages).
Office Action issued in corresponding JP Application No. 2020-532917 dated Jul. 13, 2021 (5 pages).

(Continued)

*Primary Examiner* — Theodore R. Howell
*Assistant Examiner* — George W Kosturko
(74) *Attorney, Agent, or Firm* — Osha Bergman Watanabe & Burton LLP

(57) ABSTRACT

A compound of formula (I) and its antitumor application are disclosed. The compounds of formula (I) have degradation and inhibitory effects on ALK target proteins. They are mainly composed of four parts: the first part, ALK-TKI, being compounds with ALK tyrosine kinase inhibitory activity; the second part, LIN, being different kinds of linker (Linker); the third part, the ULM, being a small molecule ligand (ULM, ubiquitin ligase binding moiety) with ubiquitination of VHL, CRBN or other proteases; and the fourth part, the group A, being a carbonyl group or absent, which covalently bond ALK-TKI to LIN, wherein LIN and ULM are covalently bonded. A series of compounds designed and synthesized by the present disclosure have wide pharmacological activities, have functions of degrading ALK protein and inhibiting ALK activity, and can be used for related tumor treatment.

Formula (I)

44 Claims, 11 Drawing Sheets

(56) References Cited

OTHER PUBLICATIONS

Asao, Tetsuhiko et al. "Sequential Use of Anaplastic Lymphoma Kinase Inhibitors in Japanese Patients With ALK-Rearranged Non-Small-Cell Lung Cancer: A Retrospective Analysis" Clinical Lung Cancer, vol. 18, No. 4, e251-e285, Jul. 2017 (8 pages).

Bordi, Paola et al. "Detection of ALK and KRAS Mutations in Circulating Tumor DNA of Patients With Advanced ALK-Positive NSCLC With Disease Progression During Crizotinib Treatment" Clinical Lung Cancer, vol. 18, No. 6, Nov. 2017, 692-697 (6 pages).

Cha, Yoon Jin et al. "Clinical outcomes in ALK-rearranged lung adenocarcinomas according to ALK fusion variants" Journal of Translational Medicine, (2016) 14:296 (10 pages).

Chan, Kin long et al. "Relationship between driver gene mutations, their relative protein expressions and survival in non-small cell lung carcinoma in Macao" Wiley, Clin Respir. J. 2018;12:1416-1423 (8 pages).

Choi, Young Lim et al. "Identification of Novel Isoforms of the EML4-ALK Transforming Gene in Non-Small Cell Lung Cancer" American Association for Cancer, Cancer Res 2008; 68: (13) Jul. 1, 2008 (7 pages).

Dagogo-Jack, I. et al. "Crizotinib resistance: implications for therapeutic strategies" Annals of Oncology 27 (Supplement 3): iii42-iii50, 2016 (9 pages).

Drizou, M. et al. "Treating patients with ALK-rearranged non-small-cell lung cancer: mechanisms of resistance and strategies to overcome it" Clin Transl Oncol (2017) 19:658-666 (9 pages).

Fujishita, Takashi et al. "Sensitivity of Non-Small-Cell Lung Cancer Cell Lines Established from Patients Treated with Prolonged Infusions of Paclitaxel" Oncology 2003;64:399-406 DOI: 10 1159/000070299 (8 pages).

Ju, Young Seok et al. "A transforming KIF5B and RET gene fusion in lung adenocarcinoma revealed from whole-genome and transcriptome sequencing" Genome Research, 22:436-445, 2012 (11 pages).

Nishio, Makoto et al. "Crizotinib versus Chemotherapy in Asian Patients with ALK-Positive Advanced Non-small Cell Lung Cancer" Cancer Res Treat. 2018;50(3):691-700 (10 pages).

Shaw, Alice T. et al. "Ceritinib versus chemotherapy in patients with ALK-rearranged non-small-cell lung cancer previously given chemotherapy and crizotinib (ASCEND-5): a randomised, controlled, open-label, phase 3 trial" Lancet Oncol 2017; 18: 874-86 (13 pages).

Soda, Manabu et al. "Identification of the transforming EML4-ALK fusion gene in non-small-cell lung cancer" Nature PublishingGroup, vol. 448, Aug. 2, 2007, doi:10.1038/nature05945 (7 pages).

Song, Xiaoling et al. "ERBB3-Independent Activation of the PI3K Pathway in EGFR-Mutant Lung Adenocarcinomas" American Association for Cancer Research 2015; DOI: 10 1158/0008-5472.CAN-13-1625 (12 pages).

Takeuchi, Kengo et al. "KIF5B-ALK, a Novel Fusion Oncokinase Identified by an Immunohistochemistry-based Diagnostic System for ALK-positive Lung Cancer" Clin Cancer Res 3143 2009;15(9)May 1, 2009 (8 pages).

Wellman, Axel et al. "The activated anaplastic lymphoma kinase increases cellular proliferation and oncogene up-regulation in rat la fibroblasts" The FASEB Journal, vol. Oct. 11, 1997, 965-972 (9 pages).

Zhang, Sen et al. "The Potent ALK Inhibitor Brigatinib (AP26113) Overcomes Mechanisms of Resistance to First- and Second-Generation ALK Inhibitors in Preclinical Models" Clin Cancer Res; 22(22) Oct. 25, 2016, 5527-5538 (13 pages).

P. Sabbatini et al., "GSK 1838705A inhibits the insulin-like growth factor-1 receptor and anaplastic lymhoma kinase and shows anti-tumor activity in experimental models of human cancers" Mol Cancer Ther, Oct. 2009, vol. 8, No. 10, pp. 2812-2820 (10 pages).

Office Action issued in corresponding Korean Application No. 10-2020-7019861, dated Aug. 11, 2022 (21 pages).

Office Action issued in corresponding Canadian Application No. 3085645, dated Nov. 8, 2022 (3 pages).

* cited by examiner

A) SR

B) H2228

A

B

ALK PROTEIN DEGRADATION AGENT AND ANTI-TUMOR APPLICATION THEREOF

FIELD

The present disclosure relates generally to compounds of formula (I) for cancer prevention and therapy, and their use in anti-cancer therapy, especially against cancer-related proteins including ALK, MET, ROS1, EGFR and FLT3.

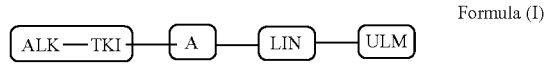

Formula (I)

BACKGROUND

Lung cancer is the leading cause of cancer related death in China and the world wide. In China, the incidence of lung cancer is already surpassed other types of cancer, and each year there are about 800,000 people died from lung cancer. The five-year survival rate of lung cancer is also very low, and it is only about 17%. And this rate have doesn't change too much since 70s in the last century. This is because traditional chemotherapy and radio-therapy killed normal cells together with cancer cells, which causes decreased immunity and dysfunction of patients physiology. Recently precision medicine provides targeted therapy to patients with specific driver genes which greatly reduced the toxic effect or traditional chemotherapy and radio-therapy and greatly improved patients quality of life.

Treating ALK (Anaplastic Lymphoma Kinase) mutation positive non-small cell lung cancer with specific small molecular tyrosine kinsae inhibitors greatly improved the efficacy of cancer therapy and patient quality of life. In lung cancer, patients with EML4-ALK gene fusion are about 3-7% of the total number of non-small cell lung cancer patients. The incidence ratio has no significant difference in Asian and western caucasion populations. In clinics, such mutations are often observed in young non-smoker patients (Soda et al. 2007; Nishio et al. 2017; Chan et al., 2017). ALK is a typrosine kinase. Gene fusion of this gene is a strong cancer driver gene which was firstly discovered in anaplastic large cell lymphoma patients, and later were found in many other diseases including diffused large B-cell lymphoma and Inflammatory Myofibroblastic Tumor (IMT) (Wellmann et al., 1997). ALK forms fusion genes with different partners and leads to consitutively activated ALK kinase activities to transform normal cells become cancer cells (Soda et al., 2007; Choi et al., 2008; Cha et al., 2016). In lung cancer, the major fusion partner with ALK is Echinoderm microtubule-associated protein-like 4, EML4. ALK can form fusion proteins with many other different partners, such as KIF5B, to drive cancer formation (Takeuchi et al. 2008). Such ALK fusion positive cancer cells are highly dependent on ALK kinase activities and inhibition of ALK kinase activity leads to death of these cells. Several ALK kinase inhibitors have been approved to treat ALKmutant positive cancer. In 2011, Crizotinib developed by Pfizer was approved by FDA to treat ALK positive non-small cell lung cancer. In 2016, Crizotinib was approved to treat non-small cell lung cancer patients with ROS1 (c-ros oncogene 1 receptor tyrosine kinase,c-ros) mutation. With this drug, the progression free survival of the patients was increased to about 10 months (Nishio et al, 2017). Regardless of with or without pretreatment, Crizotinib showed greater benefit to patients. It increased median progression free survival from 7.2 months with chemotherapy to 9.6 months, and which was increased to 13.6 months in Asian patients (Nishio et al., 2017). And the objective response rate was increased from 20% to 65% comparing those treated with chemotherapy. Treating ALK fusion positive patients with specific tyrosing kinase inhibitors provides great benefit to patients in clinics and it made a new milestone in lung cancer therapy.

There are more than 20 different genes were reported serve as partners of ALK. These different forms of ALK fusion proteins are also highly depend on ALK kinase activity and sensitive to ALK kinase inhibitors. In addition, ALK gene fusions not only play important role in non-small cell lung cancer, they are also found be critical in for many other diseases such as in including patients with ALCL patients, colorectal cancer (Lin et al., 2009; Lipson et al., 2012), IMT (Lawrence et al., 2000); ovarian cancer (Ren et al., 2012) diseases. ALK gene amplification and activating mutants were also reported in glioblastoma (Chen et al., 2008; George et al., 2008; Janoueix-Lerosey et al., 2008; Mosse et al., 2008). Different ALK fusion forms were found for different diseases. For example, the most frequently observed form is EML4-ALK in non-small cell lung cancer and the most frequently found form is NPM-ALK in ALCL. Furthermore, ALK gene amplification and mutation were also reported in glioblastma. Some of these ALK mutations are also sensitive to ALK inhibitors, and potentially benefit from ALK inhibitor development.

Although there are great benefit for patients of using ALK kinase inhibitors in clinic, drug resistance eventually developed usually about one year after drug treatment initiation. Part of the reason is because ALK gene amplification or acquired resistance mutation in ALK protein, including L1196M, L1198F, L1152R, L1151TIN, C1156Y, F1174C, G1202R, D1203N, S1206Y (Bordi et al., 2017; Dagogo-Jack and Shaw, 2016; Drizou et al., 2017). The most frequent mutation is the Point mutation L1196M which was called gatekeeper mutation. Because Crizotinib is hard to reach the brain, resistance was also developed after the occurrence of brain metasis. Other resistance mechanisms are activation of other driver genes, including EGFR mutation or activation (30-35%), c-KIT amplification (10%) or Kras or other gene mutations (5%) (Bordi et al., 2017).

Studies on drug resistance mechanisms impeded the development of the second generation of ALK kinase inhibitor drugs, which include Ceritinib (Novartis, LDK378), Alectinib (Roche, CH542802) and Brigtinib (Ariad, AP26113). These drugs can overcome many acquired resistance mutations in ALK, including gatekeeper mutation L1196M. In addition, these drugs can penetrate into the brain very well and inhibit the growth of brain metasized tumor. Within these drugs, certinib was approved by FDA in 2014 to treat patients progressed on Crizotinib treatment or patients who are not Crizotinib-tolerated. Second line treatment with Ceritinib increased progression free survival for about 4 months comparing to second line chemotherapy (Shaw et al., 2017). Alectinib was approved in 2014 in Japan and 2015 by FDA in US. It is about 10 fold more potent than Crizotinib in inhibiting ALK kinase activities. The advantage of second line using Alectinib over chemotherapy after Crizotinib resistance was recently reported (Asao et al., 2017). It increased the patients' progression free survival up to 35 months. This indicated that of using ALK kinase inhibitor drugs with optimized drug treatment strategies might make the uncontrolled tumor growth to a controllable chronic diseases. Brigatinib (Takeda) was firstly approved by FDA as breakthrough designation on Apr. 28, 2017 for second line treatment ALK-positive patients who developed resistance to Crizotinib. Comparing to two other 2nd generation drugs, Brigatinib not only effectively inhibited G1269A, C1156Y, I1171S/T, V1180L, it also blocked the resistance mediated by G1202R (Zhang et al., 2016). In addition, Brigatinib can blocked the activities of both ALK and EGFR, the response rate is 55% and disease control rate was about 86%. Currently, it has been granted priority review as a first-line treatment for ALK positive non-small cell lung cancer.

Although the development of new generation specific tyrosine kinase inhibitor drugs showed high response rate in ALK mutant positive non-small cell lung cancer, drug resistance still occurrs. The $3^{rd}$ generation ALK kinase inhibitor Lorlatinib (PF-06463922) can overcome many known acquired ALK mutations, patients who developed resistance to Lortinib eventually occurred. The number of patients with ALK rearrangement mutation is big and it contuse rising. Drug resistance to target therapy become a big obstacle to improve patients survival and the development need of the society. The need for overcome drug resistance is big and development new types of drugs to overcome resistance is urgent.

Proteolysis targeting technology is a new strategy of drug design. Traditional small molecular design only inhibit the kinase activity of ALK protein, whereas the acquired resistance mutation on the protein is the basis of certain resistance mechanism. We utilize the platform of Proteolysis targeting drug (PROTAD) to develop new ALK targeting drugs. The action mechanisms of these drugs is distinct from traditional small kinase inhibitors. These PROTAD drugs not only inhibit the activity of target proteins such as ALK, but also are able to get rid of target proteins through proteolysis. By using the PROTAC technology, we would like to develop new drugs targeting cancer driver genes such as ALK fusion proteins and getting rid of these target proteins ultimately so as to treat cancer and overcome drug resistance.

SUMMARY OF THE INVENTION

The present disclosure provides a compound of formula (I):

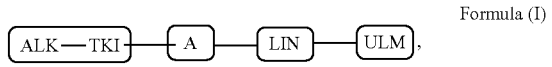

Formula (I)

or its salts, enantiomers, stereoisomers, solvates, or polymorphs, wherein all substituents or groups are as defined in the detailed description of the invention.

The present disclosure also provides a pharmaceutical composition comprising the compound of formula (I) or a pharmaceutically acceptable salt thereof, and at least one pharmaceutically acceptable carrier.

The present disclosure also provides a compound of formula (I), or a pharmaceutically acceptable salt thereof for use as a medicament:

Formula (I)

wherein all substituents or groups are as defined in the detailed description of the invention.

The present disclosure also provides the compound of formula (I) according to the present disclosure, or a pharmaceutically acceptable salt thereof for the prevention and/or treatment of cancer, especially lung cancer.

The present disclosure further provides the use of the compound of formula (I) according to the present disclosure, or a pharmaceutically acceptable salt thereof for preparing a medicament for preventing and/or treating cancer.

The Cancers include, but are not limited to, lung cancer including small cell lung cancer, non-small cell lung cancer (NSCLC) such as lung adenocarcinoma, anaplastic lymphoma kinase (ALK) mutation-positive non-small cell lung cancer, Ros1-mutation positive non-small cell lung cancer, MET mutated or amplified lung cancer, and EGFR-mutated non-small cell lung cancer; Lymphoma including anaplastic lymphoma, anaplastic large cell lymphoma (ALCL), and diffused large B-cell lymphoma; inflammatory myofibroblastic tumor (IMT); colorectal cancer; brain tumor including glioma, and glioblastoma; Acute myeloid leukemia (AML); and ovarian cancer etc.

The present disclosure also provides a method for treating or preventing cancer, which comprises administering to a subject a therapeutically effective amount of said compound of formula (I), or a pharmaceutically acceptable salt thereof, or said pharmaceutical composition according to the present disclosure.

DETAILED DESCRIPTION OF THE INVENTION

Figure 1:
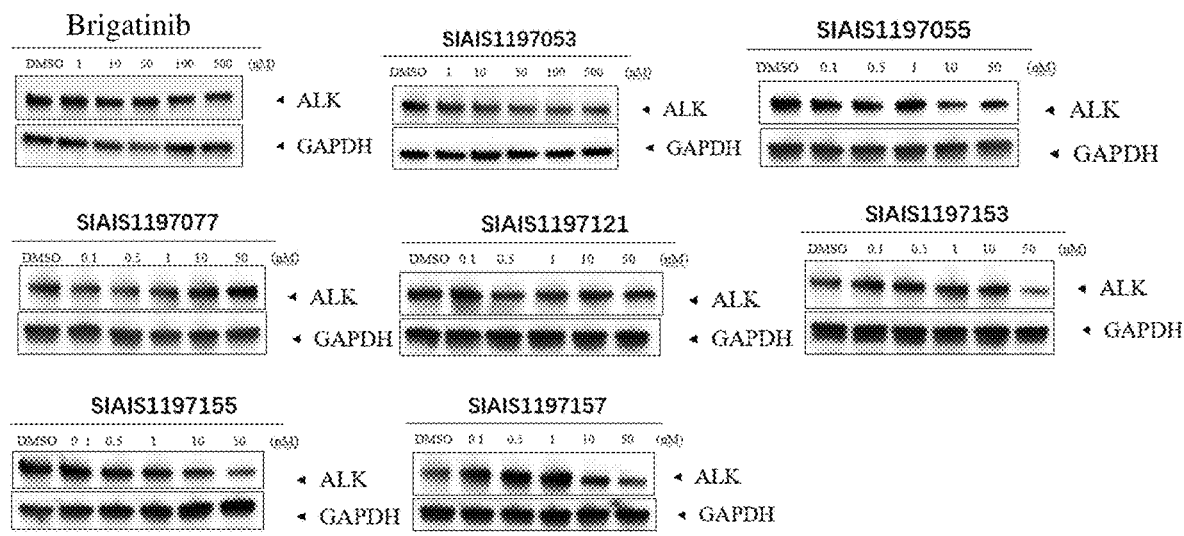
FIG. 1 shows ALK protein degradation activities for Brigatinib Analogue A-based PROTAD molecules according to the present invention in ALCL cell line SR.

The compounds of the present disclosure are very effective in degrading ALK tyrosine kinases associated with lung cancer in the cellular environment. These compounds of the present disclosure are based on PROteolytic TArgeted Chimeras (PROTAC) technology, in which one end of the compound is bound to VHL or CRBN protease with ubiquitination function, and the other end is bound to a targeted tyrosine kinase. When the compound of the present disclosure is combined with a tyrosine kinase and VHL or CRBN protease, a complex is formed, so that VHL or CRBN protease is in close proximity to the tyrosine kinase, resulting in the ubiquitination of the tyrosine kinase and its subsequent proteasome degradation.

Accordingly, in a first aspect the present disclosure provides a compound of formula (I):

Formula (I)

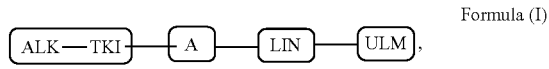

or a salt, enantiomer, stereoisomer, solvate, or polymorph thereof, in which:
ALK-TKI is covalently connected to LIN via group A, and ULM is covalently connected to LIN; wherein ALK-TKI is an ALK tyrosine kinase inhibitor or an analogue thereof with the same function;
LIN is a linking group, which represents a linear or branched alkylene chain, a spiro-cycloalkylene, a 1,4-piperazinylene, or a 1,3-dialkynyl group, wherein the linear or branched alkylene chain is optionally interrupted one or more times (e.g., 1-20, 1-15, 1-10, 1-9, 1-8, 1-7, 1-6, 1-5, 1-4, 1-3, or 1-2 times, or 1 time) by one or more selected from the group consisting of O, C(O)NH, NHC(O), NHC(O)NH, NH, S, sulfinyl, sulfonyl, aminosulfonylamino, alkynylene, alkenylene, cycloalkylene, arylene, heterocyclylene, or heteroarylene group, or any combination thereof, wherein the linear or branched alkylene chain is optionally substituted with one or more substituents (e.g., as described herein);
ULM is a small molecule ligand of VHL or CRBN protease with ubiquitination function; and
the group A is C(O) or absent.

In the present disclosure, the term "alkylene" (which is used interchangeably with "alkylene chain") used alone or in combination refers to a linear or branched chain divalent saturated hydrocarbon group composed of carbon and hydrogen atoms. The term "$C_x$-$C_y$ alkylene" or "$C_{x-y}$ alkylene" (x and y are each an integer) as used herein refers to a linear or branched alkylene group containing from x to y carbon atoms. In another embodiment, an "alkylene" radical includes, but are not limited to, $C_1$-$C_{30}$ alkylene group (i.e., $C_{1-30}$ alkylene group), or $C_1$-$C_{29}$ alkylene, $C_1$-$C_{28}$ alkylene, $C_1$-$C_{27}$ alkylene, $C_1$-$C_{26}$ alkylene, $C_1$-$C_{25}$ alkylene, $C_1$-$C_{24}$ alkylene, $C_1$-$C_{23}$ alkylene, $C_1$-$C_{22}$ alkylene, $C_1$-$C_{21}$ alkylene, $C_1$-$C_{20}$ alkylene, $C_1$-$C_{19}$ alkylene, $C_1$-$C_8$ alkylene, $C_1$-$C_{17}$ alkylene, $C_1$-$C_{16}$ alkylene, $C_1$-$C_{15}$ alkylene, $C_1$-$C_{14}$ alkylene, $C_1$-$C_{13}$ alkylene, $C_1$-$C_{12}$ alkylene, $C_1$-$C_{11}$ alkylene, $C_1$-$C_{10}$ alkylene, $C_1$-$C_9$ alkylene, $C_1$-$C_8$ alkylene, $C_1$-$C_7$ alkylene, $C_1$-$C_6$ alkylene, $C_1$-$C_5$ alkylene, $C_1$-$C_4$ alkylene, $C_1$-$C_3$ alkylene, or $C_1$-$C_2$ alkylene. Representative examples of "alkylene" group include, but are not limited to, methylene, ethylene, propylene, isopropylidene, butylene, isobutylene, sec-butylene, tert-butylene, n-pentylene, isopentylene, neopentylene, tert-pentylene, hexylene, heptylene, octylene, nonylene, decylene, undecylene, dodecylene, tridecylene, tetradecylene, pentadecylene, hexadecylene, heptadecylene, octadecylene, nonadecylene, eicosylene, heneicosylene, docosylene, tricosylene, tetracosylene, pentacosylene, hexacosylene, heptacosylene, octacosylene, nonacosylene, and triacontylene.

In the present disclosure, the term "arylene" used alone or in combination refers to a divalent aromatic hydrocarbon group containing from 5 to 14 carbon atoms and optionally one or more fused rings, such as phenylene group, naphthylene group or fluorenylene group. In the present disclosure, the "arylene" is an optionally substituted arylene. A substituted arylene group refers to an arylene group optionally substituted 1-3 times with a substituent(s) (that is, the arylene group optionally has 1-3 same or different substituent(s)). In a further embodiment, the substituent can be any one optionally selected from the group consisting of $C_{1-3}$ alkyl, $C_{1-3}$ alkoxy, halogen, amino, hydroxyl, or any combination thereof.

In the present disclosure, the term "aryl" used alone or in combination refers to a monovalent aromatic hydrocarbon group containing 5 to 14 carbon atoms and optionally one or more fused rings, such as phenyl or naphthyl or fluorenyl. In the present disclosure, the "aryl" is an optionally substituted aryl. A substituted aryl refers to an aryl group optionally substituted 1-3 times with a substituent(s) (that is, the aryl group optionally has 1-3 same or different substituent(s)). In a further embodiment, the substituent can be any one optionally selected from the group consisting of $C_{1-3}$ alkyl, $C_{1-3}$ alkoxy, halogen, amino, hydroxyl, or any combination thereof.

In the present disclosure, the term "$C_{1-3}$alkoxy group" used alone or in combination refers to a linear or branched alkoxy group containing from 1 to 3 carbon atoms. Representative examples of $C_{1-3}$alkoxy include, but are not limited to, methoxy, ethoxy, n-propoxy, and isopropoxy. In a further embodiment, examples of $C_{1-3}$alkoxy are methoxy and ethoxy.

In the present disclosure, the term "cycloalkyl" used alone or in combination refers to a saturated or partially unsaturated (e.g., containing one or more double bonds but not having a completely conjugated it-electron system) monovalent monocyclic or bicyclic cyclic hydrocarbon radical, which may include fused, bridged, or spiro ring system, having from 3 to 12 carbon atoms, e.g., having from 3 to 10 carbon atoms, or from 3 to 8 carbon atoms, or from 3 to 6 carbon atoms. Representative examples of "cycloalkyl" include, but are not limited to, cyclopropyl, cyclobutyl, cyclopentyl, cyclopentenyl, cyclohexyl, cyclohexenyl, cycloheptyl, cyclooctyl, decalinyl, octahydropentalenyl, octahydro-1H-indenyl, and spiro-cycloalkyl.

In the present disclosure, the cycloalkyl group may be unsubstituted or substituted. A substituted cycloalkyl group refers to a cycloalkyl group optionally substituted 1-3 times by a substituent(s) (that is, the cycloalkyl group optionally has 1-3 same or different substituent(s)). In a further embodiment, the substituent can be any one optionally selected from the group consisting of $C_{1-3}$ alkyl, $C_{1-3}$ alkoxy, cyano, trifluoromethyl, heterocyclyl, halogen, amino, hydroxyl, or any combination thereof.

In the present disclosure, the term "cycloalkylene", used alone or in combination, refers to a saturated and partially unsaturated (e.g., containing one or more double bonds, but not having a fully conjugated π-electron system) divalent monocyclic or bicyclic cyclic hydrocarbon group, which may include fused, bridged, or spiro ring system, having from 3 to 12 carbon atoms, e.g., having from 3 to 10 carbon atoms, or from 3 to 8 carbon atoms, or from 3 to 6 carbon atoms. Representative examples of "cycloalkylene" include, but are not limited to, cyclopropylene, cyclobutylene, cyclopentylene, cyclopentenylene, cyclohexylene, cyclohexenylene, cycloheptylene, cyclooctylene, decalinylene, octahydropentalenylene, octahydro-1H-indenylene, and spiro-cycloalkylene.

In the present disclosure, the cycloalkylene group may be unsubstituted or substituted. A substituted cycloalkylene group refers to a cycloalkylene group optionally substituted 1-3 times by a substituent(s) (that is, the cycloalkylene group optionally has 1-3 same or different substituent(s)). In a further embodiment, the substituent can be any one optionally selected from the group consisting of $C_{1-3}$ alkyl, $C_{1-3}$ alkoxy, cyano, trifluoromethyl, heterocyclyl, halogen, amino, hydroxyl, or any combination thereof.

In the present disclosure, the term "heteroarylene" used alone or in combination refers to a 5- to 10-membered monocyclic or bicyclic divalent aromatic ring group containing one or more (e.g., from 1 to 6, or from 1 to 5, or from 1 to 4, or from 1 to 3) heteroatoms independently selected from the group consisting of oxygen, nitrogen, and sulfur. Representative examples of such heteroarylene groups include, but are not limited to, furanylene, oxazolylene, isoxazolylene, oxadiazolylene, thienylene, thiazolylene, isothiazolylene, thiadiazolylene, pyrrolylene, imidazolylene, triazolylene, pyridylene, pyrimidinylene, pyridazinylene, pyrazinylene, indolylene, isoindolylene, benzofuranylene, isobenzofuranylene, benzothienylene, indazolylene, benzimidazolylene, benzoxazolylene, benzoisoxazolylene, benzothiazolylene, benzoisothiazolylene, benzotriazolylene, benzo[2,1,3]oxadiazolylene, benzo[2,1,3]thiadiazolylene, benzo[1,2,3]thiadiazolylene, quinolylene, isoquinolylene, naphthyridinylene, cinnolinylene, quinazolinylene, quinoxalinylene, phthalazinylene, pyrazolo[1,5-a]pyridinylene, pyrazolo[1,5-a]pyrimidinylene, imidazo[1,2-a]pyridinylene, 1H-pyrrolo[3,2-b]pyridinylene, 1H-pyrrolo[2,3-b]pyridinylene, 4H-fluoro[3,2-b]pyrrolylene, pyrrolo[2,1-b]thiazolylene, and imidazo[2,1-b]thiazolylene. In the present disclosure, the heteroarylene group may be unsubstituted or substituted. A substituted heteroarylene group refers to a heteroarylene group optionally substituted 1-3 times by a substituent(s) (that is, the heteroarylene group optionally has 1-3 same or different substituent(s)). In a further embodiment, the substituent can be any one optionally selected from the group consisting of $C_{1-3}$ alkyl, $C_{1-3}$ alkoxy, cyano, trifluoromethyl, heterocyclyl, halogen, amino, hydroxyl, or any combination thereof.

In the present disclosure, the term "heteroaryl" used alone or in combination refers to a 5- to 10-membered monocyclic or bicyclic monovalent aromatic ring containing one or more (eg, from 1 to 6, or from 1 to 5, or from 1 to 4, or from 1 to 3) heteroatoms independently selected from the group consisting of oxygen, nitrogen and sulfur. Representative examples of such heteroaryl groups include, but are not limited to, furyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidinyl, pyridazinyl, pyrazinyl, indolyl, isoindolyl, benzofuranyl, isobenzofuranyl, benzothienyl, indazolyl, benzimidazolyl, benzoxazolyl, benzoisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolyl, isoquinolyl, naphthyridinyl, cinnolinyl, quinazolinyl, quinoxalinyl, phthalazinyl, pyrazolo[1,5-a]pyridyl, pyrazolo[1,5-a]pyrimidyl, imidazo[1,2-a]pyridyl, 1H-pyrrolo[3,2-b]pyridyl, 1H-pyrrolo[2,3-b]pyridyl, 4H-fluoro[3,2-b]pyrrolyl, pyrrolo[2,1-b]thiazolyl and imidazo[2,1-b]thiazolyl. In the present disclosure, the heteroaryl groups may be unsubstituted or substituted. A substituted heteroaryl group refers to a heteroaryl group optionally substituted 1-3 times with a substituent(s) (that is, the heteroaryl group optionally has 1-3 same or different substituent(s)). In a further embodiment, the substituent can be any one optionally selected from the group consisting of $C_{1-3}$ alkyl, $C_{1-3}$ alkoxy, cyano, trifluoromethyl, heterocyclyl, halogen, amino, hydroxyl, or any combination thereof.

In the present disclosure, the term "heterocyclylene" used alone or in combination refers to a 4- to 6-membered saturated monocyclic divalent cyclic hydrocarbon group containing one or more (e.g., from 1 to 4, or from 1 to 3, or from 1 to 2, or 1) heteroatoms independently selected from the group consisting of sulfur, oxygen, and nitrogen. Examples of the heterocyclylene group include, but are not limited to, azetidinylene, oxetanylene, pyrrolidinylene, imidazolidylene, pyrazolidylene, triazolylend, tetrahydrofuranylene, tetrahydrothienylene, tetrahydrothiopyranylene, oxazolidinylene, thiazolidinylene, piperidinylene, piperazinylene, morpholinylene, thiomorpholinylene, and dioxanylene. In the present disclosure, the heterocyclylene group may be unsubstituted or substituted as explicitly defined. A substituted heterocycloalkylene refers to a heterocycloalkylene group optionally substituted 1-3 times by a substituent(s) (that is, the heterocycloalkylene group optionally has 1-3 same or different substituent(s)). In a further embodiment, the substituent can be any one optionally selected from the group consisting of $C_{1-3}$ alkyl, $C_{1-3}$ alkoxy, cyano, trifluoromethyl, heterocyclyl, halogen, amino, hydroxyl, or any combination thereof.

In the present disclosure, the term "heterocyclyl" used alone or in combination refers to a 4- to 6-membered saturated monocyclic monovalent cyclic hydrocarbon group containing one or more (e.g., from 1 to 4, or from 1 to 3, or from 1 to 2, or 1) heteroatoms independently selected from the group consisting of sulfur, oxygen, and nitrogen. Examples of the heterocyclyl group include, but are not limited to, azetidinyl, oxetanyl, pyrrolidinyl, imidazolidinyl, pyrazolidyl, triazolyl, tetrahydrofuranyl, tetrahydrothienyl, tetrahydrothiopyranyl, oxazolidinyl, thiazolidinyl, piperidinyl, piperazinyl, morpholinyl, thiomorpholinyl, and dioxanyl. In the present disclosure, the heterocyclyl may be unsubstituted or substituted as explicitly defined. A substituted heterocyclyl group refers to a heterocyclyl group optionally substituted 1-3 times with a substituent(s) (that is, the heterocycloalkylene group optionally has 1-3 same or different substituent(s)). In a further embodiment, the substituent may be any one optionally selected from the group consisting of $C_{1-3}$ alkyl, $C_{1-3}$ alkoxy, cyano, trifluoromethyl, heterocyclyl, halogen, amino, hydroxy, or any combination thereof.

In the present disclosure, the term "spiro-cycloalkylene" used alone or in combination refers to a divalent alicyclic hydrocarbon group derived by removing two hydrogen atoms from any one or two free valence carbon atom(s) of the alicyclic hydrocarbon group in which two rings share one common carbon atom. Representative examples of spiro-cycloalkylene group include, but are not limited to, spiro[3.3]heptanylene (for example

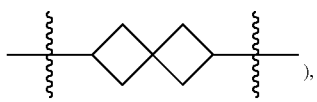), spiro[4.5]decanylene, spiro[5.5]undecanylene, 4-methyl-spiro[2.4]heptanylene etc.

In the present disclosure, the term "spiro-cycloalkyl" used alone or in combination refers to a monovalent alicyclic hydrocarbon group derived by removing one hydrogen atom from a free valence carbon atom of the alicyclic hydrocarbon group in which two rings share one common atom. Representative examples of spiro-cycloalkyl group include, but are not limited to, spiro[3.3]heptanyl, spiro[4.5]decanyl, spiro[5.5]undecanyl, 4-methylspiro[2.4]heptanyl etc.

In the present disclosure, the term "alkynylene" used alone or in combination refers to a linear or branched divalent hydrocarbon group containing one or more carbon-carbon triple bonds and containing from 2 to 10 (e.g., from 2 to 6, or from 2 to 4, or from 2 to 3, or 2) carbon atoms. Examples of the alkynylene group include, but are not limited to, ethynylene, 1-propynylene, 1-butynylene, and 1,3-diynylene.

In the present disclosure, the term "alkynyl" used alone or in combination refers to a linear or branched monovalent hydrocarbon group containing one or more carbon-carbon triple bonds and containing 2 to 10 (e.g., from 2 to 6, or from 2 to 4, or from 2 to 3, or 2) carbon atoms. Examples of the alkynyl group include, but are not limited to, ethynyl, 1-propynyl, 1-butynyl, and 1,3-dialkynyl.

In the present disclosure, the term "alkenylene" used alone or in combination refers to a linear or branched divalent hydrocarbon group containing one or more carbon-carbon double bonds and containing from 2 to 10 (e.g., from 2 to 6, or from 2 to 4, or from 2 to 3, or 2) carbon atoms. Examples of the alkenylene group include, but are not limited to, vinylidene (e.g., —CH═CH—), 1-propenylene, and 1-butenylene.

In the present disclosure, the term "alkenyl" used alone or in combination refers to a linear or branched monovalent hydrocarbon group containing one or more carbon-carbon double bonds and containing from 2 to 10 (e.g., from 2 to 6, or from 2 to 4, or from 2 to 3, or 2) carbon atoms. Examples of the alkenyl group include, but are not limited to, vinyl, 1-propenyl, and 1-butenyl.

In the present disclosure, the term "halogen atom" or "halogen" used alone or in combination refers to fluorine, chlorine, bromine or iodine, and is preferably F, Cl or Br.

In the present disclosure, the term "alkyl" used alone or in combination refers to a linear or branched alkyl group. The term "$(C_x$-$C_y)$ alkyl" or "$C_{x-y}$ alkyl" (x and y are each an integer) as used herein refers to a linear or branched chain alkyl group containing from x to y carbon atoms. The term "$C_{1-10}$ alkyl" used alone or in combination in the present disclosure refers to a linear or branched chain alkyl group containing from 1 to 10 carbon atoms. The $C_{1-10}$ alkyl group of the present disclosure includes, but are not limited to, a $C_{1-9}$ alkyl group, or a $C_{1-8}$ alkyl group, or a $C_{2-8}$ alkyl group, or a $C_{1-7}$ alkyl group, or a $C_{1-6}$ alkyl, $C_{1-5}$ alkyl, or $C_{1-4}$ alkyl. Representative examples of the alkyl include, but are not limited to, methyl, ethyl, n-propyl, isopropyl, n-butyl, isobutyl, sec-butyl, tert-butyl, pentyl, isopentyl, neopentyl, tert-pentyl, hexyl, heptyl, octyl, nonyl and decyl. The term "$C_{1-3}$ alkyl group" in the present disclosure refers to an alkyl group containing from 1 to 3 carbon atoms, and its representative examples include methyl, ethyl, n-propyl, and isopropyl.

In the present disclosure, the "alkyl" is optionally substituted, and the substituent(s) can be one or more selected from the group consisting of halogen, cyano, $C_{1-3}$ alkyl, $C_{1-3}$ alkoxy, trifluoromethyl, heterocyclyl, or any combination thereof.

In one embodiment of the present disclosure, the ALK-TKI represents the compound moiety represented by the following general formula:

(Ia)

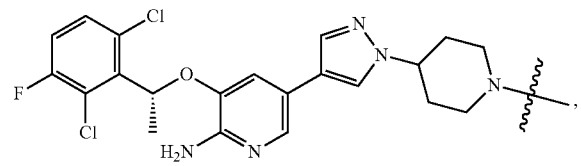

(Ib)

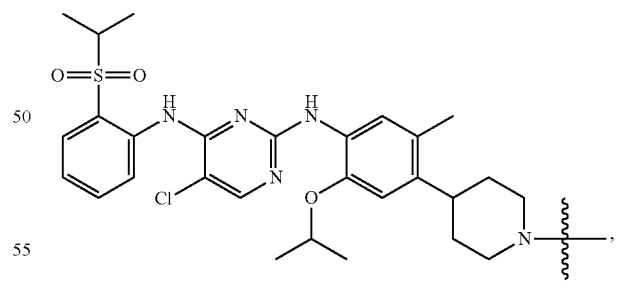

(Ic)

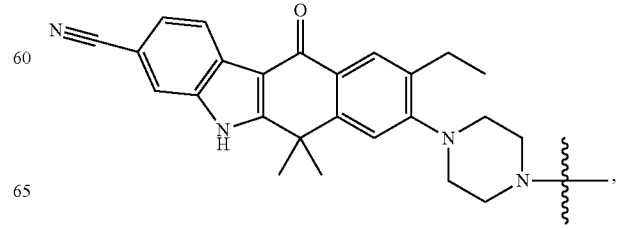

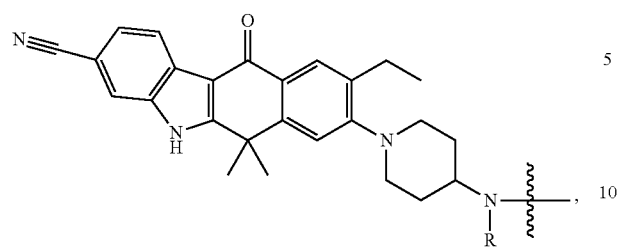(Id),
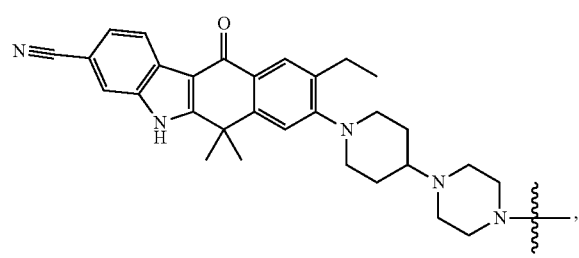(Ie),
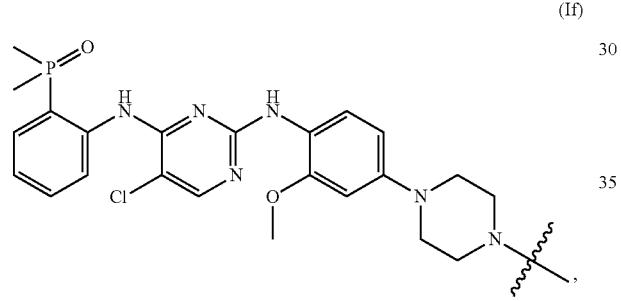(If),
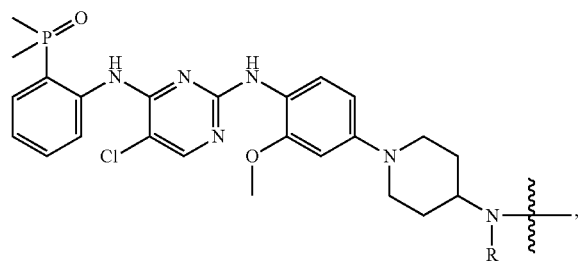(Ig),
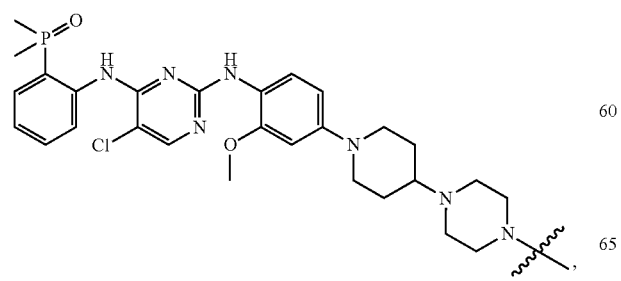(Ih),
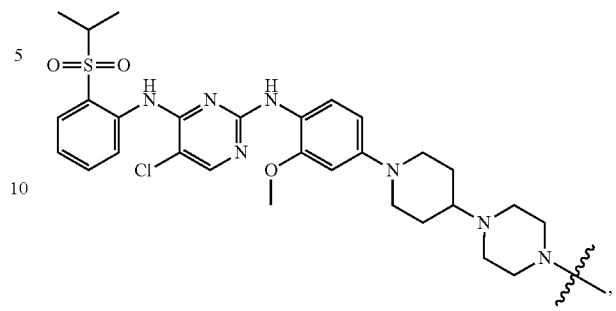(Ii),
(Ij)
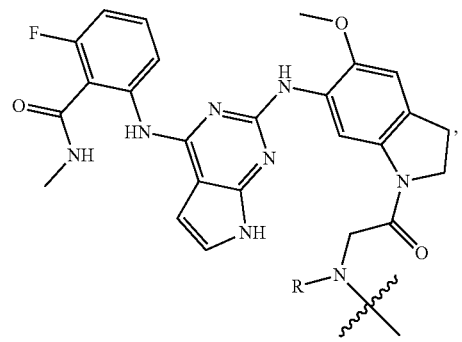(Ik),
(Il),
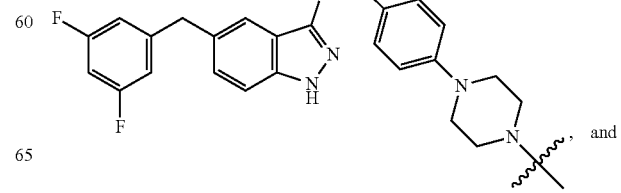(Im) and -continued

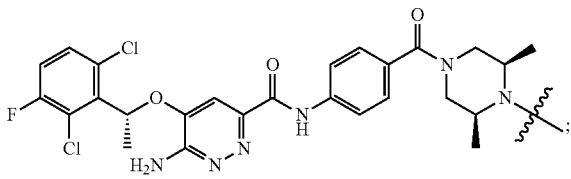
(In)

wherein, R represents an alkyl group or H. In a sub-embodiment of the present disclosure, R represents a linear or branched $C_{1-10}$ alkyl group. In a further sub-embodiment of the present disclosure, the $C_{1-10}$ alkyl group is preferably a $C_{1-9}$ alkyl group, more preferably a $C_{1-8}$ alkyl group, still more preferably a $C_{2-8}$ alkyl group, and more preferably a $C_{1-7}$ alkyl group, even more preferably $C_{1-6}$ alkyl, $C_{1-5}$ alkyl, or $C_{1-4}$ alkyl. Representative examples include, but are not limited to, methyl, ethyl, n-propyl, isopropyl, n-butyl, isobutyl, sec-butyl, tert-butyl, n-pentyl, isopentyl, neopentyl, and tert-pentyl.

In one embodiment of the present disclosure, the ULM represents a structure represented by the following formula (II):

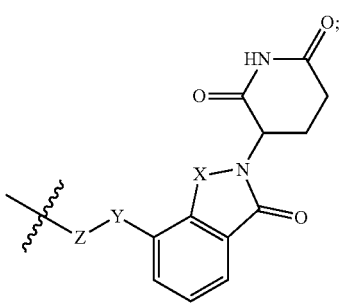
Formula (II)

wherein X represents $CH_2$ or $C(O)$, Y represents $CH_2$, NH or O, and Z represents a carbonyl group (i.e., $C(O)$) or is absent.

In a sub-embodiment of the present disclosure, in the structure of formula (II), X represents $C(O)$, Y represents N—, and Z is absent.

In a sub-embodiment of the present disclosure, in the structure of the formula (II), X represents $C(O)$, Y represents NH, and Z represents a carbonyl group.

In a sub-embodiment of the present disclosure, in the structure of formula (II), X represents $CH_2$, Y represents NH, and Z is absent.

In a sub-embodiment of the present disclosure, in the structure of formula (II), X represents $CH_2$, Y represents NH, and Z represents a carbonyl group.

In a sub-embodiment of the present disclosure, in the structure of formula (II), X represents $C(O)$, Y represents O, and Z is absent.

In a sub-embodiment of the present disclosure, in the structure of formula (II), X represents $CH_2$, Y represents O, and Z is absent.

In a sub-embodiment of the present disclosure, in the structure of the formula (II), X represents $C(O)$, Y represents O, and Z represents a carbonyl group.

In a sub-embodiment of the present disclosure, in the structure of formula (II), X represents $CH_2$, Y represents O, and Z represents a carbonyl group.

In a sub-embodiment of the present disclosure, in the structure of formula (II), X represents $CH_2$, Y represents $CH_2$, and Z is absent.

In a sub-embodiment of the present disclosure, in the structure of formula (II), X represents $CH_2$, Y represents $CH_2$, and Z represents a carbonyl group.

In a sub-embodiment of the present disclosure, in the structure of formula (II), X represents $C(O)$, Y represents $CH_2$, and Z is absent.

In a sub-embodiment of the present disclosure, in the structure of formula (II), X represents $C(O)$, Y represents $CH_2$, and Z represents a carbonyl group.

In one embodiment of the present disclosure, the ULM represents a structure represented by the following formula (III):

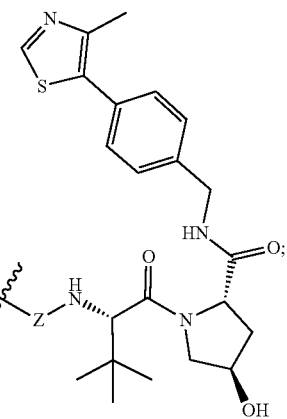
Formula (III)

wherein Z represents a carbonyl group or is absent.

In one embodiment of the present disclosure, the LIN represents: a linear or branched $C_1$-$C_{20}$ alkylene chain; —$(CH_2)_{n1}$—$(O(CH_2)_{n2})_{m1}$—; —$(CH_2)_{n1}$—$(O(CH_2)_{n2})_{m1}$—O—$(CH_2)_{n3}$—; —$(CR_1R_2)_{n1}$—$(O(CR_1R_2)_{n2})_{m1}$—O—$(CR_1R_2)_{n3}$—; —$(CH_2)_{n1}$—$(C(O)NH—(CH_2)_{n2})_{m1}$—; —$(CH_2)_{n1}$—$(C(O)NH—(CH_2)_{n2})_{m1}$—$(CH_2)_{n3}$—; —$(CH_2)_{n1}$—$(O(CH_2)_{n2})_{m1}$—O—$(CH_2)_{n3}$—C(O)NH—$(CH_2)_{n4}$—$(O(CH_2)_{n5})_{m2}$—O—$(CH_2)_{n6}$—; —$(CR_1R_2)_{n1}$—$(O(CR_1R_2)_{n2})_{m1}$—O—$(CR_1R_2)_{n3}$—C(O)NH—$(CR_1R_2)_{n4}$—$(O(CR_1R_2)_{n5})_{m2}$—O—$(CR_1R_2)_{n6}$—; $(CH_2)_{n1}$—C(O)NH—$(O(CR_1R_2)_{n2})_{m1}$—; a linear or branched alkylene chain interrupted one or more times (e.g., 1-20, 1-15, 1-10, 1-9, 1-8, 1-7, 1-6, 1-5, 1-4, 1-3, or 1-2 times, or 1 time) by one or more selected from the group consisting of NHC(O), NHC(O)NH, S, sulfinyl, sulfonyl, alkynylene, alkenylene, cycloalkylene, arylene, heterocyclylene, or heteroarylene, or any combination thereof; or —$(CH_2)_{n1}$—$(O(CH_2)_{n2})_{m1}$— in which carbon chain is interrupted one or more times (e.g., 1-20, 1-15, 1-10, 1-9, 1-8, 1-7, 1-6, 1-5, 1-4, 1-3, or 1-2 times, or 1 time) by one or more selected from the group consisting of arylene, heterocyclylene, heteroarylene group or any combination thereof;

wherein $R_1$ and $R_2$ each independently represent a linear or branched $C_1$-$C_{10}$ alkyl group or a cycloalkyl group; and n1, n2, n3, n4, n5, n6, m1, and m2 each independently represent an integer of 1, 2, 3, 4, 5, 6, 7, 8, 9, 10, 11, 12, 13, 14, 15, 16, 17, 18, 19, or 20.

Herein, when LIN represents a linear or branched alkylene chain which is optionally substituted and optionally interrupted one or more times by one or more selected from the group consisting of O, C(O)NH, NHC(O), NHC(O)NH, NH, S, sulfinyl, sulfonyl, aminosulfonylamino, alkynylene, alkenylene, cycloalkylene, arylene, heterocyclylene, or heteroarylene group, or any combination thereof, as described herein, any one of the two ends of the backbone chain of the alkylene group can be bonded to the group A, and the other end is bonded to the ULM moiety, and vice versa.

In an embodiment of the present disclosure, the LIN represents:

—(CH$_2$)$_2$O(CH$_2$)$_2$OCH$_2$—; —CH$_2$O(CH$_2$)$_2$OCH$_2$—;
—(CH$_2$)$_3$O(CH$_2$)$_2$—;
—(CH$_2$)$_3$O(CH$_2$)$_2$O(CH$_2$)$_2$—; —(CH$_2$)$_3$O(CH$_2$)$_3$—;
—(CH$_2$)$_2$O(CH$_2$)$_2$—;
—(CH$_2$)$_2$O(CH$_2$)$_2$O(CH$_2$)$_2$—; —(CH$_2$)$_2$O(CH$_2$)$_2$O(CH$_2$)$_2$—;
—(CH$_2$)$_2$O(CH$_2$)$_2$O(CH$_2$)$_2$O(CH$_2$)$_2$—; —(CH$_2$)$_2$O(CH$_2$)$_2$O(CH$_2$)$_3$—;
—(CH$_2$)$_2$O(CH$_2$)$_2$O(CH$_2$)$_2$O(CH$_2$)$_2$O(CH$_2$)$_2$—;
—(CH$_2$)$_2$O(CH$_2$)$_2$O(CH$_2$)$_2$O(CH$_2$)$_2$O(CH$_2$)$_2$O(CH$_2$)$_2$—;
—(CH$_2$)$_3$O(CH$_2$)$_2$O(CH$_2$)$_2$O(CH$_2$)$_2$O(CH$_2$)$_2$O(CH$_2$)$_2$—;
or
—(CH$_2$)$_3$O(CH$_2$)$_2$O(CH$_2$)$_2$O(CH$_2$)$_2$O(CH$_2$)$_2$O(CH$_2$)$_3$—.

In an embodiment of the present disclosure, the LIN represents:

—CH$_2$—; —(CH$_2$)$_2$—; —(CH$_2$)$_3$—; —(CH$_2$)$_4$—;
—(CH$_2$)$_5$—; —(CH$_2$)$_6$—; —(CH$_2$)$_7$—; —(CH$_2$)$_8$—;
—(CH$_2$)$_9$—; —(CH$_2$)$_{10}$—; —(CH$_2$)$_{11}$—; —(CH$_2$)$_{12}$—;
—(CH$_2$)$_{13}$—; —(CH$_2$)$_{14}$—; —(CH$_2$)$_{15}$—; —(CH$_2$)$_{16}$—;
—(CH$_2$)$_{17}$—; —(CH$_2$)$_{18}$—; —(CH$_2$)$_{19}$—; or —(CH$_2$)$_{20}$—.

In one embodiment of the present disclosure, the linear or branched alkylene chain is substituted one or more times (e.g., 1-20, 1-15, 1-10, 1-9, 1-8, 1-7, 1-6, 1-5, 1-4, 1-3, or 1-2 times, or 1 time) with one or more substituents, wherein the substituents are selected from the group consisting of hydroxyl, amino, mercapto, halogen, or any combination thereof.

In one embodiment of the present disclosure, the LIN represents a linear or branched $C_1$-$C_{20}$ alkylene chain substituted with one or more substituents selected from the group consisting of hydroxyl, amino, mercapto, halogen, or any combination thereof. In a sub-embodiment of the present disclosure, the number of the substituent may be, for example, 1-20, or 1-10, 1-9, 1-8, 1-7, 1-6, 1-5, 1-4, 1-3, 1-2 or 1.

In one embodiment of the present disclosure, the LIN represents -(CH$_2$)$_3$CH(OH)CH(OH)(CH$_2$)$_4$—.

In an embodiment of the present disclosure, the LIN represents: —(CH$_2$)$_{n1}$-triazolylene-(CH$_2$)$_{n2}$—; —(CH$_2$)$_{n1}$—(O(CH$_2$)$_{n2}$)$_{m1}$—O—(CH$_2$)$_{n3}$-triazolylene-(CH$_2$)$_{n4}$—(O(CH$_2$)$_{n5}$)$_{m2}$—O—(CH$_2$)$_{n6}$; —(CH$_2$)$_{n1}$-triazolylene-(CH$_2$)$_{n2}$—(O(CH$_2$)$_{n3}$)$_{m1}$—O—(CH$_2$)$_{n4}$—; or —(CH$_2$)$_{n1}$—(O(CH$_2$)$_{n2}$)$_{m1}$—O—(CH$_2$)$_{n3}$-triazolylene-(CH$_2$)$_{n4}$—; and n1, n2, n3, n4, n5, n6, m1, and m2 each independently represent an integer of 1, 2, 3, 4, 5, 6, 7, 8, 9, 10, 11, 12, 13, 14, 15, 16, 17, 18, 19, or 20.

In an embodiment of the present disclosure, the LIN represents:

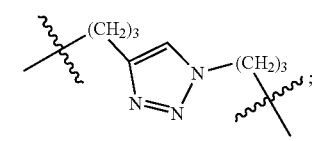

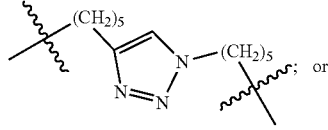

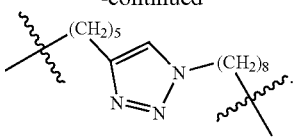

In an embodiment of the present disclosure, the LIN represents: —(CH$_2$)$_2$C(O)NH(CH$_2$)$_2$—; —(CH$_2$)$_3$C(O)NH(CH$_2$)$_3$—; —(CH$_2$)$_3$C(O)NH(CH$_2$)$_4$—; —(CH$_2$)$_6$C(O)NH(CH$_2$)$_7$—; or —(CH$_2$)$_8$C(O)NH(CH$_2$)$_8$—.

In one embodiment of the present disclosure, the LIN is —(CH$_2$)$_{n1}$—NHC(O)—(CH$_2$)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

In one embodiment of the present disclosure, the LIN is —(CH$_2$)$_3$NHC(O)(CH$_2$)$_3$—.

In an embodiment of the present disclosure, the LIN is —(CH$_2$)$_{n1}$—NHC(O)NH—(CH$_2$)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

In one embodiment of the present disclosure, the LIN is —(CH$_2$)$_4$NHC(O)NH(CH$_2$)$_4$—.

In one embodiment of the present disclosure, the LIN is —(CH$_2$)$_{n1}$—S—(CH$_2$)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

In one embodiment of the present disclosure, the LIN represents: —(CH$_2$)$_5$S(CH$_2$)$_5$— or —(CH$_2$)$_6$S(CH$_2$)$_5$—.

In one embodiment of the present disclosure, the LIN is —(CH$_2$)$_{n1}$—S(O)—(CH$_2$)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

In one embodiment of the present disclosure, the LIN represents: —(CH$_2$)$_5$S(O)(CH$_2$)$_5$— or —(CH$_2$)$_6$S(O)(CH$_2$)$_5$—.

In one embodiment of the present disclosure, the LIN is —(CH$_2$)$_{n1}$—S(O)$_2$—(CH$_2$)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

In one embodiment of the present disclosure, the LIN represents: —(CH$_2$)$_5$S(O)$_2$(CH$_2$)$_5$— or —(CH$_2$)$_6$S(O)$_2$(CH$_2$)$_5$—.

In an embodiment of the present disclosure, the LIN is —(CH$_2$)$_{n1}$—CH═CH—(CH$_2$)$_{n2}$—, wherein n1 and n2 each independently represent an integer of 1, 2, 3, 4, 5, 6, 7, 8, 9, 9, 10, 11, 12, 13, 14, 15, 16, 17, 18, 19, or 20.

In one embodiment of the present disclosure, the LIN is —(CH$_2$)$_4$CH═CH(CH$_2$)$_3$—.

In one embodiment of the present disclosure, the LIN is —(CH$_2$)$_{n1}$—C≡C—(CH$_2$)$_{n2}$— or —(CH$_2$)$_{n1}$—C≡C—C≡C—(CH$_2$)$_{n2}$—, wherein n1, n2 independently represents an integer of 1, 2, 3, 4, 5, 6, 7, 8, 9, 10, 11, 12, 13, 14, 15, 16, 17, 18, 19, or 20.

In one embodiment of the present disclosure, the LIN represents —(CH$_2$)$_2$C═C(CH$_2$)$_2$— or —(CH$_2$)$_8$C═C(CH$_2$)$_4$—.

In one embodiment of the present disclosure, the LIN represents a linear or branched alkylene chains interrupted one or more times (e.g., 1-20, 1-15, 1-10, 1-9, 1-8, 1-7, 1-6, 1-5, 1-4, 1-3, or 1-2 times, or 1 time) by one or more selected from the group consisting of NHC(O), NHC(O)NH, S, sulfinyl, sulfonyl, alkynylene, alkenylene, spiro-cycloalkylene, arylene, heterocyclylene, heteroarylene group, or any combination thereof.

In one embodiment of the present disclosure, the LIN represents —(CH$_2$)$_{n1}$-piperazinylene-(CH$_2$)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

In one embodiment of the present disclosure, the LIN represents —CH$_2$-piperazinylene-CH$_2$—, —(CH$_2$)$_2$-piperazinylene-(CH$_2$)$_2$—, —(CH$_2$)$_3$-piperazinylene-(CH$_2$)$_3$—, —(CH$_2$)$_2$-piperazinylene-(CH$_2$)$_3$—, —CH$_2$-piperazinylene-(CH$_2$)$_2$—, —CH$_2$-piperazinylene-(CH$_2$)$_3$—, or —(CH$_2$)$_2$-piperazinylene-(CH$_2$)$_3$—.

In an embodiment of the present disclosure, the LIN represents —(CH$_2$)$_{n1}$-phenylene-(CH$_2$)$_{n2}$—, wherein n1 and n2 each independently represent an integer of 1, 2, 3, 4, 5, 6, 7, 8, 9, 9, 10, 11, 12, 13, 14, 15, 16, 17, 18, 19, or 20.

In one embodiment of the present disclosure, the LIN represents —CH$_2$-phenylene-CH$_2$—, —(CH$_2$)$_2$-phenylene-(CH$_2$)$_2$—, —CH$_2$-phenylene-(CH$_2$)$_2$—, —(CH$_2$)$_2$-phenylene-CH$_2$—, —(CH$_2$)$_3$-phenylene-(CH$_2$)$_3$—, —CH$_2$-phenylene-(CH$_2$)$_3$—, —(CH$_2$)$_2$-Phenylene-(CH$_2$)$_3$—, —(CH$_2$)$_3$-phenylene-(CH$_2$)$_2$—, or —(CH$_2$)$_3$-phenylene-CH$_2$—.

In one embodiment of the present disclosure, the LIN represents a 1,4-piperazinylene, a spiro-cycloalkylene, or a 1,3-dialkynylene group, wherein when LIN is a 1,4-piperazinylene, the group A of the compound of formula (I) is a carbonyl group.

In one embodiment of the present disclosure, the LIN represents

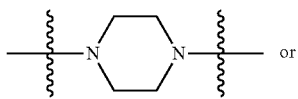 or

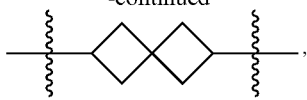

wherein when the LIN is a 1,4-piperazinylene, the group A of the compound of the formula (I) is a carbonyl group.

In one embodiment of the present disclosure, the LIN represents a spiro-cycloalkylene, and the spiro-cycloalkylene may be a spiro[3.3]heptanylene (for example

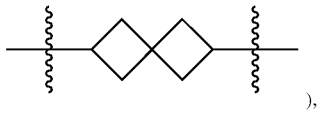), spiro[4.5]decanylene, spiro[5.5]undecanylene, or 4-methyl-spiro[2.4]heptanylene.

In an embodiment of the present disclosure, the LIN represents:

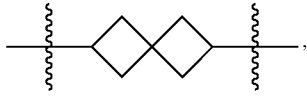 [SMILES: *C1CC2(C1)CC(*)C2]

and the group A is C(O).

Particularly preferred are the following compounds of formula I and their salts (especially pharmaceutically acceptable salts) in Tables 1 and 2 of the present disclosure:

TABLE 1

Structural formulas and names of the compounds of the present disclosure

| Compound ID | Structure of the compound | Name of the compound |
|---|---|---|
| SIAI S119 7065 | 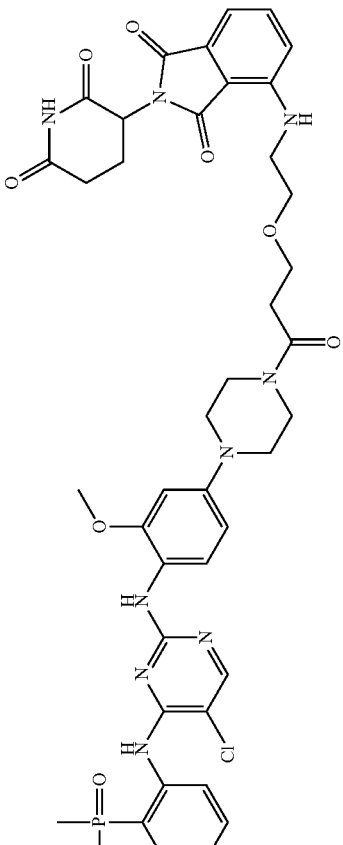 | 4-((2-(3-(4-(4-((5-chloro-4-((2-(dimethylphosphoryl)phenyl)amino)pyrimidin-2-yl)amino)-3-methoxyphenyl)piperazin-1-yl)-3-oxopropoxy)ethyl)amino)-2-(2,6-dioxopiperidin-3-yl)isoindoline-1,3-dione |
| SIAI S119 7067 | 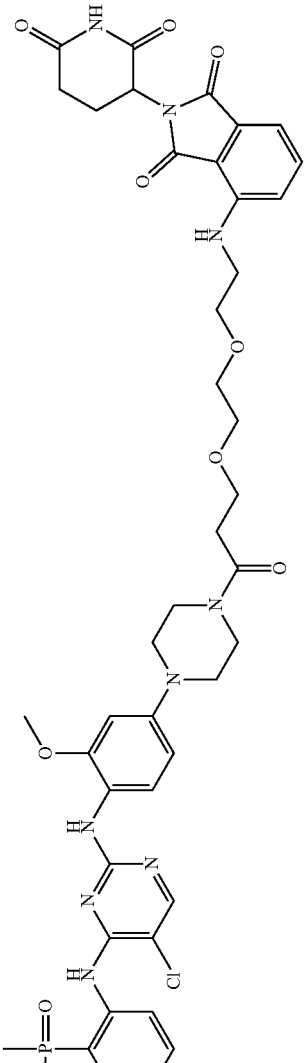 | 4-((2-(2-(3-(4-(4-((5-chloro-4-((2-(dimethylphosphoryl)phenyl)amino)pyrimidin-2-yl)amino)-3-methoxyphenyl)piperazin-1-yl)-3-oxopropoxy)ethoxy)ethyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| SIAI S119 7069 | | 4-((2-(2-(2-(3-(4-(4-(4-((2-(dimethylphosphoryl)phenyl)amino)-5-methylpyrimidin-2-yl)amino)-3-methoxyphenyl)piperazin-1-yl)-3-oxopropoxy)ethoxy)ethoxy)ethyl)amino)-2-(2,6-dioxopiperidin-3-yl)isoindoline-1,3-dione |
| SIAI S119 7071 | | 4-((15-(4-(4-((5-chloro-4-((2-(dimethylphosphoryl)phenyl)amino)pyrimidin-2-yl)amino)-3-methoxyphenyl)piperazin-1-yl)-15-oxo-3,6,9,12-tetraoxapentadecyl)amino)-2-(2,6-dioxopiperidin-3-yl)isoindoline-1,3-dione |
| SIAI S119 7073 | | 4-((18-(4-(4-((5-chloro-4-((2-(dimethylphosphoryl)phenyl)amino)pyrimidin-2-yl)amino)-3-methoxyphenyl)piperazin-1-yl)-18-oxo-3,6,9,12,15-pentaoxaoctadecyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| | | 4-((18-(4-(4-((5-chloro-4-((2-(dimethylphosphoryl)phenyl)amino)pyrimidin-2-yl)amino)-3-methoxyphenyl)piperazin-1-yl)-3,6,9,12,15-pentaoxaoctadecyl)amino)-2-(2,6-dioxopiperidin-3-yl)isoindoline-1,3-dione |
| | | 3-(4-((2-(3-(4-(4-((5-chloro-4-((2-(dimethylphosphoryl)phenyl)amino)pyrimidin-2-yl)amino)-3-methoxyphenyl)piperazin-1-yl)-3-oxopropoxy)ethyl)amino)-1-oxoisoindolin-2-yl)piperidine-2,6-dione |
| | | 3-(4-((2-(2-(3-(4-(4-((5-chloro-4-((2-(dimethylphosphoryl)phenyl)amino)pyrimidin-2-yl)amino)-3-methoxyphenyl)piperazin-1-yl)-3-oxopropoxy)ethoxy)ethyl)amino)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| | | 3-(4-((2-(2-(2-(3-(4-(4-(4-((2-(dimethylphosphoryl)phenyl)amino)-5-methylpyrimidin-2-yl)amino)-3-methoxyphenyl)piperazin-1-yl)-3-oxopropoxy)ethoxy)ethoxy)ethyl)amino)-1-oxoisoindolin-2-yl)piperidine-2,6-dione |
| | | 3-(4-((15-(4-(4-((5-chloro-4-((2-(dimethylphosphoryl)phenyl)amino)pyrimidin-2-yl)amino)-3-methoxyphenyl)piperazin-1-yl)-15-oxo-3,6,9,12-tetraoxapentadecyl)amino)-1-oxoisoindolin-2-yl)piperidine-2,6-dione |
| | | 3-(4-((18-(4-(4-((5-chloro-4-((2-(dimethylphosphoryl)phenyl)amino)pyrimidin-2-yl)amino)-3-methoxyphenyl)piperazin-1-yl)-18-oxo-3,6,9,12,15-pentaoxaoctadecyl)amino)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| | | 3-(4-(18-((4-(4-((5-chloro-4-((2-(dimethylphosphoryl)phenyl)amino)pyrimidin-2-yl)amino)-3-methoxyphenyl)piperazin-1-yl)-3,6,9,12,15-pentaoxaoctadecyl)amino)-1-oxoisoindolin-2-yl)piperidine-2,6-dione |
| | | 4-((2-(2-(3-(4-(4-((5-chloro-4-((2-(dimethylphosphoryl)phenyl)amino)pyrimidin-2-yl)amino)-3-methoxyphenyl)piperazin-1-yl)propoxy)ethoxy)ethyl)amino)-2-(2,6-dioxopiperidin-3-yl)isoindoline-1,3-dione |
| | | 4-(2-(2-(3-(4-(4-((5-chloro-4-((2-(dimethylphosphoryl)phenyl)amino)pyrimidin-2-yl)amino)-3-methoxyphenyl)piperazin-1-yl)-3-oxopropoxy)ethoxy)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| | | 3-(4-(2-(2-(3-(4-(4-((5-chloro-4-((2-(dimethylphosphoryl)phenyl)amino)pyrimidin-2-yl)amino)-3-methoxyphenyl)piperazin-1-yl)-3-oxopropoxy)ethoxy)ethoxy)-1-oxoisoindolin-2-yl)piperidine-2,6-dione |
| | | 3-(4-(19-(4-(4-((5-chloro-4-((2-(dimethylphosphoryl)phenyl)amino)pyrimidin-2-yl)amino)-3-methoxyphenyl)piperazin-1-yl)-4,7,10,13,16-pentaoxanonadecyl)-1-oxoisoindolin-2-yl)piperidine-2,6-dione |
| SIAIS1197055 | | 4-(2-(4-(4-((5-chloro-4-((2-(dimethylphosphoryl)phenyl)amino)pyrimidin-2-yl)amino)-3-methoxyphenyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
| --- | --- | --- |
| SIAI S119 7057 | | 4-((3-(4-(4-((5-chloro-4-((2-(dimethylphosphoryl)phenyl)amino)pyrimidin-2-yl)amino)-3-methoxyphenyl)piperazin-1-yl)-3-oxopropyl)amino)-2-(2,6-dioxopiperidin-3-yl)isoindoline-1,3-dione |
| SIAI S119 7059 | | 4-((4-(4-(4-((5-chloro-4-((2-(dimethylphosphoryl)phenyl)amino)pyrimidin-2-yl)amino)-3-methoxyphenyl)piperazin-1-yl)-4-oxobutyl)amino)-2-(2,6-dioxopiperidin-3-yl)isoindoline-1,3-dione |
| SIAI S119 7061 | | 4-((5-(4-(4-((5-chloro-4-((2-(dimethylphosphoryl)phenyl)amino)pyrimidin-2-yl)amino)-3-methoxyphenyl)piperazin-1-yl)-5-oxopentyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| SIAIS1197063 | | 4-((6-(4-(4-((5-chloro-4-((2-(dimethylphosphoryl)phenyl)amino)pyrimidin-2-yl)amino)-3-methoxyphenyl)piperazin-1-yl)-6-oxohexyl)amino)-2-(2,6-dioxopiperidin-3-yl)isoindoline-1,3-dione |
| SIAIS1197077 | | 4-((7-(4-(4-((5-chloro-4-((2-(dimethylphosphoryl)phenyl)amino)pyrimidin-2-yl)amino)-3-methoxyphenyl)piperazin-1-yl)-7-oxoheptyl)amino)-2-(2,6-dioxopiperidin-3-yl)isoindoline-1,3-dione |
| | | 3-(4-(2-(4-(4-((5-chloro-4-((2-(dimethylphosphoryl)phenyl)amino)pyrimidin-2-yl)amino)-3-methoxyphenyl)piperazin-1-yl)-2-oxoethyl)amino)-1-oxoisoindolin-2-yl)piperidine-2,6-dione |

| Compound ID | Structure of the compound | Name of the compound |
|---|---|---|
| | 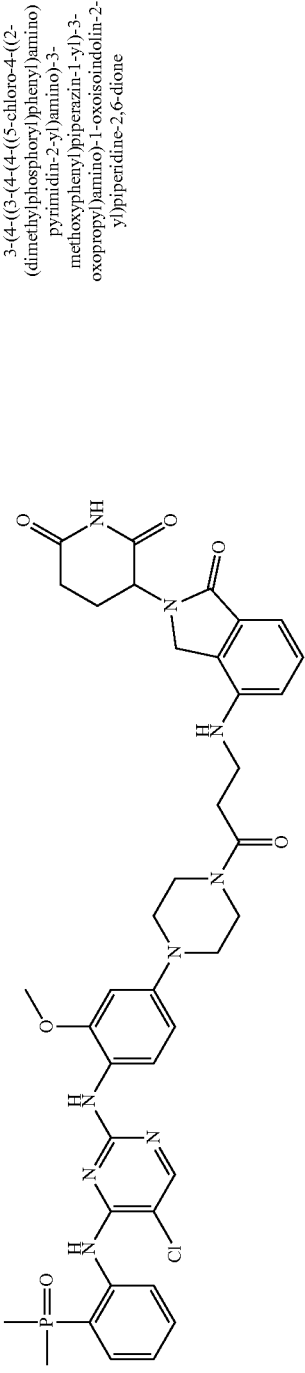 | 3-(4-((3-(4-(4-((5-chloro-4-((2-(dimethylphosphoryl)phenyl)amino)pyrimidin-2-yl)amino)-3-methoxyphenyl)piperazin-1-yl)-3-oxopropyl)amino)-1-oxoisoindolin-2-yl)piperidine-2,6-dione |
| | | 3-(4-((4-(4-(4-((5-chloro-4-((2-(dimethylphosphoryl)phenyl)amino)pyrimidin-2-yl)amino)-3-methoxyphenyl)piperazin-1-yl)-4-oxobutyl)amino)-1-oxoisoindolin-2-yl)piperidine-2,6-dione |
| | 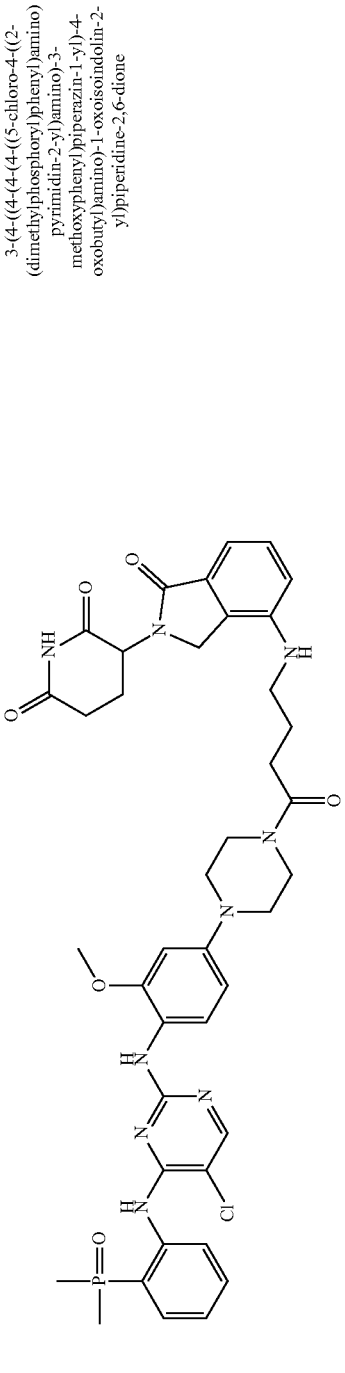 | 3-(4-((5-(4-(4-((5-chloro-4-((2-(dimethylphosphoryl)phenyl)amino)pyrimidin-2-yl)amino)-3-methoxyphenyl)piperazin-1-yl)-5-oxopentyl)amino)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| | | 3-(4-((6-(4-(4-((5-chloro-4-((2-(dimethylphosphoryl)phenyl)amino)pyrimidin-2-yl)amino)-3-methoxyphenyl)piperazin-1-yl)-6-oxohexyl)amino)-1-oxoisoindolin-2-yl)piperidine-2,6-dione |
| | | 3-(4-((7-(4-(4-((5-chloro-4-((2-(dimethylphosphoryl)phenyl)amino)pyrimidin-2-yl)amino)-3-methoxyphenyl)piperazin-1-yl)-7-oxoheptyl)amino)-1-oxoisoindolin-2-yl)piperidine-2,6-dione |
| | | 7-(4-(4-((5-chloro-4-((2-(dimethylphosphoryl)phenyl)amino)pyrimidin-2-yl)amino)-3-methoxyphenyl)piperazin-1-yl)-N-(2-(2,6-dioxopiperidin-3-yl)-1,3-dioxoisoindolin-4-yl)-7-oxoheptanamide |

TABLE 1-continued

Structural formulas and names of the compounds of the present disclosure

| Compound ID | Structure of the compound | Name of the compound |
|---|---|---|
| | | 7-(4-(4-((5-chloro-4-((2-(dimethylphosphoryl)phenyl)amino)pyrimidin-2-yl)amino)-3-methoxyphenyl)piperazin-1-yl)-N-(2-(2,6-dioxopiperidin-3-yl)-1-oxoisoindolin-4-yl)-7-oxoheptanamide |
| | | 4-(2-(4-(4-((5-chloro-4-((2-(dimethylphosphoryl)phenyl)amino)pyrimidin-2-yl)amino)-3-methoxyphenyl)piperazin-1-yl)ethyl)amino)-2-(2,6-dioxopiperidin-3-yl)isoindoline-1,3-dione |
| | | 3-(4-((2-(4-(4-((5-chloro-4-((2-(dimethylphosphoryl)phenyl)amino)pyrimidin-2-yl)amino)-3-methoxyphenyl)piperazin-1-yl)ethyl)amino)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| | | 4-(7-(4-(4-((5-chloro-4-((2-(dimethylphosphoryl)phenyl)amino)pyrimidin-2-yl)amino)-3-methoxyphenyl)piperazin-1-yl)heptyl)amino)-2-(2,6-dioxopiperidin-3-yl)isoindoline-1,3-dione |
| | | 3-(4-(7-(4-(4-((5-chloro-4-((2-(dimethylphosphoryl)phenyl)amino)pyrimidin-2-yl)amino)-3-methoxyphenyl)piperazin-1-yl)heptyl)amino)-1-oxoisoindolin-2-yl)piperidine-2,6-dione |
| | | 7-(4-(4-((5-chloro-4-((2-(dimethylphosphoryl)phenyl)amino)pyrimidin-2-yl)amino)-3-methoxyphenyl)piperazin-1-yl)-N-(2-(2,6-dioxopiperidin-3-yl)-1-oxoisoindolin-4-yl)heptanamide |

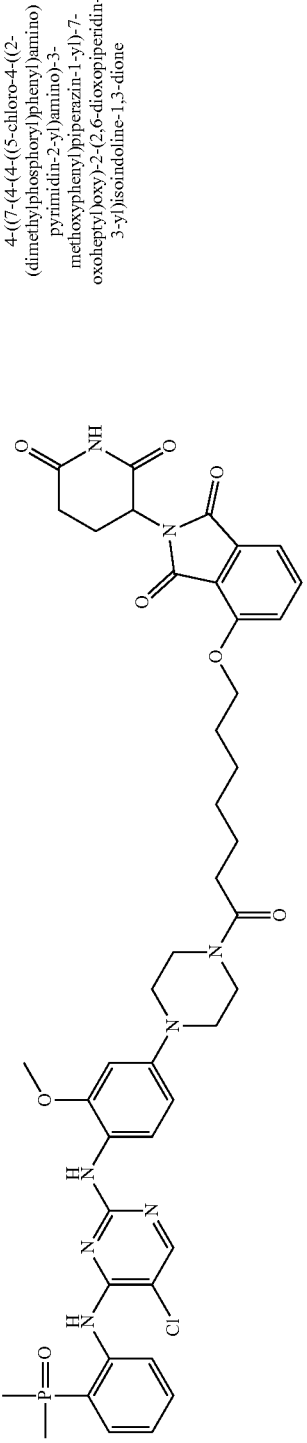

TABLE 1-continued

Structural formulas and names of the compounds of the present disclosure

| Compound ID | Structure of the compound | Name of the compound |
|---|---|---|
| | | 3-(4-(3-(4-(4-((5-chloro-4-((2-(dimethylphosphoryl)phenyl)amino)pyrimidin-2-yl)amino)-3-methoxyphenyl)piperazin-1-yl)-3-oxopropyl)-1-oxoisoindolin-2-yl)piperidine-2,6-dione |
| | | 3-(4-(8-(4-(4-((5-chloro-4-((2-(dimethylphosphoryl)phenyl)amino)pyrimidin-2-yl)amino)-3-methoxyphenyl)piperazin-1-yl)-8-oxooctyl)-1-oxoisoindolin-2-yl)piperidine-2,6-dione |
| | | 4-((5-((7-(4-(4-((5-chloro-4-((2-(dimethylphosphoryl)phenyl)amino)pyrimidin-2-yl)amino)-3-methoxyphenyl)piperazin-1-yl)-7-oxoheptyl)thio)pentyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| | | 4-((5-((7-(4-(4-((5-chloro-4-((2-(dimethylphosphoryl)phenyl)amino)pyrimidin-2-yl)amino)-3-methoxyphenyl)piperazin-1-yl)-7-oxoheptyl)sulfinyl)pentyl)amino)-2-(2,6-dioxopiperidin-3-yl)isoindoline-1,3-dione |
| | | 4-((5-((7-(4-(4-((5-chloro-4-((2-(dimethylphosphoryl)phenyl)amino)pyrimidin-2-yl)amino)-3-methoxyphenyl)piperazin-1-yl)-7-oxoheptyl)sulfonyl)pentyl)amino)-2-(2,6-dioxopiperidin-3-yl)isoindoline-1,3-dione |
| | | 4-((12-(4-(4-((5-chloro-4-((2-(dimethylphosphoryl)phenyl)amino)pyrimidin-2-yl)amino)-3-methoxyphenyl)piperazin-1-yl)-12-oxododec-5-yn-1-yl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| | | 4-((8-(4-(6-(4-(4-((5-chloro-4-((2-(dimethylphosphoryl)phenyl)amino)pyrimidin-2-yl)amino)-3-methoxyphenyl)piperazin-1-yl)-6-oxohexyl)-1H-1,2,3-triazol-1-yl)octyl)amino)-2-(2,6-dioxopiperidin-3-yl)isoindoline-1,3-dione |
| SIAIS1197087 | | (2S,4R)-1-((S)-2-(2-(2-(2-(4-(4-((5-chloro-4-((2-(dimethylphosphoryl)phenyl)amino)pyrimidin-2-yl)amino)-3-methoxyphenyl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAIS1197079 | 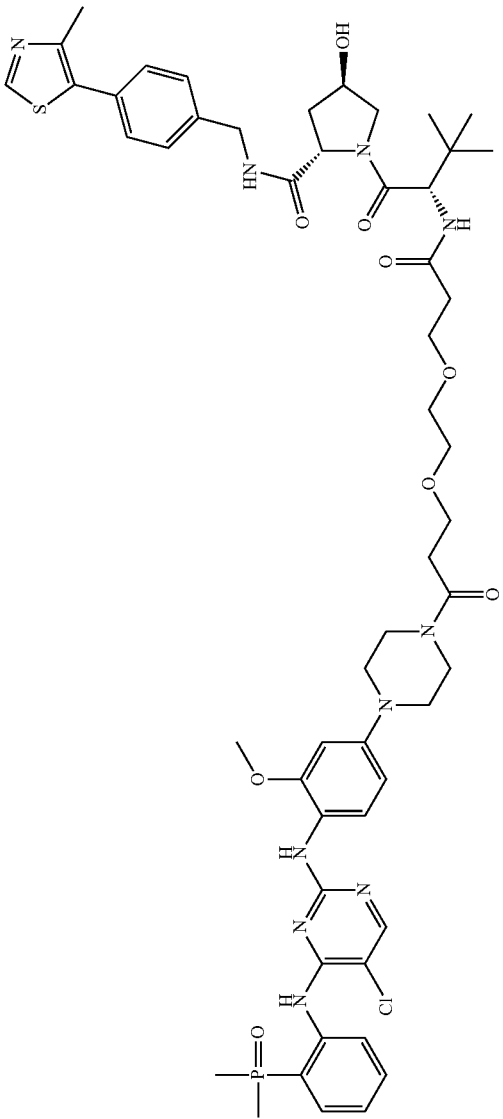 | (2S,4R)-1-((S)-2-(3-(2-(3-(4-(4-((5-chloro-4-((2-(dimethylphosphoryl)phenyl)amino)pyrimidin-2-yl)amino)-3-methoxyphenyl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide |
| | 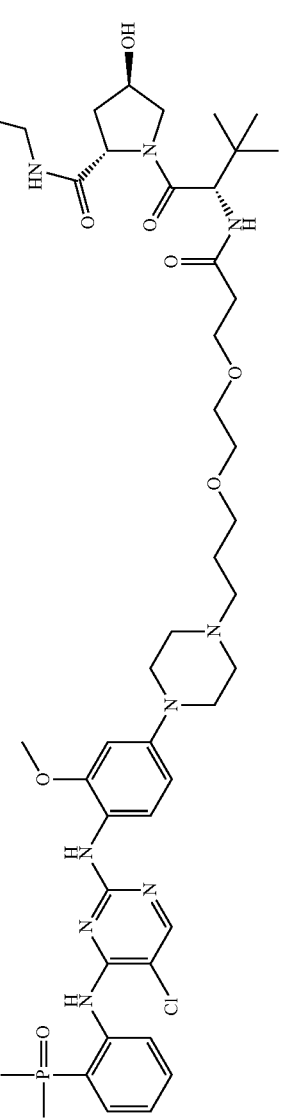 | (2S,4R)-1-((S)-2-(3-(2-(3-(4-(4-((5-chloro-4-((2-(dimethylphosphoryl)phenyl)amino)pyrimidin-2-yl)amino)-3-methoxyphenyl)piperazin-1-yl)propoxy)ethoxy)propanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S119 7081 | | (2S,4R)-1-((S)-2-(tert-butyl)-16-(4-((5-chloro-4-((2-(dimethylphosphoryl)phenyl)amino)pyrimidin-2-yl)amino)-3-methoxyphenyl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide |
| SIAI S119 7083 | | (2S,4R)-1-((S)-2-(tert-butyl)-19-(4-((5-chloro-4-((2-(dimethylphosphoryl)phenyl)amino)pyrimidin-2-yl)amino)-3-methoxyphenyl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S119 7085 | | (2S,4R)-1-((S)-2-(tert-butyl)-22-(4-(4-((5-chloro-4-((2-(dimethylphosphoryl)phenyl)amino)pyrimidin-2-yl)amino)-3-methoxyphenyl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide |
| SIAI S119 7145 | | (2S,4R)-1-((S)-2-(4-(4-((5-chloro-4-((2-(dimethylphosphoryl)phenyl)amino)pyrimidin-2-yl)amino)-3-methoxyphenyl)piperazin-1-yl)-4-oxobutanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S119 7147 | | (2S,4R)-1-((S)-2-(5-(4-(4-((5-chloro-4-((2-(dimethylphosphoryl)phenyl)amino)pyrimidin-2-yl)amino)-3-methoxyphenyl)piperazin-1-yl)-5-oxopentanamido)-3,3-dimethylbutanoyl)-4-hydroxy-N-(4-(4-methylthiazol-5-yl)benzyl)pyrrolidine-2-carboxamide |
| SIAI S119 7149 | | (2S,4R)-1-((S)-2-(6-(4-(4-((5-chloro-4-((2-(dimethylphosphoryl)phenyl)amino)pyrimidin-2-yl)amino)-3-methoxyphenyl)piperazin-1-yl)-6-oxohexanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAIS1197151 | | (2S,4R)-1-((S)-2-(7-(4-(4-((5-chloro-4-((2-(dimethylphosphoryl)phenyl)amino)pyrimidin-2-yl)amino)-3-methoxyphenyl)piperazin-1-yl)-7-oxoheptanamido)-3,3-dimethylbutanoyl)-4-hydroxy-N-(4-(4-methylthiazol-5-yl)benzyl)pyrrolidine-2-carboxamide |
|  | | (2S,4R)-1-((S)-2-(7-(4-(4-((5-chloro-4-((2-(dimethylphosphoryl)phenyl)amino)pyrimidin-2-yl)amino)-3-methoxyphenyl)piperazin-1-yl)heptanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S119 7153 | 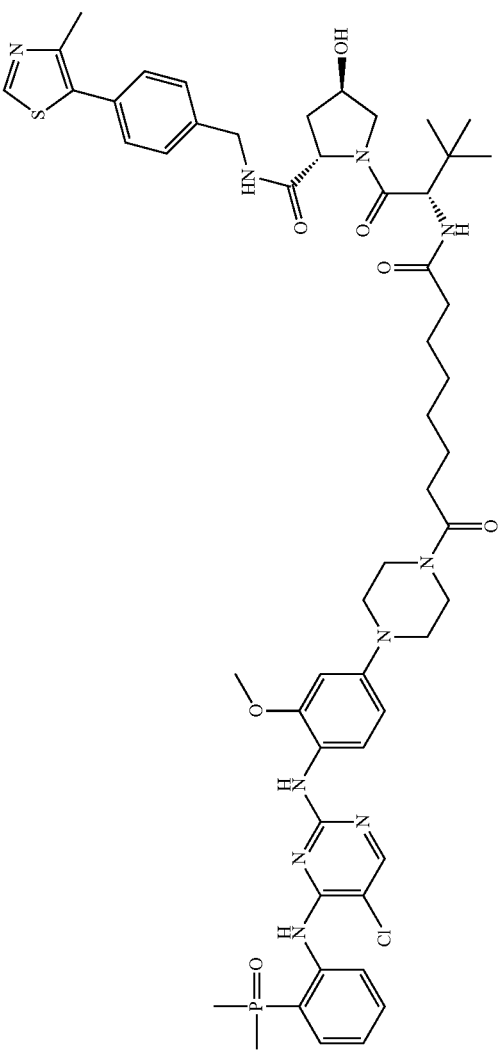 | (2S,4R)-1-((S)-2-(8-(4-(4-((5-chloro-4-((2-(dimethylphosphoryl)phenyl)amino)pyrimidin-2-yl)amino)-3-methoxyphenyl)piperazin-1-yl)-8-oxooctanamido)-3,3-dimethylbutanoyl)-4-hydroxy-N-(4-(4-methylthiazol-5-yl)benzyl)pyrrolidine-2-carboxamide |
| SIAI S119 7155 | 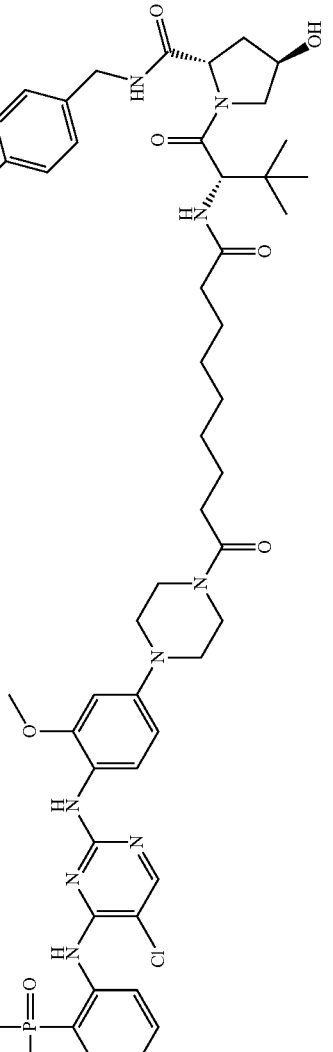 | (2S,4R)-1-((S)-2-(9-(4-(4-((5-chloro-4-((2-(dimethylphosphoryl)phenyl)amino)pyrimidin-2-yl)amino)-3-methoxyphenyl)piperazin-1-yl)-9-oxononanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S119 7157 | 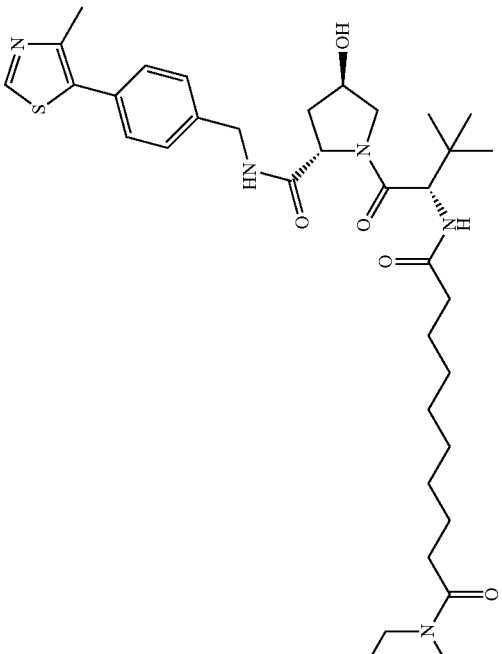 | (2S,4R)-1-((S)-2-(10-(4-(4-((5-chloro-4-((2-(dimethylphosphoryl)phenyl)amino)pyrimidin-2-yl)amino)-3-methoxyphenyl)piperazin-1-yl)-10-oxodecanamido)-3,3-dimethylbutanoyl)-4-hydroxy-N-(4-(4-methylthiazol-5-yl)benzyl)pyrrolidine-2-carboxamide |
| | 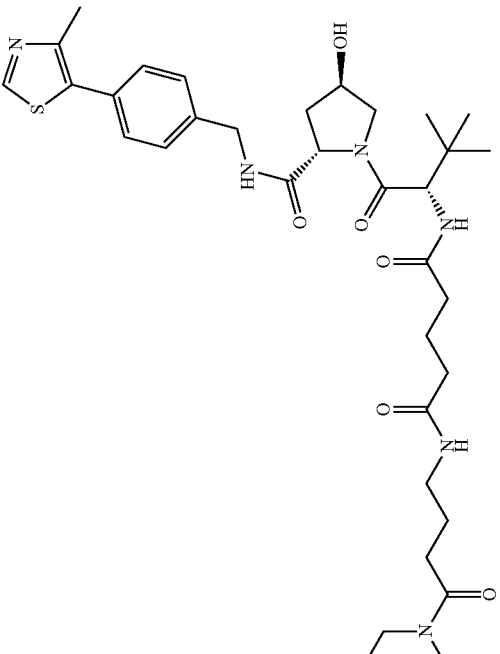 | N1-(4-(4-((5-chloro-4-((2-(dimethylphosphoryl)phenyl)amino)pyrimidin-2-yl)amino)-3-methoxyphenyl)piperazin-1-yl)-4-oxobutyl)-N5-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide |

TABLE 1-continued

Structural formulas and names of the compounds of the present disclosure

| Compound ID | Structure of the compound | Name of the compound |
| --- | --- | --- |
| SIAI S151 113 | | N-(1-(4-((5-chloro-4-((2-(dimethylphosphoryl)phenyl)amino)pyrimidin-2-yl)amino)-3-methoxyphenyl)piperidin-4-yl)-3-(2-((2-(2,6-dioxopiperidin-3-yl)-1,3-dioxoisoindolin-4-yl)amino)ethoxy)propanamide |
| SIAI S151 114 | | N-(1-(4-((5-chloro-4-((2-(dimethylphosphoryl)phenyl)amino)pyrimidin-2-yl)amino)-3-methoxyphenyl)piperidin-4-yl)-3-(2-(2-((2-(2,6-dioxopiperidin-3-yl)-1,3-dioxoisoindolin-4-yl)amino)ethoxy)ethoxy)propanamide |
| SIAI S151 115 | | N-(1-(4-((5-chloro-4-((2-(dimethylphosphoryl)phenyl)amino)pyrimidin-2-yl)amino)-3-methoxyphenyl)piperidin-4-yl)-3-(2-(2-((2-(2,6-dioxopiperidin-3-yl)-1,3-dioxoisoindolin-4-yl)amino)ethoxy)ethoxy)ethoxy)propanamide |

TABLE 1-continued

Structural formulas and names of the compounds of the present disclosure

| Compound ID | Structure of the compound | Name of the compound |
|---|---|---|
| SIAI S151 116 | | N-(1-(4-((5-chloro-4-((2-(dimethylphosphoryl)phenyl)amino)pyrimidin-2-yl)amino)-3-methoxyphenyl)piperidin-4-yl)-1-((2-(2,6-dioxopiperidin-3-yl)-1,3-dioxoisoindolin-4-yl)amino)-3,6,9,12-tetraoxapentadecan-15-amide |
| SIAI S151 117 | | N-(1-(4-((5-chloro-4-((2-(dimethylphosphoryl)phenyl)amino)pyrimidin-4-yl)amino)-3-methoxyphenyl)piperidin-4-yl)-1-((2-(2,6-dioxopiperidin-3-yl)-1,3-dioxoisoindolin-4-yl)amino)-3,6,9,12,15-pentaoxaoctadecan-18-amide |
| | | N-(1-(4-((5-chloro-4-((2-(dimethylphosphoryl)phenyl)amino)pyrimidin-4-yl)amino)-3-methoxyphenyl)piperidin-4-yl)-3-(2-((2-(2,6-dioxopiperidin-3-yl)-1-oxoisoindolin-4-yl)amino)ethoxy)propanamide |

TABLE 1-continued

Structural formulas and names of the compounds of the present disclosure

| Compound ID | Structure of the compound | Name of the compound |
|---|---|---|
| | | N-(1-(4-((5-chloro-4-((2-(dimethylphosphoryl)phenyl)amino)pyrimidin-2-yl)amino)-3-methoxyphenyl)piperidin-4-yl)-3-(2-(2-((2-(2,6-dioxopiperidin-3-yl)-1-oxoisoindolin-4-yl)amino)ethoxy)ethoxy)propanamide |
| | | N-(1-(4-((5-chloro-4-((2-(dimethylphosphoryl)phenyl)amino)pyrimidin-2-yl)amino)-3-methoxyphenyl)piperidin-4-yl)-3-(2-(2-((2-(2,6-dioxopiperidin-3-yl)-1-oxoisoindolin-4-yl)amino)ethoxy)ethoxy)propanamide |
| | | N-(1-(4-((5-chloro-4-((2-(dimethylphosphoryl)phenyl)amino)pyrimidin-2-yl)amino)-3-methoxyphenyl)piperidin-4-yl)-1-((2-(2,6-dioxopiperidin-3-yl)-1-oxoisoindolin-4-yl)amino)-3,6,9,12-tetraoxapentadecan-15-amide |

TABLE 1-continued

Structural formulas and names of the compounds of the present disclosure

| Compound ID | Structure of the compound | Name of the compound |
|---|---|---|
| | | N-(1-(4-((5-chloro-4-((2-(dimethylphosphoryl)phenyl)amino)pyrimidin-2-yl)amino)-3-methoxyphenyl)piperidin-4-yl)-1-((2-(2,6-dioxopiperidin-3-yl)-1-oxoisoindolin-4-yl)amino)-3,6,9,12,15-pentaoxaoctadecan-18-amide |
| | | N-(1-(4-((5-chloro-4-((2-(dimethylphosphoryl)phenyl)amino)pyrimidin-2-yl)amino)-3-methoxyphenyl)piperidin-4-yl)-3-(2-(2-((2-(2,6-dioxopiperidin-3-yl)-1,3-dioxoisoindolin-4-yl)oxy)ethoxy)ethoxy)propanamide |
| | | N-(1-(4-((5-chloro-4-((2-(dimethylphosphoryl)phenyl)amino)pyrimidin-2-yl)amino)-3-methoxyphenyl)piperidin-4-yl)-3-(2-(2-((2-(2,6-dioxopiperidin-3-yl)-1-oxoisoindolin-4-yl)oxy)ethoxy)ethoxy)propanamide |

TABLE 1-continued

Structural formulas and names of the compounds of the present disclosure

| Compound ID | Structure of the compound | Name of the compound |
|---|---|---|
| | | 4-((2-(2-(2-(3-((1-(4-((5-chloro-4-((2-(dimethylphosphoryl)phenyl)amino)pyrimidin-2-yl)amino)-3-methoxyphenyl)piperidin-4-yl)amino)propoxy)ethoxy)ethyl)amino)-2-(2,6-dioxopiperidin-3-yl)isoindoline-1,3-dione |
| | | 3-(4-((2-(2-(2-(3-((1-(4-((5-chloro-4-((2-(dimethylphosphoryl)phenyl)amino)pyrimidin-2-yl)amino)-3-methoxyphenyl)piperidin-4-yl)amino)propoxy)ethoxy)ethyl)amino)-1-oxoisoindolin-2-yl)piperidine-2,6-dione |
| | | N-(1-(4-((5-chloro-4-((2-(dimethylphosphoryl)phenyl)amino)pyrimidin-2-yl)amino)-3-methoxyphenyl)piperidin-4-yl)-3-(2-(2-(3-(2-(2,6-dioxopiperidin-3-yl)-1-oxoisoindolin-4-yl)propoxy)ethoxy)ethoxy)propanamide |

TABLE 1-continued

Structural formulas and names of the compounds of the present disclosure

| Compound ID | Structure of the compound | Name of the compound |
|---|---|---|
| SIAI S151 120 | | N-(1-(4-((5-chloro-4-((2-(dimethylphosphoryl)phenyl)amino)pyrimidin-2-yl)amino)-3-methoxyphenyl)piperidin-4-yl)-2-((2-(2,6-dioxopiperidin-3-yl)-1,3-dioxoisoindolin-4-yl)amino)acetamide |
| SIAI S151 121 | | N-(1-(4-((5-chloro-4-((2-(dimethylphosphoryl)phenyl)amino)pyrimidin-2-yl)amino)-3-methoxyphenyl)piperidin-4-yl)-3-((2-(2,6-dioxopiperidin-3-yl)-1,3-dioxoisoindolin-4-yl)amino)propanamide |
| SIAI S151 118 | | N-(1-(4-((5-chloro-4-((2-(dimethylphosphoryl)phenyl)amino)pyrimidin-2-yl)amino)-3-methoxyphenyl)piperidin-4-yl)-4-((2-(2,6-dioxopiperidin-3-yl)-1,3-dioxoisoindolin-4-yl)amino)butanamide |

TABLE 1-continued

Structural formulas and names of the compounds of the present disclosure

| Compound ID | Structure of the compound | Name of the compound |
|---|---|---|
| SIAI S151 119 | | N-(1-(4-((5-chloro-4-((2-(dimethyl)phosphoryl)phenyl)amino)pyrimidin-2-yl)amino)-3-methoxyphenyl)piperidin-4-yl)-5-((2-(2,6-dioxopiperidin-3-yl)-1,3-dioxoisoindolin-4-yl)amino)pentanamide |
| SIAI S151 122 | | N-(1-(4-((5-chloro-4-((2-(dimethyl)phosphoryl)phenyl)amino)pyrimidin-2-yl)amino)-3-methoxyphenyl)piperidin-4-yl)-6-((2-(2,6-dioxopiperidin-3-yl)-1,3-dioxoisoindolin-4-yl)amino)hexanamide |
| SIAI S151 123 | | N-(1-(4-((5-chloro-4-((2-(dimethyl)phosphoryl)phenyl)amino)pyrimidin-2-yl)amino)-3-methoxyphenyl)piperidin-4-yl)-7-((2-(2,6-dioxopiperidin-3-yl)-1,3-dioxoisoindolin-4-yl)amino)heptanamide |

TABLE 1-continued

Structural formulas and names of the compounds of the present disclosure

| Compound ID | Structure of the compound | Name of the compound |
|---|---|---|
| SIAI S219 151 | | N-(1-(4-((5-chloro-4-((2-(dimethylphosphoryl)phenyl)amino)pyrimidin-4-yl)amino)-3-methoxyphenyl)piperidin-4-yl)-2-((2-(2,6-dioxopiperidin-3-yl)-1-oxoisoindolin-4-yl)amino)acetamide |
| | | N-(1-(4-((5-chloro-4-((2-(dimethylphosphoryl)phenyl)amino)pyrimidin-4-yl)amino)-3-methoxyphenyl)piperidin-4-yl)-3-((2-(2,6-dioxopiperidin-3-yl)-1-oxoisoindolin-4-yl)amino)propanamide |
| SIAI S219 128 | | N-(1-(4-((5-chloro-4-((2-(dimethylphosphoryl)phenyl)amino)pyrimidin-4-yl)amino)-3-methoxyphenyl)piperidin-4-yl)-4-((2-(2,6-dioxopiperidin-3-yl)-1-oxoisoindolin-4-yl)amino)butanamide |

TABLE 1-continued

Structural formulas and names of the compounds of the present disclosure

| Compound ID | Structure of the compound | Name of the compound |
|---|---|---|
| SIAI S219 152 | | N-(1-(4-((5-chloro-4-((2-(dimethylphosphoryl)phenyl)amino)pyrimidin-2-yl)amino)-3-methoxyphenyl)piperidin-4-yl)-5-((2-(2,6-dioxopiperidin-3-yl)-1-oxoisoindolin-4-yl)amino)pentanamide |
| SIAI S219 153 | | N-(1-(4-((5-chloro-4-((2-(dimethylphosphoryl)phenyl)amino)pyrimidin-2-yl)amino)-3-methoxyphenyl)piperidin-4-yl)-6-((2-(2,6-dioxopiperidin-3-yl)-1-oxoisoindolin-4-yl)amino)hexanamide |
| SIAI S219 154 | | N-(1-(4-((5-chloro-4-((2-(dimethylphosphoryl)phenyl)amino)pyrimidin-2-yl)amino)-3-methoxyphenyl)piperidin-4-yl)-7-((2-(2,6-dioxopiperidin-3-yl)-1-oxoisoindolin-4-yl)amino)heptanamide |

TABLE 1-continued

Structural formulas and names of the compounds of the present disclosure

| Compound ID | Structure of the compound | Name of the compound |
|---|---|---|
| | | N-(1-(4-((5-chloro-4-((2-(dimethylphosphoryl)phenyl)amino)pyrimidin-2-yl)amino)-3-methoxyphenyl)piperidin-4-yl)-7-((2-(2,6-dioxopiperidin-3-yl)-1,3-dioxoisoindolin-4-yl)oxy)heptanamide |
| | | N-(1-(4-((5-chloro-4-((2-(dimethylphosphoryl)phenyl)amino)pyrimidin-2-yl)amino)-3-methoxyphenyl)piperidin-4-yl)-7-((2-(2,6-dioxopiperidin-3-yl)-1-oxoisoindolin-4-yl)oxy)heptanamide |
| SIAI S220 330 | | N-(1-(4-((5-chloro-4-((2-(dimethylphosphoryl)phenyl)amino)pyrimidin-2-yl)amino)-3-methoxyphenyl)piperidin-4-yl)-4-((2-(2,6-dioxopiperidin-3-yl)-1,3-dioxoisoindolin-4-yl)amino)-N-methylbutanamide |

TABLE 1-continued

Structural formulas and names of the compounds of the present disclosure

| Compound ID | Structure of the compound | Name of the compound |
|---|---|---|
|  |  | N-(1-(4-((5-chloro-4-((2-(dimethylphosphoryl)phenyl)amino)pyrimidin-2-yl)amino)-3-methoxyphenyl)piperidin-4-yl)-4-((2-(2,6-dioxopiperidin-3-yl)-1-oxoisoindolin-4-yl)amino)-N-methylbutanamide |
|  |  | 4-((4-((1-(4-((5-chloro-4-((2-(dimethylphosphoryl)phenyl)amino)pyrimidin-2-yl)amino)-3-methoxyphenyl)piperidin-4-yl)amino)butyl)amino)-2-(2,6-dioxopiperidin-3-yl)isoindoline-1,3-dione |
| SIAIS220026 |  | 3-(4-((4-((1-(4-((5-chloro-4-((2-(dimethylphosphoryl)phenyl)amino)pyrimidin-2-yl)amino)-3-methoxyphenyl)piperidin-4-yl)amino)butyl)amino)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| | | 4-((4-((1-(4-((5-chloro-4-((2-(dimethylphosphoryl)phenyl)amino)pyrimidin-2-yl)amino)-3-methoxyphenyl)piperidin-4-yl)(methyl)amino)butyl)amino)-2-(2,6-dioxopiperidin-3-yl)isoindoline-1,3-dione |
| | | 4-((7-((1-(4-((5-chloro-4-((2-(dimethylphosphoryl)phenyl)amino)pyrimidin-2-yl)amino)-3-methoxyphenyl)piperidin-4-yl)amino)heptyl)amino)-2-(2,6-dioxopiperidin-3-yl)isoindoline-1,3-dione |
| SIAIS219170 | | N-(1-(4-((5-chloro-4-((2-(dimethylphosphoryl)phenyl)amino)pyrimidin-2-yl)amino)-3-methoxyphenyl)piperidin-4-yl)-3-(2-(2,6-dioxopiperidin-3-yl)-1,3-dioxoisoindolin-4-yl)propanamide |

TABLE 1-continued

Structural formulas and names of the compounds of the present disclosure

| Compound ID | Structure of the compound | Name of the compound |
|---|---|---|
| | 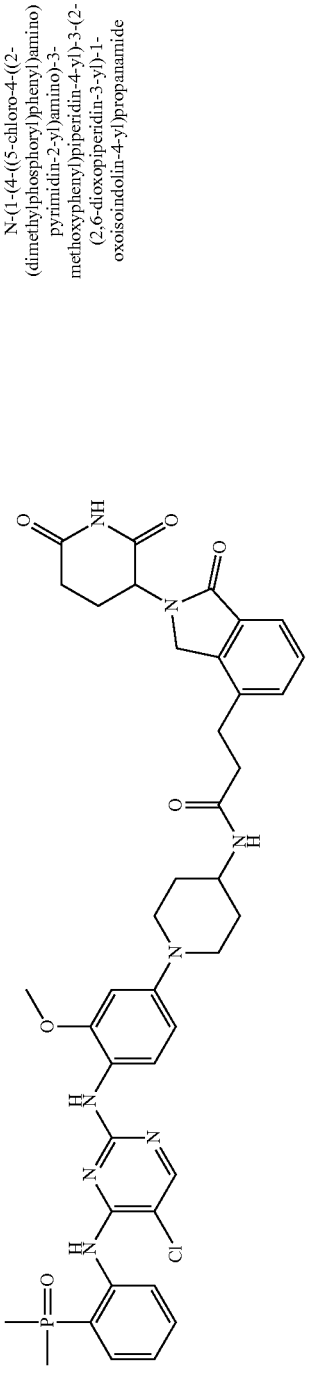 | N-(1-(4-(5-chloro-4-((2-(dimethylphosphoryl)phenyl)amino)pyrimidin-2-yl)amino)-3-methoxyphenyl)piperidin-4-yl)-3-(2-(2,6-dioxopiperidin-3-yl)-1-oxoisoindolin-4-yl)propanamide |
| | | N1-(1-(4-((5-chloro-4-((2-(dimethylphosphoryl)phenyl)amino)pyrimidin-2-yl)amino)-3-methoxyphenyl)piperidin-4-yl)-N7-(2-(2,6-dioxopiperidin-3-yl)-1,3-dioxoisoindolin-4-yl)heptanediamide |

TABLE 1-continued

Structural formulas and names of the compounds of the present disclosure

| Compound ID | Structure of the compound | Name of the compound |
|---|---|---|
| SIAIS151128 | 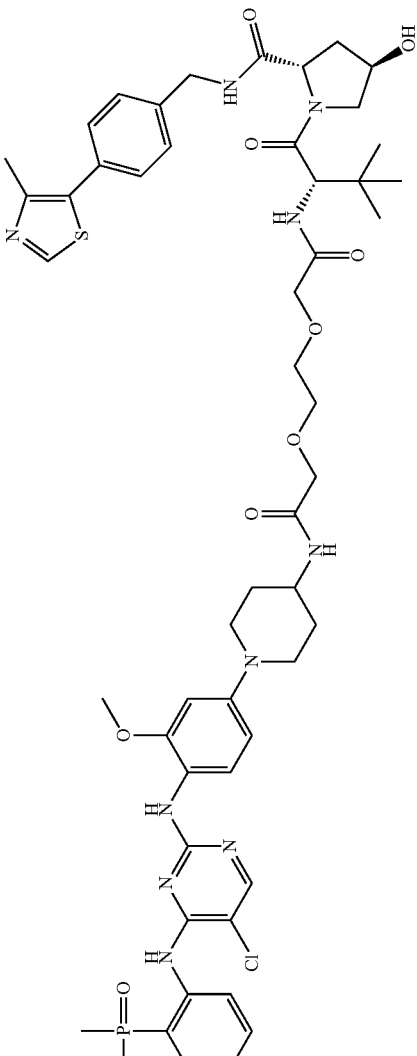 | (2S,4R)-1-((S)-2-(2-(2-(2-((1-(4-((5-chloro-4-((2-(dimethylphosphoryl)phenyl)amino)pyrimidin-2-yl)amino)-3-methoxyphenyl)piperidin-4-yl)amino)-2-oxoethoxy)ethoxy)acetamido)-3,3-dimethylbutanoyl)-4-hydroxy-N-(4-(4-methylthiazol-5-yl)benzyl)pyrrolidine-2-carboxamide |
| SIAIS151124 | 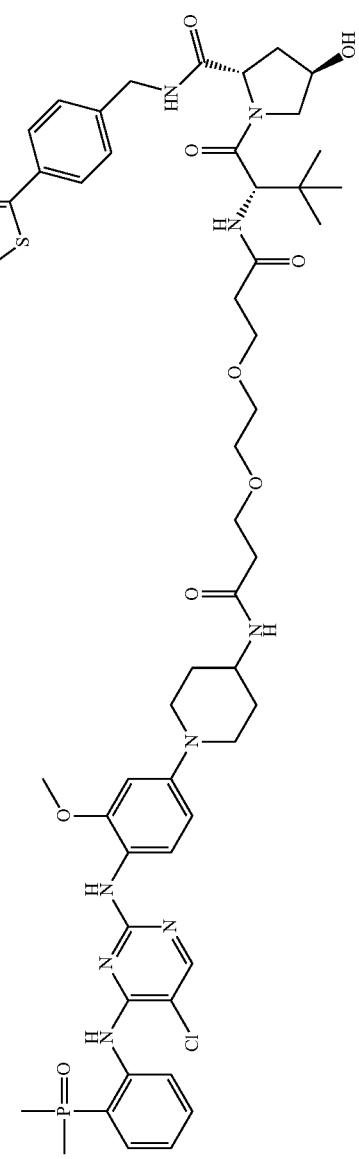 | (2S,4R)-1-((S)-2-(3-(2-(3-((1-(4-((5-chloro-4-((2-(dimethylphosphoryl)phenyl)amino)pyrimidin-2-yl)amino)-3-methoxyphenyl)piperidin-4-yl)amino)-3-oxopropoxy)ethoxy)propanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S151 125 | | (2S,4R)-1-((S)-2-(tert-butyl)-16-((1-(4-((5-chloro-4-((2-(dimethylphosphoryl)phenyl)amino)pyrimidin-2-yl)amino)-3-methoxyphenyl)piperidin-4-yl)amino)-4,16-dioxo-7,10,13-trioxa-3-azahexadecanoyl)-4-hydroxy-N-(4-(4-methylthiazol-5-yl)benzyl)pyrrolidine-2-carboxamide |
| SIAI S151 126 | | N1-(1-(4-((5-chloro-4-((2-(dimethylphosphoryl)phenyl)amino)pyrimidin-2-yl)amino)-3-methoxyphenyl)piperidin-4-yl)-N16-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13-tetraoxahexadecanediamide |

TABLE 1-continued

Structural formulas and names of the compounds of the present disclosure

| Compound ID | Structure of the compound | Name of the compound |
|---|---|---|
| SIAI S151 127 | 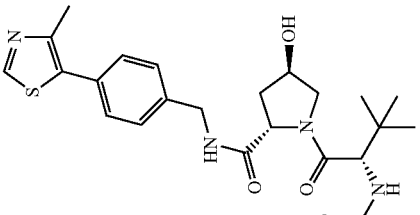 | N1-(1-(4-((5-chloro-4-((2-(dimethylphosphoryl)phenyl)amino)pyrimidin-2-yl)amino)-3-methoxyphenyl)piperidin-4-yl)-N19-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13,16-pentaoxanonadecanediamide |
| SIAI S164 143 | 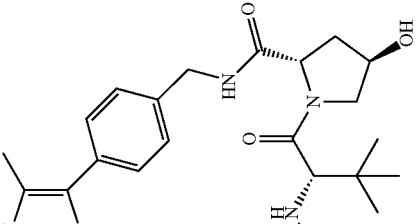 | N1-(1-(4-((5-chloro-4-((2-(dimethylphosphoryl)phenyl)amino)pyrimidin-2-yl)amino)-3-methoxyphenyl)piperidin-4-yl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide |

TABLE 1-continued

Structural formulas and names of the compounds of the present disclosure

| Compound ID | Structure of the compound | Name of the compound |
|---|---|---|
| SIAI S164 144 | 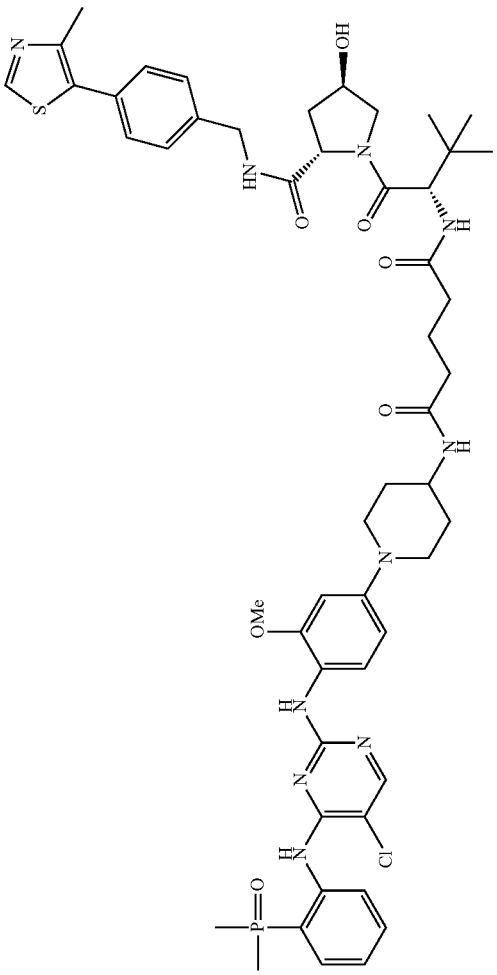 | N1-(1-(4-((5-chloro-4-((2-(dimethylphosphoryl)phenyl)amino)pyrimidin-2-yl)amino)-3-methoxyphenyl)piperidin-4-yl)-N5-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide |
| SIAI S164 145 | 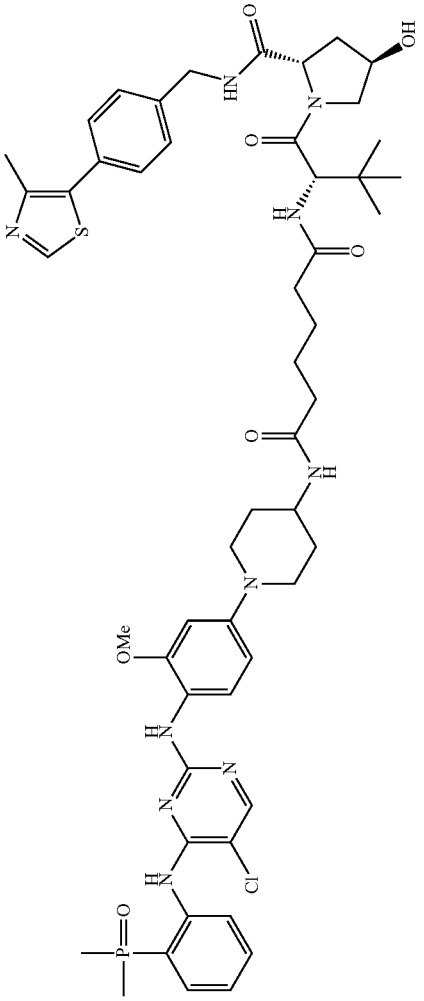 | N1-(1-(4-((5-chloro-4-((2-(dimethylphosphoryl)phenyl)amino)pyrimidin-2-yl)amino)-3-methoxyphenyl)piperidin-4-yl)-N6-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)adipamide |

TABLE 1-continued

Structural formulas and names of the compounds of the present disclosure

| Compound ID | Structure of the compound | Name of the compound |
|---|---|---|
| SIAI S164 146 | 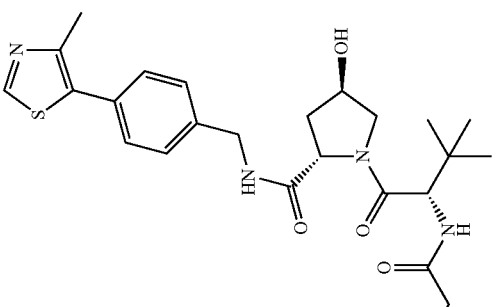 | N1-(1-(4-((5-chloro-4-((2-(dimethylphosphoryl)phenyl)amino)pyrimidin-2-yl)amino)-3-methoxyphenyl)piperidin-4-yl)-N7-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)heptanediamide |
| SIAI S164 147 | 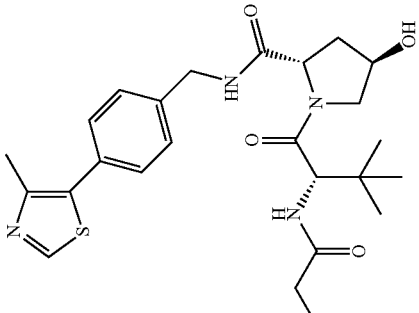 | N1-(1-(4-((5-chloro-4-((2-(dimethylphosphoryl)phenyl)amino)pyrimidin-2-yl)amino)-3-methoxyphenyl)piperidin-4-yl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide |

TABLE 1-continued

Structural formulas and names of the compounds of the present disclosure

| Compound ID | Structure of the compound | Name of the compound |
|---|---|---|
| SIAI S164 148 | 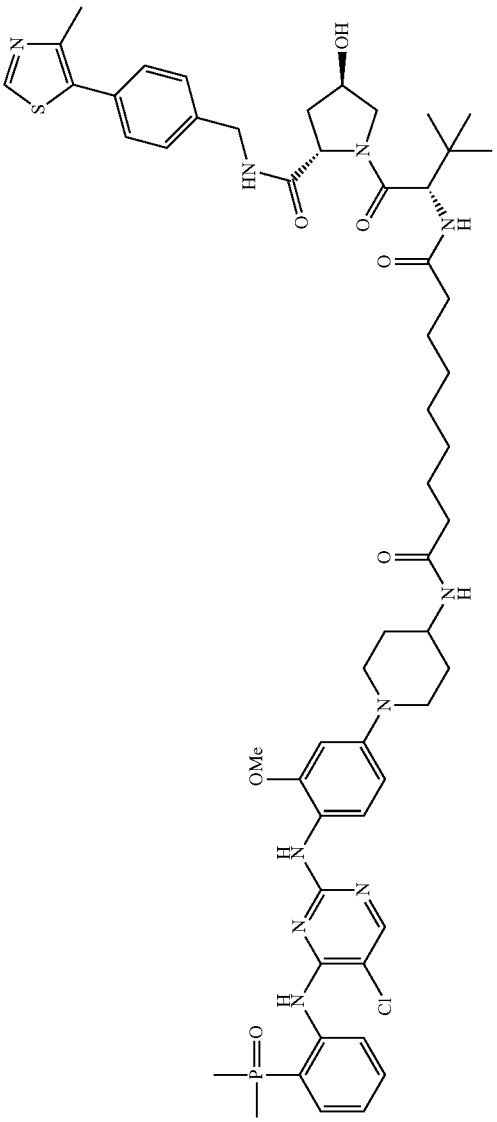 | N1-(1-(4-((5-chloro-4-((2-(dimethylphosphoryl)phenyl)amino)pyrimidin-2-yl)amino)-3-methoxyphenyl)piperidin-4-yl)-N9-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)nonanediamide |
| SIAI S164 149 | 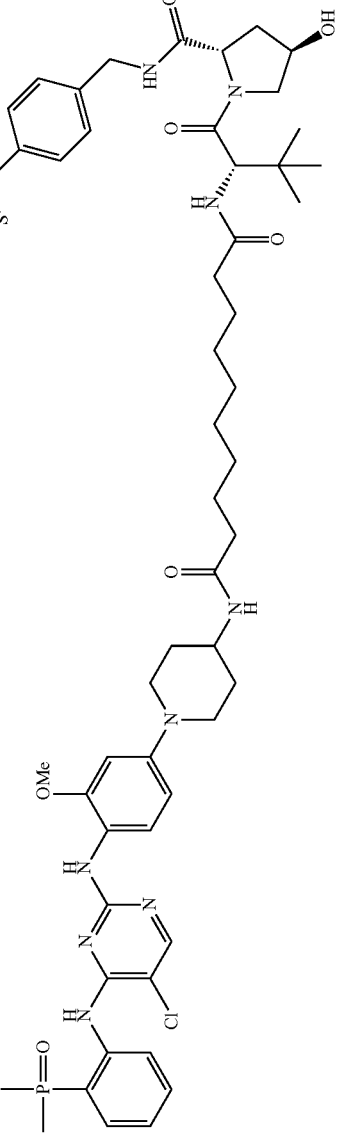 | N1-(1-(4-((5-chloro-4-((2-(dimethylphosphoryl)phenyl)amino)pyrimidin-2-yl)amino)-3-methoxyphenyl)piperidin-4-yl)-N10-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide |

TABLE 1-continued

Structural formulas and names of the compounds of the present disclosure

| Compound ID | Structure of the compound | Name of the compound |
|---|---|---|
| SIAI S121 0117 | 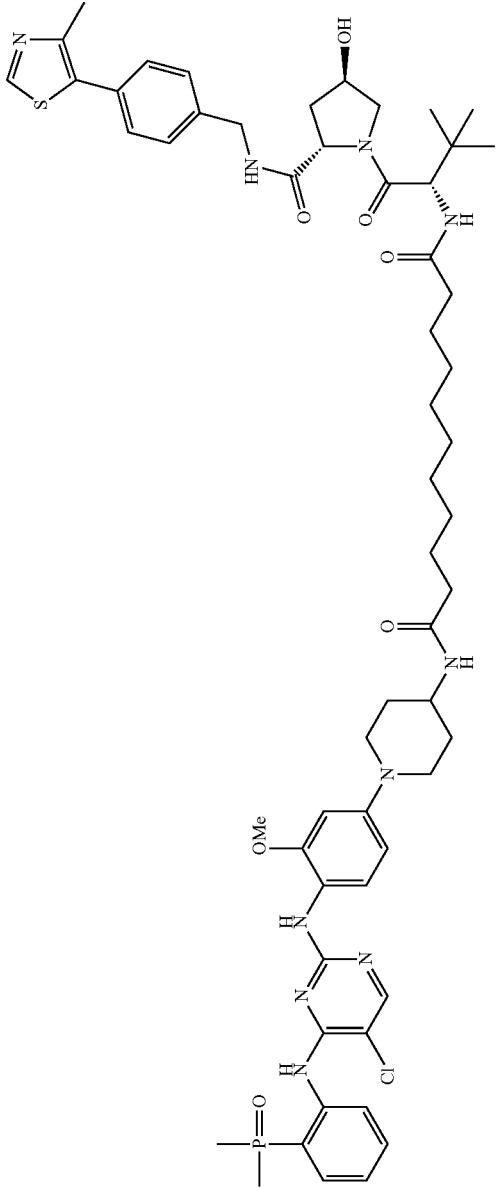 | N1-(1-(4-((5-chloro-4-((2-(dimethylphosphoryl)phenyl)amino)pyrimidin-2-yl)amino)-3-methoxyphenyl)piperidin-4-yl)-N11-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)undecanediamide |
| | | (2S,4R)-1-((S)-2-(8-((1-(4-((5-chloro-4-((2-(dimethylphosphoryl)phenyl)amino)pyrimidin-2-yl)amino)-3-methoxyphenyl)piperidin-4-yl)amino)octanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | 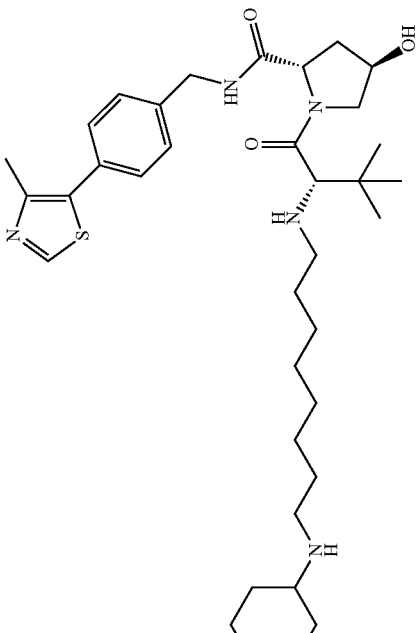 | (2S,4R)-1-((S)-2-((8-((1-(4-((5-chloro-4-((2-(dimethylphosphoryl)phenyl)amino)pyrimidin-2-yl)amino)-3-methoxyphenyl)piperidin-4-yl)amino)octyl)amino)-3,3-dimethylbutanoyl)-4-hydroxy-N-(4-(4-methylthiazol-5-yl)benzyl)pyrrolidine-2-carboxamide |
| | 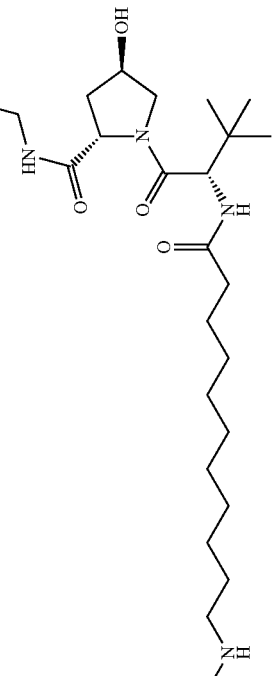 | (2S,4R)-1-((S)-2-((11-((1-(4-((5-chloro-4-((2-(dimethylphosphoryl)phenyl)amino)pyrimidin-2-yl)amino)-3-methoxyphenyl)piperidin-4-yl)amino)undecanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | 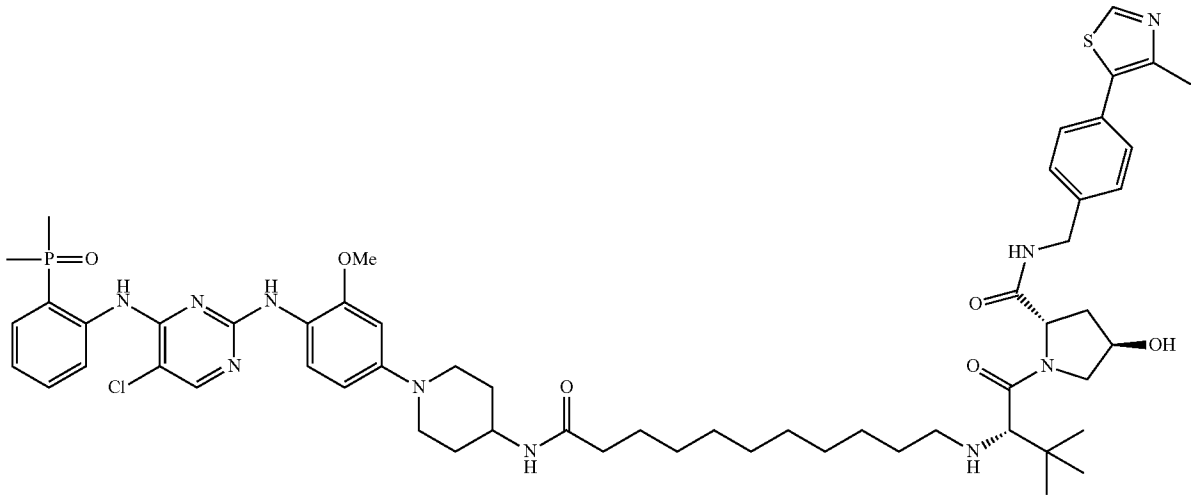 | (2S,4R)-1-((S)-2-((11-((1-(4-((5-chloro-4-((2-(dimethylphosphoryl)phenyl)amino)pyrimidin-2-yl)amino)-3-methoxyphenyl)piperidin-4-yl)amino)-11-oxoundecyl)amino)-3,3-dimethylbutanoyl)-4-hydroxy-N-(4-(4-methylthiazol-5-yl)benzyl)pyrrolidine-2-carboxamide |
| | 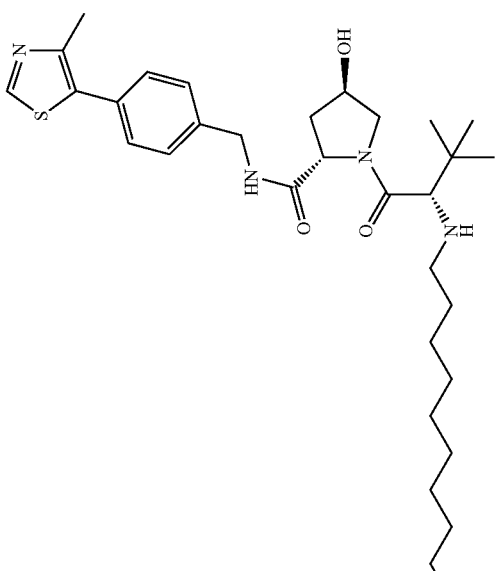 | (2S,4R)-1-((S)-2-((11-((1-(4-((5-chloro-4-((2-(dimethylphosphoryl)phenyl)amino)pyrimidin-2-yl)amino)-3-methoxyphenyl)piperidin-4-yl)amino)undecyl)amino)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | 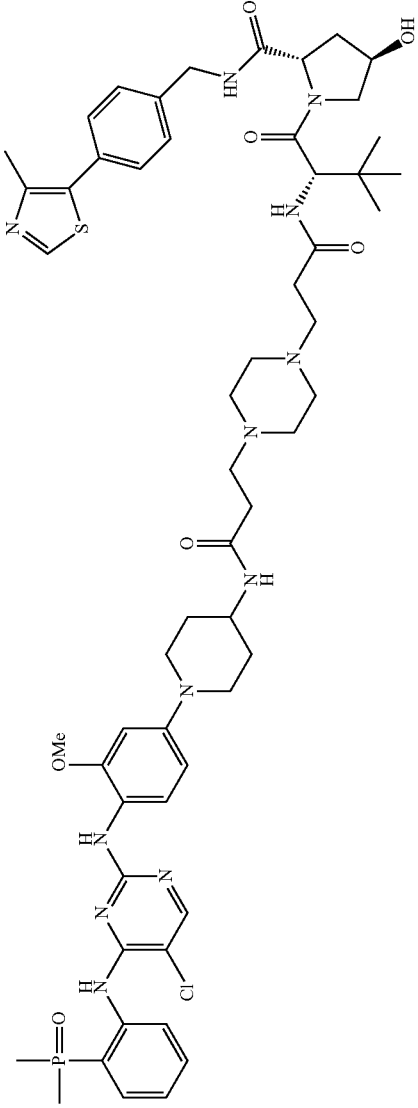 | (2S,4R)-1-((S)-2-(3-(4-(3-((1-(4-((5-chloro-4-((2-(dimethylphosphoryl)phenyl)amino)pyrimidin-2-yl)amino)-3-methoxyphenyl)piperidin-4-yl)amino)-3-oxopropyl)piperazin-1-yl)propanamido)-3,3-dimethylbutanoyl)-4-hydroxy-N-(4-(4-methylthiazol-5-yl)benzyl)pyrrolidine-2-carboxamide |
| | | (2S,4R)-1-((S)-2-(3-(4-(3-((1-(4-((5-chloro-4-((2-(dimethylphosphoryl)phenyl)amino)pyrimidin-2-yl)amino)-3-methoxyphenyl)piperidin-4-yl)amino)-3-oxopropyl)phenyl)propanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S164 157 | | N1-(1-(4-(5-chloro-4-((2-(dimethylphosphoryl)phenyl)amino)pyrimidin-2-yl)amino)-3-methoxyphenyl)piperidin-4-yl)-N4-(2-((2-(2,6-dioxopiperidin-3-yl)-1,3-dioxoisoindolin-4-yl)amino)ethyl)succinamide |
| SIAI S164 007 | | 4-((2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| SIAI S164 008 | | 4-((2-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethyl)amino)-2-(2,6-dioxopiperidin-3-yl)isoindoline-1,3-dione |
| SIAI S164 009 | | 4-((2-(2-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethoxy)ethyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| SIAI S164 016 | | 4-((15-(4-(1-(4-(4-((5-chloro-4-((2-(dimethylphosphoryl)phenyl)amino)pyrimidin-2-yl)amino)-3-methoxyphenyl)piperidin-4-yl)piperazin-1-yl)-15-oxo-3,6,9,12-tetraoxapentadecyl)amino)-2-(2,6-dioxopiperidin-3-yl)isoindoline-1,3-dione |
| SIAI S164 017 | | 4-((18-(4-(1-(4-(4-((5-chloro-4-((2-(dimethylphosphoryl)phenyl)amino)pyrimidin-2-yl)amino)-3-methoxyphenyl)piperidin-4-yl)piperazin-1-yl)-18-oxo-3,6,9,12,15-pentaoxaoctadecyl)amino)-2-(2,6-dioxopiperidin-3-yl)isoindoline-1,3-dione |
| | | 3-(4-((2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethyl)amino)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| | 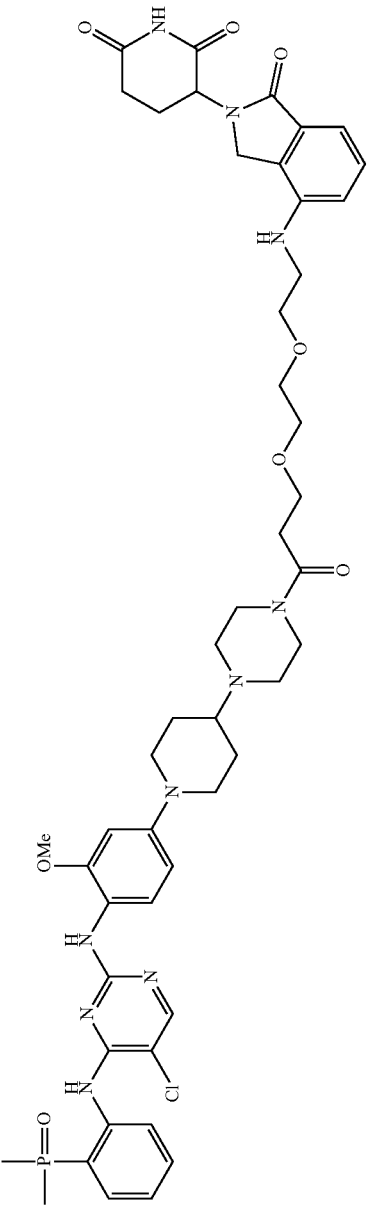 | 3-(4-((2-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethoxy)ethyl)amino)-1-oxoisoindolin-2-yl)piperidine-2,6-dione |
| | | 3-(4-((2-(2-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethoxy)ethoxy)ethyl)amino)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| |  | 3-(4-((15-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-15-oxo-3,6,9,12-tetraoxapentadecyl)amino)-1-oxoisoindolin-2-yl)piperidine-2,6-dione |
| | 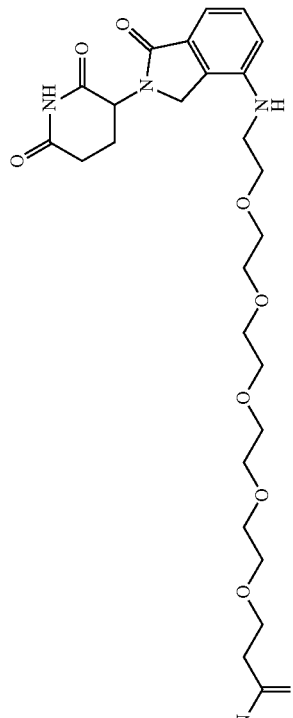 | 3-(4-((18-(4-(1-(4-((5-chloro-4-((2-(dimethylphosphoryl)phenyl)amino)pyrimidin-2-yl)amino)-3-methoxyphenyl)piperazin-1-yl)piperazin-1-yl)-18-oxo-3,6,9,12,15-pentaoxaoctadecyl)amino)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| | 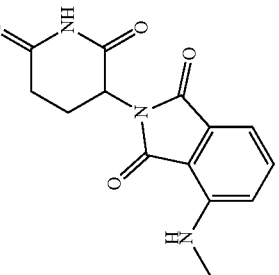 | 4-((2-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)propoxy)ethoxy)ethyl)amino)-2-(2,6-dioxopiperidin-3-yl)isoindoline-1,3-dione |
| | 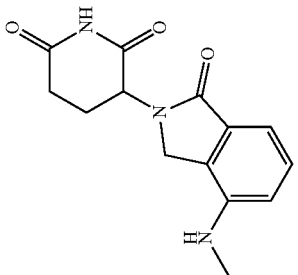 | 3-(4-((2-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)propoxy)ethoxy)ethyl)amino)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| | 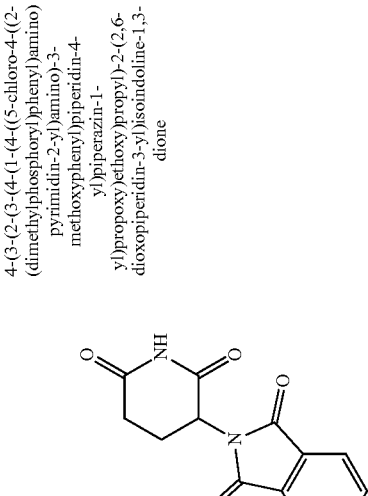 | 4-(3-(2-(3-(4-(1-(4-(4-((5-chloro-4-((2-(dimethylphosphoryl)phenyl)amino)pyrimidin-2-yl)amino)-3-methoxyphenyl)piperidin-4-yl)piperazin-1-yl)propoxy)ethoxy)propyl)-2-(2,6-dioxopiperidin-3-yl)isoindoline-1,3-dione |
| | | 3-(4-(3-(2-(3-(4-(1-(4-(4-((5-chloro-4-((2-(dimethylphosphoryl)phenyl)amino)pyrimidin-2-yl)amino)-3-methoxyphenyl)piperidin-4-yl)piperazin-1-yl)propoxy)ethoxy)propyl)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| | 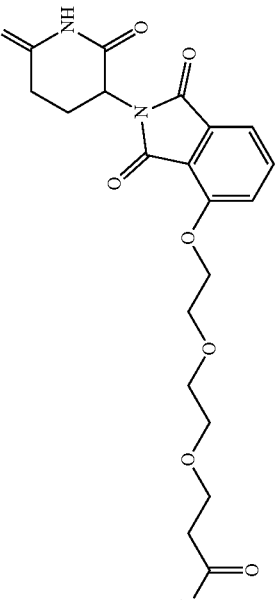 | 4-(2-(2-(3-(4-(1-(4-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethoxy)ethoxy)-2-(2,6-dioxopiperidin-3-yl)isoindoline-1,3-dione |
| | | 3-(4-(2-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethoxy)ethoxy)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| SIAI S164 018 | | 4-((2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-2-oxoethyl)amino)-2-(2,6-dioxopiperidin-3-yl)isoindoline-1,3-dione |
| SIAI S164 019 | | 4-((3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| SIAI S164 020 | | 4-((4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4-oxobutyl)amino)-2-(2,6-dioxopiperidin-3-yl)isoindoline-1,3-dione |
| SIAI S164 021 | | 4-((5-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-5-oxopentyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| SIAI S164 022 | | 4-((6-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-6-oxohexyl)amino)-2-(2,6-dioxopiperidin-3-yl)isoindoline-1,3-dione |
| SIAI S164 023 | | 4-((7-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-7-oxoheptyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| SIAI S164 073 | | 3-(4-((2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-2-oxoethyl)amino)-1-oxoisoindolin-2-yl)piperidine-2,6-dione |
| | | 3-(4-((3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)amino)-1-oxoisoindolin-2-yl)piperidine-2,6-dione |

TABLE 1-continued

Structural formulas and names of the compounds of the present disclosure

| Compound ID | Structure of the compound | Name of the compound |
| --- | --- | --- |
| SIAIS219155 | | 3-(4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4-oxobutyl)amino)-1-oxoisoindolin-2-yl)piperidine-2,6-dione |
| SIAIS219156 | | 3-(4-(5-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-5-oxopentyl)amino)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| SIAIS219157 | 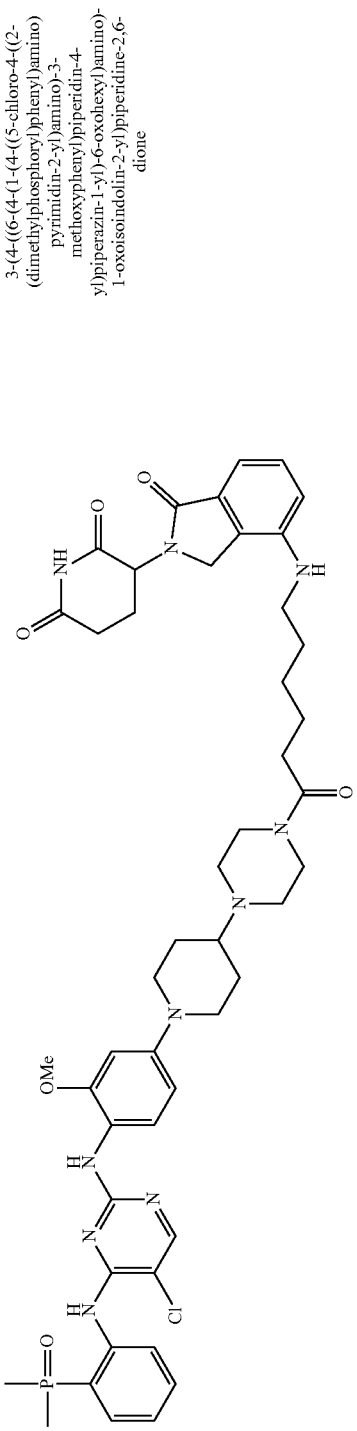 | 3-(4-((6-((4-(1-(4-((5-chloro-4-((2-(dimethylphosphoryl)phenyl)amino)pyrimidin-2-yl)amino)-3-methoxyphenyl)piperidin-4-yl)piperazin-1-yl)-6-oxohexyl)amino)-1-oxoisoindolin-2-yl)piperidine-2,6-dione |
| SIAIS219124 | 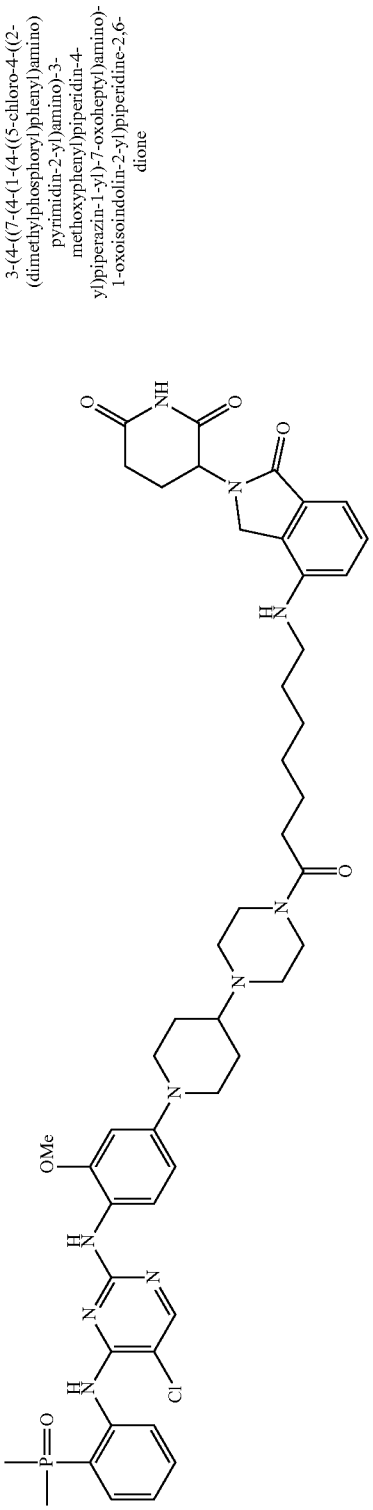 | 3-(4-((7-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-7-oxoheptyl)amino)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| SIAIS219158 | 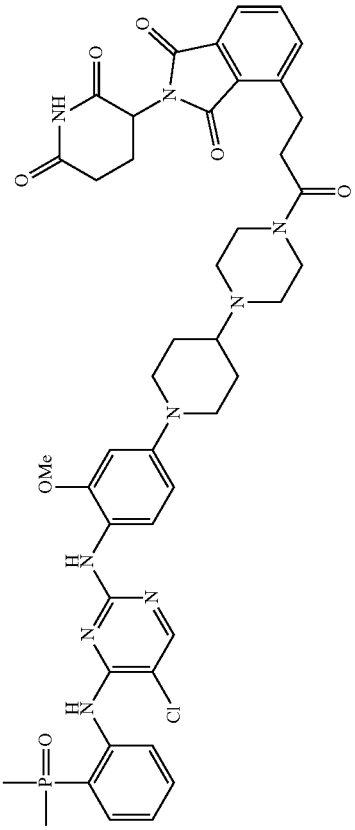 | 4-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)-2-(2,6-dioxopiperidin-3-yl)isoindoline-1,3-dione<br><br>3-(4-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| | 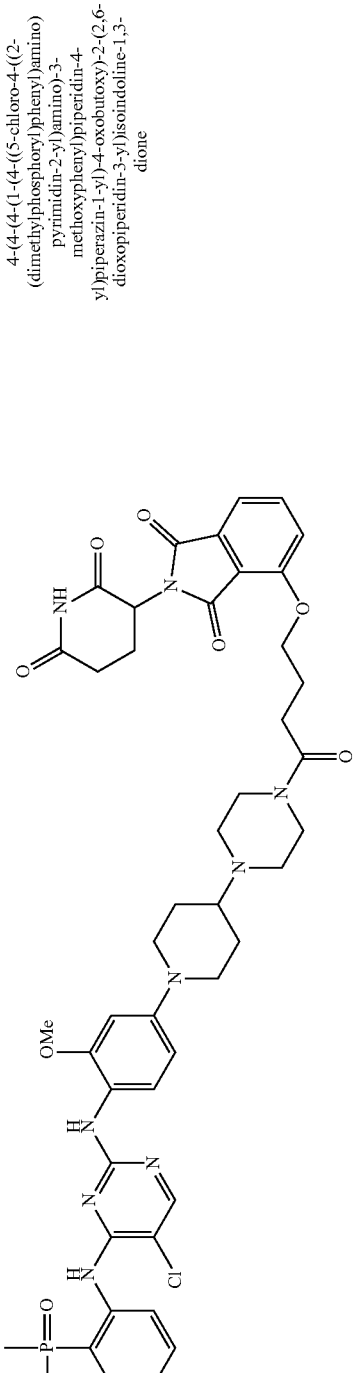 | 4-(4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4-oxobutoxy)-2-(2,6-dioxopiperidin-3-yl)isoindoline-1,3-dione |
| | 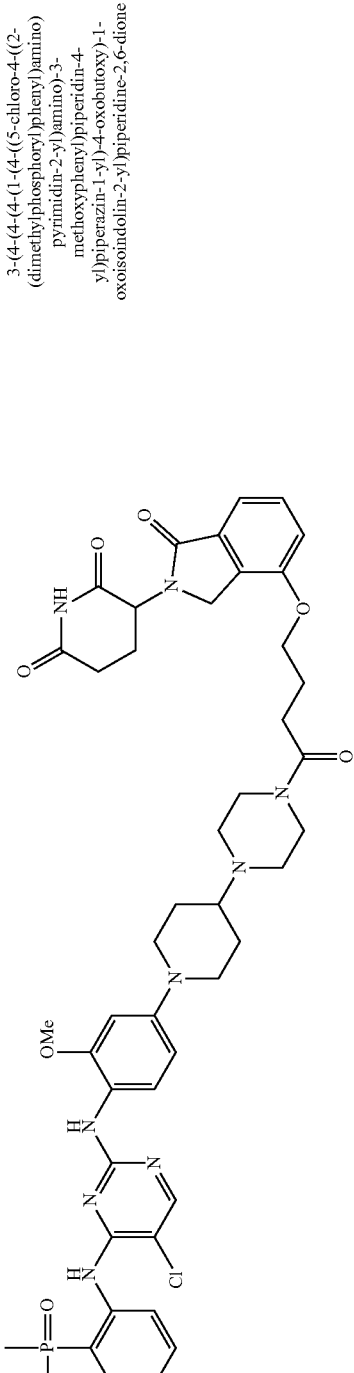 | 3-(4-(4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4-oxobutoxy)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| | 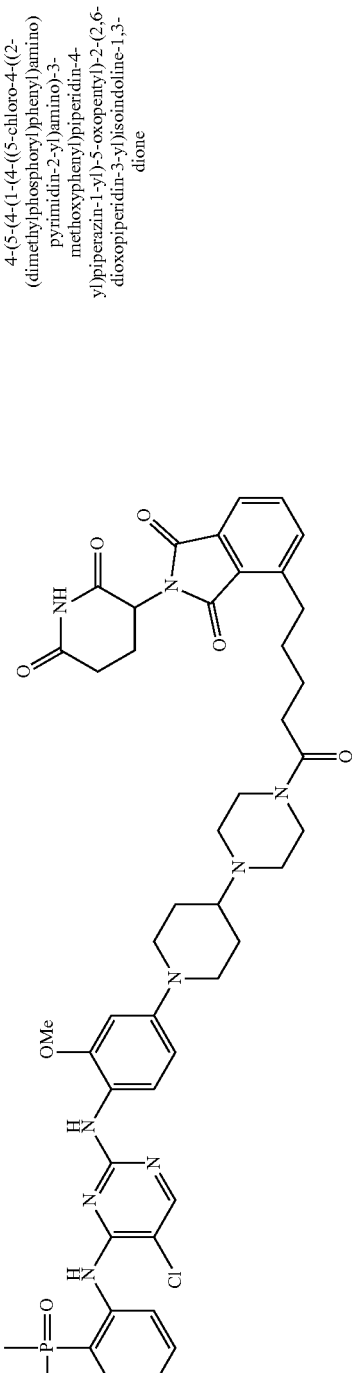 | 4-(5-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-5-oxopentyl)-2-(2,6-dioxopiperidin-3-yl)isoindoline-1,3-dione |
| | 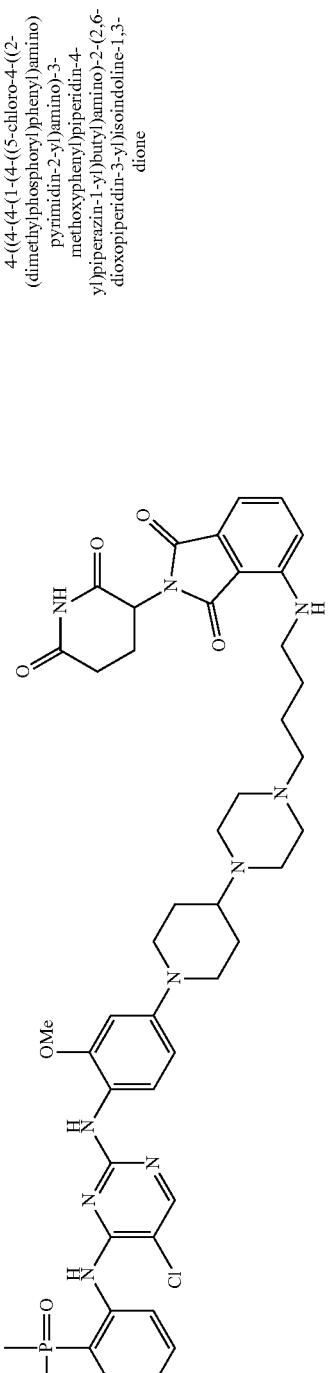 | 4-((4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)butyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| SIAIS220027 | 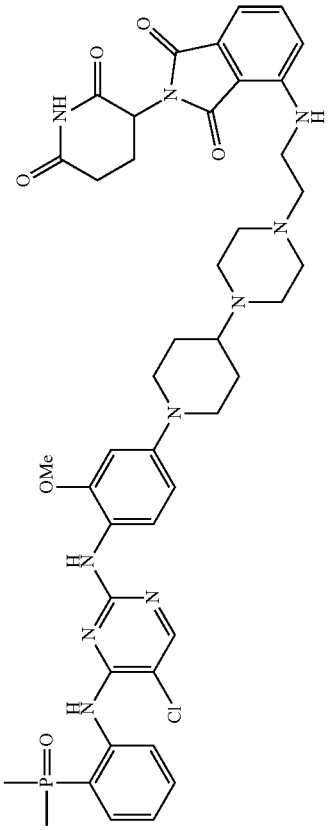 | 4-((2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)ethyl)amino)-2-(2,6-dioxopiperidin-3-yl)isoindoline-1,3-dione |
| | 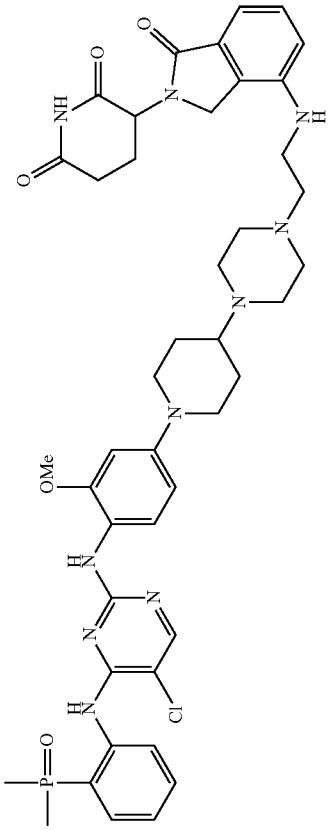 | 3-(4-((2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)ethyl)amino)-1-oxoisoindolin-2-yl)piperidine-2,6-dione |

TABLE 1-continued

Structural formulas and names of the compounds of the present disclosure

| Compound ID | Structure of the compound | Name of the compound |
| --- | --- | --- |
| SIAI S164 041 | 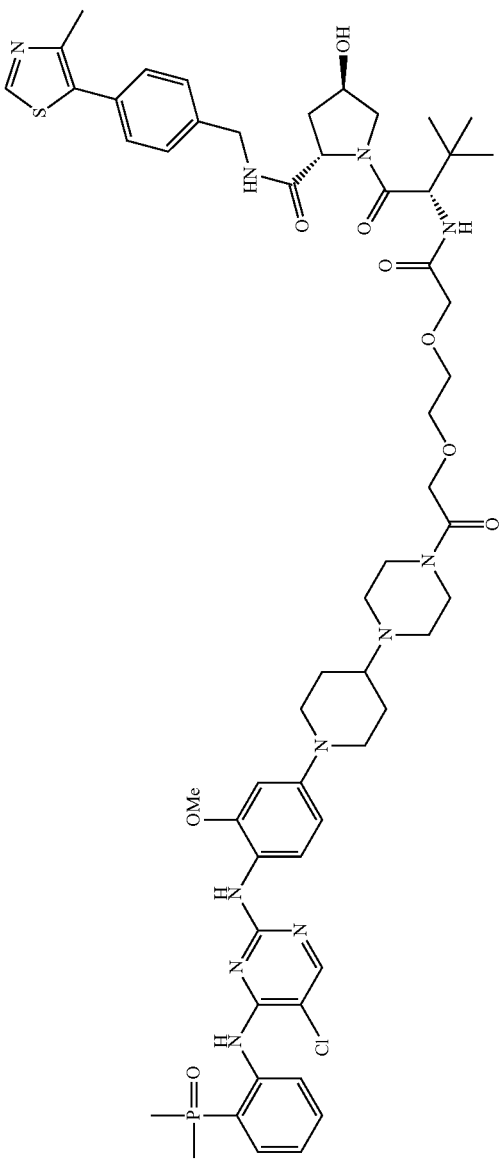 | (2S,4R)-1-((S)-2-(2-(2-(2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide |
| SIAI S164 032 | 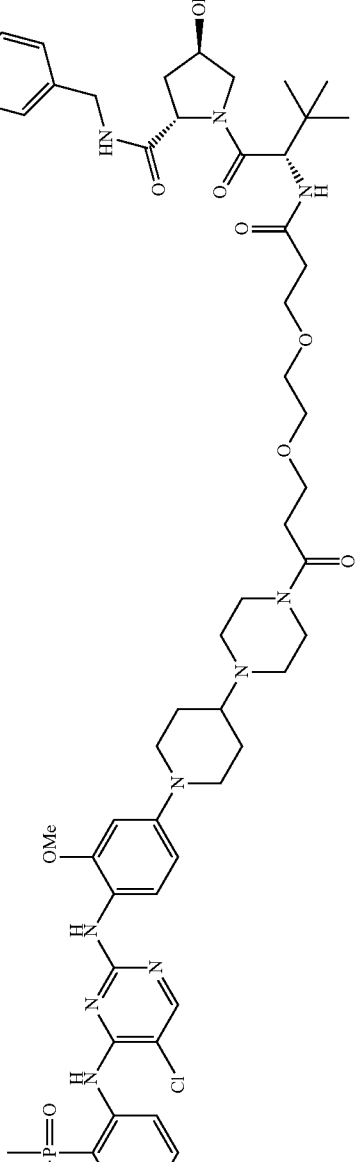 | (2S,4R)-1-((S)-2-(3-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
|  |  | (2S,4R)-1-((S)-2-(3-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)propoxy)ethoxy)propanamido)-3,3-dimethylbutanoyl)-4-hydroxy-N-(4-(4-methylthiazol-5-yl)benzyl)pyrrolidine-2-carboxamide |
| SIAIS164033 |  | (2S,4R)-1-((S)-2-(tert-butyl)-16-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S164 034 | | (2S,4R)-1-((S)-2-(tert-butyl)-19-(4-(1-(4-((5-phosphoryl)amino)pyrimidin-2-yl)amino)-3-methoxyphenyl)piperidin-4-yl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide |
| SIAI S164 035 | | (2S,4R)-1-((S)-2-(tert-butyl)-22-(4-(1-(4-((5-phosphoryl)amino)pyrimidin-2-yl)amino)-3-methoxyphenyl)piperidin-4-yl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S164 120 | 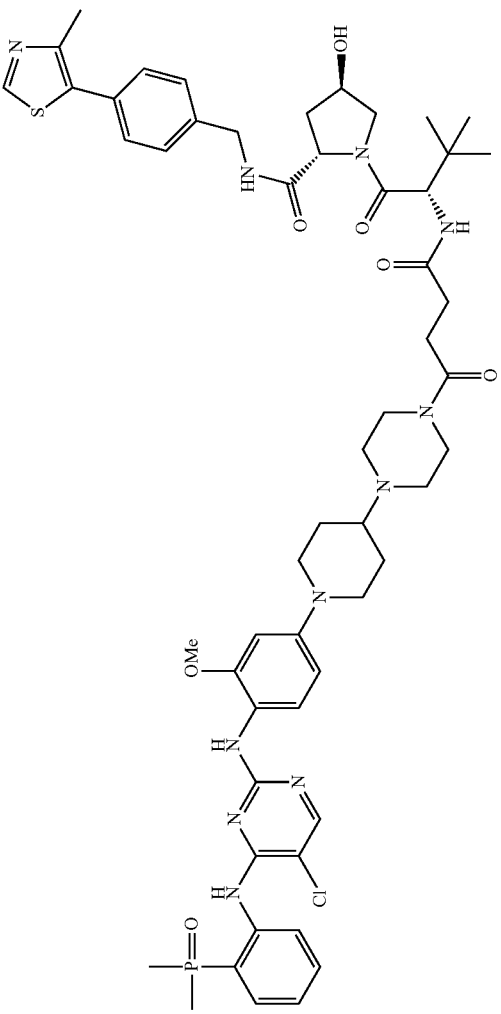 | (2S,4R)-1-((S)-2-(4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide |
| SIAI S164 121 | 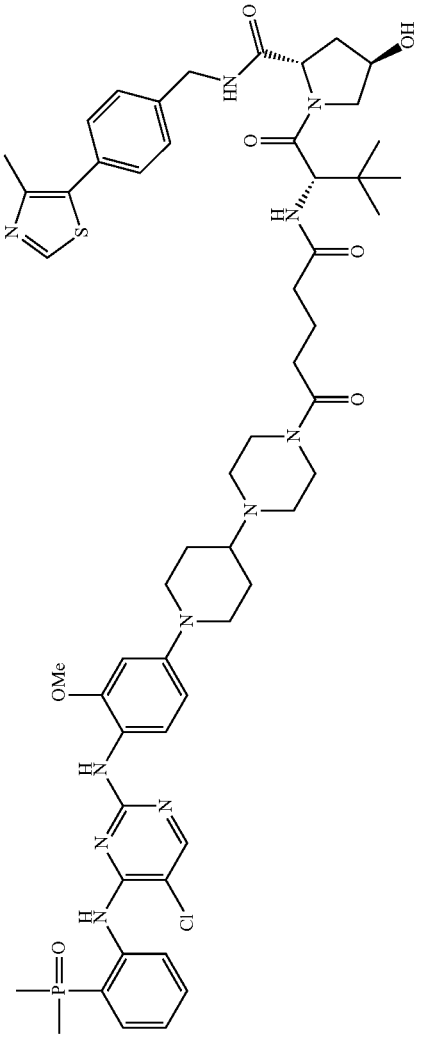 | (2S,4R)-1-((S)-2-(5-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S164 122 | 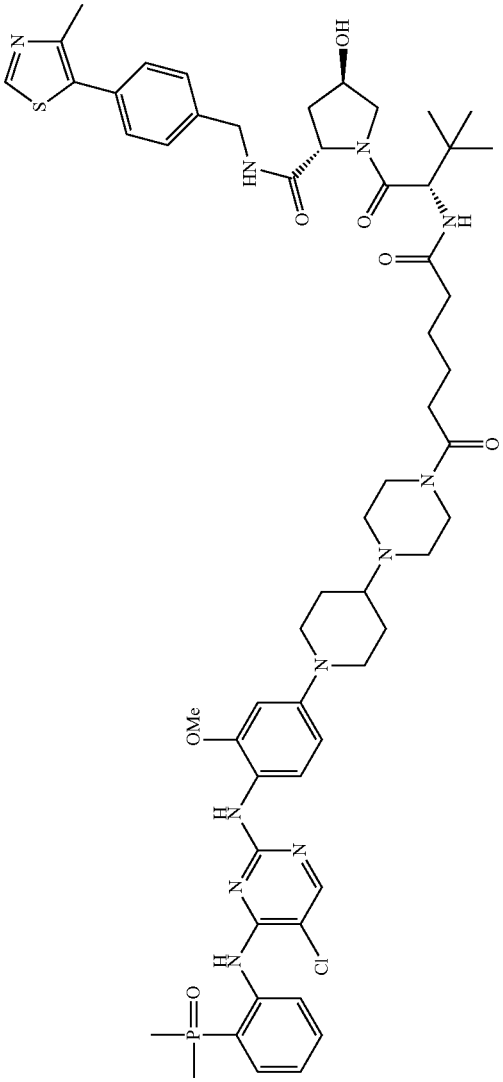 | (2S,4R)-1-((S)-2-(6-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide |
| SIAI S164 123 | 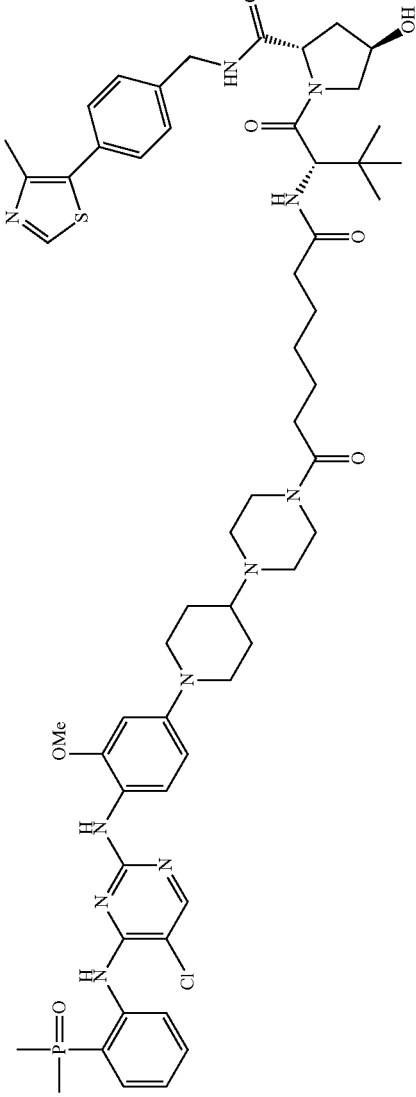 | (2S,4R)-1-((S)-2-(7-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-7-oxoheptanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | 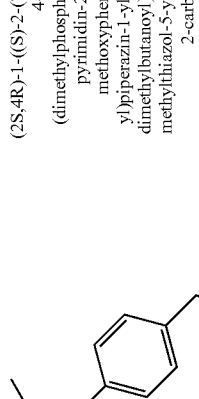 | (2S,4R)-1-((S)-2-(7-(4-(1-(4-((5-chloro-4-(4-(2-(dimethylphosphoryl)phenyl)amino)pyrimidin-2-yl)amino)-3-methoxyphenyl)piperidin-4-yl)piperazin-1-yl)heptanamido)-3,3-dimethylbutanoyl)-4-hydroxy-N-(4-methylthiazol-5-yl)benzyl)pyrrolidine-2-carboxamide |
| SIAIS164124 | 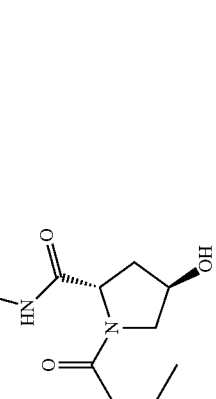 | (2S,4R)-1-((S)-2-(8-(4-(4-((5-chloro-4-(4-(2-(dimethylphosphoryl)phenyl)amino)pyrimidin-2-yl)amino)-3-methoxyphenyl)piperazin-1-yl)piperidin-4-yl)-8-oxooctanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S164 125 | 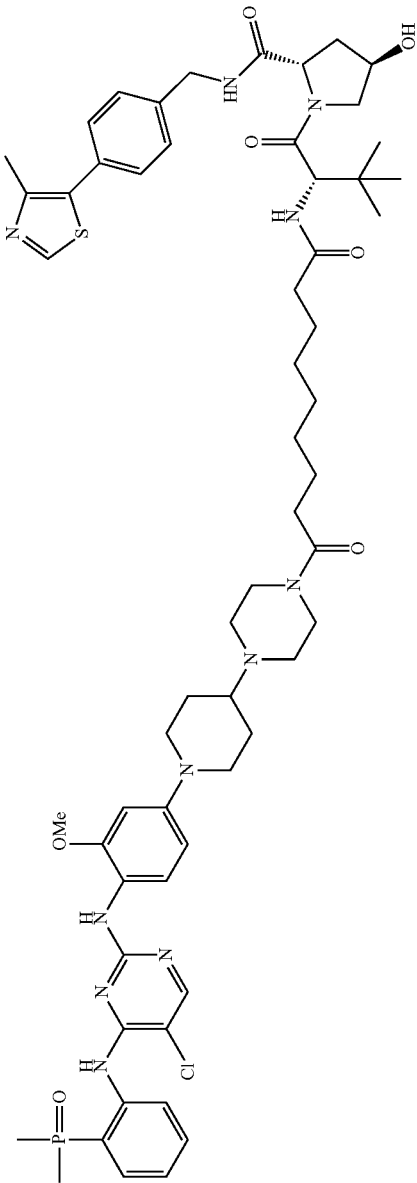 | (2S,4R)-1-((S)-2-(9-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-9-oxononanamido)-3,3-dimethylbutanoyl)-4-hydroxy-N-(4-(4-methylthiazol-5-yl)benzyl)pyrrolidine-2-carboxamide |
| SIAI S164 126 | 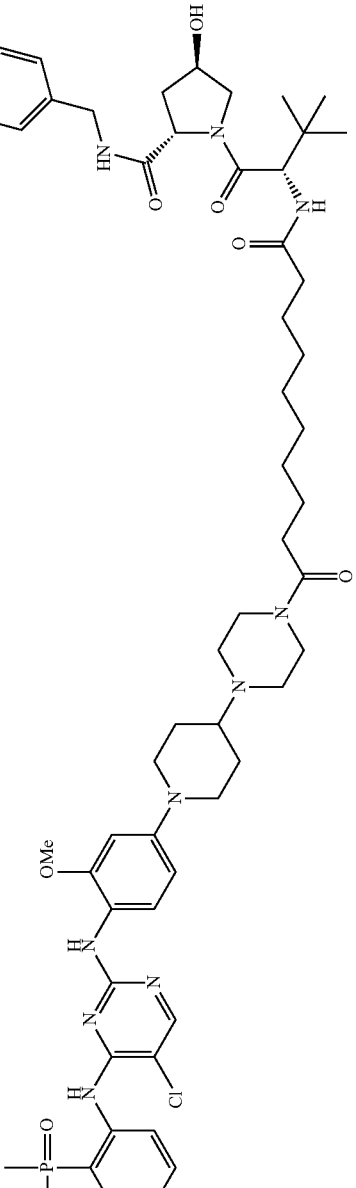 | (2S,4R)-1-((S)-2-(10-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S164 152 | | 4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-N-(2-((2-(2,6-dioxopiperidin-3-yl)-1,3-dioxoisoindolin-4-yl)amino)ethyl)-4-oxobutanamide |
| SIAI S164 153 | | (2S,4R)-1-((S)-2-(4-(4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4-oxobutyl)-1H-1,2,3-triazol-1-yl)butanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | 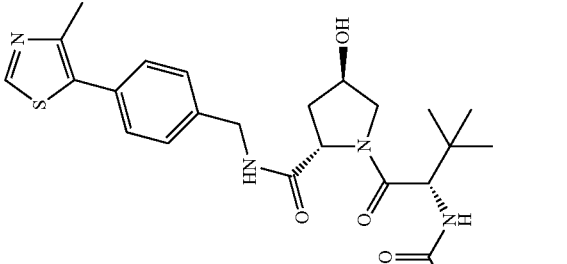 | (2S,4R)-1-((S)-2-(3-(4-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)piperazin-1-yl)propanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | 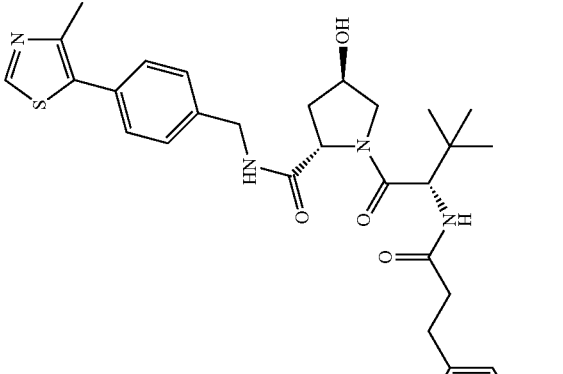 | (2S,4R)-1-((S)-2-(3-(4-(3-(4-(1-(4-(3-(4-(5-chloro-4-((2-(dimethylphosphoryl)phenyl)amino)pyrimidin-2-yl)amino)-3-methoxyphenyl)piperidin-4-yl)piperazin-1-yl)-3-oxopropyl)phenyl)propanamido)-3,3-dimethylbutanoyl)-4-hydroxy-N-(4-(4-methylthiazol-5-yl)benzyl)pyrrolidine-2-carboxamide |
| | | 3-(4-((2-(4-(3-(4-(1-(4-(5-chloro-4-((2-(dimethylphosphoryl)phenyl)amino)pyrimidin-2-yl)amino)-3-methoxyphenyl)piperidin-4-yl)piperazin-1-yl)-3-oxopropyl)piperazin-1-yl)ethyl)amino)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| | 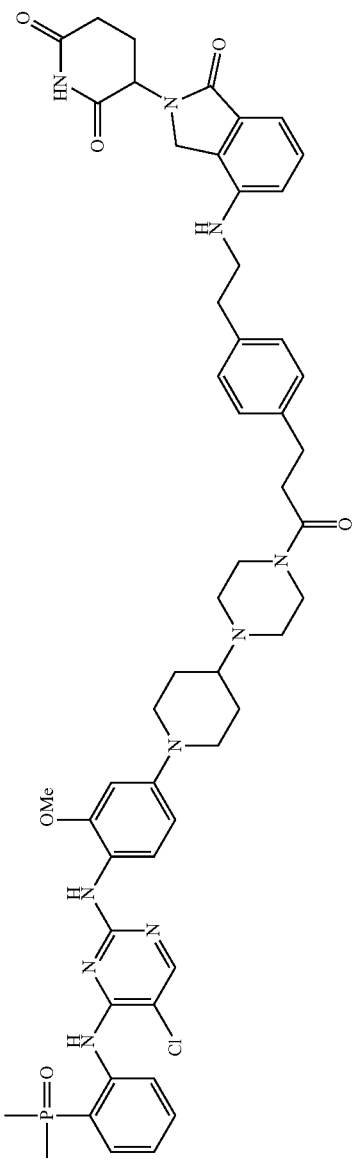 | 3-(4-(4-(3-(4-(1-(4-(5-chloro-4-((2-(dimethylphosphoryl)phenyl)amino)pyrimidin-2-yl)amino)-3-methoxyphenyl)piperidin-4-yl)piperazin-1-yl)-3-oxopropyl)phenethyl)amino)-1-oxoisoindolin-2-yl)piperidine-2,6-dione |
| SIAI S164 011 | | 8-(4-(3-(2-((2-(2,6-dioxopiperidin-3-yl)-1,3-dioxoisoindolin-4-yl)amino)ethoxy)propanoyl)piperazin-1-yl)-9-ethyl-6,6-dimethyl-11-oxo-6,11-dihydro-5H-benzo[b]carbazole-3-carbonitrile |

TABLE 1-continued

Structural formulas and names of the compounds of the present disclosure

| Compound ID | Structure of the compound | Name of the compound |
|---|---|---|
| SIAI S164 012 | | 8-(4-(3-(2-(2-(2-(2-(2,6-dioxopiperidin-3-yl)-1,3-dioxoisoindolin-4-yl)amino)ethoxy)ethoxy)propanoyl)piperazin-1-yl)-9-ethyl-6,6-dimethyl-11-oxo-6,11-dihydro-5H-benzo[b]carbazole-3-carbonitrile |
| SIAI S164 013 | | 8-(4-(3-(2-(2-(2-(2,6-dioxopiperidin-3-yl)-1,3-dioxoisoindolin-4-yl)amino)ethoxy)ethoxy)propanoyl)piperazin-1-yl)-9-ethyl-6,6-dimethyl-11-oxo-6,11-dihydro-5H-benzo[b]carbazole-3-carbonitrile |
| SIAI S164 014 | | 8-(4-(1-((2-(2,6-dioxopiperidin-3-yl)-1,3-dioxoisoindolin-4-yl)amino)-3,6,9,12-tetraoxapentadecan-15-oyl)piperazin-1-yl)-9-ethyl-6,6-dimethyl-11-oxo-6,11-dihydro-5H-benzo[b]carbazole-3-carbonitrile |

TABLE 1-continued

Structural formulas and names of the compounds of the present disclosure

| Compound ID | Structure of the compound | Name of the compound |
|---|---|---|
| SIAI S164 015 | | 8-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)-9-ethyl-6,6-dimethyl-11-oxo-6,11-dihydro-5H-benzo[b]carbazole-3-carbonitrile |
| | | 8-(4-(3-(2-((2-(2,6-dioxopiperidin-3-yl)-1-oxoisoindolin-4-yl)amino)ethoxy)propanoyl)piperazin-1-yl)-9-ethyl-6,6-dimethyl-11-oxo-6,11-dihydro-5H-benzo[b]carbazole-3-carbonitrile |
| | | 8-(4-(3-(2-((2-(2,6-dioxopiperidin-3-yl)-1,3-dioxoisoindolin-4-yl)amino)ethoxy)propyl)piperazin-1-yl)-9-ethyl-6,6-dimethyl-11-oxo-6,11-dihydro-5H-benzo[b]carbazole-3-carbonitrile |

TABLE 1-continued

Structural formulas and names of the compounds of the present disclosure

| Compound ID | Structure of the compound | Name of the compound |
| --- | --- | --- |
| SIAIS164028 | | 8-(4-((2-(2,6-dioxopiperidin-3-yl)-1,3-dioxoisoindolin-4-yl)glycyl)piperazin-1-yl)-9-ethyl-6,6-dimethyl-11-oxo-6,11-dihydro-5H-benzo[b]carbazole-3-carbonitrile |
| SIAIS164029 | | 8-(4-(3-((2-(2,6-dioxopiperidin-3-yl)-1,3-dioxoisoindolin-4-yl)amino)propanoyl)piperazin-1-yl)-9-ethyl-6,6-dimethyl-11-oxo-6,11-dihydro-5H-benzo[b]carbazole-3-carbonitrile |

TABLE 1-continued

Structural formulas and names of the compounds of the present disclosure

| Compound ID | Structure of the compound | Name of the compound |
|---|---|---|
| SIAI S164 024 | | 8-(4-(4-((2-(2,6-dioxopiperidin-3-yl)-1,3-dioxoisoindolin-4-yl)amino)butanoyl)piperazin-1-yl)-9-ethyl-6,6-dimethyl-11-oxo-6,11-dihydro-5H-benzo[b]carbazole-3-carbonitrile |
| SIAI S164 025 | | 8-(4-(5-((2-(2,6-dioxopiperidin-3-yl)-1,3-dioxoisoindolin-4-yl)amino)pentanoyl)piperazin-1-yl)-9-ethyl-6,6-dimethyl-11-oxo-6,11-dihydro-5H-benzo[b]carbazole-3-carbonitrile |
| SIAI S164 026 | | 8-(4-(6-((2-(2,6-dioxopiperidin-3-yl)-1,3-dioxoisoindolin-4-yl)amino)hexanoyl)piperazin-1-yl)-9-ethyl-6,6-dimethyl-11-oxo-6,11-dihydro-5H-benzo[b]carbazole-3-carbonitrile |

TABLE 1-continued

Structural formulas and names of the compounds of the present disclosure

| Compound ID | Structure of the compound | Name of the compound |
|---|---|---|
| SIAI S164 030 | 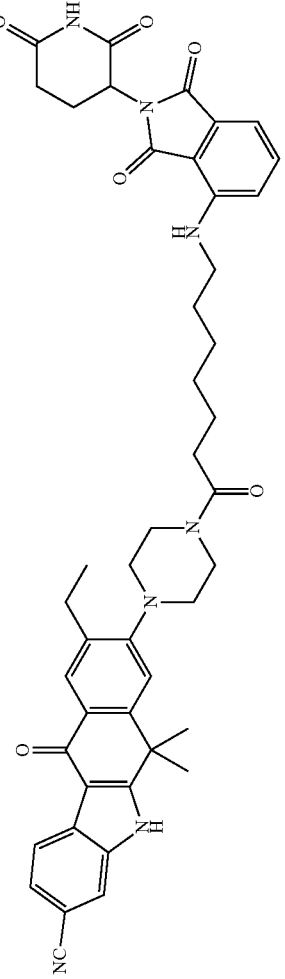 | 8-(4-(7-((2-(2,6-dioxopiperidin-3-yl)-1,3-dioxoisoindolin-4-yl)amino)heptanoyl)piperazin-1-yl)-9-ethyl-6,6-dimethyl-11-oxo-6,11-dihydro-5H-benzo[b]carbazole-3-carbonitrile |
| | | 8-(4-((2-(2,6-dioxopiperidin-3-yl)-1-oxoisoindolin-4-yl)glycyl)piperazin-1-yl)-9-ethyl-6,6-dimethyl-11-oxo-6,11-dihydro-5H-benzo[b]carbazole-3-carbonitrile |
| | | 8-(4-(2-((2-(2,6-dioxopiperidin-3-yl)-1,3-dioxoisoindolin-4-yl)amino)ethyl)piperazin-1-yl)-9-ethyl-6,6-dimethyl-11-oxo-6,11-dihydro-5H-benzo[b]carbazole-3-carbonitrile |

TABLE 1-continued

Structural formulas and names of the compounds of the present disclosure

| Compound ID | Structure of the compound | Name of the compound |
|---|---|---|
| | 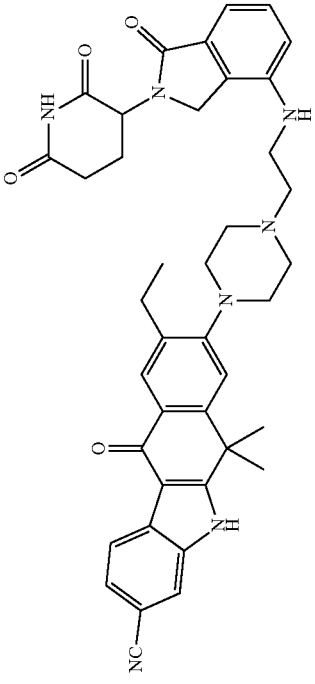 | 8-(4-(2-((2-(2,6-dioxopiperidin-3-yl)-1-oxoisoindolin-4-yl)amino)ethyl)piperazin-1-yl)-9-ethyl-6,6-dimethyl-11-oxo-6,11-dihydro-5H-benzo[b]carbazole-3-carbonitrile |
| | 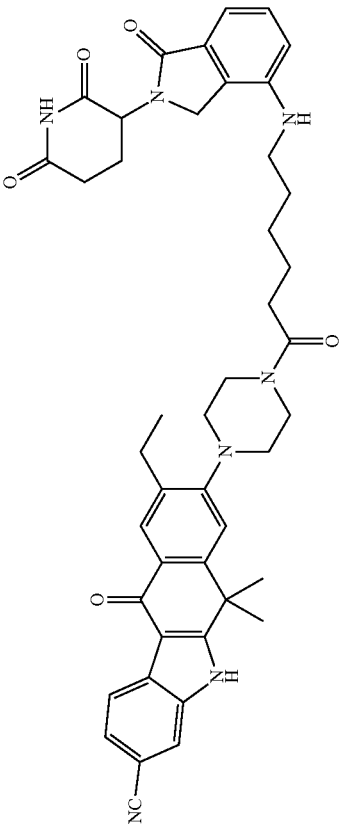 | 8-(4-(6-((2-(2,6-dioxopiperidin-3-yl)-1-oxoisoindolin-4-yl)amino)hexanoyl)piperazin-1-yl)-9-ethyl-6,6-dimethyl-11-oxo-6,11-dihydro-5H-benzo[b]carbazole-3-carbonitrile |

TABLE 1-continued

Structural formulas and names of the compounds of the present disclosure

| Compound ID | Structure of the compound | Name of the compound |
|---|---|---|
| SIAI S164 040 | 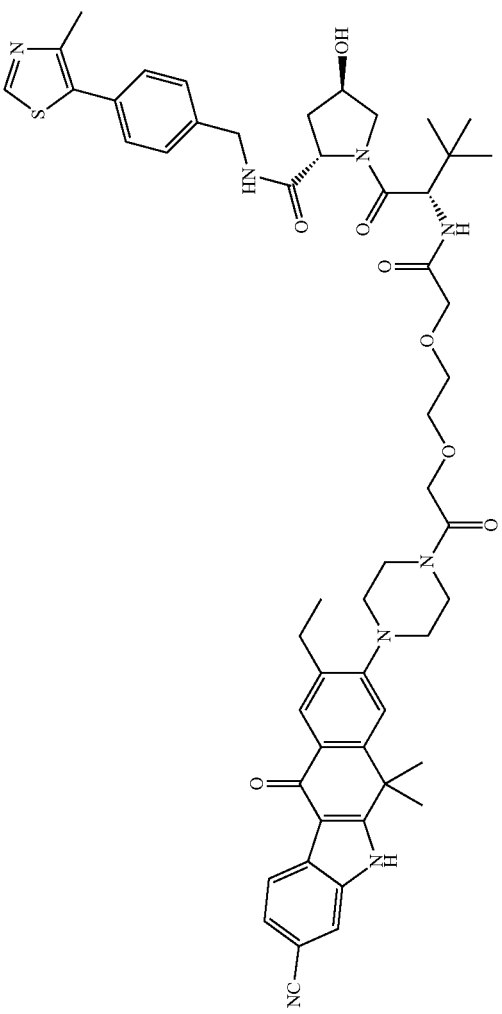 | (2S,4R)-1-((S)-2-(2-(2-(2-(4-(3-cyano-9-ethyl-6,6-dimethyl-11-oxo-6,11-dihydro-5H-benzo[b]carbazol-8-yl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide |
| SIAI S164 036 | 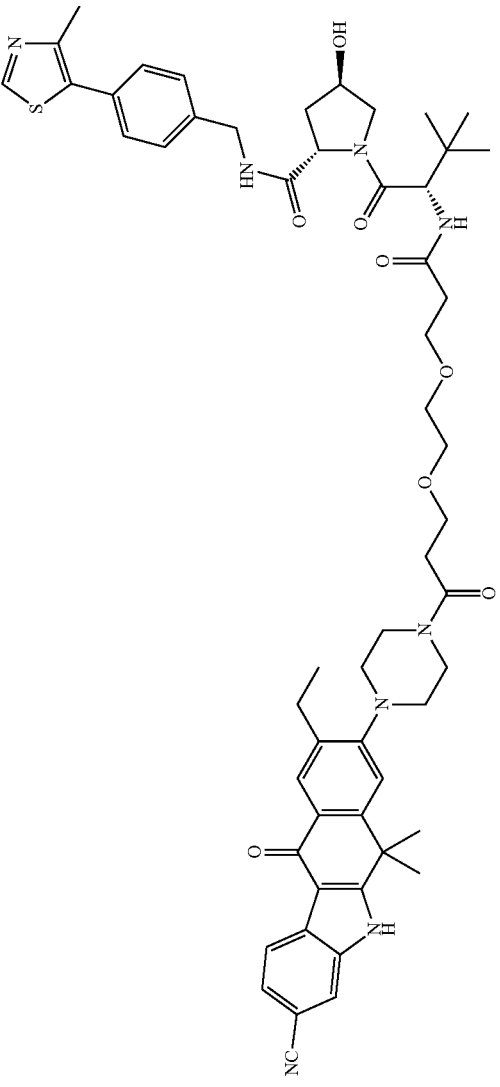 | (2S,4R)-1-((S)-2-(3-(2-(3-(4-(3-cyano-9-ethyl-6,6-dimethyl-11-oxo-6,11-dihydro-5H-benzo[b]carbazol-8-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S164 037 | 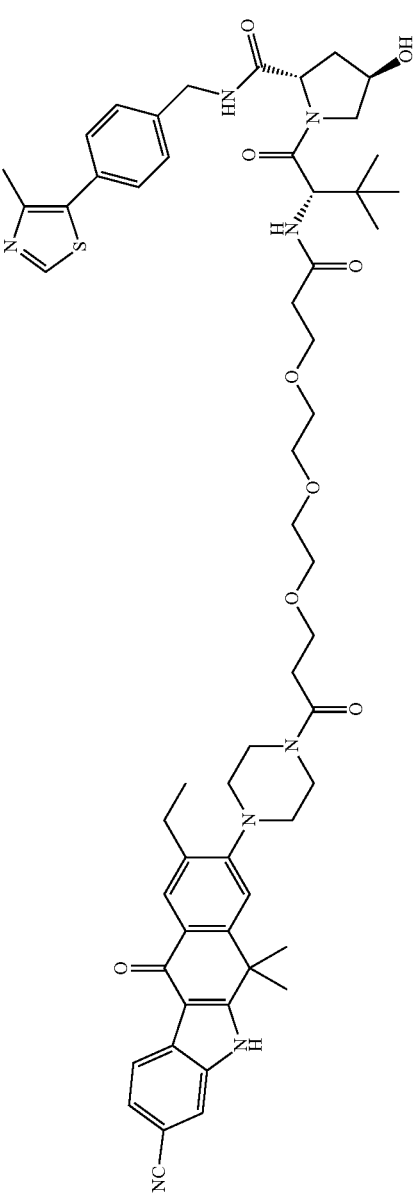 | (2S,4R)-1-((S)-2-(tert-butyl)-16-(4-(3-cyano-9-ethyl-6,6-dimethyl-11-oxo-6,11-dihydro-5H-benzo[b]carbazol-8-yl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide |
| SIAI S164 038 | 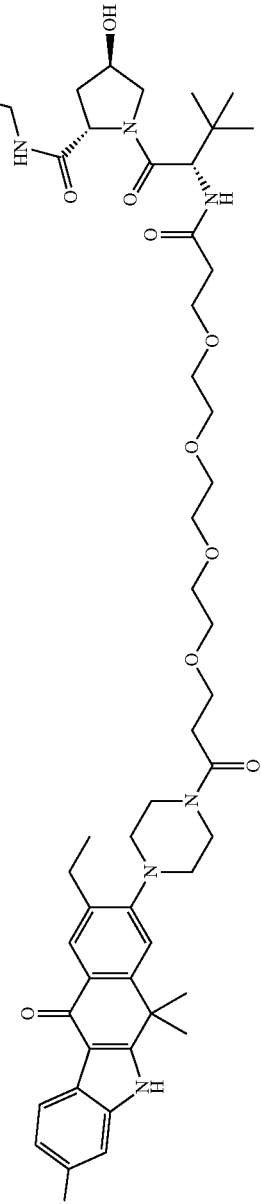 | (2S,4R)-1-((S)-2-(tert-butyl)-19-(4-(3-cyano-9-ethyl-6,6-dimethyl-11-oxo-6,11-dihydro-5H-benzo[b]carbazol-8-yl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S164 039 | | (2S,4R)-1-((S)-2-(tert-butyl)-22-(4-(3-cyano-9-ethyl-6,6-dimethyl-11-oxo-6,11-dihydro-5H-benzo[b]carbazol-8-yl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide |
| SIAI S164 093 | | (2S,4R)-1-((S)-2-(4-(4-(3-cyano-9-ethyl-6,6-dimethyl-11-oxo-6,11-dihydro-5H-benzo[b]carbazol-8-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S164 094 | 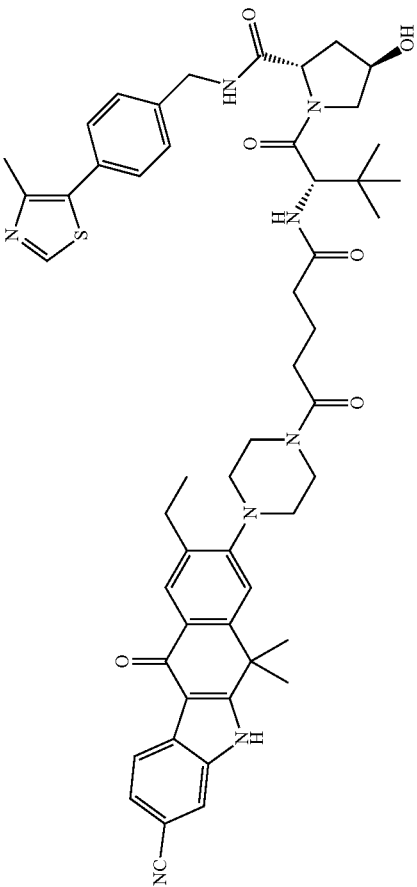 | (2S,4R)-1-((S)-2-(5-(4-(3-cyano-9-ethyl-6,6-dimethyl-11-oxo-6,11-dihydro-5H-benzo[b]carbazol-8-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide |
| SIAI S164 095 | 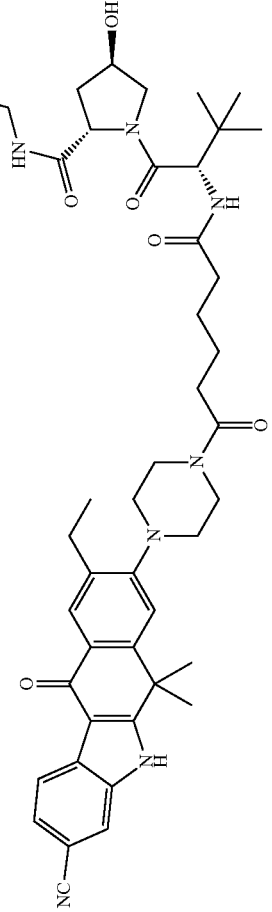 | (2S,4R)-1-((S)-2-(6-(4-(3-cyano-9-ethyl-6,6-dimethyl-11-oxo-6,11-dihydro-5H-benzo[b]carbazol-8-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S164 096 | 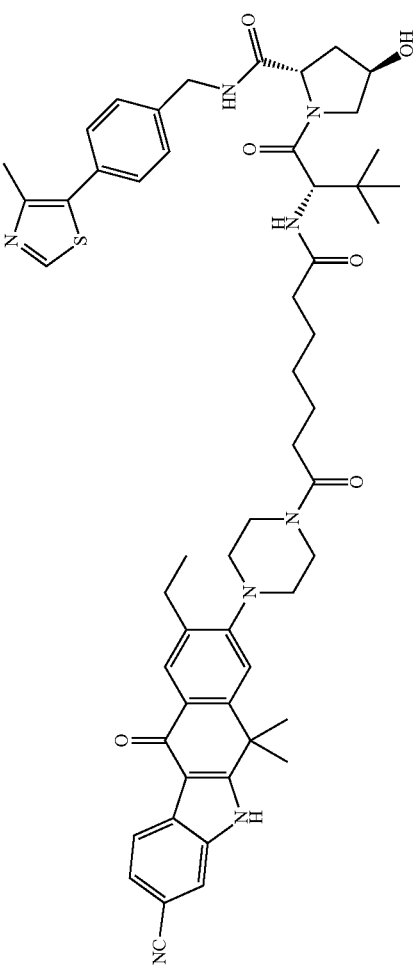 | (2S,4R)-1-((S)-2-(7-(4-(3-cyano-9-ethyl-6,6-dimethyl-11-oxo-6,11-dihydro-5H-benzo[b]carbazol-8-yl)piperazin-1-yl)-7-oxoheptanamido)-3,3-dimethylbutanoyl)-4-hydroxy-N-(4-(4-methylthiazol-5-yl)benzyl)pyrrolidine-2-carboxamide |
| SIAI S164 097 | 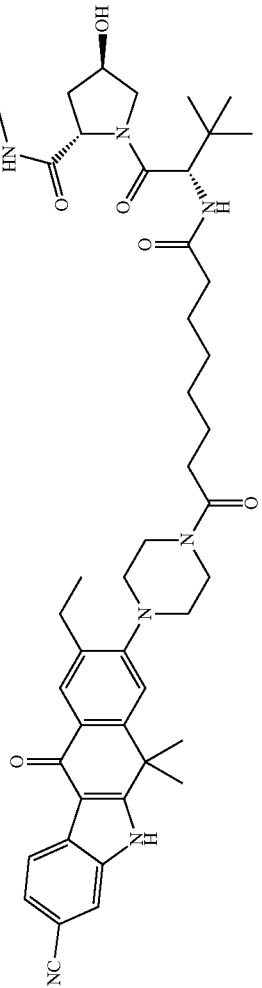 | (2S,4R)-1-((S)-2-(8-(4-(3-cyano-9-ethyl-6,6-dimethyl-11-oxo-6,11-dihydro-5H-benzo[b]carbazol-8-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S164 098 | | (2S,4R)-1-((S)-2-(9-(4-(3-cyano-9-ethyl-6,6-dimethyl-11-oxo-6,11-dihydro-5H-benzo[b]carbazol-8-yl)piperazin-1-yl)-9-oxononanamido)-3,3-dimethylbutanoyl)-4-hydroxy-N-(4-(4-methylthiazol-5-yl)benzyl)pyrrolidine-2-carboxamide |
| SIAI S164 099 | | (2S,4R)-1-((S)-2-(10-(4-(3-cyano-9-ethyl-6,6-dimethyl-11-oxo-6,11-dihydro-5H-benzo[b]carbazol-8-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S164 154 | | 4-(4-(3-cyano-9-ethyl-6,6-dimethyl-11-oxo-6,11-dihydro-5H-benzo[b]carbazol-8-yl)piperazin-1-yl)-N-(2-((2-(2,6-dioxopiperidin-3-yl)-1,3-dioxoisoindolin-4-yl)amino)ethyl)-4-oxobutanamide |
| SIAI S164 155 | | (2S,4R)-1-((S)-2-(4-(4-(4-(4-(3-cyano-9-ethyl-6,6-dimethyl-11-oxo-6,11-dihydro-5H-benzo[b]carbazol-8-yl)piperazin-1-yl)-4-oxobutyl)-1H-1,2,3-triazol-1-yl)butanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | 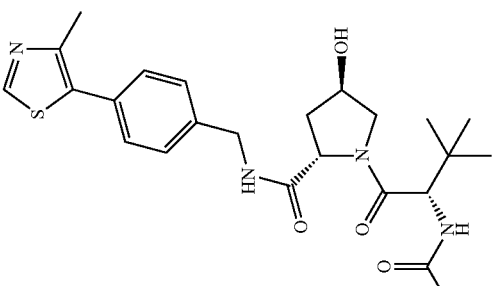 | (2S,4R)-1-((S)-2-(8-(4-(3-cyano-9-ethyl-6,6-dimethyl-11-oxo-6,11-dihydro-5H-benzo[b]carbazol-8-yl)piperazin-1-yl)octanamido)-3,3-dimethylbutanoyl)-4-hydroxy-N-(4-(4-methylthiazol-5-yl)benzyl)pyrrolidine-2-carboxamide |
| |  | N-(1-(3-cyano-9-ethyl-6,6-dimethyl-11-oxo-6,11-dihydro-5H-benzo[b]carbazol-8-yl)piperidin-4-yl)-3-(2-((2-(2,6-dioxopiperidin-3-yl)-1,3-dioxoisoindolin-4-yl)amino)ethoxy)propanamide |

TABLE 1-continued

Structural formulas and names of the compounds of the present disclosure

| Compound ID | Structure of the compound | Name of the compound |
|---|---|---|
| SIAI S219 023 | | N-(1-(3-cyano-9-ethyl-6,6-dimethyl-11-oxo-6,11-dihydro-5H-benzo[b]carbazol-8-yl)piperidin-4-yl)-3-(2-(2-(2-((2-(2,6-dioxopiperidin-3-yl)-1,3-dioxoisoindolin-4-yl)amino)ethoxy)ethoxy)ethoxy)propanamide |
| | | N-(1-(3-cyano-9-ethyl-6,6-dimethyl-11-oxo-6,11-dihydro-5H-benzo[b]carbazol-8-yl)piperidin-4-yl)-3-(2-(2-(2-((2-(2,6-dioxopiperidin-3-yl)-1,3-dioxoisoindolin-4-yl)amino)ethoxy)ethoxy)ethoxy)propanamide |
| SIAI S219 024 | | N-(1-(3-cyano-9-ethyl-6,6-dimethyl-11-oxo-6,11-dihydro-5H-benzo[b]carbazol-8-yl)piperidin-4-yl)-1-((2-(2,6-dioxopiperidin-3-yl)-1,3-dioxoisoindolin-4-yl)amino)-3,6,9,12-tetraoxapentadecan-15-amide |

TABLE 1-continued

Structural formulas and names of the compounds of the present disclosure

| Compound ID | Structure of the compound | Name of the compound |
|---|---|---|
| | 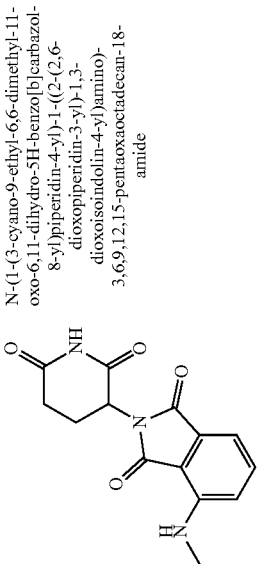 | N-(1-(3-cyano-9-ethyl-6,6-dimethyl-11-oxo-6,11-dihydro-5H-benzo[b]carbazol-8-yl)piperidin-4-yl)-1-((2-(2,6-dioxopiperidin-3-yl)-1,3-dioxoisoindolin-4-yl)amino)-3,6,9,12,15-pentaoxaoctadecan-18-amide |
| | | N-(1-(3-cyano-9-ethyl-6,6-dimethyl-11-oxo-6,11-dihydro-5H-benzo[b]carbazol-8-yl)piperidin-4-yl)-2-((2-(2,6-dioxopiperidin-3-yl)-1,3-dioxoisoindolin-4-yl)amino)acetamide |
| SIAI S219 001 | 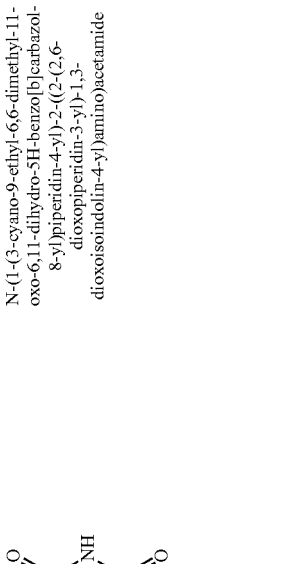 | N-(1-(3-cyano-9-ethyl-6,6-dimethyl-11-oxo-6,11-dihydro-5H-benzo[b]carbazol-8-yl)piperidin-4-yl)-3-((2-(2,6-dioxopiperidin-3-yl)-1,3-dioxoisoindolin-4-yl)amino)propanamide |

TABLE 1-continued

Structural formulas and names of the compounds of the present disclosure

| Compound ID | Structure of the compound | Name of the compound |
|---|---|---|
| SIAI S219 010 | | N-(1-(3-cyano-9-ethyl-6,6-dimethyl-11-oxo-6,11-dihydro-5H-benzo[b]carbazol-8-yl)piperidin-4-yl)-4-((2-(2,6-dioxopiperidin-3-yl)-1,3-dioxoisoindolin-4-yl)amino)butanamide |
| | | N-(1-(3-cyano-9-ethyl-6,6-dimethyl-11-oxo-6,11-dihydro-5H-benzo[b]carbazol-8-yl)piperidin-4-yl)-5-((2-(2,6-dioxopiperidin-3-yl)-1,3-dioxoisoindolin-4-yl)amino)pentanamide |
| SIAI S219 011 | | N-(1-(3-cyano-9-ethyl-6,6-dimethyl-11-oxo-6,11-dihydro-5H-benzo[b]carbazol-8-yl)piperidin-4-yl)-6-((2-(2,6-dioxopiperidin-3-yl)-1,3-dioxoisoindolin-4-yl)amino)hexanamide |

TABLE 1-continued

Structural formulas and names of the compounds of the present disclosure

| Compound ID | Structure of the compound | Name of the compound |
|---|---|---|
| | | N-(1-(3-cyano-9-ethyl-6,6-dimethyl-11-oxo-6,11-dihydro-5H-benzo[b]carbazol-8-yl)piperidin-4-yl)-2-((2-(2,6-dioxopiperidin-3-yl)-1-oxoisoindolin-4-yl)amino)acetamide |
| | | N-(1-(3-cyano-9-ethyl-6,6-dimethyl-11-oxo-6,11-dihydro-5H-benzo[b]carbazol-8-yl)piperidin-4-yl)-4-((2-(2,6-dioxopiperidin-3-yl)-1-oxoisoindolin-4-yl)amino)butanamide |
| | | N-(1-(3-cyano-9-ethyl-6,6-dimethyl-11-oxo-6,11-dihydro-5H-benzo[b]carbazol-8-yl)piperidin-4-yl)-6-((2-(2,6-dioxopiperidin-3-yl)-1-oxoisoindolin-4-yl)amino)hexanamide |

TABLE 1-continued

Structural formulas and names of the compounds of the present disclosure

| Compound ID | Structure of the compound | Name of the compound |
|---|---|---|
|  | 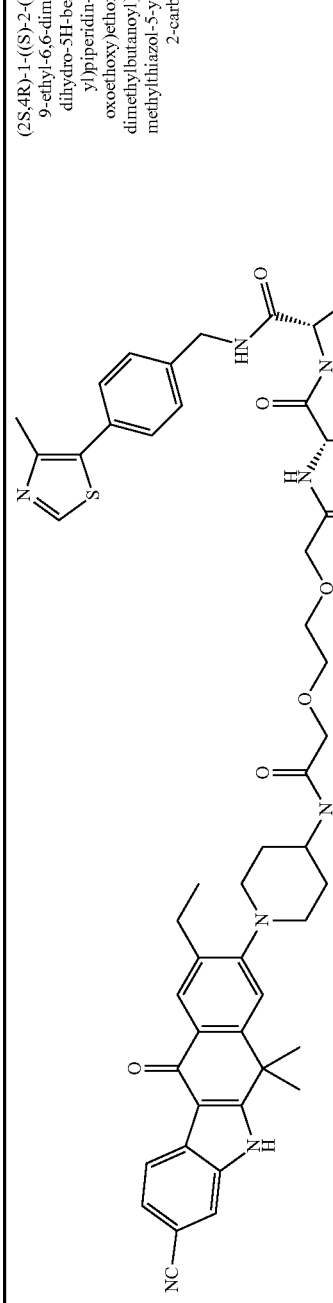 | (2S,4R)-1-((S)-2-(2-(2-(2-((1-(3-cyano-9-ethyl-6,6-dimethyl-11-oxo-6,11-dihydro-5H-benzo[b]carbazol-8-yl)piperidin-4-yl)amino)-2-oxoethoxy)ethoxy)acetamido)-3,3-dimethylbutanoyl)-4-hydroxy-N-(4-(4-methylthiazol-5-yl)benzyl)pyrrolidine-2-carboxamide |
|  | 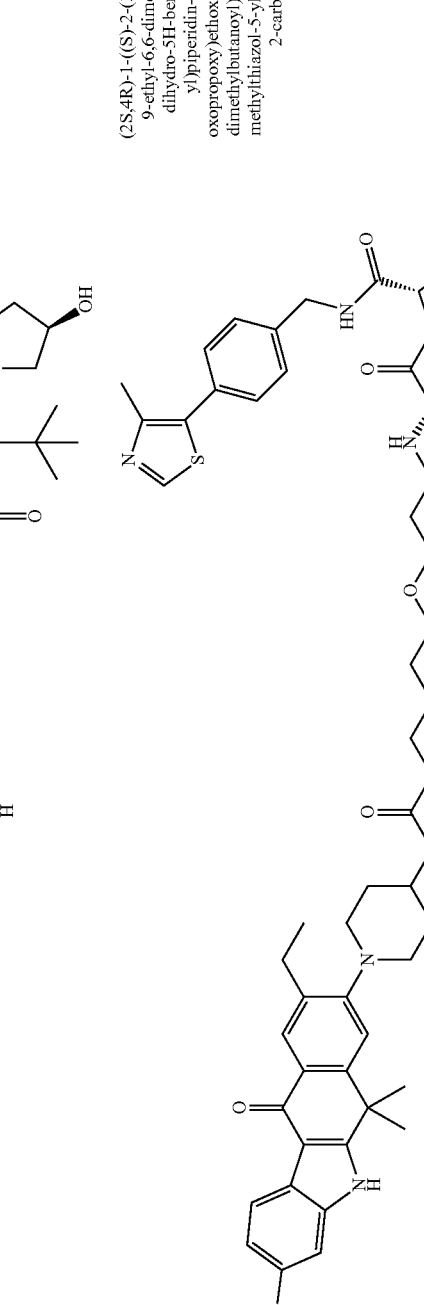 | (2S,4R)-1-((S)-2-(3-(2-(3-((1-(3-cyano-9-ethyl-6,6-dimethyl-11-oxo-6,11-dihydro-5H-benzo[b]carbazol-8-yl)piperidin-4-yl)amino)-3-oxopropoxy)ethoxy)propanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | 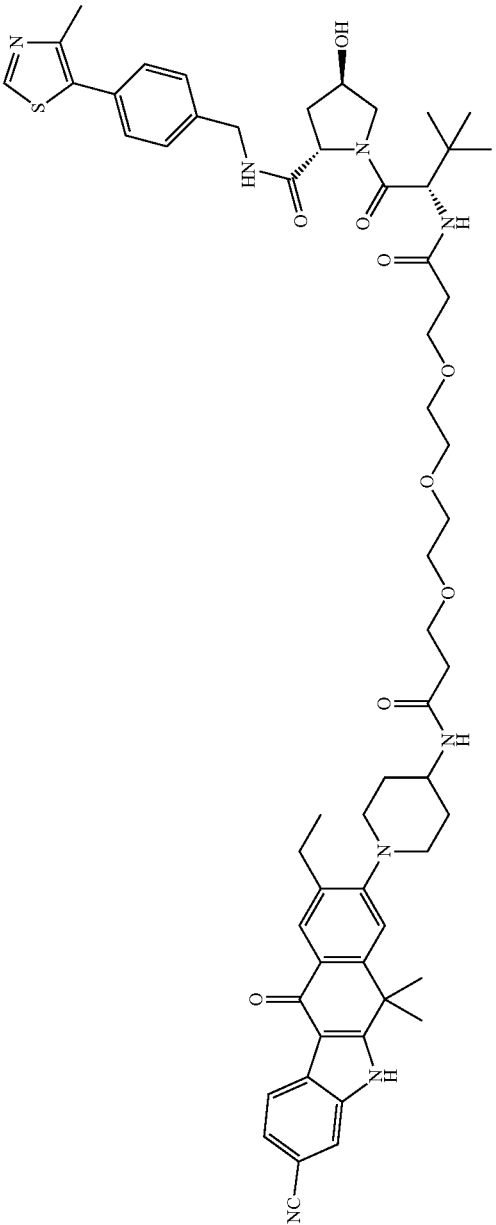 | (2S,4R)-1-((S)-2-(tert-butyl)-16-((1-(3-cyano-9-ethyl-6,6-dimethyl-11-oxo-6,11-dihydro-5H-benzo[b]carbazol-8-yl)piperidin-4-yl)amino)-4,16-dioxo-7,10,13-trioxa-3-azahexadecanoyl)-4-hydroxy-N-(4-(4-methylthiazol-5-yl)benzyl)pyrrolidine-2-carboxamide |
| | 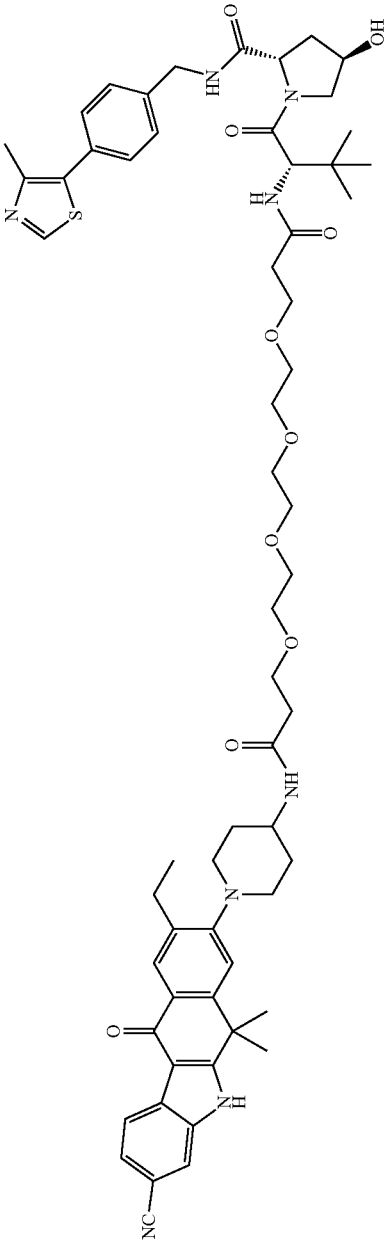 | N1-(1-(3-cyano-9-ethyl-6,6-dimethyl-11-oxo-6,11-dihydro-5H-benzo[b]carbazol-8-yl)piperidin-4-yl)-N16-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13-tetraoxahexadecanediamide |

TABLE 1-continued

Structural formulas and names of the compounds of the present disclosure

| Compound ID | Structure of the compound | Name of the compound |
|---|---|---|
| | 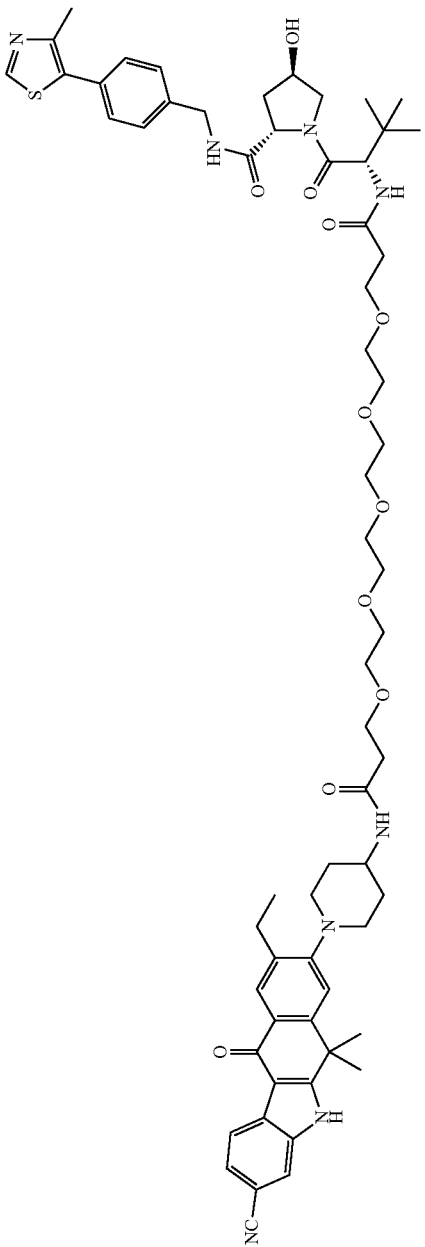 | N1-(1-(3-cyano-9-ethyl-6,6-dimethyl-11-oxo-6,11-dihydro-5H-benzo[b]carbazol-8-yl)piperidin-4-yl)-N19-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13,16-pentaoxanonadecanediamide |
| | 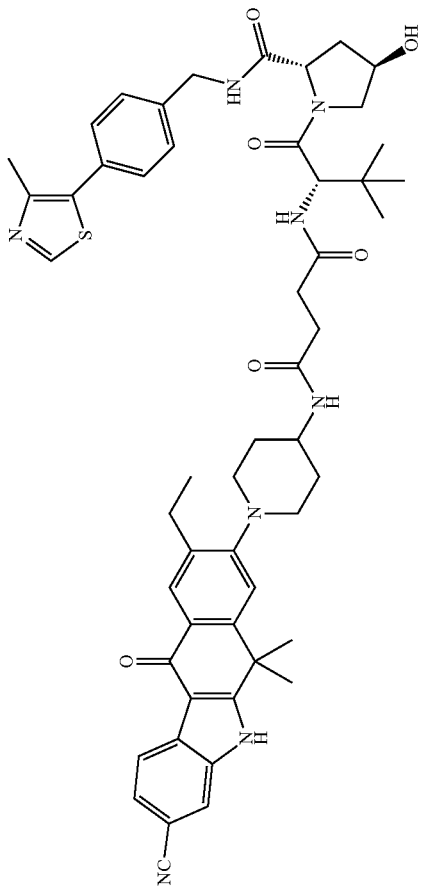 | N1-(1-(3-cyano-9-ethyl-6,6-dimethyl-11-oxo-6,11-dihydro-5H-benzo[b]carbazol-8-yl)piperidin-4-yl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide |

TABLE 1-continued

Structural formulas and names of the compounds of the present disclosure

| Compound ID | Structure of the compound | Name of the compound |
|---|---|---|
| | 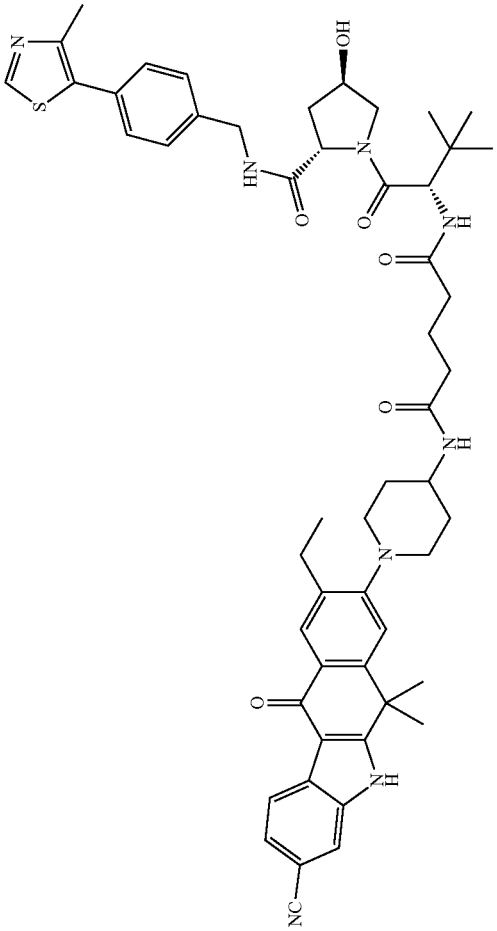 | N1-(1-(3-cyano-9-ethyl-6,6-dimethyl-11-oxo-6,11-dihydro-5H-benzo[b]carbazol-8-yl)piperidin-4-yl)-N5-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide |
| SIAI S219 020 | | N1-(1-(3-cyano-9-ethyl-6,6-dimethyl-11-oxo-6,11-dihydro-5H-benzo[b]carbazol-8-yl)piperidin-4-yl)-N6-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)adipamide |

TABLE 1-continued

Structural formulas and names of the compounds of the present disclosure

| Compound ID | Structure of the compound | Name of the compound |
|---|---|---|
| | 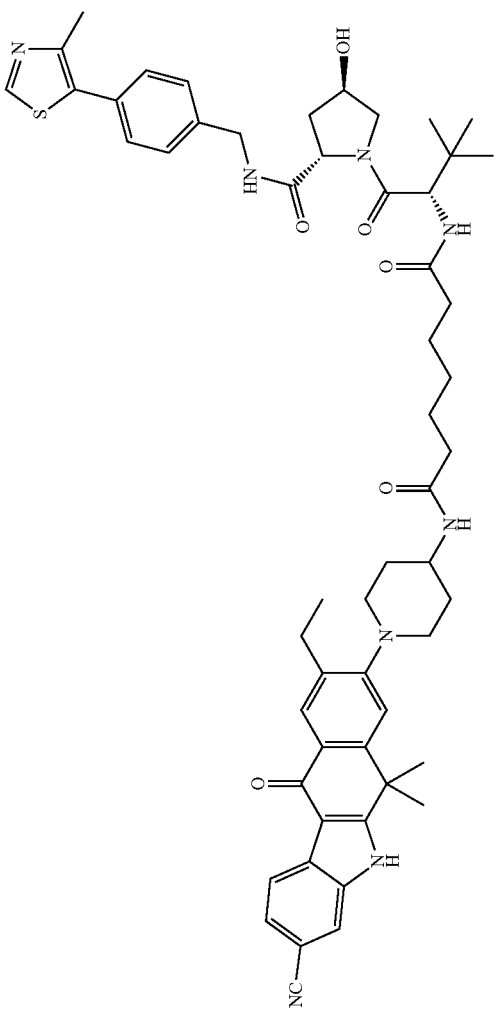 | N1-(1-(3-cyano-9-ethyl-6,6-dimethyl-11-oxo-6,11-dihydro-5H-benzo[b]carbazol-8-yl)piperidin-4-yl)-N7-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)heptanediamide |
| | 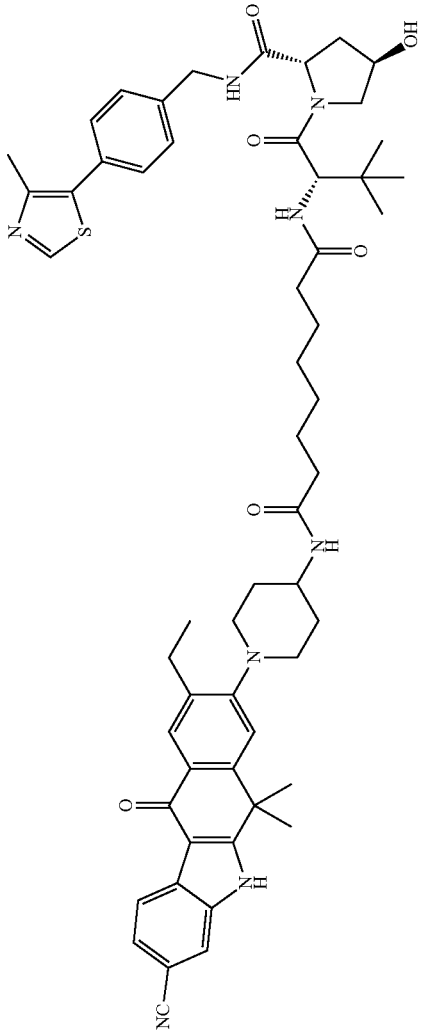 | N1-(1-(3-cyano-9-ethyl-6,6-dimethyl-11-oxo-6,11-dihydro-5H-benzo[b]carbazol-8-yl)piperidin-4-yl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide |

TABLE 1-continued

Structural formulas and names of the compounds of the present disclosure

| Compound ID | Structure of the compound | Name of the compound |
|---|---|---|
| | 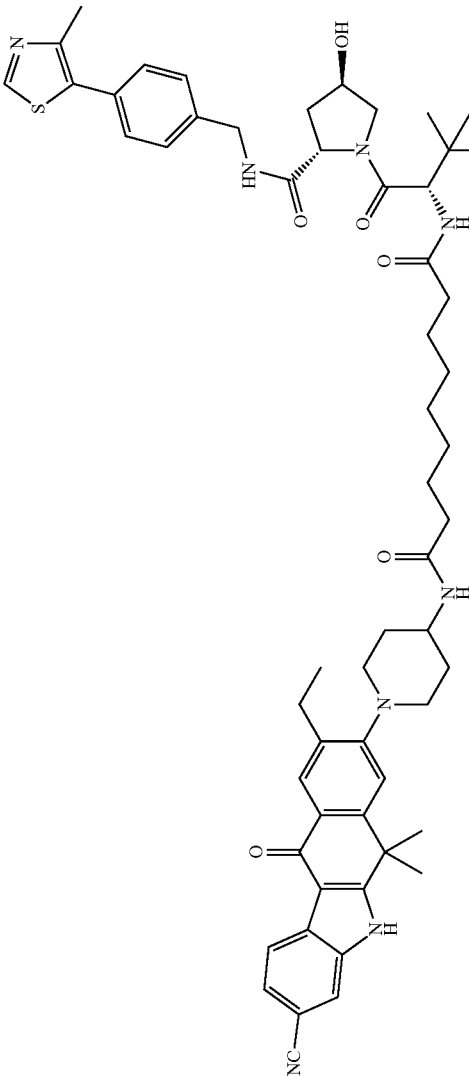 | N1-(1-(3-cyano-9-ethyl-6,6-dimethyl-11-oxo-6,11-dihydro-5H-benzo[b]carbazol-8-yl)piperidin-4-yl)-N9-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)nonanediamide |
| SIAIS219021 | | N1-(1-(3-cyano-9-ethyl-6,6-dimethyl-11-oxo-6,11-dihydro-5H-benzo[b]carbazol-8-yl)piperidin-4-yl)-N10-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide |

TABLE 1-continued

Structural formulas and names of the compounds of the present disclosure

| Compound ID | Structure of the compound | Name of the compound |
|---|---|---|
| | 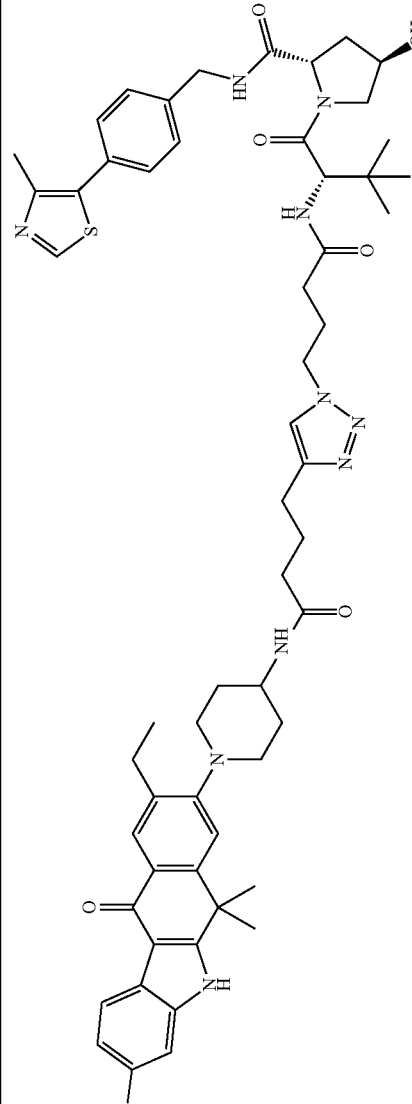 | (2S,4R)-1-((S)-2-(4-(4-(4-((1-(3-cyano-9-ethyl-6,6-dimethyl-11-oxo-6,11-dihydro-5H-benzo[b]carbazol-8-yl)piperidin-4-yl)amino)-4-oxobutyl)-1H-1,2,3-triazol-1-yl)butanamido)-3,3-dimethylbutanoyl)-4-hydroxy-N-(4-(4-methylthiazol-5-yl)benzyl)pyrrolidine-2-carboxamide |
| | | 8-(4-(4-(3-(2-(2-(2,6-dioxopiperidin-3-yl)-1,3-dioxoisoindolin-4-yl)amino)ethoxy)propanoyl)piperazin-1-yl)piperidin-1-yl)-9-ethyl-6,6-dimethyl-11-oxo-6,11-dihydro-5H-benzo[b]carbazole-3-carbonitrile |

TABLE 1-continued

Structural formulas and names of the compounds of the present disclosure

| Compound ID | Structure of the compound | Name of the compound |
|---|---|---|
| SIAI S219 018 | | 8-(4-(3-(2-(2-((2-(2,6-dioxopiperidin-3-yl)-1,3-dioxoisoindolin-4-yl)amino)ethoxy)ethoxy)propanoyl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)piperidin-1-yl)-9-ethyl-6,6-dimethyl-11-oxo-6,11-dihydro-5H-benzo[b]carbazole-3-carbonitrile |
| SIAI S219 019 | | 8-(4-(4-(1-((2-(2,6-dioxopiperidin-3-yl)-1,3-dioxoisoindolin-4-yl)amino)-3,6,9,12-tetraoxapentadecan-15-oyl)piperazin-1-yl)piperidin-1-yl)-9-ethyl-6,6-dimethyl-11-oxo-6,11-dihydro-5H-benzo[b]carbazole-3-carbonitrile |

TABLE 1-continued

Structural formulas and names of the compounds of the present disclosure

| Compound ID | Structure of the compound | Name of the compound |
|---|---|---|
| | 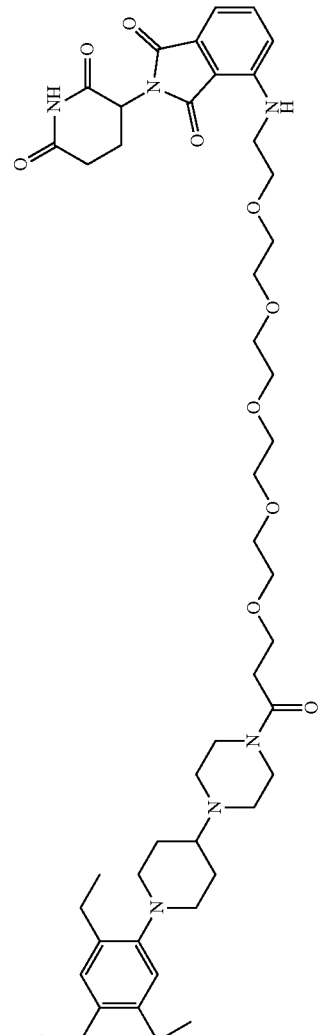 | 8-(4-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)piperidin-1-yl)-9-ethyl-6,6-dimethyl-11-oxo-6,11-dihydro-5H-benzo[b]carbazole-3-carbonitrile |
| | 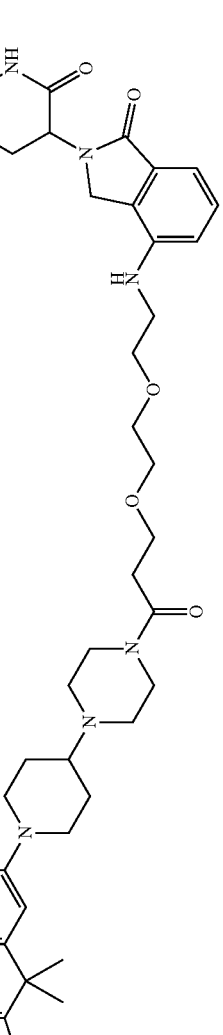 | 8-(4-(4-(3-(2-(2-((2-(2,6-dioxopiperidin-3-yl)-1-oxoisoindolin-4-yl)amino)ethoxy)ethoxy)propanoyl)piperazin-1-yl)piperidin-1-yl)-9-ethyl-6,6-dimethyl-11-oxo-6,11-dihydro-5H-benzo[b]carbazole-3-carbonitrile |

TABLE 1-continued

Structural formulas and names of the compounds of the present disclosure

| Compound ID | Structure of the compound | Name of the compound |
| --- | --- | --- |
|  |  | 8-(4-(3-(2-(2-((2-(2,6-dioxopiperidin-3-yl)-1,3-dioxoisoindolin-4-yl)oxy)ethoxy)ethoxy)propanoyl)piperazin-1-yl)piperidin-1-yl)-9-ethyl-6,6-dimethyl-11-oxo-6,11-dihydro-5H-benzo[b]carbazole-3-carbonitrile |
| SIAIS184194 |  | 8-(4-(4-((2-(2,6-dioxopiperidin-3-yl)-1,3-dioxoisoindolin-4-yl)glycyl)piperazin-1-yl)piperidin-1-yl)-9-ethyl-6,6-dimethyl-11-oxo-6,11-dihydro-5H-benzo[b]carbazole-3-carbonitrile |

TABLE 1-continued

Structural formulas and names of the compounds of the present disclosure

| Compound ID | Structure of the compound | Name of the compound |
|---|---|---|
| | 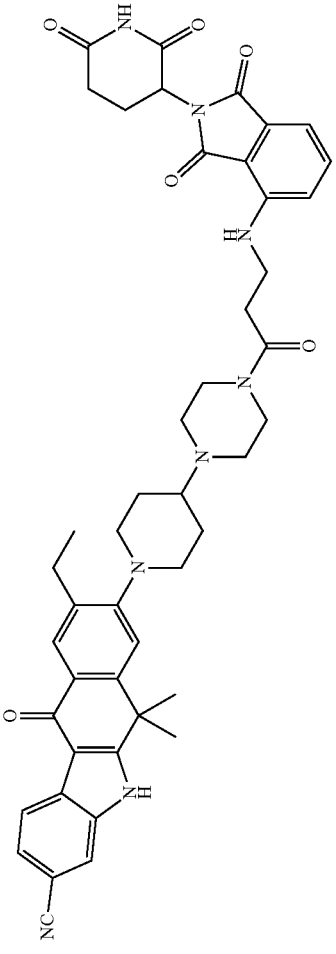 | 8-(4-(4-(3-((2-(2,6-dioxopiperidin-3-yl)-1,3-dioxoisoindolin-4-yl)amino)propanoyl)piperazin-1-yl)piperidin-1-yl)-9-ethyl-6,6-dimethyl-11-oxo-6,11-dihydro-5H-benzo[b]carbazole-3-carbonitrile |
| SIAI S219 003 | | 8-(4-(4-(4-((2-(2,6-dioxopiperidin-3-yl)-1,3-dioxoisoindolin-4-yl)amino)butanoyl)piperazin-1-yl)piperidin-1-yl)-9-ethyl-6,6-dimethyl-11-oxo-6,11-dihydro-5H-benzo[b]carbazole-3-carbonitrile |

TABLE 1-continued

Structural formulas and names of the compounds of the present disclosure

| Compound ID | Structure of the compound | Name of the compound |
|---|---|---|
| | 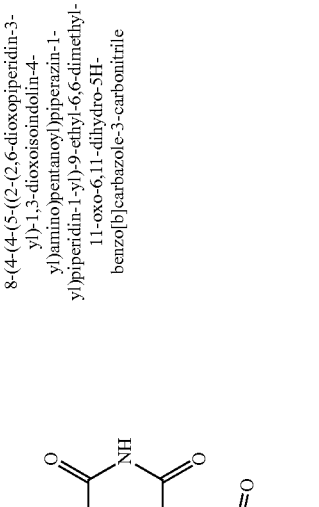 | 8-(4-(4-(5-((2-(2,6-dioxopiperidin-3-yl)-1,3-dioxoisoindolin-4-yl)amino)pentanoyl)piperazin-1-yl)piperidin-1-yl)-9-ethyl-6,6-dimethyl-11-oxo-6,11-dihydro-5H-benzo[b]carbazole-3-carbonitrile |
| SIAI S219 004 | | 8-(4-(4-(6-((2-(2,6-dioxopiperidin-3-yl)-1,3-dioxoisoindolin-4-yl)amino)hexanoyl)piperazin-1-yl)piperidin-1-yl)-9-ethyl-6,6-dimethyl-11-oxo-6,11-dihydro-5H-benzo[b]carbazole-3-carbonitrile |

TABLE 1-continued

Structural formulas and names of the compounds of the present disclosure

| Compound ID | Structure of the compound | Name of the compound |
|---|---|---|
| | 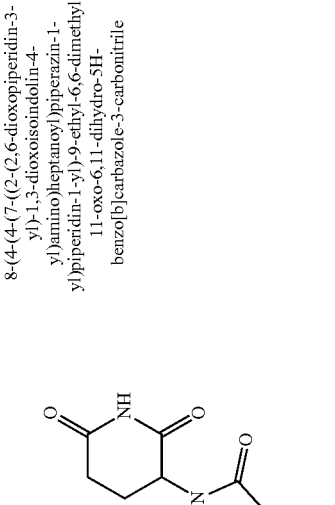 | 8-(4-(4-(7-((2-(2,6-dioxopiperidin-3-yl)-1,3-dioxoisoindolin-4-yl)amino)heptanoyl)piperazin-1-yl)piperidin-1-yl)-9-ethyl-6,6-dimethyl-11-oxo-6,11-dihydro-5H-benzo[b]carbazole-3-carbonitrile |
| | 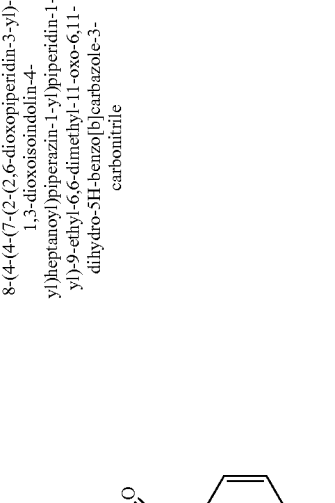 | 8-(4-(4-(7-(2-(2,6-dioxopiperidin-3-yl)-1,3-dioxoisoindolin-4-yl)heptanoyl)piperazin-1-yl)piperidin-1-yl)-9-ethyl-6,6-dimethyl-11-oxo-6,11-dihydro-5H-benzo[b]carbazole-3-carbonitrile |

TABLE 1-continued

Structural formulas and names of the compounds of the present disclosure

| Compound ID | Structure of the compound | Name of the compound |
|---|---|---|
| | 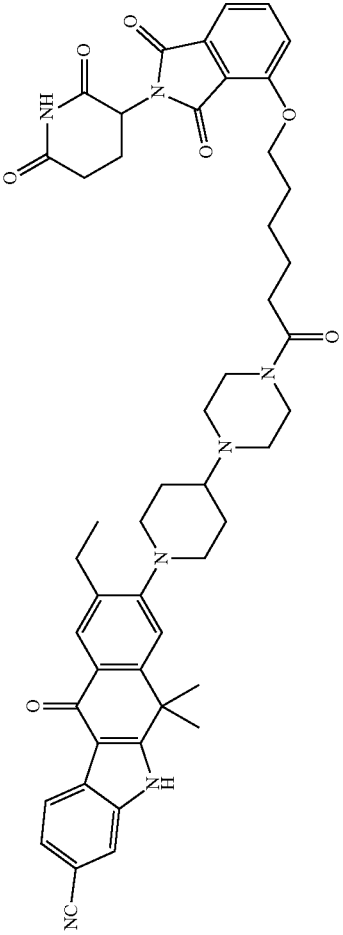 | 8-(4-(4-(6-((2-(2,6-dioxopiperidin-3-yl)-1,3-dioxoisoindolin-4-yl)oxy)hexanoyl)piperazin-1-yl)piperidin-1-yl)-9-ethyl-6,6-dimethyl-11-oxo-6,11-dihydro-5H-benzo[b]carbazole-3-carbonitrile |
| | 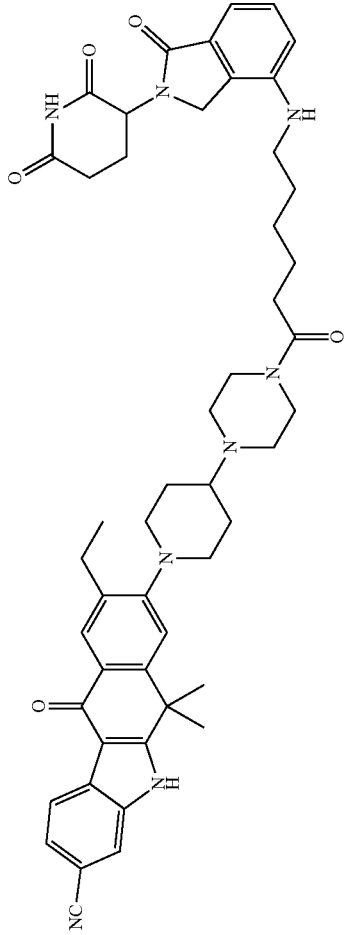 | 8-(4-(4-(6-((2-(2,6-dioxopiperidin-3-yl)-1-oxoisoindolin-4-yl)amino)hexanoyl)piperazin-1-yl)piperidin-1-yl)-9-ethyl-6,6-dimethyl-11-oxo-6,11-dihydro-5H-benzo[b]carbazole-3-carbonitrile |

TABLE 1-continued

Structural formulas and names of the compounds of the present disclosure

| Compound ID | Structure of the compound | Name of the compound |
|---|---|---|
| | | 8-(4-(4-(2-((2-(2,6-dioxopiperidin-3-yl)-1,3-dioxoisoindolin-4-yl)amino)ethyl)piperazin-1-yl)piperidin-1-yl)-9-ethyl-6,6-dimethyl-11-oxo-6,11-dihydro-5H-benzo[b]carbazole-3-carbonitrile |
| | | 8-(4-(4-(6-((2-(2,6-dioxopiperidin-3-yl)-1-oxoisoindolin-4-yl)amino)hexyl)piperazin-1-yl)piperidin-1-yl)-9-ethyl-6,6-dimethyl-11-oxo-6,11-dihydro-5H-benzo[b]carbazole-3-carbonitrile |

TABLE 1-continued

Structural formulas and names of the compounds of the present disclosure

| Compound ID | Structure of the compound | Name of the compound |
|---|---|---|
| | 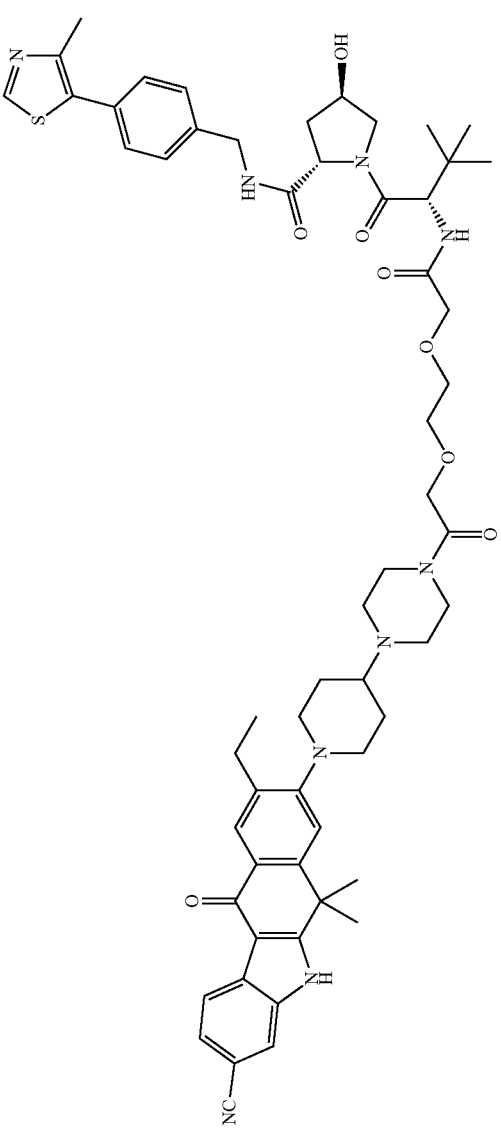 | (2S,4R)-1-((S)-2-(2-(2-(2-(4-(1-(3-cyano-9-ethyl-6,6-dimethyl-11-oxo-6,11-dihydro-5H-benzo[b]carbazol-8-yl)piperidin-4-yl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide |
| | 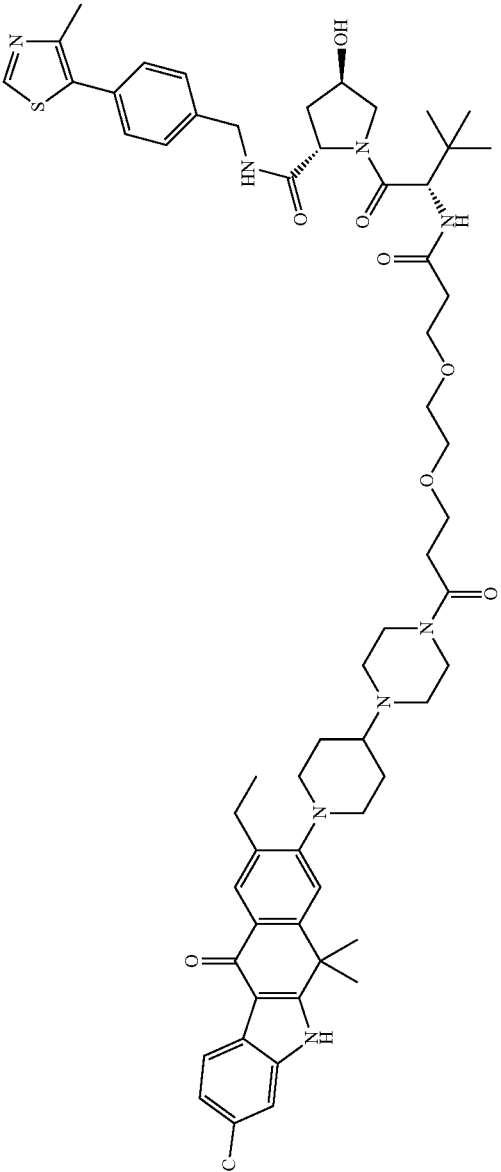 | (2S,4R)-1-((S)-2-(3-(2-(3-(4-(1-(3-cyano-9-ethyl-6,6-dimethyl-11-oxo-6,11-dihydro-5H-benzo[b]carbazol-8-yl)piperidin-4-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | 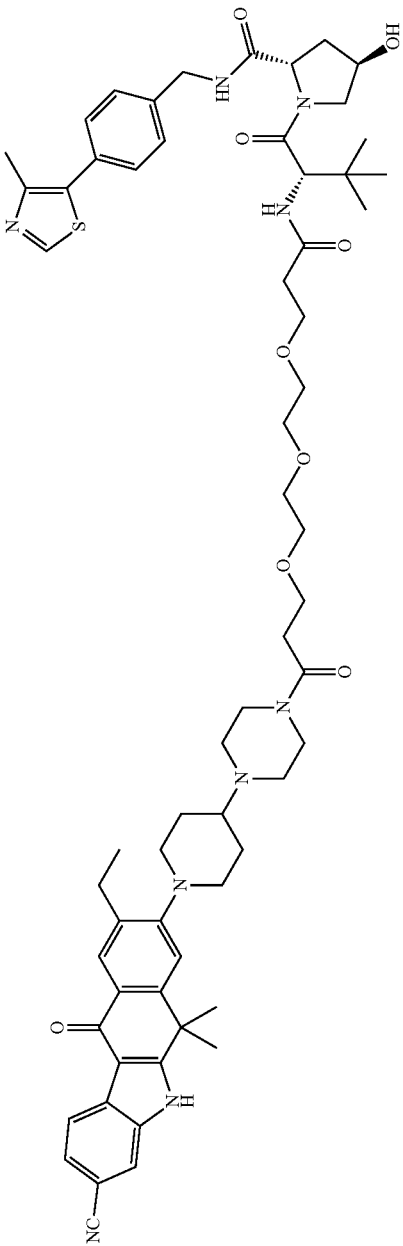 | (2S,4R)-1-((S)-2-(tert-butyl)-16-(4-(1-(3-cyano-9-ethyl-6,6-dimethyl-11-oxo-6,11-dihydro-5H-benzo[b]carbazol-8-yl)piperidin-4-yl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide |
| | | (2S,4R)-1-((S)-2-(tert-butyl)-19-(4-(1-(3-cyano-9-ethyl-6,6-dimethyl-11-oxo-6,11-dihydro-5H-benzo[b]carbazol-8-yl)piperidin-4-yl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | 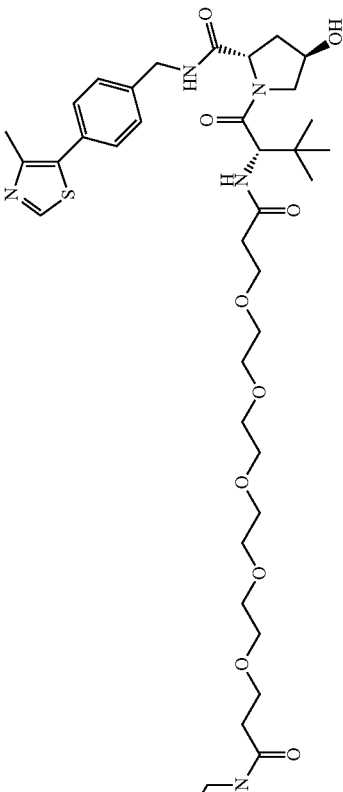 | (2S,4R)-1-((S)-2-(tert-butyl)-22-(4-(1-(3-cyano-9-ethyl-6,6-dimethyl-11-oxo-6,11-dihydro-5H-benzo[b]carbazol-8-yl)piperidin-4-yl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide |
| | | (2S,4R)-1-((S)-2-(4-(4-(1-(3-cyano-9-ethyl-6,6-dimethyl-11-oxo-6,11-dihydro-5H-benzo[b]carbazol-8-yl)piperidin-4-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | 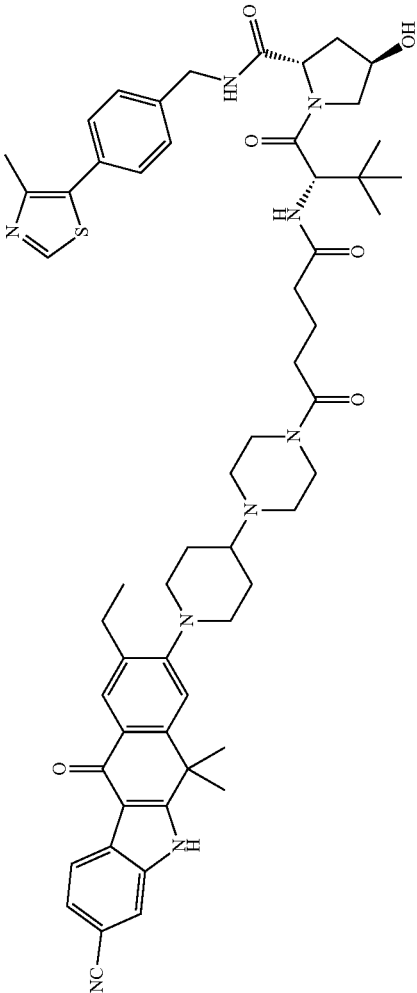 | (2S,4R)-1-((S)-2-(5-(4-(1-(3-cyano-9-ethyl-6,6-dimethyl-11-oxo-6,11-dihydro-5H-benzo[b]carbazol-8-yl)piperidin-4-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide |
| SIAIS219015 | 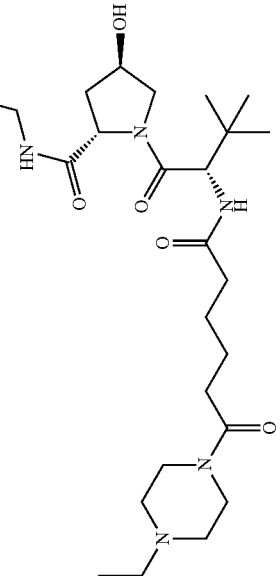 | (2S,4R)-1-((S)-2-(6-(4-(1-(3-cyano-9-ethyl-6,6-dimethyl-11-oxo-6,11-dihydro-5H-benzo[b]carbazol-8-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | | (2S,4R)-1-((S)-2-(7-(4-(1-(3-cyano-9-ethyl-6,6-dimethyl-11-oxo-6,11-dihydro-5H-benzo[b]carbazol-8-yl)piperidin-4-yl)piperazin-1-yl)-7-oxoheptanamido)-3,3-dimethylbutanoyl)-4-hydroxy-N-(4-(4-methylthiazol-5-yl)benzyl)pyrrolidine-2-carboxamide |
| | | (2S,4R)-1-((S)-2-(8-(4-(1-(3-cyano-9-ethyl-6,6-dimethyl-11-oxo-6,11-dihydro-5H-benzo[b]carbazol-8-yl)piperidin-4-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | 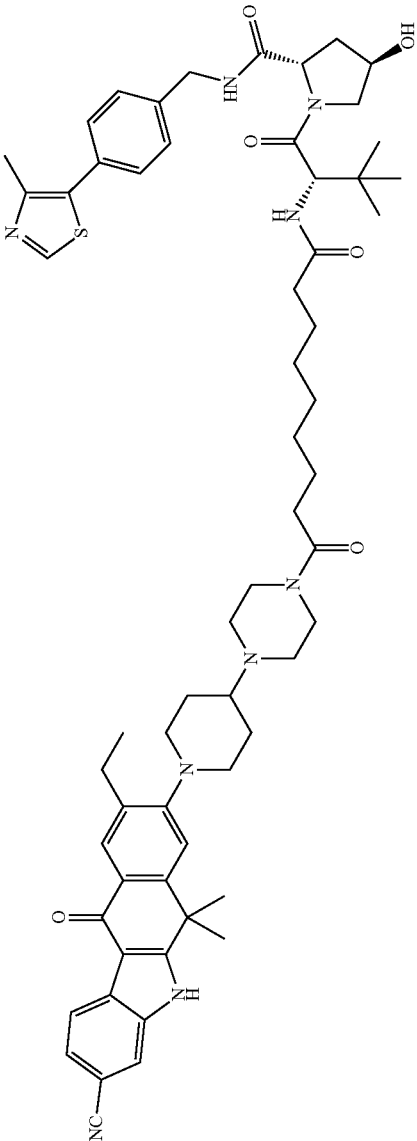 | (2S,4R)-1-((S)-2-(9-(4-(1-(3-cyano-9-ethyl-6,6-dimethyl-11-oxo-6,11-dihydro-5H-benzo[b]carbazol-8-yl)piperidin-4-yl)piperazin-1-yl)-9-oxononanamido)-3,3-dimethylbutanoyl)-4-hydroxy-N-(4-(4-methylthiazol-5-yl)benzyl)pyrrolidine-2-carboxamide |
| SIAIS219016 | | (2S,4R)-1-((S)-2-(10-(4-(1-(3-cyano-9-ethyl-6,6-dimethyl-11-oxo-6,11-dihydro-5H-benzo[b]carbazol-8-yl)piperidin-4-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
|  |  | (2S,4R)-1-((S)-2-(4-(4-(4-(1-(3-cyano-9-ethyl-6,6-dimethyl-11-oxo-6,11-dihydro-5H-benzo[b]carbazol-8-yl)piperidin-4-yl)piperazin-1-yl)-4-oxobutyl)-1H-1,2,3-triazol-1-yl)butanamido)-3,3-dimethylbutanoyl)-4-hydroxy-N-(4-(4-methylthiazol-5-yl)benzyl)pyrrolidine-2-carboxamide |
| SIAIS151031 |  | 4-((2-(3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropoxy)ethyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| SIAI S151 023 | | 4-((2-(3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropoxy)ethoxy)amino)-2-(2,6-dioxopiperidin-3-yl)isoindoline-1,3-dione |
| | | 4-((2-(2-(3-(4-(4-((5-chloro-4-((2-(isopropylsulfonyl)phenyl)amino)pyrimidin-2-yl)amino)-5-isopropoxy-2-methylphenyl)piperidin-1-yl)propoxy)ethoxy)ethyl)amino)-2-(2,6-dioxopiperidin-3-yl)isoindoline-1,3-dione |
| | | 4-(2-(2-(3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropoxy)ethoxy)ethoxy)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| | 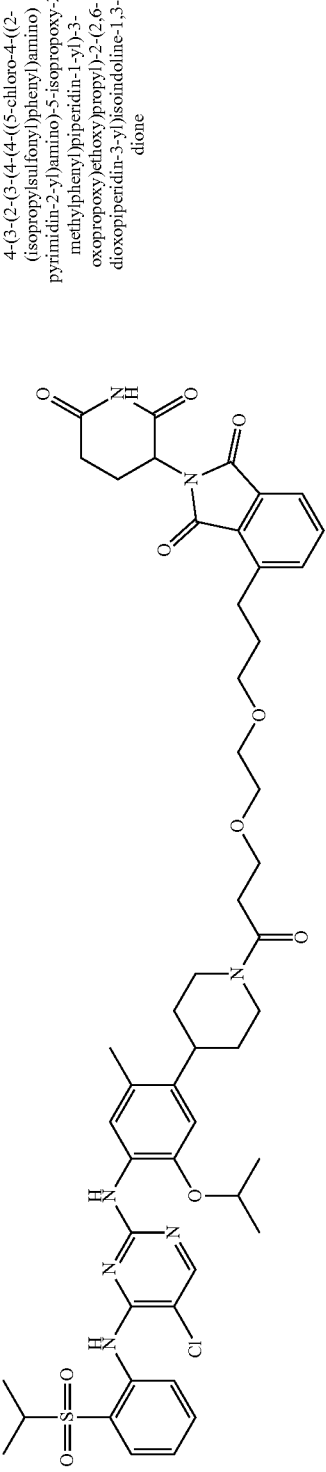 | 4-(3-(2-(3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropoxy)ethoxy)propyl)-2-(2,6-dioxopiperidin-3-yl)isoindoline-1,3-dione |
| | 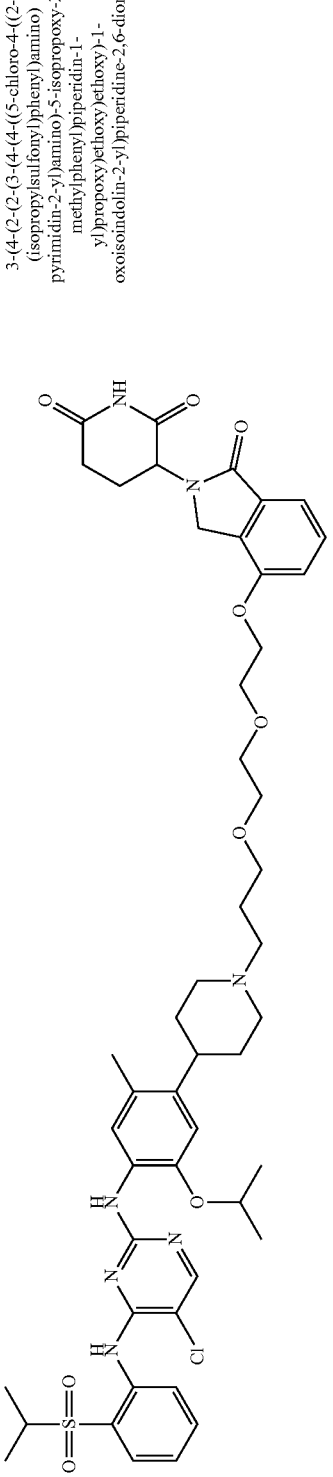 | 3-(4-(2-(2-(3-(4-(4-((5-chloro-4-((2-(isopropylsulfonyl)phenyl)amino)pyrimidin-2-yl)amino)-5-isopropoxy-2-methylphenyl)piperidin-1-yl)propoxy)ethoxy)ethoxy)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
|  | 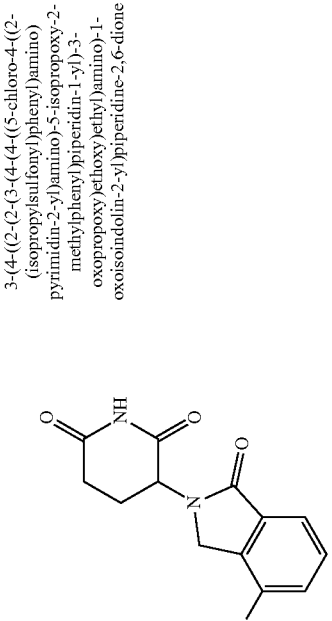 | 3-(4-((2-(2-(3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropoxy)ethoxy)ethyl)amino)-1-oxoisoindolin-2-yl)piperidine-2,6-dione |
| SIAIS151028 | 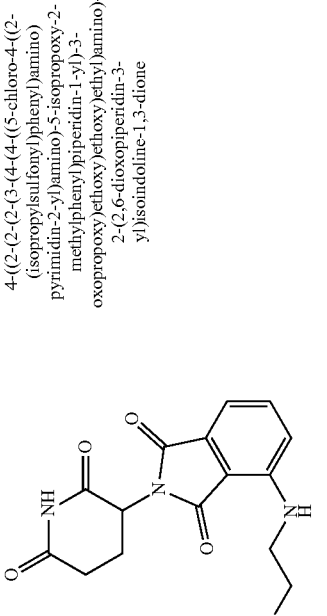 | 4-((2-(2-(2-(3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropoxy)ethoxy)ethoxy)ethyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
| --- | --- | --- |
| SIAIS151029 | | 4-((18-(4-(4-((5-chloro-4-((2-(isopropylsulfonyl)phenyl)amino)pyrimidin-2-yl)amino)-5-isopropoxy-2-methylphenyl)piperidin-1-yl)-18-oxo-3,6,9,12,15-pentaoxaoctadecyl)amino)-2-(2,6-dioxopiperidin-3-yl)isoindoline-1,3-dione |
| SIAIS151037 | | 4-((2-(4-(4-((5-chloro-4-((2-(isopropylsulfonyl)phenyl)amino)pyrimidin-2-yl)amino)-5-isopropoxy-2-methylphenyl)piperidin-1-yl)-2-oxoethyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| SIAIS151034 | 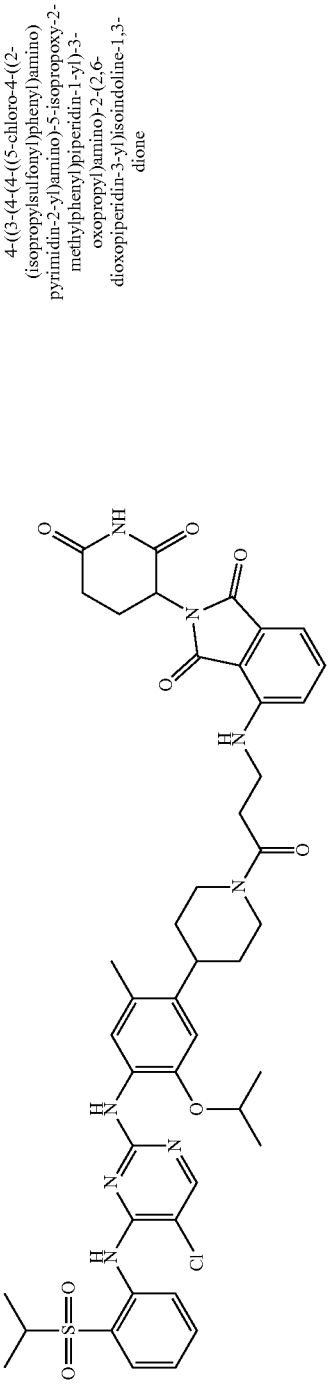 | 4-((3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropyl)amino)-2-(2,6-dioxopiperidin-3-yl)isoindoline-1,3-dione |
| | | 4-(4-(4-(4-((5-chloro-4-((2-(isopropylsulfonyl)phenyl)amino)pyrimidin-2-yl)amino)-5-isopropoxy-2-methylphenyl)piperidin-1-yl)-4-oxobutyl)-2-(2,6-dioxopiperidin-3-yl)isoindoline-1,3-dione |
| | | 4-((3-(4-(4-((5-chloro-4-((2-(isopropylsulfonyl)phenyl)amino)pyrimidin-2-yl)amino)-5-isopropoxy-2-methylphenyl)piperidin-1-yl)propyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| | 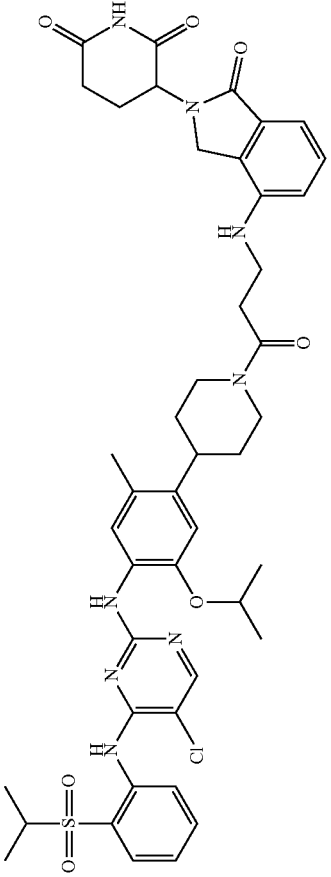 | 3-(4-((3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropyl)amino)-1-oxoisoindolin-2-yl)piperidine-2,6-dione |
| SIAIS151035 | | 4-((4-(4-(4-((5-chloro-4-((2-(isopropylsulfonyl)phenyl)amino)pyrimidin-2-yl)amino)-5-isopropoxy-2-methylphenyl)piperidin-1-yl)-4-oxobutyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
| --- | --- | --- |
| SIAI S151 036 | | 4-((5-(4-(4-((5-chloro-4-((2-(isopropylsulfonyl)phenyl)amino)pyrimidin-2-yl)amino)-5-isopropoxy-2-methylphenyl)piperidin-1-yl)-5-oxopentyl)amino)-2-(2,6-dioxopiperidin-3-yl)isoindoline-1,3-dione |
| SIAI S151 043 | | 4-((6-(4-(4-((5-chloro-4-((2-(isopropylsulfonyl)phenyl)amino)pyrimidin-2-yl)amino)-5-isopropoxy-2-methylphenyl)piperidin-1-yl)-6-oxohexyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| | | 4-((6-(4-(4-((5-chloro-4-((2-(isopropylsulfonyl)phenyl)amino)pyrimidin-2-yl)amino)-5-isopropoxy-2-methylphenyl)piperidin-1-yl)-6-oxohexyl)oxy)-2-(2,6-dioxopiperidin-3-yl)isoindoline-1,3-dione |
| SIAI S151 042 | | (2S,4R)-1-((S)-2-(2-(2-(2-(4-(4-((5-chloro-4-((2-(isopropylsulfonyl)phenyl)amino)pyrimidin-2-yl)amino)-5-isopropoxy-2-methylphenyl)piperidin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | 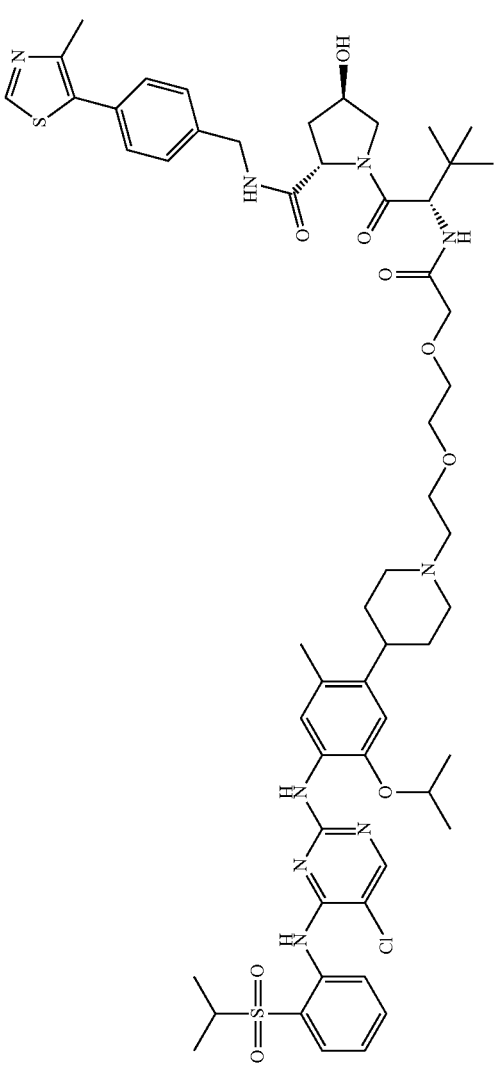 | (2S,4R)-1-((S)-2-(2-(2-(2-(4-(4-((5-chloro-4-(2-(isopropylsulfonyl)phenyl)amino)pyrimidin-2-yl)amino)-5-isopropoxy-2-methylphenyl)piperidin-1-yl)ethoxy)ethoxy)acetamido)-3,3-dimethylbutanoyl)-4-hydroxy-N-(4-(4-methylthiazol-5-yl)benzyl)pyrrolidine-2-carboxamide |
| SIAIS151038 | | (2S,4R)-1-((S)-2-(3-(2-(3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S151 039 | 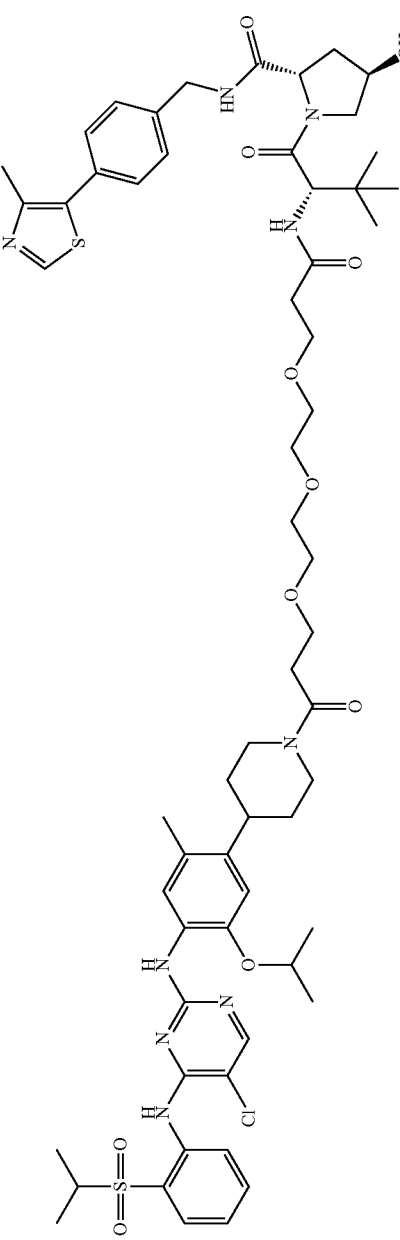 | (2S,4R)-1-((S)-2-(tert-butyl)-16-(4-((5-chloro-4-((2-(isopropylsulfonyl)phenyl)amino)pyrimidin-2-yl)amino)-5-isopropoxy-2-methylphenyl)piperidin-1-yl)-4,16-dioxo-7,10,13-trioxa-3-azahexadecanoyl)-4-hydroxy-N-(4-(4-methylthiazol-5-yl)benzyl)pyrrolidine-2-carboxamide |
| SIAI S151 040 | 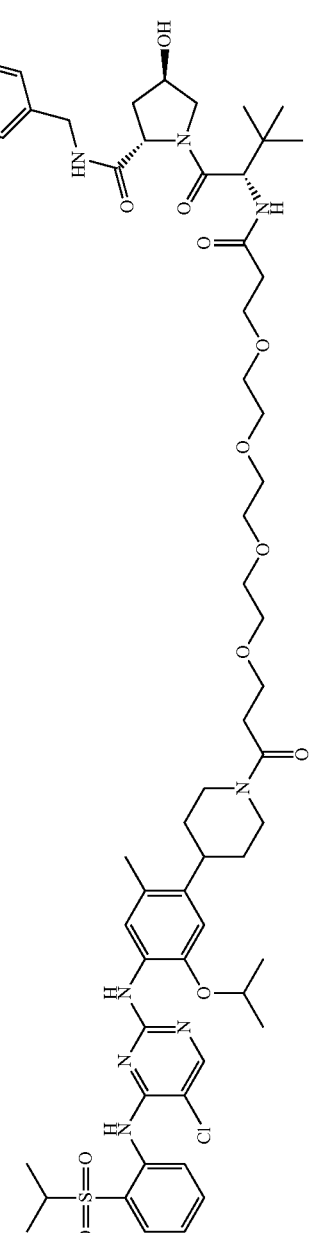 | (2S,4R)-1-((S)-2-(tert-butyl)-19-(4-((5-chloro-4-((2-(isopropylsulfonyl)phenyl)amino)pyrimidin-2-yl)amino)-5-isopropoxy-2-methylphenyl)piperidin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S151 041 | 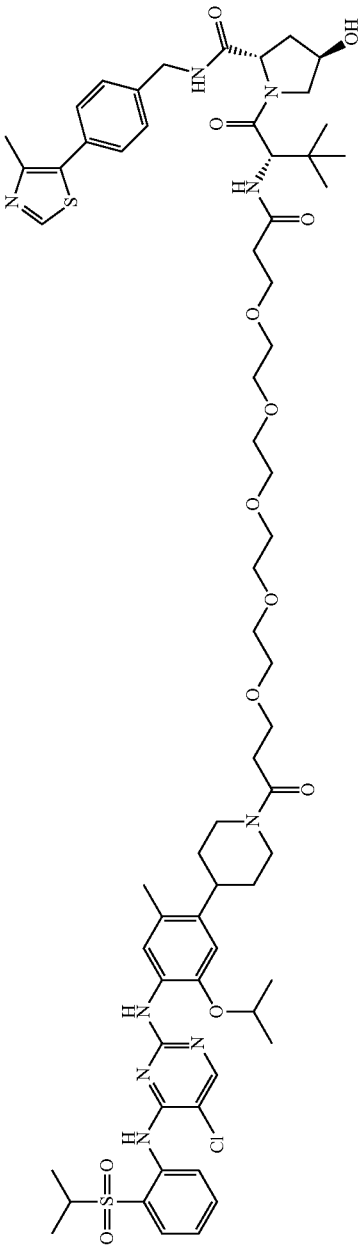 | (2S,4R)-1-((S)-2-(tert-butyl)-22-(4-(4-((5-chloro-4-((2-(isopropylsulfonyl)phenyl)amino)pyrimidin-2-yl)amino)-5-isopropoxy-2-methylphenyl)piperidin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide |
| | | (2S,4R)-1-((S)-2-(6-(4-(4-((5-chloro-4-((2-(isopropylsulfonyl)phenyl)amino)pyrimidin-2-yl)amino)-5-isopropoxy-2-methylphenyl)piperidine-1-carbonyl)spiro[3.3]heptane-2-carboxamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S074 017 | 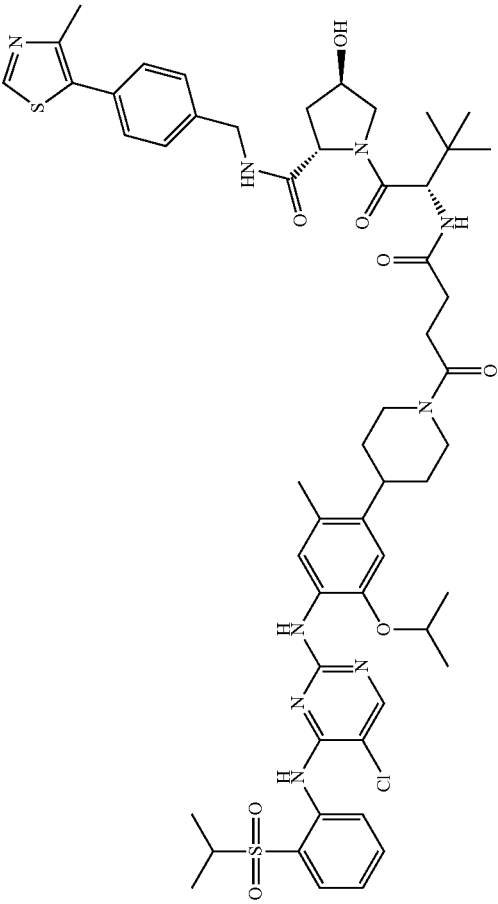 | (2S,4R)-1-((S)-2-(4-(4-(4-((5-chloro-4-((2-(isopropylsulfonyl)phenyl)amino)pyrimidin-2-yl)amino)-5-isopropoxy-2-methylphenyl)piperidin-1-yl)-4-oxobutanamido)-3,3-dimethylbutanoyl)-4-hydroxy-N-(4-(4-methylthiazol-5-yl)benzyl)pyrrolidine-2-carboxamide<br><br>(2S,4R)-1-((S)-2-(4-(4-(4-((5-chloro-4-((2-(isopropylsulfonyl)phenyl)amino)pyrimidin-2-yl)amino)-5-isopropoxy-2-methylphenyl)piperidin-1-yl)butanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | 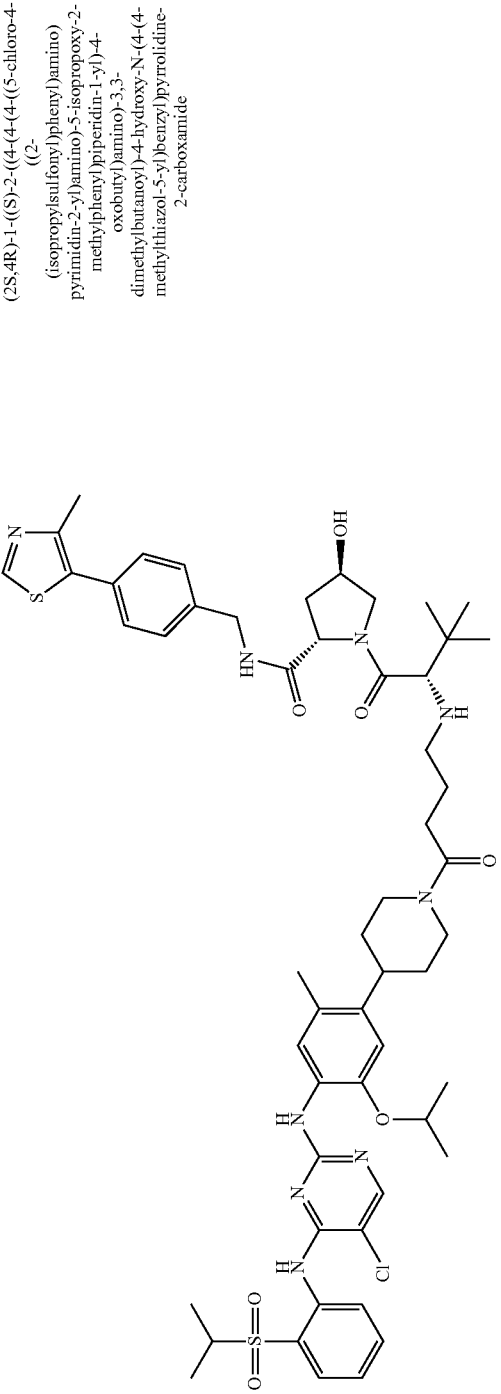 | (2S,4R)-1-((S)-2-((4-(4-(4-((5-chloro-4-((2-(isopropylsulfonyl)phenyl)amino)pyrimidin-2-yl)amino)-5-isopropoxy-2-methylphenyl)piperidin-1-yl)-4-oxobutyl)amino)-3,3-dimethylbutanoyl)-4-hydroxy-N-(4-(4-methylthiazol-5-yl)benzyl)pyrrolidine-2-carboxamide |
| SIAIS074018 | | (2S,4R)-1-((S)-2-(5-(4-(4-((5-chloro-4-((2-(isopropylsulfonyl)phenyl)amino)pyrimidin-2-yl)amino)-5-isopropoxy-2-methylphenyl)piperidin-1-yl)-5-oxopentanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S074 021 | 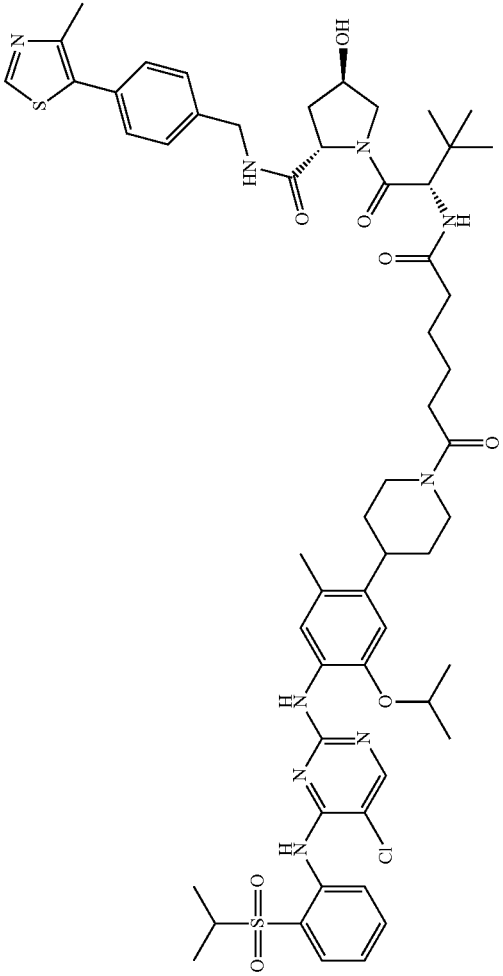 | (2S,4R)-1-((S)-2-(6-(4-(4-((5-chloro-4-((2-(isopropylsulfonyl)phenyl)amino)pyrimidin-2-yl)amino)-5-isopropoxy-2-methylphenyl)piperidin-1-yl)-6-oxohexanamido)-3,3-dimethylbutanoyl)-4-hydroxy-N-(4-(4-methylthiazol-5-yl)benzyl)pyrrolidine-2-carboxamide |
| SIAI S074 022 | 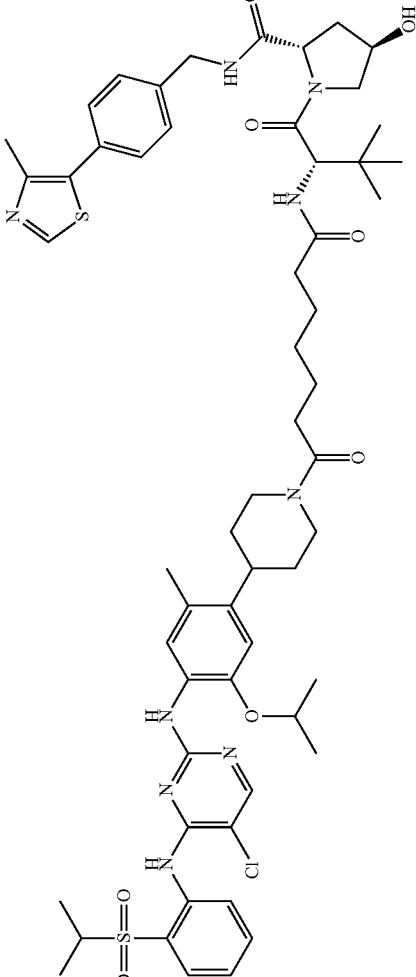 | (2S,4R)-1-((S)-2-(7-(4-(4-((5-chloro-4-((2-(isopropylsulfonyl)phenyl)amino)pyrimidin-2-yl)amino)-5-isopropoxy-2-methylphenyl)piperidin-1-yl)-7-oxoheptanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAI S074 008 | 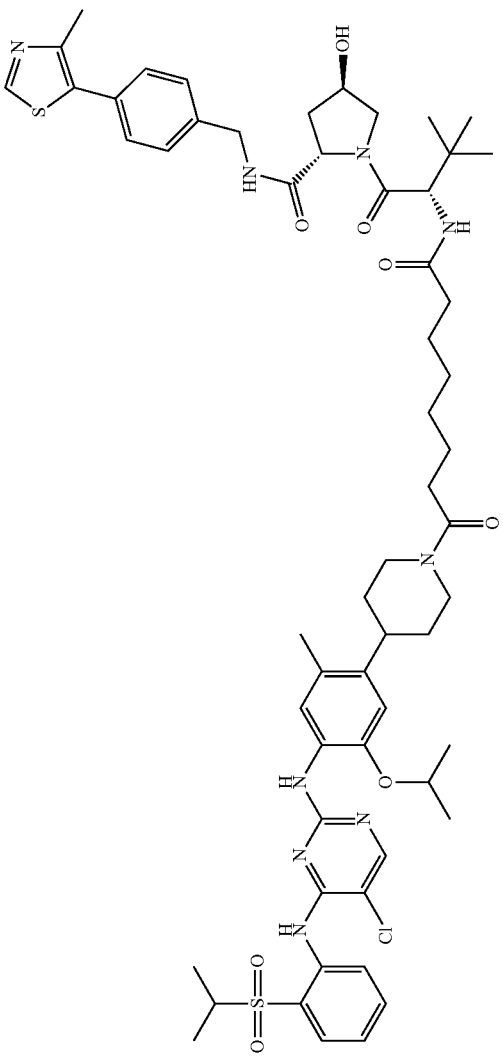 | (2S,4R)-1-((S)-2-(8-(4-(4-(5-chloro-4-((2-(isopropylsulfonyl)phenyl)amino)pyrimidin-2-yl)amino)-5-isopropoxy-2-methylphenyl)piperidin-1-yl)-8-oxooctanamido)-3,3-dimethylbutanoyl)-4-hydroxy-N-(4-(4-methylthiazol-5-yl)benzyl)pyrrolidine-2-carboxamide |
| SIAI S074 024 | 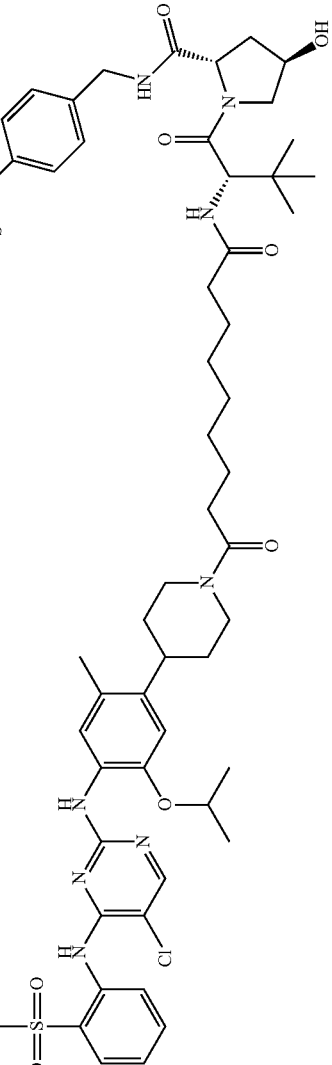 | (2S,4R)-1-((S)-2-(9-(4-(4-(5-chloro-4-((2-(isopropylsulfonyl)phenyl)amino)pyrimidin-2-yl)amino)-5-isopropoxy-2-methylphenyl)piperidin-1-yl)-9-oxononanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| SIAIS074 025 | 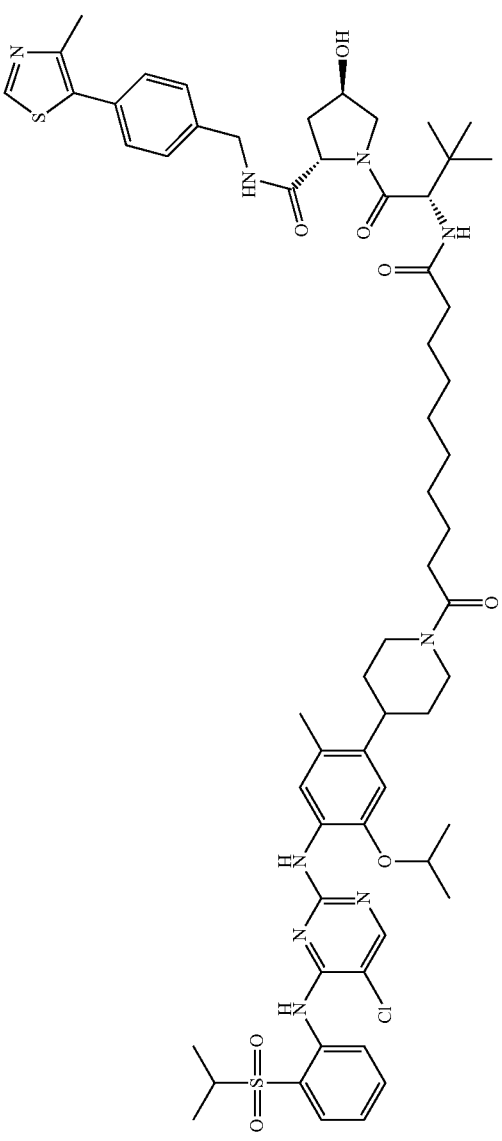 | (2S,4R)-1-((S)-2-(10-(4-(4-((5-chloro-4-((2-(isopropylsulfonyl)phenyl)amino)pyrimidin-2-yl)amino)-5-isopropoxy-2-methylphenyl)piperidin-1-yl)-10-oxodecanamido)-3,3-dimethylbutanoyl)-4-hydroxy-N-(4-(4-methylthiazol-5-yl)benzyl)pyrrolidine-2-carboxamide |
| SIAIS074 026 | 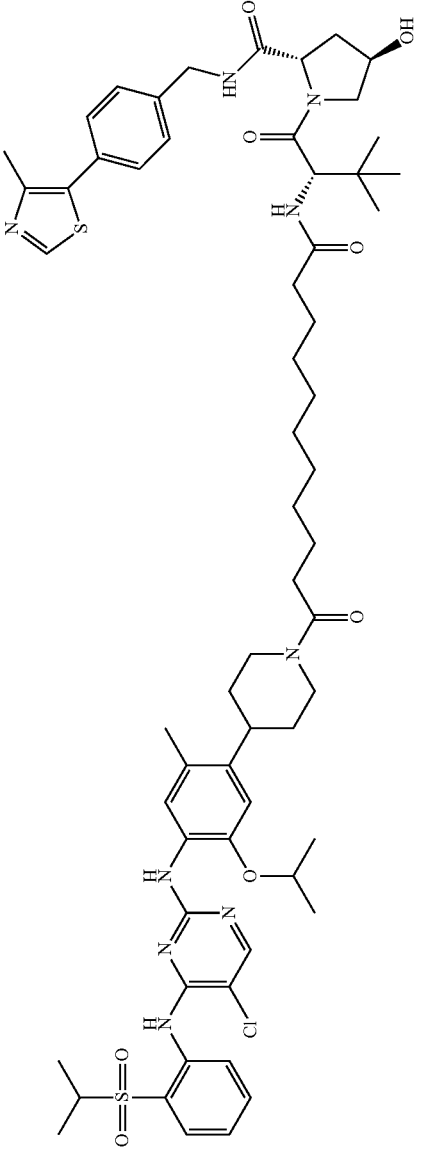 | (2S,4R)-1-((S)-2-(11-(4-(4-((5-chloro-4-((2-(isopropylsulfonyl)phenyl)amino)pyrimidin-2-yl)amino)-5-isopropoxy-2-methylphenyl)piperidin-1-yl)-11-oxoundecanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | | (2S,4R)-1-((S)-2-(5-(4-(4-((5-chloro-4-((2-(isopropylsulfonyl)phenyl)amino)pyrimidin-2-yl)amino)-5-isopropoxy-2-methylphenyl)piperidin-1-yl)-5-oxopentanamido)pentanamido)-3,3-dimethylbutanoyl)-4-hydroxy-N-(4-(4-methylthiazol-5-yl)benzyl)pyrrolidine-2-carboxamide |
| SIAIS151049 | | 4-((2-(3-(4-(4-(6-amino-5-((R)-1-(2,6-dichloro-3-fluorophenyl)ethoxy)pyridin-3-yl)-1H-pyrazol-1-yl)piperidin-1-yl)-3-oxopropoxy)ethyl)amino)-2-(2,6-dioxopiperidin-3-yl)isoindoline-1,3-dione |

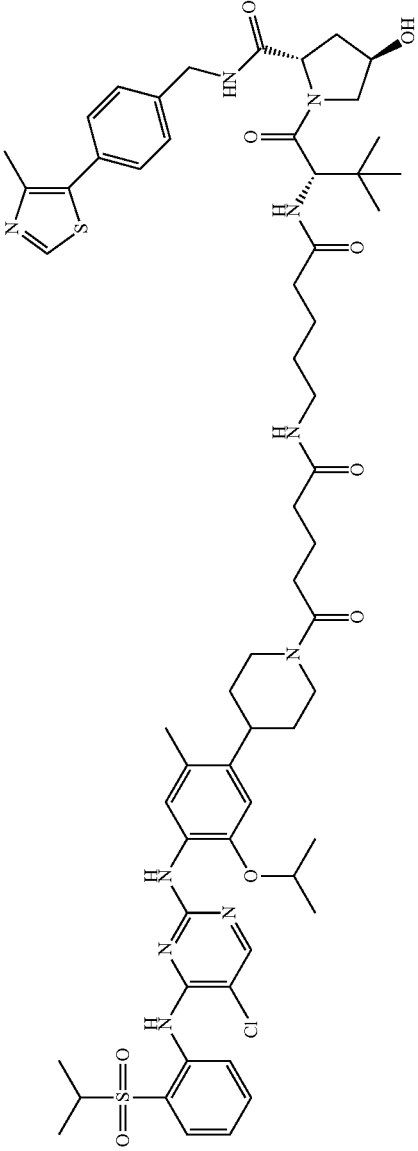

TABLE 1-continued

Structural formulas and names of the compounds of the present disclosure

| Compound ID | Structure of the compound | Name of the compound |
|---|---|---|
| | | 4-(2-(3-(4-(4-(6-amino-5-((R)-1-(2,6-dichloro-3-fluorophenyl)ethoxy)pyridin-3-yl)-1H-pyrazol-1-yl)piperidin-1-yl)-3-oxopropoxy)ethoxy)-2-(2,6-dioxopiperidin-3-yl)isoindoline-1,3-dione |
| | | 4-((2-(3-(4-(4-(6-amino-5-((R)-1-(2,6-dichloro-3-fluorophenyl)ethoxy)pyridin-3-yl)-1H-pyrazol-1-yl)piperidin-1-yl)propoxy)ethyl)amino)-2-(2,6-dioxopiperidin-3-yl)isoindoline-1,3-dione |
| | | 3-(4-((2-(3-(4-(4-(6-amino-5-((R)-1-(2,6-dichloro-3-fluorophenyl)ethoxy)pyridin-3-yl)-1H-pyrazol-1-yl)piperidin-1-yl)propoxy)ethyl)amino)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| | 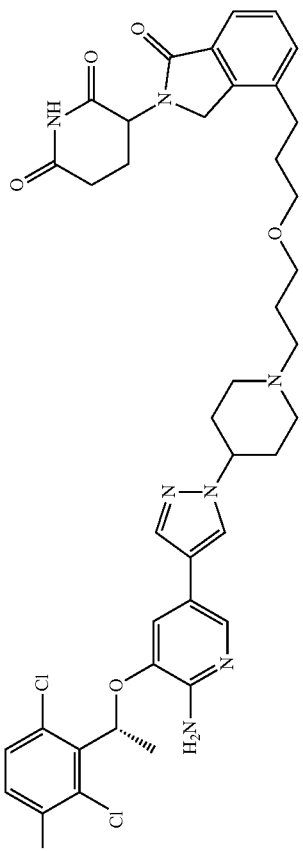 | 3-(4-(3-(4-(4-(6-amino-5-((R)-1-(2,6-dichloro-3-fluorophenyl)ethoxy)pyridin-3-yl)-1H-pyrazol-1-yl)piperidin-1-yl)propoxy)propyl)-1-oxoisoindolin-2-yl)piperidine-2,6-dione |
| SIAIS151050 | | 4-((2-(2-(3-(4-(4-(6-amino-5-((R)-1-(2,6-dichloro-3-fluorophenyl)ethoxy)pyridin-3-yl)-1H-pyrazol-1-yl)piperidin-1-yl)-3-oxopropoxy)ethoxy)ethyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| SIAIS151051 | | 4-((2-(2-(2-(3-(4-(4-(6-amino-5-((R)-1-(2,6-dichloro-3-fluorophenyl)ethoxy)pyridin-3-yl)-1H-pyrazol-1-yl)piperidin-1-yl)-3-oxopropoxy)ethoxy)ethyl)amino)-2-(2,6-dioxopiperidin-3-yl)isoindoline-1,3-dione |
| SIAIS151060 | | 4-((15-(4-(4-(6-amino-5-((R)-1-(2,6-dichloro-3-fluorophenyl)ethoxy)pyridin-3-yl)-1H-pyrazol-1-yl)piperidin-1-yl)-15-oxo-3,6,9,12-tetraoxapentadecyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
| --- | --- | --- |
| SIAIS151061 | | 4-((18-(4-(4-(6-amino-5-((R)-1-(2,6-dichloro-3-fluorophenyl)ethoxy)pyridin-3-yl)-1H-pyrazol-1-yl)piperidin-1-yl)-18-oxo-3,6,9,12,15-pentaoxaoctadecyl)amino)-2-(2,6-dioxopiperidin-3-yl)isoindoline-1,3-dione |
| SIAIS151083 | | 4-((2-(4-(4-(6-amino-5-((R)-1-(2,6-dichloro-3-fluorophenyl)ethoxy)pyridin-3-yl)-1H-pyrazol-1-yl)piperidin-1-yl)-2-oxoethyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| SIAI S151 084 | | 4-((3-(4-(4-(6-amino-5-((R)-1-(2,6-dichloro-3-fluorophenyl)ethoxy)pyridin-3-yl)-1H-pyrazol-1-yl)piperidin-1-yl)-3-oxopropyl)amino)-2-(2,6-dioxopiperidin-3-yl)isoindoline-1,3-dione |
| SIAI S151 081 | | 4-((4-(4-(6-amino-5-((R)-1-(2,6-dichloro-3-fluorophenyl)ethoxy)pyridin-3-yl)-1H-pyrazol-1-yl)piperidin-1-yl)-4-oxobutyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| SIAI S151 082 | | 4-((5-(4-(4-(6-amino-5-((R)-1-(2,6-dichloro-3-fluorophenyl)ethoxy)pyridin-3-yl)-1H-pyrazol-1-yl)piperidin-1-yl)-5-oxopentyl)amino)-2-(2,6-dioxopiperidin-3-yl)isoindoline-1,3-dione |
| SIAI S151 085 | | 4-((6-(4-(4-(6-amino-5-((R)-1-(2,6-dichloro-3-fluorophenyl)ethoxy)pyridin-3-yl)-1H-pyrazol-1-yl)piperidin-1-yl)-6-oxohexyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| | 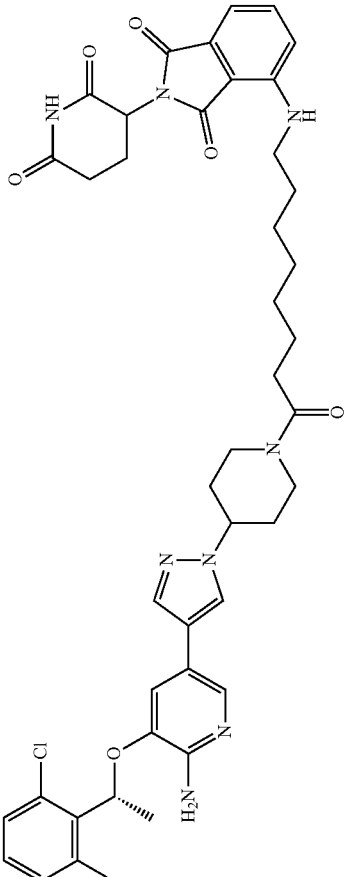 | 4-((8-(4-(4-(6-amino-5-((R)-1-(2,6-dichloro-3-fluorophenyl)ethoxy)pyridin-3-yl)-1H-pyrazol-1-yl)piperidin-1-yl)-8-oxooctyl)amino)-2-(2,6-dioxopiperidin-3-yl)isoindoline-1,3-dione |
| | 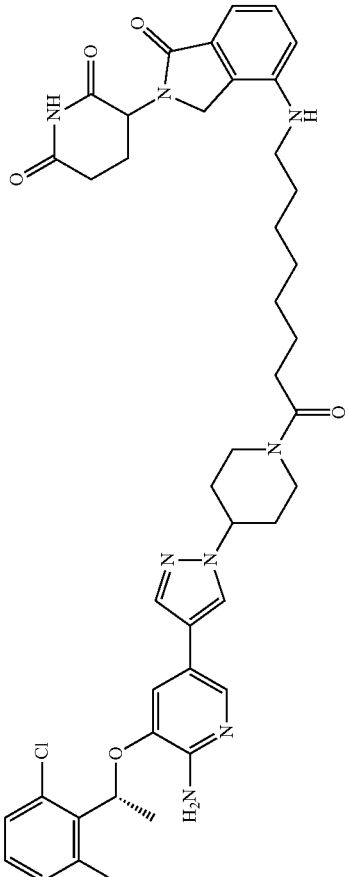 | 3-(4-(4-(8-(4-(4-(6-amino-5-((R)-1-(2,6-dichloro-3-fluorophenyl)ethoxy)pyridin-3-yl)-1H-pyrazol-1-yl)piperidin-1-yl)-8-oxooctyl)amino)-1-oxoisoindolin-2-yl)piperidine-2,6-dione |

TABLE 1-continued

Structural formulas and names of the compounds of the present disclosure

| Compound ID | Structure of the compound | Name of the compound |
|---|---|---|
| | 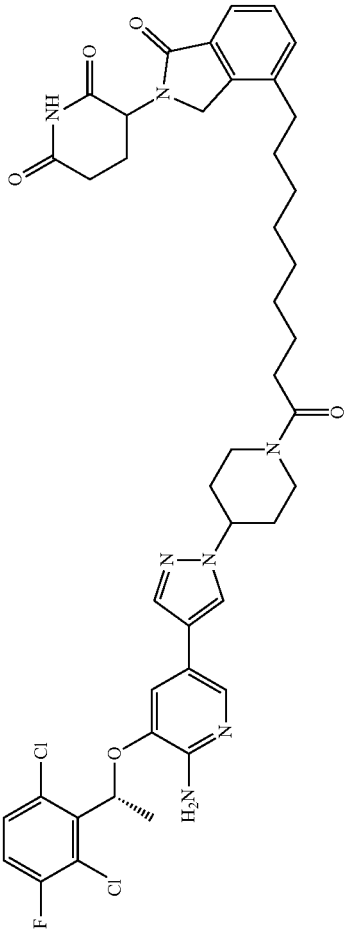 | 3-(4-(9-(4-(4-(6-amino-5-((R)-1-(2,6-dichloro-3-fluorophenyl)ethoxy)pyridin-3-yl)-1H-pyrazol-1-yl)piperidin-1-yl)-9-oxononyl)-1-oxoisoindolin-2-yl)piperidine-2,6-dione |
| | 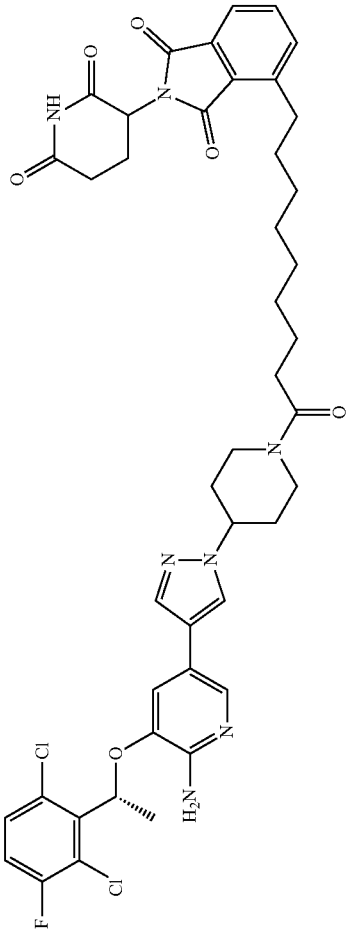 | 4-(9-(4-(4-(6-amino-5-((R)-1-(2,6-dichloro-3-fluorophenyl)ethoxy)pyridin-3-yl)-1H-pyrazol-1-yl)piperidin-1-yl)-9-oxononyl)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| | 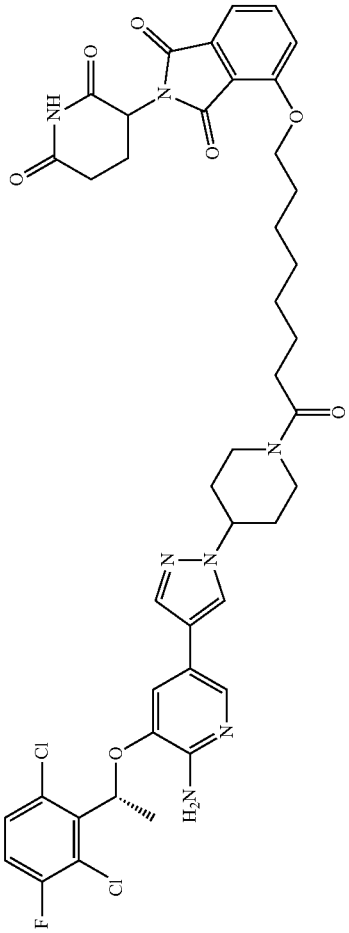 | 4-((8-(4-(4-(6-amino-5-((R)-1-(2,6-dichloro-3-fluorophenyl)ethoxy)pyridin-3-yl)-1H-pyrazol-1-yl)piperidin-1-yl)-8-oxooctyl)oxy)-2-(2,6-dioxopiperidin-3-yl)isoindoline-1,3-dione |
| | 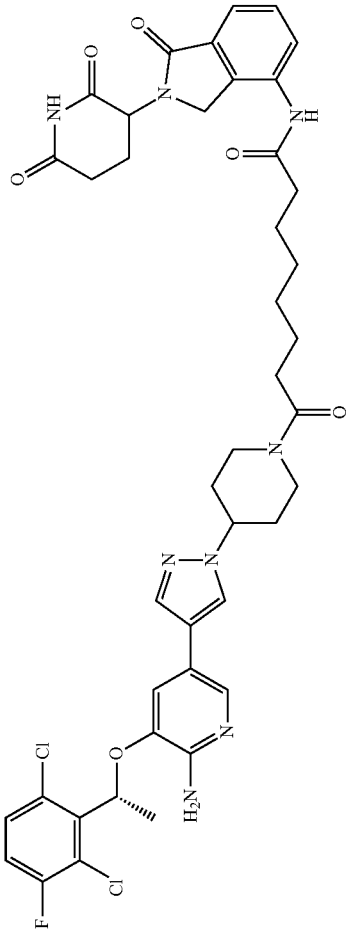 | 8-(4-(4-(6-amino-5-((R)-1-(2,6-dichloro-3-fluorophenyl)ethoxy)pyridin-3-yl)-1H-pyrazol-1-yl)piperidin-1-yl)-N-(2-(2,6-dioxopiperidin-3-yl)-1-oxoisoindolin-4-yl)-8-oxooctanamide |

TABLE 1-continued

Structural formulas and names of the compounds of the present disclosure

| Compound ID | Structure of the compound | Name of the compound |
|---|---|---|
| 301 | | 4-((8-(4-(4-(6-amino-5-((R)-1-(2,6-dichloro-3-fluorophenyl)ethoxy)pyridin-3-yl)-1H-pyrazol-1-yl)piperidin-1-yl)octyl)amino)-2-(2,6-dioxopiperidin-3-yl)isoindoline-1,3-dione |
| | | 3-(4-((8-(4-(4-(6-amino-5-((R)-1-(2,6-dichloro-3-fluorophenyl)ethoxy)pyridin-3-yl)-1H-pyrazol-1-yl)piperidin-1-yl)octyl)amino)-1-oxoisoindolin-2-yl)piperidine-2,6-dione |
| 302 | | 4-((12-(4-(4-(6-amino-5-((R)-1-(2,6-dichloro-3-fluorophenyl)ethoxy)pyridin-3-yl)-1H-pyrazol-1-yl)piperidin-1-yl)-12-oxododecyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| | 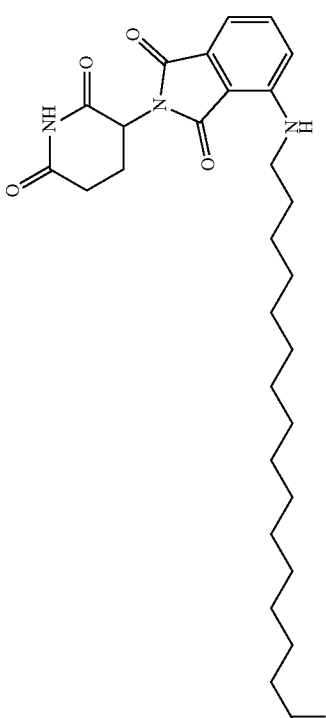 | 4-((16-(4-(4-(6-amino-5-((R)-1-(2,6-dichloro-3-fluorophenyl)ethoxy)pyridin-3-yl)-1H-pyrazol-1-yl)piperidin-1-yl)-16-oxohexadecyl)amino)-2-(2,6-dioxopiperidin-3-yl)isoindoline-1,3-dione |
| | | 8-(4-(4-(6-amino-5-((R)-1-(2,6-dichloro-3-fluorophenyl)ethoxy)pyridin-3-yl)-1H-pyrazol-1-yl)piperidin-1-yl)-N-(7-((2-(2,6-dioxopiperidin-3-yl)-1,3-dioxoisoindolin-4-yl)amino)heptyl)-8-oxooctanamide |

TABLE 1-continued

Structural formulas and names of the compounds of the present disclosure

| Compound ID | Structure of the compound | Name of the compound |
|---|---|---|
| | 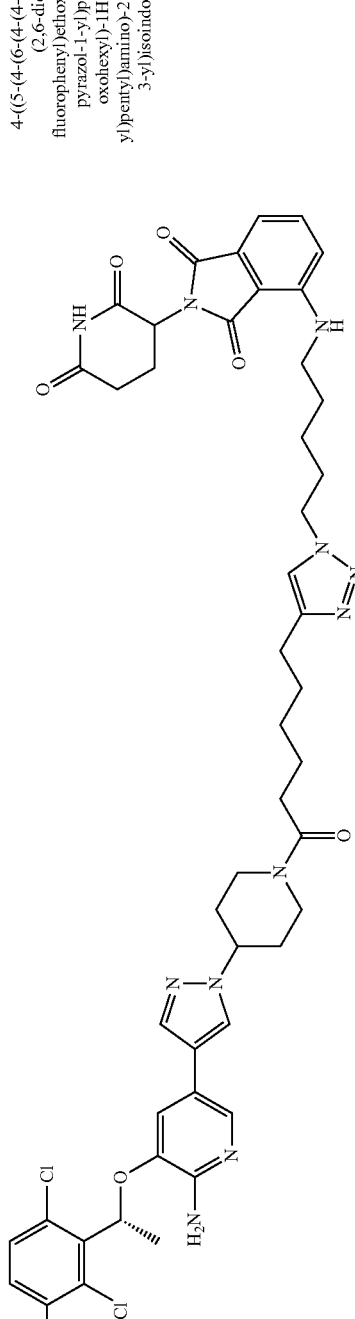 | 4-((5-(4-(6-(4-(4-(6-amino-5-((R)-1-(2,6-dichloro-3-fluorophenyl)ethoxy)pyridin-3-yl)-1H-pyrazol-1-yl)piperidin-1-yl)-6-oxohexyl)-1H-1,2,3-triazol-1-yl)pentyl)amino)-2-(2,6-dioxopiperidin-3-yl)isoindoline-1,3-dione |
| | | 4-((5-((6-(4-(4-(6-amino-5-((R)-1-(2,6-dichloro-3-fluorophenyl)ethoxy)pyridin-3-yl)-1H-pyrazol-1-yl)piperidin-1-yl)-6-oxohexyl)thio)pentyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| | 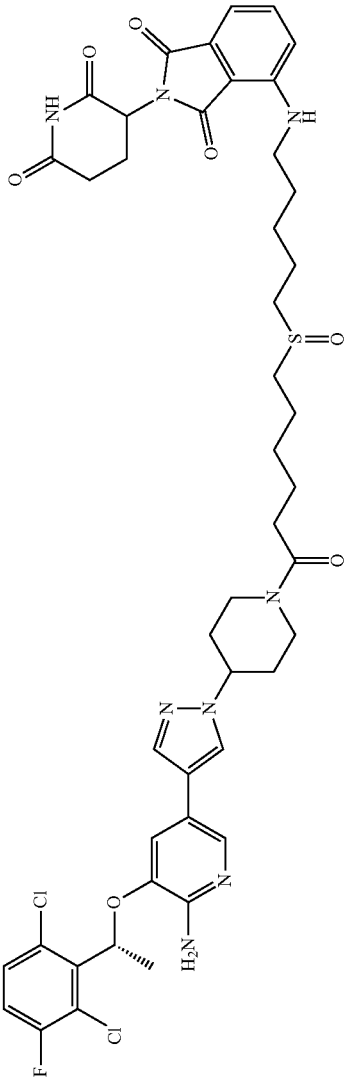 | 4-((5-((6-(4-(4-(6-amino-5-((R)-1-(2,6-dichloro-3-fluorophenyl)ethoxy)pyridin-3-yl)-1H-pyrazol-1-yl)piperidin-1-yl)-6-oxohexyl)sulfinyl)pentyl)amino)-2-(2,6-dioxopiperidin-3-yl)isoindoline-1,3-dione |
| | | 4-((5-((6-(4-(4-(6-amino-5-((R)-1-(2,6-dichloro-3-fluorophenyl)ethoxy)pyridin-3-yl)-1H-pyrazol-1-yl)piperidin-1-yl)-6-oxohexyl)sulfonyl)pentyl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| | 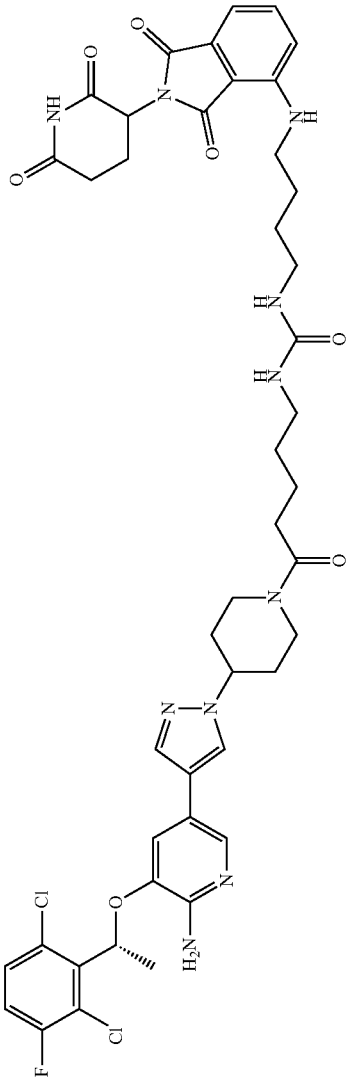 | 1-(5-(4-(4-(6-amino-5-((R)-1-(2,6-dichloro-3-fluorophenyl)ethoxy)pyridin-3-yl)-1H-pyrazol-1-yl)piperidin-1-yl)-5-oxopentyl)-3-(4-((2-(2,6-dioxopiperidin-3-yl)-1,3-dioxoisoindolin-4-yl)amino)butyl)urea |
| | | 4-(((E)-10-(4-(4-(6-amino-5-((R)-1-(2,6-dichloro-3-fluorophenyl)ethoxy)pyridin-3-yl)-1H-pyrazol-1-yl)piperidin-1-yl)-10-oxodec-4-en-1-yl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| | 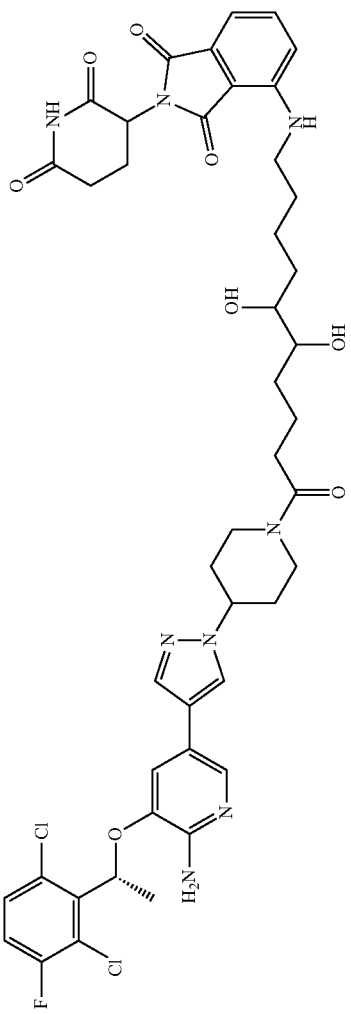 | 4-((10-(4-(4-(6-amino-5-((R)-1-(2,6-dichloro-3-fluorophenyl)ethoxy)pyridin-3-yl)-1H-pyrazol-1-yl)piperidin-1-yl)-5,6-dihydroxy-10-oxodecyl)amino)-2-(2,6-dioxopiperidin-3-yl)isoindoline-1,3-dione |
| | | 4-((7-(4-(4-(6-amino-5-((R)-1-(2,6-dichloro-3-fluorophenyl)ethoxy)pyridin-3-yl)-1H-pyrazol-1-yl)piperidin-1-yl)-7-oxohept-3-yn-1-yl)amino)-2-(2,6-dioxopiperidin-3-yl)isoindoline-1,3-dione |

TABLE 1-continued

Structural formulas and names of the compounds of the present disclosure

| Compound ID | Structure of the compound | Name of the compound |
|---|---|---|
| | 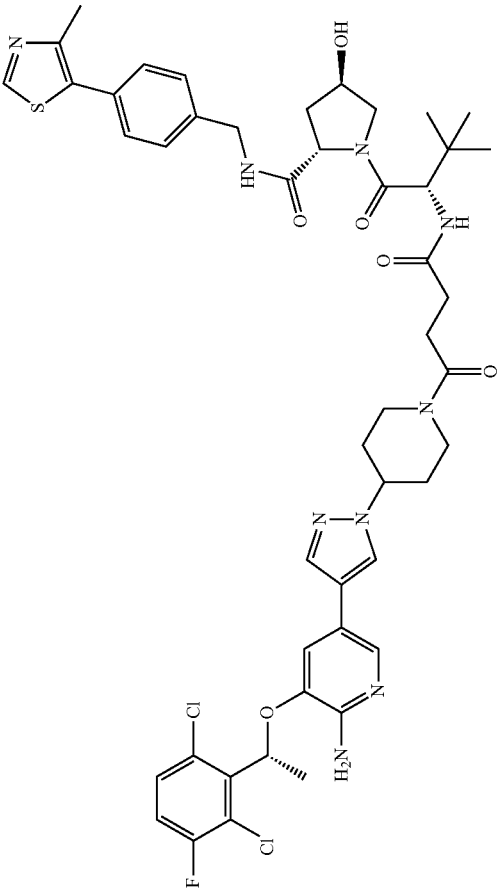 | (2S,4R)-1-((S)-2-(4-(4-(6-amino-5-((R)-1-(2,6-dichloro-3-fluorophenyl)ethoxy)pyridin-3-yl)-1H-pyrazol-1-yl)piperidin-1-yl)-4-oxobutanamido)-3,3-dimethylbutanoyl)-4-hydroxy-N-(4-(4-methylthiazol-5-yl)benzyl)pyrrolidine-2-carboxamide |
| | | (2S,4R)-1-((S)-2-(6-(4-(4-(6-amino-5-((R)-1-(2,6-dichloro-3-fluorophenyl)ethoxy)pyridin-3-yl)-1H-pyrazol-1-yl)piperidin-1-yl)-6-oxohexanamido)-3,3-dimethylbutanoyl)-4-hydroxy-N-(4-(4-methylthiazol-5-yl)benzyl)pyrrolidine-2-carboxamide |

TABLE 1-continued
Structural formulas and names of the compounds of the present disclosure
| Compound ID | Structure of the compound | Name of the compound |
|---|---|---|
| | 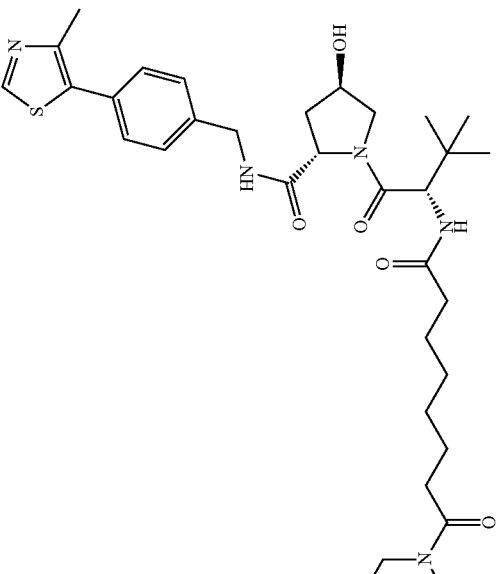 | (2S,4R)-1-((S)-2-(8-(4-(4-(6-amino-5-((R)-1-(2,6-dichloro-3-fluorophenyl)ethoxy)pyridin-3-yl)-1H-pyrazol-1-yl)piperidin-1-yl)-8-oxooctanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | 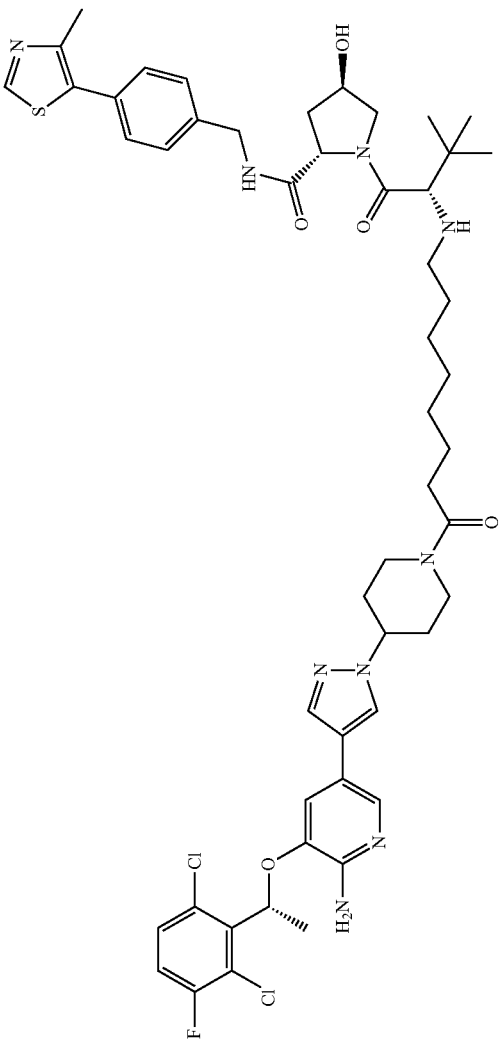 | (2S,4R)-1-((S)-2-((8-(4-(4-(6-amino-5-((R)-1-(2,6-dichloro-3-fluorophenyl)ethoxy)pyridin-3-yl)-1H-pyrazol-1-yl)piperidin-1-yl)-8-oxooctyl)amino)-3,3-dimethylbutanoyl)-4-hydroxy-N-(4-(4-methylthiazol-5-yl)benzyl)pyrrolidine-2-carboxamide |
| | 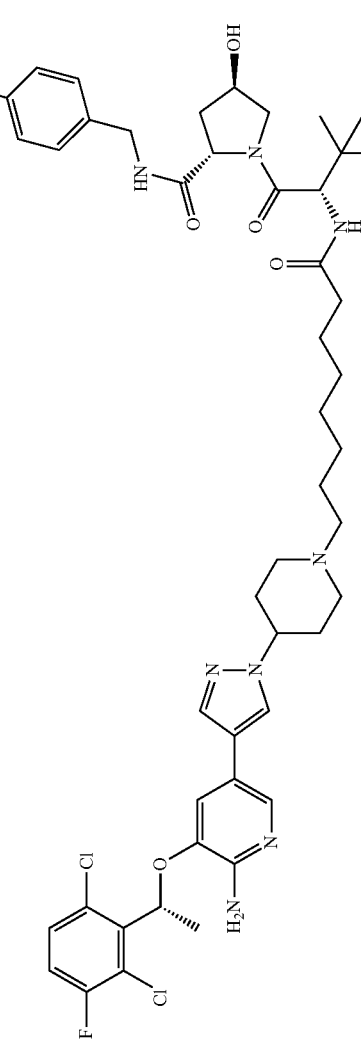 | (2S,4R)-1-((S)-2-(8-(4-(4-(6-amino-5-((R)-1-(2,6-dichloro-3-fluorophenyl)ethoxy)pyridin-3-yl)-1H-pyrazol-1-yl)piperidin-1-yl)octanamido)-3,3-dimethylbutanoyl)-4-hydroxy-N-(4-(4-methylthiazol-5-yl)benzyl)pyrrolidine-2-carboxamide |

TABLE 1-continued
Structural formulas and names of the compounds of the present disclosure
| Compound ID | Structure of the compound | Name of the compound |
|---|---|---|
| |  | (2S,4R)-1-((S)-2-((8-(4-(4-(6-amino-5-((R)-1-(2,6-dichloro-3-fluorophenyl)ethoxy)pyridin-3-yl)-1H-pyrazol-1-yl)piperidin-1-yl)octyl)amino)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | 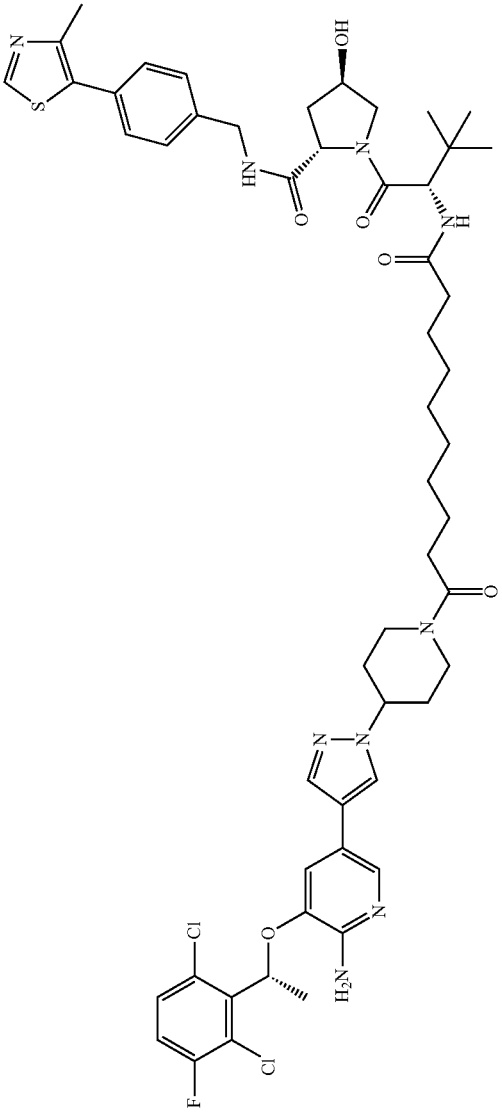 | (2S,4R)-1-((S)-2-(10-(4-(4-(6-amino-5-((R)-1-(2,6-dichloro-3-fluorophenyl)ethoxy)pyridin-3-yl)-1H-pyrazol-1-yl)piperidin-1-yl)-10-oxodecanamido)-3,3-dimethylbutanoyl)-4-hydroxy-N-(4-(4-methylthiazol-5-yl)benzyl)pyrrolidine-2-carboxamide |
| | 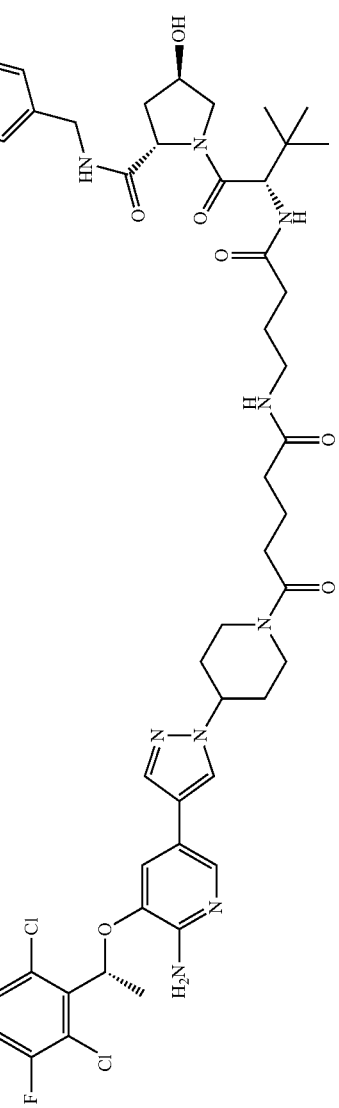 | (2S,4R)-1-((S)-2-(4-(5-(4-(4-(6-amino-5-((R)-1-(2,6-dichloro-3-fluorophenyl)ethoxy)pyridin-3-yl)-1H-pyrazol-1-yl)piperidin-1-yl)-5-oxopentanamido)butanamido)-3,3-dimethylbutanoyl)-4-hydroxy-N-(4-(4-methylthiazol-5-yl)benzyl)pyrrolidine-2-carboxamide |

TABLE 1-continued
Structural formulas and names of the compounds of the present disclosure
| Compound ID | Structure of the compound | Name of the compound |
|---|---|---|
| | 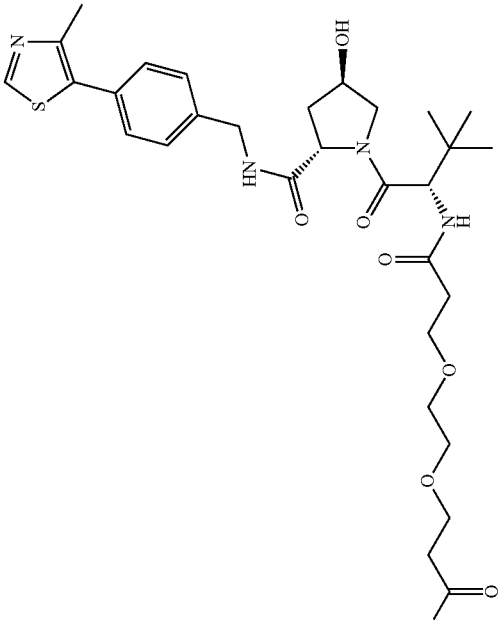 | (2S,4R)-1-((S)-2-(3-(2-(3-(4-(4-(6-amino-5-((R)-1-(2,6-dichloro-3-fluorophenyl)ethoxy)pyridin-3-yl)-1H-pyrazol-1-yl)piperidin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | | (2S,4R)-1-((S)-2-(3-(2-(3-(2-(4-(4-(6-amino-5-((R)-1-(2,6-dichloro-3-fluorophenyl)ethoxy)pyridin-3-yl)-1H-pyrazol-1-yl)piperidin-1-yl)propoxy)ethoxy)propanamido)-3,3-dimethylbutanoyl)-4-hydroxy-N-(4-(4-methylthiazol-5-yl)benzyl)pyrrolidine-2-carboxamide |
| | | (2S,4R)-1-((S)-16-(4-(4-(6-amino-5-((R)-1-(2,6-dichloro-3-fluorophenyl)ethoxy)pyridin-3-yl)-1H-pyrazol-1-yl)piperidin-1-yl)-2-(tert-butyl)-4,16-dioxo-7,10,13-trioxa-3-azahexadecanoyl)-4-hydroxy-N-(4-(4-methylthiazol-5-yl)benzyl)pyrrolidine-2-carboxamide |

TABLE 1-continued

Structural formulas and names of the compounds of the present disclosure

| Compound ID | Structure of the compound | Name of the compound |
|---|---|---|
| | 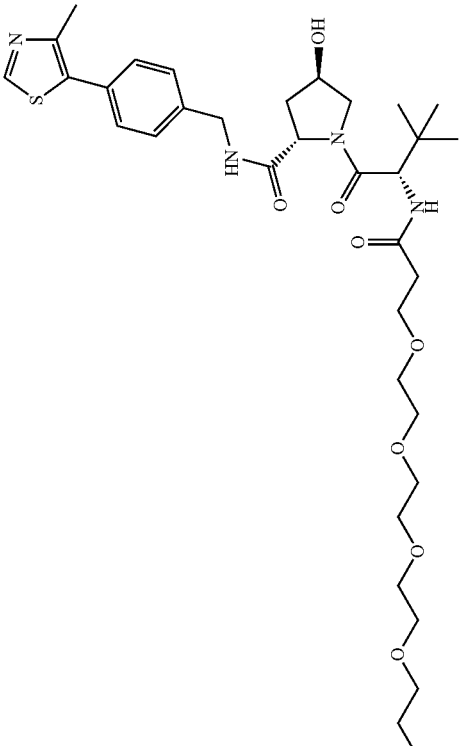 | (2S,4R)-1-((S)-19-(4-(4-(6-amino-5-((R)-1-(2,6-dichloro-3-fluorophenyl)ethoxy)pyridin-3-yl)-1H-pyrazol-1-yl)piperidin-1-yl)-2-(tert-butyl)-4,19-dioxo-7,10,13,16-tetraoxa-3-azanonadecanoyl)-4-hydroxy-N-(4-(4-methylthiazol-5-yl)benzyl)pyrrolidine-2-carboxamide |
| | 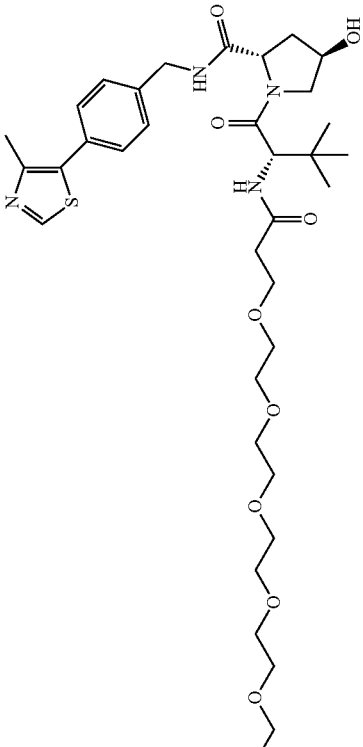 | (2S,4R)-1-((S)-22-(4-(4-(6-amino-5-((R)-1-(2,6-dichloro-3-fluorophenyl)ethoxy)pyridin-3-yl)-1H-pyrazol-1-yl)piperidin-1-yl)-2-(tert-butyl)-4,22-dioxo-7,10,13,16,19-pentaoxa-3-azanonadecanoyl)-4-hydroxy-N-(4-(4-methylthiazol-5-yl)benzyl)pyrrolidine-2-carboxamide |

TABLE 2

| Structural formulas and names of the compounds of the present disclosure | |
|---|---|
| Structure of the compound | Name of the compound |
| | 4-((2-(3-(4-(1-(4-((5-chloro-4-((2-(isopropyl-sulfonyl)phenyl)amino)-pyrimidin-2-yl)amino)-3-methoxyphenyl)-piperidin-4-yl)piperazin-1-yl)-3-oxopropoxy)-ethyl)amino)-2-(2,6-dioxopiperidin-3-yl)-isoindoline-1,3-dione |
| | 4-((2-(2-(3-(4-(1-(4-((5-chloro-4-((2-(isopropyl-sulfonyl)phenyl)amino)-pyrimidin-2-yl)amino)-3-methoxyphenyl)-piperidin-4-yl)piperazin-1-yl)-3-oxopropoxy)-ethoxy)ethyl)amino)-2-(2,6-dioxopiperidin-3-yl)isoindoline-1,3-dione |
| | 4-((2-(2-(2-(3-(4-(1-(4-((5-chloro-4-((2-(isopropylsulfonyl)-phenyl)amino)pyrimidin-2-yl)amino)-3-methoxy-phenyl)piperidin-4-yl)-piperazin-1-yl)-3-oxo-propoxy)ethoxy)-ethoxy)ethyl)amino)-2-(2,6-dioxopiperidin-3-yl)isoindoline-1,3-dione |
| | 4-((18-(4-(1-(4-((5-chloro-4-((2-(isopropyl-sulfonyl)phenyl)amino)-pyrimidin-2-yl)amino)-3-methoxyphenyl)piper-idin-4-yl)piperazin-1-yl)-18-oxo-3,6,9,12,15-pentaoxaoctadecyl)-amino)-2-(2,6-dioxo-piperidin-3-yl)isoindoline-1,3-dione |
| | 4-((2-(4-(1-(4-((5-chloro-4-((2-(isopropyl-sulfonyl)phenyl)amino)-pyrimidin-2-yl)amino)-3-methoxyphenyl)piper-idin-4-yl)piperazin-1-yl)-2-oxoethyl)amino)-2-(2,6-dioxopiperidin-3-yl)isoindoline-1,3-dione |

TABLE 2-continued

Structural formulas and names of the compounds of the present disclosure

| Structure of the compound | Name of the compound |
| --- | --- |
| | 4-((3-(4-(1-(4-((5-chloro-4-((2-(isopropyl-sulfonyl)phenyl)amino)-pyrimidin-2-yl)amino)-3-methoxyphenyl)piper-idin-4-yl)piperazin-1-yl)-3-oxopropyl)amino)-2-(2,6-dioxopiperidin-3-yl)isoindoline-1,3-dione |
| | 4-((4-(4-(1-(4-((5-chloro-4-((2-(isopropyl-sulfonyl)phenyl)amino)-pyrimidin-2-yl)amino)-3-methoxyphenyl)piper-idin-4-yl)piperazin-1-yl)-4-oxobutyl)amino)-2-(2,6-dioxopiperidin-3-yl)isoindoline-1,3-dione |
| | 4-((5-(4-(1-(4-((5-chloro-4-((2-(isopropyl-sulfonyl)phenyl)amino)-pyrimidin-2-yl)amino)-3-methoxyphenyl)piper-idin-4-yl)piperazin-1-yl)-5-oxopentyl)amino)-2-(2,6-dioxopiperidin-3-yl)isoindoline-1,3-dione |
| | 4-((6-(4-(1-(4-((5-chloro-4-((2-(isopropyl-sulfonyl)phenyl)amino)-pyrimidin-2-yl)amino)-3-methoxyphenyl)piper-idin-4-yl)piperazin-1-yl)-6-oxohexyl)amino)-2-(2,6-dioxopiperidin-3-yl)isoindoline-1,3-dione |
| | 4-((7-(4-(1-(4-((5-chloro-4-((2-(isopropyl-sulfonyl)phenyl)amino)-pyrimidin-2-yl)amino)-3-methoxyphenyl)piper-idin-4-yl)piperazin-1-yl)-7-oxoheptyl)amino)-2-(2,6-dioxopiperidin-3-yl)isoindoline-1,3-dione |

TABLE 2-continued

Structural formulas and names of the compounds of the present disclosure

| Structure of the compound | Name of the compound |
| --- | --- |
| 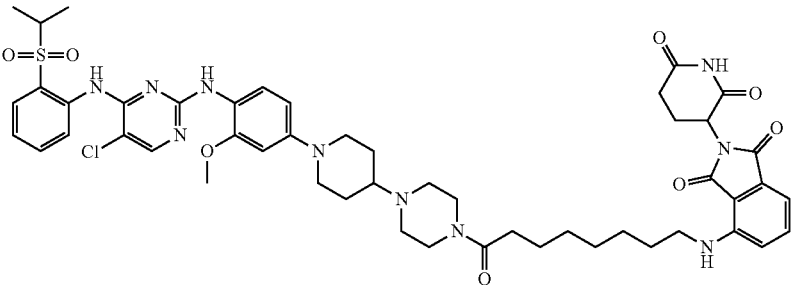 [SMILES: COc1cc(N2CCC(N3CCN(C(=O)CCCCCCCNc4cccc5c4C(=O)N(C4CCC(=O)NC4=O)C5=O)CC3)CC2)ccc1Nc1ncc(Cl)c(Nc2ccccc2S(=O)(=O)C(C)C)n1] | 4-((8-(4-(1-(4-((5-chloro-4-((2-(isopropyl-sulfonyl)phenyl)amino)-pyrimidin-2-yl)amino)-3-methoxyphenyl)piper-idin-4-yl)piperazin-1-yl)-8-oxooctyl)amino)-2-(2,6-dioxopiperidin-3-yl)isoindoline-1,3-dione |
| 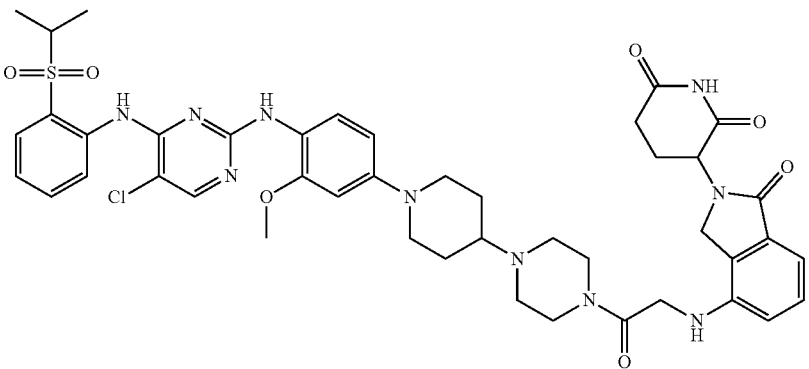 [SMILES: COc1cc(N2CCC(N3CCN(C(=O)CNc4cccc5c4CN(C4CCC(=O)NC4=O)C5=O)CC3)CC2)ccc1Nc1ncc(Cl)c(Nc2ccccc2S(=O)(=O)C(C)C)n1] | 3-(4-((2-(4-(1-(4-((5-chloro-4-((2-(isopropyl-sulfonyl)phenyl)amino)-pyrimidin-2-yl)amino)-3-methoxyphenyl)piper-idin-4-yl)piperazin-1-yl)-2-oxoethyl)amino)-1-oxoisoindolin-2-yl)-piperidine-2,6-dione |
| 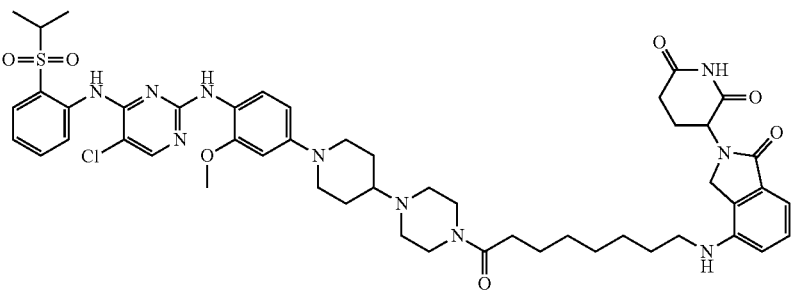 [SMILES: COc1cc(N2CCC(N3CCN(C(=O)CCCCCCCNc4cccc5c4CN(C4CCC(=O)NC4=O)C5=O)CC3)CC2)ccc1Nc1ncc(Cl)c(Nc2ccccc2S(=O)(=O)C(C)C)n1] | 3-(4-((8-(4-(2-(4-((5-chloro-4-((2-(isopropyl-sulfonyl)phenyl)amino)-pyrimidin-2-yl)amino)-3-methoxyphenyl)piper-idin-4-yl)piperazin-1-yl)-8-oxooctyl)amino)-1-oxoisoindolin-2-yl)-piperidine-2,6-dione |
| 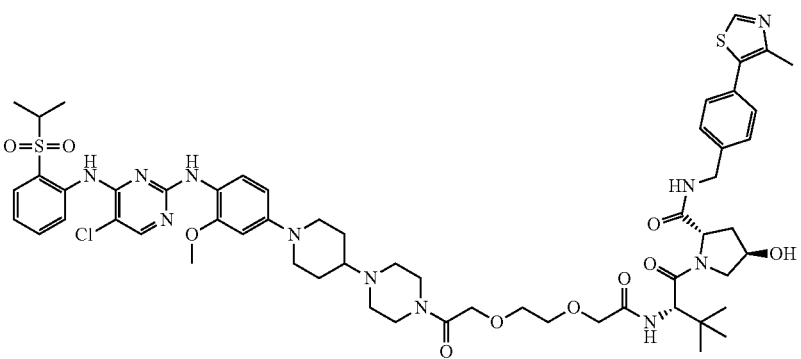 [SMILES: COc1cc(N2CCC(N3CCN(C(=O)COCCOCC(=O)N[C@H](C(=O)N4C[C@H](O)C[C@H]4C(=O)NCc4ccc(-c5scnc5C)cc4)C(C)(C)C)CC3)CC2)ccc1Nc1ncc(Cl)c(Nc2ccccc2S(=O)(=O)C(C)C)n1] | (2S,4R)-1-((S)-2-(2-(2-(2-(4-(1-(4-((5-chloro-4-((2-(isopropyl-sulfonyl)phenyl)amino)-pyrimidin-2-yl)amino)-3-methoxyphenyl)piper-idin-4-yl)piperazin-1-yl)-2-oxoethoxy)ethoxy)-acetamido)-3,3-dimethyl-butanoyl)-4-hydroxy-N-(4-(4-methylthiazol-5-yl)benzyl)pyrrolidine-2-carboxamide |

TABLE 2-continued

Structural formulas and names of the compounds of the present disclosure

| Structure of the compound | Name of the compound |
|---|---|
| | (2S,4R)-1-((S)-2-(3-(2-(3-(4-(1-(4-((5-chloro-4-((2-(isopropylsulfonyl)phenyl)amino)-pyrimidin-2-yl)amino)-3-methoxyphenyl)piperidin-4-yl)piperazin-1-yl)-3-oxopropoxy)-ethoxy)propanamido)-3,3-dimethylbutanoyl)-4-hydroxy-N-(4-(4-methylthiazol-5-yl)-benzyl)pyrrolidine-2-carboxamide |
| | (2S,4R)-1-((S)-2-(tert-butyl)-16-(4-(1-(4-((5-chloro-4-((2-(isopropylsulfonyl)phenyl)amino)-pyrimidin-2-yl)amino)-3-methoxyphenyl)piperidin-4-yl)piperazin-1-yl)-4,16-dioxo-7,10,13-trioxa-3-azahexadecanoyl)-4-hydroxy-N-(4-(4-methyl-thiazol-5-yl)benzyl)pyrrolidine-2-carboxamide |
| | (2S,4R)-1-((S)-2-(tert-butyl)-19-(4-(1-(4-((5-chloro-4-((2-(isopropylsulfonyl)phenyl)amino)-pyrimidin-2-yl)amino)-3-methoxyphenyl)piperidin-4-yl)piperazin-1-yl)-4,19-dioxo-7,10,13,16-tetraoxa-3-azanonadecanoyl)-4-hydroxy-N-(4-(4-methylthiazol-5-yl)-benzyl)pyrrolidine-2-carboxamide |
| | (2S,4R)-1-((S)-2-(tert-butyl)-22-(4-(1-(4-((5-chloro-4-((2-(isopropylsulfonyl)phenyl)amino)-pyrimidin-2-yl)amino)-3-methoxyphenyl)piperidin-4-yl)piperazin-1-yl)-4,22-dioxo-7,10,13,16,19-pentaoxa-3-azadocosanoyl)-4-hydroxy-N-(4-(4-methyl-thiazol-5-yl)benzyl)-pyrrolidine-2-carboxamide |

TABLE 2-continued

Structural formulas and names of the compounds of the present disclosure

| Structure of the compound | Name of the compound |
|---|---|
| | (2S,4R)-1-((S)-2-(4-(4-(1-(4-((5-chloro-4-((2-(isopropylsulfonyl)-phenyl)amino)pyrimidin-2-yl)amino)-3-methoxy-phenyl)piperidin-4-yl)-piperazin-1-yl)-4-oxo-butanamido)-3,3-dimethylbutanoyl)-4-hydroxy-N-(4-(4-methylthiazol-5-yl)-benzyl)pyrrolidine-2-carboxamide |
| | (2S,4R)-1-((S)-2-(5-(4-(1-(4-((5-chloro-4-((2-(isopropylsulfonyl)-phenyl)amino)pyrimidin-2-yl)amino)-3-methoxy-phenyl)piperidin-4-yl)-piperazin-1-yl)-5-oxopentanamido)-3,3-dimethylbutanoyl)-4-hydroxy-N-(4-(4-methylthiazol-5-yl)-benzyl)pyrrolidine-2-carboxamide |
| | (2S,4R)-1-((S)-2-(6-(4-(1-(4-((5-chloro-4-((2-(isopropylsulfonyl)-phenyl)amino)pyrimidin-2-yl)amino)-3-methoxy-phenyl)piperidin-4-yl)-piperazin-1-yl)-6-oxohexanamido)-3,3-dimethylbutanoyl)-4-hydroxy-N-(4-(4-methylthiazol-5-yl)-benzyl)pyrrolidine-2-carboxamide |
| | (2S,4R)-1-((S)-2-(6-(4-(1-(4-((5-chloro-4-((2-(isopropylsulfonyl)-phenyl)amino)pyrimidin-2-yl)amino)-3-methoxy-phenyl)piperidin-4-yl)piperazin-1-yl)-hexanamido)-3,3-dimethylbutanoyl)-4-hydroxy-N-(4-(4-methylthiazol-5-yl)-benzyl)pyrrolidine-2-carboxamide |

TABLE 2-continued

Structural formulas and names of the compounds of the present disclosure

| Structure of the compound | Name of the compound |
|---|---|
| | (2S,4R)-1-((S)-2-(7-(4-(1-(4-((5-chloro-4-((2-(isopropylsulfonyl)-phenyl)amino)pyrimidin-2-yl)amino)-3-methoxy-phenyl)piperidin-4-yl)-piperazin-1-yl)-7-oxoheptanamido)-3,3-dimethylbutanoyl)-4-hydroxy-N-(4-(4-methylthiazol-5-yl)-benzyl)pyrrolidine-2-carboxamide |
| | (2S,4R)-1-((S)-2-(8-(4-(1-(4-((5-chloro-4-((2-(isopropylsulfonyl)-phenyl)amino)pyrimidin-2-yl)amino)-3-methoxy-phenyl)piperidin-4-yl)-piperazin-1-yl)-8-oxooctanamido)-3,3-dimethylbutanoyl)-4-hydroxy-N-(4-(4-methylthiazol-5-yl)-benzyl)pyrrolidine-2-carboxamide |
| | (2S,4R)-1-((S)-2-(9-(4-(1-(4-((5-chloro-4-((2-(isopropylsulfonyl)-phenyl)amino)pyrimidin-2-yl)amino)-3-methoxy-phenyl)piperidin-4-yl)piperazin-1-yl)-9-oxononanamido)-3,3-dimethylbutanoyl)-4-hydroxy-N-(4-(4-methyl-thiazol-5-yl)benzyl)-pyrrolidine-2-carbox-amide |
| | (2S,4R)-1-((S)-2-(10-(4-(1-(4-((5-chloro-4-((2-(isopropylsulfonyl)-phenyl)amino)pyrimidin-2-yl)amino)-3-methoxy-phenyl)piperidin-4-yl)-piperazin-1-yl)-10-oxodecanamido)-3,3-dimethylbutanoyl)-4-hydroxy-N-(4-(4-methylthiazol-5-yl)-benzyl)pyrrolidine-2-carboxamide |

TABLE 2-continued

Structural formulas and names of the compounds of the present disclosure

| Structure of the compound | Name of the compound |
|---|---|
| | 2-(2,6-dioxopiperidin-3-yl)-4-((2-(3-(4-(1-(4-((4-((2-(isopropyl-sulfonyl)phenyl)amino)-1,3,5-triazin-2-yl)-amino)-3-methoxy-phenyl)piperidin-4-yl)-piperazin-1-yl)-3-oxopropoxy)ethyl)-amino)isoindoline-1,3-dione |
| | 2-(2,6-dioxopiperidin-3-yl)-4-((2-(2-(3-(4-(1-(4-((4-((2-(isopropyl-sulfonyl)phenyl)amino)-1,3,5-triazin-2-yl)amino)-3-methoxyphenyl)piper-idin-4-yl)piperazin-1-yl)-3-oxopropoxy)ethoxy)-ethyl)amino)isoindoline-1,3-dione |
| | 2-(2,6-dioxopiperidin-3-yl)-4-((2-(2-(2-(3-(4-(1-(4-((4-((2-(isopropyl-sulfonyl)phenyl)amino)-1,3,5-triazin-2-yl)amino)-3-methoxyphenyl)piper-idin-4-yl)piperazin-1-yl)-3-oxopropoxy)-ethoxy)ethoxy)ethyl)-amino)isoindoline-1,3-dione |
| | 2-(2,6-dioxopiperidin-3-yl)-4-((15-(4-(1-(4-((4-((2-(isopropylsulfonyl)-phenyl)amino)-1,3,5-triazin-2-yl)amino)-3-methoxyphenyl)piper-idin-4-yl)piperazin-1-yl)-15-oxo-3,6,9,12-tetraoxapentadecyl)-amino)isoindoline-1,3-dione |
| | 2-(2,6-dioxopiperidin-3-yl)-4-((18-(4-(1-(4-((4-((2-(isopropylsulfonyl)-phenyl)amino)-1,3,5-triazin-2-yl)amino)-3-methoxyphenyl)piper-idin-4-yl)piperazin-1-yl)-18-oxo-3,6,9,12,15-pentaoxaoctadecyl)-amino)isoindoline-1,3-dione |

TABLE 2-continued

Structural formulas and names of the compounds of the present disclosure

| Structure of the compound | Name of the compound |
|---|---|
|  | 2-(2,6-dioxopiperidin-3-yl)-4-((2-(4-(1-(4-((4-((2-(isopropylsulfonyl)-phenyl)amino)-1,3,5-triazin-2-yl)amino)-3-methoxyphenyl)piperidin-4-yl)piperazin-1-yl)-2-oxoethyl)amino)-isoindoline-1,3-dione |
|  | 2-(2,6-dioxopiperidin-3-yl)-4-((3-(4-(1-(4-((4-((2-(isopropylsulfonyl)-phenyl)amino)-1,3,5-triazin-2-yl)amino)-3-methoxyphenyl)piperidin-4-yl)piperazin-1-yl)-3-oxopropyl)amino)-isoindoline-1,3-dione |
|  | 2-(2,6-dioxopiperidin-3-yl)-4-((4-(4-(1-(4-((4-((2-(isopropylsulfonyl)-phenyl)amino)-1,3,5-triazin-2-yl)amino)-3-methoxyphenyl)piperidin-4-yl)piperazin-1-yl)-4-oxobutyl)amino)-isoindoline-1,3-dione |
|  | 2-(2,6-dioxopiperidin-3-yl)-4-((5-(4-(1-(4-((4-((2-(isopropylsulfonyl)-phenyl)amino)-1,3,5-triazin-2-yl)amino)-3-methoxyphenyl)piperidin-4-yl)piperazin-1-yl)-5-oxopentyl)amino)-isoindoline-1,3-dione |

TABLE 2-continued

Structural formulas and names of the compounds of the present disclosure

| Structure of the compound | Name of the compound |
|---|---|
| | 2-(2,6-dioxopiperidin-3-yl)-4-((6-(4-(1-(4-((4-((2-(isopropylsulfonyl)-phenyl)amino)-1,3,5-triazin-2-yl)amino)-3-methoxyphenyl)piperidin-4-yl)piperazin-1-yl)-6-oxohexyl)amino)-isoindoline-1,3-dione |
| | 2-(2,6-dioxopiperidin-3-yl)-4-((7-(4-(1-(4-((4-((2-(isopropylsulfonyl)-phenyl)amino)-1,3,5-triazin-2-yl)amino)-3-methoxyphenyl)piperidin-4-yl)piperazin-1-yl)-7-oxoheptyl)amino)-isoindoline-1,3-dione |
| | 2-(2,6-dioxopiperidin-3-yl)-4-((12-(4-(1-(4-((4-((2-(isopropylsulfonyl)-phenyl)amino)-1,3,5-triazin-2-yl)amino)-3-methoxyphenyl)piperidin-4-yl)piperazin-1-yl)-12-oxododecyl)-amino)isoindoline-1,3-dione |
| | 3-(4-((12-(4-(1-(4-((4-((2-(isopropylsulfonyl)-phenyl)amino)-1,3,5-triazin-2-yl)amino)-3-methoxyphenyl)piperidin-4-yl)piperazin-1-yl)-12-oxododecyl)-amino)-1-oxoisoindolin-2-yl)piperidine-2,6-dione |
| | N-(2-(2,6-dioxopiperidin-3-yl)-1-oxoisoindolin-4-yl)-12-(4-(1-(4-((4-((2-(isopropylsulfonyl)-phenyl)amino)-1,3,5-triazin-2-yl)amino)-3-methoxyphenyl)piperidin-4-yl)piperazin-1-yl)-12-oxododecanamide |

TABLE 2-continued

Structural formulas and names of the compounds of the present disclosure

| Structure of the compound | Name of the compound |
| --- | --- |
| | 3-(4-((2-(4-(1-(4-((4-((2-(isopropylsulfonyl)-phenyl)amino)-1,3,5-triazin-2-yl)amino)-3-methoxyphenyl)piperidin-4-yl)piperazin-1-yl)-2-oxoethyl)amino)-1-oxoisoindolin-2-yl)-piperidine-2,6-dione |
| | (2S,4R)-4-hydroxy-1-((S)-2-(2-(2-(2-(4-(1-(4-((4-((2-(isopropyl-sulfonyl)phenyl)-amino)-1,3,5-triazin-2-yl)amino)-3-methoxy-phenyl)piperidin-4-yl)piperazin-1-yl)-2-oxoethoxy)ethoxy)-acetamido)-3,3-dimethylbutanoyl)-N-(4-(4-methylthiazol-5-yl)benzyl)pyrrolidine-2-carboxamide |
| | (2S,4R)-4-hydroxy-1-((S)-2-(3-(2-(3-(4-(1-(4-((4-((2-(isopropyl-sulfonyl)phenyl)-amino)-1,3,5-triazin-2-yl)amino)-3-methoxy-phenyl)piperidin-4-yl)-piperazin-1-yl)-3-oxopropoxy)ethoxy)-propanamido)-3,3-dimethylbutanoyl)-N-(4-(4-methylthiazol-5-yl)benzyl)pyrrolidine-2-carboxamide |
| | (2S,4R)-1-((S)-2-(tert-butyl)-16-(4-(1-(4-((4-((2-(isopropylsulfonyl)-phenyl)amino)-1,3,5-triazin-2-yl)amino)-3-methoxyphenyl)piperidin-4-yl)piperazin-1-yl)-4,16-dioxo-7,10,13-trioxa-3-azahexadeca-noyl)-4-hydroxy-N-(4-(4-methylthiazol-5-yl)-benzyl)pyrrolidine-2-carboxamide |

TABLE 2-continued

Structural formulas and names of the compounds of the present disclosure

| Structure of the compound | Name of the compound |
|---|---|
| | (2S,4R)-1-((S)-2-(tert-butyl)-16-(4-(1-(4-((4-((2-(isopropylsulfonyl)-phenyl)amino)-1,3,5-triazin-2-yl)amino)-3-methoxyphenyl)piperidin-4-yl)piperazin-1-yl)-4-oxo-7,10,13-trioxa-3-azahexadecanoyl)-4-hydroxy-N-(4-(4-methylthiazol-5-yl)benzyl)pyrrolidine-2-carboxamide |
| | (2S,4R)-1-((S)-2-(tert-butyl)-19-(4-(1-(4-((4-((2-(isopropylsulfonyl)-phenyl)amino)-1,3,5-triazin-2-yl)amino)-3-methoxyphenyl)piperidin-4-yl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide |
| | (2S,4R)-1-((S)-2-(tert-butyl)-22-(4-(1-(4-((4-((2-(isopropylsulfonyl)-phenyl)amino)-1,3,5-triazin-2-yl)amino)-5-methoxy-2-methyl-phenyl)piperidin-4-yl)-piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide |
| | (2S,4R)-4-hydroxy-1-((S)-2-(4-(4-(1-(4-((4-((2-(isopropylsulfonyl)-phenyl)amino)-1,3,5-triazin-2-yl)amino)-3-methoxyphenyl)piperidin-4-yl)piperazin-1-yl)-4-oxobutanamido)-3,3-dimethylbutanoyl)-N-(4-(4-methylthiazol-5-yl)benzyl)pyrrolidine-2-carboxamide |

TABLE 2-continued

Structural formulas and names of the compounds of the present disclosure

| Structure of the compound | Name of the compound |
|---|---|
| | (2S,4R)-4-hydroxy-1-((S)-2-(5-(4-(1-(4-((4-((2-(isopropylsulfonyl)-phenyl)amino)-1,3,5-triazin-2-yl)amino)-5-methoxy-2-methyl-phenyl)piperidin-4-yl)-piperazin-1-yl)-5-oxopentanamido)-3,3-dimethylbutanoyl)-N-(4-(4-methylthiazol-5-yl)benzyl)pyrrolidine-2-carboxamide |
| | (2S,4R)-4-hydroxy-1-((S)-2-(6-(4-(1-(5-isopropoxy-4-((4-((2-(isopropylsulfonyl)-phenyl)amino)-1,3,5-triazin-2-yl)amino)-2-methylphenyl)piperidin-4-yl)piperazin-1-yl)-6-oxohexanamido)-3,3-dimethylbutanoyl)-N-(4-(4-methylthiazol-5-yl)benzyl)pyrrolidine-2-carboxamide |
| | (2S,4R)-4-hydroxy-1-((S)-2-(7-(4-(1-(4-((4-((2-(isopropylsulfonyl)-phenyl)amino)-1,3,5-triazin-2-yl)amino)-3-methoxyphenyl)piper-idin-4-yl)piperazin-1-yl)-7-oxoheptanamido)-3,3-dimethylbutanoyl)-N-(4-(4-methylthiazol-5-yl)benzyl)pyrrolidine-2-carboxamide |
| | (2S,4R)-4-hydroxy-1-((S)-2-(8-(4-(1-(4-((4-((2-(isopropylsulfonyl)-phenyl)amino)-1,3,5-triazin-2-yl)amino)-5-methoxy-2-methyl-phenyl)-piperidin-4-yl)piperazin-1-yl)-8-oxooctanamido)-3,3-dimethylbutanoyl)-N-(4-(4-methylthiazol-5-yl)benzyl)pyrrolidine-2-carboxamide |

TABLE 2-continued

Structural formulas and names of the compounds of the present disclosure

| Structure of the compound | Name of the compound |
|---|---|
| | (2S,4R)-4-hydroxy-1-((S)-2-(9-(4-(1-(5-isopropoxy-4-((4-((2-(isopropylsulfonyl)-phenyl)amino)-1,3,5-triazin-2-yl)amino)-2-methylphenyl)piperidin-4-yl)piperazin-1-yl)-9-oxononanamido)-3,3-dimethylbutanoyl)-N-(4-(4-methylthiazol-5-yl)benzyl)pyrrolidine-2-carboxamide |
| | (2S,4R)-4-hydroxy-1-((S)-2-(10-(4-(1-(5-isopropoxy-4-((4-((2-(isopropylsulfonyl)-phenyl)amino)-1,3,5-triazin-2-yl)amino)-2-methylphenyl)piperidin-4-yl)piperazin-1-yl)-10-oxodecanamido)-3,3-dimethylbutanoyl)-N-(4-(4-methylthiazol-5-yl)benzyl)pyrrolidine-2-carboxamide |
| | (2S,4R)-4-hydroxy-1-((S)-2-(13-(4-(1-(5-isopropoxy-4-((4-((2-(isopropylsulfonyl)-phenyl)amino)-1,3,5-triazin-2-yl)amino)-2-methylphenyl)piperidin-4-yl)piperazin-1-yl)-13-oxotridecanamido)-3,3-dimethylbutanoyl)-N-(4-(4-methylthiazol-5-yl)benzyl)pyrrolidine-2-carboxamide |
| | 2-((2-((1-(N-(3-(2-((2-(2,6-dioxopiperidin-3-yl)-1,3-dioxoisoindolin-4-yl)amino)ethoxy)-propanoyl)-N-methyl-glycyl)-5-methoxy-indolin-6-yl)amino)-7H-pyrrolo[2,3-d]pyrimidin-4-yl)amino)-6-fluoro-N-methylbenzamide |

TABLE 2-continued

Structural formulas and names of the compounds of the present disclosure

| Structure of the compound | Name of the compound |
|---|---|
|  | 2-((2-((1-(N-(3-(2-(2-((2-(2,6-dioxopiperidin-3-yl)-1,3-dioxoisoindolin-4-yl)amino)ethoxy)-ethoxy)propanoyl)-N-methylglycyl)-5-methoxy-indolin-6-yl)amino)-7H-pyrrolo[2,3-d]pyrimidin-4-yl)amino)-6-fluoro-N-methylbenzamide |
|  | 2-((2-((1-(1-((2-(2,6-dioxopiperidin-3-yl)-1,3-dioxoisoindolin-4-yl)-amino)-13-methyl-12-oxo-3,6,9-trioxa-13-azapentadecan-15-oyl)-5-methoxyindolin-6-yl)-amino)-7H-pyrrolo[2,3-d]pyrimidin-4-yl)amino)-6-fluoro-N-methyl-benzamide |
|  | 1-((2-(2,6-dioxopiper-idin-3-yl)-1,3-dioxoiso-indolin-4-yl)amino)-N-(2-(6-((4-((3-fluoro-2-(methylcarbamoyl)-phenyl)amino)-7H-pyrrolo[2,3-d]pyrimidin-2-yl)amino)-5-methoxy-indolin-1-yl)-2-oxoethyl)-N-methyl-3,6,9,12-tetra-oxapentadecan-15-amide |
|  | 1-((2-(2,6-dioxopiper-idin-3-yl)-1,3-dioxoiso-indolin-4-yl)amino)-N-(2-(6-((4-((3-fluoro-2-(methylcarbamoyl)-phenyl)amino)-7H-pyrrolo[2,3-d]pyrimidin-2-yl)amino)-5-methoxy-indolin-1-yl)-2-oxoethyl)-N-methyl-3,6,9,12,15-pentaoxaoctadecan-18-amide |

TABLE 2-continued

Structural formulas and names of the compounds of the present disclosure

| Structure of the compound | Name of the compound |
| --- | --- |
|  | 2-((2-((1-(N-((2-(2,6-dioxopiperidin-3-yl)-1,3-dioxoisoindolin-4-yl)-glycyl)-N-methylglycyl)-5-methoxyindolin-6-yl)amino)-7H-pyrrolo-[2,3-d]pyrimidin-4-yl)-amino)-6-fluoro-N-methylbenzamide |
|  | 2-((2-((1-(N-(3-((2-(2,6-dioxopiperidin-3-yl)-1,3-dioxoisoindolin-4-yl)amino)propanoyl)-N-methylglycyl)-5-methoxy-indolin-6-yl)amino)-7H-pyrrolo[2,3-d]pyrimidin-4-yl)amino)-6-fluoro-N-methylbenzamide |
|  | 2-((2-((1-(N-(4-((2-(2,6-dioxopiperidin-3-yl)-1,3-dioxoisoindolin-4-yl)amino)butanoyl)-N-methylglycyl)-5-methoxy-indolin-6-yl)amino)-7H-pyrrolo[2,3-d]pyrimidin-4-yl)amino)-6-fluoro-N-methylbenzamide |

TABLE 2-continued

Structural formulas and names of the compounds of the present disclosure

| Structure of the compound | Name of the compound |
| --- | --- |
|  | 2-((2-((1-(N-(5-((2-(2,6-dioxopiperidin-3-yl)-1,3-dioxoisoindolin-4-yl)amino)pentanoyl)-N-methylglycyl)-5-methoxy-indolin-6-yl)amino)-7H-pyrrolo[2,3-d]pyrimidin-4-yl)amino)-6-fluoro-N-methylbenzamide |
|  | 2-((2-((1-(N-(6-((2-(2,6-dioxopiperidin-3-yl)-1,3-dioxoisoindolin-4-yl)amino)hexanoyl)-N-methylglycyl)-5-methoxy-indolin-6-yl)amino)-7H-pyrrolo[2,3-d]pyrimidin-4-yl)amino)-6-fluoro-N-methylbenzamide |
|  | 2-((2-((1-(N-(7-((2-(2,6-dioxopiperidin-3-yl)-1,3-dioxoisoindolin-4-yl)amino)heptanoyl)-N-methylglycyl)-5-methoxy-indolin-6-yl)amino)-7H-pyrrolo[2,3-d]pyrimidin-4-yl)amino)-6-fluoro-N-methylbenzamide |

TABLE 2-continued

Structural formulas and names of the compounds of the present disclosure

| Structure of the compound | Name of the compound |
|---|---|
| 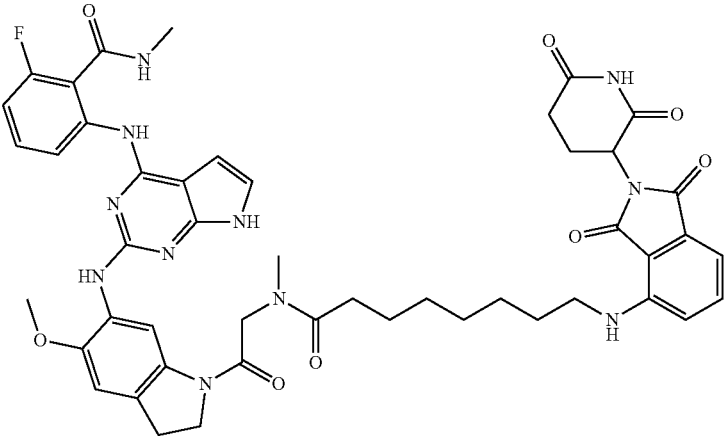 [SMILES: CNC(=O)c1c(F)cccc1Nc1nc(Nc2cc3c(cc2OC)CCN3C(=O)CN(C)C(=O)CCCCCCCNc2cccc3c2C(=O)N(C2CCC(=O)NC2=O)C3=O)nc2[nH]ccc12] | 2-((2-((1-(N-(8-((2-(2,6-dioxopiperidin-3-yl)-1,3-dioxoisoindolin-4-yl)amino)octanoyl)-N-methylglycyl)-5-methoxy-indolin-6-yl)amino)-7H-pyrrolo[2,3-d]pyrimidin-4-yl)amino)-6-fluoro-N-methylbenzamide |
| 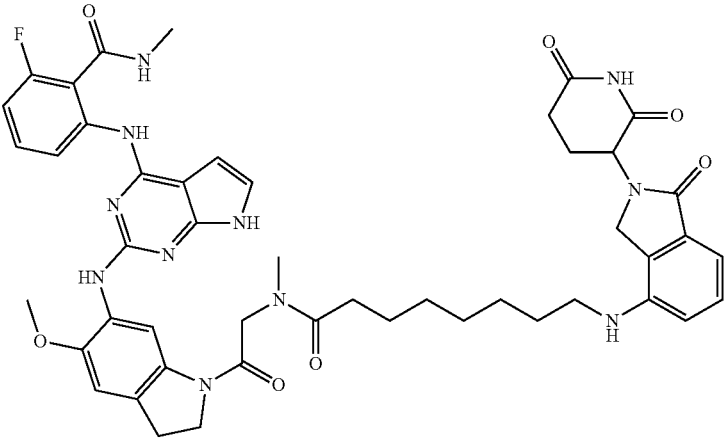 [SMILES: CNC(=O)c1c(F)cccc1Nc1nc(Nc2cc3c(cc2OC)CCN3C(=O)CN(C)C(=O)CCCCCCCNc2cccc3c2CN(C2CCC(=O)NC2=O)C3=O)nc2[nH]ccc12] | 2-((2-((1-(N-(8-((2-(2,6-dioxopiperidin-3-yl)-1-oxoisoindolin-4-yl)-amino)octanoyl)-N-methylglycyl)-5-methoxy-indolin-6-yl)amino)-7H-pyrrolo[2,3-d]pyrimidin-4-yl)amino)-6-fluoro-N-methylbenzamide |
| 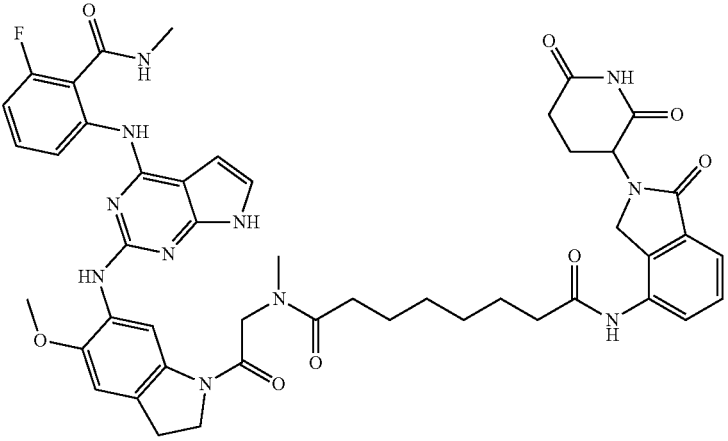 [SMILES: CNC(=O)c1c(F)cccc1Nc1nc(Nc2cc3c(cc2OC)CCN3C(=O)CN(C)C(=O)CCCCCCC(=O)Nc2cccc3c2CN(C2CCC(=O)NC2=O)C3=O)nc2[nH]ccc12] | N1-(2-(2,6-dioxopiperidin-3-yl)-1-oxoisoindolin-4-yl)-N8-(2-(6-((4-((3-fluoro-2-(methylcarbamoyl)phenyl)amino)-7H-pyrrolo[2,3-d]pyrimidin-2-yl)amino)-5-methoxyindolin-1-yl)-2-oxoethyl)-N8-methyloctanediamide |

TABLE 2-continued

Structural formulas and names of the compounds of the present disclosure

| Structure of the compound | Name of the compound |
|---|---|
|  | (2S,4R)-1-((S)-2-(tert-butyl)-14-(6-((4-((3-fluoro-2-(methylcarbamoyl)phenyl)amino)-7H-pyrrolo[2,3-d]pyrimidin-2-yl)amino)-5-methoxyindolin-1-yl)-12-methyl-4,11,14-trioxo-6,9-dioxa-3,12-diazatetradecanoyl)-4-hydroxy-N-(4-(4-methylthiazol-5-yl)benzyl)-pyrrolidine-2-carboxamide |
|  | (2S,4R)-1-((S)-2-(tert-butyl)-16-(6-((4-((3-fluoro-2-(methylcarbamoyl)phenyl)amino)-7H-pyrrolo[2,3-d]pyrimidin-2-yl)amino)-5-methoxyindolin-1-yl)-14-methyl-4,13,16-trioxo-7,10-dioxa-3,14-diazahexadecanoyl)-4-hydroxy-N-(4-(4-methylthiazol-5-yl)benzyl)pyrrolidine-2-carboxamide |
|  | (2S,4R)-1-((S)-2-(tert-butyl)-19-(6-((4-((3-fluoro-2-(methylcarbamoyl)phenyl)amino)-7H-pyrrolo-[2,3-d]pyrimidin-2-yl)amino)-5-methoxyindolin-1-yl)-17-methyl-4,16,19-trioxo-7,10,13-trioxa-3,17-diazanonadecanoyl)-4-hydroxy-N-(4-(4-methyl-thiazol-5-yl)phenyl)pyrrolidine-2-carboxamide |

TABLE 2-continued

Structural formulas and names of the compounds of the present disclosure

| Structure of the compound | Name of the compound |
|---|---|
| | N1-(2-(6-((4-((3-fluoro-2-(methylcarbamoyl)-phenyl)amino)-7H-pyrrolo[2,3-d]pyrimidin-2-yl)amino)-5-methoxy-indolin-1-yl)-2-oxoethyl)-N16-((S)-1-((2S,4R)-4-hydroxy-2-((4-(4-methyl-thiazol-5-yl)benzyl)-carbamoyl)pyrrolidin-1-yl)-3,3-dimethyl-1-oxobutan-2-yl)-N1-methyl-4,7,10,13-tetra-oxahexadecanediamide |
| | N1-(2-(6-((4-((3-fluoro-2-(methylcarbamoyl)-phenyl)amino)-7H-pyrrolo[2,3-d]pyrimidin-2-yl)amino)-5-methoxy-indolin-1-yl)-2-oxoethyl)-N19-((S)-1-((2S,4R)-4-hydroxy-2-((4-(4-methyl-thiazol-5-yl)benzyl)-carbamoyl)pyrrolidin-1-yl)-3,3-dimethyl-1-oxobutan-2-yl)-N1-methyl-4,7,10,13,16-pentaoxanonadecane-diamide |
| | N1-(2-(6-((4-((3-fluoro-2-(methylcarbamoyl)-phenyl)amino)-7H-pyrrolo[2,3-d]pyrimidin-2-yl)amino)-5-methoxy-indolin-1-yl)-2-oxoethyl)-N4-((S)-1-((2S,4R)-4-hydroxy-2-((4-(4-methyl-thiazol-5-yl)benzyl)-carbamoyl)pyrrolidin-1-yl)-3,3-dimethyl-1-oxobutan-2-yl)-N1-methylsuccinamide |

TABLE 2-continued

Structural formulas and names of the compounds of the present disclosure

| Structure of the compound | Name of the compound |
|---|---|
| | N1-(2-(6-((4-((3-fluoro-2-(methylcarbamoyl)-phenyl)amino)-7H-pyrrolo[2,3-d]pyrimidin-2-yl)amino)-5-methoxy-indolin-1-yl)-2-oxoethyl)-N5-((S)-1-((2S,4R)-4-hydroxy-2-((4-(4-methyl-thiazol-5-yl)benzyl)-carbamoyl)pyrrolidin-1-yl)-3,3-dimethyl-1-oxobutan-2-yl)-N1-methylglutaramide |
| | N1-(2-(6-((4-((3-fluoro-2-(methylcarbamoyl)-phenyl)amino)-7H-pyrrolo[2,3-d]pyrimidin-2-yl)amino)-5-methoxy-indolin-1-yl)-2-oxoethyl)-N6-((S)-1-((2S,4R)-4-hydroxy-2-((4-(4-methyl-thiazol-5-yl)benzyl)-carbamoyl)pyrrolidin-1-yl)-3,3-dimethyl-1-oxobutan-2-yl)-N1-methyladipamide |
| | N1-(2-(6-((4-((3-fluoro-2-(methylcarbamoyl)-phenyl)amino)-7H-pyrrolo[2,3-d]pyrimidin-2-yl)amino)-5-methoxy-indolin-1-yl)-2-oxoethyl)-N7-((S)-1-((2S,4R)-4-hydroxy-2-((4-(4-methyl-thiazol-5-yl)benzyl)-carbamoyl)pyrrolidin-1-yl)-3,3-dimethyl-1-oxobutan-2-yl)-N1-methylheptanediamide |

TABLE 2-continued

Structural formulas and names of the compounds of the present disclosure

| Structure of the compound | Name of the compound |
|---|---|
| | N1-(2-(6-((4-((3-fluoro-2-(methylcarbamoyl)-phenyl)amino)-7H-pyrrolo[2,3-d]pyrimidin-2-yl)amino)-5-methoxy-indolin-1-yl)-2-oxoethyl)-N8-((S)-1-((2S,4R)-4-hydroxy-2-((4-(4-methyl-thiazol-5-yl)benzyl)-carbamoyl)pyrrolidin-1-yl)-3,3-dimethyl-1-oxobutan-2-yl)-N1-methyloctanediamide |
| | N1-(2-(6-((4-((3-fluoro-2-(methylcarbamoyl)-phenyl)amino)-7H-pyrrolo[2,3-d]pyrimidin-2-yl)amino)-5-methoxy-indolin-1-yl)-2-oxoethyl)-N9-((S)-1-((2S,4R)-4-hydroxy-2-((4-(4-methyl-thiazol-5-yl)benzyl)-carbamoyl)pyrrolidin-1-yl)-3,3-dimethyl-1-oxobutan-2-yl)-N1-methylnonanediamide |
| | N1-(2-(6-((4-((3-fluoro-2-(methylcarbamoyl)-phenyl)amino)-7H-pyrrolo[2,3-d]pyrimidin-2-yl)amino)-5-methoxy-indolin-1-yl)-2-oxoethyl)-N10-((S)-1-((2S,4R)-4-hydroxy-2-((4-(4-methyl-thiazol-5-yl)benzyl)-carbamoyl)pyrrolidin-1-yl)-3,3-dimethyl-1-oxobutan-2-yl)-N1-methyldecanediamide |

TABLE 2-continued

Structural formulas and names of the compounds of the present disclosure

| Structure of the compound | Name of the compound |
|---|---|
| 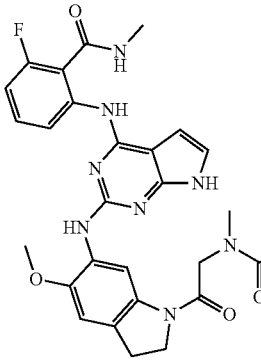 | N1-(2-(6-((4-((3-fluoro-2-(methylcarbamoyl)-phenyl)amino)-7H-pyrrolo[2,3-d]pyrimidin-2-yl)amino)-5-methoxy-indolin-1-yl)-2-oxoethyl)-N13-((S)-1-((2S,4R)-4-hydroxy-2-((4-(4-methyl-thiazol-5-yl)benzyl)-carbamoyl)pyrrolidin-1-yl)-3,3-dimethyl-1-oxobutan-2-yl)-N1-methyltridecanediamide |
| 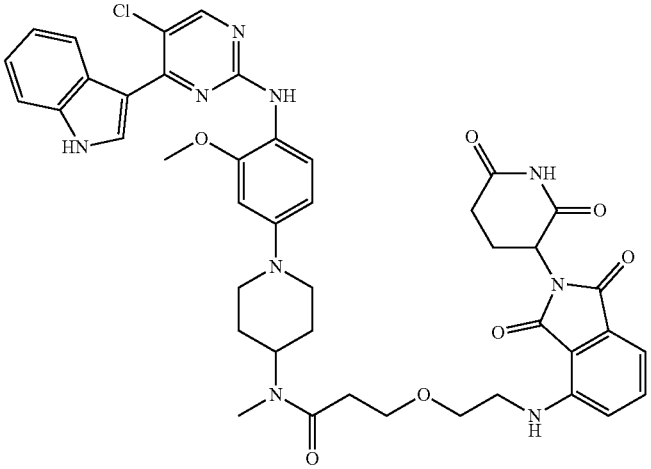 [SMILES: COc1cc(N2CCC(N(C)C(=O)CCOCCNc3cccc4c3C(=O)N(C3CCC(=O)NC3=O)C4=O)CC2)ccc1Nc1ncc(Cl)c(-c2c[nH]c3ccccc23)n1] | N-(1-(4-((5-chloro-4-(1H-indol-3-yl)pyrimidin-2-yl)amino)-3-methoxy-phenyl)piperidin-4-yl)-3-(2-((2-(2,6-dioxo-piperidin-3-yl)-1,3-dioxoisoindolin-4-yl)-amino)ethoxy)-N-methylpropanamide |
| 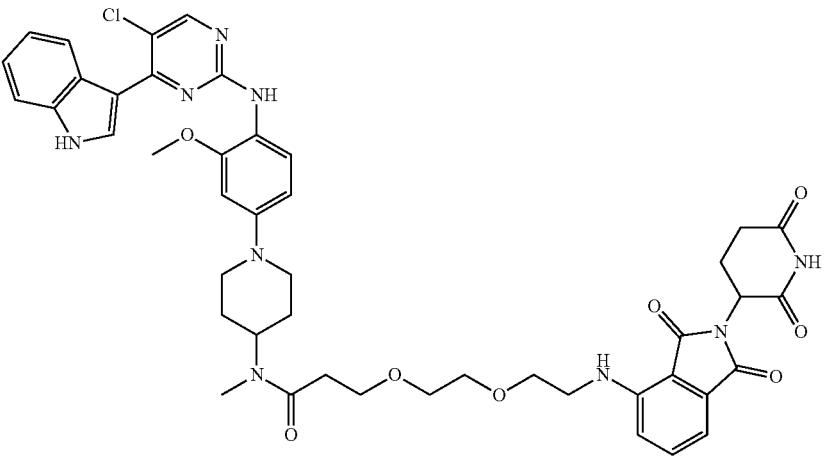 [SMILES: COc1cc(N2CCC(N(C)C(=O)CCOCCOCCNc3cccc4c3C(=O)N(C3CCC(=O)NC3=O)C4=O)CC2)ccc1Nc1ncc(Cl)c(-c2c[nH]c3ccccc23)n1] | N-(1-(4-((5-chloro-4-(1H-indol-3-yl)pyrimidin-2-yl)amino)-3-methoxy-phenyl)piperidin-4-yl)-3-(2-(2-((2-(2,6-dioxo-piperidin-3-yl)-1,3-dioxoisoindolin-4-yl)-amino)ethoxy)ethoxy)-N-methylpropanamide |

TABLE 2-continued

Structural formulas and names of the compounds of the present disclosure

| Structure of the compound | Name of the compound |
|---|---|
| 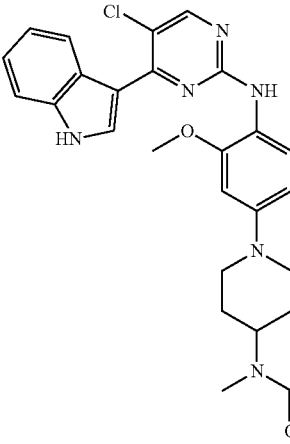 | N-(1-(4-((5-chloro-4-(1H-indol-3-yl)pyrimidin-2-yl)amino)-3-methoxy-phenyl)piperidin-4-yl)-3-(2-(2-(2-((2-(2,6-dioxopiperidin-3-yl)-1,3-dioxoisoindolin-4-yl)amino)ethoxy)-ethoxy)ethoxy)-N-methylpropanamide |
| 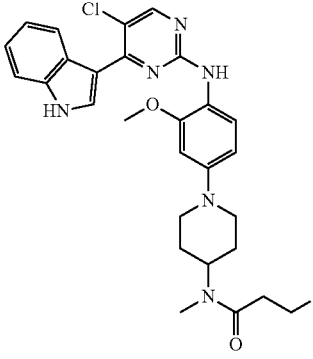 | N-(1-(4-((5-chloro-4-(1H-indol-3-yl)pyrimidin-2-yl)amino)-3-methoxy-phenyl)piperidin-4-yl)-1-((2-(2,6-dioxopiperidin-3-yl)-1,3-dioxoisoindolin-4-yl)amino)-N-methyl-3,6,9,12-tetraoxapenta-decan-5-amide |
| 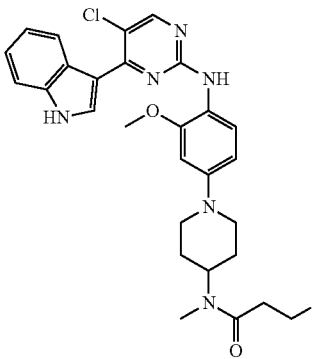 | N-(1-(4-((5-chloro-4-(1H-indol-3-yl)pyrimidin-2-yl)amino)-3-methoxy-phenyl)piperidin-4-yl)-1-((2-(2,6-dioxopiperidin-3-yl)-1,3-dioxoisoindolin-4-yl)amino)-N-methyl-3,6,9,12,15-pentaoxa-octadecan-18-amide |

TABLE 2-continued

Structural formulas and names of the compounds of the present disclosure

| Structure of the compound | Name of the compound |
|---|---|
| 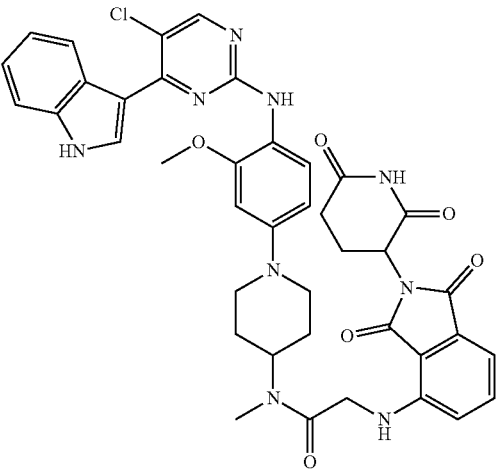 [SMILES: COc1cc(N2CCC(N(C)C(=O)CNc3cccc4c3C(=O)N(C3CCC(=O)NC3=O)C4=O)CC2)ccc1Nc1ncc(Cl)c(-c2c[nH]c3ccccc23)n1] | N-(1-(4-((5-chloro-4-(1H-indol-3-yl)pyrimidin-2-yl)amino)-3-methoxy-phenyl)piperidin-4-yl)-2-((2-(2,6-dioxopiperidin-3-yl)-1,3-dioxoisoindolin-4-yl)amino)-N-methyl-acetamide |
| 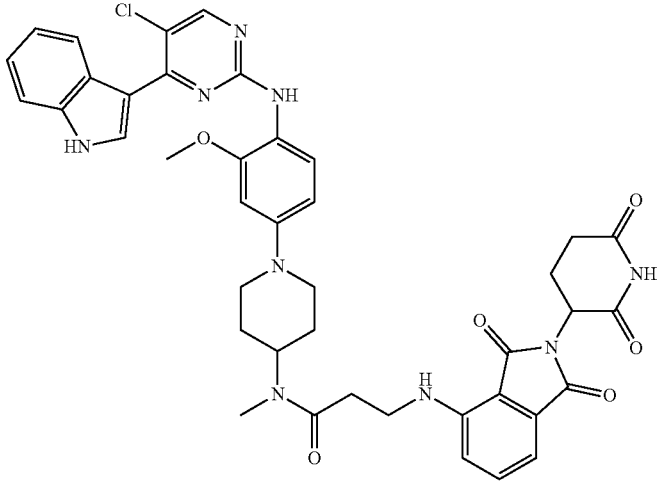 [SMILES: COc1cc(N2CCC(N(C)C(=O)CCNc3cccc4c3C(=O)N(C3CCC(=O)NC3=O)C4=O)CC2)ccc1Nc1ncc(Cl)c(-c2c[nH]c3ccccc23)n1] | N-(1-(4-((5-chloro-4-(1H-indol-3-yl)pyrimidin-2-yl)amino)-3-methoxy-phenyl)piperidin-4-yl)-3-((2-(2,6-dioxopiperidin-3-yl)-1,3-dioxoisoindolin-4-yl)amino)-N-methyl-propanamide |
| 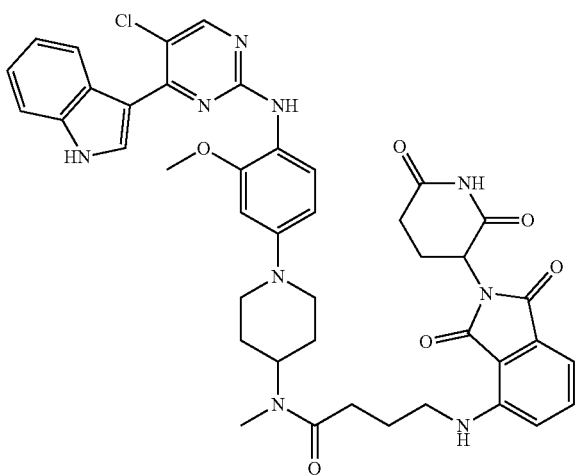 [SMILES: COc1cc(N2CCC(N(C)C(=O)CCCNc3cccc4c3C(=O)N(C3CCC(=O)NC3=O)C4=O)CC2)ccc1Nc1ncc(Cl)c(-c2c[nH]c3ccccc23)n1] | N-(1-(4-((5-chloro-4-(1H-indol-3-yl)pyrimidin-2-yl])amino)-3-methoxy-phenyl)-piperidin-4-yl)-4-((2-(2,6-dioxopiperidin-3-yl)-1,3-dioxoisoindolin-4-yl)amino)-N-methyl-butanamide |

TABLE 2-continued

Structural formulas and names of the compounds of the present disclosure

| Structure of the compound | Name of the compound |
| --- | --- |
|  | N-(1-(4-((5-chloro-4-(1H-indol-3-yl)pyrimidin-2-yl)amino)-3-methoxy-phenyl)piperidin-4-yl)-5-((2-(2,6-dioxopiperidin-3-yl)-1,3-dioxoisoindolin-4-yl)amino)-N-methyl-pentanamide |
|  | N-(1-(4-((5-chloro-4-(1H-indol-3-yl)pyrimidin-2-yl)amino)-3-methoxy-phenyl)piperidin-4-yl)-6-((2-(2,6-dioxopiperidin-3-yl)-1,3-dioxoisoindolin-4-yl)amino)-N-methyl-hexanamide |
|  | N-(1-(4-((5-chloro-4-(1H-indol-3-yl)pyrimidin-2-yl)amino)-3-methoxy-phenyl)piperidin-4-yl)-7-((2-(2,6-dioxopiperidin-3-yl)-1,3-dioxoisoindolin-4-yl)amino)-N-methyl-heptanamide |

TABLE 2-continued

Structural formulas and names of the compounds of the present disclosure

| Structure of the compound | Name of the compound |
| --- | --- |
|  | N-(1-(4-((5-chloro-4-(1H-indol-3-yl)pyrimidin-2-yl)amino)-3-methoxyphenyl)piperidin-4-yl)-12-((2-(2,6-dioxopiperidin-3-yl)-1,3-dioxoisoindolin-4-yl)amino)-N-methyl-dodecanamide |
|  | N-(1-(4-((5-chloro-4-(1H-indol-3-yl)pyrimidin-2-yl)amino)-3-methoxyphenyl)piperidin-4-yl)-12-((2-(2,6-dioxopiperidin-3-yl)-1-oxoisoindolin-4-yl)amino)-N-methyl-dodecanamide |
|  | N1-(1-(4-((5-chloro-4-(1H-indol-3-yl)pyrimidin-2-yl)amino)-3-methoxyphenyl)piperidin-4-yl)-N12-(2-(2,6-dioxopiperidin-3-yl)-1-oxoisoindolin-4-yl)-N1-methyl-dodecanediamide |

TABLE 2-continued

Structural formulas and names of the compounds of the present disclosure

| Structure of the compound | Name of the compound |
| --- | --- |
| | (2S,4R)-1-((S)-12-(tert-butyl)-2-(1-(4-((5-chloro-4-(1H-indol-3-yl)pyrimidin-2-yl)-amino)-3-methoxy-phenyl)piperidin-4-yl)-3,10-dioxo-5,8-dioxa-2,11-diazatridecan-13-oyl)-4-hydroxy-N-(4-(4-methylthiazol-5-yl)-benzyl)pyrrolidine-2-carboxamide |
| | (2S,4R)-1-((S)-17-(tert-butyl)-2-(1-(4-((5-chloro-4-(1H-indol-3-yl)pyrimidin-2-yl)-amino)-3-methoxy-phenyl)piperidin-4-yl)-3,15-dioxo-6,9,12-trioxa-2,16-diazaoctadecan-18-oyl)-4-hydroxy-N-(4-(4-methylthiazol-5-yl)benzyl)pyrrolidine-2-carboxamide |
| | N1-(1-(4-((5-chloro-4-(1H-indol-3-yl)pyrimidin-2-yl)amino)-3-methoxy-phenyl)piperidin-4-yl)-N19-((S)-1-((2S,4R)-4-hydroxy-2-((4-(4-methyl-thiazol-5-yl)benzyl)-carbamoyl)pyrrolidin-1-yl)-3,3-dimethyl-1-oxobutan-2-yl)-N1-methyl-4,7,10,13,16-pentaoxanonadecane-diamide |

TABLE 2-continued

Structural formulas and names of the compounds of the present disclosure

| Structure of the compound | Name of the compound |
| --- | --- |
|  | N1-(1-(4-((5-chloro-4-(1H-indol-3-yl)pyrimidin-2-yl)amino)-3-methoxyphenyl)piperidin-4-yl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methylsuccinamide |
|  | N1-(1-(4-((5-chloro-4-(1H-indol-3-yl)pyrimidin-2-yl)amino)-3-methoxyphenyl)piperidin-4-yl)-N6-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyladipamide |
|  | (2S,4R)-1-((S)-2-(6-((1-(4-((5-chloro-4-(1H-indol-3-yl)pyrimidin-2-yl)amino)-3-methoxyphenyl)piperidin-4-yl)(methyl)amino)hexanamido)-3,3-dimethylbutanoyl)-4-hydroxy-N-(4-(4-methylthiazol-5-yl)benzyl)pyrrolidine-2-carboxamide |

TABLE 2-continued

Structural formulas and names of the compounds of the present disclosure

| Structure of the compound | Name of the compound |
| --- | --- |
|  | N1-(1-(4-((5-chloro-4-(1H-indol-3-yl)pyrimidin-2-yl)amino)-3-methoxy-phenyl)piperidin-4-yl)-N8-((S)-1-((2S,4R)-4-hydroxy-2-((4-(4-methyl-thiazol-5-yl)benzyl)-carbamoyl)pyrrolidin-1-yl)-3,3-dimethyl-1-oxobutan-2-yl)-N1-methyloctanediamide |
|  | N1-(1-(4-((5-chloro-4-(1H-indol-3-yl)pyrimidin-2-yl)amino)-3-methoxy-phenyl)piperidin-4-yl)-N10-((S)-1-((2S,4R)-4-hydroxy-2-((4-(4-methyl-thiazol-5-yl)benzyl)-carbamoyl)pyrrolidin-1-yl)-3,3-dimethyl-1-oxobutan-2-yl)-N1-methyldecanediamide |
|  | N-(5-(3,5-difluorobenzyl)-1H-indazol-3-yl)-4-(4-(3-(2-((2-(2,6-dioxo-piperidin-3-yl)-1,3-dioxoisoindolin-4-yl)-amino)ethoxy)propanoyl)-piperazin-1-yl)-2-((tetra-hydro-2H-pyran-4-yl)-amino)benzamide |

TABLE 2-continued

Structural formulas and names of the compounds of the present disclosure

| Structure of the compound | Name of the compound |
| --- | --- |
|  | N-(5-(3,5-difluorobenzyl)-1H-indazol-3-yl)-4-(4-(3-(2-(2-((2-(2,6-dioxo-piperidin-3-yl)-1,3-dioxoisoindolin-4-yl)-amino)ethoxy)ethoxy)-propanoyl)piperazin-1-yl)-2-((tetrahydro-2H-pyran-4-yl)amino)-benzamide |
|  | N-(5-(3,5-difluorobenzyl)-1H-indazol-3-yl)-4-(4-(3-(2-(2-(2-((2-(2,6-dioxopiperidin-3-yl)-1,3-dioxoisoindolin-4-yl)amino)ethoxy)ethoxy)-ethoxy)propanoyl)piper-azin-1-yl)-2-((tetrahydro-2H-pyran-4-yl)amino)-benzamide |
|  | N-(5-(3,5-difluorobenzyl)-1H-indazol-3-yl)-4-(4-(3-(2-(2-(2-((2-(2,6-dioxopiperidin-3-yl)-1-oxoisoindolin-4-yl)-amino)ethoxy)ethoxy)-ethoxy)propanoyl)-piperazin-1-yl)-2-((tetrahydro-2H-pyran-4-yl)amino)benzamide |
|  | N-(5-(3,5-difluorobenzyl)-1H-indazol-3-yl)-4-(4-(3-(2-(2-(3-(2-(2,6-dioxopiperidin-3-yl)-1,3-dioxoisoindolin-4-yl)-propoxy)ethoxy)ethoxy)-propanoyl)piperazin-1-yl)-2-((tetrahydro-2H-pyran-4-yl)amino)-benzamide |
|  | N-(5-(3,5-difluorobenzyl)-1H-indazol-3-yl)-4-(4-(1-((2-(2,6-dioxopiperidin-3-yl)-1,3-dioxoisoindolin-4-yl)amino)-3,6,9,12-tetraoxapentadecan-15-oyl)piperazin-1-yl)-2-((tetrahydro-2H-pyran-4-yl)amino)benzamide |

TABLE 2-continued

Structural formulas and names of the compounds of the present disclosure

| Structure of the compound | Name of the compound |
|---|---|
| | N-(5-(3,5-difluorobenzyl)-1H-indazol-3-yl)-4-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)-2-((tetrahydro-2H-pyran-4-yl)amino)benzamide |
| | N-(5-(3,5-difluorobenzyl)-1H-indazol-3-yl)-4-(4-((2-(2,6-dioxopiperidin-3-yl)-1,3-dioxoisoindolin-4-yl)glycyl)piperazin-1-yl)-2-((tetrahydro-2H-pyran-4-yl)amino)-benzamide |
| | N-(5-(3,5-difluorobenzyl)-1H-indazol-3-yl)-4-(4-(3-((2-(2,6-dioxopiperidin-3-yl)-1,3-dioxoisoindolin-4-yl)amino)propanoyl)-piperazin-1-yl)-2-((tetrahydro-2H-pyran-4-yl)-amino)benzamide |
| | N-(5-(3,5-difluorobenzyl)-1H-indazol-3-yl)-4-(4-(4-((2-(2,6-dioxopiperidin-3-yl)-1,3-dioxoisoindolin-4-yl)amino)butanoyl)-piperazin-1-yl)-2-((tetrahydro-2H-pyran-4-yl)-amino)benzamide |

TABLE 2-continued

Structural formulas and names of the compounds of the present disclosure

| Structure of the compound | Name of the compound |
|---|---|
|  | N-(5-(3,5-difluorobenzyl)-1H-indazol-3-yl)-4-(4-(5-((2-(2,6-dioxopiperidin-3-yl)-1,3-dioxoisoindolin-4-yl)amino)pentanoyl)-piperazin-1-yl)-2-((tetrahydro-2H-pyran-4-yl)-amino)benzamide |
|  | N-(5-(3,5-difluorobenzyl)-1H-indazol-3-yl)-4-(4-(6-((2-(2,6-dioxopiperidin-3-yl)-1,3-dioxoisoindolin-4-yl)amino)hexanoyl)-piperazin-1-yl)-2-((tetrahydro-2H-pyran-4-yl)-amino)benzamide |
|  | N-(5-(3,5-difluorobenzyl)-1H-indazol-3-yl)-4-(4-(7-((2-(2,6-dioxopiperidin-3-yl)-1,3-dioxoisoindolin-4-yl)amino)heptanoyl)-piperazin-1-yl)-2-((tetrahydro-2H-pyran-4-yl)-amino)benzamide |
|  | N-(5-(3,5-difluorobenzyl)-1H-indazol-3-yl)-4-(4-(12-((2-(2,6-dioxo-piperidin-3-yl)-1,3-dioxoisoindolin-4-yl)-amino)dodecanoyl)-piperazin-1-yl)-2-((tetrahydro-2H-pyran-4-yl)-amino)benzamide |

TABLE 2-continued

Structural formulas and names of the compounds of the present disclosure

| Structure of the compound | Name of the compound |
|---|---|
|  | (2S,4R)-1-((S)-2-(2-(2-(2-(4-(4-((5-(3,5-difluorobenzyl)-1H-indazol-3-yl)carbamoyl)-3-((tetrahydro-2H-pyran-4-yl)amino)phenyl)-piperazin-1-yl)-2-oxoethoxy)ethoxy)-acetamido)-3,3-dimethyl-butanoyl)-4-hydroxy-N-(4-(4-methylthiazol-5-yl)benzyl)pyrrolidine-2-carboxamide |
|  | (2S,4R)-1-((S)-2-(tert-butyl)-16-(4-(4-((5-(3,5-difluorobenzyl)-1H-indazol-3-yl)carbamoyl)-3-((tetrahydro-2H-pyran-4-yl)amino)phenyl)-piperazin-1-yl)-4,16-dioxo-7,10,13-trioxa-3-azahexadecanoyl)-4-hydroxy-N-(4-(4-methyl-thiazol-5-yl)benzyl)-pyrrolidine-2-carboxamide |
|  | (2S,4R)-1-((S)-2-(tert-butyl)-22-(4-(4-((5-(3,5-difluorobenzyl)-1H-indazol-3-yl)carbamoyl)-3-((tetrahydro-2H-pyran-4-yl)amino)phenyl)-piperazin-1-yl)-4,22-dioxo-7,10,13,16,19-pentaoxa-3-azadoco-sanoyl)-4-hydroxy-N-(4-(4-methylthiazol-5-yl)benzyl)pyrrolidine-2-carboxamide |
|  | (2S,4R)-1-((S)-2-(4-(4-(4-((5-(3,5-difluoro-benzyl)-1H-indazol-3-yl)carbamoyl)-3-((tetra-hydro-2H-pyran-4-yl)-amino)phenyl)piperazin-1-yl)-4-oxobutanamido)-3,3-dimethylbutanoyl)-4-hydroxy-N-(4-(4-methylthiazol-5-yl)-benzyl)pyrrolidine-2-carboxamide |

TABLE 2-continued

Structural formulas and names of the compounds of the present disclosure

| Structure of the compound | Name of the compound |
|---|---|
| 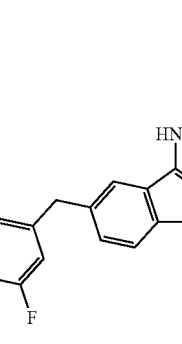 | (2S,4R)-1-((S)-2-(6-(4-(4-((5-(3,5-difluoro-benzyl)-1H-indazol-3-yl)carbamoyl)-3-((tetra-hydro-2H-pyran-4-yl)-amino)phenyl)piperazin-1-yl)-6-oxohexanamido)-3,3-dimethylbutanoyl)-4-hydroxy-N-(4-(4-methylthiazol-5-yl)-benzyl)pyrrolidine-2-carboxamide |
|  | (2S,4R)-1-((S)-2-(8-(4-(4-((5-(3,5-difluoro-benzyl)-1H-indazol-3-yl)carbamoyl)-3-((tetra-hydro-2H-pyran-4-yl)-amino)phenyl)piperazin-1-yl)-8-oxooctanamido)-3,3-dimethylbutanoyl)-4-hydroxy-N-(4-(4-methylthiazol-5-yl)-benzyl)pyrrolidine-2-carboxamide |
|  | (2S,4R)-1-((S)-2-(10-(4-(4-((5-(3,5-difluoro-benzyl)-1H-indazol-3-yl)carbamoyl)-3-((tetra-hydro-2H-pyran-4-yl)-amino)phenyl)piperazin-1-yl)-10-oxodecanamido)-3,3-dimethylbutanoyl)-4-hydroxy-N-(4-(4-methyl-thiazol-5-yl)-benzyl)pyrrolidine-2-carboxamide |
| 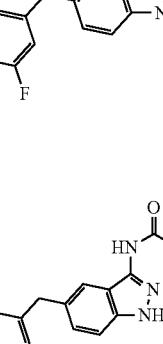 | (2S,4R)-1-((S)-2-(13-(4-(4-((5-(3,5-difluoro-benzyl)-1H-indazol-3-yl)carbamoyl)-3-((tetra-hydro-2H-pyran-4-yl)-amino)phenyl)piperazin-1-yl)-13-oxotridecan-amido)-3,3-dimethyl-butanoyl)-4-hydroxy-N-(4-(4-methylthiazol-5-yl)benzyl)pyrrolidine-2-carboxamide |

TABLE 2-continued

Structural formulas and names of the compounds of the present disclosure

| Structure of the compound | Name of the compound |
| --- | --- |
| | (2S,4R)-1-((S)-2-(13-(4-(4-((5-(3,5-difluoro-benzyl)-1H-indazol-3-yl)carbamoyl)-3-((tetra-hydro-2H-pyran-4-yl)-amino)phenyl)piperazin-1-yl)tridecanamido)-3,3-dimethylbutanoyl)-4-hydroxy-N-(4-(4-methylthiazol-5-yl)-benzyl)pyrrolidine-2-carboxamide |
| | 6-amino-5-((R)-1-(2,6-dichloro-3-fluorophenyl)-ethoxy)-N-(4-((3S,5R)-4-(3-(2-((2-(2,6-dioxo-piperidin-3-yl)-1,3-dioxoisoindolin-4-yl)-amino)ethoxy)propanoyl)-3,5-dimethylpiperazine-1-carbonyl)phenyl)-pyridazine-3-carboxamide |
| | 6-amino-5-((R)-1-(2,6-dichloro-3-fluorophenyl)-ethoxy)-N-(4-((3S,5R)-4-(3-(2-(2-((2-(2,6-dioxopiperidin-3-yl)-1,3-dioxoisoindolin-4-yl)-amino)ethoxy)ethoxy)-propanoyl)-3,5-dimethyl-piperazine-1-carbonyl)-phenyl)pyridazine-3-carboxamide |
| | 6-amino-5-((R)-1-(2,6-dichloro-3-fluorophenyl)-ethoxy)-N-(4-((3S,5R)-4-(3-(2-(2-(2-((2-(2,6-dioxopiperidin-3-yl)-1,3-dioxoisoindolin-4-yl)-amino)ethoxy)ethoxy)-ethoxy)propanoyl)-3,5-dimethylpiperazine-1-carbonyl)phenyl)pyrida-zine-3-carboxamide |
| | 6-amino-5-((R)-1-(2,6-dichloro-3-fluorophenyl)-ethoxy)-N-(4-((3S,5R)-4-(1-((2-(2,6-dioxo-piperidin-3-yl)-1,3-dioxo-isoindolin-4-yl)amino)-3,6,9,12-tetraoxapenta-decan-15-oyl)-3,5-dimethylpiperazine-1-carbonyl)phenyl)pyrida-zine-3-carboxamide |

TABLE 2-continued

Structural formulas and names of the compounds of the present disclosure

| Structure of the compound | Name of the compound |
|---|---|
| | 6-amino-5-((R)-1-(2,6-dichloro-3-fluorophenyl)-ethoxy)-N-(4-((3S,5R)-4-(1-((2-(2,6-dioxo-piperidin-3-yl)-1,3-dioxoisoindolin-4-yl)-amino)-3,6,9,12,15-pentaoxaoctadecan-18-oyl)-3,5-dimethyl-piperazine-1-carbonyl)-phenyl)pyridazine-3-carboxamide |
| | 6-amino-5-((R)-1-(2,6-dichloro-3-fluoro-phenyl)ethoxy)-N-(4-((3S,5R)-4-((2-(2,6-dioxopiperidin-3-yl)-1,3-dioxoisoindolin-4-yl)glycyl)-3,5-dimethyl-piperazine-1-carbonyl)-phenyl)pyridazine-3-carboxamide |
| | 6-amino-5-((R)-1-(2,6-dichloro-3-fluoro-phenyl)ethoxy)-N-(4-((3S,5R)-4-(3-((2-(2,6-dioxopiperidin-3-yl)-1,3-dioxoisoindolin-4-yl)amino)propanoyl)-3,5-dimethylpiperazine-1-carbonyl)phenyl)-pyridazine-3-carboxamide |
| | 6-amino-5-((R)-1-(2,6-dichloro-3-fluorophenyl)-ethoxy)-N-(4-((3S,5R)-4-(4-((2-(2,6-dioxo-piperidin-3-yl)-1,3-dioxoisoindolin-4-yl)-amino)butanoyl)-3,5-dimethylpiperazine-1-carbonyl)phenyl)pyrida-zine-3-carboxamide |
| | 6-amino-5-((R)-1-(2,6-dichloro-3-fluorophenyl)-ethoxy)-N-(4-((3S,5R)-4-(5-((2-(2,6-dioxo-piperidin-3-yl)-1,3-dioxoisoindolin-4-yl)-amino)pentanoyl)-3,5-dimethylpiperazine-1-carbonyl)phenyl)pyrida-zine-3-carboxamide |

TABLE 2-continued

Structural formulas and names of the compounds of the present disclosure

| Structure of the compound | Name of the compound |
|---|---|
| | 6-amino-5-((R)-1-(2,6-dichloro-3-fluorophenyl)-ethoxy)-N-(4-((3S,5R)-4-(6-((2-(2,6-dioxo-piperidin-3-yl)-1,3-dioxoisoindolin-4-yl)-amino)hexanoyl)-3,5-dimethylpiperazine-1-carbonyl)phenyl)pyridazine-3-carboxamide |
| | 6-amino-5-((R)-1-(2,6-dichloro-3-fluorophenyl)-ethoxy)-N-(4-((3S,5R)-4-(7-((2-(2,6-dioxo-piperidin-3-yl)-1,3-dioxoisoindolin-4-yl)-amino)heptanoyl)-3,5-dimethylpiperazine-1-carbonyl)phenyl)pyridazine-3-carboxamide |
| | 6-amino-5-((R)-1-(2,6-dichloro-3-fluorophenyl)-ethoxy)-N-(4-((3S,5R)-4-(10-((2-(2,6-dioxo-piperidin-3-yl)-1,3-dioxoisoindolin-4-yl)-amino)decanoyl)-3,5-dimethylpiperazine-1-carbonyl)phenyl)pyridazine-3-carboxamide |
| | 6-amino-5-((R)-1-(2,6-dichloro-3-fluorophenyl)-ethoxy)-N-(4-((3S,5R)-4-(10-((2-(2,6-dioxo-piperidin-3-yl)-1-oxoiso-indolin-4-yl)amino)-decanoyl)-3,5-dimethyl-piperazine-1-carbonyl)-phenyl)pyridazine-3-carboxamide |
| | 6-amino-5-((R)-1-(2,6-dichloro-3-fluorophenyl)-ethoxy)-N-(4-((3S,5R)-4-(10-((2-(2,6-dioxo-piperidin-3-yl)-1-oxoiso-indolin-4-yl)amino)-decyl)-3,5-dimethyl-piperazine-1-carbonyl)-phenyl)pyridazine-3-carboxamide |

TABLE 2-continued

Structural formulas and names of the compounds of the present disclosure

| Structure of the compound | Name of the compound |
|---|---|
| | 6-amino-5-((R)-1-(2,6-dichloro-3-fluorophenyl)-ethoxy)-N-(4-((3S,5R)-4-(11-(2-(2,6-dioxo-piperidin-3-yl)-1,3-dioxoisoindolin-4-yl)-undecanoyl)-3,5-dimethyl-piperazine-1-carbonyl)-phenyl)pyridazine-3-carboxamide |
| | 6-amino-5-((R)-1-(2,6-dichloro-3-fluorophenyl)-ethoxy)-N-(4-((3S,5R)-4-(2-(2-(2-(((S)-1-((2S,4R)-4-hydroxy-2-((4-(4-methylthiazol-5-yl)-benzyl)carbamoyl)-pyrrolidin-1-yl)-3,3-dimethyl-1-oxobutan-2-yl)amino)-2-oxoethoxy)-ethoxy)acetyl)-3,5-dimethylpiperazine-1-carbonyl)phenyl)pyridazine-3-carboxamide |
| | 6-amino-5-((R)-1-(2,6-dichloro-3-fluorophenyl)-ethoxy)-N-(4-((3S,5R)-4-((S)-15-((2S,4R)-4-hydroxy-2-((4-(4-methyl-thiazol-5-yl)benzyl)-carbamoyl)pyrrolidine-1-carbonyl)-16,16-dimethyl-13-oxo-4,7,10-trioxa-14-azaheptadecanoyl)-3,5-dimethylpiperazine-1-carbonyl)phenyl)pyridazine-3-carboxamide |
| | 6-amino-5-((R)-1-(2,6-dichloro-3-fluorophenyl)-ethoxy)-N-(4-((3S,5R)-4-((S)-21-((2S,4R)-4-hydroxy-2-((4-(4-methyl-thiazol-5-yl)benzyl)-carbamoyl)pyrrolidine-1-carbonyl)-22,22-dimethyl-19-oxo-4,7,10,13,16-pentaoxa-20-azatricosanoyl)-3,5-dimethylpiperazine-1-carbonyl)phenyl)pyridazine-3-carboxamide |

TABLE 2-continued

Structural formulas and names of the compounds of the present disclosure

| Structure of the compound | Name of the compound |
|---|---|
| | 6-amino-5-((R)-1-(2,6-dichloro-3-fluorophenyl)-ethoxy)-N-(4-((3S,5R)-4-(4-(((S)-1-((2S,4R)-4-hydroxy-2-((4-(4-methyl-thiazol-5-yl)benzyl)-carbamoyl)pyrrolidin-1-yl)-3,3-dimethyl-1-oxobutan-2-yl)amino)-4-oxobutanoyl)-3,5-dimethylpiperazine-1-carbonyl)phenyl)pyridazine-3-carboxamide |
| | 6-amino-5-((R)-1-(2,6-dichloro-3-fluorophenyl)-ethoxy)-N-(4-((3S,5R)-4-(6-(((S)-1-((2S,4R)-4-hydroxy-2-((4-(4-methyl-thiazol-5-yl)benzyl)-carbamoyl)pyrrolidin-1-yl)-3,3-dimethyl-1-oxobutan-2-yl)amino)-6-oxohexanoyl)-3,5-dimethylpiperazine-1-carbonyl)phenyl)pyridazine-3-carboxamide |
| | 6-amino-5-((R)-1-(2,6-dichloro-3-fluoro-phenyl)ethoxy)-N-(4-((3S,5R)-4-(8-(((S)-1-((2S,4R)-4-hydroxy-2-((4-(4-methylthiazol-5-yl)benzyl)carbamoyl)-pyrrolidin-1-yl)-3,3-dimethyl-1-oxobutan-2-yl)amino)-8-oxo-octanoyl)-3,5-dimethyl-piperazine-1-carbonyl)-phenyl)pyridazine-3-carboxamide |
| | 6-amino-5-((R)-1-(2,6-dichloro-3-fluoro-phenyl)ethoxy)-N-(4-((3S,5R)-4-(10-(((S)-1-((2S,4R)-4-hydroxy-2-((4-(4-methylthiazol-5-yl)benzyl)carbamoyl)-pyrrolidin-1-yl)-3,3-dimethyl-1-oxobutan-2-yl)amino)-10-oxo-decanoyl)-3,5-dimethyl-piperazine-1-carbonyl)-phenyl)pyridazine-3-carboxamide |

It should be recognized that the compounds of formula (I) of the present disclosure may have a stereo configuration and can therefore exist in more than one stereoisomer form. The disclosure also relates to compounds of formula (I) having a stereo configuration in pure or substantially pure isomeric form, e.g., greater than about 90% enantiomeric/diastereomeric excess ("ee"), such as greater than about 95% ee or 97% ee, or greater than about 99% ee, and mixtures thereof, including racemic mixtures. The purification of said isomers and the separation of said isomeric mixtures may be achieved by standard techniques known in the art (e.g., column chromatography, preparative TLC, preparative HPLC, asymmetric synthesis (for example, by using chiral intermediates) and/or chiral resolution and the like).

The present disclosure also provides a pharmaceutical composition comprising, as an active ingredient, the compound of formula (I) according to the present disclosure or a pharmaceutically acceptable salt thereof, and a pharmaceutically acceptable carrier.

The pharmaceutical composition of the present disclosure further includes at least one additional medicine for treating or preventing cancer.

In another aspect of the present disclosure, the compound of formula (I) according to the disclosure, or a pharmaceutically acceptable salt thereof, is for use as a medicament.

In another aspect of the present disclosure, the compound of formula (I) according to the present disclosure, or a pharmaceutically acceptable salt thereof, is used for preventing and/or treating cancer.

Cancers include but are not limited to lung cancer including small cell lung cancer, non-small cell lung cancer (NSCLC) such as lung adenocarcinoma, anaplastic lymphoma kinase (ALK) mutation-positive non-small cell lung cancer, ROS1-mutation positive non-small cell lung cancer, MET mutated or amplified lung cancer, and EGFR-mutated non-small cell lung cancer; Lymphoma including anaplastic lymphoma, anaplastic large cell lymphoma (ALCL), and diffused large B-cell lymphoma; inflammatory myofibroblastic tumor (IMT); colorectal cancer; brain tumor including glioma, and glioblastoma; Acute myeloid leukemia (AML); and ovarian cancer etc.

In one embodiment of the present disclosure, the compound of formula (I) according to the present disclosure, or a pharmaceutically acceptable salt thereof, is used for preventing and/or treating lung cancer.

In one embodiment of the present disclosure, the lung cancer is e.g., selected from the group consisting of small cell lung cancer, non-small cell lung cancer (NSCLC) such as lung adenocarcinoma, anaplastic lymphoma kinase (ALK) mutation-positive non-small cell lung cancer (NSCLC), ROS1-mutation positive non-small cell lung cancer, MET mutated or amplified lung cancer, and EGFR-mutated non-small cell lung cancer.

Another aspect of the present disclosure provides the use of the compound of formula (I) according to the present disclosure, or a pharmaceutically acceptable salt thereof, for the preparation of a medicament for the prevention and/or treatment of cancer.

In one embodiment of the use of compound of formula (I) of the present disclosure, the cancers include but are not limited to lung cancer including small cell lung cancer, non-small cell lung cancer (NSCLC) such as lung adenocarcinoma, anaplastic lymphoma kinase (ALK) mutation-positive non-small cell lung cancer, ROS1-mutation positive non-small cell lung cancer, MET mutated or amplified lung cancer, and EGFR-mutated non-small cell lung cancer; Lymphoma including anaplastic lymphoma, anaplastic large cell lymphoma (ALCL), and diffused large B-cell lymphoma; inflammatory myofibroblastic tumor (IMT); colorectal cancer; brain tumor including glioma, and glioblastoma; Acute myeloid leukemia (AML); and ovarian cancer etc.

In one embodiment, the lung cancer is e.g., selected from the group consisting of small cell lung cancer, non-small cell lung cancer (NSCLC) such as lung adenocarcinoma, anaplastic lymphoma kinase (ALK) mutation-positive non-small cell lung cancer (NSCLC), ROS1-mutation positive non-small cell lung cancer, MET mutated or amplified lung cancer, and EGFR-mutated non-small cell lung cancer.

A further aspect of the present disclosure also provides a method for treating or preventing cancer, which comprises administering to a subject a therapeutically effective amount of the compound of formula (I) according to the present disclosure, or a pharmaceutically acceptable salt thereof, or the pharmaceutical composition.

In the method for treating or preventing cancer according to the present disclosure, the compound of formula (I) according to the present disclosure, or a pharmaceutically acceptable salt thereof, or the pharmaceutical composition is administered to the subject by at least one mode of administration selected from the group consisting of nasal administration, inhalation administration, topical administration, oral administration, oral mucosal administration, rectal administration, Pleural, peritoneal, vaginal, intramuscular, subcutaneous, transdermal, epidural, intrathecal, and intravenous administration.

In one embodiment of the method for treating or preventing cancer according to the present disclosure, the cancers include but are not limited to lung cancer including small cell lung cancer, non-small cell lung cancer (NSCLC) such as lung adenocarcinoma, anaplastic lymphoma kinase (ALK) mutation-positive non-small cell lung cancer, ROS1-mutation positive non-small cell lung cancer, MET mutated or amplified lung cancer, and EGFR-mutated non-small cell lung cancer; Lymphoma including anaplastic lymphoma, anaplastic large cell lymphoma (ALCL), and diffused large B-cell lymphoma; inflammatory myofibroblastic tumor (IMT); colorectal cancer; brain tumor including glioma, and glioblastoma; Acute myeloid leukemia (AML); and ovarian cancer etc.

In one embodiment of the method for treating or preventing cancer according to the present disclosure, the lung cancer is e.g., selected from the group consisting of small cell lung cancer, non-small cell lung cancer (NSCLC) such as lung adenocarcinoma, anaplastic lymphoma kinase (ALK) mutation-positive non-small cell lung cancer (NSCLC), ROS1-mutation positive non-small cell lung cancer, MET mutated or amplified lung cancer, and EGFR-mutated non-small cell lung cancer.

Definition

Generally, the nomenclature used herein and the laboratory procedures described below comprising those for cell culture, organic chemistry, analytical chemistry, and pharmacology and the like are those well known and commonly used in the art. Unless otherwise defined, all the scientific and technical terms used herein in combination with the present disclosure described herein have the same meaning commonly understood by those skilled in the art. In addition, the use of the word "a" or "an" when used in combination with the term "comprising" or a noun word in the claims and/or the specification may mean "one", but it is also consistent with the meaning of "one or more", "at least one", and "one or more than one". Similarly, the word "another" or "other" may mean at least a second or more.

It should be understood that whenever various aspects are described herein with term "comprising", other similar aspects described with "consisting of" and/or "consisting essentially of" are also provided.

The term "about" used herein refers to approximately, roughly, approximately, or around. When the term "about" is used in combination with a numerical range, it modifies that range by extending the boundaries above and below the stated numerical value. For example, the term "about" used herein may modify a numerical value above and below the stated value by a variance of, for example, ±20%, or ±15%, or ±10%, ±5%, or ±1%.

The term "absent" used herein in combination with a substituent(s) or group(s) means that the substituent(s) or group(s) is not present. In other words, when the substituent(s) or group(s) is not present, it becomes a bond or a bond connector. For example, in the compound of formula (I) according to the present disclosure, when the group A is absent, the ALK-TKI moiety is directly covalently bonded (or connected) to the LIN.

As used herein, the term "interrupted" of "the linear or branched alkylene chain interrupted . . . by . . . " used alone or in combination has a definition known in the art, i.e., can refer to there is a group as defined herein (e.g., a group selected from the group consisting of O, C(O)NH, NHC(O), NHC(O)NH, NH, S, sulfinyl, sulfonyl, aminosulfonylamino, alkynylene, alkenylene, cycloalkylene, arylene, heterocyclylene, or heteroarylene group, or any combination thereof, as described herein) inserted between any two adjacent carbon atoms in the backbone chain of the linear or branched alkylene chain. For example, the term "the linear or branched alkylene chain interrupted one or more times by one or more "O" radicals" used alone or in combination refers to one or more pairs of any two adjacent carbon atoms in the backbone chain of the linear or branched alkylene chain are inserted therebetween with the —O— radical, to from a linear or branched oxaalkylene radical containing one or more (e.g., 1-10, 1-8, 1-7, 1-6, 1-5, 1-4, 1-3, 1-2, or 1) "—CH$_2$—O—CH$_2$—" fragments.

Herein, the compound of the formula (I) of the present disclosure is also referred to as a PROTAD (small) molecule, a PROTAD compound as an ALK protein degradation agent, a PROTAD compound, a degradation agent, ALK PROTAD (compound(s)) or an ALK protein modulator, which can be used interchangeably.

Herein, the structure represented by formula (Ia) as described above is a monovalent chemical moiety (or a monovalent group) formed or derived from Crizotinib by removing a single hydrogen atom on the nitrogen of piperidinyl. The structure represented by formula (Ib) as described above is a monovalent chemical moiety (or a monovalent group) derived from Ceritinib by removing a single hydrogen atom on the nitrogen of piperidinyl.

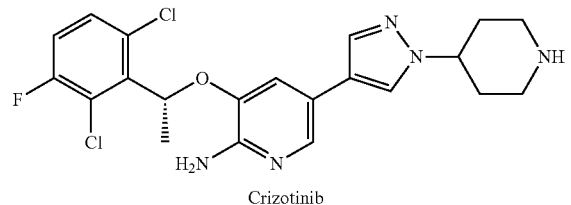

Crizotinib

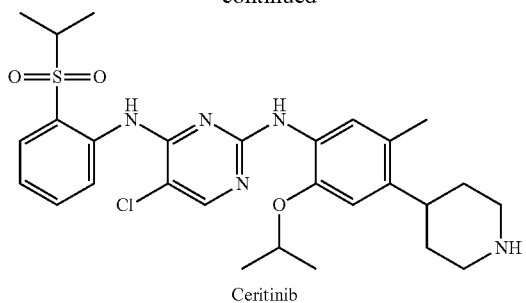

Ceritinib

Herein, the structures represented by formulae (Ic), (Id), and (Ie) as described above are all analogs of Alectinib.

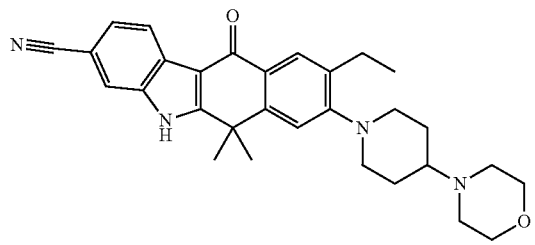

Alectinib

Herein, the structures represented by the formulas (If), (Ig), and (Ih) as described above are all analogs of Brigatinib.

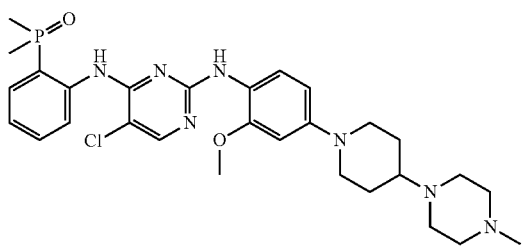

Brigatinib

Herein, the structure represented by the formula (Ii) is a monovalent chemical moiety (or a monovalent group) derived from TAE684 (NVP-TAE684) by removing the methyl group on the nitrogen of piperazinyl.

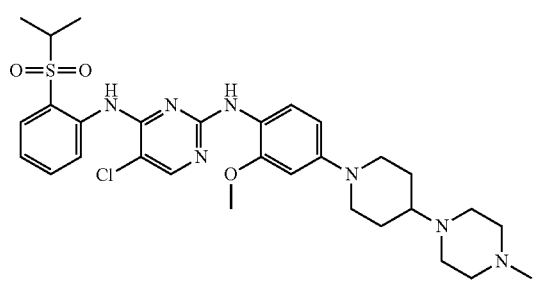

TAE684 (NVP-TAE684)

Herein, the structure represented by the formula (Ij) is a monovalent chemical moiety (or a monovalent group) derived from ASP3026 by removing the methyl group on the nitrogen of piperazinyl.

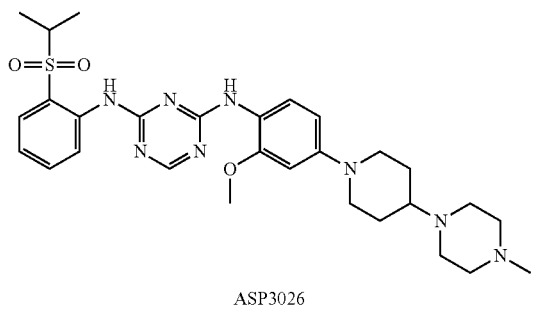 [SMILES: COc1cc(N2CCC(N3CCN(C)CC3)CC2)ccc1Nc1ncnc(Nc2ccccc2S(=O)(=O)C(C)C)n1]

ASP3026

Herein, the structure represented by formula (Ik) is a monovalent chemical moiety (or a monovalent group) derived from GSK1838705A by removing one or two methyl groups on the dimethylamino group.

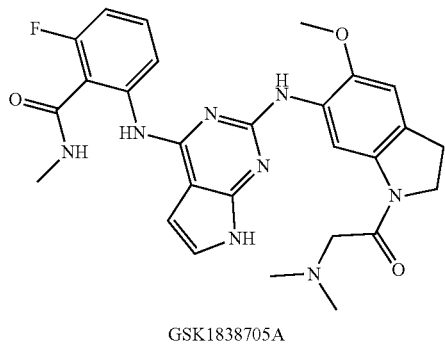 [SMILES: CNC(=O)c1c(F)cccc1Nc1nc(Nc2cc3c(cc2OC)CCN3C(=O)CN(C)C)nc2[nH]ccc12]

GSK1838705A

Herein, the structure represented by the formula (Ii) is a monovalent chemical moiety (or a monovalent group) derived from AZD3463 by removing a single hydrogen atom from the primary amine group (—NH$_2$).

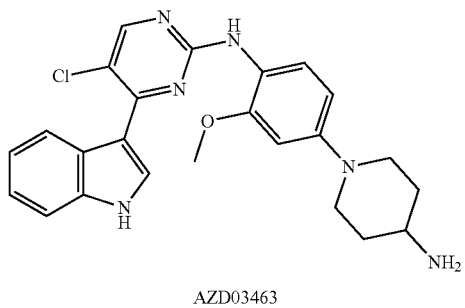 [SMILES: COc1cc(N2CCC(N)CC2)ccc1Nc1ncc(Cl)c(-c2c[nH]c3ccccc23)n1]

AZD03463

Herein, the structure represented by formula (Im) is a monovalent chemical moiety (or a monovalent group) derived from Entrectinib (RXDX-101) by removing the methyl group on the nitrogen of piperazinyl.

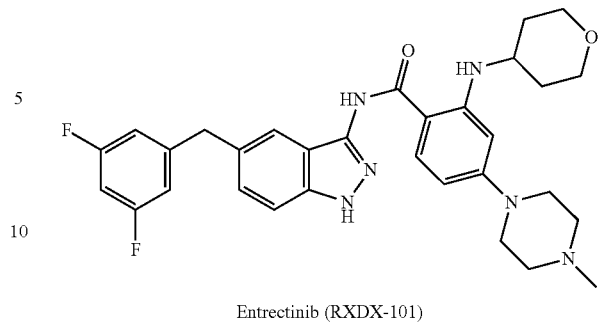

Entrectinib (RXDX-101)

Herein, the structure represented by formula (In) is a monovalent chemical moiety (or a monovalent group) derived from Ensartinib (X-396) by removing a single hydrogen atom on the nitrogen of piperazinyl.

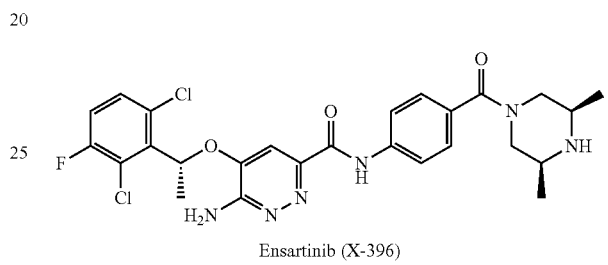

Ensartinib (X-396)

Herein, a bond interrupted by a wavy line shows the point of attachment of the radical depicted. For example, the group depicted below

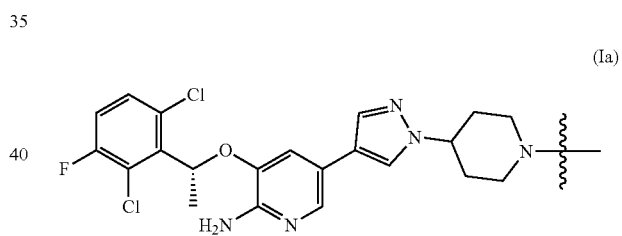

(Ia)

is the chemical moiety represented by formula (Ia), which is connected to the rest part of the compound of formula (I) through the N atom of piperidinyl.

Herein, the ULM can represents a structure of the following formula (II)

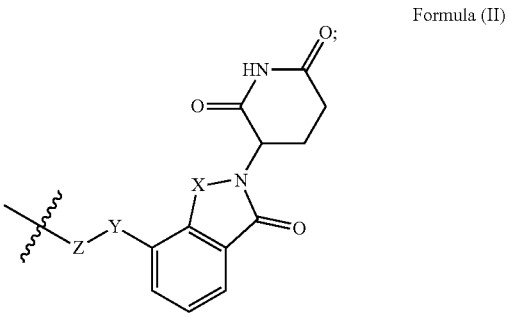

Formula (II)

wherein X represents CH$_2$ or C(O), Y represents CH$_2$, NH or O, and Z represents a carbonyl group or is absent. The structure of the following formula (II) is a derivative of Thalidomide, Lenalidomide, or Pomalidomide.

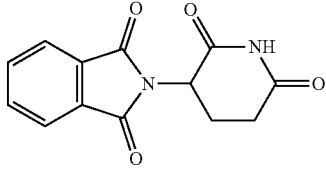
Thalidomide

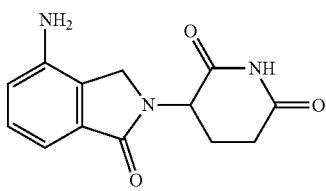
Lenalidomide

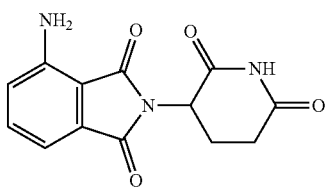
Pomalidomide

Herein, the ULM can also represents a structure of the following formula (III)

Formula (III)

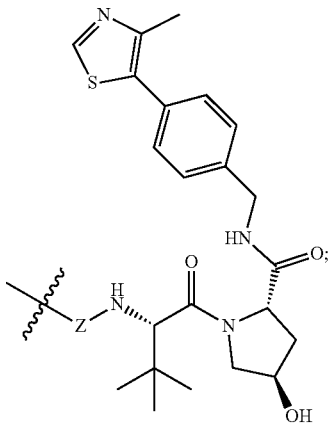

where Z represents a carbonyl group or is absent. The structure of the following formula (III) is a derivative of VHL-1.

VHL-1

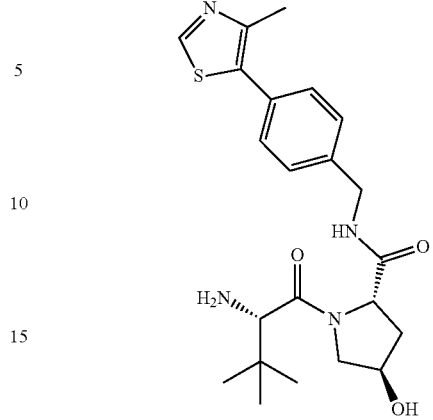

As used herein, the terms "LIN" and "linker" are used interchangeably and both refers to a linking group in a compound of formula (I).

As used herein, the term "intermediate LM" refers to an intermediate compound in the following schemes for synthesizing the target compounds of the present disclosure by reacting with ALK-TKIs, for example, Brigatinib derivatives, Erlotinib derivatives, Ceritinib, or Crizotinib derivatives.

As used herein, the term "halogen atom" or "halogen" used alone or in combination refers to fluorine, chlorine, bromine or iodine, and is preferably F, Cl or Br.

As used herein, the term "alkyl" used alone or in combination refers to a linear or branched alkyl group. The term "$(C_x-C_y)$ alkyl" or "$C_{x-y}$ alkyl" (x and y are each an integer) refers to a linear or branched chain alkyl group containing x to y carbon atoms. The term "$C_{1-10}$ alkyl" used alone or in combination in the present disclosure refers to a linear or branched chain alkyl group containing 1 to 10 carbon atoms. The $C_{1-10}$ alkyl group of the present disclosure includes, but are not limited to, a $C_{1-9}$ alkyl group, or a $C_{1-8}$ alkyl group, or a $C_{2-8}$ alkyl group, or a $C_{1-7}$ alkyl group, or a $C_{1-6}$ alkyl, $C_{1-5}$ alkyl, or $C_{1-4}$ alkyl. Representative examples include, but are not limited to, methyl, ethyl, n-propyl, isopropyl, n-butyl, isobutyl, sec-butyl, tert-butyl, pentyl, isopentyl, neopentyl, tert-pentyl, hexyl, heptyl, octyl, nonyl and decyl. The term "$C_{1-3}$ alkyl group" in the present disclosure refers to an alkyl group containing 1 to 3 carbon atoms, and its representative examples include methyl, ethyl, n-propyl, and isopropyl.

As used herein, the "alkyl" is optionally substituted, and the substituent can be one or more selected from the group consisting of halogen, cyano, $C_{1-3}$ alkyl, $C_{1-3}$ alkoxy, trifluoromethyl, heterocyclyl, or any combination thereof.

As used herein, the term "alkylene" (which is used interchangeably with "alkylene chain") used alone or in combination refers to a linear or branched divalent saturated hydrocarbon group composed of carbon and hydrogen atoms. The term "$C_x-C_y$ alkylene" or "$C_{x-y}$ alkylene" (x and y are each an integer) refers to a linear or branched alkylene group containing from x to y carbon atoms. The $C_{1-30}$ alkylene group in the present disclosure includes, but are not limited to, $C_1-C_{29}$ alkylene, $C_1-C_{28}$ alkylene, $C_1-C_{27}$ alkylene, $C_1-C_{26}$ alkylene, $C_1-C_{25}$ alkylene, $C_1-C_{24}$ alkylene, $C_1-C_{23}$ alkylene, $C_1-C_{22}$ alkylene, $C_1-C_{21}$ alkylene, $C_1-C_{20}$ alkylene, $C_1-C_{19}$ alkylene, $C_1-C_8$ alkylene, $C_1-C_{17}$ alkylene, $C_1-C_{16}$ alkylene, $C_1-C_{15}$ alkylene, $C_1-C_{14}$ alkylene, $C_1$-$C_{13}$ alkylene, $C_1$-$C_{12}$ alkylene, $C_1$-$C_{11}$ alkylene, $C_1$-$C_{10}$ alkylene, $C_1$-$C_9$ alkylene, $C_1$-$C_8$ alkylene, $C_1$-$C_7$ alkylene, $C_1$-$C_6$ alkylene, $C_1$-$C_5$ alkylene, $C_1$-$C_4$ alkylene, $C_1$-$C_3$ alkylene, or $C_1$-$C_2$ alkylene.

Representative examples include, but are not limited to, methylene, ethylene, propylene, isopropylidene, butylene, isobutylene, sec-butylene, tert-butylene, n-pentylene, isopentylene, neopentylene, tert-pentylene, hexylene, heptylene, octylene, nonylene, decylene, undecylene, dodecylene, tridecylene, tetradecylene, pentadecylene, hexadecylene, heptadecylene, octadecylene, nonadecylene, eicosylene, heneicosylene, docosylene, tricosylene, tetracosylene, pentacosylene, hexacosylene, peptacosylene, octacosylene, nonacosylene, and triacontylene.

As used herein, the term "aryl" used alone or in combination refers to a monovalent aromatic hydrocarbon group containing 5 to 14 carbon atoms and optionally one or more fused rings, such as phenyl or naphthyl or fluorenyl. In the present disclosure, the "aryl" is an optionally substituted aryl. A substituted aryl refers to an aryl group optionally substituted 1-3 times with a substituent(s) (that is, the aryl group optionally has 1-3 same or different substituent(s)). In a further embodiment, the substituent can be any one optionally selected from the group consisting of $C_{1-3}$ alkyl, $C_{1-3}$ alkoxy, halogen, amino, hydroxyl, or any combination thereof.

As used herein, the term "arylene" used alone or in combination refers to a divalent aromatic hydrocarbon group containing from 5 to 14 carbon atoms and optionally one or more fused rings, such as phenylene group, naphthylene group or fluorenylene group. In the present disclosure, the "arylene" is an optionally substituted arylene. A substituted arylene group refers to an arylene group optionally substituted 1-3 times with a substituent(s) (that is, the arylene group optionally has 1-3 same or different substituent(s)). In a further embodiment, the substituent can be any one optionally selected from the group consisting of $C_{1-3}$ alkyl, $C_{1-3}$ alkoxy, halogen, amino, hydroxyl, or any combination thereof.

As used herein, the term "$C_{1-3}$ alkoxy group" used alone or in combination refers to a linear or branched alkoxy group containing from 1 to 3 carbon atoms. Representative examples of $C_{1-3}$ alkoxy include, but are not limited to, methoxy, ethoxy, n-propoxy, and isopropoxy. Preferred are methoxy and ethoxy.

As used herein, the term "cycloalkyl" used alone or in combination refers to a saturated or partially unsaturated (e.g., containing one or more double bonds, but not having a completely conjugated π-electron system) monovalent monocyclic or bicyclic cyclic hydrocarbon radical, which may include fused, bridged, or spiro ring system, having from 3 to 12 carbon atoms, e.g., having from 3 to 10 carbon atoms, or from 3 to 8 carbon atoms, or from 3 to 6 carbon atoms. Representative examples include, but are not limited to, cyclopropyl, cyclobutyl, cyclopentyl, cyclopentenyl, cyclohexyl, cyclohexenyl, cycloheptyl, cyclooctyl, decalinyl, octahydropentalenyl, octahydro-1H-indenyl, and spiro-cycloalkyl. The cycloalkyl group may be unsubstituted or substituted. A substituted cycloalkyl group refers to a cycloalkyl group optionally substituted 1-3 times by a substituent(s) (that is, the cycloalkyl group optionally has 1-3 same or different substituent(s)). In a further embodiment, the substituent can be any one optionally selected from the group consisting of $C_{1-3}$ alkyl, $C_{1-3}$ alkoxy, cyano, trifluoromethyl, heterocyclyl, halogen, amino, hydroxyl, or any combination thereof.

As used herein, the term "cycloalkylene", used alone or in combination, refers to a saturated and partially unsaturated (e.g., containing one or more double bonds, but not having a fully conjugated π-electron system) divalent monocyclic or bicyclic cyclic hydrocarbon group, which may include fused, bridged, or spiro ring system, having from 3 to 12 carbon atoms, e.g., having from 3 to 10 carbon atoms, or from 3 to 8 carbon atoms, or from 3 to 6 carbon atoms.

Representative examples include, but are not limited to, cyclopropylene, cyclobutylene, cyclopentylene, cyclopentenylene, cyclohexylene, cyclohexenylene, cycloheptylene, cyclooctylene, decalinylene, octahydropentalenylene, octahydro-1H-indenylene, and spiro-cycloalkylene. The cycloalkylene group may be unsubstituted or substituted. A substituted cycloalkylene group refers to a cycloalkylene group optionally substituted 1-3 times by a substituent(s) (that is, the cycloalkylene group optionally has 1-3 same or different substituent(s)).

In a further embodiment, the substituent can be any one optionally selected from the group consisting of $C_{1-3}$ alkyl, $C_{1-3}$ alkoxy, cyano, trifluoromethyl, heterocyclyl, halogen, amino, hydroxyl, or any combination thereof.

As used herein, the term "heteroaryl" used alone or in combination refers to a 5- to 10-membered monovalent monocyclic or bicyclic aromatic ring containing one or more (eg, from 1 to 6, or from 1 to 5, or from 1 to 4, or from 1 to 3) heteroatoms independently selected from the group consisting of oxygen, nitrogen and sulfur. Representative examples of such heteroaryl groups include, but are not limited to, furyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidinyl, pyridazinyl, pyrazinyl, indolyl, isoindolyl, benzofuranyl, isobenzofuranyl, benzothienyl, indazolyl, benzimidazolyl, benzoxazolyl, benzoisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolyl, isoquinolyl, naphthyridinyl, cinnolinyl, quinazolinyl, quinoxalinyl, phthalazinyl, pyrazolo[1,5-a]pyridyl, pyrazolo[1,5-a]pyrimidyl, imidazo[1,2-a]pyridyl, 1H-pyrrolo[3,2-b]pyridyl, 1H-pyrrolo[2,3-b]pyridyl, 4H-fluoro[3,2-b]pyrrolyl, pyrrolo[2,1-b]thiazolyl and imidazo[2,1-b]thiazolyl. According to a clear definition, heteroaryl groups may be unsubstituted or substituted. A substituted heteroaryl group refers to a heteroaryl group optionally substituted 1-3 times with a substituent(s) (that is, the heteroaryl group optionally has 1-3 same or different substituent(s)). In a further embodiment, the substituent can be any one optionally selected from the group consisting of $C_{1-3}$ alkyl, $C_{1-3}$ alkoxy, cyano, trifluoromethyl, heterocyclyl, halogen, amino, hydroxyl, or any combination thereof.

As used herein, the term "heteroarylene" used alone or in combination refers to a 5- to 10-membered monocyclic or bicyclic divalent aromatic ring group containing one or more (eg, from 1 to 6, or from 1 to 5, or from 1 to 4, or from 1 to 3) heteroatoms independently selected from the group consisting of oxygen, nitrogen, and sulfur. Representative examples of such heteroarylene groups include, but are not limited to, furanylene, oxazolylene, isoxazolylene, oxadiazolylene, thienylene, thiazolylene, isothiazolylene, thiadiazolylene, pyrrolylene, imidazolylene, triazolylene, pyridylene, pyrimidinylene, pyridazinylene, pyrazinylene, indolylene, isoindolylene, benzofuranylene, isobenzofuranylene, benzothienylene, indazolylene, benzimidazolylene, benzoxazolylene, benzoisoxazolylene, benzothiazolylene, benzoisothiazolylene, benzotriazolylene, benzo[2,1,3]oxadiazolylene, benzo[2,1,3]thiadiazolylene, benzo[1,2,3]thiadiazolylene, quinolylene, isoquinolylene, naphthyridinylene, cinnolinylene, quinazolinylene, quinoxalinylene, phthalazinylene, pyrazolo[1,5-a]pyridinylene, pyrazolo[1,5-a]pyrimidinylene, imidazo[1,2-a]pyridinylene, 1H-pyrrolo[3,2-b]pyridinylene, 1H-pyrrolo[2,3-b]pyridinylene, 4H-fluoro[3,2-b]pyrrolylene, pyrrolo[2,1-b]thiazolylene, and imidazo[2,1-b]thiazolylene. According to a clear definition, the heteroarylene group may be unsubstituted or substituted. A substituted heteroarylene group refers to a heteroarylene group optionally substituted 1-3 times by a substituent(s) (that is, the heteroarylene group optionally has 1-3 same or different substituent(s)). In a further embodiment, the substituent can be any one optionally selected from the group consisting of $C_{1-3}$ alkyl, $C_{1-3}$ alkoxy, cyano, trifluoromethyl, heterocyclyl, halogen, amino, hydroxyl, or any combination thereof.

As used herein, the term "heterocyclyl" used alone or in combination refers to a 4- to 6-membered saturated monocyclic monovalent cyclic hydrocarbon group containing one or more (e.g., from 1 to 4, or from 1 to 3, or from 1 to 2, or 1) heteroatoms independently selected from the group consisting of sulfur, oxygen, and nitrogen. Examples of the heterocyclyl include, but are not limited to, azetidinyl, oxetanyl, pyrrolidinyl, imidazolidinyl, pyrazolidyl, triazolyl, tetrahydrofuranyl, tetrahydrothienyl, tetrahydrothiopyranyl, oxazolidinyl, thiazolidinyl, piperidinyl, piperazinyl, morpholinyl, thiomorpholinyl, and dioxanyl. The heterocyclyl may be unsubstituted or substituted as explicitly defined. A substituted heterocyclyl group refers to a heterocyclyl group optionally substituted 1-3 times with a substituent(s) (that is, the heterocycloalkylene group optionally has 1-3 same or different substituent(s)). In a further embodiment, the substituent may be any one optionally selected from the group consisting of $C_1$-3 alkyl, $C_{1-3}$ alkoxy, cyano, trifluoromethyl, heterocyclyl, halogen, amino, hydroxy, or any combination thereof.

As used herein, the term "heterocyclylene" used alone or in combination refers to a 4- to 6-membered saturated monocyclic divalent cyclic hydrocarbon group containing one or more (e.g., from 1 to 4, or from 1 to 3, or from 1 to 2, or 1) heteroatoms independently selected from the group consisting of sulfur, oxygen, and nitrogen. Examples of the heterocyclylene group include, but are not limited to, azetidinylene, oxetanylene, pyrrolidinylene, imidazolidylene, pyrazolidylene, triazolylend, tetrahydrofuranylene, tetrahydrothienylene, tetrahydrothiopyranylene, oxazolidinylene, thiazolidinylene, piperidinylene, piperazinylene, morpholinylene, thiomorpholinylene, and dioxanylene. The heterocyclylene group may be unsubstituted or substituted as explicitly defined. A substituted heterocycloalkylene refers to a heterocycloalkylene group optionally substituted 1-3 times by a substituent(s) (that is, the heterocycloalkylene group optionally has 1-3 same or different substituent(s)). In a further embodiment, the substituent can be any one optionally selected from the group consisting of $C_{1-3}$ alkyl, $C_{1-3}$ alkoxy, cyano, trifluoromethyl, heterocyclyl, halogen, amino, hydroxyl, or any combination thereof.

As used herein, the term "spiro-cycloalkylene" used alone or in combination refers to a divalent alicyclic hydrocarbon group derived by removing two hydrogen atoms from any one or two free valence carbon atom(s) of the alicyclic hydrocarbon group in which two rings share one common carbon atom. Representative examples include, but are not limited to, spiro[3.3]heptanylene (for example

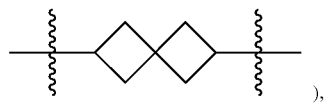 [SMILES: *C1CC2(C1)CC(*)C2]

), spiro[4.5]decanylene, spiro[5.5]undecanylene, 4-methyl-spiro[2.4] heptanylene etc.

As used herein, the term "alkynyl" used alone or in combination refers to a linear or branched monovalent hydrocarbon group containing one or more carbon-carbon triple bonds and containing from 2 to 10 (e.g., from 2 to 6, or from 2 to 4, or from 2 to 3, or 2) carbon atoms. Examples of the alkynyl include, but are not limited to, ethynyl, 1-propynyl, 1-butynyl, and 1,3-dialkynyl.

As used herein, the term "alkynylene" used alone or in combination refers to a linear or branched divalent hydrocarbon group containing one or more carbon-carbon triple bonds and containing from 2 to 10 (e.g., from 2 to 6, or from 2 to 4, or from 2 to 3, or 2) carbon atoms. Examples of the alkynylene group include, but are not limited to, ethynylene, 1-propynylene, 1-butynylene, and 1,3-diynylene.

As used herein, the term "alkenyl" used alone or in combination refers to a linear or branched monovalent hydrocarbon group containing one or more carbon-carbon double bonds and containing from 2 to 10 (e.g., from 2 to 6, or from 2 to 4, or from 2 to 3, or 2) carbon atoms. Examples of the alkenyl group include, but are not limited to, vinyl, 1-propenyl, and 1-butenyl.

As used herein, the term "alkenylene" used alone or in combination refers to a linear or branched divalent hydrocarbon group containing one or more carbon-carbon double bonds and containing from 2 to 10 (e.g., from 2 to 6, or from 2 to 4, or from 2 to 3, or 2) carbon atoms. Examples of the alkenylene group include, but are not limited to, vinylidene (e.g., —CH=CH—), 1-propenylene, and 1-butenylene.

Salts or pharmaceutically acceptable salts, enantiomers, stereoisomers, solvates, polymorphs of the compounds of formula I according to the disclosure are also encompassed within the scope of the invention.

In all embodiments of the disclosure, the salt or pharmaceutically acceptable salt of the compound of formula I refers to a non-toxic inorganic or organic acid and/or base addition salt. Examples include, but are not limited to, sulfate, hydrochloride, citrate, maleate, sulfonate, or p-toluenesulfonate etc.

"Pharmaceutically acceptable carrier" refers to a pharmaceutically acceptable material, such as a filler, stabilizer, dispersant, suspending agent, diluent, excipient, thickener, solvent, or encapsulating material, with which the useful compounds according to the present disclosure are carried or transported into or administered to a patient so that they can perform their intended function. Generally, such constructs are carried or transported from one organ or part of the body to another organ or part of the body. The carrier is compatible with the other ingredients of the formulation, including the compounds useful in the present disclosure, and is not harmful to the patient, and the carrier must be "acceptable." Some examples of materials that can be used as pharmaceutically acceptable carriers include, but are not limited to, sugars such as lactose, glucose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository wax; oils such as peanut oil, cottonseed oil, safflower oil, sesame oil, olive oil, corn oil and soybean oil; glycols such as propylene glycol; polyols such as glycerol, sorbitol, mannitol, and polyethylene glycol; esters such as ethyl oleate and ethyl laurate; agar; buffers such as magnesium hydroxide and aluminum hydroxide; surfactant phosphate buffer solution; and other common non-toxic compatible substances used in pharmaceutical preparations.

A "therapeutically effective amount" of a compound of the disclosure depends on the age, sex, and weight of the patient, the patient's current medical condition, and the cancer progression of the patient being treated. Those skilled in the art will be able to determine a suitable dosage based on these and other factors.

The term "room temperature" used herein refers to the ambient temperature, such as a temperature of 20-30° C.

The compound developed by the present invention belongs to a specific protein-degrading agent, which is composed of three parts: a target protein anchoring part, a protein degradation system (such as an E3 ligase) recruitment part, and a linker. In the present disclosure, an inhibitor targeting ALK protein is selected as an anchoring part, and an E3 ligase ligand is combined with an ALK protein inhibitor through a linker to develop a degradation agent targeting ALK protein. Through the specific recognition of target proteins by ALK-TKIs, the tyrosine kinase activity of ALK is inhibited, and at the same time, E3 ligase specifically ubiquitinates ALK protein to achieve degradation and elimination, and finally can remove the target protein from tumor cells. Because ALK mutation-positive lung cancer cells are highly dependent on the presence and activity of ALK protein, completely degrading ALK protein and inhibiting residual ALK activity can not only inhibit tumorigenesis and progression, but also potentially overcome resistance to targeted drugs. In addition, the degrading agent designed and developed by the present invention can also target and inhibit other tyrosine kinase receptors including ROS1, c-MET, insulin receptor, IGFIR and EGFR with lung cancer driving mutation, etc. The compounds developed by the present invention provide potentially alternative treatments for cancers that are positive for these targets. This research will provide a new treatment strategy for lung cancer patients in the context of precision medicine.

EXAMPLES

In the following description, numerous specific details are set forth in order to provide a thorough understanding of the invention. The invention may be practiced without some or all of these specific details. In other cases, well-known process operations have not been described in detail in order not to unnecessarily obscure the present invention. Although the present invention will be described in conjunction with specific embodiments, it should be understood that this is not intended to limit the present invention to these embodiments.

The following abbreviations are used throughout the description and examples:
Boc Tert-butoxycarbonyl
Con. concentration
DCM Dichloromethane
DMF N, N-dimethylformamide
DMSO Dimethyl sulfoxide
DIPEA N, N-diisopropylethylamine
EDCI 1-(3-Dimethylaminopropyl)-3-ethylcarbodiimide
ESI Electrospray ionization
equiv equivalent
EtOH Ethanol
HOAT 1-hydroxy-7-azobenzotriazole
HPLC High performance liquid chromatography
HRMS High resolution mass spectrometry
LC-MS Liquid chromatography-mass spectrometry
LRMS Low resolution mass spectrometry
LC Liquid chromatography
Me methyl
MeCN Acetonitrile
MeOH Methanol
MS Mass spectrometry
MW microwave
NMM N-methylmorpholine
NMP N-methylpyrrolidone
$^1$H NMR Proton nuclear magnetic resonance
rt Room temperature
TFA Trifluoroacetate
TLC Thin layer chromatography
TMS Trimethylsilyl
Xantphos; or X-Phos 4,5-bis (diphenylphosphine)-9,9-dimethylxanthene In the present disclosure, the $^1$H NMR spectrum is measured using a Bruker-500 MHz nuclear magnetic resonance instrument, and $CD_3OD$ containing 0.1% TMS is used as a solvent, wherein the $^1$H NMR spectrum uses CD3OD (δ=3.31 ppm) as an internal standard; or $CDCl_3$ containing 0.1% TMS is used as the solvent, wherein the $^1$H NMR spectrum uses $CDCl_3$ (δ=7.26 ppm) as the internal standard; or DMSO-$d_6$ containing 0.03% TMS as the solvent, wherein the $^1$H NMR spectrum uses DMSO-$d_6$ (δ=2.50 ppm) as the internal standard; LRMS spectrum was measured on an AB Triple 4600 mass spectrometer, HPLC preparation was measured on a SHIMADZU LC-20AP type instrument, and HPLC purity was measured on a SHIMADZU LC-30AP or Waters 1525 type instrument. All reactions were performed in the air without special instructions; the reactions were followed by TLC or LC-MS.

Solvents and reagents are processed as follows:
The solvents used in the reaction: DCM, DMF, anhydrous EtOH, and anhydrous MeOH were purchased from Chinese Sinopharm Group;
Preparative grade $CH_3CN$ and deionized water are used in HPLC preparation;
Unless otherwise stated, Alectinib, Alectinib analogue A, Crizotinib, Ceritinib, Brigatinib, TAE684 (NVP-TAE684), ASP3026, GSK1838705A, AZD3463, Entrectinib (RXDX-101), Ensartinib (X-396)) and various kinds of carbon chain linking unit (linker group of the compound of the formula (I) of the present disclosure) were directly purchased.

Other reagents and medicines were purchased from the manufacturer and used directly without special instructions.

General Synthesis Procedure
General Synthesis Procedure for Brigatinib Analogue a, B, C (ALK Inhibitors)

Scheme 1

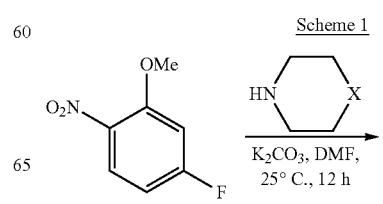

-continued

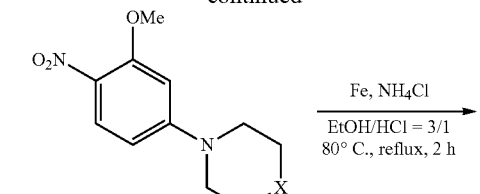

X = NHBoc, SIAIS1197111
X = CHNH₂Boc, SIAIS151054
X = CHpiperazineBoc, SIAIS151059

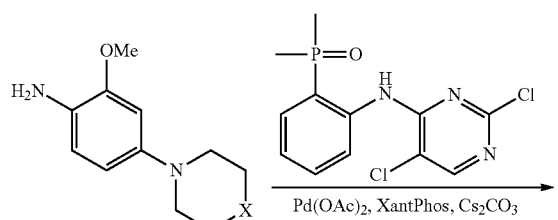

X = NHBoc, SIAIS1197129
X = CHNH₂Boc, SIAIS151062
X = CHpiperazineBoc, SIAIS164003

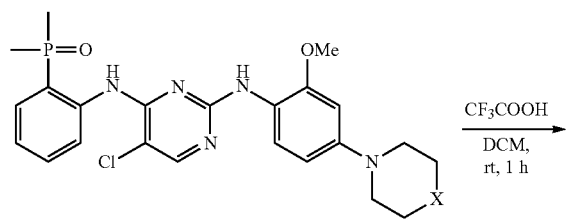

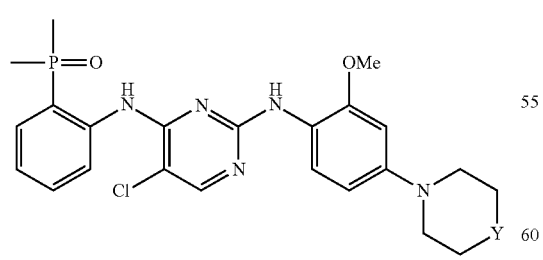

Y = NH, SIAIS1197135, Brigatinib Analogue A
Y = CHNH₂, SIAIS151101, Brigatinib Analogue B
Y = CHpiperizine, SIAIS164005, Brigatinib Analogue C Wherein group X and Y are as shown in Scheme 1.

General Synthesis Procedure for Alectinib Analogue B, C (ALK Inhibitors):

Scheme 2

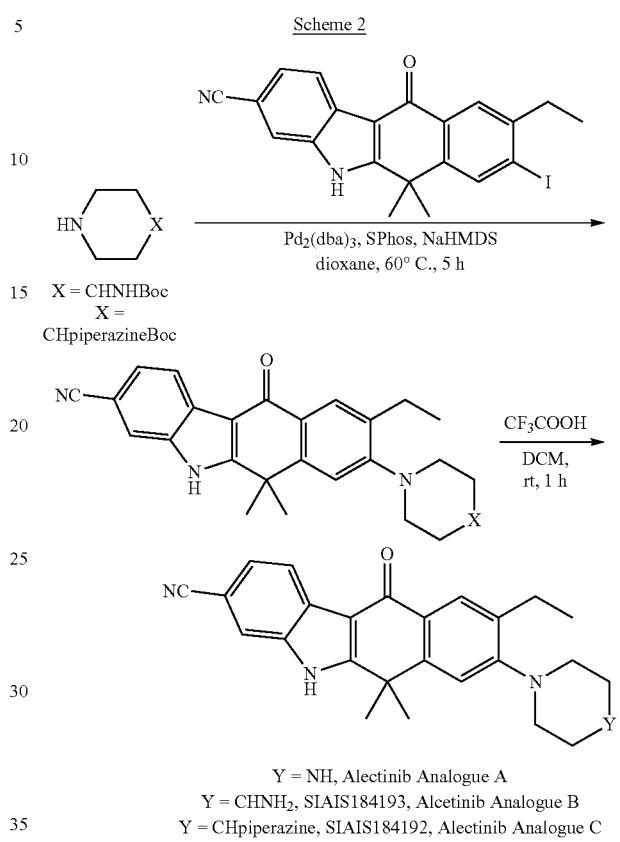

Y = NH, Alectinib Analogue A
Y = CHNH₂, SIAIS184193, Alcetinib Analogue B
Y = CHpiperazine, SIAIS184192, Alectinib Analogue C Wherein group X and Y are as shown in Scheme 2.

In addition, the Alectinib amalogue A (9-ethyl-6,6-dimethyl-11-oxo-8-(piperazin-1-yl)-6,11-dihydro-5H-benzo[b]carbazole-3-carbonitrile) can also be purchased directly.

General Synthesis Procedure for Intermediate LM (Pomalidomide PEG Linker):

Scheme 3

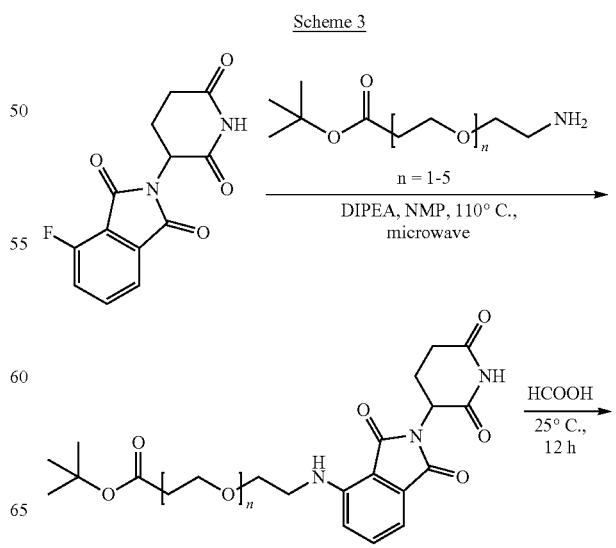

423

-continued

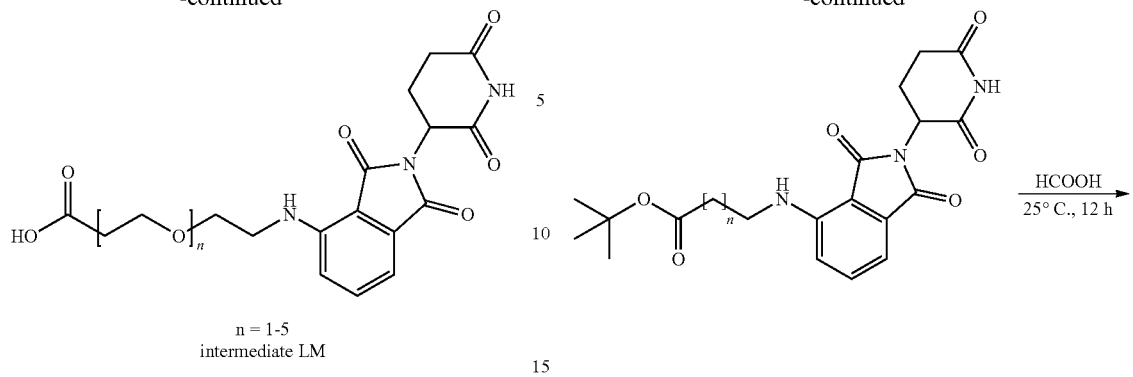

n = 1-5
intermediate LM

Wherein n is an integer of from 1 to 5, as shown in Scheme 3.

General Synthesis Procedure for Intermediate LM (Pomalidomide Alkyl Carbon Chain Linker)

Scheme 4

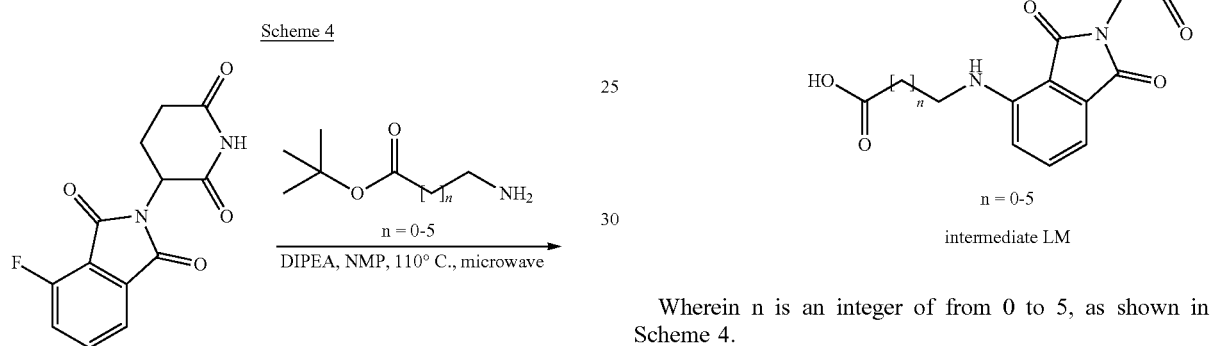

424

-continued n = 0-5
intermediate LM

Wherein n is an integer of from 0 to 5, as shown in Scheme 4.

General Synthesis Procedure for Intermediate LM (VHL-1 PEG Linker):

Scheme 5

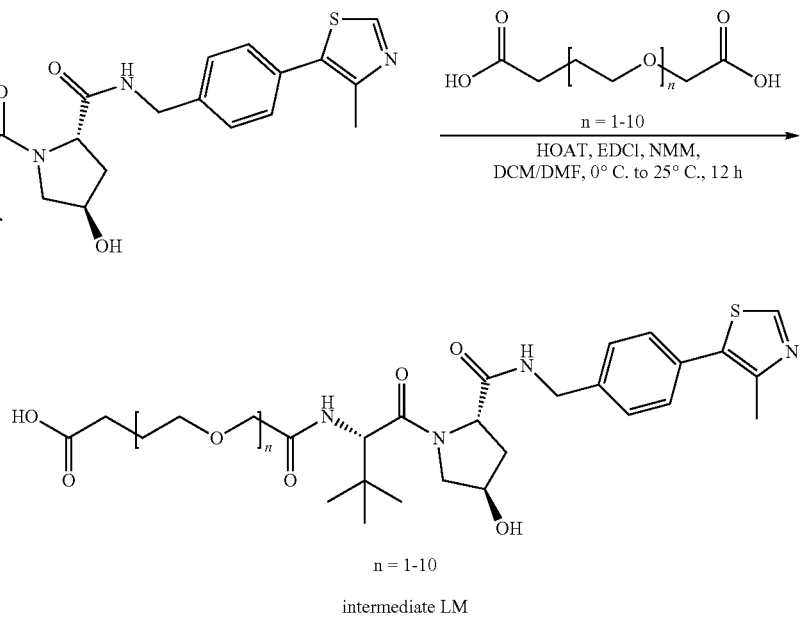

n = 1-10
intermediate LM

Wherein n is an integer of from 0 to 10, as shown in Scheme 5.

General Synthesis Procedure for Intermediate LM (VHL-1 Alkyl Carbon Chain Linker):

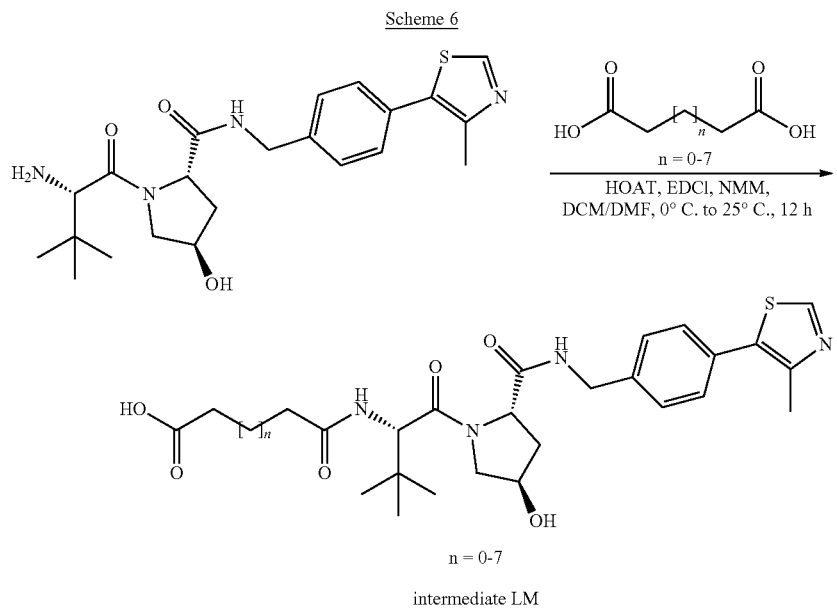

Scheme 6

Wherein n is an integer of from 0 to 7, as shown in Scheme 6.

General Synthesis Procedure for Intermediate LM (Lenalidomide Carbonyl Alkyl Carbon Chain Linker):

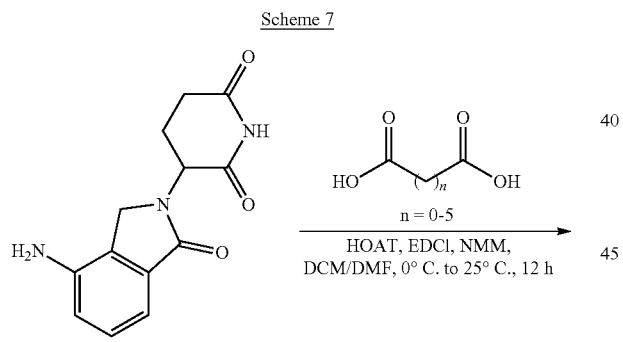

Scheme 7

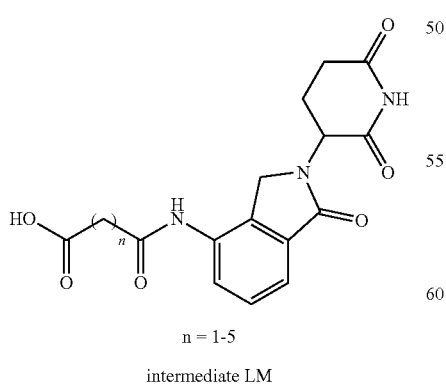

intermediate LM

Wherein n is an integer of from 1 to 5, as shown in Scheme 7.

General Synthesis Procedure for Intermediate LM (Lenalidomide Alkyl Carbon Chain Linker)

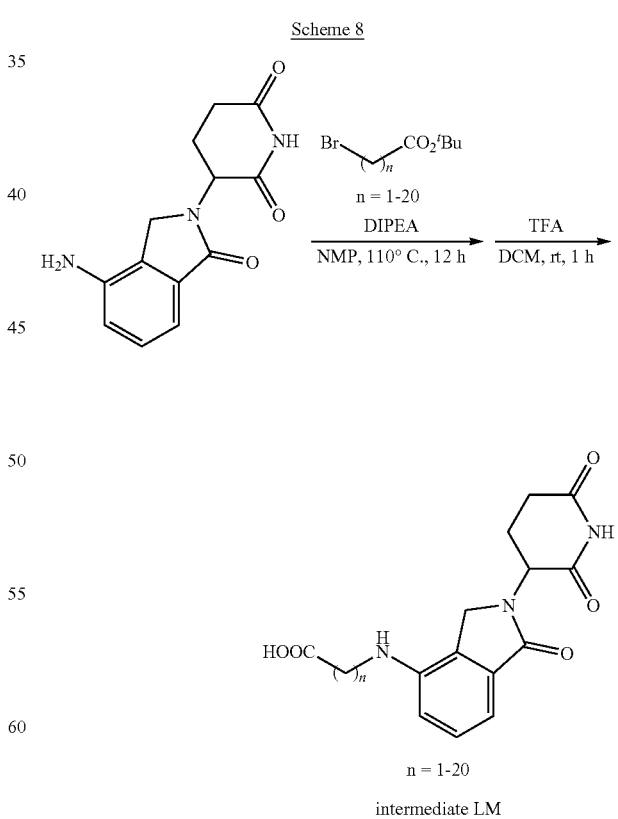

Scheme 8

Wherein n is an integer of from 1 to 20, as shown in Scheme 8.

General Synthesis Procedure for Special Intermediate LM (SIAIS151103):
Scheme 9
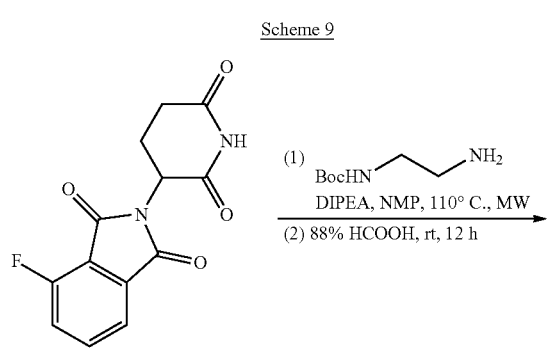
SIAIS151103
intermediate LM
General Synthesis Procedure for Special Intermediate LM (SIAIS164119):
Scheme 10
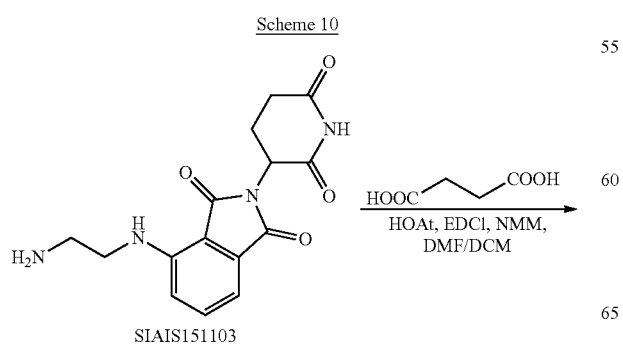
SIAIS151103
-continued
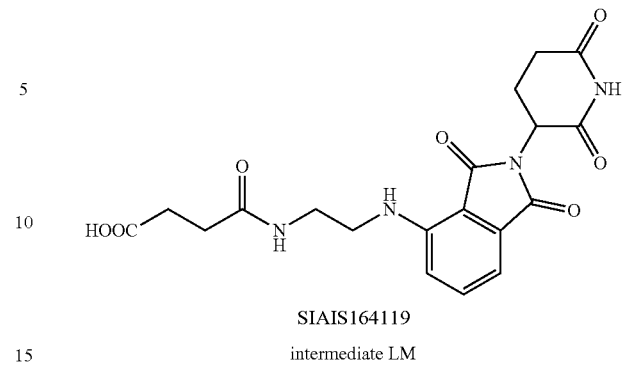
SIAIS164119
intermediate LM
General Synthesis Procedure for Special Intermediate LM (SIAIS164050):
Scheme 11
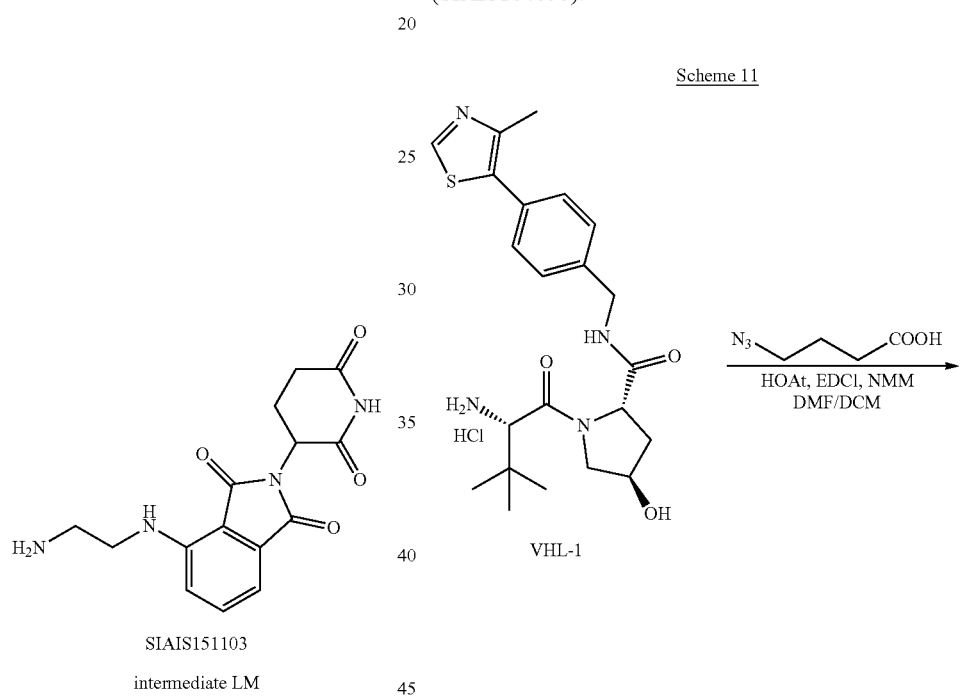
VHL-1
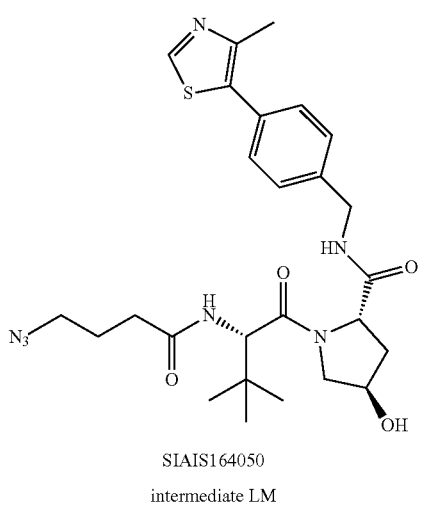
SIAIS164050
intermediate LM General Synthesis Procedure for Special Intermediate LM (SIAIS164128):
Scheme 12
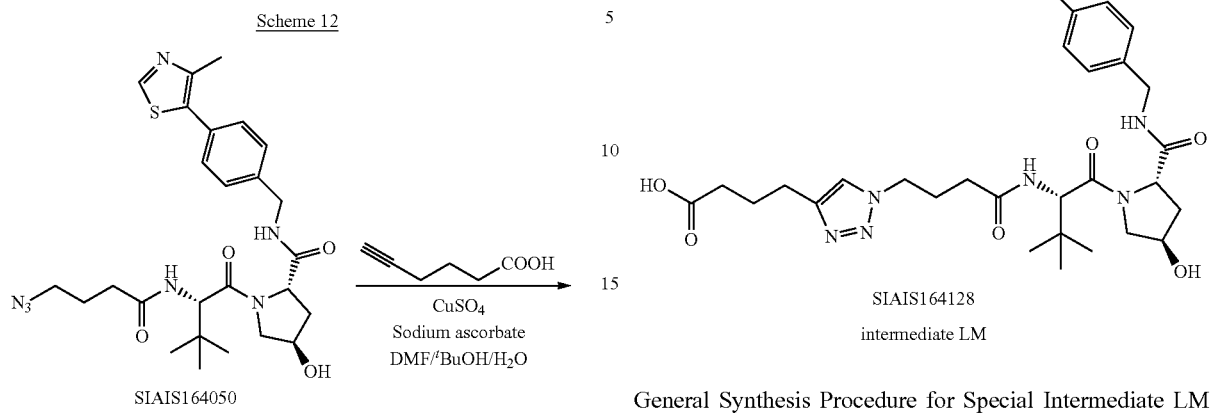
General Synthesis Procedure for Special Intermediate LM (SIAIS219048):
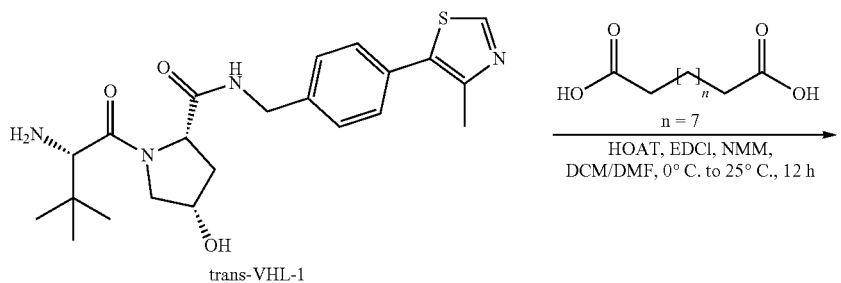
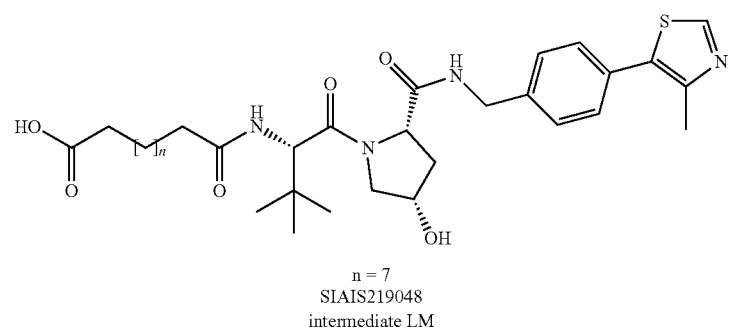
Wherein n is 7, as shown in Scheme 13.

General Synthesis Procedure for Special Intermediate LM (SIAIS172147):
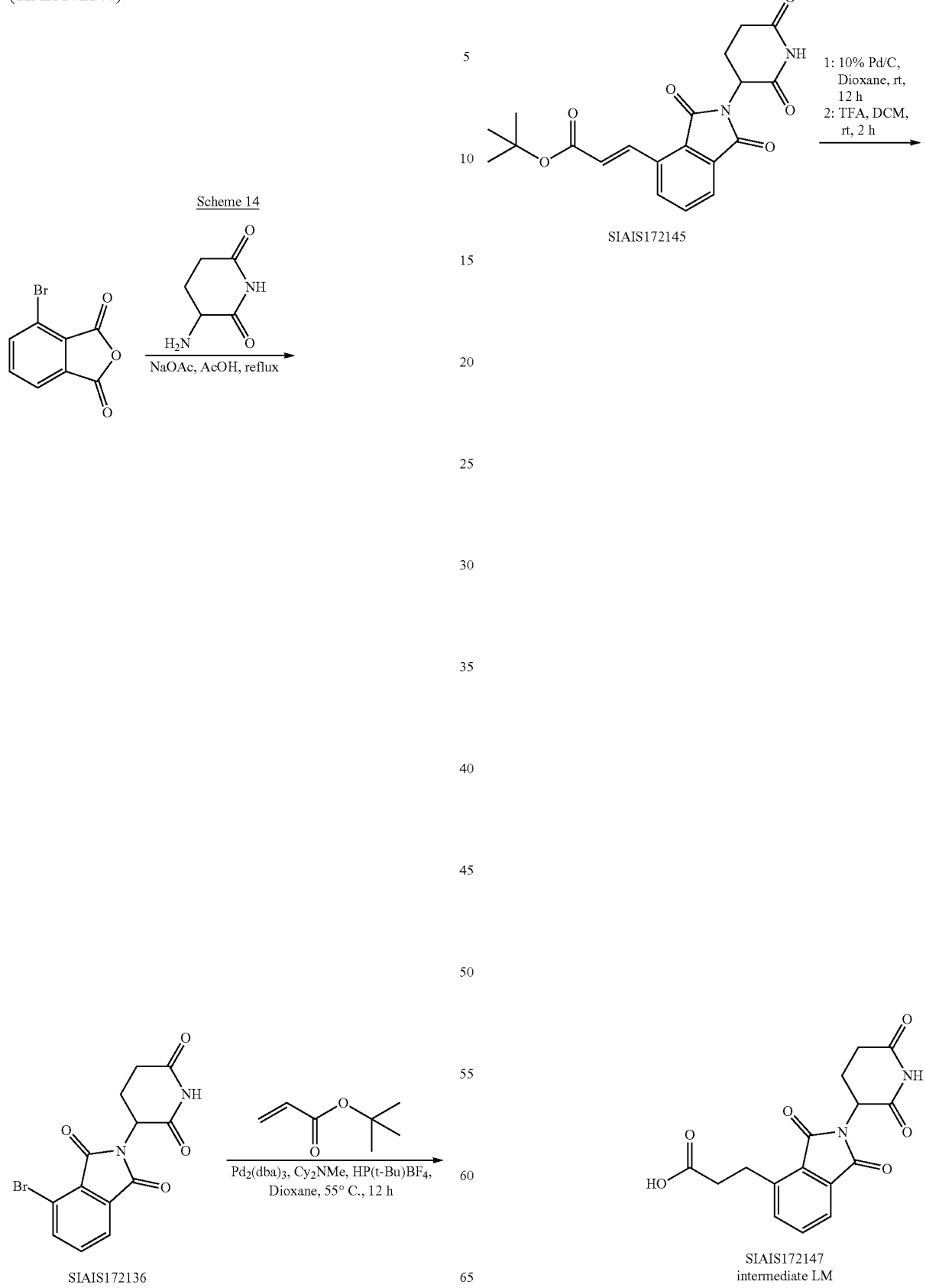

General Synthesis Procedure for Compounds in this Patent:
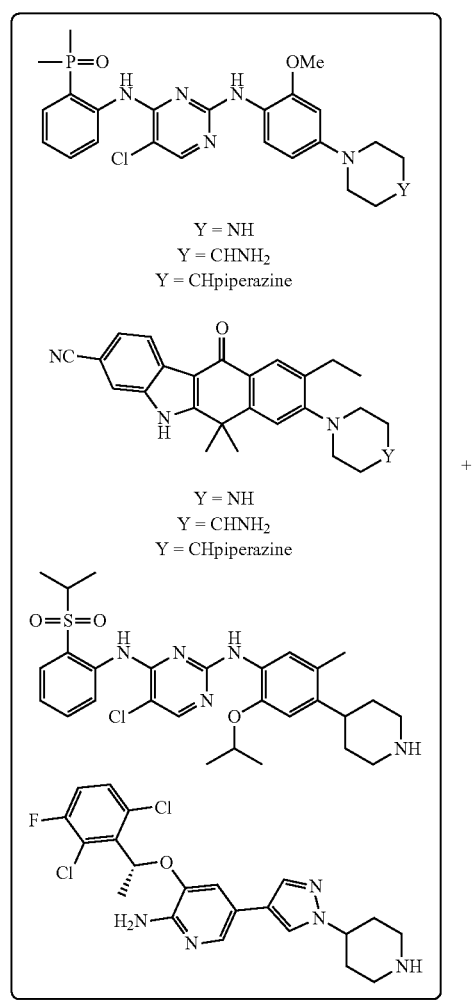
Scheme 15
ALK inhibitors -continued
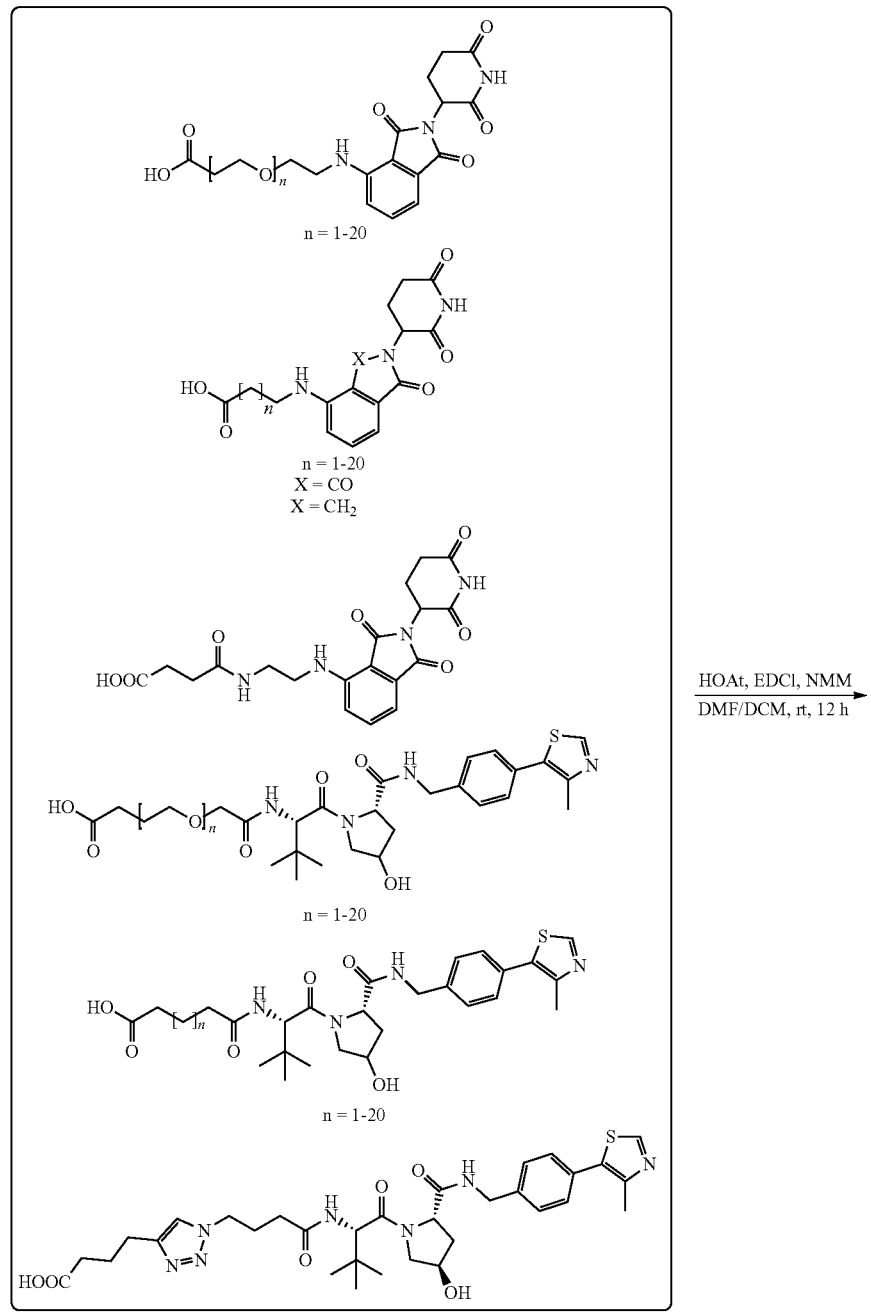
LM

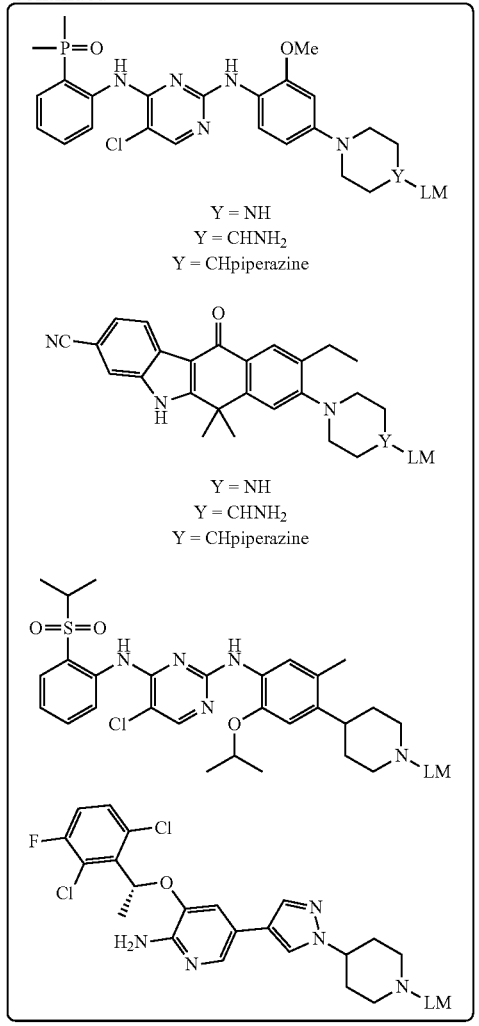

Compound in this dicvovery

INTERMEDIATE EXAMPLES

Intermediate Example 1: Synthesis of Brigatinib Analogue A (SIAIS1197135)

Brigatinib Analogue A (SIAIS1197135) was synthesized according to scheme 1.

Synthesis of tert-butyl 4-(3-methoxy-4-nitrophenyl)piperazine-1-carboxylate (SIAIS1197111)

To a solution of 5-fluoro-2-nitroanisole (7 g, 40.9 mmol) in DMF (60 mL) were added $K_2CO_3$ (8.4 g, 60.8 mmol) and tert-butyl piperazine-1-carboxylate (9.1 g, 48.9 mmol) at room temperature under air. After stirring at the same temperature overnight, the reaction mixture was quenched with water, extracted with ethyl acetate, washed with brine and dried over anhydrous $Na_2SO_4$. The solvent was evaporated under the reduced pressure and the residue was purified by recrystallization (eluent: petroleum ether/ethyl acetate=5:1) to afford SIAIS1197111 in 80% yield (11.1 g) as a yellow solid. $^1$H NMR (500 MHz, DMSO) δ 7.89 (d, J=9.3 Hz, 1H), 6.57 (d, J=9.5 Hz, 1H), 6.52 (s, 1H), 3.90 (s, 3H), 3.46 (s, 8H), 1.42 (s, 9H). HRMS (ESI) calcd for $C_{16}H_{24}N_3O_5^+$ $[M+H]^+$, 338.1710; found, 338.1610.

Synthesis of tert-butyl 4-(4-amino-3-methoxyphenyl)piperazine-1-carboxylate (SIAIS1197129)

To a stirred solution of SIAIS1197111 (10 g, 29.6 mmol) in EtOH (90 mL) and $H_2O$ (30 mL) were added $NH_4Cl$ (6.3 g, 118.6 mmol) and Fe powder (8.3 g, 148.2 mmol). Then the resulting mixture was refluxed at 80° C. for 2 h under an atmosphere of nitrogen. When the reaction was complete, the crude mixture was cooled down to room temperature, filtered by silica, after solvent evaporation, extracted with DCM (3×50 mL), the combined organic layer was washed with brine (20 mL), then dried over $Na_2SO_4$ and concentrated in vacuum to afford SIAIS1197129 in 85% yield (7.7 g) as a gray solid. $^1$H NMR (500 MHz, MeOD) δ 6.72 (d, J=8.3 Hz, 1H), 6.63 (d, J=2.2 Hz, 1H), 6.47 (d, J=7.0 Hz, 1H), 3.86 (s, 3H), 3.57 (s, 4H), 2.99 (s, 4H), 1.50 (s, 9H). HRMS (ESI) calcd for $C_{16}H_{26}N_3O_3^+$ $[M+H]^+$, 308.1969; found, 308.1882.

Synthesis of (2-((5-chloro-2-((2-methoxy-4-(piperazin-1-yl)phenyl)amino)pyrimidin-4-yl)amino)phenyl) dimethylphosphine oxide. (SIAIS1197135)

To a solution of 2,5-dichloro-N-(2-(dimethylphosphoryl)phenyl)pyrimidin-4-amine (2 g, 6.3 mmol) in DMF (30 mL) were added SIAIS1197129 (2.4 g, 7.8 mmol), Pd(OAc)$_2$ (176 mg, 0.78 mmol), Xantphos (810 mg, 1.4 mmol) and Cs$_2$CO$_3$ (6.4 g, 19.6 mmol) in microwave tube, the solution was purged and refilled with nitrogen three times. Then the mixture was stirred at 110° C. for 2 h in the microwave. After the starting material was consumed, the reaction mixture was filtered through a pad of silica gel and most of the solvent of the filtrate was removed under the reduced pressure. Then the mixture was quenched with water, extracted with ethyl acetate, washed with water and brine, dried over anhydrous Na$_2$SO$_4$. The solvent was evaporated under the reduced pressure and the residue was purified by reverse phase ISCO (C18) to give the title compound (900 mg) as a brown solid.

To a solution of above compound (900 mg) in DCM (6 mL) was added TFA (2 mL) under air. The resulting solution was stirred at room temperature for 1 h. Then most of the solvent was removed under the reduced pressure, the pH of the solution was adjusted to 8-9 with saturated NaHCO$_3$ solution, then extracted with DCM, dried over anhydrous Na$_2$SO$_4$. The solvent was evaporated under the reduced pressure and the residue was purified by reverse phase ISCO (C18), eluent (v/v): MeOH/water=10%-100%, to afford SIAIS1197135 as a yellow solid (701 mg, 23% yield over two steps). $^1$H NMR (500 MHz, MeOD) δ 8.32 (dd, J=8.2, 4.4 Hz, 1H), 8.04 (s, 1H), 7.70 (d, J=8.7 Hz, 1H), 7.61 (dd, J=14.1, 7.7 Hz, 1H), 7.52 (t, J=7.9 Hz, 1H), 7.26 (t, J=7.5, 1H), 6.67 (d, J=2.5 Hz, 1H), 6.45 (dd, J=8.8, 2.5 Hz, 1H), 3.86 (s, 3H), 3.24-3.17 (m, 4H), 3.17-3.11 (m, 4H), 1.83 (d, J=13.5 Hz, 6H). HRMS (ESI) calcd for C$_{23}$H$_{29}$ClN$_6$O$_2$P$^+$ [M+H]$^+$, 487.1773; found, 487.1773.

Intermediate Example 2: Synthesis of Brigatinib Analogue B

Brigatinib Analogue B was synthesized according to scheme 1, using similar procedures for the preparation of Brigatinib Analogue A in Intermediate Example 1, the synthesis data and structural characterization data are as follows:

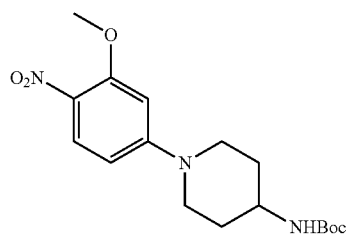

tert-butyl (1-(3-methoxy-4-nitrophenyl)piperazine-4-yl) carbamate (SIAIS151054)

(yellow solid, 1.81 g, 88%) $^1$H NMR (500 MHz, CDCl$_3$) δ 7.99 (t, J=8.9 Hz, 1H), 6.41 (dd, J=9.4, 2.5 Hz, 1H), 6.30 (d, J=2.5 Hz, 1H), 4.49 (s, 1H), 3.94 (s, 3H), 3.86-3.82 (m, 2H), 3.71 (s, 1H), 3.09-3.00 (m, 2H), 2.11-2.03 (m, 2H), 1.89-1.75 (m, 2H), 1.45 (s, 9H).

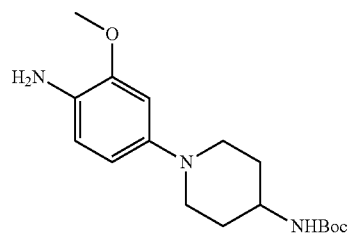 [SMILES: COc1cc(N2CCC(NC(=O)OC(C)(C)C)CC2)ccc1[N+](=O)[O-]]

tert-butyl (1-(4-amino-3-methoxyphenyl)piperazine-4-yl)carbamate (SIAIS151062)

(gray solid, 411.6 mg, 90%) $^1$H NMR (500 MHz, DMSO) δ 6.82 (d, J=7.6 Hz, 1H), 6.50 (d, J=8.5 Hz, 1H), 6.48 (d, J=2.5 Hz, 1H), 6.28 (dd, J=8.4, 2.4 Hz, 1H), 4.20 (s, 2H), 3.73 (s, 3H), 3.33-3.26 (m, 3H), 2.56-2.50 (m, 2H), 1.77 (d, J=11.4 Hz, 2H), 1.53-1.45 (m, 2H), 1.39 (s, 9H).

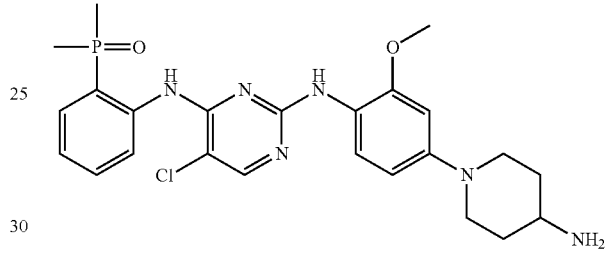

(2-((2-((4-(4-aminopiperidin-1-yl)-2-methoxyphenyl)amino)-5-chloropyrimidin-4-yl)amino)phenyl) dimethylphosphine oxide (SIAIS151101)

(yellow solid, 330 mg, 33% yield over two steps) $^1$H NMR (500 MHz, DMSO) δ 8.49 (s, 1H), 8.08 (s, 1H), 8.06 (s, 1H), 7.53 (ddd, J=14.0, 7.7, 1.3 Hz, 1H), 7.38-7.32 (m, 2H), 7.10 (t, J=7.1 Hz, 1H), 6.62 (d, J=2.5 Hz, 1H), 6.46 (dd, J=8.7, 2.5 Hz, 1H), 3.75 (s, 3H), 3.65-3.61 (m, 2H), 2.78-2.67 (m, 3H), 1.82-1.79 (m, 2H), 1.78 (s, 3H), 1.75 (s, 3H), 1.42-1.34 (m, 2H). HRMS (ESI) calcd for C$_{24}$H$_{31}$ClN$_6$O$_2$P [M+H]$^+$: 501.1913, found, 501.1900.

Intermediate Example 3: Synthesis of Brigatinib Analogue C

Brigatinib Analogue C was synthesized according to scheme 1, using similar procedures for the preparation of Brigatinib Analogue A in Intermediate Example 1, the synthesis data and structural characterization data are as follows:

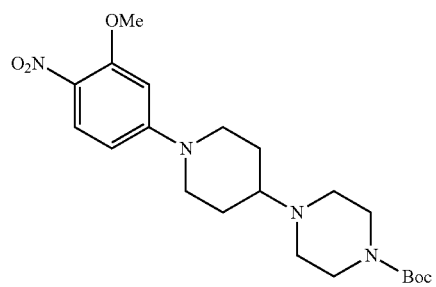 [SMILES: COc1cc(N2CCC(N3CCN(C(=O)OC(C)(C)C)CC3)CC2)ccc1[N+](=O)[O-]]

tert-butyl 4-(1-(3-methoxy-4-nitrophenyl)piperidine-4-yl)piperazine-1-carboxylate (SIAIS151059)

(yellow solid, 1.02 g, 83%) $^1$H NMR (500 MHz, MeOD) δ 7.93 (d, J=9.4 Hz, 1H), 6.55 (dt, J=13.4, 6.7 Hz, 1H), 6.50 (d, J=2.5 Hz, 1H), 4.10 (s, 1H), 4.07 (s, 1H), 3.94 (d, J=6.6 Hz, 3H), 3.43 (s, 4H), 3.02-2.93 (m, 2H), 2.60-2.55 (m, 5H), 2.02-1.95 (m, 2H), 1.57 (qd, J=12.4, 4.0 Hz, 2H), 1.46 (s, 9H). HRMS (ESI) calcd for $C_{21}H_{33}N_4O_5$ [M+H]$^+$: 421.2445, found, 421.2442.

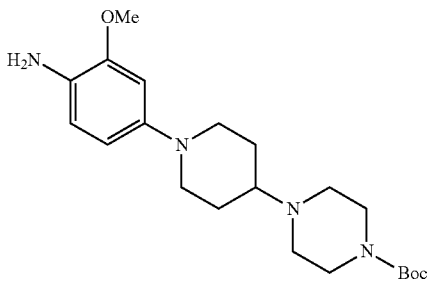

tert-butyl 4-(1-(4-amino-3-methoxyphenyl)piperidine-4-yl)piperazine-1-carboxylate (SIAIS164003)

(gray solid, 745 mg, 79%). $^1$H NMR (500 MHz, MeOD) δ 6.59 (t, J=56.8 Hz, 3H), 3.78 (s, 3H), 3.46 (s, 6H), 2.62 (d, J=4.3 Hz, 6H), 2.42 (s, 1H), 1.98 (s, 2H), 1.69 (d, J=9.7 Hz, 2H), 1.46 (s, 9H). HRMS (ESI) calcd for $C_{21}H_{35}N_4O_3$ [M+H]$^+$: 391.2704, found, 391.3048.

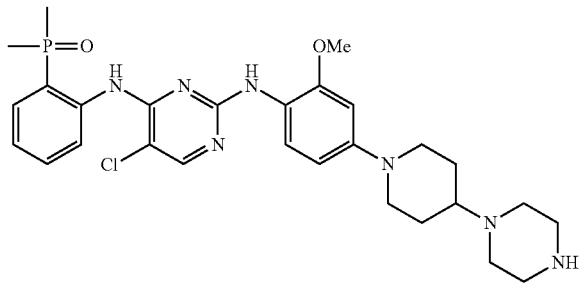 [SMILES: COc1cc(N2CCC(N3CCNCC3)CC2)ccc1Nc1ncc(Cl)c(Nc2ccccc2P(C)(C)=O)n1]

(2-((5-chloro-2-((2-methoxy-4-(4-(piperazin-1-yl)piperidin-1-yl)phenyl)amino)pyrimidin-4-yl)amino)phenyl)dimethylphosphine oxide. (SIAIS164005)

(yellow solid, 350 mg, 37% yield over two steps). $^1$H NMR (500 MHz, MeOD) δ 8.33 (dd, J=8.2, 4.4 Hz, 1H), 8.03 (s, 1H), 7.69-7.64 (m, 1H), 7.60 (ddd, J=14.0, 7.7, 1.4 Hz, 1H), 7.51 (t, J=7.9 Hz, 1H), 7.26 (td, J=7.6, 1.2 Hz, 1H), 6.66 (d, J=2.4 Hz, 1H), 6.45 (dd, J=8.8, 2.5 Hz, 1H), 3.85 (s, 3H), 3.73-3.63 (m, 2H), 3.11-3.02 (m, 4H), 2.79-2.66 (m, 6H), 2.48-2.43 (m, 1H), 1.99 (d, J=12.5 Hz, 2H), 1.84 (d, J=13.5 Hz, 6H), 1.72-1.63 (m, 2H). HRMS (ESI) calcd for $C_{28}H_{38}ClN_7O_2P$ [M+H]$^+$: 570.2508, found, 570.2498.

Intermediate Example 4: Synthesis of Alectinib Analogue B (SIAIS184193)

Alectinib Analogue B 8-(4-aminopiperidin-1-yl)-9-ethyl-6,6-dimethyl-11-oxo-6,11-dihydro-5H-benzo[b]carbazole-3-carbonitrile (SIAIS184193) was synthesized according to scheme 2:

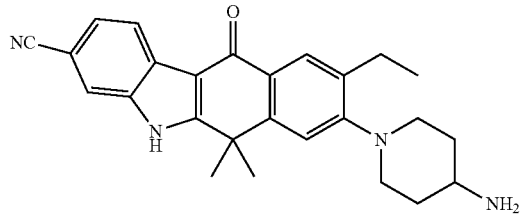 [SMILES: CCc1cc2c(cc1N1CCC(N)CC1)C(C)(C)c1[nH]c3cc(C#N)ccc3c1C2=O]

At room temperature, 9-ethyl-8-iodo-6,6-dimethyl-11-oxo-6,11-dihydro-5H-benzo[b]carbazole-3-carbonitrile (440 mg, 1 mmol), 4-tert-butoxycarbonylaminopiperidine (377 mg, 1.4 mmol), Pd$_2$(dba)$_3$ (45.8 mg, 0.05 mmol), Sphos (82.1 mg, 0.2 mmol) anad dioxane (10 mL) was added sequentially in a 25 mL egg-shaped flask, the mixture was evacuated and replaced with argon, then NaHMDS (4 mL, 4 mmol, 1.0 M in THF) was added, the mixture was heated to 60° C. and stirred for 5 h. When the reaction was complete detected by TLC, the resulting solution was concentrated under reduced pressure and the residue was purified by silica gel chromatography (eluent: hexanes/EA=1:1) to give a brown solid.

To a solution of above brown solid (350 mg) in DCM (6 mL) was added TFA (2 mL) under air. The resulting solution was stirred at room temperature for 1 h. Then most of the solvent was removed under the reduced pressure, the pH of the solution was adjusted to 8-9 with saturated NaHCO$_3$ solution, extracted with DCM, dried over anhydrous sodium sulfate. The solvent was evaporated under reduced pressure and the residue was purified by reverse phase ISCO (C18), eluent (v/v): MeOH/water=10%-100%, to afford the desired product SIAIS184193 as yellow solid (310 mg, 60% over 2 steps). $^1$H NMR (500 MHz, DMSO) δ 12.91 (s, 1H), 8.32 (d, J=8.1 Hz, 1H), 8.17 (d, J=4.2 Hz, 2H), 8.05 (d, J=8.2 Hz, 1H), 8.01 (s, 1H), 7.61 (dd, J=8.1, 1.3 Hz, 1H), 7.38 (s, 1H), 3.22 (d, J=12.2 Hz, 3H), 2.86 (t, J=11.4 Hz, 2H), 2.70 (q, J=7.5 Hz, 2H), 2.06 (d, J=10.0 Hz, 2H), 1.81-1.73 (m, 8H), 1.28 (t, J=7.5 Hz, 3H). HRMS (ESI) calcd for $C_{26}H_{29}N4O$ [M+H]$^+$: 413.2336, found 413.2339.

Intermediate Example 5: Synthesis of Alectinib Analogue C

Alectinib Analogue C was synthesized according to scheme 2, using similar procedures for the preparation of Alectinib Analogue B in Intermediate Example 4, the structural characterization data are as follows:

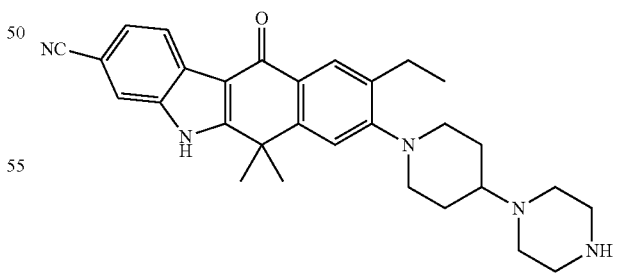

9-ethyl-6,6-dimethyl-11-oxo-8-(4-(piperazin-1-yl)piperidin-1-yl)-6,11-dihydro-5H-benzo[b]carbazole-3-carbonitrile. (SIAIS184192)

(yellow solid, 280 mg, 48%) $^1$H NMR (500 MHz, DMSO) δ 12.76 (s, 1H), 8.32 (d, J=8.1 Hz, 1H), 8.06 (s, 1H), 8.01

(s, 1H), 7.61 (d, J=9.0 Hz, 1H), 6.69 (d, J=8.4 Hz, 1H), 3.94 (s, 8H), 3.61 (s, 1H), 3.49-3.29 (m, 4H), 2.70 (q, J=7.8 Hz, 2H), 1.76 (s, 6H), 1.61 (s, 4H), 1.28 (t, J=7.5 Hz, 3H). HRMS (ESI) calcd for $C_{30}H_{36}N_5O$ $[M+H]^+$: 482.2914, found 482.2911.

Intermediate Example 6: Synthesis of 3-(2-((2-(2,6-dioxopiperidin-3-yl)-1,3-dioxoisoindolin-4-yl)amino)ethoxy)propanoic acid (SIAIS151001)

According to Scheme 3, a solution of 2-(2,6-dioxopiperidin-3-yl)-4-fluoroisoindolin-1,3-dione (5 mmol, 1 equiv), tert-butyl 3-(2-aminoethoxy)propionate (6 mmol, 1.2 equiv) and DIPEA (25 mmol, 5 equiv) in NMP (8 mL) was stirred in a 30 mL microwave tube for 10 min at room temperature, then charged with argon and heated to 110° C. in a microwave reactor for 2 h. After cooling to RT, the reaction mixture was poured into 90% saline, extracted with EA (4×50 mL), the combined organic phase was washed with water (2×30 mL), brine (50 mL), dried over anhydrous sodium sulfate and concentrated under reduced pressure. The resulting residue was purified by silica gel chromatography (eluent: hexanes/EA=1:1) to give the desired tert-butyl ester intermediate. This intermediate was treated with 88% formic acid (20 mL) overnight at room temperature. After concentration under reduced pressure and freeze-drying, the desired product SIAIS151001 was obtained as yellow solid (1.0 g, 48% yield). $^1$H NMR (500 MHz, DMSO) δ 12.17 (s, 1H), 11.09 (s, 1H), 7.57 (dd, J=8.5, 7.5 Hz, 1H), 7.13 (d, J=8.6 Hz, 1H), 7.04 (d, J=7.0 Hz, 1H), 6.59 (t, J=5.7 Hz, 1H), 5.05 (dd, J=12.8, 5.4 Hz, 1H), 3.65 (t, J=6.3 Hz, 2H), 3.59 (t, J=5.5 Hz, 2H), 3.46 (q, J=5.5 Hz, 2H), 2.91-2.83 (m, 1H), 2.61-2.52 (m, 2H), 2.46 (t, J=6.3 Hz, 2H), 2.05-2.00 (m, 1H); HRMS (ESI) calcd for $C_{18}H_{20}N_3O_7^+$ $[M+H]^+$, 390.1301; found, 390.1261.

Intermediate Example 7: Synthesis of 3-(2-(2-((2-(2,6-dioxopiperidin-3-yl)-1,3-dioxoisoindolin-4-yl)amino)ethoxy)ethoxy)propanoic acid (SIAIS151004)

According to the procedures for the preparation of Intermediate Example 6, tert-Butyl 3-(2-(2-aminoethoxy)ethoxy)propanoate was used to prepare SIAIS151004 (yellow solid, 0.95 g, 51% yield). $^1$H NMR (500 MHz, DMSO) δ 11.09 (s, 1H), 7.58 (dd, J=8.0, 7.5 Hz, 1H), 7.14 (d, J=8.6 Hz, 1H), 7.04 (d, J=7.0 Hz, 1H), 6.60 (t, J=5.7 Hz, 1H), 5.05 (dd, J=12.8, 5.4 Hz, 1H), 3.62-3.58 (m, 4H), 3.56-3.54 (m, 2H), 3.52-3.49 (m, 2H), 3.46 (dd, J=11.1, 5.5 Hz, 2H), 2.92-2.84 (m, 1H), 2.66-2.51 (m, 2H), 2.42 (t, J=6.4 Hz, 2H), 2.06-1.98 (m, 1H); HRMS (ESI) calcd for $C_{20}H_{24}N_3O_8^+$ $[M+H]^+$, 434.1558; found, 434.1445.

Intermediate Example 8: Synthesis of 3-(2-(2-(2-((2-(2,6-dioxopiperidin-3-yl)-1,3-dioxoisoindolin-4-yl)amino)ethoxy)ethoxy)ethoxy)propanoic acid (SIAIS151005)

According to the procedures for the preparation of Intermediate Example 6, tert-Butyl 3-(2-(2-(2-aminoethoxy)ethoxy)ethoxy)propanoate was used to prepare SIAIS151005 (yellow solid, 0.95 g, 61% yield). $^1$H NMR (500 MHz, DMSO) δ 11.09 (s, 1H), 7.58 (dd, J=8.0, 7.0 Hz, 1H), 7.15 (d, J=8.6 Hz, 1H), 7.04 (d, J=7.0 Hz, 1H), 6.61 (t, J=5.8 Hz, 1H), 5.05 (dd, J=12.8, 5.4 Hz, 1H), 3.63-3.48 (m, 14H), 2.92-2.83 (m, 1H), 2.64-2.52 (m, 2H), 2.18 (t, J=8.1 Hz, 2H), 2.07-1.99 (m, 1H). HRMS (ESI) calcd for $C_{22}H_{28}N_3O_9^+$ $[M+H]^+$, 478.1820; found, 478.1159.

Intermediate Example 9: Synthesis of 1-((2-(2,6-dioxopiperidin-3-yl)-1,3-dioxoisoindolin-4-yl)amino)-3,6,9,12-tetraoxapentadecan-15-oic acid (SIAIS151006)

According to the procedures for the preparation of Intermediate Example 6, tert-Butyl 1-amino-3,6,9,12-tetraoxapentadecan-15-oate was used to prepare SIAIS151006 (yellow solid, 0.87 g, 53% yield). $^1$H NMR (500 MHz, DMSO) δ 11.09 (s, 1H), 7.58 (dd, J=8.5, 7.5 Hz, 1H), 7.15 (d, J=8.6 Hz, 1H), 7.04 (d, J=7.0 Hz, 1H), 6.60 (t, J=5.7 Hz, 1H), 5.05 (dd, J=12.8, 5.4 Hz, 1H), 3.63-3.48 (m, 18H), 2.92-2.84 (m, 1H), 2.63-2.52 (m, 2H), 2.41 (t, J=6.4 Hz, 2H), 2.07-1.98 (m, 1H). HRMS (ESI) calcd for $C_{24}H_{32}N_3O_{10}^+$ $[M+H]^+$, 522.2082; found, 522.2178.

Intermediate Example 10: Synthesis of 1-((2-(2,6-dioxopiperidin-3-yl)-1,3-dioxoisoindolin-4-yl)amino)-3,6,9,12,15-pentaoxaoctadecan-18-oic acid (SIAIS151007)

According to the procedures for the preparation of Intermediate Example 6, tert-Butyl 1-amino-3,6,9,12,15-pentaoxaoctadecan-18-oate was used to prepare SIAIS151007 (yellow solid, 0.8 g, 51% yield). $^1$H NMR (500 MHz, DMSO) δ 11.09 (s, 1H), 7.58 (t, J=8.0 Hz, 1H), 7.14 (d, J=8.6 Hz, 1H), 7.04 (d, J=7.0 Hz, 1H), 6.60 (t, J=5.7 Hz, 1H), 5.05 (dd, J=12.8, 5.4 Hz, 1H), 3.63-3.54 (m, 8H), 3.54-3.48 (m, 12H), 3.30 (dd, J=7.0 Hz, 4H), 2.92-2.84 (m, 1H), 2.63-2.52 (m, 2H), 2.06-1.99 (m, 1H). HRMS (ESI) calcd for $C_{26}H_{36}N_3O_{11}^+$ $[M+H]^+$, 566.2344; found, 566.2679.

Intermediate Example 11: Synthesis of (2-(2,6-dioxopiperidin-3-yl)-1,3-dioxoisoindolin-4-yl)glycine (SIAIS151025)

According to Scheme 4, a solution of 2-(2,6-dioxopiperidin-3-yl)-4-fluoroisoindolin-1,3-dione (7 mmol, 1 equiv), tert-butyl 3-(2-aminoethoxy)propionate (8.4 mmol, 1.2 equiv) and DIPEA (35 mmol, 5 equiv) in NMP (8 mL) was stirred in a microwave tube for 10 min at room temperature, then charged with argon and heated to 110° C. in a microwave reactor for 2 h. After cooling to RT, the reaction mixture was poured into 90% saline, extracted with ethyl acetate (4×50 mL), the combined organic phase was washed with water (2×30 mL), brine (50 mL), dried over anhydrous sodium sulfate and concentrated under reduced pressure. The resulting residue was purified by silica gel chromatography (eluent (v/v): hexanes/EA=1:1) to give the desired tert-butyl ester intermediate. This intermediate was treated with 88% formic acid (20 mL) overnight at room temperature. After concentration under reduced pressure and freeze-drying, the desired product SIAIS151025 was obtained as yellow solid (1.2 g, 48% yield). $^1$H NMR (500 MHz, DMSO) δ 11.10 (s, 1H), 7.59 (dd, J=15.9, 8.5 Hz, 1H), 7.07 (d, J=7.0 Hz, 1H), 6.99 (d, J=8.6 Hz, 1H), 6.86 (t, J=5.7 Hz, 1H), 5.06 (dt, J=15.1, 7.6 Hz, 1H), 4.08 (d, J=5.7 Hz, 2H), 2.92-2.84 (m, 1H), 2.63-2.52 (m, 2H), 2.07-2.02 (m, 1H). HRMS (ESI) calcd for $C_{18}H_{20}N_3O_6^+$ $[M+H]^+$, 332.0877; found, 332.0720.

Intermediate Example 12: Synthesis of 3-((2-(2,6-dioxopiperidin-3-yl)-1,3-dioxoisoindolin-4-yl)amino)propanoic acid (SIAIS151026)

According to the procedures for the preparation of Intermediate Example 11, tert-Butyl 3-amino-propanoate was used to prepare SIAIS151026 (yellow solid, 0.93 g, 39% yield). $^1$H NMR (500 MHz, DMSO) δ 11.09 (s, 1H), 7.59 (dd, J=8.0, 7.5 Hz, 1H), 7.15 (d, J=8.6 Hz, 1H), 7.04 (d, J=7.0 Hz, 1H), 6.67 (t, J=6.0 Hz, 1H), 5.05 (dd, J=12.8, 5.4 Hz, 1H), 3.53 (dd, J=12.6, 6.3 Hz, 2H), 2.92-2.84 (m, 1H), 2.65-2.53 (m, 4H), 2.08-1.98 (m, 1H). HRMS (ESI) calcd for $C_{16}H_{16}N_3O_6^+$ [M+H]$^+$, 346.1034; found, 346.0868.

Intermediate Example 13: Synthesis of 4-((2-(2,6-dioxopiperidin-3-yl)-1,3-dioxoisoindolin-4-yl)amino)butanoic acid (SIAIS151019)

According to the procedures for the preparation of Intermediate Example 11, tert-Butyl 4-amino-butanoate was used to prepare SIAIS151019 (yellow solid, 0.8 g, 61% yield). $^1$H NMR (500 MHz, DMSO) δ 12.14 (s, 1H), 11.09 (s, 1H), 7.58 (dd, J=8.4, 7.3 Hz, 1H), 7.13 (d, J=8.6 Hz, 1H), 7.02 (d, J=7.0 Hz, 1H), 6.65 (t, J=6.0 Hz, 1H), 5.05 (dd, J=12.8, 5.4 Hz, 1H), 3.32 (dd, J=13.7, 6.7 Hz, 2H), 2.94-2.82 (m, 1H), 2.66-2.51 (m, 2H), 2.30 (t, J=7.2 Hz, 2H), 2.05-2.00 (m, 1H), 1.82-1.75 (m, 2H). HRMS (ESI) calcd for $C_{17}H_{18}N_3O_6^+$ [M+H]$^+$, 360.1190; found, 360.1223.

Intermediate Example 14: Synthesis of 5-((2-(2,6-dioxopiperidin-3-yl)-1,3-dioxoisoindolin-4-yl)amino)pentanoic acid (SIAIS151020)

According to the procedures for the preparation of Intermediate Example 11, tert-Butyl 5-amino-pentanoate was used to prepare SIAIS151020 (yellow solid, 0.9 g, 50% yield). $^1$H NMR (500 MHz, DMSO) δ 12.05 (s, 1H), 11.11 (s, 1H), 7.57 (dd, J=8.3, 7.4 Hz, 1H), 7.09 (d, J=8.6 Hz, 1H), 7.02 (d, J=7.0 Hz, 1H), 6.56 (t, J=5.9 Hz, 1H), 5.05 (dd, J=12.7, 5.4 Hz, 1H), 3.32-3.28 (m, 2H), 2.94-2.82 (m, 1H), 2.62-2.51 (m, 2H), 2.27-2.25 (m, 2H), 2.06-1.99 (m, 1H), 1.62-1.53 (m, 4H). HRMS (ESI) calcd for $C_{18}H_{20}N_3O_6^+$ [M+H]$^+$, 374.1347; found, 374.1384.

Intermediate Example 15: Synthesis of 6-((2-(2,6-dioxopiperidin-3-yl)-1,3-dioxoisoindolin-4-yl)amino)hexanoic acid (SIAIS151027)

According to the procedures for the preparation of Intermediate Example 11, tert-Butyl 6-amino-hexanoate was used to prepare SIAIS151027 (yellow solid, 1.26 g, 61% yield). $^1$H NMR (500 MHz, DMSO) δ 12.00 (s, 1H), 11.09 (s, 1H), 7.58 (dd, J=8.3, 7.4 Hz, 1H), 7.09 (d, J=8.6 Hz, 1H), 7.02 (d, J=7.0 Hz, 1H), 6.54 (t, J=5.9 Hz, 1H), 5.05 (dd, J=12.8, 5.4 Hz, 1H), 3.30-3.27 (m, 2H), 2.92-2.84 (m, 1H), 2.63-2.51 (m, 2H), 2.21 (t, J=7.5 Hz, 2H), 2.08-1.98 (m, 1H), 1.60-1.50 (m, 4H), 1.38-1.31 (m, 2H). HRMS (ESI) calcd for $C_{19}H_{22}N_3O_6^+$ [M+H]$^+$, 388.1503; found, 388.1119.

Intermediate Example 16: Synthesis of 7-((2-(2,6-dioxopiperidin-3-yl)-1,3-dioxoisoindolin-4-yl)amino)heptanoic acid (SIAIS151086)

According to the procedures for the preparation of Intermediate Example 11, tert-Butyl 7-amino-heptanoate was used to prepare SIAIS151086 (yellow solid, 1.3 g, 64% yield). $^1$H NMR (500 MHz, DMSO) δ 12.04 (s, 1H), 11.09 (s, 1H), 7.58 (dd, J=8.3, 7.3 Hz, 1H), 7.09 (d, J=8.6 Hz, 1H), 7.02 (d, J=7.0 Hz, 1H), 6.53 (t, J=5.9 Hz, 1H), 5.05 (dd, J=12.7, 5.4 Hz, 1H), 3.28 (dd, J=13.4, 6.7 Hz, 2H), 2.94-2.82 (m, 1H), 2.65-2.51 (m, 2H), 2.19 (t, J=7.3 Hz, 2H), 2.05-2.00 (m, 1H), 1.60-1.53 (m, 2H), 1.53-1.46 (m, 2H), 1.37-1.28 (m, 4H). HRMS (ESI) calcd for $C_{20}H_{24}N_3O_6^+$ [M+H]$^+$, 402.1660; found, 402.1643.

Intermediate Example 17: Synthesis of 2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)acetic acid (SIAIS151010)

According to scheme 5, to a solution of diacid (2,2'-(ethane-1,2-diylbis(oxy))diacetic acid, 5.0 mmol, 2.5 equiv) in anhydrous DMF (10 mL) and anhydrous DCM (150 mL) was added NMM (10.0 mmol, 5 equiv), VHL-1 (2 mmol, 1 equiv), HOAt (2.4 mmol, 1.2 equiv) and EDCI (2.4 mmol, 1.2 equiv) at 0° C. The resulting reaction solution was stirred at 0° C. for 5 h and then at room temperature overnight. After VHL-1 was totally consumed, the reaction was quenched with water (1 mL) and then concentrated under reduced pressure, the residue was purified by reverse-phase chromatography, eluent (v/v): acetonitrile/(water+0.1% TFA)=10%-100%, to yield the desired product SIAIS151010 as white solid (0.2 g, 23%). $^1$H NMR (500 MHz, DMSO) δ 8.98 (s, 1H), 8.60 (t, J=5.9 Hz, 1H), 7.48 (d, J=9.5 Hz, 1H), 7.40 (s, 4H), 4.57 (d, J=9.6 Hz, 1H), 4.47-4.37 (m, 2H), 4.35 (s, 1H), 4.29-4.22 (m, 1H), 4.07 (d, J=12.5 Hz, 1H), 3.97 (s, 2H), 3.69-3.59 (m, 8H), 2.44 (s, 3H), 2.07-2.03 (m, 1H), 1.93-1.87 (m, 1H), 0.94 (s, 9H). HRMS (ESI) calcd for $C_{28}H_{39}N_4O_8S^+$ [M+H]$^+$, 591.2483; found, 591.2365.

Intermediate Example 18: Synthesis of 3-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethoxy)propanoic acid (SIAIS151002)

According to the procedures for the preparation of Intermediate Example 17, 3,3'-(ethane-1,2-diylbis(oxy))dipropionic acid was used to prepare SIAIS151002 (white solid, 0.53 g, 44% yield). $^1$H NMR (500 MHz, DMSO) δ 12.17 (s, 1H), 8.99 (s, 1H), 8.57 (t, J=6.0 Hz, 1H), 7.92 (d, J=9.3 Hz, 1H), 7.41 (dd, J=18.5, 8.2 Hz, 4H), 4.55 (d, J=9.5 Hz, 1H), 4.46-4.40 (m, 2H), 4.36 (s, 1H), 4.23 (dd, J=15.8, 5.4 Hz, 1H), 3.69-3.56 (m, 7H), 3.49-3.46 (m, 4H), 2.58-2.53 (m, 1H), 2.47-2.42 (m, 2H), 2.45 (s, 3H), 2.39-2.32 (m, 1H), 2.06-2.01 (m, 1H), 1.95-1.88 (m, 1H), 0.94 (s, 9H). HRMS (ESI) calcd for $C_{30}H_{43}N_4O_8S^+$ [M+H]$^+$, 619.2796; found, 619.2973.

Intermediate Example 19: Synthesis of (S)-15-((2S,4R)-4-hydroxy-2-((4-(4-methylthiazol-5-yl)benzyl)carbamoyl)pyrrolidin-1-carbonyl)-16,16-dimethyl-13-oxo-4,7,10-trioxa-14-azaheptadecanoic acid (SIAIS151003)

According to the procedures for the preparation of Intermediate Example 17, 3,3'-((oxybis(ethane-2,1-diyl))bis(oxy))dipropionic acid was used to prepare SIAIS151003 (white solid, 0.63 g, 59% yield). $^1$H NMR (500 MHz, DMSO) δ 8.99 (s, 1H), 8.57 (t, J=6.0 Hz, 1H), 7.92 (d, J=9.4 Hz, 1H), 7.41 (dd, J=18.5, 8.2 Hz, 4H), 4.56 (d, J=9.4 Hz, 1H), 4.47-4.41 (m, 2H), 4.36 (s, 1H), 4.23 (dd, J=15.9, 5.5 Hz, 1H), 3.70-3.57 (m, 8H), 3.51-3.47 (m, 7H), 2.58-2.52 (m, 1H), 2.47-2.42 (m, 2H), 2.45 (s, 3H), 2.39-2.32 (m, 1H), 2.08-2.00 (m, 1H), 1.94-1.88 (m, 1H), 0.94 (s, 9H). HRMS (ESI) calcd for $C_{32}H_{47}N_4O_9S^+$ [M+H]$^+$, 663.3058; found, 663.3008.

Intermediate Example 20: Synthesis of (S)-18-((2S,4R)-4-hydroxy-2-((4-(4-methylthiazol-5-yl)benzyl)carbamoyl)pyrrolidin-1-carbonyl)-19,19-dimethyl-16-oxo-4,7,10,13-tetraoxa-17-azaicosanoic acid (SIAIS151008)

According to the procedures for the preparation of Intermediate Example 17, 4,7,10,13-tetraoxahexadecanedioic acid was used to prepare SIAIS151008 (white solid, 0.53 g, 51% yield). $^1$H NMR (500 MHz, DMSO) δ 8.98 (s, 1H), 8.56 (t, J=6.0 Hz, 1H), 7.91 (d, J=9.4 Hz, 1H), 7.40 (dd, J=18.8, 8.3 Hz, 4H), 4.55 (d, J=9.4 Hz, 1H), 4.45-4.40 (m, 2H), 4.35 (s, 1H), 4.22 (dd, J=15.8, 5.5 Hz, 1H), 3.69-3.54 (m, 10H), 3.48 (d, J=2.7 Hz, 9H), 2.56-2.52 (m, 1H), 2.45-2.41 (m, 2H), 2.45 (s, 3H), 2.38-2.32 (m, 1H), 2.06-2.00 (m, 1H), 1.94-1.88 (m, 1H), 0.93 (s, 9H). HRMS (ESI) calcd for $C_{34}H_{51}N_4O_{10}S^+$ [M+H]$^+$, 707.3320; found, 707.2945.

Intermediate Example 21: Synthesis of (S)-21-((2S,4R)-4-hydroxy-2-((4-(4-methylthiazol-5-yl)benzyl)carbamoyl)pyrrolidin-1-carbonyl)-22,22-dimethyl-19-oxo-4,7,10,13,16-pentaoxa-20-azatricosanoic acid (SIAIS151009)

According to the procedures for the preparation of Intermediate Example 17, 4,7,10,13,16-pentaoxanonadecanedioic acid was used to prepare SIAIS151009 (white solid, 0.82 g, 85% yield). $^1$H NMR (500 MHz, DMSO) δ 8.98 (s, 1H), 8.56 (d, J=5.7 Hz, 1H), 7.91 (d, J=9.3 Hz, 1H), 7.40 (dd, J=18.6, 7.9 Hz, 4H), 4.55 (d, J=9.3 Hz, 1H), 4.47-4.40 (m, 2H), 4.35 (s, 1H), 4.22 (dd, J=15.7, 5.2 Hz, 1H), 3.68-3.56 (m, 11H), 3.51-3.49 (s, 9H), 2.56-2.53 (m, 1H), 2.45-2.41 (m, 5H), 2.44 (s, 3H), 2.36 (dd, J=13.4, 7.0 Hz, 1H), 2.08-2.00 (m, 1H), 1.94-1.86 (m, 1H), 0.93 (s, 9H). HRMS (ESI) calcd for $C_{36}H_{55}N_4O_{11}S^+$ [M+H]$^+$, calcd for 751.3583; found, 751.3199.

Intermediate Example 22: Synthesis of 4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoic acid (SIAIS074011)

According to scheme 6, to a solution of diacid (succinic acid, 5.0 mmol, 2.5 equiv) in anhydrous DMF (10 mL) and anhydrous DCM (150 mL) was added NMM (10.0 mmol, 5 equiv), VHL-1 (2 mmol, 1 equiv), HOAt (2.4 mmol, 1.2 equiv) and EDCI (2.4 mmol, 1.2 equiv) at 0° C. The resulting reaction solution was stirred at 0° C. for 5 h and then at room temperature overnight. After VHL-1 was totally consumed, the reaction was quenched with water (1 mL) and then concentrated under reduced pressure, the residue was purified by reverse-phase chromatography, eluent (v/v): acetonitrile/(water+0.1% TFA)=10%-100%, to yield the desired product SIAIS074011 as white solid (0.82 g, 65%). $^1$H NMR (500 MHz, CDCl$_3$) δ 11.88 (s, 1H), 8.85 (s, J=11.2 Hz, 1H), 7.69 (s, 1H), 7.37-7.29 (m, 4H), 6.09 (br, 1H), 4.67-4.54 (m, 3H), 4.49 (s, 1H), 4.29 (dd, J=15.0, 5.0 Hz, 1H), 4.05 (d, J=11.3 Hz, 1H), 3.73-3.63 (m, 1H), 2.73-2.58 (m, 1H), 2.57-2.41 (m, 3H), 2.50 (s, 3H), 2.31-2.14 (m, 2H), 0.96 (s, 9H). HRMS (ESI) calcd for $C_{26}H_{35}N_4O_6S^+$ [M+H]$^+$, 531.2272; found, 531.2275.

Intermediate Example 23: Synthesis of 5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoic acid (SIAIS074012)

According to the procedures for the preparation of Intermediate Example 22, glutaric acid was used to prepare SIAIS074012 (white solid, 0.85 g, 67% yield). $^1$H NMR (500 MHz, CDCl$_3$) δ 9.08 (s, 1H), 8.65 (br, 1H), 8.10 (s, 1H), 7.38-7.29 (m, 4H), 4.72-4.64 (m, 3H), 4.52 (s, 1H), 4.25 (dd, J=15.4, 5.0 Hz, 1H), 4.09 (d, J=10.5 Hz, 1H), 3.73 (d, J=10.0 Hz, 1H), 2.48 (s, 3H), 2.39-2.13 (m, 6H), 1.92-1.74 (m, 2H), 0.96 (s, 9H). HRMS (ESI) calcd for $C_{27}H_{37}N_4O_6S^+$[M+H]$^+$, 545.2428; found, 545.2428.

Intermediate Example 24: Synthesis of 6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoic acid (SIAIS074013)

According to the procedures for the preparation of Intermediate Example 22, adipic acid was used to prepare SIAIS074013 (white solid, 0.79 g, 55% yield). $^1$H NMR (500 MHz, CDCl$_3$) δ 8.99 (s, 1H), 7.66 (s, 1H), 7.39-7.33 (m, 4H), 7.30 (d, J=7.5 Hz, 1H). 7.14 (br, 1H), 4.67-4.61 (m, 3H), 4.52 (s, 1H). 4.28 (dd, J=15.4, 5.0 Hz, 1H), 4.09 (d, J=11.4 Hz, 1H), 3.74-3.63 (m, 1H), 2.52 (s, 3H), 2.31-2.17 (m, 6H), 1.65-1.53 (m, 4H), 0.96 (s, 9H). HRMS (ESI) calcd for calcd for $C_{28}H_4ON_4O_6S^+$ [M+H]$^+$, 559.2585; found, 559.3632.

Intermediate Example 25: Synthesis of 7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoic acid (SIAIS074014)

According to the procedures for the preparation of Intermediate Example 22, pimelic acid was used to prepare SIAIS074014 (white solid, 0.8 g, 57% yield). $^1$H NMR (500 MHz, CDCl$_3$) δ 8.90 (s, 1H), 7.42-7.38 (m, 1H), 7.41-7.33 (m, 4H), 7.31 (d, J=9.0 Hz, 1H), 6.38 (br, 1H), 4.79-4.46 (m, 3H), 4.55 (s, 1H), 4.28 (dd, J=15.2, 5.1 Hz, 1H), 4.12 (d, J=11.3 Hz, 1H), 3.72-3.63 (m, 1H), 2.51 (s, 3H), 2.38-2.33 (m, 1H), 2.28-2.21 (m, 4H), 2.18-2.12 (m, 1H), 1.62-1.52 (m, 3H), 1.33-1.23 (m, 3H), 0.96 (s, 9H). HRMS (ESI) calcd for $C_{29}H_{41}N_4O_6S^+$ [M+H]$^+$, 573.2741; found, 573.3804.

Intermediate Example 26: Synthesis of 8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoic acid (SIAIS074015)

According to the procedures for the preparation of Intermediate Example 22, suberic acid was used to prepare SIAIS074015 (white solid, 0.95 g, 68% yield). $^1$H NMR (500 MHz, CDCl$_3$) δ 8.82 (s, 1H), 7.43 (t, J=6.0 Hz, 1H), 7.34 (s, 4H), 6.98 (d, J=8.5 Hz, 1H), 6.10 (s, 1H), 4.69-4.65 (m, 1H), 4.63-4.51 (m, 2H), 4.55-4.50 (m, 1H), 4.38-4.27 (m, 1H), 4.11 (d, J=16.7 Hz, 1H), 3.72-3.62 (m, 1H), 2.51 (s, 3H), 2.39-2.13 (m, 6H), 1.58-1.54 (m, 4H), 1.33-1.21 (m, 4H), 0.95 (s, 9H). HRMS (ESI) calcd for $C_{30}H_{43}N_4O_6S^+$ [M+H]$^+$, 587.2898; found, 587.2917.

Intermediate Example 27: Synthesis of 9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoic acid (SIAIS074016)

According to the procedures for the preparation of Intermediate Example 22, azelaic acid was used to prepare SIAIS074016 (white solid, 0.92 g, 64% yield). $^1$H NMR (500 MHz, CDCl$_3$) δ 8.82 (s, 1H), 7.35 (s, 4H), 7.02 (t, J=14.3 Hz, 1H), 5.99 (s, 1H), 4.74-4.49 (m, 4H), 4.30 (dd, J=15.2, 5.1 Hz, 1H), 4.13 (d, J=11.3 Hz, 1H), 3.67 (dd, J=11.5, 3.5 Hz, 1H), 2.51 (s, 3H), 2.42-2.36 (m, 1H), 2.28 (t, J=7.5 Hz, 2H), 2.24-2.12 (m, 3H), 1.67-1.48 (m, 4H), 1.35-1.22 (m, 6H), 0.95 (s, 9H). HRMS (ESI) calcd for C$_{31}$H$_{45}$N$_4$O$_6$S$^+$ [M+H]$^+$, 601.3054; found, 601.3150.

Intermediate Example 28: Synthesis of 10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoic acid (SIAIS074019)

According to the procedures for the preparation of Intermediate Example 22, sebacic acid was used to prepare SIAIS074019 (white solid, 0.96 g, 66% yield). $^1$H NMR (500 MHz, CDCl$_3$) δ 8.79 (s, 1H), 7.39-7.36 (m, 1H), 7.35 (s, 4H), 7.01 (d, J=9.0 Hz, 1H), 5.80 (s, 1H), 4.68-4.52 (m, 4H), 4.29 (dd, J=15.2, 5.0 Hz, 1H), 4.12 (d, J=11.2 Hz, 1H), 3.72-3.62 (m, 1H), 2.51 (s, 3H), 2.41-2.33 (m, 1H), 2.32-2.23 (m, 2H), 2.23-2.11 (m, 3H), 1.65-1.48 (m, 4H), 1.32-1.21 (m, 8H), 0.95 (s, 9H). HRMS (ESI) calcd for C$_{32}$H$_{47}$N$_4$O$_6$S$^+$ [M+H]$^+$: 615.3211; found, 615.4391.

Intermediate Example 29: Synthesis of 11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoic acid (SIAIS074020)

According to the procedures for the preparation of Intermediate Example 22, 1,11-undecanedioic acid was used to prepare SIAIS074020 (white solid, 1 g, 67% yield). $^1$H NMR (500 MHz, CDCl$_3$) δ 8.77 (s, 1H), 7.39-7.32 (m, 4H), 7.30 (m, 1H), 7.01 (d, J=8.8 Hz, 1H), 5.52 (br, 1H), 4.69-4.59 (m, 3H), 4.53 (s, 1H), 4.29 (dd, J=15.2, 5.0 Hz, 1H), 4.14 (d, J=11.3 Hz, 1H), 3.68-3.64 (m, 1H), 2.51 (s, 3H), 2.44-2.40 (m, 1H), 2.29 (t, J=7.1 Hz, 2H), 2.26-2.12 (m, 3H), 1.68-1.48 (m, 4H), 1.30-1.20 (m, 10H), 0.95 (s, 9H). HRMS (ESI) calcd for C$_{33}$H$_{49}$N$_4$O$_6$S$^+$ [M+H]$^+$, 629.3367; found, 629.4540.

Intermediate Example 30: Synthesis of 3-((2-(2,6-dioxopiperidin-3-yl)-1-oxoisoindolin-4-yl)amino)-3-oxopropanoic acid (SIAIS171004)

According to scheme 7, to a solution of diacid (malonic acid, 5.0 mmol, 2.5 equiv) in anhydrous DMF (10 mL) and anhydrous DCM (150 mL) was added NMM (10.0 mmol, 5 equiv), lenalidomide (2 mmol, 1 equiv), HOAt (2.4 mmol, 1.2 equiv) and EDCI (2.4 mmol, 1.2 equiv) at 0° C. The resulting reaction solution was then stirred at room temperature overnight. After lenalidomide was totally consumed, the reaction was quenched with water (1 mL) and then concentrated under reduced pressure, the residue was purified by reverse-phase chromatography, eluent (v/v): acetonitrile/(water+0.1% TFA)=10%-100%, to yield the desired product SIAIS171004 as white solid (0.32 g, 24%). $^1$H NMR (500 MHz, DMSO) δ 11.02 (s, 1H), 10.03 (s, 1H), 7.86 (d, J=7.1 Hz, 1H), 7.62-7.43 (m, 2H), 5.15 (dd, J=13.4, 4.9 Hz, 1H), 4.36 (dd, J=35.5, 17.5 Hz, 2H), 3.42 (d, 1H), 2.95-2.87 (m, 1H), 2.63-2.59 (m, 1H), 2.38-2.28 (m, 1H), 2.07-2.01 (m, 1H). HRMS (ESI) calcd for C$_{16}$H$_{16}$N$_3$O$_6$$^+$ [M+H]$^+$, 346.1034; found, 346.1015.

Intermediate Example 31: Synthesis of 4-((2-(2,6-dioxopiperidin-3-yl)-1-oxoisoindolin-4-yl)amino)-4-oxobutanoic acid (SIAIS164084)

According to the procedures for the preparation of Intermediate Example 30, succinic acid was used to prepare SIAIS164084 (white solid, 0.11 g, 44% yield). $^1$H NMR (500 MHz, DMSO) δ 12.16 (s, 1H), 11.02 (s, 1H), 9.86 (s, 1H), 7.81 (dd, J=7.1, 1.7 Hz, 1H), 7.57-7.40 (m, 2H), 5.15 (dd, J=13.3, 5.1 Hz, 1H), 4.35 (dd, J=35.5, 17.5 Hz, 2H), 2.96-2.87 (m, 1H), 2.65-2.58 (m, 3H), 2.55-2.53 (m, 2H), 2.37-2.29 (m, 1H), 2.06-2.00 (m, 1H). HRMS (ESI) calcd for C$_{17}$H$_{18}$N$_3$O$_6$$^+$ [M+H]$^+$, 360.1190; found, 360.1198.

Intermediate Example 32: Synthesis of 5-((2-(2,6-dioxopiperidin-3-yl)-1-oxoisoindolin-4-yl)amino)-5-oxopentanoic acid (SIAIS171005)

According to the procedures for the preparation of Intermediate Example 30, glutaric acid was used to prepare SIAIS171005 (white solid, 0.52 g, 35% yield). $^1$H NMR (500 MHz, DMSO) δ 11.01 (s, 1H), 9.80 (s, 1H), 7.81 (d, J=5.8 Hz, 1H), 7.54-7.46 (m, 2H), 5.15 (dd, J=13.3, 5.1 Hz, 1H), 4.36 (dd, J=35.5, 17.5 Hz, 2H), 2.97-2.85 (m, 1H), 2.77-2.75 (m, 2H), 2.66-2.57 (m, 1H), 2.42-2.39 (m, 1H), 2.35 (dd, J=13.1, 4.4 Hz, 1H), 2.30-2.27 (m, 1H), 2.03-1.97 (m, 1H), 1.85-1.79 (m, 2H). HRMS (ESI) calcd for C$_{18}$H$_{20}$N$_3$O$_6$$^+$ [M+H]$^+$, 374.1347; found, 374.1526.

Intermediate Example 33: Synthesis of 6-((2-(2,6-dioxopiperidin-3-yl)-1-oxoisoindolin-4-yl)amino)-6-oxohexanoic acid (SIAIS164101)

According to the procedures for the preparation of Intermediate Example 30, adipic acid was used to prepare SIAIS164101 (white solid, 0.4 g, 27% yield). $^1$H NMR (500 MHz, MeOD) δ 7.70 (d, J=7.9 Hz, 1H), 7.66 (d, J=7.4 Hz, 1H), 7.52 (t, J=7.7 Hz, 1H), 5.16 (dd, J=13.4, 5.2 Hz, 1H), 4.53-4.43 (m, 2H), 2.95-2.87 (m, 1H), 2.81-2.76 (m, 1H), 2.55-2.48 (m, 1H), 2.46 (t, J=7.2 Hz, 2H), 2.36 (t, J=7.0 Hz, 2H), 2.22-2.16 (m, 1H), 1.79-1.66 (m, 4H). HRMS (ESI) calcd for C$_{19}$H$_{22}$N$_3$O$_6$$^+$ [M+H]$^+$, 388.1503; found, 388.1714.

Intermediate Example 34: Synthesis of 7-((2-(2,6-dioxopiperidin-3-yl)-1-oxoisoindolin-4-yl)amino)-7-oxoheptanoic acid (SIAIS164102)

According to the procedures for the preparation of Intermediate Example 30, pimelic acid was used to prepare SIAIS164102 (white solid, 0.45 g, 28% yield). $^1$H NMR (500 MHz, MeOD) δ 7.70 (d, J=7.9 Hz, 1H), 7.65 (d, J=7.4 Hz, 1H), 7.52 (t, J=7.7 Hz, 1H), 5.16 (dd, J=13.4, 5.2 Hz, 1H), 4.49 (t, J=10.1 Hz, 2H), 2.94-2.87 (m, 1H), 2.81-2.76 (m, 1H), 2.54-2.48 (m, 1H), 2.45 (t, J=7.5 Hz, 2H), 2.32 (t, J=7.0 Hz, 2H), 2.22-2.16 (m, 1H), 1.77-1.72 (m, 2H), 1.70-1.63 (m, 2H), 1.48-1.42 (m, 2H). HRMS (ESI) calcd for C$_{20}$H$_{24}$N$_3$O$_6$$^+$ [M+H]$^+$, 402.1660; found, 402.1890.

Intermediate Example 35: Synthesis of (2-(2,6-dioxopiperidin-3-yl)-1-oxoisoindolin-4-yl)aminoacetic acid (SIAIS1204057)

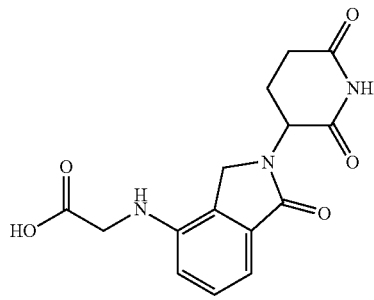 [SMILES: O=C(O)CNc1cccc2c1CN(C1CCC(=O)NC1=O)C2=O]

According to scheme 8, to a solution of lenalidomide (2 mmol, 1 equiv) in NMP (8 mL) was added tert-butyl 2-bromoacetate (2.4 mmol, 1.2 equiv) and DIPEA (6 mmol, 3 equiv), then stirred at 110° C. overnight. After cooling to room temperature, the resulting solution was purified by reverse-phase chromatography, eluent (v/v): acetonitrile/(water+0.1% TFA)=10%-100%, to yield the desired tert-butyl ester intermediate. This intermediate was treated with TFA (2 mL) in DCM (6 mL) for 1 h at room temperature. After concentration under reduced pressure and freeze-drying, the desired product SIAIS1204057 was obtained as yellow solid, 1.0 g, 48%. $^1$H NMR (500 MHz, DMSO) δ 11.01 (s, 1H), 7.28 (t, J=7.7 Hz, 1H), 6.98 (d, J=7.3 Hz, 1H), 6.66 (d, J=8.0 Hz, 1H), 5.94 (s, 1H), 5.12 (dd, J=13.3, 5.1 Hz, 1H), 4.26 (d, J=17.0 Hz, 1H), 4.16 (d, J=17.0 Hz, 1H), 3.92 (s, 2H), 2.98-2.85 (m, 1H), 2.62 (d, J=17.3 Hz, 1H), 2.39-2.26 (m, 1H), 2.08-1.99 (m, 1H). HRMS (ESI) calcd for $C_{15}H_{16}N_3O_5^+$ [M+H]$^+$, 318.1084; found, 318.1098.

Intermediate Example 36: Synthesis of 4-((2-(2,6-dioxopiperidin-3-yl)-1-oxoisoindolin-4-yl)amino)butanoic acid (SIAIS1204085)

According to the procedures for the preparation of Intermediate Example 35, tert-butyl 4-bromobutanoate was used to prepare SIAIS1204085 (yellow solid, 215 mg, 62% yield). $^1$H NMR (500 MHz, DMSO) δ 11.01 (s, 1H), 7.28 (t, J=7.7 Hz, 1H), 6.93 (d, J=7.3 Hz, 1H), 6.77 (d, J=8.0 Hz, 1H), 5.11 (dd, J=13.3, 5.1 Hz, 1H), 4.23 (d, J=17.0 Hz, 1H), 4.13 (d, J=17.0 Hz, 1H), 4.01 (s, 1H), 3.14 (t, J=7.0 Hz, 2H), 2.98-2.86 (m, 1H), 2.66-2.58 (d, J=17.6 Hz, 1H), 2.34 (t, J=7.3 Hz, 2H), 2.32-2.24 (m, 1H), 2.08-1.98 (m, 1H), 1.85-1.75 (m, 2H). HRMS (ESI) calcd for $C_{17}H_{20}N_3O_5^+$ [M+H]$^+$, 346.1379; found, 346.1414.

Intermediate Example 37: Synthesis of 5-((2-(2,6-dioxopiperidin-3-yl)-1-oxoisoindolin-4-yl)amino)pentanoic acid (SIAIS1210133)

According to the procedures for the preparation of Intermediate Example 35, tert-butyl 5-bromopentanoate was used to prepare SIAIS1210133 (yellow solid, 215 mg, 60% yield). $^1$H NMR (500 MHz, DMSO) δ 11.01 (s, 1H), 7.28 (t, J=7.7 Hz, 1H), 6.92 (t, J=10.9 Hz, 1H), 6.76 (d, J=8.0 Hz, 1H), 5.11 (dd, J=13.3, 5.1 Hz, 1H), 5.07 (s, 1H), 4.23 (d, J=17.2 Hz, 1H), 4.13 (d, J=17.1 Hz, 1H), 3.13 (d, J=6.4 Hz, 2H), 2.97-2.87 (m, 1H), 2.61 (d, J=16.7 Hz, 1H), 2.38-2.21 (m, 3H), 2.06-1.98 (m, 1H), 1.67-1.55 (m, 4H). HRMS (ESI) calcd for $C_{15}H_{22}N_3O_5^+$ [M+H]$^+$, 360.1554; found, 360.1551.

Intermediate Example 38: Synthesis of 6-((2-(2,6-dioxopiperidin-3-yl)-1-oxoisoindolin-4-yl)amino)hexanoic acid (SIAIS1204061)

According to the procedures for the preparation of Intermediate Example 35, tert-butyl 6-bromohexanoate was used to prepare SIAIS1204061 (yellow solid, 268 mg, 72% yield). $^1$H NMR (500 MHz, DMSO) δ 11.01 (s, 1H), 7.29 (t, J=7.7 Hz, 1H), 6.94 (d, J=7.4 Hz, 1H), 6.76 (d, J=8.0 Hz, 1H), 5.11 (dd, J=13.3, 5.1 Hz, 1H), 4.24 (d, J=17.0 Hz, 1H), 4.14 (d, J=17.0 Hz, 1H), 4.05 (s, 1H), 3.12 (t, J=7.0 Hz, 2H), 2.98-2.87 (m, 1H), 2.66-2.58 (m, 1H), 2.35-2.25 (m, 1H), 2.22 (t, J=7.0 Hz, 2H), 2.07-2.00 (m, 1H), 1.63-1.50 (m, 4H), 1.43-1.37 (m, 2H). HRMS (ESI) calcd for $C_{19}H_{24}N_3O_5^+$ [M+H]$^+$, 374.1710; found, 374.1720.

Intermediate Example 39: Synthesis of 7-((2-(2,6-dioxopiperidin-3-yl)-1-oxoisoindolin-4-yl)amino)heptanoic acid (SIAIS1204063)

According to the procedures for the preparation of Intermediate Example 35, tert-butyl 7-bromoheptanoate was used to prepare SIAIS1204063 (yellow solid, 252 mg, 65% yield). $^1$H NMR (500 MHz, DMSO) δ 11.00 (s, 1H), 7.28 (t, J=7.7 Hz, 1H), 6.93 (d, J=7.3 Hz, 1H), 6.75 (d, J=8.0 Hz, 1H), 5.11 (dd, J=13.2, 5.0 Hz, 1H), 4.23 (d, J=17.0 Hz, 1H), 4.13 (d, J=17.0 Hz, 1H), 3.11 (t, J=7.0 Hz, 2H), 2.98-2.84 (m, 1H), 2.67-2.57 (m, 1H), 2.35-2.25 (m, 1H), 2.20 (t, J=7.3 Hz, 2H), 2.07-1.99 (m, 1H), 1.63-1.46 (m, 4H), 1.42-1.27 (m, 4H). HRMS (ESI) calcd for $C_{20}H_{26}N_3O_5^+$ [M+H]$^+$, 388.1867; found, 388.1878.

Intermediate Example 40: Synthesis of 4-((2-aminoethyl)amino)-2-(2,6-dioxopiperidin-3-yl) isoindolin-1,3-dione (SIAIS151103)

According to Scheme 9, a solution of 2-(2,6-dioxopiperidin-3-yl)-4-fluoroisoindolin-1,3-dione (7.2 mmol, 1 equiv), 叔丁基(2-氨基乙基)氨基甲酸酯 (8.1 mmol, 1.2 equiv) and DIPEA (36.4 mmol, 5 equiv) in NMP (10 mL) was stirred in a microwave tube for 10 min at room temperature, then charged with argon and heated to 110° C. in a microwave reactor for 2 h. After cooling to RT, the reaction mixture was poured into 90% saline, extracted with EA (4×50 mL), the combined organic phase was washed with water (2×30 mL), brine (50 mL), dried over anhydrous sodium sulfate and concentrated under reduced pressure. The resulting residue was purified by silica gel chromatography (eluent (v/v): hexanes/EA=1:1) to give the desired tert-butyl ester intermediate. This intermediate was treated with 88% formic acid (20 mL) overnight at room temperature. After concentration under reduced pressure and freeze-drying, the desired product SIAIS151103 was obtained as yellow solid (1.1 g, 48% yield). $^1$H NMR (500 MHz, DMSO) δ 8.36 (s, 2H), 7.64-7.58 (m, 1H), 7.18 (t, J=6.2 Hz, 1H), 7.07 (d, J=7.1 Hz, 1H), 6.84 (t, J=6.2 Hz, 1H), 5.06 (dd, J=12.7, 5.4 Hz, 1H), 3.56 (dd, J=12.2, 6.0 Hz, 2H), 2.96 (t, J=6.1 Hz, 2H), 2.93-2.85 (m, 1H), 2.61-2.51 (m, 2H), 2.06-2.00 (m, 1H). HRMS (ESI) calcd for $C_{15}H_{17}N_4O_4^+$ [M+H]$^+$, 317.1244; found, 317.1236.

Intermediate Example 41: Synthesis of 4-((2-((2-(2,6-dioxopiperidin-3-yl)-1,3-dioxoisoindolin-4-yl)amino)ethyl)amino)-4-oxobutanoic acid (SIAIS164119)

According to scheme 10, to a solution of succinic acid (295.2 mg, 2.5 mmol, 2.5 equiv) in anhydrous DMF (5 mL) and anhydrous DCM (50 mL) was added NMM (1.01 g, 10.0 mmol, 10 equiv), SIAIS151103 (316.3 mg, 1 mmol, 1 equiv), HOAt (163.3 mg, 1.2 mmol, 1.2 equiv) and EDCI (230 mg, 1.2 mmol, 1.2 equiv) at 0° C. The resulting reaction solution was stirred at 0° C. for 5 h and then at room temperature overnight. After the reaction was complete, the resulting solution was quenched with water (1 mL) and then concentrated under reduced pressure, the residue was purified by reverse-phase chromatography, eluent (v/v) acetonitrile/(water+0.1% TFA)=10%-100%, to yield the desired product SIAIS164119 as yellow solid (170 mg, 41%). $^1$H NMR (500 MHz, MeOD) δ 7.55-7.50 (m, 1H), 7.10 (d, J=8.6 Hz, 1H), 7.04 (t, J=6.3 Hz, 1H), 5.05 (dd, J=12.4, 5.5 Hz, 1H), 3.47-3.39 (m, 4H), 2.89-2.82 (m, 1H), 2.79-2.65 (m, 2H), 2.58 (t, J=7.0 Hz, 2H), 2.45 (t, J=7.0 Hz, 2H), 2.16-2.05 (m, 1H). HRMS (ESI) calcd for $C_{19}H_{21}N_4O_7^+$ [M+H]$^+$, 417.1405; found, 417.0916.

Intermediate Example 42: Synthesis of (2S,4R)-1-((S)-2-(4-azidobutyrylamino-3,3-dimethylbutyryl)-4-hydroxy-N-(4-(4-methylthiazol-5-yl)benzyl)pyrrolidin-2-carboxamide (SIAIS164050)

According to scheme 11, to a solution of VHL-1 (934 mg, 2 mmol, 1 equiv) and 4-azidobutanoic acid (258.2 mg, 2 mmol, 1 equiv) in DMF (5 mL) and DCM (20 mL) was added HOAt (54.4 mg, 0.4 mmol, 0.2 equiv), EDCI (766.8 mg, 4 mmol, 2 equiv) and NMM (2.02 g, 20 mmol, 10 equiv) at room temperature. The resulting reaction solution was stirred at room temperature overnight. After the reaction was complete detected by LC-MS, the resulting solution was concentrated under reduced pressure, the residue was poured into 90% saline, extracted with EA (4×50 mL), the combined organic phase was washed with water (2×30 mL), brine (50 mL), dried over anhydrous sodium sulfate and concentrated under reduced pressure. The resulting residue was purified by silica gel chromatography (eluent (v/v): DCM/MeOH=40:1) to give the desired product SIAIS164050 as pale yellow liquid (734 mg, 68%). $^1$H NMR (500 MHz, MeOD) δ 8.87 (s, 1H), 7.48-7.41 (m, 4H), 4.62 (s, 1H), 4.58-4.50 (m, 3H), 4.38-4.33 (m, 1H), 3.91 (d, J=11.0 Hz, 1H), 3.80 (dd, J=10.9, 3.9 Hz, 1H), 3.33 (t, J=5.0 Hz, 2H), 2.48 (d, J=5.3 Hz, 3H), 2.41-2.32 (m, 2H), 2.22 (dd, J=13.1, 7.6 Hz, 1H), 2.11-2.06 (m, 1H), 1.90-1.82 (m, 2H), 1.04 (s, 9H). HRMS (ESI) calcd for $C_{26}H_{36}N_7O_4S^+$ [M+H]$^+$, 542.2544; found, 542.2256.

Intermediate Example 43: Synthesis of 4-(1-(4-(((S)-1-((2S,4R)-4-hydroxy-2-((4-(4-methylthiazol-5-yl)benzyl)carbamoyl)pyrrolidin-1-yl)-3,3-dimethyl-1-oxobut-2-yl)amino)-4-oxobutyl)-1H-1,2,3-triazol-4-yl)butanoic acid (SIAIS164128)

According to scheme 12, to a solution of 5-hexynoic acid (22.4 mg, 0.2 mmol, 1 equiv) and SIAIS164050 (108.3 mg, 0.2 mmol, 1 equiv) in DMF (1 mL), tBuOH (1 mL) and water (1 mL) was added CuSO$_4$ (31.9 mg, 0.2 mmol, 1 equiv) and sodium ascorbate (39.6 mg, 0.2 mmol, 1 equiv) at room temperature. The resulting reaction solution was stirred at room temperature for 2 h. After the reaction was complete detected by LC-MS, the resulting solution was purified by reverse-phase chromatography (eluent (v/v): acetonitrile/(water+0.1% TFA)=10%-100%), to yield the desired product SIAIS164128 as white solid (100 mg, 76%). $^1$H NMR (500 MHz, MeOD) δ 9.19 (d, J=3.4 Hz, 1H), 7.87 (s, 1H), 7.51-7.42 (m, 4H), 4.60 (s, 1H), 4.59-4.54 (m, 2H), 4.51 (s, 1H), 4.43 (t, J=6.8 Hz, 2H), 4.36 (d, J=15.3 Hz, 1H), 3.93 (d, J=11.1 Hz, 1H), 3.80 (dd, J=11.0, 3.8 Hz, 1H), 2.77 (t, J=7.6 Hz, 2H), 2.51 (d, J=3.8 Hz, 3H), 2.36 (t, J=7.3 Hz, 2H), 2.32-2.28 (m, 2H), 2.25-2.15 (m, 3H), 2.11-2.06 (m, 1H), 2.00-1.94 (m, 2H), 1.04 (s, 9H). HRMS (ESI) calcd for $C_{32}H_{44}N_7O_6S^+$ [M+H]$^+$, 654.3068; found, 654.2990.

Intermediate Example 44: Synthesis of 11-(((S)-1-((2S,4S)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoic acid (SIAIS219048)

According to scheme 13, to a solution of diacid (1,11-undecanedioic acid, 0.25 mmol, 2.5 equiv) in anhydrous DMF (4 mL) and anhydrous DCM (10 mL) was added NMM (0.5 mmol, 5 equiv), trans-VHL-1 (0.1 mmol, 1 equiv), HOAt (0.15 mmol, 1.5 equiv) and EDCI (0.15 mmol, 1.5 equiv) at 0° C. The resulting reaction solution was stirred at 0° C. for 2 h and then at room temperature overnight. After trans-VHL-1 was totally consumed, the reaction was quenched with water (1 mL) and then concentrated under reduced pressure, the residue was purified by reverse-phase chromatography, eluent (v/v): acetonitrile/(water+0.1% TFA)=10%-100%, to yield the desired product SIAIS219048 as white solid (48 mg, 76%). $^1$H NMR (500 MHz, CDCl$_3$) δ 8.78 (s, 1H), 7.38-7.31 (m, 4H), 7.31-7.28 (m, 1H), 7.00 (d, J=8.8 Hz, 1H), 5.50 (br, 1H), 4.67-4.56 (m, 3H), 4.51 (s, 1H), 4.26 (dd, J=15.2, 5.0 Hz, 1H), 4.13 (d, J=11.3 Hz, 1H), 3.64-3.62 (m, 1H), 2.50 (s, 3H), 2.43-2.40 (m, 1H), 2.27 (t, J=7.1 Hz, 2H), 2.25-2.11 (m, 3H), 1.67-1.46 (m, 4H), 1.30-1.21 (m, 10H), 0.93 (s, 9H). HRMS (ESI) calcd for $C_{33}H_{49}N_4O_6S^+$ [M+H]$^+$, 629.3367; found, 629.3377.

Intermediate Example 45: Synthesis of 3-(2-(2,6-dioxopiperidin-3-yl)-1,3-dioxoisoindololin-4-yl)propionic acid (SIAIS172147)

Synthesis of 4-bromo-2-(2,6-dioxopiperidin-3-yl)isoindolin-1,3-dione (SIAIS172136)

According to scheme 14, 4-bromoisobenzofuran-1,3-dione (500 mg, 2.20 mmol), 3-aminopiperidine-2,6-dione (400 mg, 2.42 mmol) and anhydrous sodium acetate was added in a 100 mL egg-shaped flask, followed by glacial acetic acid (10 mL). The resulting reaction solution was slowly heated to 140° C. and stirred for 12 h. After the reaction was complete, the reaction solution was cooled to room temperature, a large amount of white solid was precipitated. After filtration, the filter cake, water (10 mL) and methanol (2 mL) were added to a flask and stirred for 0.5 h. After filtration, the filter cake was washed with water, concentrated under reduced pressure to yield the desired product SIAIS172136 as white solid (700 mg, 94%). $^1$H NMR (500 MHz, DMSO) δ 11.14 (s, 1H), 8.14 (d, J=1.4 Hz, 1H), 8.09 (dd, J=7.9, 1.7 Hz, 1H), 7.86 (d, J=7.9 Hz, 1H), 5.16 (dd, J=12.9, 5.4 Hz, 1H), 2.93-2.85 (m, 1H), 2.65-2.50

Synthesis of tert-butyl (E)-3-(2-(2,6-dioxopiperidin-3-yl)-1,3-dioxoisoindolin-4-yl)acrylate (SIAIS172145)

According to scheme 14, tri-tert-butylphosphine tetrafluoroborate (110 mg, 0.38 mmol), N-methyldicyclohexylamine (250 mg, 1.28 mmol), Pd$_2$(dba)$_3$(163 mg, 0.64 mmol) and anhydrous dioxane was added in a 50 mL egg-shaped flask and stirred at room temperature for 30 min, then SIAIS172136 (300 mg, 0.89 mmol) and tert-butyl acrylate were added. The resulting reaction solution was slowly heated to 55° C. under an atmosphere of nitrogen and stirred for 12 h. After the reaction was complete, the reaction solution was concentrated under reduced pressure, the residue was purified by silica gel chromatography (eluent (v/v): EA/PE=2:3) to yield the desired product SIAIS172145 as light yellow solid (270 mg, 79%). $^1$H NMR (500 MHz, CDCl$_3$) δ 8.11 (s, 1H), 8.02 (s, 1H), 7.89 (d, J=7.7 Hz, 1H), 7.84 (dd, J=7.8, 1.2 Hz, 1H), 7.65 (d, J=16.0 Hz, 1H), 6.54 (d, J=16.0 Hz, 1H), 5.00 (dd, J=12.5, 5.3 Hz, 1H), 2.94-2.72 (m, 3H), 2.20-2.13 (m, 1H), 1.54 (s, 9H). HRMS (ESI) calcd for C$_{20}$H$_{21}$N$_2$O$_6$$^+$ [M+H]$^+$, 385.1394; found, 385.1389.

Synthesis of 3-(2-(2,6-dioxopiperidin-3-yl)-1,3-dioxoisoindololin-4-yl) propionic acid (SIAIS172147)

According to scheme 14, SIAIS172145 (250 mg, 0.65 mmol) was added in a 100 mL egg-shaped flask, followed by dioxane (20 mL) anad 10% wet Pd/C. After extracting and recharging with H$_2$ (25 psi) 3 times, the reaction solution was allowed to stir at RT overnight. After the reaction was complete, the reaction solution was filtrated, washed with dioxane, the filtrate was concentrated under reduced pressure to give a light yellow oil, the crude was used for the following reaction without further purification. The crude, TFA (1 mL) and anhydrous DCM were added in a 50 mL egg-shaped flask, and stirred at RT for 2 h, when the reaction was complete, the resulting solution was concentrated under reduced pressure, the residue was purified by reverse-phase chromatography, eluent (v/v): acetonitrile/(water+0.1% TFA)=10%-100%, to yield the desired product SIAIS172147 after concentration and freeze-drying, (white solid, 180 mg, 84% over 2 steps). $^1$H NMR (500 MHz, DMSO) δ 12.22 (s, 1H), 11.12 (s, 1H), 7.86-7.79 (m, 2H), 7.77-7.70 (m, 1H), 5.13 (dd, J=12.8, 5.4 Hz, 1H), 3.01 (t, J=7.4 Hz, 2H), 2.93-2.85 (m, 1H), 2.64 (t, J=7.4 Hz, 2H), 2.62-2.50 (m, 2H), 2.08-2.02 (m, 1H). HRMS (ESI) calcd for C$_{16}$H$_{15}$N$_2$O$_6$$^+$ [M+H]$^+$, 331.0925; found, 331.0919.

COMPOUND EXAMPLES

Compound Example 1: Synthesis of 4-((2-(3-(4-(4-((5-chloro-4-((2-(dimethylphosphoryl)phenyl)amino)pyrimidin-2-yl)amino)-3-methoxyphenyl)piperazin-1-yl)-3-oxopropoxy)ethyl)amino)-2-(2,6-dioxopiperidin-3-yl)isoindoline-1,3-dione. (SIAIS1197065)

According to scheme 15, to a stirred solution of corresponding ALK inhibitor (Brigatinib Analogue A, 0.02 mmol, 1 equiv) and intermediate LM (SIAIS151001, 1 equiv), in DMF (1 mL) and DCM (5 mL) was added HOAt (0.04 mmol, 2 equiv), EDCI (0.04 mmol, 2 equiv) and NMM (0.2 mmol, 10 equiv) sequentially at RT. The resulting reaction mixture was stirred at room temperature overnight. After the reaction was complete detected by LC-MS, the resulting solution was purified by preparative HPLC, eluent (v/v): acetonitrile/(water+0.05% HCl)=10%-100%, after concentration under reduced pressure and freeze-drying, the desired product SIAIS1197065 was obtained as yellow solid (16.2 mg, 60%). $^1$H NMR (500 MHz, MeOD) δ 8.38 (s, 1H), 8.05 (s, 1H), 7.65 (dd, J=13.8, 7.7 Hz, 1H), 7.54 (s, 1H), 7.50 (dd, J=8.4, 7.2 Hz, 1H), 7.35 (t, J=7.3 Hz, 1H), 7.26 (s, 1H), 7.04 (d, J=8.6 Hz, 1H), 7.00 (d, J=7.1 Hz, 1H), 6.65 (s, 1H), 6.46 (d, J=7.9 Hz, 1H), 4.97 (dd, J=12.4, 5.4 Hz, 1H), 3.84 (t, J=5.8 Hz, 4H), 3.80 (s, 3H), 3.72 (t, J=5.0 Hz, 4H), 3.48 (t, J=5.0 Hz, 2H), 3.20 (s, 4H), 2.80-2.68 (m, 3H), 2.66-2.58 (m, 2H), 2.04-1.96 (m, 1H), 1.88 (d, J=13.6 Hz, 6H). HRMS (ESI) calcd for C$_{41}$H$_{46}$ClN$_9$O$_8$P$^+$ [M+H]$^+$, 858.2890; found, 858.3506.

Compound Example 2: Synthesis of 4-((2-(2-(3-(4-(4-((5-chloro-4-((2-(dimethylphosphoryl)phenyl)amino)pyrimidin-2-yl)amino)-3-methoxyphenyl)piperazin-1-yl)-3-oxopropoxy)ethoxy)ethyl)amino)-2-(2,6-dioxopiperidin-3-yl)isoindoline-1,3-dione. (SIAIS1197067)

According to the procedures for the preparation of Compound Example 1, Brigatinib Analogue A and intermediate LM (SIAIS151004) was used to prepare SIAIS1197067 (yellow solid, 16.7 mg, 62% yield). $^1$H NMR (500 MHz, MeOD) δ 8.37 (s, 1H), 8.04 (s, 1H), 7.66 (dd, J=13.9, 7.7 Hz, 1H), 7.55 (s, 1H), 7.50 (dd, J=8.5, 7.2 Hz, 1H), 7.37 (t, J=7.0 Hz, 1H), 7.28 (d, J=6.7 Hz, 1H), 7.02 (d, J=8.6 Hz, 1H), 7.00 (d, J=7.0 Hz, 1H), 6.68 (s, 1H), 6.51 (d, J=6.4 Hz, 1H), 5.02 (dd, J=12.5, 5.5 Hz, 1H), 3.82 (s, 3H), 3.79 (t, J=6.1 Hz, 2H), 3.74 (d, J=4.2 Hz, 4H), 3.68 (t, J=5.3 Hz, 2H), 3.66-3.59 (m, 4H), 3.43 (t, J=5.2 Hz, 2H), 3.28-3.18 (m, 4H), 2.86-2.76 (m, 1H), 2.75-2.61 (m, 4H), 2.11-2.03 (m, 1H), 1.88 (d, J=13.6 Hz, 6H). HRMS (ESI) calcd for C$_{43}$H$_{50}$ClN$_9$O$_9$P$^+$ [M+H]$^+$, 902.3152; found, 902.3791.

Compound Example 3: Synthesis of 4-((2-(2-(2-(3-(4-(4-((2-(dimethylphosphoryl)phenyl)amino)-5-methylpyrimidin-2-yl)amino)-3-methoxyphenyl)piperazin-1-yl)-3-oxopropoxy)ethoxy)ethoxy)ethyl)amino)-2-(2,6-dioxopiperidin-3-yl)isoindoline-1,3-dione. (SIAIS1197069)

According to the procedures for the preparation of Compound Example 1, Brigatinib Analogue A and intermediate LM (SIAIS151005) was used to prepare SIAIS1197069 (yellow solid, 13.7 mg, 51% yield). $^1$H NMR (500 MHz, MeOD) δ 8.36 (s, 1H), 8.03 (s, 1H), 7.66 (dd, J=14.0, 7.7 Hz, 1H), 7.55 (s, 1H), 7.51 (t, J=7.8 Hz, 1H), 7.37 (t, J=7.4 Hz, 1H), 7.30 (s, 1H), 7.03 (d, J=8.7 Hz, 1H), 7.01 (d, J=7.1 Hz, 1H), 6.70 (s, 1H), 6.56 (s, 1H), 5.02 (dd, J=12.6, 5.5 Hz, 1H), 3.83 (s, 3H), 3.80-3.71 (m, 6H), 3.68-3.57 (m, 10H), 3.44 (t, J=5.0 Hz, 2H), 3.28 (s, 2H), 3.23 (s, 2H), 2.87-2.78 (m, 1H), 2.75-2.62 (m, 4H), 2.12-2.04 (m, 1H), 1.88 (d, J=13.6 Hz, 6H). HRMS (ESI) calcd for C$_{45}$H$_{54}$ClN$_9$O$_{10}$P$^+$ [M+H]$^+$, 946.3961; found, 946.1771.

Compound Example 4: Synthesis of 4-((15-(4-(4-((5-chloro-4-((2-(dimethylphosphoryl)phenyl)amino)pyrimidin-2-yl)amino)-3-methoxyphenyl)piperazin-1-yl)-15-oxo-3,6,9,12-tetraoxapentadecyl)amino)-2-(2,6-dioxopiperidin-3-yl)isoindoline-1,3-dione. (SIAIS1197071)

According to the procedures for the preparation of Compound Example 1, Brigatinib Analogue A and intermediate LM (SIAIS151006) was used to prepare SIAIS1197071 (yellow solid, 4.8 mg, 18% yield). $^1$H NMR (500 MHz, MeOD) δ 8.38 (s, 1H), 8.03 (s, 1H), 7.66 (dd, J=15.0, 7.4 Hz, 1H), 7.58-7.49 (m, 2H), 7.37 (t, J=8.4 Hz, 1H), 7.30 (t, J=7.5 Hz, 1H), 7.07-7.00 (m, 2H), 6.72 (s, 1H), 6.56 (s, 1H), 5.02 (dd, J=12.6, 5.5 Hz, 1H), 3.84 (s, 3H), 3.80-3.73 (m, 6H), 3.64-3.55 (m, 14H), 3.46 (t, J=5.5 Hz, 2H), 3.24 (s, 4H), 2.87-2.78 (m, 1H), 2.74-2.67 (m, 4H), 2.10-2.04 (m, 1H), 1.88 (d, J=13.6 Hz, 6H). HRMS (ESI) calcd for $C_{47}H_{58}ClN_9O_{11}P^+$ [M+H]$^+$, 990.3676; found, 990.4374.

Compound Example 5: Synthesis of 4-((18-(4-(4-((5-chloro-4-((2-(dimethylphosphoryl)phenyl)amino) pyrimidin-2-yl)amino)-3-methoxyphenyl)piperazin-1-yl)-18-oxo-3,6,9,12,15-pentaoxaoctadecyl)amino)-2-(2,6-dioxopiperidin-3-yl)isoindoline-1,3-dione. (SIAIS1197073)

According to the procedures for the preparation of Compound Example 1, Brigatinib Analogue A and intermediate LM (SIAIS151007) was used to prepare SIAIS1197073 (yellow solid, 4.5 mg, 17% yield). $^1$H NMR (500 MHz, MeOD) δ 8.39 (s, 1H), 8.03 (s, 1H), 7.66 (dd, J=14.0, 7.5 Hz, 1H), 7.59-7.48 (m, 2H), 7.38 (t, J=7.1 Hz, 1H), 7.29 (s, 1H), 7.06 (d, J=8.7 Hz, 1H), 7.02 (d, J=7.0 Hz, 1H), 6.73 (s, 1H), 6.57 (s, 1H), 5.02 (dd, J=12.6, 5.5 Hz, 1H), 3.84 (s, 3H), 3.80-3.72 (m, 6H), 3.71-3.54 (m, 18H), 3.46 (t, J=5.5 Hz, 2H), 3.24 (s, 4H), 2.86-2.77 (m, 1H), 2.76-2.62 (m, 4H), 2.11-2.04 (m, 1H), 1.88 (d, J=13.6 Hz, 6H). HRMS (ESI) calcd for $C_{49}H_{62}ClN_9O_{12}P^+$ [M+H]$^+$, 1034.3939; found, 1034.3055.

Compound Example 6: Synthesis of 4-((2-(4-(4-((5-chloro-4-((2-(dimethylphosphoryl)phenyl)amino) pyrimidin-2-yl)amino)-3-methoxyphenyl)piperazin-1-yl)-2-oxoethyl)amino)-2-(2,6-dioxopiperidin-3-yl) isoindoline-1,3-dione. (SIAIS1197055)

According to the procedures for the preparation of Compound Example 1, Brigatinib Analogue A and intermediate LM (SIAIS151025) was used to prepare SIAIS1197055 (yellow solid, 18.8 mg, 69% yield). $^1$H NMR (500 MHz, DMSO) δ 11.12 (s, 1H), 8.43 (s, 1H), 8.11 (s, 1H), 7.64 (dd, J=8.4, 7.2 Hz, 1H), 7.59-7.54 (m, 1H), 7.43 (d, J=9.4 Hz, 1H), 7.39 (s, 1H), 7.14 (d, J=8.6 Hz, 1H), 7.09 (d, J=7.1 Hz, 1H), 6.73 (d, J=2.1 Hz, 1H), 6.55 (dd, J=8.5, 2.2 Hz, 1H), 5.08 (dd, J=12.9, 5.1 Hz, 1H), 3.80 (s, 3H), 3.71 (s, 4H), 3.28 (s, 2H), 3.20 (s, 4H), 1.78 (d, J=13.6 Hz, 6H). HRMS (ESI) calcd for $C_{38}H_{40}ClN_9O_7P^+$ [M+H]$^+$, 800.2471; found, 800.2478.

Compound Example 7: Synthesis of 4-((3-(4-(4-((5-chloro-4-((2-(dimethylphosphoryl)phenyl)amino) pyrimidin-2-yl)amino)-3-methoxyphenyl)piperazin-1-yl)-3-oxopropyl)amino)-2-(2,6-dioxopiperidin-3-yl)isoindoline-1,3-dione. (SIAIS1197057)

According to the procedures for the preparation of Compound Example 1, Brigatinib Analogue A and intermediate LM (SIAIS151026) was used to prepare SIAIS1197057 (yellow solid, 13.5 mg, 50% yield). $^1$H NMR (500 MHz, MeOD) δ 8.37 (s, 1H), 8.04 (s, 1H), 7.66 (dd, J=14.0, 7.6 Hz, 1H), 7.58 (t, J=7.8 Hz, 2H), 7.36 (t, J=7.4 Hz, 1H), 7.29 (d, J=8.2 Hz, 1H), 7.14 (d, J=8.7 Hz, 1H), 7.05 (d, J=7.1 Hz, 1H), 6.68 (s, 1H), 6.54 (d, J=7.5 Hz, 1H), 4.99 (dd, J=12.8, 5.5 Hz, 1H), 3.83 (s, 3H), 3.78-3.68 (m, 6H), 3.18 (s, 4H), 2.84-2.74 (m, 3H), 2.71-2.59 (m, 2H), 2.02-1.94 (m, 1H), 1.88 (d, J=13.6 Hz, 6H). HRMS (ESI) calcd for $C_{39}H_{42}ClN_9O_7P^+$ [M+H]$^+$, 814.2628; found, 814.3219.

Compound Example 8: Synthesis of 4-((4-(4-(4-((5-chloro-4-((2-(dimethylphosphoryl)phenyl)amino) pyrimidin-2-yl)amino)-3-methoxyphenyl)piperazin-1-yl)-4-oxobutyl)amino)-2-(2,6-dioxopiperidin-3-yl) isoindoline-1,3-dione. (SIAIS1197059)

According to the procedures for the preparation of Compound Example 1, Brigatinib Analogue A and intermediate LM (SIAIS151019) was used to prepare SIAIS1197059 (yellow solid, 14.4 mg, 53% yield). $^1$H NMR (500 MHz, MeOD) δ 8.38 (s, 1H), 8.04 (s, 1H), 7.66 (dd, J=13.8, 7.3 Hz, 1H), 7.54 (dd, J=8.5, 7.1 Hz, 2H), 7.36 (t, J=7.6 Hz, 1H), 7.30 (d, J=8.5 Hz, 1H), 7.11 (d, J=8.6 Hz, 1H), 7.01 (d, J=7.1 Hz, 1H), 6.69 (s, 1H), 6.54 (d, J=7.5 Hz, 1H), 5.03 (dd, J=12.6, 5.5 Hz, 1H), 3.84 (s, 3H), 3.78-3.65 (m, 4H), 3.44 (t, J=6.6 Hz, 2H), 3.18 (s, 4H), 2.89-2.77 (m, 1H), 2.75-2.63 (m, 2H), 2.58 (t, J=7.0 Hz, 2H), 2.11-2.04 (m, 1H), 2.04-1.97 (m, 2H), 1.88 (d, J=13.6 Hz, 6H). HRMS (ESI) calcd for $C_{40}H_{44}ClN_9O_7P^+$ [M+H]$^+$, 828.2784; found, 828.2783.

Compound Example 9: Synthesis of 4-((5-(4-(4-((5-chloro-4-((2-(dimethylphosphoryl)phenyl)amino) pyrimidin-2-yl)amino)-3-methoxyphenyl)piperazin-1-yl)-5-oxopentyl)amino)-2-(2,6-dioxopiperidin-3-yl)isoindoline-1,3-dione. (SIAIS1197061)

According to the procedures for the preparation of Compound Example 1, Brigatinib Analogue A and intermediate LM (SIAIS151020) was used to prepare SIAIS1197061 (yellow solid, 12.6 mg, 45% yield). $^1$H NMR (500 MHz, MeOD) δ 8.37 (s, 1H), 8.04 (s, 1H), 7.64 (dd, J=14.1, 7.8 Hz, 1H), 7.54 (t, J=7.8 Hz, 2H), 7.41-7.30 (m, 2H), 7.07 (d, J=8.5 Hz, 1H), 7.01 (d, J=7.1 Hz, 1H), 6.69 (s, 1H), 6.53 (s, 1H), 5.00 (dd, J=12.6, 5.5 Hz, 1H), 3.85 (s, 3H), 3.78-3.66 (m, 4H), 3.39 (t, J=5.6 Hz, 2H), 3.19 (s, 4H), 2.85-2.74 (m, 1H), 2.73-2.60 (m, 2H), 2.53 (t, J=6.6 Hz, 2H), 2.07-2.00 (m, 1H), 1.87 (d, J=13.5 Hz, 6H), 1.81-1.71 (m, 4H). HRMS (ESI) calcd for $C_{41}H_{46}ClN_9O_7P^+$ [M+H]$^+$, 842.2941; found, 842.2951.

Compound Example 10: Synthesis of 4-((6-(4-(4-((5-chloro-4-((2-(dimethylphosphoryl)phenyl)amino) pyrimidin-2-yl)amino)-3-methoxyphenyl)piperazin-1-yl)-6-oxohexyl)amino)-2-(2,6-dioxopiperidin-3-yl) isoindoline-1,3-dione. (SIAIS1197063)

According to the procedures for the preparation of Compound Example 1, Brigatinib Analogue A and intermediate LM (SIAIS151027) was used to prepare SIAIS1197063 (yellow solid, 15.6 mg, 58% yield). $^1$H NMR (500 MHz, MeOD) δ 8.38 (s, 1H), 8.04 (s, 1H), 7.66 (dd, J=13.5, 7.0 Hz, 1H), 7.53 (dd, J=8.6, 7.1 Hz, 2H), 7.36 (t, J=6.8 Hz, 1H), 7.32 (d, J=6.8 Hz, 1H), 7.05 (d, J=8.5 Hz, 1H), 7.00 (d, J=6.9 Hz, 1H), 6.71 (s, 1H), 6.55 (d, J=7.7 Hz, 1H), 5.01 (dd, J=12.5, 5.4 Hz, 1H), 3.85 (s, 3H), 3.78-3.68 (m, 4H), 3.36 (t, J=6.8 Hz, 2H), 3.22 (s, 4H), 2.86-2.74 (m, 1H), 2.74-2.62 (m, 2H), 2.49 (t, J=7.4 Hz, 2H), 2.10-2.03 (m, 1H), 1.88 (d, J=13.6 Hz, 6H), 1.76-1.66 (m, 4H), 1.54-1.46 (m, 2H). HRMS (ESI) calcd for $C_{42}H_{48}ClN_9O_7P^+$ [M+H]$^+$, 856.3097; found, 856.3109.

Compound Example 11: Synthesis of 4-((7-(4-(4-((5-chloro-4-((2-(dimethylphosphoryl)phenyl)amino) pyrimidin-2-yl)amino)-3-methoxyphenyl)piperazin-1-yl)-7-oxoheptyl)amino)-2-(2,6-dioxopiperidin-3-yl)isoindoline-1,3-dione. (SIAIS1197077)

According to the procedures for the preparation of Compound Example 1, Brigatinib Analogue A and intermediate LM (SIAIS151086) was used to prepare SIAIS1197077 (yellow solid, 17.6 mg, 65% yield). $^1$H NMR (500 MHz, MeOD) δ 8.38 (s, 1H), 8.04 (s, 1H), 7.66 (dd, J=13.8, 7.7 Hz, 1H), 7.53 (dd, J=8.6, 7.1 Hz, 2H), 7.37 (t, J=7.1 Hz, 1H), 7.31 (d, J=8.6 Hz, 1H), 7.04 (d, J=8.6 Hz, 1H), 7.02 (d, J=7.0 Hz, 1H), 6.72 (s, 1H), 6.56 (d, J=8.5 Hz, 1H), 5.03 (dd, J=12.5, 5.5 Hz, 1H), 3.85 (s, 3H), 3.79-3.67 (m, 4H), 3.34 (t, J=6.9 Hz, 2H), 3.24 (d, J=14.7 Hz, 4H), 2.87-2.77 (m, 1H), 2.75-2.64 (m, 2H), 2.46 (t, J=7.5 Hz, 2H), 2.12-2.04 (m, 1H), 1.88 (d, J=13.6 Hz, 6H), 1.74-1.62 (m, 4H), 1.54-1.40 (m, 4H). HRMS (ESI) calcd for $C_{43}H_{50}ClN_9O_7P^+$ [M+H]$^+$, 870.3254; found, 870.3009.

Compound Example 12: Synthesis of (2S,4R)-1-((S)-2-(2-(2-(2-(4-(4-((5-chloro-4-((2-(dimethylphosphoryl)phenyl)amino)pyrimidin-2-yl)amino)-3-methoxyphenyl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide. (SIAIS1197087)

According to the procedures for the preparation of Compound Example 1, Brigatinib Analogue A and intermediate LM (SIAIS151010) was used to prepare SIAIS1197087 (white solid, 15.7 mg, 58%). $^1$H NMR (500 MHz, MeOD) δ 8.85 (s, 1H), 8.37 (s, 1H), 8.04 (s, 1H), 7.65 (dd, J=14.1, 7.4 Hz, 1H), 7.54 (s, 1H), 7.44-7.32 (m, 5H), 6.69 (s, 1H), 6.55 (s, 1H), 4.71 (d, J=9.4 Hz, 1H), 4.60-4.44 (m, 2H), 4.50 (s, 1H), 4.41-4.31 (m, 3H), 4.07 (d, J=10.4 Hz, 2H), 3.87 (d, J=9.8 Hz, 1H), 3.83 (s, 3H), 3.80-3.64 (m, 9H), 3.25 (s, 4H), 2.44 (s, 3H), 2.27-2.17 (m, 1H), 2.13-2.04 (m, 1H), 1.87 (d, J=13.5 Hz, 6H), 1.03 (s, 9H). HRMS (ESI) calcd for $C_{51}H_{65}ClN_{10}O_9PS^+$ [M+H]$^+$, 1059.4077; found, 1059.4091.

Compound Example 13: Synthesis of (2S,4R)-1-((S)-2-(3-(2-(3-(4-(4-((5-chloro-4-((2-(dimethylphosphoryl)phenyl)amino)pyrimidin-2-yl)amino)-3-methoxyphenyl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide. (SIAIS1197079)

According to the procedures for the preparation of Compound Example 1, Brigatinib Analogue A and intermediate LM (SIAIS151002) was used to prepare SIAIS1197079 (white solid, 14.9 mg, 55%). $^1$H NMR (500 MHz, MeOD) δ 8.89 (s, 1H), 8.40 (s, 1H), 8.03 (s, 1H), 7.66 (dd, J=14.0, 7.7 Hz, 1H), 7.55 (s, 1H), 7.46 (d, J=8.2 Hz, 2H), 7.42-7.33 (m, 3H), 7.29 (d, J=7.8 Hz, 1H), 6.72 (s, 1H), 6.58 (d, J=8.5 Hz, 1H), 4.64 (s, 1H), 4.60-4.52 (m, 2H), 4.49 (s, 1H), 4.34 (d, J=15.5 Hz, 1H), 3.88 (d, J=10.9 Hz, 1H), 3.84 (s, 3H), 3.81-3.66 (m, 9H), 3.62-3.58 (m, 4H), 3.31 (s, 2H), 3.21 (s, 2H), 2.77-2.66 (m, 2H), 2.46 (s, 3H), 2.51-2.43 (m, 1H), 2.43-2.36 (m, 1H), 2.25-2.18 (m, 1H), 2.12-2.04 (m, 1H), 1.88 (d, J=13.6 Hz, 6H), 1.03 (s, 9H). HRMS (ESI) calcd for $C_{53}H_{69}ClN_{10}O_9PS^+$ [M+H]$^+$, 1087.4390; found, 1087.3478.

Compound Example 14: Synthesis of (2S,4R)-1-((S)-2-(tert-butyl)-16-(4-(4-((5-chloro-4-((2-(dimethylphosphoryl)phenyl)amino)pyrimidin-2-yl)amino)-3-methoxyphenyl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide. (SIAIS1197081)

According to the procedures for the preparation of Compound Example 1, Brigatinib Analogue A and intermediate LM (SIAIS151003) was used to prepare SIAIS1197081 (white solid, 17.1 mg, 63%). $^1$H NMR (500 MHz, MeOD) δ 8.91 (s, 1H), 8.39 (s, 1H), 8.04 (s, 1H), 7.66 (dd, J=14.1, 7.8 Hz, 1H), 7.54 (s, 1H), 7.46 (d, J=8.2 Hz, 2H), 7.44-7.35 (m, 3H), 7.29 (d, J=8.2 Hz, 1H), 6.73 (d, J=2.1 Hz, 1H), 6.59 (d, J=8.4 Hz, 1H), 4.64 (s, 1H), 4.59-4.51 (m, 2H), 4.49 (s, 1H), 4.35 (d, J=15.5 Hz, 1H), 3.88 (d, J=11.1 Hz, 1H), 3.85 (s, 3H), 3.82-3.73 (m, 7H), 3.72-3.65 (m, 2H), 3.63-3.54 (m, 8H), 3.44 (t, J=7.0 Hz, 1H), 3.31 (s, 2H), 3.24 (s, 2H), 2.71 (t, J=6.2 Hz, 2H), 2.60-2.50 (m, 1H), 2.47 (s, 3H), 2.49-2.40 (m, 1H), 2.25-2.18 (m, 1H), 2.11-2.05 (m, 1H), 1.88 (d, J=13.6 Hz, 6H), 1.03 (s, 9H). HRMS (ESI) calcd for $C_{55}H_{73}ClN_{10}O_{10}PS^+$ [M+H]$^+$, 1131.4652; found, 1131.4651.

Compound Example 15: Synthesis of (2S,4R)-1-((S)-2-(tert-butyl)-19-(4-(4-((5-chloro-4-((2-(dimethylphosphoryl)phenyl)amino)pyrimidin-2-yl)amino)-3-methoxyphenyl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide. (SIAIS1197083)

According to the procedures for the preparation of Compound Example 1, Brigatinib Analogue A and intermediate LM (SIAIS151008) was used to prepare SIAIS1197083 (white solid, 16.7 mg, 62%). $^1$H NMR (500 MHz, MeOD) δ 8.89 (s, 1H), 8.39 (s, 1H), 8.04 (s, 1H), 7.66 (dd, J=13.5, 8.1 Hz, 1H), 7.54 (s, 1H), 7.46 (d, J=8.1 Hz, 2H), 7.42-7.35 (m, 3H), 7.31 (d, J=8.6 Hz, 1H), 6.73 (s, 1H), 6.58 (d, J=7.5 Hz, 1H), 4.64 (s, 1H), 4.59-4.50 (m, 2H), 4.49 (s, 1H), 4.35 (d, J=15.5 Hz, 1H), 3.87 (d, J=12.2 Hz, 1H), 3.85 (s, 3H), 3.82-3.72 (m, 7H), 3.73-3.65 (m, 2H), 3.64-3.53 (m, 12H), 3.31 (s, 2H), 3.24 (s, 2H), 2.72 (t, J=6.2 Hz, 2H), 2.59-2.51 (m, 1H), 2.46 (s, 3H), 2.49-2.40 (m, 1H), 2.25-2.16 (m, 1H), 2.11-2.04 (m, 1H), 1.88 (d, J=13.6 Hz, 6H), 1.03 (s, 9H). HRMS (ESI) calcd for $C_{57}H_{77}ClN_{10}O_{11}PS^+$ [M+H]$^+$, 1175.4915; found, 1175.4981.

Compound Example 16: Synthesis of (2S,4R)-1-((S)-2-(tert-butyl)-22-(4-(4-((5-chloro-4-((2-(dimethylphosphoryl)phenyl)amino)pyrimidin-2-yl)amino)-3-methoxyphenyl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide. (SIAIS1197085)

According to the procedures for the preparation of Compound Example 1, Brigatinib Analogue A and intermediate LM (SIAIS151009) was used to prepare SIAIS1197085 (white solid, 16.5 mg, 61%). $^1$H NMR (500 MHz, MeOD) δ 8.90 (s, 1H), 8.39 (s, 1H), 8.03 (s, 1H), 7.67 (dd, J=14.0, 6.9 Hz, 1H), 7.55 (s, 1H), 7.46 (d, J=8.1 Hz, 2H), 7.44-7.34 (m, 3H), 7.30 (d, J=8.5 Hz, 1H), 6.74 (s, 1H), 6.59 (d, J=8.1 Hz, 1H), 4.64 (s, 1H), 4.59-4.51 (m, 2H), 4.49 (s, 1H), 4.35 (d, J=15.6 Hz, 1H), 3.88 (d, J=11.1 Hz, 1H), 3.85 (s, 3H), 3.82-3.4 (m, 7H), 3.74-3.67 (m, 2H), 3.65-3.54 (m, 16H), 3.31 (s, 2H), 3.25 (s, 2H), 2.72 (t, J=6.1 Hz, 2H), 2.60-2.51 (m, 1H), 2.47 (s, 3H), 2.50-2.40 (m, 1H), 2.25-2.17 (m, 1H), 2.11-2.04 (m, 1H), 1.88 (d, J=13.6 Hz, 6H), 1.03 (s, 9H). HRMS (ESI) calcd for $C_{59}H_{81}ClN_{10}O_{12}PS^+$ [M+H]$^+$, 1219.5177; found, 1219.5229.

Compound Example 17: Synthesis of (2S,4R)-1-((S)-2-(4-(4-(4-((5-chloro-4-((2-(dimethylphosphoryl)phenyl)amino)pyrimidin-2-yl)amino)-3-methoxyphenyl)piperazin-1-yl)-4-oxobutanamido)-3,3-dimethylbutanoyl)-4-hydroxy-N-(4-(4-methylthiazol-5-yl)benzyl)pyrrolidine-2-carboxamide. (SIAIS1197145)

According to the procedures for the preparation of Compound Example 1, Brigatinib Analogue A and intermediate LM (SIAIS074011) was used to prepare SIAIS1197145 (white solid, 10.1 mg, 37%). $^1$H NMR (500 MHz, MeOD) δ 9.98 (s, 1H), 8.22 (s, 1H), 8.18 (s, 1H), 7.80-7.45 (m, 8H), 7.39 (s, 1H), 7.13 (d, J=8.5 Hz, 1H), 4.66-4.35 (m, 5H), 4.05 (s, 4H), 3.96 (s, 3H), 3.89 (d, J=10.7 Hz, 1H), 3.80 (d, J=8.1 Hz, 1H), 3.70 (s, 2H), 3.61 (s, 2H), 2.91-2.63 (m, 4H), 2.61 (s, 3H), 2.23 (s, 1H), 2.07 (s, 1H), 1.87 (d, J=13.4 Hz, 6H), 1.05 (s, 9H). HRMS (ESI) calcd for $C_{49}H_{61}ClN_{10}O_7PS^+$ [M+H]$^+$, 999.3866; found, 999.1918.

Compound Example 18: Synthesis of (2S,4R)-1-((S)-2-(5-(4-(4-((5-chloro-4-((2-(dimethylphosphoryl)phenyl)amino)pyrimidin-2-yl)amino)-3-methoxyphenyl)piperazin-1-yl)-5-oxopentanamido)-3,3-dimethylbutanoyl)-4-hydroxy-N-(4-(4-methylthiazol-5-yl)benzyl)pyrrolidine-2-carboxamide. (SIAIS1197147)

According to the procedures for the preparation of Compound Example 1, Brigatinib Analogue A and intermediate LM (SIAIS074012) was used to prepare SIAIS1197147 (white solid, 9.4 mg, 35%). $^1$H NMR (500 MHz, MeOD) δ 10.00 (s, 1H), 8.25 (s, 1H), 8.14 (s, 1H), 7.79-7.63 (m, 3H), 7.61-7.46 (m, 6H), 7.22 (d, J=8.6 Hz, 1H), 4.65-4.47 (m, 4H), 4.41 (d, J=15.7 Hz, 1H), 4.07 (s, 4H), 3.97 (s, 3H), 3.93 (d, J=11.1 Hz, 1H), 3.80 (dd, J=11.0, 3.6 Hz, 1H), 3.74 (s, 2H), 3.66 (s, 2H), 2.60 (s, 3H), 2.53 (t, J=7.4 Hz, 2H), 2.40 (t, J=7.1 Hz, 2H), 2.28-2.20 (m, 1H), 2.11-2.02 (m, 1H), 2.01-1.92 (m, 2H), 1.87 (d, J=13.6 Hz, 6H), 1.05 (s, 9H). HRMS (ESI) calcd for $C_{50}H_{63}ClN_{10}O_7PS^+$ [M+H]$^+$, 1013.4023; found, 1013.2012.

Compound Example 19: Synthesis of (2S,4R)-1-((S)-2-(6-(4-(4-((5-chloro-4-((2-(dimethylphosphoryl)phenyl)amino)pyrimidin-2-yl)amino)-3-methoxyphenyl)piperazin-1-yl)-6-oxohexanamido)-3,3-dimethylbutanoyl)-4-hydroxy-N-(4-(4-methylthiazol-5-yl)benzyl)pyrrolidine-2-carboxamide. (SIAIS1197149)

According to the procedures for the preparation of Compound Example 1, Brigatinib Analogue A and intermediate LM (SIAIS074013) was used to prepare SIAIS1197149 (white solid, 11.4 mg, 42%). $^1$H NMR (500 MHz, MeOD) δ 10.02 (d, J=2.9 Hz, 1H), 8.26 (s, 1H), 8.13 (m, 1H), 7.80-7.63 (m, 3H), 7.60-7.49 (m, 6H), 7.25 (d, J=8.8 Hz, 1H), 4.64-4.46 (m, 4H), 4.40 (dd, J=15.7, 3.7 Hz, 1H), 4.10 (s, 4H), 3.97 (s, 3H), 3.90 (d, J=11.1 Hz, 1H), 3.80 (dd, J=11.0, 3.9 Hz, 1H), 3.76 (s, 2H), 3.68 (s, 2H), 2.61 (s, 3H), 2.59-2.48 (m, 2H), 2.38-2.32 (m, 2H), 2.27-2.21 (m, 1H), 2.10-2.03 (m, 1H), 1.87 (d, J=13.6 Hz, 6H), 1.77-1.64 (m, 4H), 1.04 (s, 9H). HRMS (ESI) calcd for $C_{51}H_{65}ClN_{10}O_7PS^+$ [M+H]$^+$, 1027.4179; found, 1027.2037.

Compound Example 20: Synthesis of (2S,4R)-1-((S)-2-(7-(4-(4-((5-chloro-4-((2-(dimethylphosphoryl)phenyl)amino)pyrimidin-2-yl)amino)-3-methoxyphenyl)piperazin-1-yl)-7-oxoheptanamido)-3,3-dimethylbutanoyl)-4-hydroxy-N-(4-(4-methylthiazol-5-yl)benzyl)pyrrolidine-2-carboxamide. (SIAIS1197151)

According to the procedures for the preparation of Compound Example 1, Brigatinib Analogue A and intermediate LM (SIAIS074014) was used to prepare SIAIS1197151 (white solid, 12.7 mg, 47%). $^1$H NMR (500 MHz, MeOD) δ 10.03 (d, J=1.2 Hz, 1H), 8.26 (s, 1H), 8.13 (s, 1H), 7.78-7.65 (m, 3H), 7.61-7.48 (m, 6H), 7.25 (d, J=8.6 Hz, 1H), 4.63 (d, J=7.6 Hz, 1H), 4.59-4.53 (m, 2H), 4.50 (s, 1H), 4.40 (dd, J=15.8, 6.4 Hz, 1H), 4.11 (s, 4H), 3.98 (s, 3H), 3.90 (d, J=11.0 Hz, 1H), 3.80 (dd, J=11.0, 3.7 Hz, 1H), 3.77-3.60 (m, 4H), 2.61 (s, 3H), 2.52 (t, J=7.5 Hz, 2H), 2.36-2.19 (m, 3H), 2.12-2.04 (m, 1H), 1.87 (d, J=13.6 Hz, 6H), 1.72-1.57 (m, 4H), 1.47-1.29 (m, 2H), 1.03 (s, 9H). HRMS (ESI) calcd for $C_{52}H_{67}ClN_{10}O_7PS^+$ [M+H]$^+$, 1041.4336; found, 1041.2125.

Compound Example 21: Synthesis of (2S,4R)-1-((S)-2-(8-(4-(4-((5-chloro-4-((2-(dimethylphosphoryl)phenyl)amino)pyrimidin-2-yl)amino)-3-methoxyphenyl)piperazin-1-yl)-8-oxooctanamido)-3,3-dimethylbutanoyl)-4-hydroxy-N-(4-(4-methylthiazol-5-yl)benzyl)pyrrolidine-2-carboxamide. (SIAIS1197153)

According to the procedures for the preparation of Compound Example 1, Brigatinib Analogue A and intermediate LM (SIAIS074015) was used to prepare SIAIS1197153 (white solid, 6.8 mg, 25%). $^1$H NMR (500 MHz, MeOD) δ 9.99 (d, J=4.4 Hz, 1H), 8.23 (s, 1H), 8.18 (s, 1H), 7.74 (dd, J=13.0, 7.6 Hz, 1H), 7.66 (t, J=7.5 Hz, 2H), 7.60-7.46 (m, 5H), 7.40 (s, 1H), 7.14 (d, J=8.7 Hz, 1H), 4.63 (d, J=6.1 Hz, 1H), 4.60-4.52 (m, 2H), 4.50 (s, 1H), 4.40 (dd, J=15.8, 7.7 Hz, 1H), 4.05 (s, 4H), 3.96 (s, 3H), 3.91 (d, J=11.0 Hz, 1H), 3.80 (dd, J=11.1, 3.7 Hz, 1H), 3.68 (s, 2H), 3.62 (s, 2H), 2.61 (s, 3H), 2.51 (t, J=7.5 Hz, 2H), 2.40-2.17 (m, 3H), 2.11-2.03 (m, 1H), 1.87 (d, J=13.5 Hz, 6H), 1.70-1.55 (m, 4H), 1.45-1.30 (m, 4H), 1.04 (s, 9H). HRMS (ESI) calcd for $C_{53}H_{69}ClN_{10}O_7PS^+$ [M+H]$^+$, 1055.4492; found, 1055.2208.

Compound Example 22: Synthesis of (2S,4R)-1-((S)-2-(9-(4-(4-((5-chloro-4-((2-(dimethylphosphoryl)phenyl)amino)pyrimidin-2-yl)amino)-3-methoxyphenyl)piperazin-1-yl)-9-oxononanamido)-3,3-dimethylbutanoyl)-4-hydroxy-N-(4-(4-methylthiazol-5-yl)benzyl)pyrrolidine-2-carboxamide. (SIAIS1197155)

According to the procedures for the preparation of Compound Example 1, Brigatinib Analogue A and intermediate LM (SIAIS074016) was used to prepare SIAIS1197155 (white solid, 8.3 mg, 31%). $^1$H NMR (500 MHz, MeOD) δ 9.96 (s, 1H), 8.19 (d, J=14.1 Hz, 2H), 7.73 (dd, J=14.0, 6.8 Hz, 1H), 7.67-7.45 (m, 6H), 7.31 (s, 1H), 7.07 (d, J=8.7 Hz, 1H), 4.64 (s, 1H), 4.60-4.52 (m, 2H), 4.50 (s, 1H), 4.41 (d, J=15.8 Hz, 1H), 4.00 (s, 4H), 3.95 (s, 3H), 3.91 (d, J=11.1 Hz, 1H), 3.80 (dd, J=11.0, 3.8 Hz, 1H), 3.63 (s, 2H), 3.57 (s, 2H), 2.60 (s, 3H), 2.50 (t, J=7.6 Hz, 2H), 2.37-2.18 (m, 3H), 2.11-2.03 (m, 1H), 1.87 (d, J=13.6 Hz, 6H), 1.70-1.55 (m, 4H), 1.45-1.30 (m, 6H), 1.02 (s, 9H). HRMS (ESI) calcd for $C_{54}H_{71}ClN_{10}O_7PS^+$ [M+H]$^+$, 1069.4649; found, 1069.2386.

Compound Example 23: Synthesis of (2S,4R)-1-((S)-2-(10-(4-(4-((5-chloro-4-((2-(dimethylphosphoryl)phenyl)amino)pyrimidin-2-yl)amino)-3-methoxyphenyl)piperazin-1-yl)-10-oxodecanamido)-3,3-dimethylbutanoyl)-4-hydroxy-N-(4-(4-methylthiazol-5-yl)benzyl)pyrrolidine-2-carboxamide. (SIAIS1197157)

According to the procedures for the preparation of Compound Example 1, Brigatinib Analogue A and intermediate LM (SIAIS074019) was used to prepare SIAIS1197157 (white solid, 10.6 mg, 39%). $^1$H NMR (500 MHz, MeOD) δ 9.56 (d, J=4.2 Hz, 1H), 8.35 (s, 1H), 8.08 (s, 1H), 7.70 (s, 1H), 7.62-7.30 (m, 6H), 6.86 (s, 1H), 6.71 (s, 1H), 4.64 (d, J=3.5 Hz, 1H), 4.60-4.47 (m, 3H), 4.39 (dd, J=15.7, 3.2 Hz, 1H), 4.00-3.69 (m, 9H), 3.36 (s, 4H), 2.55 (d, J=3.8 Hz, 3H), 2.51-2.40 (m, 2H), 2.38-2.18 (m, 3H), 2.12-2.02 (m, 1H), 1.89 (dd, J=13.6, 3.5 Hz, 6H), 1.62 (s, 4H), 1.35 (s, 8H), 1.03 (t, J=5.8 Hz, 9H). HRMS (ESI) calcd for $C_{55}H_{73}ClN_{10}O_7PS^+$ [M+H]$^+$, 1083.4805; found, 1083.2486.

Compound Example 24: Synthesis of N-(1-(4-((5-chloro-4-((2-(dimethylphosphoryl)phenyl)amino)pyrimidin-2-yl)amino)-3-methoxyphenyl)piperidin-4-yl)-3-(2-((2-(2,6-dioxopiperidin-3-yl)-1,3-dioxoisoindolin-4-yl)amino)ethoxy)propenamide. (SIAIS151113)

According to the procedures for the preparation of Compound Example 1, Brigatinib Analogue B and intermediate LM (SIAIS151001) was used to prepare SIAIS151113 (yellow solid, 10.4 mg, 60%). $^1$H NMR (500 MHz, MeOD) δ 8.29 (dd, J=8.1, 3.8 Hz, 1H), 8.13 (s, 1H), 7.74-7.67 (m, 2H), 7.63-7.59 (m, 1H), 7.55 (dd, J=8.6, 7.1 Hz, 1H), 7.41-7.31 (m, 1H), 7.09 (d, J=8.5 Hz, 1H), 7.04 (d, J=6.8 Hz, 1H), 7.00 (d, J=1.9 Hz, 1H), 6.81 (dd, J=8.8, 2.4 Hz, 1H), 5.03 (dd, J=12.5, 5.5 Hz, 1H), 4.10-3.85 (m, 2H), 3.92 (s, 3H), 3.79 (t, J=5.9 Hz, 2H), 3.71 (t, J=5.1 Hz, 2H), 3.68-3.64 (m, 2H), 3.50 (t, J=5.0 Hz, 2H), 2.93-2.61 (m, 4H), 2.48 (t, J=5.9 Hz, 2H), 2.10-2.01 (m, 3H), 1.88 (s, 3H), 1.85 (s, 3H), 1.83-1.75 (m, 2H). HRMS (ESI) calcd for $C_{42}H_{48}ClN_9O_8P^+$ [M+H]$^+$: 872.3047, found, 872.2645.

Compound Example 25: Synthesis of N-(1-(4-((5-chloro-4-((2-(dimethylphosphoryl)phenyl)amino)pyrimidin-2-yl)amino)-3-methoxyphenyl)piperidin-4-yl)-3-(2-(2-((2-(2,6-dioxopiperidin-3-yl)-1,3-dioxoisoindolin-4-yl)amino)ethoxy)ethoxy)propenamide. (SIAIS151114)

According to the procedures for the preparation of Compound Example 1, Brigatinib Analogue B and intermediate LM (SIAIS151004) was used to prepare SIAIS151114 (yellow solid, 9.8 mg, 53%). $^1$H NMR (500 MHz, MeOD) δ 8.29 (dd, J=7.5, 3.5 Hz, 1H), 8.13 (s, 1H), 7.72-7.67 (m, 2H), 7.62-7.59 (m, 1H), 7.52 (dd, J=8.5, 7.1 Hz, 1H), 7.41-7.37 (m, 1H), 7.07 (d, J=8.5 Hz, 1H), 7.01 (d, J=6.9 Hz, 1H), 6.99 (s, 1H), 6.79 (d, J=8.8 Hz, 1H), 5.04 (dd, J=12.6, 5.5 Hz, 1H), 4.00-3.94 (m, 1H), 3.90 (s, 3H), 3.76 (t, J=6.1 Hz, 2H), 3.72 (t, J=5.3 Hz, 2H), 3.70-3.62 (m, 8H), 3.48 (t, J=5.3 Hz, 2H), 2.87-2.80 (m, 1H), 2.75-2.67 (m, 2H), 2.46 (t, J=6.0 Hz, 2H), 2.13-2.07 (m, 3H), 1.88 (s, 3H), 1.86 (s, 3H), 1.84-1.77 (m, 2H). HRMS (ESI) calcd for $C_{44}H_{52}ClN_9O_9P^+$ [M+H]$^+$: 916.3309, found, 916.2857.

Compound Example 26: Synthesis of N-(1-(4-((5-chloro-4-((2-(dimethylphosphoryl)phenyl)amino)pyrimidin-2-yl)amino)-3-methoxyphenyl)piperidin-4-yl)-3-(2-(2-(2-((2-(2,6-dioxopiperidin-3-yl)-1,3-dioxoisoindolin-4-yl)amino)ethoxy)ethoxy)ethoxy)propenamide. (SIAIS151115)

According to the procedures for the preparation of Compound Example 1, Brigatinib Analogue B and intermediate LM (SIAIS151005) was used to prepare SIAIS151115 (yellow solid, 16.8 mg, 87%). $^1$H NMR (500 MHz, MeOD) δ 8.30 (dd, J=7.5, 3.5 Hz, 1H), 8.12 (s, 1H), 7.73-7.66 (m, 2H), 7.61 (t, J=7.8 Hz, 1H), 7.52 (dd, J=8.5, 7.1 Hz, 1H), 7.39 (t, J=7.1 Hz, 1H), 7.06 (d, J=8.6 Hz, 1H), 7.02 (d, J=7.0 Hz, 1H), 7.00 (s, 1H), 6.81 (d, J=6.9 Hz, 1H), 5.04 (dd, J=12.7, 5.5 Hz, 1H), 4.02-3.96 (m, 1H), 3.90 (s, 3H), 3.75-3.67 (m, 7H), 3.65 (s, 3H), 3.64-3.63 (m, 3H), 3.61-3.59 (m, 2H), 3.48 (t, J=5.2 Hz, 2H), 3.38-3.35 (m, 1H), 2.89-2.81 (m, 1H), 2.76-2.67 (m, 2H), 2.45 (t, J=6.0 Hz, 2H), 2.16-2.07 (m, 3H), 1.88 (s, 3H), 1.85 (s, 3H), 1.84-1.78 (m, 2H). HRMS (ESI) calcd for $C_{46}H_{56}ClN_9O_{10}P^+$ [M+H]$^+$: 960.3571, found, 960.3920.

Compound Example 27: Synthesis of N-(1-(4-((5-chloro-4-((2-(dimethylphosphoryl)phenyl)amino)pyrimidin-2-yl)amino)-3-methoxyphenyl)piperidin-4-yl)-1-((2-(2,6-dioxopiperidin-3-yl)-1,3-dioxoisoindolin-4-yl)amino)-3,6,9,12-tetraoxapentadecan-15-amide. (SIAIS151116)

According to the procedures for the preparation of Compound Example 1, Brigatinib Analogue B and intermediate LM (SIAIS151006) was used to prepare SIAIS151116 (yellow solid, 13.5 mg, 67%). $^1$H NMR (500 MHz, MeOD) δ 8.30 (dd, J=7.5, 3.5 Hz, 1H), 8.12 (s, 1H), 7.75-7.66 (m, 2H), 7.60 (t, J=7.8 Hz, 1H), 7.51 (dd, J=8.5, 7.1 Hz, 1H), 7.38 (dd, J=7.0, 6.0 Hz, 1H), 7.05-6.99 (m, 3H), 6.82 (d, J=8.2 Hz, 1H), 5.03 (dd, J=12.7, 5.5 Hz, 1H), 4.03-3.96 (m, 1H), 3.90 (s, 3H), 3.75-3.68 (m, 6H), 3.65-3.59 (m, 12H), 3.45 (t, J=5.3 Hz, 2H), 3.39-3.34 (m, 2H), 2.88-2.81 (m, 1H), 2.77-2.62 (m, 2H), 2.45 (t, J=6.0 Hz, 2H), 2.16-2.12 (m, 2H), 2.11-2.06 (m, 1H), 1.88 (s, 3H), 1.85 (s, 3H), 1.85-1.78 (m, 2H). HRMS (ESI) calcd for $C_{48}H_{60}ClN_9O_{11}P^+$ [M+H]$^+$: 1004.3833, found, 1004.4184.

Compound Example 28: Synthesis of N-(1-(4-((5-chloro-4-((2-(dimethylphosphoryl)phenyl)amino)pyrimidin-2-yl)amino)-3-methoxyphenyl)piperidin-4-yl)-1-((2-(2,6-dioxopiperidin-3-yl)-1,3-dioxoisoindolin-4-yl)amino)-3,6,9,12,15-pentaoxaoctadecan-18-amide. (SIAIS151117)

According to the procedures for the preparation of Compound Example 1, Brigatinib Analogue B and intermediate LM (SIAIS151007) was used to prepare SIAIS151117 (yellow solid, 15.8 mg, 75%). $^1$H NMR (500 MHz, MeOD) δ 8.24 (dd, J=7.5, 3.5 Hz, 1H), 8.16 (s, 1H), 7.76 (d, J=8.7 Hz, 1H), 7.69 (ddd, J=13.9, 7.7, 1.4 Hz, 1H), 7.63-7.59 (m, 1H), 7.52 (dd, J=8.5, 7.1 Hz, 1H), 7.42-7.38 (m, 1H), 7.16-7.11 (m, 1H), 7.03 (dd, J=15.1, 7.8 Hz, 2H), 6.92 (d, J=8.7 Hz, 1H), 5.03 (dd, J=12.8, 5.5 Hz, 1H), 4.06-4.00 (m, 1H), 3.92 (s, 3H), 3.75-3.71 (m, 4H), 3.69 (t, J=5.3 Hz, 2H), 3.64-3.60 (m, 16H), 3.53-3.48 (m, 2H), 3.45 (t, J=5.3 Hz, 2H), 2.88-2.80 (m, 1H), 2.75-2.64 (m, 2H), 2.46 (t, J=6.0 Hz, 2H), 2.20-2.17 (m, 2H), 2.11-2.06 (m, 1H), 1.95-1.89 (m, 2H), 1.88 (s, 3H), 1.85 (s, 3H). HRMS (ESI) calcd for $C_{50}H_{64}ClN_9O_{12}P^+$ [M+H]$^+$: 1049.5400, found, 1049.4482.

Compound Example 29: Synthesis of N-(1-(4-((5-chloro-4-((2-(dimethylphosphoryl)phenyl)amino)pyrimidin-2-yl)amino)-3-methoxyphenyl)piperidin-4-yl)-2-((2-(2,6-dioxopiperidin-3-yl)-1,3-dioxoisoindolin-4-yl)amino)acetamide. (SIAIS151120)

According to the procedures for the preparation of Compound Example 1, Brigatinib Analogue B and intermediate LM (SIAIS151025) was used to prepare SIAIS151120 (yellow solid, 11.1 mg, 68%). $^1$H NMR (500 MHz, MeOD) δ 8.31 (dd, J=7.5, 3.5 Hz, 1H), 8.10 (s, 1H), 7.72-7.66 (m, 2H), 7.62-7.57 (m, 2H), 7.40-7.36 (m, 1H), 7.13 (d, J=7.0 Hz, 1H), 6.97 (s, 1H), 6.92 (d, J=8.5 Hz, 1H), 6.79 (d, J=8.2 Hz, 1H), 5.08 (dd, J=12.6, 5.5 Hz, 1H), 4.07-4.01 (m, 3H), 3.90 (s, 3H), 3.74-3.69 (m, 2H), 3.38-3.31 (m, 2H), 2.88-2.83 (m, 1H), 2.78-2.76 (m, 1H), 2.75-2.71 (m, 1H), 2.15-2.08 (m, 3H), 1.88 (s, 3H), 1.85 (s, 3H), 1.85-1.78 (m, 2H). HRMS (ESI) calcd for $C_{39}H_{42}ClN_9O_7P^+$ [M+H]$^+$: 814.2628, found, 814.3211.

Compound Example 30: Synthesis of N-(1-(4-((5-chloro-4-((2-(dimethylphosphoryl)phenyl)amino)pyrimidin-2-yl)amino)-3-methoxyphenyl)piperidin-4-yl)-3-((2-(2,6-dioxopiperidin-3-yl)-1,3-dioxoisoindolin-4-yl)amino)propenamide. (SIAIS151121)

According to the procedures for the preparation of Compound Example 1, Brigatinib Analogue B and intermediate LM (SIAIS151026) was used to prepare SIAIS151121 (yellow solid, 14 mg, 85%). $^1$H NMR (500 MHz, MeOD) δ 8.29 (dd, J=7.5, 3.5 Hz, 1H), 8.12 (s, 1H), 7.75 (d, J=8.7 Hz, 1H), 7.69 (ddd, J=13.9, 7.8, 1.4 Hz, 1H), 7.62-7.57 (m, 2H), 7.41-7.36 (m, 1H), 7.14 (d, J=8.5 Hz, 1H), 7.07 (d, J=6.9 Hz, 1H), 7.02 (d, J=2.0 Hz, 1H), 6.83 (dd, J=8.8, 2.4 Hz, 1H), 5.03 (dd, J=12.4, 5.5 Hz, 1H), 4.02-3.96 (m, 1H), 3.92 (s, 3H), 3.71-3.67 (m, 4H), 3.40-3.34 (m, 2H), 2.86-2.79 (m, 1H), 2.75-2.65 (m, 2H), 2.56 (dd, J=6.9, 5.3 Hz, 2H), 2.12-2.05 (m, 3H), 1.88 (s, 3H), 1.85 (s, 3H), 1.81-1.72 (m, 2H). HRMS (ESI) calcd for $C_{40}H_{44}ClN_9O_7P^+$ [M+H]$^+$: 828.2784, found, 828.3370.

Compound Example 31: Synthesis of N-(1-(4-((5-chloro-4-((2-(dimethylphosphoryl)phenyl)amino)pyrimidin-2-yl)amino)-3-methoxyphenyl)piperidin-4-yl)-4-((2-(2,6-dioxopiperidin-3-yl)-1,3-dioxoisoindolin-4-yl)amino)butanamide. (SIAIS151118)

According to the procedures for the preparation of Compound Example 1, Brigatinib Analogue B and intermediate LM (SIAIS151019) was used to prepare SIAIS151118 (yellow solid, 13.2 mg, 78%). $^1$H NMR (500 MHz, MeOD) δ 8.30 (dd, J=7.5, 3.5 Hz, 1H), 8.11 (s, 1H), 7.75-7.73 (m, 1H), 7.69 (ddd, J=13.9, 7.7, 1.4 Hz, 1H), 7.62-7.58 (m, 1H), 7.56 (dd, J=9.0, 7.5 Hz, 1H), 7.41-7.36 (m, 1H), 7.09 (d, J=8.5 Hz, 1H), 7.05 (d, J=6.8 Hz, 1H), 6.99 (s, 1H), 6.81 (d, J=8.4 Hz, 1H), 5.06 (dd, J=12.6, 5.5 Hz, 1H), 3.96-3.89 (m, 1H), 3.91 (s, 3H), 3.71-3.68 (m, 2H), 3.41 (t, J=6.7 Hz, 2H), 3.37-3.33 (m, 2H), 2.89-2.81 (m, 1H), 2.77-2.69 (m, 2H), 2.34 (t, J=7.0 Hz, 2H), 2.14-2.05 (m, 3H), 2.03-1.97 (m, 2H), 1.88 (s, 3H), 1.85 (s, 3H), 1.81-1.72 (m, 2H). HRMS (ESI) calcd for $C_{41}H_{46}ClN_9O_7P^+$ [M+H]$^+$: 842.2941, found, 842.3294.

Compound Example 32: Synthesis of N-(1-(4-((5-chloro-4-((2-(dimethylphosphoryl)phenyl)amino)pyrimidin-2-yl)amino)-3-methoxyphenyl)piperidin-4-yl)-5-((2-(2,6-dioxopiperidin-3-yl)-1,3-dioxoisoindolin-4-yl)amino)pentanamide. (SIAIS151119)

According to the procedures for the preparation of Compound Example 1, Brigatinib Analogue B and intermediate LM (SIAIS151020) was used to prepare SIAIS151119 (yellow solid, 12 mg, 70%). $^1$H NMR (500 MHz, MeOD) δ 8.30 (dd, J=7.5, 3.5 Hz, 1H), 8.11 (s, 1H), 7.71-7.66 (m, 2H), 7.61 (t, J=7.9 Hz, 1H), 7.55 (dd, J=8.6, 7.1 Hz, 1H), 7.41-7.37 (m, 1H), 7.05 (dd, J=9.8, 7.8 Hz, 2H), 7.00 (d, J=2.0 Hz, 1H), 6.82 (dd, J=8.8, 2.3 Hz, 1H), 5.05 (dd, J=12.5, 5.5 Hz, 1H), 4.00-3.94 (m, 1H), 3.92 (s, 3H), 3.75-3.70 (m, 2H), 3.39-3.33 (m, 4H), 2.88-2.80 (m, 1H), 2.76-2.66 (m, 2H), 2.28 (t, J=7.1 Hz, 2H), 2.15-2.08 (m, 3H), 1.88 (s, 3H), 1.85 (s, 3H), 1.83-1.68 (m, 6H). HRMS (ESI) calcd for $C_{42}H_{48}ClN_9O_7P^+$ [M+H]$^+$: 856.3097, found, 856.3403.

Compound Example 33: Synthesis of N-(1-(4-((5-chloro-4-((2-(dimethylphosphoryl)phenyl)amino)pyrimidin-2-yl)amino)-3-methoxyphenyl)piperidin-4-yl)-6-((2-(2,6-dioxopiperidin-3-yl)-1,3-dioxoisoindolin-4-yl)amino)hexanamide. (SIAIS151122)

According to the procedures for the preparation of Compound Example 1, Brigatinib Analogue B and intermediate LM (SIAIS151027) was used to prepare SIAIS151122 (yellow solid, 4.5 mg, 30%). $^1$H NMR (500 MHz, MeOD) δ 8.32 (dd, J=7.5, 3.5 Hz, 1H), 8.10 (s, 1H), 7.69 (ddd, J=14.0, 7.8, 1.4 Hz, 2H), 7.61 (t, J=7.8 Hz, 1H), 7.55 (dd, J=8.6, 7.1 Hz, 1H), 7.40-7.36 (m, 1H), 7.05 (dd, J=10.9, 7.7 Hz, 2H), 6.96 (s, 1H), 6.79 (d, J=8.6 Hz, 1H), 5.04 (dd, J=12.5, 5.5 Hz, 1H), 3.97-3.93 (m, 1H), 3.91 (s, 3H), 3.72-3.68 (m, 2H), 3.36 (t, J=6.8 Hz, 2H), 3.30-3.23 (m, 2H), 2.85-2.76 (m, 1H), 2.75-2.65 (m, 2H), 2.24 (t, J=7.2 Hz, 2H), 2.11-2.05 (m, 3H), 1.88 (s, 3H), 1.85 (s, 3H), 1.79-1.73 (m, 2H), 1.73-1.67 (m, 4H), 1.51-1.43 (m, 2H). HRMS (ESI) calcd for $C_{43}H_{50}ClN_9O_7P^+$ [M+H]$^+$: 870.3254, found, 870.3881.

Compound Example 34: Synthesis of N-(1-(4-((5-chloro-4-((2-(dimethylphosphoryl)phenyl)amino)pyrimidin-2-yl)amino)-3-methoxyphenyl)piperidin-4-yl)-7-((2-(2,6-dioxopiperidin-3-yl)-1,3-dioxoisoindolin-4-yl)amino)heptanamide. (SIAIS151123)

According to the procedures for the preparation of Compound Example 1, Brigatinib Analogue B and intermediate LM (SIAIS151086) was used to prepare SIAIS151123 (yellow solid, 12.3 mg, 70%). $^1$H NMR (500 MHz, MeOD) δ 8.30 (dd, J=7.5, 3.5 Hz, 1H), 8.11 (s, 1H), 7.75-7.66 (m, 2H), 7.61 (t, J=7.9 Hz, 1H), 7.55 (dd, J=8.6, 7.1 Hz, 1H), 7.41-7.37 (m, 1H), 7.04 (t, J=7.5 Hz, 2H), 7.00 (s, 1H) 6.82 (d, J=7.7 Hz, 1H), 5.05 (dd, J=12.5, 5.5 Hz, 1H), 4.01-3.93 (m, 1H), 3.92 (s, 3H), 3.72-3.70 (m, 2H), 3.37-3.32 (m, 4H), 2.89-2.79 (m, 1H), 2.76-2.69 (m, 2H), 2.22 (t, J=7.4 Hz, 2H), 2.14-2.05 (m, 3H), 1.88 (s, 3H), 1.85 (s, 3H), 1.84-1.76

(m, 2H), 1.72-1.64 (m, 4H), 1.50-1.40 (m, 4H). HRMS (ESI) calcd for $C_{44}H_{52}ClN_9O_7P^+$ [M+H]$^+$: 884.3410, found, 884.3420.

Compound Example 35: Synthesis of N-(1-(4-((5-chloro-4-((2-(dimethylphosphoryl)phenyl)amino) pyrimidin-2-yl)amino)-3-methoxyphenyl)piperidin-4-yl)-2-((2-(2,6-dioxopiperidin-3-yl)-1-oxoisoindolin-4-yl)amino)acetamide. (SIAIS219151)

According to the procedures for the preparation of Compound Example 1, Brigatinib Analogue B and intermediate LM (SIAIS1204057) was used to prepare SIAIS219151 (yellow solid, 7.2 mg, 45%). $^1$H NMR (500 MHz, MeOD) δ 8.19 (s, 2H), 7.72 (dd, J=13.7, 7.6 Hz, 2H), 7.63 (t, J=7.6 Hz, 1H), 7.44 (s, 1H), 7.36 (t, J=7.8 Hz, 1H), 7.26 (s, 1H), 7.17 (d, J=7.5 Hz, 1H), 6.99 (s, 1H), 6.72 (d, J=8.1 Hz, 1H), 5.18 (dd, J=13.3, 5.1 Hz, 1H), 4.44 (d, J=16.8 Hz, 1H), 4.39 (d, J=16.9 Hz, 1H), 4.15 (s, 1H), 3.95 (s, 3H), 3.73-3.68 (m, 2H), 3.63-3.50 (m, 4H), 2.97-2.90 (m, 1H), 2.85-2.77 (m, 1H), 2.55-2.46 (m, 1H), 2.22-2.15 (m, 3H), 2.00 (s, 2H), 1.86 (d, J=13.5 Hz, 6H). HRMS (ESI) calcd for $C_{39}H_{44}ClN_9O_7P^+$ [M+H]$^+$: 800.2835, found, 800.2831.

Compound Example 36: Synthesis of N-(1-(4-((5-chloro-4-((2-(dimethylphosphoryl)phenyl)amino) pyrimidin-2-yl)amino)-3-methoxyphenyl)piperidin-4-yl)-4-((2-(2,6-dioxopiperidin-3-yl)-1-oxoisoindolin-4-yl)amino)butanamide. (SIAIS219128)

According to the procedures for the preparation of Compound Example 1, Brigatinib Analogue B and intermediate LM (SIAIS1204085) was used to prepare SIAIS219128 (yellow solid, 10 mg, 40%). $^1$H NMR (500 MHz, MeOD) δ 8.24 (s, 1H), 8.12 (s, 1H), 7.79-7.71 (m, 2H), 7.67 (t, J=7.6 Hz, 1H), 7.51 (t, J=7.1 Hz, 1H), 7.44 (s, 1H), 7.41 (t, J=7.8 Hz, 1H), 7.21-7.15 (m, 2H), 7.00 (d, J=8.1 Hz, 1H), 5.20 (dd, J=13.3, 5.0 Hz, 1H), 4.44 (d, J=17.0 Hz, 1H), 4.37 (d, J=17.0 Hz, 1H), 3.98 (s, 4H), 3.82-3.62 (m, 4H), 3.41-3.37 (m, 2H), 3.01-2.89 (m, 1H), 2.83 (d, J=16.7 Hz, 1H), 2.58-2.48 (m, 1H), 2.41 (t, J=6.7 Hz, 2H), 2.28-2.13 (m, 2H), 2.07-1.96 (m, 4H), 1.87 (d, J=13.5 Hz, 6H), 1.77 (d, J=14.2 Hz, 1H). HRMS (ESI) calcd for $C_{41}H_{48}ClN_9O_6P^+$ [M+H]$^+$: 828.3148, found, 828.3141.

Compound Example 37: Synthesis of N-(1-(4-((5-chloro-4-((2-(dimethylphosphoryl)phenyl)amino) pyrimidin-2-yl)amino)-3-methoxyphenyl)piperidin-4-yl)-5-((2-(2,6-dioxopiperidin-3-yl)-1-oxoisoindolin-4-yl)amino)pentanamide (SIAIS219152)

According to the procedures for the preparation of Compound Example 1, Brigatinib Analogue B and intermediate LM (SIAIS1210133) was used to prepare SIAIS219152 (yellow solid, 8.0 mg, 47%). $^1$H NMR (500 MHz, MeOD) δ 8.25 (s, 1H), 8.13 (s, 1H), 7.80-7.71 (m, 2H), 7.68 (t, J=7.7 Hz, 1H), 7.55-7.41 (m, 3H), 7.37-7.25 (m, 1H), 7.22-7.17 (m, 1H), 7.14-7.08 (m, 1H), 5.17 (dd, J=13.2, 5.1 Hz, 1H), 4.53-4.38 (m, 2H), 4.08 (s, 1H), 3.99 (s, 3H), 3.73 (s, 4H), 3.35-3.32 (m, 2H), 2.93-2.90 (m, 1H), 2.83-2.81 (m, 1H), 2.59-2.46 (m, 1H), 2.32 (s, 2H), 2.23-2.07 (m, 5H), 1.87 (d, J=13.6 Hz, 6H), 1.81-1.71 (m, 4H). HRMS (ESI) calcd for $C_{42}H_{50}ClN_9O_6P^+$ [M+H]$^+$: 842.3305, found, 842.3301.

Compound Example 38: Synthesis of N-(1-(4-((5-chloro-4-((2-(dimethylphosphoryl)phenyl)amino) pyrimidin-2-yl)amino)-3-methoxyphenyl)piperidin-4-yl)-6-((2-(2,6-dioxopiperidin-3-yl)-1-oxoisoindolin-4-yl)amino)hexanamide. (SIAIS219153)

According to the procedures for the preparation of Compound Example 1, Brigatinib Analogue B and intermediate LM (SIAIS1204061) was used to prepare SIAIS219153 (yellow solid, 8.2 mg, 48%). $^1$H NMR (500 MHz, MeOD) δ 8.25 (s, 1H), 8.14 (s, 1H), 7.80-7.71 (m, 2H), 7.68 (t, J=7.4 Hz, 1H), 7.54-7.40 (m, 3H), 7.31-7.25 (m, 1H), 7.21-7.17 (m, 1H), 7.15-7.03 (m, 1H), 5.17 (dd, J=13.3, 5.1 Hz, 1H), 4.48-4.38 (m, 2H), 4.06 (s, 1H), 3.99 (s, 3H), 3.72 (s, 4H), 3.33-3.31 (m, 2H), 2.93-2.90 (m, 1H), 2.82-2.81 (m, 1H), 2.58-2.47 (m, 1H), 2.27 (t, J=6.7 Hz, 2H), 2.24-2.16 (m, 2H), 2.05-2.04 (m, 3H), 1.87 (d, J=13.5 Hz, 6H), 1.76-1.68 (m, 4H), 1.52-1.45 (m, 2H). HRMS (ESI) calcd for $C_{43}H_{52}ClN_9O_6P^+$ [M+H]$^+$: 856.3461, found, 856.3449.

Compound Example 39: Synthesis of N-(1-(4-((5-chloro-4-((2-(dimethylphosphoryl)phenyl)amino) pyrimidin-2-yl)amino)-3-methoxyphenyl)piperidin-4-yl)-7-((2-(2,6-dioxopiperidin-3-yl)-1-oxoisoindolin-4-yl)amino)heptanamide. (SIAIS219154)

According to the procedures for the preparation of Compound Example 1, Brigatinib Analogue B and intermediate LM (SIAIS1204063) was used to prepare SIAIS219154 (yellow solid, 7.9 mg, 45%). $^1$H NMR (500 MHz, MeOD) δ 8.22 (s, 1H), 8.17 (s, 1H), 7.79-7.70 (m, 2H), 7.66 (t, J=7.8 Hz, 1H), 7.47 (t, J=7.1 Hz, 1H), 7.39 (dd, J=16.2, 8.4 Hz, 2H), 7.20 (d, J=7.5 Hz, 1H), 7.10 (d, J=8.3 Hz, 1H), 6.99 (d, J=8.0 Hz, 1H), 5.17 (dd, J=13.3, 5.2 Hz, 1H), 4.42 (d, J=17.0 Hz, 1H), 4.37 (d, J=17.0 Hz, 1H), 4.06 (t, J=10.9 Hz, 1H), 3.98 (s, 3H), 3.69-3.62 (m, 4H), 3.30-3.26 (m, 2H), 2.99-2.89 (m, 1H), 2.85-2.76 (m, 1H), 2.58-2.46 (m, 1H), 2.26-2.15 (m, 5H), 2.04-2.00 (m, 2H), 1.87 (d, J=13.5 Hz, 6H), 1.74-1.65 (m, 4H), 1.51-1.46 (m, 2H), 1.44-1.40 (m, 2H). HRMS (ESI) calcd for $C_{44}H_{54}ClN_9O_6P^+$ [M+H]$^+$: 870.3618, found, 870.3611.

Compound Example 40: Synthesis of (2S,4R)-1-((S)-2-(2-(2-(2-((1-(4-((5-chloro-4-((2-(dimethylphosphoryl)phenyl)amino)pyrimidin-2-yl)amino)-3-methoxyphenyl)piperidin-4-yl)amino)-2-oxoethoxy)ethoxy)acetamido)-3,3-dimethylbutanoyl)-4-hydroxy-N-(4-(4-methylthiazol-5-yl)benzyl)pyrrolidine-2-carboxamide. (SIAIS151128)

According to the procedures for the preparation of Compound Example 1, Brigatinib Analogue B and intermediate LM (SIAIS151010) was used to prepare SIAIS151128 (white solid, 14.7 mg, 68%). $^1$H NMR (500 MHz, MeOD) δ 8.92 (s, 1H), 8.30 (dd, J=8.0, 4.1 Hz, 1H), 8.11 (s, 1H), 7.71-7.64 (m, 2H), 7.61-7.57 (m, 1H), 7.43-7.38 (m, 5H), 7.00 (s, 1H), 6.82 (dd, J=8.5, 2.0 Hz, 1H), 4.72 (s, 1H), 4.59-4.56 (m, 1H), 4.53-4.46 (m, 2H), 4.38 (d, J=15.7 Hz, 1H), 4.13-4.02 (m, 5H), 3.91-3.90 (m, 1H), 3.90 (s, 3H), 3.85-3.65 (m, 8H), 3.37-3.34 (m, 1H), 2.46 (s, 3H), 2.28-2.23 (m, 1H), 2.15-2.07 (m, 3H), 1.99-1.91 (m, 2H), 1.88 (s, 3H), 1.85 (s, 3H), 1.05 (s, 9H). HRMS (ESI) calcd for $C_{52}H_{67}ClN_{10}O_9PS^+$ [M+H]$^+$: 1073.4234, found, 1073.4229.

Compound Example 41: Synthesis of (2S,4R)-1-((S)-2-(3-(2-(3-((1-(4-((5-chloro-4-((2-(dimethylphosphoryl)phenyl)amino)pyrimidin-2-yl)amino)-3-methoxyphenyl)piperidin-4-yl)amino)-3-oxopropoxy)ethoxy)propanamido)-3,3-dimethylbutanoyl)-4-hydroxy-N-(4-(4-methylthiazol-5-yl)benzyl)pyrrolidine-2-carboxamide. (SIAIS151124)

According to the procedures for the preparation of Compound Example 1, Brigatinib Analogue B and intermediate LM (SIAIS151002) was used to prepare SIAIS151124 (white solid, 6.1 mg, 28%). $^1$H NMR (500 MHz, MeOD) δ 8.93 (s, 1H), 8.30 (dd, J=7.5, 3.5 Hz, 1H), 8.12 (s, 1H), 7.73-7.66 (m, 2H), 7.63-7.59 (m, 1H), 7.47-7.45 (m, 2H), 7.43-7.38 (m, 3H), 7.03 (d, J=2.0 Hz, 1H), 6.84 (dd, J=8.8, 2.4 Hz, 1H), 4.66 (s, 1H), 4.60-4.54 (m, 1H), 4.51-4.47 (m, 2H), 4.39-4.34 (m, 1H), 4.03-3.96 (m, 1H), 3.91-3.87 (m, 1H), 3.92 (s, 3H), 3.80 (dd, J=11.0, 3.8 Hz, 1H), 3.75-3.70 (m, 6H), 3.64-3.60 (m, 4H), 3.40-3.34 (m, 2H), 2.61-2.53 (m, 1H), 2.49-2.44 (m, 3H), 2.47 (s, 3H), 2.25-2.20 (m, 1H), 2.16-2.05 (m, 3H), 1.88 (s, 3H), 1.85 (s, 3H), 1.84-1.78 (m, 2H), 1.04 (s, 9H). HRMS (ESI) calcd for $C_{54}H_{71}ClN_{10}O_9PS^+$ [M+H]$^+$: 1101.4547, found, 1101.4558.

Compound Example 42: Synthesis of (2S,4R)-1-((S)-2-(tert-butyl)-16-((1-(4-((5-chloro-4-((2-(dimethylphosphoryl)phenyl)amino)pyrimidin-2-yl)amino)-3-methoxyphenyl)piperidin-4-yl)amino)-4,16-dioxo-7,10,13-trioxa-3-azahexadecanoyl)-4-hydroxy-N-(4-(4-methylthiazol-5-yl)benzyl)pyrrolidine-2-carboxamide. (SIAIS151125)

According to the procedures for the preparation of Compound Example 1, Brigatinib Analogue B and intermediate LM (SIAIS151003) was used to prepare SIAIS151125 (white solid, 13.2 mg, 58%). $^1$H NMR (500 MHz, MeOD) δ 8.94 (s, 1H), 8.29 (dd, J=7.5, 3.5 Hz, 1H), 8.12 (s, 1H), 7.73-7.67 (m, 2H), 7.62-7.58 (m, 1H), 7.47-7.44 (m, 2H), 7.43-7.37 (m, 3H), 7.04 (s, 1H), 6.86 (d, J=8.6 Hz, 1H), 4.65 (s, 1H), 4.59-4.50 (m, 2H), 4.50-4.47 (m, 1H), 4.38-4.33 (m, 1H), 4.03-3.97 (m, 1H), 3.92 (s, 3H), 3.89-3.86 (m, 1H), 3.80 (dd, J=10.9, 3.9 Hz, 1H), 3.76-3.70 (m, 6H), 3.64-3.58 (m, 9H), 3.44-3.35 (m, 2H), 2.60-2.54 (m, 1H), 2.50-2.44 (m, 3H), 2.47 (s, 3H), 2.24-2.20 (m, 1H), 2.17-2.13 (m, 2H), 2.10-2.05 (m, 1H), 1.88 (s, 3H), 1.86-1.80 (m, 2H), 1.85 (s, 3H), 1.04 (s, 9H). HRMS (ESI) calcd for $C_{56}H_{75}ClN_{10}O_{10}PS^+$ [M+H]$^+$: 1145.4809, found, 1145.4807.

Compound Example 43: Synthesis of N1-(1-(4-((5-chloro-4-((2-(dimethylphosphoryl)phenyl)amino)pyrimidin-2-yl)amino)-3-methoxyphenyl)piperidin-4-yl)-N16-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13-tetraoxahexadecanediamide. (SIAIS151126)

According to the procedures for the preparation of Compound Example 1, Brigatinib Analogue B and intermediate LM (SIAIS151008) was used to prepare SIAIS151126 (white solid, 13.0 mg, 55%). $^1$H NMR (500 MHz, MeOD) δ 8.99 (s, 1H), 8.25 (dd, J=8.1, 4.0 Hz, 1H), 8.16 (s, 1H), 7.76 (d, J=8.8 Hz, 1H), 7.70 (dd, J=13.9, 7.7 Hz, 1H), 7.63-7.59 (m, 1H), 7.48-7.46 (m, 2H), 7.44-7.41 (m, 3H), 7.15 (d, J=2.3 Hz, 1H), 6.94 (dd, J=8.8, 2.5 Hz, 1H), 4.64 (s, 1H), 4.59-4.51 (m, 2H), 4.50-4.47 (m, 1H), 4.36 (d, J=15.5 Hz, 1H), 4.08-4.01 (m, 1H), 3.93 (s, 3H), 3.90-3.87 (m, 1H), 3.79 (dd, J=10.9, 3.7 Hz, 1H), 3.76-3.71 (m, 6H), 3.62-3.60 (m, 12H), 3.50 (t, J=11.1 Hz, 2H), 2.58-2.53 (m, 1H), 2.49-2.45 (m, 3H), 2.48 (s, 3H), 2.24-2.16 (m, 3H), 2.11-2.05 (m, 1H), 1.94-1.90 (m, 2H), 1.88 (s, 3H), 1.85 (s, 3H), 1.03 (s, 9H). HRMS (ESI) calcd for $C_{58}H_{79}ClN_{10}O_{11}PS^+$ [M+H]$^+$: 1189.5071, found, 1189.5091.

Compound Example 44: Synthesis of N1-(1-(4-((5-chloro-4-((2-(dimethylphosphoryl)phenyl)amino)pyrimidin-2-yl)amino)-3-methoxyphenyl)piperidin-4-yl)-N19-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13,16-pentaoxanonadecanediamide. (SIAIS151127)

According to the procedures for the preparation of Compound Example 1, Brigatinib Analogue B and intermediate LM (SIAIS151009) was used to prepare SIAIS151127 (white solid, 19.5 mg, 79%). $^1$H NMR (500 MHz, MeOD) δ 9.05 (s, 1H), 8.23 (dd, J=8.0, 4.1 Hz, 1H), 8.17 (s, 1H), 7.76 (d, J=8.8 Hz, 1H), 7.71 (ddd, J=13.9, 7.8, 1.4 Hz, 1H), 7.64-7.59 (m, 1H), 7.50-7.46 (m, 2H), 7.44-7.40 (m, 3H), 7.19 (d, J=2.4 Hz, 1H), 6.97 (dd, J=8.8, 2.5 Hz, 1H), 4.64 (s, 1H), 4.58-4.51 (m, 2H), 4.51-4.48 (m, 1H), 4.36 (d, J=15.6 Hz, 1H), 4.09-4.03 (m, 1H), 3.94 (s, 3H), 3.90-3.87 (m, 1H), 3.80 (dd, J=11.0, 3.9 Hz, 1H), 3.76-3.69 (m, 6H), 3.62-3.60 (m, 16H), 3.54 (t, J=12.0 Hz, 2H), 2.59-2.54 (m, 1H), 2.50-2.45 (m, 3H), 2.49 (s, 3H), 2.24-2.18 (m, 3H), 2.11-2.05 (m, 1H), 1.98-1.91 (m, 2H), 1.88 (s, 3H), 1.85 (s, 3H), 1.03 (s, 9H). HRMS (ESI) calcd for $C_{60}H_{83}ClN_{10}O_{12}PS^+$ [M+H]$^+$: 1233.5333, found, 1233.5335.

Compound Example 45: Synthesis of N1-(1-(4-((5-chloro-4-((2-(dimethylphosphoryl)phenyl)amino)pyrimidin-2-yl)amino)-3-methoxyphenyl)piperidin-4-yl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl) succinamide. (SIAIS164143)

According to the procedures for the preparation of Compound Example 1, Brigatinib Analogue B and intermediate LM (SIAIS074011) was used to prepare SIAIS164143 (white solid, 12.8 mg, 63%). $^1$H NMR (500 MHz, MeOD) δ 9.95 (s, 1H), 8.27 (s, 1H), 8.11 (s, 1H), 7.78-7.73 (m, 2H), 7.68 (t, J=7.5 Hz, 1H), 7.60-7.50 (m, 6H), 7.29 (d, J=8.2 Hz, 1H), 4.62-4.47 (m, 4H), 4.41 (d, J=15.6 Hz, 1H), 4.19-4.11 (m, 1H), 4.00 (s, 3H), 3.91-3.89 (m, 1H), 3.81-3.78 (m, 5H), 2.67-2.53 (m, 4H), 2.59 (s, 3H), 2.31-2.15 (m, 5H), 2.11-2.04 (m, 1H), 1.88 (s, 3H), 1.86 (s, 3H), 1.04 (s, 9H). HRMS (ESI) calcd for $C_{50}H_{63}ClN_{10}O_7PS^+$ [M+H]$^+$: 1013.4023, found, 1013.3452.

Compound Example 46: Synthesis of N1-(1-(4-((5-chloro-4-((2-(dimethylphosphoryl)phenyl)amino)pyrimidin-2-yl)amino)-3-methoxyphenyl)piperidin-4-yl)-N5-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide. (SIAIS164144)

According to the procedures for the preparation of Compound Example 1, Brigatinib Analogue B and intermediate LM (SIAIS074012) was used to prepare SIAIS164144 (white solid, 12.2 mg, 59%). $^1$H NMR (500 MHz, MeOD) δ 9.96 (s, 1H), 8.28 (s, 1H), 8.11 (s, 1H), 7.78-7.73 (m, 2H), 7.68 (t, J=7.8 Hz, 1H), 7.61-7.56 (m, 3H), 7.55-7.49 (m, 3H), 7.30 (d, J=8.7 Hz, 1H), 4.64 (s, 1H), 4.69-4.51 (m, 3H), 4.45-4.40 (m, 1H), 4.20-4.12 (m, 1H), 4.00 (s, 3H), 3.93 (d, J=11.2 Hz, 1H), 3.86-3.73 (m, 5H), 2.60 (s, 3H), 2.38-2.17 (m, 9H), 2.11-2.05 (m, 1H), 1.96-1.91 (m, 2H), 1.88 (s, 3H), 1.85 (s, 3H), 1.05 (s, 9H). HRMS (ESI) calcd for $C_{51}H_{65}ClN_{10}O_7PS^+$ [M+H]$^+$: 1027.4179, found, 1027.3585.

Compound Example 47: Synthesis of N1-(1-(4-((5-chloro-4-((2-(dimethylphosphoryl)phenyl)amino)pyrimidin-2-yl)amino)-3-methoxyphenyl)piperidin-4-yl)-N6-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)adipamide. (SIAIS164145)

According to the procedures for the preparation of Compound Example 1, Brigatinib Analogue B and intermediate LM (SIAIS074013) was used to prepare SIAIS164145 (white solid, 13.1 mg, 63%). $^1$H NMR (500 MHz, MeOD) δ 10.01 (s, 1H), 8.28 (s, 1H), 8.11 (s, 1H), 7.78-7.74 (m, 2H), 7.69 (t, J=7.9 Hz, 1H), 7.63 (s, 1H), 7.59-7.57 (m, 2H), 7.55-7.50 (m, 3H), 7.32 (d, J=6.9 Hz, 1H), 4.64 (s, 1H), 4.61-4.47 (m, 3H), 4.43-4.39 (m, 1H), 4.21-4.13 (m, 1H), 4.00 (s, 3H), 3.92 (d, J=11.1 Hz, 1H), 3.85-3.71 (m, 5H), 2.61 (s, 3H), 2.36-2.17 (m, 9H), 2.10-2.04 (m, 1H), 1.88 (s, 3H), 1.86 (s, 3H), 1.70-1.62 (m, 4H), 1.04 (s, 9H). HRMS (ESI) calcd for $C_{52}H_{67}ClN_{10}O_7PS^+$ [M+H]$^+$: 1041.4336, found, 1041.3764.

Compound Example 48: Synthesis of N1-(1-(4-((5-chloro-4-((2-(dimethylphosphoryl)phenyl)amino)pyrimidin-2-yl)amino)-3-methoxyphenyl)piperidin-4-yl)-N7-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)heptanediamide. (SIAIS164146)

According to the procedures for the preparation of Compound Example 1, Brigatinib Analogue B and intermediate LM (SIAIS074014) was used to prepare SIAIS164146 (white solid, 12.3 mg, 58%). $^1$H NMR (500 MHz, MeOD) δ 9.97 (s, 1H), 8.27 (s, 1H), 8.11 (s, 1H), 7.77-7.73 (m, 2H), 7.68 (t, J=7.8 Hz, 1H), 7.61-7.50 (m, 6H), 7.29 (d, J=8.7 Hz, 1H), 4.64 (s, 1H), 4.61-4.48 (m, 3H), 4.44-4.38 (m, 1H), 4.18-4.12 (m, 1H), 4.00 (s, 3H), 3.91 (d, J=11.1 Hz, 1H), 3.85-3.70 (m, 5H), 2.60 (s, 3H), 2.36-2.15 (m, 9H), 2.10-2.05 (m, 1H), 1.88 (s, 3H), 1.85 (s, 3H), 1.69-1.61 (m, 4H), 1.42-1.33 (m, 2H), 1.04 (s, 9H). HRMS (ESI) calcd for $C_{53}H_{69}ClN_{10}O_7PS^+$ [M+H]$^+$: 1055.4492, found, 1055.3854.

Compound Example 49: Synthesis of N1-(1-(4-((5-chloro-4-((2-(dimethylphosphoryl)phenyl)amino)pyrimidin-2-yl)amino)-3-methoxyphenyl)piperidin-4-yl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide. (SIAIS164147)

According to the procedures for the preparation of Compound Example 1, Brigatinib Analogue B and intermediate LM (SIAIS074015) was used to prepare SIAIS164147 (white solid, 14.8 mg, 69%). $^1$H NMR (500 MHz, MeOD) δ 9.91 (s, 1H), 8.27 (s, 1H), 8.11 (s, 1H), 7.77-7.73 (m, 2H), 7.69 (t, J=7.8 Hz, 1H), 7.61 (d, J=2.1 Hz, 1H), 7.58-7.51 (m, 5H), 7.31 (d, J=8.7 Hz, 1H), 4.64 (s, 1H), 4.60-4.49 (m, 3H), 4.43-4.38 (m, 1H), 4.20-4.13 (m, 1H), 4.00 (s, 3H), 3.92 (d, J=11.1 Hz, 1H), 3.86-3.75 (m, 5H), 2.60 (s, 3H), 2.33-2.18 (m, 9H), 2.11-2.05 (m, 1H), 1.88 (s, 3H), 1.85 (s, 3H), 1.68-1.59 (m, 4H), 1.41-1.34 (m, 4H), 1.04 (s, 9H). HRMS (ESI) calcd for $C_{54}H_{71}ClN_{10}O_7PS^+$ [M+H]$^+$: 1069.4649, found, 1069.4001.

Compound Example 50: Synthesis of N1-(1-(4-((5-chloro-4-((2-(dimethylphosphoryl)phenyl)amino)pyrimidin-2-yl)amino)-3-methoxyphenyl)piperidin-4-yl)-N9-((S)-1-((2,4R)-4-hydroxy-2-2S,4R)-((4-(4-methylthiazol-5-yl)benzyl)carbamoyl)pyrrolidin-1-yl)-3,3-dimethyl-1-oxobutan-2-yl)nonanediamide. (SIAIS164148)

According to the procedures for the preparation of Compound Example 1, Brigatinib Analogue B and intermediate LM (SIAIS074016) was used to prepare SIAIS164148 (white solid, 12.8 mg, 59%). $^1$H NMR (500 MHz, MeOD) δ 10.01 (s, 1H), 8.28 (s, 1H), 8.11 (s, 1H), 7.78-7.73 (m, 2H), 7.69 (t, J=7.9 Hz, 1H), 7.63 (d, J=2.0 Hz, 1H), 7.60-7.57 (m, 2H), 7.55-7.49 (m, 3H), 7.31 (d, J=8.8 Hz, 1H), 4.64 (s, 1H), 4.60-4.49 (m, 3H), 4.44-4.38 (m, 1H), 4.21-4.13 (m, 1H), 4.00 (s, 3H), 3.91 (d, J=11.1 Hz, 1H), 3.85-2.73 (m, 5H), 2.61 (s, 3H), 2.33-2.18 (m, 9H), 2.10-2.04 (m, 1H), 1.88 (s, 3H), 1.86 (s, 3H), 1.66-1.59 (m, 4H), 1.36 (s, 6H), 1.04 (s, 9H). HRMS (ESI) calcd for $C_{55}H_{73}ClN_{10}O_7PS^+$ [M+H]$^+$: 1083.4805, found, 1083.4133.

Compound Example 51: Synthesis of N1-(1-(4-((5-chloro-4-((2-(dimethylphosphoryl)phenyl)amino)pyrimidin-2-yl)amino)-3-methoxyphenyl)piperidin-4-yl)-N10-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide. (SIAIS164149)

According to the procedures for the preparation of Compound Example 1, Brigatinib Analogue B and intermediate LM (SIAIS074019) was used to prepare SIAIS164149 (white solid, 10.2 mg, 46%). $^1$H NMR (500 MHz, MeOD) δ 10.02 (s, 1H), 8.28 (s, 1H), 8.11 (s, 1H), 7.79-7.73 (m, 2H), 7.69 (t, J=7.9 Hz, 1H), 7.63 (d, J=2.0 Hz, 1H), 7.58 (d, J=8.3 Hz, 2H), 7.54-7.50 (m, 3H), 7.32 (d, J=8.6 Hz, 1H), 4.64 (s, 1H), 4.60-4.49 (m, 3H), 4.44-4.38 (m, 1H), 4.20-4.14 (m, 1H), 4.00 (s, 3H), 3.91 (d, J=11.2 Hz, 1H), 3.81 (dd, J=10.9, 3.9 Hz, 5H), 2.61 (s, 3H), 2.33-2.18 (m, 9H), 2.10-2.05 (m, 1H), 1.88 (s, 3H), 1.86 (s, 3H), 1.67-1.57 (m, 4H), 1.35 (s, 9H), 1.04 (s, 9H). HRMS (ESI) calcd for $C_{56}H_{75}ClN_{10}O_7PS^+$ [M+H]$^+$: 1097.4962, found, 1097.4296.

Compound Example 52: Synthesis of N1-(1-(4-((5-chloro-4-((2-(dimethylphosphoryl)phenyl)amino)pyrimidin-2-yl)amino)-3-methoxyphenyl)piperidin-4-yl)-N11-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)undecanediamide. (SIAIS1210117)

According to the procedures for the preparation of Compound Example 1, Brigatinib Analogue B and intermediate LM (SIAIS074020) was used to prepare SIAIS1210117 (white solid, 10.6 mg, 48%). $^1$H NMR (500 MHz, MeOD) δ 8.94 (s, 1H), 8.30 (s, 1H), 8.15 (s, 1H), 7.78 (s, 1H), 7.72 (dd, J=14.0, 6.7 Hz, 1H), 7.64 (t, J=7.9 Hz, 1H), 7.48 (d, J=8.2 Hz, 2H), 7.43 (d, J=8.3 Hz, 3H), 7.11 (s, 1H), 6.91 (d, J=7.8 Hz, 1H), 4.66 (s, 1H), 4.62-4.55 (m, 2H), 4.58-4.50 (m, 2H), 4.41-4.36 (m, 1H), 3.95 (s, 3H), 3.92 (d, J=11.1 Hz, 1H), 3.82 (dd, J=11.0, 3.9 Hz, 1H), 3.75 (d, J=12.6 Hz, 2H), 3.47-3.40 (m, 2H), 2.49 (s, 3H), 2.26-2.21 (m, 4H), 2.17 (d, J=12.5 Hz, 2H), 1.90-1.85 (m, 8H), 1.68-1.57 (m, 6H), 1.39-1.33 (m, 10H), 1.05 (s, 9H). HRMS (ESI) calcd for $C_{57}H_{77}ClN_{10}O_7PS^+$ [M+H]$^+$: 1111.5118, found, 1111.5109.

Comparative Example 53: Synthesis of N1-(1-(4-((5-chloro-4-((2-(dimethylphosphoryl)phenyl)amino)pyrimidin-2-yl)amino)-3-methoxyphenyl)piperidin-4-yl)-N11-((S)-1-((2S,4S)-4-hydroxy-2-((4-(4-methylthiazol-5-yl)benzyl)carbamoyl)pyrrolidin-1-yl)-3,3-dimethyl-1-oxobutan-2-yl)undecanediamide. (SIAIS219050)

According to the procedures for the preparation of Compound Example 1, Brigatinib Analogue B and intermediate LM (SIAIS219048) was used to prepare SIAIS219050 (white solid, 8.2 mg, 37%). $^1$H NMR (500 MHz, MeOD) δ 9.34 (s, 1H), 8.23 (s, 1H), 8.15 (s, 1H), 7.82-7.71 (m, 2H), 7.67 (t, J=7.8 Hz, 1H), 7.50-7.45 (m, 6H), 7.18 (d, J=8.6 Hz, 1H), 4.56-4.50 (m, 3H), 4.45-4.36 (m, 2H), 4.14-4.10 (m, 1H), 4.04 (dd, J=10.5, 5.1 Hz, 1H), 3.98 (s, 3H), 3.75-3.68 (m, 6H), 2.53 (s, 3H), 2.50-2.40 (m, 1H), 2.34-2.20 (m, 8H), 2.13-2.08 (m, 2H), 2.01-1.94 (m, 1H), 1.87 (d, J=13.5 Hz, 6H), 1.62 (d, J=7.3 Hz, 5H), 1.33 (s, 12H), 1.04 (s, 9H). HRMS (ESI) calcd for $C_{57}H_{77}ClN_{10}O_7PS^+$ [M+H]$^+$: 1111.5118, found, 1111.5111.

Compound Example 54: Synthesis of N1-(1-(4-((5-chloro-4-((2-(dimethylphosphoryl)phenyl)amino)pyrimidin-2-yl)amino)-3-methoxyphenyl)piperidin-4-yl)-N4-(2-((2-(2,6-dioxopiperidin-3-yl)-1,3-dioxoisoindolin-4-yl)amino)ethyl)succinamide. (SIAIS164157)

According to the procedures for the preparation of Compound Example 1, Brigatinib Analogue B and intermediate LM (SIAIS164119) was used to prepare SIAIS164157 (yellow solid, 11.0 mg, 61%). $^1$H NMR (500 MHz, MeOD) δ 8.23 (s, 1H), 8.16 (s, 1H), 7.80-7.70 (m, 2H), 7.66 (t, J=7.8 Hz, 1H), 7.55 (dd, J=8.4, 7.2 Hz, 1H), 7.47 (t, J=7.6 Hz, 1H), 7.38 (s, 1H), 7.14-7.10 (m, 2H), 7.04 (d, J=7.1 Hz, 1H), 5.08-5.03 (m, 1H), 4.08-4.04 (m, 1H), 3.98 (s, 3H), 3.77-3.61 (m, 4H), 3.49-3.41 (m, 4H), 2.89-2.82 (m, 1H), 2.78-2.68 (m, 2H), 2.53-2.49 (m, 1H), 2.51 (s, 3H), 2.23-2.17 (m, 2H), 2.12-2.00 (m, 3H), 1.88 (s, 3H), 1.85 (s, 3H). HRMS (ESI) calcd for $C_{43}H_{49}ClN_{10}O_8P^+$ [M+H]$^+$: 899.3155, found, 899.0580.

Compound Example 55: Synthesis of N-(1-(4-((5-chloro-4-((2-(dimethylphosphoryl)phenyl)amino)pyrimidin-2-yl)amino)-3-methoxyphenyl)piperidin-4-yl)-3-(2-(2,6-dioxopiperidin-3-yl)-1,3-dioxoisoindolin-4-yl)propenamide. (SIAIS219170)

According to the procedures for the preparation of Compound Example 1, Brigatinib Analogue B and intermediate LM (SIAIS172147) was used to prepare SIAIS219170 (white solid, 6.4 mg, 39%). $^1$H NMR (500 MHz, MeOD) δ 8.24-8.12 (m, 2H), 7.83 (d, J=7.7 Hz, 1H), 7.78-7.71 (m, 4H), 7.65 (s, 1H), 7.47 (d, J=6.7 Hz, 1H), 7.37-7.28 (m, 1H), 7.10-7.04 (m, 1H), 5.12 (dd, J=12.5, 5.4 Hz, 1H), 4.04 (s, 1H), 3.97 (d, J=4.3 Hz, 3H), 3.68-3.61 (m, 4H), 3.16 (t, J=7.2 Hz, 2H), 2.91-2.82 (m, 1H), 2.78-2.66 (m, 2H), 2.63 (s, 2H), 2.16-2.06 (m, 3H), 1.87 (d, J=13.5 Hz, 6H), 1.89-1.85 (m, 2H). HRMS (ESI) calcd for $C_{40}H_{43}ClN_8O_7P^+$ [M+H]$^+$: 813.2675, found, 813.2670.

Compound Example 56: Synthesis of 4-((2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethyl)amino)-2-(2,6-dioxopiperidin-3-yl)isoindoline-1,3-dione. (SIAIS164007)

According to the procedures for the preparation of Compound Example 1, Brigatinib Analogue C and intermediate LM (SIAIS151001) was used to prepare SIAIS164007 (yellow solid, 17.5 mg, 71%). $^1$H NMR (500 MHz, MeOD) δ 8.38 (s, 1H), 8.06 (s, 1H), 7.72-7.65 (m, 1H), 7.61-7.54 (m, 2H), 7.39 (t, J=7.5 Hz, 1H), 7.32 (d, J=8.1 Hz, 1H), 7.11 (d, J=8.5 Hz, 1H), 7.05 (d, J=7.0 Hz, 1H), 6.68 (d, J=2.4 Hz, 1H), 6.52 (d, J=8.5 Hz, 1H), 5.10 (dd, J=12.7, 5.5 Hz, 1H), 3.86 (s, 3H), 3.84-3.75 (m, 6H), 3.53-3.51 (m, 4H), 3.43-3.32 (m, 2H), 3.30-2.95 (m, 5H), 2.90-2.83 (m, 2H), 2.81-2.54 (m, 5H), 2.21-2.01 (m, 3H), 1.89 (d, J=13.6 Hz, 6H), 1.83-1.63 (m, 2H). HRMS (ESI) calcd for $C_{46}H_{55}ClN_{10}O_8P$ [M+H]$^+$: 941.3625, found, 941.2930.

Compound Example 57: Synthesis of 4-((2-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethoxy)ethyl)amino)-2-(2,6-dioxopiperidin-3-yl)isoindoline-1,3-dione. (SIAIS164008)

According to the procedures for the preparation of Compound Example 1, Brigatinib Analogue C and intermediate LM (SIAIS151004) was used to prepare SIAIS164008 (yellow solid, 18.4 mg, 71%). $^1$H NMR (500 MHz, MeOD) δ 8.38 (s, 1H), 8.06 (s, 1H), 7.68 (dd, J=14.7, 7.1 Hz, 1H), 7.60-7.54 (m, 2H), 7.37 (t, J=7.0 Hz, 1H), 7.32 (d, J=8.2 Hz, 1H), 7.11 (d, J=8.5 Hz, 1H), 7.06 (d, J=7.0 Hz, 1H), 6.69 (d, J=2.4 Hz, 1H), 6.52 (d, J=8.2 Hz, 1H), 5.07 (dd, J=12.5, 5.5 Hz, 1H), 3.89 (s, 1H), 3.87 (s, 1H), 3.84 (s, 3H), 3.78 (t, J=5.8 Hz, 2H), 3.73 (t, J=5.1 Hz, 2H), 3.69-3.68 (m, 2H), 3.67-3.63 (m, 2H), 3.51 (t, J=5.1 Hz, 3H), 3.38-3.31 (m, 8H), 2.91-2.63 (m, 7H), 2.18 (d, J=10.2 Hz, 2H), 2.15-2.05 (m, 1H), 1.88 (d, J=13.6 Hz, 6H), 1.86-1.73 (m, 2H). HRMS (ESI) calcd for $C_{48}H_{59}ClN_{10}O_9P$ [M+H]$^+$: 985.3887, found, 985.3166.

Compound Example 58: Synthesis of 4-((2-(2-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethoxy)ethoxy)ethyl)amino)-2-(2,6-dioxopiperidin-3-yl)isoindoline-1,3-dione. (SIAIS164009)

According to the procedures for the preparation of Compound Example 1, Brigatinib Analogue C and intermediate LM (SIAIS151005) was used to prepare SIAIS164009 (yellow solid, 20 mg, 74%). $^1$H NMR (500 MHz, MeOD) δ 8.38 (s, 1H), 8.07 (d, J=14.7 Hz, 1H), 7.67 (dd, J=14.7, 7.1 Hz, 1H), 7.61-7.51 (m, 2H), 7.37 (t, J=7.1 Hz, 1H), 7.32 (d, J=8.2 Hz, 1H), 7.08 (t, J=6.2 Hz, 1H), 7.05 (d, J=7.0 Hz, 1H), 6.70 (d, J=2.4 Hz, 1H), 6.53 (d, J=9.0 Hz, 1H), 5.05 (dd, J=12.5, 5.5 Hz, 1H), 3.91 (d, J=12.4 Hz, 2H), 3.84 (s, 3H), 3.80-3.70 (m, 5H), 3.70-3.63 (m, 7H), 3.63-3.57 (m, 3H), 3.51-3.49 (m, 3H), 3.46-3.35 (m, 2H), 3.32-3.31 (m, 3H), 2.92-2.77 (m, 4H), 2.77-2.62 (m, 3H), 2.22 (d, J=12.1 Hz, 2H), 2.12-2.08 (m, 1H), 1.88 (d, J=13.6 Hz, 6H), 1.86-1.79 (m, 2H). HRMS (ESI) calcd for $C_{50}H_{63}ClN_{10}O_{10}P$ [M+H]$^+$: 1029.4149, found, 1029.3401.

Compound Example 59: Synthesis of 4-((15-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-15-oxo-3,6,9,12-tetraoxapentadecyl)amino)-2-(2,6-dioxopiperidin-3-yl)isoindoline-1,3-dione. (SIAIS164016)

According to the procedures for the preparation of Compound Example 1, Brigatinib Analogue C and intermediate LM (SIAIS151006) was used to prepare SIAIS164016 (yellow solid, 13 mg, 46%). $^1$H NMR (500 MHz, MeOD) δ 8.38 (s, 1H), 8.06 (s, 1H), 7.68 (dd, J=13.3, 8.4 Hz, 1H), 7.60-7.51 (m, 2H), 7.37 (t, J=7.1 Hz, 1H), 7.30 (d, J=8.7 Hz, 1H), 7.06 (d, J=8.6 Hz, 1H), 7.03 (d, J=7.0 Hz, 1H), 6.71 (d, J=2.4 Hz, 1H), 6.55 (d, J=7.7 Hz, 1H), 5.04 (dd, J=12.7, 5.5 Hz, 1H), 3.93 (d, J=12.7 Hz, 2H), 3.84 (s, 3H), 3.75 (t, J=5.8 Hz, 3H), 3.71 (t, J=5.2 Hz, 2H), 3.69-3.55 (m, 15H), 3.54-3.36 (m, 5H), 2.86-2.80 (m, 4H), 2.77-2.63 (m, 3H), 2.25 (d, J=11.3 Hz, 2H), 2.15-2.04 (m, 1H), 1.90-1.86 (m, 8H). HRMS (ESI) calcd for $C_{52}H_{67}ClN_{10}O_{11}P$ [M+H]$^+$: 1073.4411, found, 1073.4778.

Compound Example 60: Synthesis of 4-((18-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-18-oxo-3,6,9,12,15-pentaoxaoctadecyl)amino)-2-(2,6-dioxopiperidin-3-yl)isoindoline-1,3-dione. (SIAIS164017)

According to the procedures for the preparation of Compound Example 1, Brigatinib Analogue C and intermediate LM (SIAIS151007) was used to prepare SIAIS164017 (yellow solid, 18.2 mg, 62%). $^1$H NMR (500 MHz, MeOD) δ 8.38 (s, 1H), 8.05 (s, 1H), 7.67 (dd, J=14.2, 6.5 Hz, 1H), 7.60-7.52 (m, 2H), 7.37 (t, J=6.9 Hz, 1H), 7.32 (d, J=8.9 Hz, 1H), 7.08 (d, J=8.5 Hz, 1H), 7.04 (d, J=7.0 Hz, 1H), 6.72 (d, J=2.4 Hz, 1H), 6.57 (d, J=8.8 Hz, 1H), 5.04 (dd, J=12.6, 5.5 Hz, 1H), 3.95 (d, J=12.2 Hz, 2H), 3.85 (s, 3H), 3.75 (dd, J=12.5, 6.6 Hz, 2H), 3.71 (t, J=5.2 Hz, 2H), 3.68-3.56 (m, 18H), 3.56-3.37 (m, 5H), 3.32-3.31 (m, 4H), 2.93-2.78 (m, 4H), 2.78-2.60 (m, 3H), 2.25 (d, J=10.6 Hz, 2H), 2.11-2.07 (m, 1H), 1.90-1.87 (m, 8H). HRMS (ESI) calcd for $C_{54}H_{71}ClN_{10}O_{12}P$ [M+H]$^+$: 1117.4674, found, 1117.4682.

Compound Example 61: Synthesis of 4-((2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-2-oxoethyl)amino)-2-(2,6-dioxopiperidin-3-yl)isoindoline-1,3-dione. (SIAIS164018)

According to the procedures for the preparation of Compound Example 1, Brigatinib Analogue C and intermediate LM (SIAIS151025) was used to prepare SIAIS164018 (yellow solid, 18.1 mg, 78%). $^1$H NMR (500 MHz, MeOD) δ 8.39 (s, 1H), 8.07 (d, J=17.8 Hz, 1H), 7.68 (dd, J=14.1, 7.7 Hz, 1H), 7.61-7.53 (m, 2H), 7.37 (t, J=7.5 Hz, 1H), 7.34 (d, J=8.9 Hz, 1H), 7.10 (d, J=7.0 Hz, 1H), 7.00 (d, J=8.5 Hz, 1H), 6.75 (d, J=2.4 Hz, 1H), 6.60 (d, J=7.9 Hz, 1H), 5.09 (dd, J=12.5, 5.5 Hz, 1H), 4.26 (s, 2H), 3.97 (d, J=12.4 Hz, 2H), 3.86 (s, 3H), 3.71-3.32 (m, 9H), 2.98-2.81 (m, 3H), 2.79-2.68 (m, 2H), 2.27 (d, J=11.4 Hz, 2H), 2.17-2.08 (m, 1H), 2.00-1.91 (m, 2H), 1.88 (d, J=13.6 Hz, 6H). HRMS (ESI) calcd for $C_{43}H_{49}ClN_{10}O_7P$ [M+H]$^+$: 883.3206, found, 883.3327.

Compound Example 62: Synthesis of 4-((3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)amino)-2-(2,6-dioxopiperidin-3-yl)isoindoline-1,3-dione. (SIAIS164019)

According to the procedures for the preparation of Compound Example 1, Brigatinib Analogue C and intermediate LM (SIAIS151026) was used to prepare SIAIS164019 (yellow solid, 14.2 mg, 60%). $^1$H NMR (500 MHz, MeOD) δ 8.39 (s, 1H), 8.06 (s, 1H), 7.68 (dd, J=13.4, 8.4 Hz, 1H), 7.63-7.53 (m, 2H), 7.38 (t, J=6.8 Hz, 1H), 7.33 (d, J=7.4 Hz, 1H), 7.15 (d, J=8.6 Hz, 1H), 7.10 (d, J=7.0 Hz, 1H), 6.72 (d, J=2.4 Hz, 1H), 6.57 (d, J=8.5 Hz, 1H), 5.05 (dd, J=12.5, 5.4 Hz, 1H), 3.93 (s, 2H), 3.86 (s, 3H), 3.72 (t, J=5.2 Hz, 2H), 3.40 (t, J=12.2 Hz, 2H), 3.32-3.31 (m, 6H), 2.86-2.79 (m, 5H), 2.77-2.64 (m, 3H), 2.17 (d, J=12.1 Hz, 2H), 2.14-2.06 (m, 1H), 1.90-1.83 (m, 8H). HRMS (ESI) calcd for $C_{44}H_{51}ClN_{10}O_7P$ [M+H]$^+$: 897.3363, found, 897.3679.

Compound Example 63: Synthesis of 4-((4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4-oxobutyl)amino)-2-(2,6-dioxopiperidin-3-yl)isoindoline-1,3-dione. (SIAIS164020)

According to the procedures for the preparation of Compound Example 1, Brigatinib Analogue C and intermediate LM (SIAIS151019) was used to prepare SIAIS164020 (yellow solid, 14.2 mg, 59%). $^1$H NMR (500 MHz, MeOD) δ 8.40 (s, 1H), 8.05 (s, 1H), 7.68 (dd, J=13.4, 8.5 Hz, 1H), 7.60-7.57 (m, 2H), 7.39 (t, J=7.0 Hz, 1H), 7.31 (d, J=8.5 Hz, 1H), 7.14 (d, J=8.6 Hz, 1H), 7.08 (d, J=6.9 Hz, 1H), 6.74 (d, J=2.4 Hz, 1H), 6.59 (d, J=8.5 Hz, 1H), 5.07 (dd, J=12.6, 5.5 Hz, 1H), 3.94 (d, J=12.4 Hz, 2H), 3.86 (s, 3H), 3.59-3.37 (m, 5H), 3.33-3.31 (m, 6H), 2.89-2.80 (m, 3H), 2.79-2.68 (m, 2H), 2.58 (s, 2H), 2.19 (s, 2H), 2.13-2.11 (m, 1H), 2.08-1.97 (m, 2H), 1.97-1.80 (m, 8H). HRMS (ESI) calcd for $C_{45}H_{53}ClN_{10}O_7P$ [M+H]$^+$: 911.3519, found, 911.3859.

Compound Example 64: Synthesis of 4-((5-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-5-oxopentyl)amino)-2-(2,6-dioxopiperidin-3-yl)isoindoline-1,3-dione. (SIAIS164021)

According to the procedures for the preparation of Compound Example 1, Brigatinib Analogue C and intermediate LM (SIAIS151020) was used to prepare SIAIS164021 (yellow solid, 20.6 mg, 85%). $^1$H NMR (500 MHz, MeOD) δ 8.38 (s, 1H), 8.07 (s, 1H), 7.69 (dd, J=13.9, 7.5 Hz, 1H), 7.61-7.56 (m, 2H), 7.39 (t, J=7.6 Hz, 1H), 7.34 (s, 1H), 7.09 (d, J=8.5 Hz, 1H), 7.06 (d, J=7.1 Hz, 1H), 6.78 (s, 1H), 6.63 (s, 1H), 5.07 (dd, J=12.7, 5.5 Hz, 1H), 3.95 (s, 2H), 3.86 (s, 3H), 3.66 (m, 3H), 3.52-3.37 (m, 5H), 2.97-2.80 (m, 4H), 2.80-2.66 (m, 2H), 2.54 (s, 2H), 2.36 (t, J=8.1 Hz, 1H), 2.27 (s, 2H), 2.17-2.08 (m, 1H), 2.04 (dt, J=14.8, 7.5 Hz, 1H), 1.94 (s, 2H), 1.89 (d, J=13.6 Hz, 6H), 1.75 (s, 4H). HRMS (ESI) calcd for $C_{46}H_{55}ClN_{10}O_7P$ [M+H]$^+$: 925.3676, found, 925.4004.

Compound Example 65: Synthesis of 4-((6-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-6-oxohexyl)amino)-2-(2,6-dioxopiperidin-3-yl)isoindoline-1,3-dione. (SIAIS164022)

According to the procedures for the preparation of Compound Example 1, Brigatinib Analogue C and intermediate LM (SIAIS151027) was used to prepare SIAIS164022 (yellow solid, 15.5 mg, 63%). $^1$H NMR (500 MHz, MeOD) δ 8.38 (s, 1H), 8.07 (d, J=17.1 Hz, 1H), 7.68 (dd, J=13.4, 7.1 Hz, 1H), 7.60-7.55 (m, 2H), 7.38 (t, J=7.1 Hz, 1H), 7.33 (d, J=8.2 Hz, 1H), 7.06 (dd, J=9.2, 7.9 Hz, 2H), 6.74 (d, J=2.4 Hz, 1H), 6.59 (d, J=8.7 Hz, 1H), 5.06 (dd, J=12.5, 5.5 Hz, 1H), 3.95 (d, J=11.7 Hz, 2H), 3.86 (s, 3H), 3.77-3.39 (m, 4H), 3.37 (t, J=6.8 Hz, 2H), 3.35-3.31 (m, 5H), 2.91-2.80 (m, 3H), 2.80-2.64 (m, 2H), 2.49 (t, J=7.3 Hz, 2H), 2.24 (d, J=12.1 Hz, 2H), 2.19-2.04 (m, 1H), 1.90-1.87 (m, 8H), 1.78-1.65 (m, 4H), 1.57-1.43 (m, 2H). HRMS (ESI) calcd for $C_{47}H_{57}ClN_{10}O_7P$ [M+H]$^+$: 939.3832, found, 939.4168.

Compound Example 66: Synthesis of 4-((7-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-7-oxoheptyl)amino)-2-(2,6-dioxopiperidin-3-yl)isoindoline-1,3-dione. (SIAIS164023)

According to the procedures for the preparation of Compound Example 1, Brigatinib Analogue C and intermediate LM (SIAIS151086) was used to prepare SIAIS164023 (yellow solid, 14.1 mg, 56%). $^1$H NMR (500 MHz, MeOD) δ 8.39 (s, 1H), 8.05 (s, 1H), 7.68 (dd, J=12.8, 7.8 Hz, 1H), 7.56 (dd, J=8.6, 7.1 Hz, 2H), 7.38 (t, J=7.0 Hz, 1H), 7.33 (d, J=8.4 Hz, 1H), 7.05 (t, J=7.8 Hz, 2H), 6.74 (d, J=2.4 Hz, 1H), 6.59 (d, J=8.3 Hz, 1H), 5.06 (dd, J=12.5, 5.5 Hz, 1H), 3.96 (d, J=12.7 Hz, 2H), 3.87 (s, 3H), 3.71-3.46 (m, 4H), 3.40-3.31 (m, 7H), 2.93-2.80 (m, 3H), 2.80-2.65 (m, 2H), 2.45 (t, J=7.5 Hz, 2H), 2.25 (d, J=11.5 Hz, 2H), 2.15-2.06 (m, 1H), 1.90-1.87 (m, 8H), 1.71-1.62 (m, 4H), 1.58-1.39 (m, 4H). HRMS (ESI) calcd for $C_{48}H_{59}ClN_{10}O_7P$ [M+H]$^+$: 953.3989, found, 953.4144.

Compound Example 67: Synthesis of 3-(4-((2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-2-oxoethyl)amino)-1-oxoisoindolin-2-yl)piperidine-2,6-dione. (SIAIS219073)

According to the procedures for the preparation of Compound Example 1, Brigatinib Analogue C and intermediate LM (SIAIS1204057) was used to prepare SIAIS219073 (yellow solid, 5.8 mg, 38%). $^1$H NMR (500 MHz, MeOD) δ 8.33 (s, 1H), 8.11 (s, 1H), 7.74-7.68 (m, 1H), 7.60 (s, 1H), 7.45-7.36 (m, 3H), 7.18 (d, J=7.5 Hz, 1H), 6.99 (s, 1H), 6.88 (d, J=8.1 Hz, 1H), 6.80 (d, J=7.0 Hz, 1H), 5.19-5.15 (m, 1H), 4.44 (d, J=16.8 Hz, 1H), 4.37 (d, J=16.8 Hz, 1H), 4.25 (s, 1H), 3.96 (d, J=12.7 Hz, 2H), 3.90 (s, 3H), 3.64-3.61 (m, 4H), 3.39-3.36 (m, 2H), 3.28-3.05 (m, 6H), 2.97-2.87 (m, 1H), 2.81 (d, J=2.5 Hz, 1H), 2.54-2.50 (m, 1H), 2.37 (d, J=11.1 Hz, 2H), 2.24-2.07 (m, 3H), 1.88 (d, J=13.6 Hz, 6H). HRMS (ESI) calcd for $C_{43}H_{51}ClN_{10}O_6P^+$ [M+H]$^+$: 869.3414, found, 869.3410.

Compound Example 68: Synthesis of 3-(4-((4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4-oxobutyl)amino)-1-oxoisoindolin-2-yl)piperidine-2,6-dione. (SIAIS219155)

According to the procedures for the preparation of Compound Example 1, Brigatinib Analogue C and intermediate LM (SIAIS1204085) was used to prepare SIAIS219155 (yellow solid, 7.0 mg, 45%). $^1$H NMR (500 MHz, MeOD) δ 8.33 (s, 1H), 8.09 (s, 1H), 7.70 (dd, J=14.0, 7.8 Hz, 1H), 7.60 (s, 1H), 7.43 (t, J=7.6 Hz, 2H), 7.38 (s, 1H), 7.23 (d, J=5.0 Hz, 1H), 7.05 (d, J=7.4 Hz, 1H), 6.92 (s, 1H), 6.74 (s, 1H), 5.17 (dd, J=13.2, 5.0 Hz, 1H), 4.43 (d, J=17.3 Hz, 1H), 4.34 (d, J=17.4 Hz, 1H), 3.97-3.87 (m, 4H), 3.77-3.47 (m, 2H), 3.46-3.31 (m, 8H), 3.17-3.05 (m, 4H), 2.97-2.89 (m, 1H), 2.85-2.78 (m, 1H), 2.58-2.49 (m, 3H), 2.32-2.17 (m, 3H), 2.09-1.92 (m, 4H), 1.88 (d, J=13.6 Hz, 6H). HRMS (ESI) calcd for $C_{45}H_{55}ClN_{10}O_6P^+$[M+H]$^+$: 897.3727, found, 897.3722.

Compound Example 69: Synthesis of 3-(4-((5-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-5-oxopentyl)amino)-1-oxoisoindolin-2-yl)piperidine-2,6-dione. (SIAIS219156)

According to the procedures for the preparation of Compound Example 1, Brigatinib Analogue C and intermediate LM (SIAIS1210133) was used to prepare SIAIS219156 (yellow solid, 7.5 mg, 47%). $^1$H NMR (500 MHz, MeOD) δ 8.30 (s, 1H), 8.12 (s, 1H), 7.71 (dd, J=13.4, 7.1 Hz, 1H), 7.61 (t, J=7.0 Hz, 1H), 7.47 (dt, J=12.9, 7.1 Hz, 3H), 7.37 (d, J=7.4 Hz, 1H), 7.16 (d, J=7.9 Hz, 1H), 7.04 (s, 1H), 6.84 (d, J=8.7 Hz, 1H), 5.18 (dd, J=13.3, 5.2 Hz, 1H), 4.50 (d, J=17.1 Hz, 1H), 4.43 (d, J=17.1 Hz, 1H), 3.95 (s, 1H), 3.91 (s, 3H), 3.77-3.47 (m, 4H), 3.38 (d, J=3.4 Hz, 2H), 3.30-3.22 (m, 8H), 2.97-2.88 (m, 1H), 2.84-2.78 (m, 1H), 2.56-2.49 (m, 3H), 2.36 (s, 2H), 2.26-2.18 (m, 1H), 2.12-2.10 (m, 2H), 1.88 (d, J=13.6 Hz, 6H), 1.77 (s, 4H). HRMS (ESI) calcd for $C_{46}H_{57}ClN_{10}O_6P^+$ [M+H]$^+$: 911.3883, found, 911.3878.

Compound Example 70: Synthesis of 3-(4-((6-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-6-oxohexyl)amino)-1-oxoisoindolin-2-yl)piperidine-2,6-dione. (SIAIS219157)

According to the procedures for the preparation of Compound Example 1, Brigatinib Analogue C and intermediate LM (SIAIS1204061) was used to prepare SIAIS219157 (yellow solid, 8.1 mg, 53%). $^1$H NMR (500 MHz, MeOD) δ 8.28 (s, 1H), 8.13 (s, 1H), 7.71 (dd, J=14.0, 7.7 Hz, 1H), 7.62 (t, J=7.6 Hz, 1H), 7.52 (t, J=7.8 Hz, 1H), 7.45 (t, J=6.5 Hz, 3H), 7.25 (d, J=7.9 Hz, 1H), 7.08 (s, 1H), 6.87 (d, J=8.6 Hz, 1H), 5.19 (dd, J=13.3, 5.1 Hz, 1H), 4.54 (d, J=17.1 Hz, 1H), 4.47 (d, J=17.1 Hz, 1H), 3.95 (s, 1H), 3.91 (s, 3H), 3.67-3.57 (m, 4H), 3.38 (t, J=7.1 Hz, 2H), 3.30-3.17 (m, 8H), 2.99-2.88 (m, 1H), 2.85-2.77 (m, 1H), 2.59-2.44 (m, 3H), 2.39 (d, J=10.6 Hz, 2H), 2.27-2.08 (m, 3H), 1.88 (d, J=13.6 Hz, 6H), 1.78-1.74 (m, 2H), 1.73-1.65 (m, 2H), 1.56-1.47 (m, 2H). HRMS (ESI) calcd for $C_{47}H_{59}ClN_{10}O_6P$ [M+H]$^+$: 925.4040, found, 925.4031.

Compound Example 71: Synthesis of 3-(4-((7-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-7-oxoheptyl)amino)-1-oxoisoindolin-2-yl)piperidine-2,6-dione. (SIAIS219124)

According to the procedures for the preparation of Compound Example 1, Brigatinib Analogue C and intermediate LM (SIAIS1204063) was used to prepare SIAIS219124 (yellow solid, 11.2 mg, 48%). $^1$H NMR (500 MHz, MeOD) δ 8.38 (s, 1H), 8.08 (s, 1H), 7.70 (dd, J=13.9, 7.9 Hz, 1H), 7.59 (s, 1H), 7.45-7.37 (m, 2H), 7.33 (s, 1H), 7.16 (d, J=7.3 Hz, 1H), 6.93 (d, J=8.0 Hz, 1H), 6.79 (s, 1H), 6.64 (d, J=8.4 Hz, 1H), 5.17 (dd, J=13.2, 5.0 Hz, 1H), 4.38 (d, J=17.0 Hz, 1H), 4.31 (d, J=16.9 Hz, 1H), 3.98 (d, J=12.6 Hz, 2H), 3.89 (d, J=14.3 Hz, 3H), 3.57 (s, 2H), 3.47 (s, 2H), 3.19 (s, 6H), 2.95-2.89 (m, 4H), 2.82 (d, J=15.7 Hz, 2H), 2.54-2.41 (m, 3H), 2.34-2.18 (m, 4H), 1.97-1.86 (m, 6H), 1.71-1.64 (m, 4H), 1.48 (s, 4H). HRMS (ESI) calcd for $C_{48}H_{61}ClN_{10}O_6P$ [M+H]$^+$: 939.4196, found, 939.4188.

Compound Example 72: Synthesis of (2S,4R)-1-((S)-2-(2-(2-(2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide. (SIAIS164041)

According to the procedures for the preparation of Compound Example 1, Brigatinib Analogue C and intermediate LM (SIAIS151010) was used to prepare SIAIS164041 (white solid, 18.2 mg, 61%). $^1$H NMR (500 MHz, MeOD) δ 8.91 (s, 1H), 8.39 (s, 1H), 8.05 (s, 1H), 7.68 (dd, J=14.1, 7.7 Hz, 1H), 7.60-7.55 (m, 1H), 7.46-7.37 (m, 5H), 7.30 (s, 1H), 6.72 (d, J=2.5 Hz, 1H), 6.58 (d, J=8.7 Hz, 1H), 4.72 (s, 1H), 4.60-4.49 (m, 3H), 4.48-4.23 (m, 5H), 4.14-4.00 (m, 3H), 3.95 (d, J=12.2 Hz, 2H), 3.91-3.83 (m, 5H), 3.82-3.74 (m, 7H), 3.48-3.44 (m, 2H), 2.85 (t, J=12.2 Hz, 2H), 2.46 (s, 3H), 2.29-2.23 (m, 3H), 2.14-2.05 (m, 1H), 1.90-1.87 (m, 9H), 1.04 (s, 9H). HRMS (ESI) calcd for $C_{56}H_{74}ClN_{11}O_9PS^+$ [M+H]$^+$: 1142.4812, found, 1142.4776.

Compound Example 73: Synthesis of (2S,4R)-1-((S)-2-(3-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide. (SIAIS164032)

According to the procedures for the preparation of Compound Example 1, Brigatinib Analogue C and intermediate LM (SIAIS151002) was used to prepare SIAIS164032 (white solid, 15.4 mg, 50%). $^1$H NMR (500 MHz, MeOD) δ 8.93 (s, 1H), 8.39 (s, 1H), 8.05 (s, 1H), 7.68 (dd, J=14.0, 7.6 Hz, 1H), 7.62-7.51 (m, 1H), 7.47 (d, J=8.4 Hz, 2H), 7.45-7.36 (m, 3H), 7.29 (d, J=9.4 Hz, 1H), 6.74 (d, J=2.5 Hz, 1H), 6.60 (d, J=7.4 Hz, 1H), 4.66 (s, 1H), 4.60-4.50 (m, 3H), 4.37 (d, J=15.5 Hz, 2H), 3.97 (d, J=13.1 Hz, 2H), 3.89 (d, J=11.2 Hz, 3H), 3.85 (s, 3H), 3.84-3.80 (m, 1H), 3.80-3.67 (m, 5H), 3.66-3.51 (m, 6H), 3.51-3.36 (m, 2H), 3.30 (s, 5H), 2.91-2.85 (m, 2H), 2.78-2.61 (m, 2H), 2.61-2.42 (m, 5H), 2.28-2.21 (m, 3H), 2.11-2.04 (m, 1H), 1.93-1.87 (m, 7H), 1.03 (s, 9H). HRMS (ESI) calcd for $C_{58}H_{78}ClN_{11}O_9PS^+$ [M+H]$^+$: 1170.5125, found, 1170.5152.

Compound Example 74: Synthesis of (2S,4R)-1-((S)-2-(tert-butyl)-16-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide. (SIAIS164033)

According to the procedures for the preparation of Compound Example 1, Brigatinib Analogue C and intermediate LM (SIAIS151003) was used to prepare SIAIS164033 (white solid, 24.9 mg, 78%). $^1$H NMR (500 MHz, MeOD) δ 8.98 (s, 1H), 8.40 (s, 1H), 8.05 (s, 1H), 7.68 (dd, J=14.0, 7.6 Hz, 1H), 7.62-7.52 (m, 1H), 7.51-7.46 (m, 2H), 7.45-7.42 (m, 2H), 7.39 (t, J=7.2 Hz, 1H), 7.28 (s, 1H), 6.75 (d, J=2.4 Hz, 1H), 6.61 (d, J=8.7 Hz, 1H), 4.65 (s, 1H), 4.60-4.47 (m, 3H), 4.37 (d, J=15.6 Hz, 1H), 3.98 (d, J=12.7 Hz, 2H), 3.89 (d, J=11.2 Hz, 1H), 3.85 (s, 3H), 3.83-3.69 (m, 6H), 3.66-3.57 (m, 9H), 3.52-3.41 (m, 2H), 3.32-3.31 (m, 5H), 2.92-2.86 (m, 2H), 2.65-2.63 (m, 2H), 2.62-2.53 (m, 1H), 2.53-2.43 (m, 4H), 2.33-2.18 (m, 3H), 2.10-2.05 (m, 1H), 1.94-1.87 (m, 8H), 1.03 (s, 9H). HRMS (ESI) calcd for $C_{60}H_{82}ClN_{11}O_{10}PS^+$ [M+H]$^+$: 1214.5387, found, 1214.5405.

Compound Example 75: Synthesis of (2S,4R)-1-((S)-2-(tert-butyl)-19-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide. (SIAIS164034)

According to the procedures for the preparation of Compound Example 1, Brigatinib Analogue C and intermediate LM (SIAIS151008) was used to prepare SIAIS164034 (white solid, 23.8 mg, 72%). $^1$H NMR (500 MHz, MeOD) δ 8.94 (d, J=3.1 Hz, 1H), 8.39 (s, 1H), 8.05 (s, 1H), 7.68 (dd, J=13.5, 8.4 Hz, 1H), 7.62-7.52 (m, 1H), 7.51-7.45 (m, 2H), 7.45-7.41 (m, 2H), 7.38 (t, J=7.8 Hz, 1H), 7.29 (s, 1H), 6.74 (d, J=2.3 Hz, 1H), 6.60 (d, J=8.6 Hz, 1H), 4.65 (s, 1H), 4.59-4.50 (m, 3H), 4.36 (d, J=15.5 Hz, 1H), 3.98 (d, J=12.7 Hz, 2H), 3.92-3.83 (m, 4H), 3.82-3.70 (m, 6H), 3.65-3.56 (m, 14H), 3.47-3.44 (m, 2H), 3.32 (s, 6H), 2.87 (t, J=12.5 Hz, 2H), 2.67-2.54 (m, 2H), 2.51-2.43 (m, 4H), 2.32-2.18 (m, 3H), 2.10-2.04 (m, 1H), 1.93-1.87 (m, 7H), 1.03 (s, 9H). HRMS (ESI) calcd for $C_{62}H_{86}ClN_{11}O_{11}PS^+$ [M+H]$^+$: 1258.5650, found, 1258.5713.

Compound Example 76: Synthesis of (2S,4R)-1-((S)-2-(tert-butyl)-22-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide. (SIAIS164035)

According to the procedures for the preparation of Compound Example 1, Brigatinib Analogue C and intermediate LM (SIAIS151009) was used to prepare SIAIS164035 (white solid, 18.7 mg, 55%). $^1$H NMR (500 MHz, MeOD) δ 8.94 (s, 1H), 8.52-8.25 (m, 1H), 8.05 (s, 1H), 7.68 (dd, J=14.8, 7.1 Hz, 1H), 7.60-7.55 (m, 1H), 7.51-7.46 (m, 2H), 7.45-7.41 (m, 2H), 7.39 (t, J=7.7 Hz, 1H), 7.28 (s, 1H), 6.74 (s, 1H), 6.61 (s, 1H), 4.65 (s, 1H), 4.59-4.49 (m, 3H), 4.36 (d, J=15.5 Hz, 1H), 3.98 (d, J=13.0 Hz, 2H), 3.92-3.83 (m, 4H), 3.82-3.67 (m, 7H), 3.62-3.61 (m, 20H), 3.49-3.44 (m, 2H), 3.34-3.31 (m, 2H), 2.87 (t, J=12.5 Hz, 2H), 2.68-2.53 (m, 2H), 2.51-2.44 (m, 4H), 2.28-2.20 (m, 3H), 2.10-2.04 (m, 1H), 1.94-1.87 (m, 8H), 1.04 (s, 9H). HRMS (ESI) calcd for $C_{64}H_{90}ClN_{11}O_{12}PS^+$ [M+H]$^+$: 1302.5912, found, 1302.5944.

Compound Example 77: Synthesis of (2S,4R)-1-((S)-2-(4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide. (SIAIS164120)

According to the procedures for the preparation of Compound Example 1, Brigatinib Analogue C and intermediate LM (SIAIS074011) was used to prepare SIAIS164120 (white solid, 9.1 mg, 48%). $^1$H NMR (500 MHz, MeOD) δ 9.62 (s, 1H), 8.31 (s, 1H), 8.11 (s, 1H), 7.70 (dd, J=14.0, 9.1 Hz, 1H), 7.60 (s, 1H), 7.54 (d, J=8.2 Hz, 2H), 7.49 (d, J=8.3 Hz, 2H), 7.43 (t, J=7.7 Hz, 2H), 6.98 (s, 1H), 6.80 (s, 1H), 4.61 (s, 1H), 4.59-4.54 (m, 2H), 4.50 (s, 1H), 4.40 (d, J=15.8 Hz, 1H), 4.34-4.22 (m, 1H), 3.97 (d, J=11.9 Hz, 2H), 3.92-3.86 (m, 4H), 3.81 (dd, J=11.0, 3.9 Hz, 1H), 3.67-3.60 (m, 5H), 3.17 (s, 4H), 2.84-2.57 (m, 5H), 2.56 (s, 3H), 2.37 (d, J=10.3 Hz, 2H), 2.28-2.19 (m, 1H), 2.19-2.05 (m, 3H), 1.88 (d, J=13.6 Hz, 6H), 1.03 (s, 9H). HRMS (ESI) calcd for $C_{54}H_{70}ClN_{11}O_7PS^+$ [M+H]$^+$: 1082.4601, found, 1082.1363.

Compound Example 78: Synthesis of (2S,4R)-1-((S)-2-(5-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide. (SIAIS164121)

According to the procedures for the preparation of Compound Example 1, Brigatinib Analogue C and intermediate LM (SIAIS074012) was used to prepare SIAIS164121 (white solid, 6.3 mg, 33%). $^1$H NMR (500 MHz, MeOD) δ 9.72 (s, 1H), 8.28 (s, 1H), 8.15 (s, 1H), 7.72 (dd, J=13.9, 7.9 Hz, 1H), 7.67-7.60 (m, 1H), 7.59-7.35 (m, 6H), 7.14 (s, 1H), 6.91 (s, 1H), 4.69-4.49 (m, 5H), 4.41 (d, J=15.8 Hz, 1H), 4.31-4.16 (m, 1H), 3.95-3.92 (m, 6H), 3.81 (d, J=7.8 Hz, 1H), 3.69 (s, 4H), 3.27-3.02 (m, 5H), 2.57 (s, 3H), 2.44-2.37 (m, 6H), 2.24-2.08 (m, 4H), 1.93-1.87 (m, 8H), 1.04 (s, 9H). HRMS (ESI) calcd for $C_{55}H_{72}ClN_{11}O_7PS^+$ [M+H]$^+$: 1096.4758, found, 1096.1472.

Compound Example 79: Synthesis of (2S,4R)-1-((S)-2-(6-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide. (SIAIS164122)

According to the procedures for the preparation of Compound Example 1, Brigatinib Analogue C and intermediate LM (SIAIS074013) was used to prepare SIAIS164122 (white solid, 8.6 mg, 44%). $^1$H NMR (500 MHz, MeOD) δ 9.76 (s, 1H), 8.26 (s, 1H), 8.15 (s, 1H), 7.72 (dd, J=13.9, 7.8 Hz, 1H), 7.63 (t, J=8.0 Hz, 1H), 7.59-7.43 (m, 6H), 7.17 (s, 1H), 6.95 (s, 1H), 4.64 (s, 1H), 4.61-4.49 (m, 3H), 4.41 (d, J=15.6 Hz, 1H), 4.25 (s, 1H), 3.99-3.88 (m, 6H), 3.81 (dd, J=10.8, 3.8 Hz, 1H), 3.69 (s, 4H), 3.40-3.31 (m, 3H), 3.17 (s, 3H), 2.58 (s, 3H), 2.50-2.43 (m, 4H), 2.36-2.22 (m, 5H), 2.13-2.03 (m, 1H), 1.88 (d, J=13.6 Hz, 6H), 1.67 (s, 4H), 1.05 (s, 9H). HRMS (ESI) calcd for $C_{56}H_{74}ClN_{11}O_7PS^+$ [M+H]$^+$: 1110.4914, found, 1110.1540.

Compound Example 80: Synthesis of (2S,4R)-1-((S)-2-(7-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-7-oxoheptanamido)-3,3-dimethylbutanoyl)-4-hydroxy-N-(4-(4-methylthiazol-5-yl)benzyl)pyrrolidine-2-carboxamide. (SIAIS164123)

According to the procedures for the preparation of Compound Example 1, Brigatinib Analogue C and intermediate LM (SIAIS074014) was used to prepare SIAIS164123 (white solid, 8.4 mg, 43%). $^1$H NMR (500 MHz, MeOD) δ 9.64 (s, 1H), 8.32 (s, 1H), 8.11 (s, 1H), 7.71 (dd, J=13.9, 7.7 Hz, 1H), 7.61 (s, 1H), 7.55-7.44 (m, 6H), 7.01 (s, 1H), 6.81 (s, 1H), 4.64 (s, 1H), 4.60-4.50 (m, 3H), 4.41 (d, J=15.7 Hz, 1H), 3.96 (d, J=10.3 Hz, 2H), 3.92-3.90 (m, 4H), 3.81 (dd, J=10.9, 3.9 Hz, 1H), 3.69-3.60 (m, 4H), 3.31-3.17 (m, 7H), 2.56 (s, 3H), 2.47 (t, J=7.3 Hz, 2H), 2.37 (s, 2H), 2.35-2.27 (m, 2H), 2.27-2.20 (m, 1H), 2.19-2.03 (m, 3H), 1.88 (d, J=13.6 Hz, 6H), 1.70-1.59 (m, 4H), 1.43-1.37 (m, 2H), 1.03 (s, 9H). HRMS (ESI) calcd for $C_{57}H_{76}ClN_{11}O_7PS^+$ [M+H]$^+$: 1124.5071, found, 1124.1726.

Compound Example 81: Synthesis of (2S,4R)-1-((S)-2-(8-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide. (SIAIS164124)

According to the procedures for the preparation of Compound Example 1, Brigatinib Analogue C and intermediate LM (SIAIS074015) was used to prepare SIAIS164124 (white solid, 8.3 mg, 42%). $^1$H NMR (500 MHz, MeOD) δ 9.76 (s, 1H), 8.27 (s, 1H), 8.15 (s, 1H), 7.72 (dd, J=14.0, 7.9 Hz, 1H), 7.63 (s, 1H), 7.59-7.39 (m, 6H), 7.19 (s, 1H), 6.94 (s, 1H), 4.64 (s, 1H), 4.62-4.46 (m, 3H), 4.41 (d, J=15.7 Hz, 1H), 4.26 (s, 1H), 4.03-3.86 (m, 6H), 3.81 (dd, J=10.9, 3.8 Hz, 1H), 3.69 (s, 4H), 3.33 (s, 3H), 3.17 (s, 3H), 2.58 (s, 3H), 2.53-2.38 (m, 4H), 2.38-2.17 (m, 5H), 2.13-2.02 (m, 1H), 1.88 (d, J=13.6 Hz, 6H), 1.64 (d, J=6.7 Hz, 4H), 1.39 (d, J=3.5 Hz, 4H), 1.03 (s, 9H). HRMS (ESI) calcd for $C_{58}H_{78}ClN_{11}O_7PS^+$ [M+H]$^+$: 1138.5227, found, 1138.1798.

Compound Example 82: Synthesis of (2S,4R)-1-((S)-2-(9-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-9-oxononanamido)-3,3-dimethylbutanoyl)-4-hydroxy-N-(4-(4-methylthiazol-5-yl)benzyl)pyrrolidine-2-carboxamide. (SIAIS164125)

According to the procedures for the preparation of Compound Example 1, Brigatinib Analogue C and intermediate LM (SIAIS074016) was used to prepare SIAIS164125 (white solid, 8.9 mg, 44%). $^1$H NMR (500 MHz, MeOD) δ

9.82-9.70 (m, 1H), 8.25 (s, 1H), 8.16 (s, 1H), 7.78-7.68 (m, 1H), 7.64 (s, 1H), 7.56-7.47 (m, 6H), 7.23 (s, 1H), 6.98 (s, 1H), 4.64 (s, 1H), 4.61-4.47 (m, 3H), 4.40 (d, J=15.7 Hz, 1H), 4.25 (s, 1H), 3.92 (t, J=8.1 Hz, 6H), 3.81 (dd, J=11.0, 3.8 Hz, 1H), 3.70 (s, 4H), 3.39-3.32 (m, 3H), 3.30-3.17 (m, 3H), 2.58 (s, 3H), 2.52-2.39 (m, 4H), 2.39-2.17 (m, 5H), 2.13-2.03 (m, 1H), 1.88 (d, J=13.6 Hz, 6H), 1.62 (s, 4H), 1.37 (s, 6H), 1.03 (s, 9H). HRMS (ESI) calcd for $C_{59}H_{80}ClN_{11}O_7PS^+$ [M+H]$^+$: 1152.5384, found, 1152.1936.

Compound Example 83: Synthesis of (2S,4R)-1-((S)-2-(10-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide. (SIAIS164126)

According to the procedures for the preparation of Compound Example 1, Brigatinib Analogue C and intermediate LM (SIAIS074019) was used to prepare SIAIS164126 (white solid, 7.7 mg, 38%). $^1$H NMR (500 MHz, MeOD) δ 9.88-9.79 (m, 1H), 8.19 (s, 2H), 7.73 (dd, J=13.9, 7.8 Hz, 1H), 7.65 (s, 1H), 7.57-7.48 (m, 6H), 7.33 (s, 1H), 7.06 (s, 1H), 4.64 (s, 1H), 4.61-4.46 (m, 3H), 4.44-4.37 (m, 1H), 4.27 (s, 1H), 3.95-3.90 (m, 6H), 3.85-3.48 (m, 8H), 3.20-3.04 (m, 3H), 2.60 (s, 3H), 2.53-2.43 (m, 4H), 2.42-2.19 (m, 5H), 2.10-2.05 (m, 1H), 1.88 (d, J=13.6 Hz, 6H), 1.62 (d, J=7.0 Hz, 4H), 1.36 (s, 8H), 1.03 (s, 9H). HRMS (ESI) calcd for $C_{60}H_{82}ClN_{11}O_7PS^+$ [M+H]$^+$: 1166.5540, found, 1166.2102.

Compound Example 84: Synthesis of 4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-N-(2-((2-(2,6-dioxopiperidin-3-yl)-1,3-dioxoisoindolin-4-yl)amino)ethyl)-4-oxobutanamide. (SIAIS164152)

According to the procedures for the preparation of Compound Example 1, Brigatinib Analogue C and intermediate LM (SIAIS164119) was used to prepare SIAIS164152 (yellow solid, 10.6 mg, 63%). $^1$H NMR (500 MHz, MeOD) δ 8.23 (s, 1H), 8.17 (s, 1H), 7.74 (dd, J=13.8, 7.8 Hz, 1H), 7.71-7.62 (m, 2H), 7.57 (dd, J=8.5, 7.2 Hz, 1H), 7.50 (t, J=7.3 Hz, 1H), 7.45 (s, 1H), 7.15 (t, J=6.9 Hz, 2H), 7.06 (d, J=7.1 Hz, 1H), 5.08 (dd, J=12.7, 5.5 Hz, 1H), 4.72 (s, 1H), 4.27 (s, 1H), 3.97 (s, 3H), 3.93 (d, J=12.2 Hz, 2H), 3.86-3.58 (m, 6H), 3.48 (s, 5H), 3.17 (s, 2H), 2.93-2.85 (m, 1H), 2.80-2.65 (m, 3H), 2.65-2.40 (m, 7H), 2.16-2.07 (m, 1H), 1.87 (d, J=13.6 Hz, 6H). HRMS (ESI) calcd for $C_{47}H_{56}ClN_{11}O_8P$ [M+H]$^+$: 968.3734, found, 968.1075.

Compound Example 85: Synthesis of 4-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)-2-(2,6-dioxopiperidin-3-yl)isoindoline-1,3-dione. (SIAIS219158)

According to the procedures for the preparation of Compound Example 1, Brigatinib Analogue C and intermediate LM (SIAIS172147) was used to prepare SIAIS219158 (white solid, 6.8 mg, 44%). $^1$H NMR (500 MHz, MeOD) δ 8.31 (d, J=12.2 Hz, 1H), 8.11 (s, 1H), 7.86-7.81 (m, 2H), 7.76 (dd, J=7.8, 1.2 Hz, 1H), 7.74-7.67 (m, 1H), 7.60 (t, J=7.5 Hz, 1H), 7.44 (t, J=7.1 Hz, 2H), 6.99 (s, 1H), 6.80 (d, J=8.4 Hz, 1H), 5.13 (dd, J=12.6, 5.5 Hz, 1H), 3.94 (d, J=12.8 Hz, 2H), 3.90 (s, 3H), 3.61-3.55 (m, 4H), 3.19-3.14 (m, 8H), 2.91-2.77 (m, 4H), 2.76-2.73 (m, 2H), 2.35 (d, J=11.4 Hz, 2H), 2.18-2.06 (m, 3H), 1.91-1.87 (m, 6H). HRMS (ESI) calcd for $C_{44}H_{50}ClN_9O_7P^+$ [M+H]$^+$: 882.3254, found, 882.3242.

Compound Example 86: Synthesis of (2S,4R)-1-((S)-2-(4-(4-(4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4-oxobutyl)-1H-1,2,3-triazol-1-yl)butanamido)-3,3-dimethylbutanoyl)-4-hydroxy-N-(4-(4-methylthiazol-5-yl)benzyl)pyrrolidine-2-carboxamide. (SIAIS164153)

According to the procedures for the preparation of Compound Example 1, Brigatinib Analogue C and intermediate LM (SIAIS164128) was used to prepare SIAIS164153 (white solid, 9.2 mg, 44%). $^1$H NMR (500 MHz, MeOD) δ 9.90 (s, 1H), 8.32 (s, 1H), 8.21 (s, 2H), 7.74 (dd, J=13.7, 7.7 Hz, 1H), 7.69-7.58 (m, 2H), 7.56 (d, J=8.1 Hz, 2H), 7.54-7.46 (m, 3H), 7.38 (s, 1H), 7.10 (s, 1H), 4.64-4.48 (m, 6H), 4.44-4.41 (m, 1H), 4.26 (s, 1H), 3.96-3.92 (m, 6H), 3.88-3.53 (m, 8H), 3.17 (s, 2H), 2.92 (s, 2H), 2.61-2.59 (m, 5H), 2.52 (s, 2H), 2.48-2.13 (m, 8H), 2.12-2.01 (m, 3H), 1.87 (d, J=13.6 Hz, 6H), 1.03 (s, 9H). HRMS (ESI) calcd for $C_{60}H_{79}ClN_{14}O_7PS^+$ [M+H]$^+$: 1205.5398, found, 1205.1640.

Compound Example 87: Synthesis of 8-(4-(3-(2-((2-(2,6-dioxopiperidin-3-yl)-1,3-dioxoisoindolin-4-yl)amino)ethoxy)propanoyl)piperazin-1-yl)-9-ethyl-6,6-dimethyl-11-oxo-6,11-dihydro-5H-benzo[b]carbazole-3-carbonitrile. (SIAIS164011)

According to the procedures for the preparation of Compound Example 1, Alectinib Analogue A and intermediate LM (SIAIS151001) was used to prepare SIAIS164011 (yellow solid, 16.6 mg, 47%). $^1$H NMR (500 MHz, DMSO) δ 12.70 (s, 1H), 11.09 (s, 1H), 8.32 (d, J=8.2 Hz, 1H), 8.06 (s, 1H), 8.00 (s, 1H), 7.61 (dd, J=8.1, 1.4 Hz, 1H), 7.59-7.55 (m, 1H), 7.36 (s, 1H), 7.15 (d, J=8.6 Hz, 1H), 7.04 (d, J=7.0 Hz, 1H), 6.61 (t, J=5.7 Hz, 1H), 5.04 (dd, J=12.8, 5.4 Hz, 1H), 3.73 (t, J=6.5 Hz, 2H), 3.63 (t, J=5.2 Hz, 6H), 3.48 (dd, J=10.9, 5.4 Hz, 2H), 2.98-2.90 (m, 4H), 2.89-2.81 (m, 1H), 2.73 (q, J=7.5 Hz, 2H), 2.65 (t, J=6.6 Hz, 2H), 2.56-2.49 (m, 2H), 2.00-1.97 (m, 1H), 1.73 (s, 6H), 1.27 (t, J=7.5 Hz, 3H). HRMS (ESI) calcd for $C_{43}H_{44}N_7O_7$ [M+H]$^+$: 770.3297, found, 770.2435.

Compound Example 88: Synthesis of 8-(4-(3-(2-(2-((2-(2,6-dioxopiperidin-3-yl)-1,3-dioxoisoindolin-4-yl)amino)ethoxy)ethoxy)propanoyl)piperazin-1-yl)-9-ethyl-6,6-dimethyl-11-oxo-6,11-dihydro-5H-benzo[b]carbazole-3-carbonitrile. (SIAIS164012)

According to the procedures for the preparation of Compound Example 1, Alectinib Analogue A and intermediate LM (SIAIS151004) was used to prepare SIAIS164012 (yellow solid, 28 mg, 75%). $^1$H NMR (500 MHz, CDCl$_3$) δ 9.70 (s, 1H), 8.51-8.43 (m, 2H), 8.27 (s, 1H), 7.77 (s, 1H), 7.56 (d, J=8.1 Hz, 1H), 7.46-7.43 (m, 1H), 7.13 (s, 1H), 7.03-7.02 (m, 1H), 6.84 (dd, J=8.6, 5.0 Hz, 1H), 6.43 (s, 1H), 4.96 (dd, J=11.8, 5.4 Hz, 1H), 3.88-3.83 (m, 4H), 3.71-3.65 (m, 8H), 3.37 (s, 2H), 3.03-2.93 (m, 4H), 2.90-2.88 (m, 1H), 2.77-2.71 (m, 6H), 2.13 (s, 1H), 1.70 (dd, J=7.3, 2.1 Hz, 6H), 1.34

(t, J=7.5 Hz, 3H). HRMS (ESI) calcd for $C_{45}H_{48}N_7O_8$ [M+H]$^+$: 814.3559, found, 814.2643.

Compound Example 89: Synthesis of 8-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)-9-ethyl-6,6-dimethyl-11-oxo-6,11-dihydro-5H-benzo[b]carbazole-3-carbonitrile. (SIAIS164013)

According to the procedures for the preparation of Compound Example 1, Alectinib Analogue A and intermediate LM (SIAIS151005) was used to prepare SIAIS164013 (yellow solid, 28.8 mg, 73%). $^1$H NMR (500 MHz, CDCl$_3$) δ 10.76 (s, 1H), 9.09 (s, 1H), 8.47 (d, J=8.2 Hz, 1H), 8.27 (s, 1H), 7.75 (s, 1H), 7.51 (d, J=8.2 Hz, 1H), 7.41 (dd, J=10.1, 5.5 Hz, 1H), 7.13 (s, 1H), 7.01 (d, J=7.1 Hz, 1H), 6.81 (d, J=8.6 Hz, 1H), 6.42 (s, 1H), 5.03-4.87 (m, 1H), 3.83 (t, J=6.2 Hz, 4H), 3.70-3.57 (m, 12H), 3.35 (s, 2H), 3.02-2.84 (m, 5H), 2.83-2.65 (m, 6H), 2.12 (s, 1H), 1.88-1.65 (m, 6H), 1.37-1.26 (m, 3H). HRMS (ESI) calcd for $C_{47}H_{52}N_7O_9$ [M+H]$^+$: 858.3821, found, 858.2862.

Compound Example 90: Synthesis of 8-(4-(1-((2-(2,6-dioxopiperidin-3-yl)-1,3-dioxoisoindolin-4-yl)amino)-3,6,9,12-tetraoxapentadecan-15-oyl)piperazin-1-yl)-9-ethyl-6,6-dimethyl-11-oxo-6,11-dihydro-5H-benzo[b]carbazole-3-carbonitrile. (SIAIS164014)

According to the procedures for the preparation of Compound Example 1, Alectinib Analogue A and intermediate LM (SIAIS151006) was used to prepare SIAIS164014 (yellow solid, 16.8 mg, 40%). $^1$H NMR (500 MHz, CDCl$_3$) δ 10.04 (s, 1H), 8.62 (s, 1H), 8.49 (d, J=8.2 Hz, 1H), 8.28 (s, 1H), 7.75 (s, 1H), 7.54 (dd, J=8.2, 1.3 Hz, 1H), 7.48-7.41 (m, 1H), 7.14 (s, 1H), 7.04 (d, J=7.0 Hz, 1H), 6.84 (d, J=8.6 Hz, 1H), 6.43 (s, 1H), 4.94 (dd, J=12.2, 5.4 Hz, 1H), 3.82 (t, J=6.3 Hz, 4H), 3.73-3.57 (m, 16H), 3.38 (t, J=5.1 Hz, 2H), 3.02-2.94 (m, 4H), 2.91-2.88 (m, 1H), 2.83-2.67 (m, 6H), 2.18-2.08 (m, 1H), 1.73 (d, J=5.0 Hz, 6H), 1.33 (t, J=7.5 Hz, 3H). HRMS (ESI) calcd for $C_{49}H_{56}N_7O_{10}$ [M+H]$^+$: 902.4083, found, 902.4401.

Compound Example 91: Synthesis of 8-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)-9-ethyl-6,6-dimethyl-11-oxo-6,11-dihydro-5H-benzo[b]carbazole-3-carbonitrile. (SIAIS164015)

According to the procedures for the preparation of Compound Example 1, Alectinib Analogue A and intermediate LM (SIAIS151007) was used to prepare SIAIS164015 (yellow solid, 17.8 mg, 41%). $^1$H NMR (500 MHz, CDCl$_3$) δ 10.12 (s, 1H), 8.64 (s, 1H), 8.50 (d, J=8.2 Hz, 1H), 8.28 (s, 1H), 7.74 (d, J=4.2 Hz, 1H), 7.54 (d, J=8.1 Hz, 1H), 7.45 (dd, J=12.4, 5.4 Hz, 1H), 7.17 (s, 1H), 7.09-7.02 (m, 1H), 6.84 (d, J=8.5 Hz, 1H), 6.46 (s, 1H), 4.94 (dd, J=12.0, 5.6 Hz, 1H), 3.83 (d, J=3.2 Hz, 4H), 3.74-3.60 (m, 20H), 3.41 (d, J=4.8 Hz, 2H), 2.98 (s, 4H), 2.91-2.88 (m, 1H), 2.81-2.69 (m, 6H), 2.15-2.13 (m, 1H), 1.74-1.71 (m, 6H), 1.34 (t, J=7.4 Hz, 3H). HRMS (ESI) calcd for $C_{51}H_{60}N_7O_{11}$ [M+H]$^+$: 946.4345, found, 946.4364.

Compound Example 92: Synthesis of 8-(4-((2-(2,6-dioxopiperidin-3-yl)-1,3-dioxoisoindolin-4-yl)glycyl)piperazin-1-yl)-9-ethyl-6,6-dimethyl-11-oxo-6,11-dihydro-5H-benzo[b]carbazole-3-carbonitrile. (SIAIS164028)

According to the procedures for the preparation of Compound Example 1, Alectinib Analogue A and intermediate LM (SIAIS151025) was used to prepare SIAIS164028 (yellow solid, 17.2 mg, 53%). $^1$H NMR (500 MHz, DMSO) δ 12.71 (s, 1H), 11.11 (s, 1H), 8.32 (d, J=8.2 Hz, 1H), 8.08 (s, 1H), 8.00 (s, 1H), 7.65-7.60 (m, 2H), 7.42 (s, 1H), 7.15 (d, J=8.6 Hz, 1H), 7.13 (s, 1H), 7.09 (d, J=7.1 Hz, 1H), 5.08 (dd, J=12.9, 5.3 Hz, 1H), 4.28 (d, J=4.4 Hz, 2H), 3.74 (s, 2H), 3.70 (s, 2H), 3.05 (s, 2H), 3.01 (s, 2H), 3.05-2.87 (m, 1H), 2.78 (q, J=7.5 Hz, 2H), 2.63 (s, 1H), 2.59-2.54 (m, 1H), 2.07-2.04 (m, 1H), 1.75 (s, 6H), 1.30 (t, J=7.5 Hz, 3H). HRMS (ESI) calcd for $C_{40}H_{38}N_7O_6$ [M+H]$^+$: 712.2878, found, 712.2993.

Compound Example 93: Synthesis of 8-(4-(3-((2-(2,6-dioxopiperidin-3-yl)-1,3-dioxoisoindolin-4-yl)amino)propanoyl)piperazin-1-yl)-9-ethyl-6,6-dimethyl-11-oxo-6,11-dihydro-5H-benzo[b]carbazole-3-carbonitrile. (SIAIS164029)

According to the procedures for the preparation of Compound Example 1, Alectinib Analogue A and intermediate LM (SIAIS151026) was used to prepare SIAIS164029 (yellow solid, 16.8 mg, 50%). $^1$H NMR (500 MHz, DMSO) δ 12.70 (s, 1H), 11.10 (s, 1H), 8.32 (d, J=8.1 Hz, 1H), 8.06 (s, 1H), 8.00 (s, 1H), 7.61 (t, J=7.5 Hz, 2H), 7.38 (s, 1H), 7.18 (d, J=8.6 Hz, 1H), 7.04 (d, J=7.0 Hz, 1H), 6.82 (t, J=6.3 Hz, 1H), 5.05 (dd, J=12.7, 5.4 Hz, 1H), 3.68 (s, 2H), 3.63 (s, 2H), 3.61-3.56 (m, 2H), 2.96-2.94 (m, 4H), 2.92-2.83 (m, 1H), 2.78-2.71 (m, 4H), 2.65-2.52 (m, 2H), 2.03-2.01 (m, 1H), 1.74 (s, 6H), 1.28 (t, J=7.5 Hz, 3H). HRMS (ESI) calcd for $C_{41}H_{40}N_7O_6$ [M+H]$^+$: 726.3035, found, 726.3166.

Compound Example 94: Synthesis of 8-(4-(4-((2-(2,6-dioxopiperidin-3-yl)-1,3-dioxoisoindolin-4-yl)amino)butanoyl)piperazin-1-yl)-9-ethyl-6,6-dimethyl-11-oxo-6,11-dihydro-5H-benzo[b]carbazole-3-carbonitrile. (SIAIS164024)

According to the procedures for the preparation of Compound Example 1, Alectinib Analogue A and intermediate LM (SIAIS151019) was used to prepare SIAIS164024 (yellow solid, 23.6 mg, 69%). $^1$H NMR (500 MHz, CDCl$_3$) δ 9.09 (s, 1H), 8.53 (d, J=8.2 Hz, 1H), 8.30 (s, 1H), 8.04 (s, 1H), 7.77 (s, 1H), 7.58 (dd, J=8.2, 1.3 Hz, 1H), 7.51 (dd, J=8.5, 7.2 Hz, 1H), 7.14 (s, 1H), 7.10 (d, J=7.0 Hz, 1H), 6.99 (d, J=8.6 Hz, 1H), 6.34 (s, 1H), 4.93 (dd, J=12.4, 5.4 Hz, 1H), 3.85 (s, 2H), 3.66 (s, 2H), 3.43 (s, 2H), 2.99 (d, J=4.5 Hz, 4H), 2.92-2.89 (m, 1H), 2.83-2.73 (m, 4H), 2.53 (t, J=6.9 Hz, 2H), 2.18-2.11 (m, 1H), 2.10-2.03 (m, 2H), 1.76 (s, 6H), 1.35 (t, J=7.5 Hz, 3H). HRMS (ESI) calcd for $C_{42}H_{42}N_7O_6$ [M+H]$^+$: 740.3191, found, 740.3471.

Compound Example 95: Synthesis of 8-(4-(5-((2-(2,6-dioxopiperidin-3-yl)-1,3-dioxoisoindolin-4-yl)amino)pentanoyl)piperazin-1-yl)-9-ethyl-6,6-dimethyl-11-oxo-6,11-dihydro-5H-benzo[b]carbazole-3-carbonitrile. (SIAIS164025)

According to the procedures for the preparation of Compound Example 1, Alectinib Analogue A and intermediate LM (SIAIS151020) was used to prepare SIAIS164025 (yellow solid, 21 mg, 61%). $^1$H NMR (500 MHz, CDCl$_3$) δ 9.49 (s, 1H), 8.52 (d, J=8.2 Hz, 1H), 8.30 (s, 1H), 8.09 (s, 1H), 7.77 (d, J=0.5 Hz, 1H), 7.56 (dd, J=8.2, 1.3 Hz, 1H), 7.49 (dd, J=8.5, 7.1 Hz, 1H), 7.16 (s, 1H), 7.09 (d, J=6.9 Hz, 1H), 6.89 (d, J=8.5 Hz, 1H), 6.25 (s, 1H), 4.90 (dd, J=12.4, 5.4 Hz, 1H), 3.86 (s, 2H), 3.69 (s, 2H), 3.32 (t, J=6.5 Hz, 2H), 3.07-2.95 (m, 4H), 2.89 (d, J=13.2 Hz, 1H), 2.83-2.71 (m, 4H), 2.49 (t, J=7.1 Hz, 2H), 2.16-2.12 (m, 1H), 1.86-1.82 (m, 2H), 1.78-1.75 (m, 8H), 1.35 (t, J=7.5 Hz, 3H). HRMS (ESI) calcd for C$_{43}$H$_{44}$N$_7$O$_6$ [M+H]$^+$: 754.3348, found, 754.3630.

Compound Example 96: Synthesis of 8-(4-(6-((2-(2,6-dioxopiperidin-3-yl)-1,3-dioxoisoindolin-4-yl)amino)hexanoyl)piperazin-1-yl)-9-ethyl-6,6-dimethyl-11-oxo-6,11-dihydro-5H-benzo[b]carbazole-3-carbonitrile. (SIAIS164026)

According to the procedures for the preparation of Compound Example 1, Alectinib Analogue A and intermediate LM (SIAIS151027) was used to prepare SIAIS164026 (yellow solid, 20.4 mg, 58%). $^1$H NMR (500 MHz, CDCl$_3$) δ 9.22 (s, 1H), 8.54 (d, J=8.2 Hz, 1H), 8.31 (s, 1H), 8.05 (s, 1H), 7.77 (s, 1H), 7.58 (dd, J=8.2, 1.3 Hz, 1H), 7.49 (dd, J=8.5, 7.1 Hz, 1H), 7.16 (s, 1H), 7.09 (d, J=6.9 Hz, 1H), 6.88 (d, J=8.5 Hz, 1H), 6.23 (s, 1H), 4.92 (dd, J=12.3, 5.4 Hz, 1H), 3.85 (s, 2H), 3.69 (s, 2H), 3.29 (t, J=6.8 Hz, 2H), 3.04-2.97 (m, 4H), 2.912-2.89 (m, 1H), 2.82-2.73 (m, 4H), 2.45 (t, J=7.5 Hz, 2H), 2.18-2.11 (m, 1H), 1.78-1.71 (m, 10H), 1.53-1.52 (m, 2H), 1.36 (t, J=7.5 Hz, 3H). HRMS (ESI) calcd for C$_{44}$H$_{46}$N$_7$O$_6$ [M+H]$^+$: 768.3504, found, 768.3785.

Compound Example 97: Synthesis of -(4-(7-((2-(2,6-dioxopiperidin-3-yl)-1,3-dioxoisoindolin-4-yl)amino)heptanoyl)piperazin-1-yl)-9-ethyl-6,6-dimethyl-11-oxo-6,11-dihydro-5H-benzo[b]carbazole-3-carbonitrile. (SIAIS164030)

According to the procedures for the preparation of Compound Example 1, Alectinib Analogue A and intermediate LM (SIAIS151086) was used to prepare SIAIS164030 (yellow solid, 19.4 mg, 54%). $^1$H NMR (500 MHz, CDCl$_3$) δ 10.26 (s, 1H), 8.51 (d, J=8.2 Hz, 1H), 8.30 (s, 2H), 7.76 (d, J=0.5 Hz, 1H), 7.55 (dd, J=8.2, 1.3 Hz, 1H), 7.47 (dd, J=8.5, 7.1 Hz, 1H), 7.16 (s, 1H), 7.06 (t, J=5.1 Hz, 1H), 6.86 (d, J=8.5 Hz, 1H), 6.21 (s, 1H), 4.93 (dd, J=12.2, 5.5 Hz, 1H), 3.88 (s, 2H), 3.72 (s, 2H), 3.25 (t, J=7.0 Hz, 2H), 3.02 (dd, J=9.9, 4.8 Hz, 4H), 2.91-2.88 (m, 1H), 2.85-2.70 (m, 4H), 2.46 (t, J=7.5 Hz, 2H), 2.19-2.10 (m, 1H), 1.77-1.70 (m, 8H), 1.69-1.63 (m, 2H), 1.53-1.39 (m, 4H), 1.33 (t, J=7.5 Hz, 3H). HRMS (ESI) calcd for C$_{45}$H$_{48}$N$_7$O$_6$ [M+H]$^+$: 782.3661, found, 782.3818.

Compound Example 98: Synthesis of (2S,4R)-1-((S)-2-(2-(2-(2-(4-(3-cyano-9-ethyl-6,6-dimethyl-11-oxo-6,11-dihydro-5H-benzo[b]carbazol-8-yl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide. (SIAIS164040)

According to the procedures for the preparation of Compound Example 1, Alectinib Analogue A and intermediate LM (SIAIS151010) was used to prepare SIAIS164040 (white solid, 29.7 mg, 66%). $^1$H NMR (500 MHz, CDCl$_3$) δ 10.26 (s, 1H), 8.94 (s, 1H), 8.51 (d, J=8.2 Hz, 1H), 8.29 (s, 1H), 7.78 (s, 1H), 7.56 (dd, J=8.2, 1.3 Hz, 1H), 7.41-7.31 (m, 5H), 7.16 (s, 1H), 4.72 (t, J=8.1 Hz, 1H), 4.61-4.51 (m, 3H), 4.36 (dd, J=15.2, 5.4 Hz, 1H), 4.28 (s, 2H), 4.14 (d, J=11.7 Hz, 1H), 4.11-4.00 (m, 2H), 3.85-3.58 (m, 9H), 3.46-3.39 (m, 2H), 3.00 (s, 4H), 2.88 (s, 3H), 2.76 (q, J=7.6 Hz, 2H), 2.55 (s, 3H), 2.53-2.49 (m, 1H), 2.45 (t, J=8.2 Hz, 2H), 2.09-2.00 (m, 3H), 1.73 (d, J=3.4 Hz, 6H), 1.34 (t, J=7.5 Hz, 3H), 0.97 (s, 9H). HRMS (ESI) calcd for C$_{53}$H$_{63}$N$_8$O$_8$S [M+H]$^+$: 971.4484, found, 971.4483.

Compound Example 99: Synthesis of (2S,4R)-1-((S)-2-(3-(2-(3-(4-(3-cyano-9-ethyl-6,6-dimethyl-11-oxo-6,11-dihydro-5H-benzo[b]carbazol-8-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide. (SIAIS164036)

According to the procedures for the preparation of Compound Example 1, Alectinib Analogue A and intermediate LM (SIAIS151002) was used to prepare SIAIS164036 (white solid, 16.1 mg, 35%). $^1$H NMR (500 MHz, CDCl$_3$) δ 10.34 (s, 1H), 9.08 (s, 1H), 8.50 (d, J=8.2 Hz, 1H), 8.28 (s, 1H), 7.77 (s, 1H), 7.62 (s, 1H), 7.55 (dd, J=8.2, 1.3 Hz, 1H), 7.42 (d, J=8.2 Hz, 2H), 7.36 (d, J=8.2 Hz, 2H), 7.11 (s, 1H), 4.74 (t, J=8.2 Hz, 1H), 4.66 (dd, J=15.5, 6.8 Hz, 1H), 4.58 (s, 1H), 4.54 (d, J=8.4 Hz, 1H), 4.34 (dd, J=15.4, 5.2 Hz, 1H), 4.18 (d, J=11.4 Hz, 1H), 3.85-3.72 (m, 5H), 3.71-3.58 (m, 8H), 2.96-2.95 (m, 4H), 2.77-2.72 (m, 2H), 2.70 (t, J=6.3 Hz, 2H), 2.58 (s, 3H), 2.56-2.49 (m, 2H), 2.47-2.37 (m, 1H), 2.29-2.21 (m, 1H), 1.71 (d, J=3.1 Hz, 6H), 1.32 (t, J=7.5 Hz, 3H), 0.97 (s, 9H). HRMS (ESI) calcd for C$_{55}$H$_{67}$N$_8$O$_8$S [M+H]$^+$: 999.4797, found, 999.4847.

Compound Example 100: Synthesis of (2S,4R)-1-((S)-2-(tert-butyl)-16-(4-(3-cyano-9-ethyl-6,6-dimethyl-11-oxo-6,11-dihydro-5H-benzo[b]carbazol-8-yl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide. (SIAIS164037)

According to the procedures for the preparation of Compound Example 1, Alectinib Analogue A and intermediate LM (SIAIS151003) was used to prepare SIAIS164037 (white solid, 34.6 mg, 72%). $^1$H NMR (500 MHz, CDCl$_3$) δ 10.62 (s, 1H), 9.10 (s, 1H), 8.50 (d, J=8.2 Hz, 1H), 8.28 (s, 1H), 7.78 (s, 1H), 7.54 (dd, J=8.2, 1.3 Hz, 1H), 7.46 (d, J=6.2 Hz, 1H), 7.39 (d, J=8.2 Hz, 2H), 7.34 (d, J=8.2 Hz, 2H), 7.14 (s, 1H), 4.73 (t, J=8.3 Hz, 1H), 4.63 (dd, J=15.3, 6.8 Hz, 1H), 4.57-4.54 (m, 2H), 4.34 (dd, J=15.3, 5.1 Hz, 1H), 4.17 (d, J=11.4 Hz, 1H), 3.81-3.75 (m, 5H), 3.72-3.59 (m, 12H), 2.99-2.96 (m, 4H), 2.80-2.67 (m, 4H), 2.56 (s, 3H), 2.56-2.54 (m, 2H), 2.44-2.34 (m, 1H), 2.29-2.24 (m, 1H), 1.72 (d, J=2.7 Hz, 6H), 1.33 (t, J=7.5 Hz, 3H), 0.99 (s, 9H). HRMS (ESI) calcd for C$_{57}$H$_{71}$N$_8$O$_9$S [M+H]$^+$: 1043.5059, found, 1043.5097.

Compound Example 101: Synthesis of (2S,4R)-1-((S)-2-(tert-butyl)-19-(4-(3-cyano-9-ethyl-6,6-dimethyl-11-oxo-6,11-dihydro-5H-benzo[b]carbazol-8-yl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide. (SIAIS164038)

According to the procedures for the preparation of Compound Example 1, Alectinib Analogue A and intermediate LM (SIAIS151008) was used to prepare SIAIS164038 (white solid, 32.5 mg, 65%). $^1$H NMR (500 MHz, CDCl$_3$) δ 10.78 (s, 1H), 9.08 (s, 1H), 8.50 (d, J=8.2 Hz, 1H), 8.28 (s, 1H), 7.77 (s, 1H), 7.53 (dd, J=8.2, 1.3 Hz, 1H), 7.39-7.37 (m, 3H), 7.34 (d, J=8.2 Hz, 2H), 7.15 (s, 1H), 4.73 (t, J=8.0 Hz, 1H), 4.65-4.56 (m, 2H), 4.54 (d, J=8.3 Hz, 1H), 4.35 (dd, J=15.3, 5.2 Hz, 1H), 4.14 (d, J=11.4 Hz, 1H), 3.82-3.81 (m, 4H), 3.70-3.67 (m, 5H), 3.63-3.61 (m, 12H), 3.00-2.96 (m, 4H), 2.78-2.71 (m, 4H), 2.54 (s, 3H), 2.52 (s, 2H), 2.41-2.39 (m, 1H), 2.28-2.27 (m, 1H), 1.73 (s, 6H), 1.32 (t, J=7.5 Hz, 3H), 0.98 (s, 9H). HRMS (ESI) calcd for C$_{59}$H$_{75}$N$_8$O$_{10}$S [M+H]$^+$: 1087.5321, found, 1087.5342.

Compound Example 102: Synthesis of (2S,4R)-1-((S)-2-(tert-butyl)-22-(4-(3-cyano-9-ethyl-6,6-dimethyl-11-oxo-6,11-dihydro-5H-benzo[b]carbazol-8-yl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide. (SIAIS164039)

According to the procedures for the preparation of Compound Example 1, Alectinib Analogue A and intermediate LM (SIAIS151009) was used to prepare SIAIS164039 (white solid, 40.1 mg, 77%). $^1$H NMR (500 MHz, CDCl$_3$) δ 10.84 (s, 1H), 9.03 (s, 1H), 8.50 (d, J=8.2 Hz, 1H), 8.29 (s, 1H), 7.78 (s, 1H), 7.54 (dd, J=8.2, 1.3 Hz, 1H), 7.37 (q, J=8.2 Hz, 5H), 7.22 (d, J=7.6 Hz, 1H), 7.17 (s, 1H), 4.74 (t, J=7.8 Hz, 1H), 4.63-4.59 (m, 2H), 4.54 (d, J=8.4 Hz, 1H), 4.36 (dd, J=15.2, 5.1 Hz, 1H), 4.14 (d, J=11.2 Hz, 1H), 3.83 (s, 4H), 3.75-3.68 (m, 4H), 3.65-3.61 (m, 16H), 3.01 (s, 2H), 2.97 (s, 2H), 2.79-2.76 (m, 2H), 2.75-2.71 (m, 3H), 2.54 (s, 3H), 2.53-2.52 (m, 2H), 2.44-2.43 (m, 1H), 2.26-2.25 (m, 1H), 1.75 (d, J=4.9 Hz, 6H), 1.34 (t, J=7.5 Hz, 3H), 0.98 (s, 9H). HRMS (ESI) calcd for C$_{61}$H$_{79}$N$_8$O$_{11}$S [M+H]$^+$: 1131.5584, found, 1131.5582.

Compound Example 103: Synthesis of (2S,4R)-1-((S)-2-(4-(4-(3-cyano-9-ethyl-6,6-dimethyl-11-oxo-6,11-dihydro-5H-benzo[b]carbazol-8-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide. (SIAIS164093)

According to the procedures for the preparation of Compound Example 1, Alectinib Analogue A and intermediate LM (SIAIS074011) was used to prepare SIAIS164093 (white solid, 21.2 mg, 67%). $^1$H NMR (500 MHz, DMSO) δ 12.74 (s, 1H), 8.99 (s, 1H), 8.57 (t, J=6.0 Hz, 1H), 8.32 (d, J=8.2 Hz, 1H), 8.07 (s, 1H), 8.00 (s, 1H), 7.95 (d, J=9.3 Hz, 1H), 7.63-7.58 (m, 1H), 7.41 (q, J=8.2 Hz, 5H), 4.55 (d, J=9.4 Hz, 1H), 4.43 (dd, J=14.3, 6.9 Hz, 2H), 4.36 (s, 1H), 4.22 (dd, J=16.0, 5.5 Hz, 1H), 3.64 (s, 7H), 2.99 (s, 2H), 2.93 (s, 2H), 2.76 (q, J=7.4 Hz, 2H), 2.65-2.54 (m, 3H), 2.45-2.42 (m, 4H), 2.09-1.99 (m, 1H), 1.96-1.86 (m, 1H), 1.74 (s, 6H), 1.29 (t, J=7.5 Hz, 3H), 0.94 (s, 9H). HRMS (ESI) calcd for C$_{51}$H$_{59}$N$_8$O$_6$S [M+H]$^+$: 911.4273, found, 911.4539.

Compound Example 104: Synthesis of (2S,4R)-1-((S)-2-(5-(4-(3-cyano-9-ethyl-6,6-dimethyl-11-oxo-6,11-dihydro-5H-benzo[b]carbazol-8-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide. (SIAIS164094)

According to the procedures for the preparation of Compound Example 1, Alectinib Analogue A and intermediate LM (SIAIS074012) was used to prepare SIAIS164094 (white solid, 16.7 mg, 52%). $^1$H NMR (500 MHz, DMSO) δ 12.73 (s, 1H), 8.97 (s, 1H), 8.56 (t, J=5.9 Hz, 1H), 8.32 (d, J=8.2 Hz, 1H), 8.06 (s, 1H), 8.00 (s, 1H), 7.92 (d, J=9.5 Hz, 1H), 7.61 (d, J=8.2 Hz, 1H), 7.45-7.35 (m, 5H), 4.56 (d, J=9.3 Hz, 1H), 4.42 (dd, J=16.5, 8.2 Hz, 2H), 4.35 (s, 1H), 4.21 (dd, J=15.9, 5.4 Hz, 1H), 3.73-3.59 (m, 7H), 2.98 (s, 2H), 2.92 (s, 2H), 2.75 (q, J=7.4 Hz, 2H), 2.43 (s, 3H), 2.36 (t, J=7.4 Hz, 2H), 2.33-2.19 (m, 2H), 2.06-2.02 (m, 1H), 1.93-1.88 (m, 1H), 1.75-1.72 (m, 8H), 1.28 (t, J=7.5 Hz, 3H), 0.94 (s, 9H). HRMS (ESI) calcd for C$_{52}$H$_{61}$N$_8$O$_6$S [M+H]$^+$: 925.4429, found, 925.4685.

Compound Example 105: Synthesis of (2S,4R)-1-((S)-2-(6-(4-(3-cyano-9-ethyl-6,6-dimethyl-11-oxo-6,11-dihydro-5H-benzo[b]carbazol-8-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide. (SIAIS164095)

According to the procedures for the preparation of Compound Example 1, Alectinib Analogue A and intermediate LM (SIAIS074013) was used to prepare SIAIS164095 (white solid, 19.6 mg, 60%). $^1$H NMR (500 MHz, DMSO) δ 12.76 (s, 1H), 8.98 (s, 1H), 8.56 (t, J=5.8 Hz, 1H), 8.32 (d, J=8.1 Hz, 1H), 8.07 (s, 1H), 8.00 (s, 1H), 7.88 (d, J=9.3 Hz, 1H), 7.60 (d, J=8.1 Hz, 1H), 7.44-7.36 (m, 5H), 4.56 (d, J=9.5 Hz, 1H), 4.49-4.39 (m, 2H), 4.35 (s, 1H), 4.21 (dd, J=15.8, 5.4 Hz, 1H), 3.68-3.64 (m, 8H), 2.98 (s, 2H), 2.92 (s, 2H), 2.75 (q, J=7.4 Hz, 2H), 2.44 (s, 3H), 2.37 (s, 2H), 2.34-2.28 (m, 1H), 2.20-2.12 (m, 1H), 2.07-2.00 (m, 1H), 1.94-1.87 (m, 1H), 1.75 (s, 6H), 1.53 (d, J=6.8 Hz, 4H), 1.28 (t, J=7.5 Hz, 3H), 0.94 (s, 9H). HRMS (ESI) calcd for C$_{53}$H$_{63}$N$_8$O$_6$S [M+H]$^+$: 939.4586, found, 939.4864.

Compound Example 106: Synthesis of (2S,4R)-1-((S)-2-(7-(4-(3-cyano-9-ethyl-6,6-dimethyl-11-oxo-6,11-dihydro-5H-benzo[b]carbazol-8-yl)piperazin-1-yl)-7-oxoheptanamido)-3,3-dimethylbutanoyl)-4-hydroxy-N-(4-(4-methylthiazol-5-yl)benzyl)pyrrolidine-2-carboxamide. (SIAIS164096)

According to the procedures for the preparation of Compound Example 1, Alectinib Analogue A and intermediate LM (SIAIS074014) was used to prepare SIAIS164096 (white solid, 21.6 mg, 66%). $^1$H NMR (500 MHz, DMSO) δ 12.74 (s, 1H), 8.98 (s, 1H), 8.56 (t, J=5.9 Hz, 1H), 8.32 (d, J=8.1 Hz, 1H), 8.06 (s, 1H), 8.00 (s, 1H), 7.86 (d, J=9.3 Hz, 1H), 7.61 (dd, J=8.1, 1.2 Hz, 1H), 7.44-7.36 (m, 5H), 4.55 (d, J=9.4 Hz, 1H), 4.45-4.41 (m, 2H), 4.35 (s, 1H), 4.21 (dd, J=15.9, 5.5 Hz, 1H), 3.69-3.62 (m, 7H), 2.97 (s, 2H), 2.93 (s, 2H), 2.75 (q, J=7.5 Hz, 2H), 2.44 (s, 3H), 2.37-2.32 (m, 2H), 2.31-2.24 (m, 1H), 2.18-2.11 (m, 1H), 2.06-2.00 (m, 1H), 1.94-1.87 (m, 1H), 1.75 (s, 6H), 1.55-1.49 (m, 4H), 1.32-1.25 (m, 5H), 0.93 (d, J=11.4 Hz, 9H). HRMS (ESI) calcd for C$_{54}$H$_{65}$N$_8$O$_6$S [M+H]$^+$: 953.4742, found, 953.4991.

Compound Example 107: Synthesis of (2S,4R)-1-((S)-2-(8-(4-(3-cyano-9-ethyl-6,6-dimethyl-11-oxo-6,11-dihydro-5H-benzo[b]carbazol-8-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide. (SIAIS164097)

According to the procedures for the preparation of Compound Example 1, Alectinib Analogue A and intermediate LM (SIAIS074015) was used to prepare SIAIS164097 (white solid, 22.6 mg, 68%). $^1$H NMR (500 MHz, DMSO) δ 12.76 (s, 1H), 8.99 (s, 1H), 8.56 (t, J=6.0 Hz, 1H), 8.32 (d, J=8.1 Hz, 1H), 8.06 (s, 1H), 8.00 (s, 1H), 7.85 (d, J=9.3 Hz, 1H), 7.60 (d, J=8.2 Hz, 1H), 7.45-7.36 (m, 5H), 4.55 (d, J=9.4 Hz, 1H), 4.45-4.41 (m, 2H), 4.35 (s, 1H), 4.21 (dd, J=16.0, 5.3 Hz, 1H), 3.65-3.63 (m, 7H), 2.97 (s, 2H), 2.93 (s, 2H), 2.75 (q, J=7.5 Hz, 2H), 2.44 (s, 3H), 2.38-2.33 (m, 2H), 2.30-2.24 (m, 1H), 2.16-2.10 (m, 1H), 2.06-1.99 (m, 1H), 1.94-1.86 (m, 1H), 1.75 (s, 6H), 1.52-1.47 (m, 4H), 1.30-1.27 (m, 7H), 0.93 (s, 9H). HRMS (ESI) calcd for $C_{55}H_{67}N_8O_6S$ [M+H]$^+$: 967.4899, found, 967.5164.

Compound Example 108: Synthesis of (2S,4R)-1-((S)-2-(9-(4-(3-cyano-9-ethyl-6,6-dimethyl-11-oxo-6,11-dihydro-5H-benzo[b]carbazol-8-yl)piperazin-1-yl)-9-oxononanamido)-3,3-dimethylbutanoyl)-4-hydroxy-N-(4-(4-methylthiazol-5-yl)benzyl)pyrrolidine-2-carboxamide. (SIAIS164098)

According to the procedures for the preparation of Compound Example 1, Alectinib Analogue A and intermediate LM (SIAIS074016) was used to prepare SIAIS164098 (white solid, 21.8 mg, 64%). $^1$H NMR (500 MHz, DMSO) δ 12.74 (s, 1H), 8.99 (s, 1H), 8.55 (t, J=6.0 Hz, 1H), 8.32 (d, J=8.1 Hz, 1H), 8.06 (s, 1H), 8.00 (s, 1H), 7.84 (d, J=9.3 Hz, 1H), 7.61 (dd, J=8.1, 1.2 Hz, 1H), 7.44-7.36 (m, 5H), 4.55 (d, J=9.4 Hz, 1H), 4.45-4.41 (m, 2H), 4.35 (s, 1H), 4.21 (dd, J=16.0, 5.6 Hz, 1H), 3.66-3.63 (m, 7H), 2.97 (s, 2H), 2.92 (s, 2H), 2.75 (q, J=7.5 Hz, 2H), 2.44 (s, 3H), 2.35 (t, J=7.5 Hz, 2H), 2.31-2.23 (m, 1H), 2.16-2.08 (m, 1H), 2.05-2.00 (m, 1H), 1.92-1.87 (m, 1H), 1.75 (s, 6H), 1.52-1.46 (m, 4H), 1.30-1.27 (m, 9H), 0.92 (s, 9H). HRMS (ESI) calcd for $C_{56}H_{69}N_8O_6S$ [M+H]$^+$: 981.5055, found, 981.5349.

Compound Example 109: Synthesis of (2S,4R)-1-((S)-2-(10-(4-(3-cyano-9-ethyl-6,6-dimethyl-11-oxo-6,11-dihydro-5H-benzo[b]carbazol-8-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide. (SIAIS164099)

According to the procedures for the preparation of Compound Example 1, Alectinib Analogue A and intermediate LM (SIAIS074019) was used to prepare SIAIS164099 (white solid, 20.1 mg, 59%). $^1$H NMR (500 MHz, DMSO) δ 12.77 (s, 1H), 8.99 (s, 1H), 8.56 (t, J=6.0 Hz, 1H), 8.32 (d, J=8.1 Hz, 1H), 8.06 (s, 1H), 8.00 (s, 1H), 7.84 (d, J=9.4 Hz, 1H), 7.60 (dd, J=8.1, 1.2 Hz, 1H), 7.42-7.37 (m, 5H), 4.54 (d, J=9.4 Hz, 1H), 4.45-4.41 (m, 2H), 4.35 (s, 1H), 4.21 (dd, J=15.9, 5.4 Hz, 1H), 3.69-3.63 (m, 7H), 2.97 (s, 2H), 2.92 (s, 2H), 2.75 (q, J=7.5 Hz, 2H), 2.44 (s, 3H), 2.35 (t, J=7.4 Hz, 2H), 2.30-2.22 (m, 1H), 2.11 (dt, J=14.4, 6.5 Hz, 1H), 2.06-1.99 (m, 1H), 1.93-1.87 (m, 1H), 1.75 (s, 6H), 1.53-1.46 (m, 4H), 1.30-1.27 (m, 11H), 0.92 (s, 9H). HRMS (ESI) calcd for $C_{57}H_{71}N_8O_6S$ [M+H]$^+$: 995.5212, found, 995.5518.

Compound Example 110: Synthesis of 4-(4-(3-cyano-9-ethyl-6,6-dimethyl-11-oxo-6,11-dihydro-5H-benzo[b]carbazol-8-yl)piperazin-1-yl)-N-(2-((2-(2,6-dioxopiperidin-3-yl)-1,3-dioxoisoindolin-4-yl)amino)ethyl)-4-oxobutanamide. (SIAIS164154)

According to the procedures for the preparation of Compound Example 1, Alectinib Analogue A and intermediate LM (SIAIS164119) was used to prepare SIAIS164154 (yellow solid, 9 mg, 49%). $^1$H NMR (500 MHz, DMSO) δ 12.73 (s, 1H), 11.09 (s, 1H), 8.32 (d, J=8.2 Hz, 1H), 8.11 (t, J=5.3 Hz, 1H), 8.07 (s, 1H), 8.00 (s, 1H), 7.60 (dd, J=12.1, 5.6 Hz, 2H), 7.39 (s, 1H), 7.20 (d, J=8.6 Hz, 1H), 7.03 (d, J=7.0 Hz, 1H), 6.75 (s, 1H), 5.05 (dd, J=12.8, 5.4 Hz, 1H), 3.63 (s, 4H), 3.29-3.21 (m, 2H), 2.98 (s, 2H), 2.92 (s, 2H), 2.88-2.85 (m, 1H), 2.75 (q, J=7.4 Hz, 2H), 2.66-2.51 (m, 6H), 2.35 (t, J=7.0 Hz, 2H), 2.05-1.98 (m, 1H), 1.75 (s, 6H), 1.29 (t, J=7.5 Hz, 3H). HRMS (ESI) calcd for $C_{44}H_{45}N_8O_7$ [M+H]$^+$: 797.3406, found, 797.1339.

Compound Example 111: Synthesis of (2S,4R)-1-((S)-2-(4-(4-(4-(3-cyano-9-ethyl-6,6-dimethyl-11-oxo-6,11-dihydro-5H-benzo[b]carbazol-8-yl)piperazin-1-yl)-4-oxobutyl)-1H-1,2,3-triazol-1-yl)butanamido)-3,3-dimethylbutanoyl)-4-hydroxy-N-(4-(4-methylthiazol-5-yl)benzyl)pyrrolidine-2-carboxamide. (SIAIS164155)

According to the procedures for the preparation of Compound Example 1, Alectinib Analogue A and intermediate LM (SIAIS164128) was used to prepare SIAIS164155 (white solid, 9 mg, 38%). $^1$H NMR (500 MHz, DMSO) δ 12.82 (s, 1H), 9.01 (s, 1H), 8.56 (t, J=6.0 Hz, 1H), 8.32 (d, J=8.1 Hz, 1H), 8.06 (s, 1H), 7.99 (d, J=10.0 Hz, 2H), 7.90 (s, 1H), 7.60 (dd, J=8.1, 1.2 Hz, 1H), 7.46-7.34 (m, 6H), 4.53 (d, J=9.3 Hz, 1H), 4.46-4.39 (m, 2H), 4.35 (s, 1H), 4.30 (t, J=7.1 Hz, 2H), 4.21 (dd, J=15.8, 5.4 Hz, 1H), 2.97 (s, 2H), 2.93 (s, 2H), 2.75 (q, J=7.4 Hz, 2H), 2.69-2.64 (m, 3H), 2.49-2.34 (m, 7H), 2.29-2.23 (m, 1H), 2.21-2.13 (m, 1H), 2.11-1.94 (m, 4H), 1.94-1.79 (m, 4H), 1.75 (s, 7H), 1.28 (t, J=7.5 Hz, 3H), 0.93 (s, 9H). HRMS (ESI) calcd for $C_{57}H_{68}N_{11}O_6S$ [M+H]$^+$: 1034.5069, found, 1034.2256.

Compound Example 112: Synthesis of N-(1-(3-cyano-9-ethyl-6,6-dimethyl-11-oxo-6,11-dihydro-5H-benzo[b]carbazol-8-yl)piperidin-4-yl)-3-(2-(2-((2-(2,6-dioxopiperidin-3-yl)-1,3-dioxoisoindolin-4-yl)amino)ethoxy)ethoxy)propenamide. (SIAIS219023)

According to the procedures for the preparation of Compound Example 1, Alectinib Analogue B and intermediate LM (SIAIS151004) was used to prepare SIAIS219023 (yellow solid, 9.8 mg, 49%). $^1$H NMR (500 MHz, MeOD) δ 8.41 (d, J=8.1 Hz, 1H), 8.24 (s, 1H), 7.88 (s, 1H), 7.60-7.51 (m, 3H), 7.08 (d, J=8.5 Hz, 1H), 7.03 (d, J=7.2 Hz, 1H), 5.06 (dd, J=12.5, 5.5 Hz, 1H), 4.14 (d, J=17.1 Hz, 1H), 3.96 (t, J=11.3 Hz, 1H), 3.80-3.73 (m, 2H), 3.69-3.61 (m, 6H), 3.50 (t, J=5.2 Hz, 2H), 3.20 (d, J=27.6 Hz, 4H), 2.89-2.69 (m, 6H), 2.48 (t, J=6.1 Hz, 2H), 2.10 (d, J=4.6 Hz, 2H), 1.88-1.75 (m, 8H), 1.37-1.29 (m, 2H). HRMS (ESI) calcd for $C_{46}H_{50}N_7O_8$ [M+H]$^+$: 828.3715, found, 828.3762.

Compound Example 113: Synthesis of N-(1-(3-cyano-9-ethyl-6,6-dimethyl-11-oxo-6,11-dihydro-5H-benzo[b]carbazol-8-yl)piperidin-4-yl)-1-((2-(2,6-dioxopiperidin-3-yl)-1,3-dioxoisoindolin-4-yl)amino)-3,6,9,12-tetraoxapentadecan-15-amide. (SIAIS219024)

According to the procedures for the preparation of Compound Example 1, Alectinib Analogue B and intermediate LM (SIAIS151006) was used to prepare SIAIS219024 (yellow solid, 11.2 mg, 51%). $^1$H NMR (500 MHz, MeOD) δ 8.41 (d, J=8.1 Hz, 1H), 8.33 (s, 1H), 7.88 (s, 2H), 7.58 (dd, J=8.2, 1.4 Hz, 1H), 7.50 (dd, J=8.5, 7.1 Hz, 1H), 7.02 (dd, J=14.9, 7.8 Hz, 2H), 5.06 (dd, J=12.6, 5.5 Hz, 1H), 4.10 (t, J=10.9 Hz, 1H), 3.76 (t, J=6.1 Hz, 2H), 3.69-3.54 (m, 14H), 3.47-3.41 (m, 2H), 3.17 (s, 4H), 2.94-2.83 (m, 3H), 2.77-2.67 (m, 2H), 2.49 (t, J=6.0 Hz, 2H), 2.24 (d, J=11.8 Hz, 2H), 2.14-2.00 (m, 3H), 1.83 (s, 4H), 1.42 (t, J=7.5 Hz, 3H), 1.35-1.24 (m, 2H). HRMS (ESI) calcd for $C_{50}H_{58}N_7O_{10}$ $[M+H]^+$: 916.4240, found, 916.4319.

Compound Example 114: Synthesis of N-(1-(3-cyano-9-ethyl-6,6-dimethyl-11-oxo-6,11-dihydro-5H-benzo[b]carbazol-8-yl)piperidin-4-yl)-2-((2-(2,6-dioxopiperidin-3-yl)-1,3-dioxoisoindolin-4-yl)amino)acetamide. (SIAIS219001)

According to the procedures for the preparation of Compound Example 1, Alectinib Analogue B and intermediate LM (SIAIS151025) was used to prepare SIAIS219001 (yellow solid, 7.4 mg, 42%). $^1$H NMR (500 MHz, DMSO) δ 12.71 (s, 1H), 11.11 (s, 1H), 8.31 (d, J=7.9 Hz, 1H), 8.04 (s, 1H), 7.99 (s, 1H), 7.90 (d, J=7.7 Hz, 1H), 7.63-7.59 (m, 2H), 7.37 (s, 1H), 7.08 (d, J=6.7 Hz, 1H), 6.97-6.93 (m, 1H), 6.89 (d, J=8.7 Hz, 1H), 5.07 (dd, J=12.8, 5.4 Hz, 1H), 3.97 (s, 4H), 3.82 (s, 2H), 2.86-2.84 (m, 3H), 2.70 (d, J=7.4 Hz, 4H), 1.90 (s, 2H), 1.75 (s, 6H), 1.66 (s, 2H), 1.27 (t, J=7.4 Hz, 3H). HRMS (ESI) calcd for $C_{41}H_{40}N_7O_6$ $[M+H]^+$: 726.3035, found, 726.3045.

Compound Example 115: Synthesis of N-(1-(3-cyano-9-ethyl-6,6-dimethyl-11-oxo-6,11-dihydro-5H-benzo[b]carbazol-8-yl)piperidin-4-yl)-4-((2-(2,6-dioxopiperidin-3-yl)-1,3-dioxoisoindolin-4-yl)amino)butanamide. (SIAIS219010)

According to the procedures for the preparation of Compound Example 1, Alectinib Analogue B and intermediate LM (SIAIS151019) was used to prepare SIAIS219010 (yellow solid, 7.2 mg, 40%). $^1$H NMR (500 MHz, DMSO) δ 12.70 (s, 1H), 11.10 (s, 1H), 8.32 (d, J=8.1 Hz, 1H), 8.03 (s, 1H), 8.00 (s, 1H), 7.90 (d, J=7.7 Hz, 1H), 7.63-7.58 (m, 2H), 7.36 (s, 1H), 7.14 (d, J=8.6 Hz, 1H), 7.03 (d, J=7.0 Hz, 1H), 6.64 (t, J=6.1 Hz, 1H), 5.06 (dd, J=12.7, 5.4 Hz, 1H), 3.77 (s, 1H), 3.15 (d, J=12.3 Hz, 2H), 2.88-2.83 (m, 3H), 2.69 (q, J=7.4 Hz, 2H), 2.63-2.58 (m, 2H), 2.19 (t, J=7.2 Hz, 2H), 2.05-2.00 (m, 1H), 1.89 (d, J=10.3 Hz, 2H), 1.85-1.79 (m, 2H), 1.75 (s, 6H), 1.62-1.53 (m, 2H), 1.28-1.24 (m, 5H). HRMS (ESI) calcd for $C_{43}H_{44}N_7O_6$ $[M+H]^+$: 754.3348, found, 754.3170.

Compound Example 116: Synthesis of N-(1-(3-cyano-9-ethyl-6,6-dimethyl-11-oxo-6,11-dihydro-5H-benzo[b]carbazol-8-yl)piperidin-4-yl)-6-((2-(2,6-dioxopiperidin-3-yl)-1,3-dioxoisoindolin-4-yl)amino)hexanamide. (SIAIS219011)

According to the procedures for the preparation of Compound Example 1, Alectinib Analogue B and intermediate LM (SIAIS151027) was used to prepare SIAIS219011 (yellow solid, 8.8 mg, 47%). $^1$H NMR (500 MHz, DMSO) δ 12.72 (s, 1H), 11.13 (s, 1H), 8.34 (d, J=8.1 Hz, 1H), 8.04 (s, 1H), 8.02 (s, 1H), 7.93 (d, J=7.7 Hz, 1H), 7.65-7.59 (m, 2H), 7.37 (s, 1H), 7.15 (d, J=8.6 Hz, 1H), 7.06 (d, J=7.0 Hz, 1H), 6.65 (t, J=6.1 Hz, 1H), 5.08 (dd, J=12.7, 5.4 Hz, 1H), 3.78 (s, 1H), 3.17 (d, J=12.3 Hz, 2H), 2.88-2.85 (m, 3H), 2.70 (q, J=7.4 Hz, 2H), 2.61-2.59 (m, 2H), 2.21 (t, J=7.2 Hz, 2H), 2.06-2.01 (m, 4H), 1.90 (d, J=10.3 Hz, 2H), 1.86-1.79 (m, 2H), 1.77 (s, 6H), 1.62-1.54 (m, 2H), 1.29-1.27 (m, 6H). HRMS (ESI) calcd for $C_{45}H_{48}N_7O_6$ $[M+H]^+$: 782.3661, found, 782.3465.

Compound Example 117: Synthesis of N1-(1-(3-cyano-9-ethyl-6,6-dimethyl-11-oxo-6,11-dihydro-5H-benzo[b]carbazol-8-yl)piperidin-4-yl)-N6-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)adipamide. (SIAIS219020)

According to the procedures for the preparation of Compound Example 1, Alectinib Analogue B and intermediate LM (SIAIS074013) was used to prepare SIAIS219020 (white solid, 9.9 mg, 43%). $^1$H NMR (500 MHz, MeOD) δ 9.81 (s, 1H), 8.43-8.39 (m, 1H), 8.32 (s, 1H), 7.89 (s, 1H), 7.88 (s, 1H), 7.58-7.49 (m, 5H), 4.64 (s, 1H), 4.60-4.49 (m, 3H), 4.41 (d, J=15.7 Hz, 1H), 4.08 (s, 1H), 3.92 (d, J=11.1 Hz, 1H), 3.81 (dd, J=11.0, 3.9 Hz, 1H), 3.61 (d, J=9.8 Hz, 2H), 3.54 (s, 2H), 2.94-2.86 (m, 2H), 2.58 (s, 3H), 2.39-2.19 (m, 8H), 2.08-2.05 (m, 2H), 1.85 (s, 6H), 1.67-1.66 (m, 4H), 1.41 (t, J=7.5 Hz, 3H), 1.05 (s, 9H). HRMS (ESI) calcd for $C_{54}H_{65}N_8O_6S$ $[M+H]^+$: 953.4742, found, 953.4074.

Compound Example 118: Synthesis of N1-(1-(3-cyano-9-ethyl-6,6-dimethyl-11-oxo-6,11-dihydro-5H-benzo[b]carbazol-8-yl)piperidin-4-yl)-N10-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide. (SIAIS219021)

According to the procedures for the preparation of Compound Example 1, Alectinib Analogue B and intermediate LM (SIAIS074019) was used to prepare SIAIS219021 (white solid, 11.2 mg, 46%). $^1$H NMR (500 MHz, MeOD) δ 9.60 (s, 1H), 8.41 (d, J=8.2 Hz, 1H), 8.26 (s, 1H), 7.88 (s, 1H), 7.65 (s, 1H), 7.57-7.47 (m, 5H), 4.64 (s, 1H), 4.59-4.52 (m, 2H), 4.50 (s, 1H), 4.39 (d, J=15.7 Hz, 1H), 3.98 (s, 1H), 3.91 (d, J=11.1 Hz, 1H), 3.80 (dd, J=11.0, 3.9 Hz, 1H), 3.45-3.44 (m, 2H), 3.29-3.22 (m, 2H), 2.86 (q, J=7.4 Hz, 2H), 2.55 (d, J=2.9 Hz, 3H), 2.29-2.21 (m, 5H), 2.14-2.06 (m, 3H), 1.89 (d, J=10.8 Hz, 2H), 1.83 (s, 6H), 1.63 (d, J=6.4 Hz, 4H), 1.39-1.34 (m, 12H), 1.04 (s, 9H). HRMS (ESI) calcd for $C_{58}H_{73}N_8O_6S$ $[M+H]^+$: 1009.5368, found, 1009.4649.

Compound Example 119: Synthesis of 8-(4-(4-(3-(2-(2-((2-(2,6-dioxopiperidin-3-yl)-1,3-dioxoisoindolin-4-yl)amino)ethoxy)ethoxy)propanoyl)piperazin-1-yl)piperidin-1-yl)-9-ethyl-6,6-dimethyl-11-oxo-6,11-dihydro-5H-benzo[b]carbazole-3-carbonitrile. (SIAIS219018)

According to the procedures for the preparation of Compound Example 1, Alectinib Analogue C and intermediate LM (SIAIS151004) was used to prepare SIAIS219018 (yellow solid, 8.8 mg, 47%). $^1$H NMR (500 MHz, DMSO) δ 12.81 (s, 1H), 11.10 (s, 1H), 8.32 (d, J=8.2 Hz, 1H), 8.06 (d, J=3.0 Hz, 1H), 8.01 (s, 1H), 7.62-7.58 (m, 2H), 7.35 (s, 1H), 7.16 (d, J=8.5 Hz, 1H), 7.05 (d, J=6.9 Hz, 1H), 6.61 (s, 1H), 5.06 (dd, J=12.7, 5.4 Hz, 1H), 4.51 (d, J=11.5 Hz, 1H), 4.11 (d, J=15.1 Hz, 1H), 3.67-3.46 (m, 14H), 3.33-3.24 (m, 6H), 3.12-3.05 (m, 1H), 2.92-2.78 (m, 3H), 2.73-2.68 (m, 2H), 2.66-2.53 (m, 3H), 2.25-2.16 (m, 2H), 2.06-1.99 (m, 1H), 1.96-1.85 (m, 2H), 1.76 (d, J=2.0 Hz, 6H), 1.30-1.26 (m, 3H). HRMS (ESI) calcd for $C_{50}H_{57}N_8O_8$ $[M+H]^+$: 897.4294, found, 897.3670.

Compound Example 120: Synthesis of 8-(4-(4-(1-((2-(2,6-dioxopiperidin-3-yl)-1,3-dioxoisoindolin-4-yl)amino)-3,6,9,12-tetraoxapentadecan-15-oyl)piperazin-1-yl)piperidin-1-yl)-9-ethyl-6,6-dimethyl-11-oxo-6,11-dihydro-5H-benzo[b]carbazole-3-carbonitrile. (SIAIS219019)

According to the procedures for the preparation of Compound Example 1, Alectinib Analogue C and intermediate LM (SIAIS151006) was used to prepare SIAIS219019 (yellow solid, 10.1 mg, 49%). $^1$H NMR (500 MHz, DMSO) δ 12.84 (s, 1H), 11.09 (s, 1H), 8.31 (d, J=8.2 Hz, 1H), 8.06 (d, J=3.0 Hz, 1H), 8.00 (s, 1H), 7.61-7.56 (m, 2H), 7.36 (s, 1H), 7.15 (d, J=8.7 Hz, 1H), 7.04 (d, J=7.0 Hz, 1H), 6.60 (s, 1H), 5.05 (dd, J=12.8, 5.5 Hz, 1H), 4.51 (d, J=13.5 Hz, 1H), 4.12 (d, J=13.9 Hz, 1H), 3.66-3.60 (m, 4H), 3.60-3.46 (m, 20H), 3.30 (s, 4H), 3.12 (t, J=12.9 Hz, 2H), 2.91-2.78 (m, 3H), 2.73-2.68 (m, 3H), 2.26-2.19 (m, 2H), 2.3-2.002 (m, 1H), 1.95-1.87 (m, 2H), 1.76 (s, 6H), 1.30-1.26 (m, 3H). HRMS (ESI) calcd for $C_{54}H_{65}N_8O_{10}$ [M+H]$^+$: 985.4818, found, 985.4897.

Compound Example 121: Synthesis of 8-(4-(4-((2-(2,6-dioxopiperidin-3-yl)-1,3-dioxoisoindolin-4-yl)glycyl)piperazin-1-yl)piperidin-1-yl)-9-ethyl-6,6-dimethyl-11-oxo-6,11-dihydro-5H-benzo[b]carbazole-3-carbonitrile. (SIAIS184194)

According to the procedures for the preparation of Compound Example 1, Alectinib Analogue C and intermediate LM (SIAIS151025) was used to prepare SIAIS184194 (yellow solid, 6.2 mg, 37%). $^1$H NMR (500 MHz, DMSO) δ 12.78 (s, 1H), 11.11 (s, 1H), 8.32 (d, J=8.2 Hz, 1H), 8.06 (s, 1H), 8.01 (s, 1H), 7.65-7.59 (m, 2H), 7.37 (s, 1H), 7.12 (dd, J=14.8, 7.8 Hz, 2H), 7.04 (s, 1H), 5.08 (dd, J=12.5, 5.4 Hz, 1H), 4.58-4.52 (m, 1H), 4.28-4.21 (m, 1H), 3.61 (s, 2H), 3.48 (d, J=5.2 Hz, 3H), 3.44-3.40 (m, 8H), 2.83 (s, 3H), 2.72 (d, J=7.5 Hz, 2H), 2.28-2.18 (m, 2H), 2.08-2.01 (m, 1H), 1.95-1.88 (m, 2H), 1.76 (s, 6H), 1.29 (t, J=7.5 Hz, 3H). HRMS (ESI) calcd for $C_{45}H_{47}N_8O_6$ [M+H]$^+$: 795.3613, found, 795.3622.

Compound Example 122: Synthesis of 8-(4-(4-(4-((2-(2,6-dioxopiperidin-3-yl)-1,3-dioxoisoindolin-4-yl)amino)butanoyl)piperazin-1-yl)piperidin-1-yl)-9-ethyl-6,6-dimethyl-11-oxo-6,11-dihydro-5H-benzo[b]carbazole-3-carbonitrile. (SIAIS219003)

According to the procedures for the preparation of Compound Example 1, Alectinib Analogue C and intermediate LM (SIAIS151019) was used to prepare SIAIS219003 (yellow solid, 6.6 mg, 38%). $^1$H NMR (500 MHz, DMSO) δ 12.69 (s, 1H), 11.09 (s, 1H), 8.32 (s, 1H), 8.04 (s, 1H), 7.99 (s, 1H), 7.60 (d, J=8.8 Hz, 2H), 7.33 (s, 1H), 7.18 (d, J=8.8 Hz, 1H), 7.03 (d, J=7.0 Hz, 1H), 6.66 (s, 1H), 5.06 (dd, J=12.8, 5.6 Hz, 1H), 3.26-3.18 (m, 6H), 2.78-2.68 (m, 10H), 2.40 (s, 4H), 2.07-1.99 (m, 2H), 1.89-1.78 (m, 6H), 1.75 (s, 6H), 1.61 (t, J=10.4 Hz, 2H), 1.27 (t, J=11.8 Hz, 5H). HRMS (ESI) calcd for $C_{47}H_{51}N_8O_6$ [M+H]$^+$: 823.3926, found, 823.5145.

Compound Example 123: Synthesis of 8-(4-(4-(6-((2-(2,6-dioxopiperidin-3-yl)-1,3-dioxoisoindolin-4-yl)amino)hexanoyl)piperazin-1-yl)piperidin-1-yl)-9-ethyl-6,6-dimethyl-11-oxo-6,11-dihydro-5H-benzo[b]carbazole-3-carbonitrile. (SIAIS219004)

According to the procedures for the preparation of Compound Example 1, Alectinib Analogue C and intermediate LM (SIAIS151027) was used to prepare SIAIS219004 (yellow solid, 7.1 mg, 40%). $^1$H NMR (500 MHz, DMSO) δ 12.67 (s, 1H), 11.08 (s, 1H), 8.30 (s, 1H), 8.00 (s, 1H), 7.95 (s, 1H), 7.58 (d, J=8.4 Hz, 2H), 7.31 (s, 1H), 7.14 (d, J=8.8 Hz, 1H), 7.02 (d, J=7.0 Hz, 1H), 6.58 (s, 1H), 5.07 (dd, J=12.8, 5.6 Hz, 1H), 3.24-3.13 (m, 6H), 2.75-2.65 (m, 10H), 2.36 (s, 4H), 2.05-1.97 (m, 2H), 1.86-1.77 (m, 6H), 1.73 (s, 6H), 1.60 (t, J=10.4 Hz, 2H), 1.25-1.20 (m, 9H). HRMS (ESI) calcd for $C_{49}H_{55}N_8O_6$ [M+H]$^+$:851.4239, found, 851.5517.

Compound Example 124: Synthesis of (2S,4R)-1-((S)-2-(6-(4-(1-(3-cyano-9-ethyl-6,6-dimethyl-11-oxo-6,11-dihydro-5H-benzo[b]carbazol-8-yl)piperidin-4-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide. (SIAIS219015)

According to the procedures for the preparation of Compound Example 1, Alectinib Analogue C and intermediate LM (SIAIS074013) was used to prepare SIAIS219015 (yellow solid, 10.2 mg, 48%). $^1$H NMR (500 MHz, DMSO) δ 12.79 (s, 1H), 10.63 (s, 1H), 8.98 (s, 1H), 8.57 (s, 1H), 8.32 (d, J=8.2 Hz, 1H), 8.06 (s, 1H), 8.01 (s, 1H), 7.87 (d, J=9.2 Hz, 1H), 7.62-7.59 (m, 1H), 7.42 (d, J=8.1 Hz, 2H), 7.40-7.34 (m, 3H), 4.57-4.50 (m, 2H), 4.47-4.40 (m, 2H), 4.35 (s, 1H), 4.22 (d, J=11.5 Hz, 1H), 4.09 (d, J=16.2 Hz, 1H), 3.70-3.62 (m, 2H), 3.54 (d, J=16.2 Hz, 3H), 3.14 (d, J=9.2 Hz, 1H), 3.02 (d, J=18.4 Hz, 2H), 2.81 (t, J=10.6 Hz, 2H), 2.74-2.68 (m, 2H), 2.44 (s, 3H), 2.40-2.35 (m, 2H), 2.32-2.25 (m, 1H), 2.19 (t, J=14.0 Hz, 3H), 2.04-1.99 (m, 2H), 1.93-1.88 (m, 3H), 1.76 (s, 6H), 1.55-1.46 (m, 4H), 1.30-1.23 (m, 5H), 0.94 (s, 9H). HRMS (ESI) calcd for $C_{58}H_{72}N_9O_6S$ [M+H]$^+$: 1022.5321, found, 1022.4607.

Compound Example 125: Synthesis of (2S,4R)-1-((S)-2-(10-(4-(1-(3-cyano-9-ethyl-6,6-dimethyl-11-oxo-6,11-dihydro-5H-benzo[b]carbazol-8-yl)piperidin-4-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide. (SIAIS219016)

According to the procedures for the preparation of Compound Example 1, Alectinib Analogue C and intermediate LM (SIAIS074019) was used to prepare SIAIS219016 (yellow solid, 9.8 mg, 43%). $^1$H NMR (500 MHz, MeOD) δ 9.86 (s, 1H), 8.40 (d, J=8.1 Hz, 1H), 8.20 (s, 1H), 7.87 (s, 1H), 7.57-7.54 (m, 5H), 7.43 (s, 1H), 4.64 (s, 1H), 4.59-4.53 (m, 3H), 4.41 (d, J=15.7 Hz, 1H), 4.27 (s, 1H), 3.91 (d, J=11.1 Hz, 1H), 3.81 (dd, J=11.0, 3.8 Hz, 1H), 3.72 (s, 2H), 3.43 (d, J=11.2 Hz, 3H), 3.15 (d, J=12.9 Hz, 2H), 2.99 (t, J=11.4 Hz, 2H), 2.81 (q, J=7.5 Hz, 2H), 2.59 (s, 3H), 2.47 (t, J=7.4 Hz, 2H), 2.39-2.20 (m, 6H), 2.10-2.04 (m, 4H), 1.80 (s, 6H), 1.62 (d, J=6.2 Hz, 4H), 1.35 (t, J=7.4 Hz, 12H), 1.04 (s, 9H). HRMS (ESI) calcd for $C_{62}H_{80}N_9O_6S$ [M+H]$^+$:1078.5947, found, 1078.5193.

Compound Example 126: Synthesis of 4-((2-(3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropoxy)ethyl)amino)-2-(2,6-dioxopiperidin-3-yl)isoindoline-1,3-dione. (SIAIS151031)

According to the procedures for the preparation of Compound Example 1, Ceritinib and intermediate LM (SIAIS151001) was used to prepare SIAIS151031 (yellow solid, 20.8 mg, 62%). $^1$H NMR (500 MHz, MeOD) δ 8.45 (d, J=7.8 Hz, 1H), 8.15 (s, 1H), 7.93 (dd, J=8.0, 1.5 Hz, 1H), 7.76 (s, 1H), 7.70 (t, J=7.8 Hz, 1H), 7.55-7.50 (m, 1H), 7.38 (t, J=7.4 Hz, 1H), 7.07 (dd, J=8.4, 7.0 Hz, 1H), 7.02 (t, J=7.2 Hz, 1H), 6.77 (d, J=2.2 Hz, 1H), 5.00-4.94 (m, 1H), 4.70 (d, J=13.0 Hz, 1H), 4.58 (s, 1H), 4.56-4.50 (m, 1H), 4.16 (d, J=13.4 Hz, 1H), 3.90-3.77 (m, 2H), 3.73-3.70 (m, 2H), 3.52-3.49 (m, 2H), 3.22-3.13 (m, 1H), 3.00-2.93 (m, 1H), 2.81-2.59 (m, 6H), 2.13 (d, J=1.0 Hz, 3H), 2.03-1.95 (m, 1H), 1.76 (d, J=13.1 Hz, 2H), 1.67-1.54 (m, 2H), 1.28-1.25 (m, 12H). HRMS (ESI) calcd for $C_{46}H_{54}ClN_8O_9S$ [M+H]$^+$: 929.3418, found, 929.2502.

Compound Example 127: Synthesis of 4-((2-(2-(3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropoxy)ethoxy)ethyl)amino)-2-(2,6-dioxopiperidin-3-yl)isoindoline-1,3-dione. (SIAIS151023)

According to the procedures for the preparation of Compound Example 1, Ceritinib and intermediate LM (SIAIS151004) was used to prepare SIAIS151023 (yellow solid, 32.8 mg, 94%). $^1$H NMR (500 MHz, MeOD) δ 8.45 (d, J=8.3 Hz, 1H), 8.15 (d, J=1.9 Hz, 1H), 7.92 (dd, J=8.0, 1.5 Hz, 1H), 7.74 (s, 1H), 7.69-7.66 (m, 1H), 7.51-7.47 (m, 1H), 7.37 (t, J=7.6 Hz, 1H), 7.02 (dd, J=8.5, 4.0 Hz, 1H), 7.00 (d, J=7.0 Hz, 2H), 6.79 (s, 1H), 5.01 (dd, J=12.5, 5.5 Hz, 1H), 4.69 (d, J=13.1 Hz, 1H), 4.59-4.54 (m, 1H), 4.12 (d, J=13.0 Hz, 1H), 3.81-3.74 (m, 2H), 3.71-3.60 (m, 6H), 3.45-3.41 (m, 2H), 3.36-3.32 (m, 1H), 3.21-3.13 (m, 1H), 2.99-2.93 (m, 1H), 2.84-2.64 (m, 5H), 2.63-2.55 (m, 1H), 2.13 (s, 3H), 2.07-2.03 (m, 1H), 1.79-1.71 (m, 2H), 1.67-1.52 (m, 2H), 1.31-1.28 (m, 6H), 1.26 (d, J=6.8 Hz, 6H). HRMS (ESI) calcd for $C_{48}H_{58}ClN_8O_{10}S$ [M+H]$^+$: 973.3680, found, 973.3685.

Compound Example 128: Synthesis of 4-((2-(2-(2-(3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropoxy)ethoxy)ethoxy)ethyl)amino)-2-(2,6-dioxopiperidin-3-yl)isoindoline-1,3-dione. (SIAIS151028)

According to the procedures for the preparation of Compound Example 1, Ceritinib and intermediate LM (SIAIS151005) was used to prepare SIAIS151028 (yellow solid, 32.4 mg, 89%). $^1$H NMR (500 MHz, MeOD) δ 8.45 (d, J=8.2 Hz, 1H), 8.15 (s, 1H), 7.92 (dd, J=8.0, 1.5 Hz, 1H), 7.76 (s, 1H), 7.70-7.64 (m, 1H), 7.50 (dd, J=8.4, 7.2 Hz, 1H), 7.37 (t, J=7.7 Hz, 1H), 7.02 (t, J=7.2 Hz, 2H), 6.80 (s, 1H), 5.02 (dd, J=12.5, 5.5 Hz, 1H), 4.70 (d, J=13.0 Hz, 1H), 4.61-4.54 (m, 1H), 4.14 (d, J=11.9 Hz, 1H), 3.82-3.71 (m, 2H), 3.67-3.59 (m, 10H), 3.43 (t, J=5.4 Hz, 2H), 3.35-3.31 (m, 1H), 3.22-3.16 (m, 1H), 3.01-2.95 (m, 1H), 2.83 (s, 1H), 2.81-2.67 (m, 4H), 2.63-2.56 (m, 1H), 2.15 (s, 3H), 2.10-2.04 (m, 1H), 1.80-1.75 (m, 2H), 1.70-1.52 (m, 2H), 1.29 (t, J=6.0 Hz, 6H), 1.25 (d, J=6.8 Hz, 6H). HRMS (ESI) calcd for $C_{50}H_{62}ClN_8O_{11}S$ [M+H]$^+$: 1017.3942, found, 1017.3457.

Compound Example 129: Synthesis of 4-((18-(4-(4-((5-chloro-4-((2-(isopropylsulfonyl)phenyl)amino)pyrimidin-2-yl)amino)-5-isopropoxy-2-methylphenyl)piperidin-1-yl)-18-oxo-3,6,9,12,15-pentaoxaoctadecyl)amino)-2-(2,6-dioxopiperidin-3-yl)isoindoline-1,3-dione. (SIAIS151029)

According to the procedures for the preparation of Compound Example 1, Ceritinib and intermediate LM (SIAIS151007) was used to prepare SIAIS151029 (yellow solid, 31.6 mg, 80%). $^1$H NMR (500 MHz, MeOD) δ 8.45 (d, J=8.3 Hz, 1H), 8.14 (s, 1H), 7.93-7.90 (m, 1H), 7.76 (s, 1H), 7.68-7.64 (m, 1H), 7.51 (dd, J=8.5, 7.1 Hz, 1H), 7.38-7.34 (m, 1H), 7.03 (dd, J=12.8, 7.8 Hz, 2H), 6.80 (s, 1H), 5.02 (dd, J=12.6, 5.5 Hz, 1H), 4.70 (d, J=13.4 Hz, 1H), 4.61-4.55 (m, 2H), 4.15 (d, J=14.0 Hz, 1H), 3.79-3.74 (m, 2H), 3.68 (t, J=5.3 Hz, 2H), 3.62-3.55 (m, 16H), 3.46-3.43 (m, 2H), 3.24-3.18 (m, 1H), 3.04-2.94 (m, 1H), 2.83-2.61 (m, 6H), 2.15 (s, 3H), 2.10-2.04 (m, 1H), 1.82-1.76 (m, 2H), 1.69-1.53 (m, 2H), 1.30 (t, J=6.1 Hz, 6H), 1.26 (s, 3H), 1.24 (s, 3H). HRMS (ESI) calcd for $C_{54}H_{70}ClN_8O_{13}S$ [M+H]$^+$: 1105.4466, found, 1105.3969.

Compound Example 130: Synthesis of 4-((2-(4-(4-((5-chloro-4-((2-(isopropylsulfonyl)phenyl)amino)pyrimidin-2-yl)amino)-5-isopropoxy-2-methylphenyl)piperidin-1-yl)-2-oxoethyl)amino)-2-(2,6-dioxopiperidin-3-yl)isoindoline-1,3-dione. (SIAIS151037)

According to the procedures for the preparation of Compound Example 1, Ceritinib and intermediate LM (SIAIS151025) was used to prepare SIAIS151037 (yellow solid, 20.1 mg, 64%). $^1$H NMR (500 MHz, DMSO) δ 11.11 (s, 1H), 9.46 (s, 1H), 8.47 (d, J=8.4 Hz, 1H), 8.25 (s, 1H), 8.06 (s, 1H), 7.84 (dd, J=8.0, 1.6 Hz, 1H), 7.66-7.59 (m, 2H), 7.53 (s, 1H), 7.40-7.33 (m, 1H), 7.20-7.15 (m, 2H), 7.08 (d, J=7.0 Hz, 1H), 6.86 (s, 1H), 5.08 (dd, J=12.9, 5.4 Hz, 1H), 4.60-4.54 (m, 2H), 4.35-4.13 (m, 2H), 4.05 (d, J=13.0 Hz, 1H), 3.48-3.40 (m, 1H), 3.24-3.14 (m, 1H), 3.01-2.85 (m, 2H), 2.77 (t, J=12.1 Hz, 1H), 2.63-2.52 (m, 2H), 2.17 (s, 3H), 2.08-2.00 (m, 1H), 1.74-1.71 (m, 3H), 1.59-1.48 (m, 1H), 1.20-1.15 (m, 12H). HRMS (ESI) calcd for $C_{43}H_{48}ClN_8O_8S$ [M+H]$^+$: 871.2999, found, 871.0255.

Compound Example 131: Synthesis of 4-((3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropyl)amino)-2-(2,6-dioxopiperidin-3-yl)isoindoline-1,3-dione. (SIAIS151034)

According to the procedures for the preparation of Compound Example 1, Ceritinib and intermediate LM (SIAIS151026) was used to prepare SIAIS151034 (yellow solid, 27.1 mg, 85%). $^1$H NMR (500 MHz, DMSO) δ 11.09 (s, 1H), 9.45 (s, 1H), 8.46 (d, J=8.1 Hz, 1H), 8.25 (s, 1H), 8.04 (s, 1H), 7.83 (dd, J=8.0, 1.5 Hz, 1H), 7.66-7.56 (m, 2H), 7.52 (s, 1H), 7.40-7.30 (m, 1H), 7.17 (d, J=8.6 Hz, 1H), 7.03 (d, J=7.0 Hz, 1H), 6.87-6.77 (m, 2H), 5.04 (dd, J=12.8, 5.5 Hz, 1H), 4.65-4.52 (m, 2H), 3.98 (d, J=12.6 Hz, 1H), 3.57 (dd, J=12.4, 6.1 Hz, 2H), 3.46-3.41 (m, 1H), 3.11 (t, J=11.8 Hz, 1H), 2.96-2.83 (m, 2H), 2.71 (t, J=6.3 Hz, 2H), 2.68-2.52 (m, 3H), 2.14 (s, 3H), 2.05-1.97 (m, 1H), 1.71-1.67 (m, 2H), 1.64-1.56 (m, 1H), 1.52-1.43 (m, 1H), 1.21-1.13 (m, 12H). HRMS (ESI) calcd for $C_{44}H_{50}ClN_8O_8S$ [M+H]$^+$: 885.3155, found, 885.2667.

Compound Example 132: Synthesis of 4-((4-(4-(4-((5-chloro-4-((2-(isopropylsulfonyl)phenyl)amino)pyrimidin-2-yl)amino)-5-isopropoxy-2-methylphenyl)piperidin-1-yl)-4-oxobutyl)amino)-2-(2,6-dioxopiperidin-3-yl)isoindoline-1,3-dione. (SIAIS151035)

According to the procedures for the preparation of Compound Example 1, Ceritinib and intermediate LM (SIAIS151019) was used to prepare SIAIS151035 (yellow solid, 21.5 mg, 67%). ¹H NMR (500 MHz, MeOD) δ 8.46 (d, J=8.3 Hz, 1H), 8.15 (s, 1H), 7.92 (dd, J=8.0, 1.6 Hz, 1H), 7.76 (s, 1H), 7.70-7.64 (m, 1H), 7.56 (dd, J=8.5, 7.1 Hz, 1H), 7.39-7.35 (m, 1H), 7.13 (d, J=8.6 Hz, 1H), 7.05 (d, J=7.1 Hz, 1H), 6.79 (s, 1H), 5.05-5.01 (m, 1H), 4.71 (d, J=11.6 Hz, 1H), 4.59-4.52 (m, 1H), 4.09 (d, J=12.5 Hz, 1H), 3.47-3.41 (m, 2H), 3.36-3.33 (m, 1H), 3.24-3.16 (m, 1H), 3.01-2.95 (m, 1H), 2.86-2.78 (m, 1H), 2.77-2.66 (m, 3H), 2.64-2.49 (m, 2H), 2.15 (s, 3H), 2.10-1.96 (m, 3H), 1.79 (d, J=13.1 Hz, 2H), 1.63-1.49 (m, 2H), 1.29 (d, J=6.0 Hz, 6H), 1.26 (d, J=6.8 Hz, 6H). HRMS (ESI) calcd for $C_{45}H_{52}ClN_8O_8S$ [M+H]⁺: 899.3312, found, 899.0450.

Compound Example 133: Synthesis of 4-((5-(4-(4-((5-chloro-4-((2-(isopropylsulfonyl)phenyl)amino) pyrimidin-2-yl)amino)-5-isopropoxy-2-methylphenyl)piperidin-1-yl)-5-oxopentyl)amino)-2-(2,6-dioxopiperidin-3-yl)isoindoline-1,3-dione. (SIAIS151036)

According to the procedures for the preparation of Compound Example 1, Ceritinib and intermediate LM (SIAIS151020) was used to prepare SIAIS151036 (yellow solid, 31.5 mg, 96%). ¹H NMR (500 MHz, MeOD) δ 8.46 (d, J=8.4 Hz, 1H), 8.15 (s, 1H), 7.92 (dd, J=8.0, 1.5 Hz, 1H), 7.77 (s, 1H), 7.74-7.66 (m, 1H), 7.55 (dd, J=8.5, 7.2 Hz, 1H), 7.39-7.35 (m, 1H), 7.08 (d, J=8.6 Hz, 1H), 7.03 (d, J=7.1 Hz, 1H), 6.79 (s, 1H), 5.03-4.95 (m, 1H), 4.69 (d, J=11.6 Hz, 1H), 4.61-4.53 (m, 1H), 4.08-4.04 (m, 1H), 3.46-3.32 (m, 3H), 3.24-3.16 (m, 1H), 3.01-2.97 (m, 1H), 2.82-2.61 (m, 4H), 2.57-2.44 (m, 2H), 2.15 (s, 3H), 2.05-1.99 (m, 1H), 1.82-1.72 (m, 6H), 1.65-1.51 (m, 2H), 1.31-1.27 (m, 6H), 1.26 (d, J=6.8 Hz, 6H). HRMS (ESI) calcd for $C_{46}H_{54}ClN_8O_8S$ [M+H]⁺: 913.3468, found, 913.0576.

Compound Example 134: Synthesis of 4-((6-(4-(4-((5-chloro-4-((2-(isopropylsulfonyl)phenyl)amino) pyrimidin-2-yl)amino)-5-isopropoxy-2-methylphenyl)piperidin-1-yl)-6-oxohexyl)amino)-2-(2,6-dioxopiperidin-3-yl)isoindoline-1,3-dione. (SIAIS151043)

According to the procedures for the preparation of Compound Example 1, Ceritinib and intermediate LM (SIAIS151027) was used to prepare SIAIS151043 (yellow solid, 26.3 mg, 79%). ¹H NMR (500 MHz, MeOD) δ 8.26 (d, J=8.3 Hz, 1H), 8.09 (s, 1H), 7.88 (dd, J=8.0, 1.4 Hz, 1H), 7.62 (t, J=7.5 Hz, 1H), 7.45 (dd, J=8.5, 7.1 Hz, 1H), 7.40-7.36 (m, 2H), 6.95 (dd, J=13.9, 7.8 Hz, 2H), 6.76 (d, J=2.2 Hz, 1H), 4.95-4.90 (m, 1H), 4.63-4.59 (m, 1H), 4.52-4.47 (m, 1H), 4.00 (d, J=13.1 Hz, 1H), 3.27 (t, J=6.9 Hz, 3H), 3.14-3.08 (m, 1H), 2.95-2.89 (m, 1H), 2.75-2.54 (m, 4H), 2.38 (t, J=7.4 Hz, 2H), 2.09 (s, 3H), 2.01-1.93 (m, 1H), 1.74-1.66 (m, 2H), 1.66-1.58 (m, 4H), 1.55-1.38 (m, 4H), 1.17-1.15 (m, 12H). HRMS (ESI) calcd for $C_{47}H_{56}ClN_8O_8S$ [M+H]⁺: 927.3625, found, 927.0642.

Compound Example 135: Synthesis of (2S,4R)-1-((S)-2-(2-(2-(2-(4-(4-((5-chloro-4-((2-(isopropylsulfonyl)phenyl)amino)pyrimidin-2-yl)amino)-5-isopropoxy-2-methylphenyl)piperidin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide. (SIAIS151042)

According to the procedures for the preparation of Compound Example 1, Ceritinib and intermediate LM (SIAIS151010) was used to prepare SIAIS151042 (white solid, 36.8 mg, 91%). ¹H NMR (500 MHz, MeOD) δ 8.91 (d, J=1.6 Hz, 1H), 8.28 (s, 1H), 8.19 (s, 1H), 7.99 (dd, J=8.0, 1.4 Hz, 1H), 7.75-7.69 (m, 1H), 7.53-7.49 (m, 1H), 7.47-7.34 (m, 5H), 6.86 (d, J=6.2 Hz, 1H), 4.72-4.53 (m, 4H), 4.51-4.31 (m, 5H), 4.13-4.01 (m, 3H), 3.88-3.86 (m, 1H), 3.83-3.69 (m, 5H), 3.39-3.34 (m, 1H), 3.24-3.16 (m, 1H), 3.07-2.97 (m, 1H), 2.79-2.71 (m, 1H), 2.47-2.45 (m, 3H), 2.26-2.14 (m, 1H), 2.18 (s, 3H), 2.12-2.04 (m, 1H), 1.82-1.77 (m, 2H), 1.73-1.53 (m, 2H), 1.27-1.24 (m, 12H), 1.05 (d, J=4.5 Hz, 9H). HRMS (ESI) calcd for $C_{56}H_{73}ClN_9O_{10}S_2$ [M+H]⁺: 1130.4605, found, 1130.0737.

Compound Example 136: Synthesis of (2S,4R)-1-((S)-2-(3-(2-(3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide. (SIAIS151038)

According to the procedures for the preparation of Compound Example 1, Ceritinib and intermediate LM (SIAIS151002) was used to prepare SIAIS151038 (white solid, 39.4 mg, 95%). ¹H NMR (500 MHz, MeOD) δ 8.92 (d, J=2.4 Hz, 1H), 8.32 (d, J=7.2 Hz, 1H), 8.19 (s, 1H), 7.99 (dd, J=8.0, 1.5 Hz, 1H), 7.71 (t, J=7.8 Hz, 1H), 7.54-7.49 (m, 1H), 7.48-7.35 (m, 5H), 6.87 (s, 1H), 4.72-4.69 (m, 1H), 4.67-4.64 (m, 1H), 4.64-4.47 (m, 4H), 4.35 (d, J=15.3 Hz, 1H), 4.16 (d, J=12.2 Hz, 1H), 3.88 (d, J=11.1 Hz, 1H), 3.82-3.67 (m, 5H), 3.66-3.60 (m, 4H), 3.40-3.35 (m, 1H), 3.25-3.19 (m, 1H), 3.03 (t, J=10.9 Hz, 1H), 2.77-2.65 (m, 3H), 2.58-2.52 (m, 1H), 2.50-2.43 (m, 4H), 2.24-2.18 (m, 1H), 2.20 (s, 3H), 2.11-2.05 (m, 1H), 1.86-1.75 (m, 2H), 1.71-1.52 (m, 2H), 1.28-1.24 (m, 12H), 1.03 (s, 9H). HRMS (ESI) calcd for $C_{58}H_{77}ClN_9O_{10}S_2$ [M+H]⁺: 1158.4918, found, 1158.4604.

Compound Example 137: Synthesis of (2S,4R)-1-((S)-2-(tert-butyl)-16-(4-(4-((5-chloro-4-((2-(isopropylsulfonyl)phenyl)amino)pyrimidin-2-yl)amino)-5-isopropoxy-2-methylphenyl)piperidin-1-yl)-4,16-dioxo-7,10,13-trioxa-3-azahexadecanoyl)-4-hydroxy-N-(4-(4-methylthiazol-5-yl)benzyl) pyrrolidine-2-carboxamide. (SIAIS151039)

According to the procedures for the preparation of Compound Example 1, Ceritinib and intermediate LM (SIAIS151003) was used to prepare SIAIS151039 (white solid, 40.2 mg, 93%). ¹H NMR (500 MHz, MeOD) δ 8.93 (s, 1H), 8.32 (d, J=7.6 Hz, 1H), 8.20 (s, 1H), 7.99 (dd, J=8.0, 1.5 Hz, 1H), 7.71 (t, J=7.5 Hz, 1H), 7.54-7.49 (m, 1H), 7.48-7.36 (m, 5H), 6.88 (s, 1H), 4.74-3.70 (m, 1H), 4.66-4.47 (m, 5H), 4.35 (d, J=15.5 Hz, 1H), 4.16 (d, J=12.6 Hz, 1H), 3.88 (d, J=11.1 Hz, 1H), 3.81-3.76 (m, 3H), 3.74-3.67 (m, 2H), 3.63-3.58 (m, 8H), 3.40-3.35 (m, 1H), 3.23 (t, J=12.9 Hz, 1H), 3.06-3.00 (m, 1H), 2.78-2.64 (m, 3H), 2.59-2.53 (m, 1H), 2.50-2.42 (m, 4H), 2.25-2.17 (m, 1H), 2.20 (s, 3H), 2.11-2.05 (m, 1H), 1.80 (t, J=15.3 Hz, 2H), 1.73-1.53 (m, 2H), 1.28-1.24 (m, 12H), 1.03 (s, 9H). HRMS (ESI) calcd for $C_{60}H_{81}ClN_9O_{11}S_2$[M+H]⁺: 1202.5180, found, 1203.4829.

Compound Example 138: Synthesis of (2S,4R)-1-((S)-2-(tert-butyl)-19-(4-((5-chloro-4-((2-(isopropylsulfonyl)phenyl)amino)pyrimidin-2-yl)amino)-5-isopropoxy-2-methylphenyl)piperidin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide. (SIAIS151040)

According to the procedures for the preparation of Compound Example 1, Ceritinib and intermediate LM (SIAIS151008) was used to prepare SIAIS151040 (white solid, 34.3 mg, 77%). $^1$H NMR (500 MHz, MeOD) δ 8.94 (s, 1H), 8.32 (d, J=7.8 Hz, 1H), 8.20 (s, 1H), 7.99 (dd, J=8.0, 1.5 Hz, 1H), 7.72 (t, J=7.8 Hz, 1H), 7.54-7.49 (m, 1H), 7.48-7.41 (m, 4H), 7.36 (s, 1H), 6.89 (s, 1H), 4.72 (d, J=13.5 Hz, 1H), 4.65-4.47 (m, 5H), 4.35 (d, J=15.5 Hz, 1H), 4.17 (d, J=13.7 Hz, 1H), 3.88 (d, J=11.1 Hz, 1H), 3.81-3.76 (m, 3H), 3.74-3.67 (m, 2H), 3.63-3.56 (m, 14H), 3.41-3.35 (m, 1H), 3.23 (t, J=12.3 Hz, 1H), 3.07-3.01 (m, 1H), 2.80-2.64 (m, 3H), 2.59-2.53 (m, 1H), 2.49-2.45 (m, 4H), 2.25-2.18 (m, 1H), 2.20 (s, 3H), 2.11-2.05 (m, 1H), 1.80 (t, J=15.2 Hz, 2H), 1.74-1.55 (m, 2H), 1.28-1.24 (m, 12H), 1.03 (s, 9H). HRMS (ESI) calcd for $C_{62}H_{85}ClN_9O_{12}S_2[M+H]^+$: 1246.5442, found, 1246.5029.

Compound Example 139: Synthesis of (2S,4R)-1-((S)-2-(tert-butyl)-22-(4-((5-chloro-4-((2-(isopropylsulfonyl)phenyl)amino)pyrimidin-2-yl)amino)-5-isopropoxy-2-methylphenyl)piperidin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide. (SIAIS151041)

According to the procedures for the preparation of Compound Example 1, Ceritinib and intermediate LM (SIAIS151009) was used to prepare SIAIS151041 (white solid, 40 mg, 86%). $^1$H NMR (500 MHz, MeOD) δ 8.93 (s, 1H), 8.32 (d, J=7.5 Hz, 1H), 8.19 (s, 1H), 7.99 (dd, J=8.0, 1.5 Hz, 1H), 7.72 (t, J=7.7 Hz, 1H), 7.53-7.49 (m, 1H), 7.43 (ddd, J=19.0, 15.8, 9.5 Hz, 5H), 6.89 (s, 1H), 4.72 (d, J=13.5 Hz, 1H), 4.66-4.48 (m, 5H), 4.37-4.33 (m, 1H), 4.17 (d, J=13.5 Hz, 1H), 3.88 (d, J=11.1 Hz, 1H), 3.84-3.76 (m, 3H), 3.75-3.67 (m, 2H), 3.63-3.58 (m, 16H), 3.40-3.35 (m, 1H), 3.23 (t, J=12.0 Hz, 1H), 3.07-3.01 (m, 1H), 2.78-2.65 (m, 3H), 2.61-2.52 (m, 1H), 2.50-2.42 (m, 1H), 2.47 (s, 3H), 2.24-2.18 (m, 4H), 2.10-2.05 (m, 1H), 1.81 (t, J=15.2 Hz, 2H), 1.74-1.52 (m, 2H), 1.28-1.24 (m, 12H), 1.03 (s, 9H). HRMS (ESI) calcd for $C_{64}H_{89}ClN_9O_{13}S_2[M+H]^+$: 1290.5704, found, 1290.5117.

Compound Example 140: Synthesis of (2S,4R)-1-((S)-2-(4-(4-(4-((5-chloro-4-((2-(isopropylsulfonyl)phenyl)amino)pyrimidin-2-yl)amino)-5-isopropoxy-2-methylphenyl)piperidin-1-yl)-4-oxobutanamido)-3,3-dimethylbutanoyl)-4-hydroxy-N-(4-(4-methylthiazol-5-yl)benzyl)pyrrolidine-2-carboxamide. (SIAIS074017)

According to the procedures for the preparation of Compound Example 1, Ceritinib and intermediate LM (SIAIS074011) was used to prepare SIAIS074017 (white solid, 72 mg, 75%). $^1$H NMR (500 MHz, MeOD) δ 8.86 (d, J=1.7 Hz, 1H), 8.45 (d, J=8.4 Hz, 1H), 8.15 (s, 1H), 7.92 (dd, J=8.0, 1.6 Hz, 1H), 7.76 (s, 1H), 7.69-7.64 (m, 1H), 7.48-7.44 (m, 2H), 7.42-7.40 (m, 2H), 7.38-7.35 (m, 1H), 6.80 (d, J=7.1 Hz, 1H), 4.68 (d, J=11.6 Hz, 1H), 4.63 (d, J=7.4 Hz, 1H), 4.61-4.53 (m, 3H), 4.53-4.44 (m, 2H), 4.36 (dd, J=15.4, 4.3 Hz, 1H), 4.12 (d, J=13.5 Hz, 1H), 3.90 (d, J=11.1 Hz, 1H), 3.80 (dd, J=11.0, 3.8 Hz, 1H), 3.24-3.19 (m, 1H), 3.03-2.97 (m, 1H), 2.80-2.68 (m, 3H), 2.67-2.53 (m, 2H), 2.47 (d, J=3.0 Hz, 3H), 2.25-2.18 (m, 1H), 2.16 (s, 3H), 2.11-2.05 (m, 1H), 1.83-1.76 (m, 2H), 1.71-1.63 (m, 1H), 1.59-1.51 (m, 1H), 1.32-1.29 (m, 6H), 1.25 (d, J=6.8 Hz, 6H), 1.05 (s, 9H). HRMS (ESI) calcd for $C_{54}H_{69}ClN_9O_8S_2^+$ [M+H]$^+$: 1070.4394; found, 1070.4352.

Compound Example 141: Synthesis of (2S,4R)-1-((S)-2-(5-(4-(4-((5-chloro-4-((2-(isopropylsulfonyl)phenyl)amino)pyrimidin-2-yl)amino)-5-isopropoxy-2-methylphenyl)piperidin-1-yl)-5-oxopentanamido)-3,3-dimethylbutanoyl)-4-hydroxy-N-(4-(4-methylthiazol-5-yl)benzyl)pyrrolidine-2-carboxamide. (SIAIS074018)

According to the procedures for the preparation of Compound Example 1, Ceritinib and intermediate LM (SIAIS074012) was used to prepare SIAIS074018 (white solid, 25.2 mg, 65%). $^1$H NMR (500 MHz, CDCl$_3$) δ 10.63-10.18 (m, 1H), 9.28-8.52 (m, 3H), 8.42 (d, J=7.9 Hz, 1H), 8.09-7.86 (m, 1H), 7.59-7.43 (m, 1H), 7.35 (t, J=15.5 Hz, 6H), 7.13 (s, 1H), 6.73 (d, J=14.8 Hz, 1H), 6.27 (s, 1H), 4.76 (s, 1H), 4.52 (d, J=24.2 Hz, 3H), 4.34 (d, J=13.3 Hz, 1H), 4.06 (d, J=72.7 Hz, 2H), 3.75-3.45 (m, 1H), 3.28-3.08 (m, 2H), 2.88 (d, J=43.8 Hz, 2H), 2.67 (s, 3H), 2.60-2.25 (m, 7H), 2.19 (s, 4H), 2.10-1.72 (m, 4H), 1.57 (s, 2H), 1.32 (dd, J=42.6, 36.2 Hz, 13H), 1.11-0.82 (m, 9H). HRMS (ESI) calcd for $C_{55}H_{71}ClN_9O_8S_2^+$ [M+H]$^+$: 1084.4550; found, 1084.4549.

Compound Example 142: Synthesis of (2S,4R)-1-((S)-2-(6-(4-(4-((5-chloro-4-((2-(isopropylsulfonyl)phenyl)amino)pyrimidin-2-yl)amino)-5-isopropoxy-2-methylphenyl)piperidin-1-yl)-6-oxohexanamido)-3,3-dimethylbutanoyl)-4-hydroxy-N-(4-(4-methylthiazol-5-yl)benzyl)pyrrolidine-2-carboxamide. (SIAIS074021)

According to the procedures for the preparation of Compound Example 1, Ceritinib and intermediate LM (SIAIS074013) was used to prepare SIAIS074021 (white solid, 27.3 mg, 69%). $^1$H NMR (500 MHz, CDCl$_3$) δ 10.27 (s, 1H), 10.23-10.07 (m, 1H), 8.83 (s, 1H), 8.45 (d, J=8.3 Hz, 1H), 7.99 (s, 1H), 7.91 (dd, J=7.9, 1.4 Hz, 1H), 7.47 (d, J=2.3 Hz, 1H), 7.40 (dd, J=15.4, 6.9 Hz, 1H), 7.38-7.28 (m, 4H), 6.73 (d, J=3.8 Hz, 1H), 6.42 (dd, J=25.8, 8.5 Hz, 1H), 5.35 (t, J=4.8 Hz, 1H), 4.88-4.70 (m, 2H), 4.59 (dd, J=15.0, 6.7 Hz, 1H), 4.51 (dd, J=11.9, 5.4 Hz, 2H), 4.34 (dd, J=14.9, 5.1 Hz, 1H), 4.13 (d, J=11.8 Hz, 1H), 4.00 (d, J=12.3 Hz, 1H), 3.80-3.42 (m, 6H), 3.26-3.09 (m, 2H), 2.92 (t, J=12.0 Hz, 1H), 2.65 (s, 1H), 2.57 (ddd, J=16.5, 8.1, 4.0 Hz, 1H), 2.53 (s, 2H), 2.39 (s, 1H), 2.34-2.21 (m, 2H), 2.21-2.12 (m, 3H), 2.04-1.97 (m, 1H), 1.88-1.77 (m, 2H), 1.75-1.47 (m, 5H), 1.34-1.23 (m, 12H), 1.01-0.75 (m, 7H). HRMS (ESI) calcd for $C_{56}H_{73}ClN_9O_8S_2^+$ [M+H]$^+$: 1098.4707; found, 1098.6188.

Compound Example 143: Synthesis of (2S,4R)-1-((S)-2-(7-(4-(4-((5-chloro-4-((2-(isopropylsulfonyl)phenyl)amino)pyrimidin-2-yl)amino)-5-isopropoxy-2-methylphenyl)piperidin-1-yl)-7-oxoheptanamido)-3,3-dimethylbutanoyl)-4-hydroxy-N-(4-(4-methylthiazol-5-yl)benzyl)pyrrolidine-2-carboxamide. (SIAIS074022)

According to the procedures for the preparation of Compound Example 1, Ceritinib and intermediate LM (SIAIS074014) was used to prepare SIAIS074022 (white solid, 29.5 mg, 74%). $^1$H NMR (500 MHz, CDCl$_3$) δ 10.11 (s, 1H), 9.63 (s, 1H), 8.76 (s, 1H), 8.48 (d, J=8.3 Hz, 1H), 8.02 (s, 1H), 7.92 (dd, J=7.9, 1.5 Hz, 1H), 7.58 (s, 1H), 7.45 (t, J=7.3 Hz, 1H), 7.40-7.32 (m, 4H), 7.29 (t, J=7.7 Hz, 1H), 6.72 (d, J=9.6 Hz, 1H), 6.19 (d, J=6.8 Hz, 1H), 4.77 (dd, J=19.4, 11.3 Hz, 2H), 4.64-4.46 (m, 4H), 4.34 (dd, J=15.0, 5.1 Hz, 2H), 4.05 (dd, J=56.9, 11.8 Hz, 3H), 3.60 (dd, J=11.3, 3.2 Hz, 1H), 3.27-3.18 (m, 1H), 3.14 (dd, J=19.6, 13.0 Hz, 1H), 2.91 (t, J=10.7 Hz, 1H), 2.69-2.58 (m, 1H), 2.57-2.49 (m, 3H), 2.45-2.31 (m, 2H), 2.31-2.11 (m, 6H), 1.80 (dd, J=33.7, 17.8 Hz, 2H), 1.74-1.48 (m, 6H), 1.43-1.23 (m, 15H), 1.01-0.82 (m, 9H). HRMS (ESI) calcd for C$_{57}$H$_{75}$ClN$_9$O$_8$S$_2{}^+$ [M+H]$^+$: 1112.4863, found, 1112.6343.

Compound Example 144: Synthesis of (2S,4R)-1-((S)-2-(8-(4-(4-((5-chloro-4-((2-(isopropylsulfonyl)phenyl)amino)pyrimidin-2-yl)amino)-5-isopropoxy-2-methylphenyl)piperidin-1-yl)-8-oxooctanamido)-3,3-dimethylbutanoyl)-4-hydroxy-N-(4-(4-methylthiazol-5-yl)benzyl)pyrrolidine-2-carboxamide. (SIAIS074008)

According to the procedures for the preparation of Compound Example 1, Ceritinib and intermediate LM (SIAIS074015) was used to prepare SIAIS074008 (white solid, 30.1 mg, 75%). $^1$H NMR (500 MHz, CDCl$_3$) δ 9.89 (s, 1H), 8.92 (s, 1H), 8.71 (s, 1H), 8.51 (d, J=8.4 Hz, 1H), 8.08 (d, J=17.2 Hz, 1H), 7.92 (dd, J=8.0, 1.5 Hz, 1H), 7.74 (s, 1H), 7.51 (t, J=7.3 Hz, 1H), 7.37 (p, J=8.3 Hz, 3H), 7.29 (dd, J=11.4, 4.4 Hz, 1H), 6.70 (d, J=4.5 Hz, 1H), 6.18-6.05 (m, 1H), 5.35 (dd, J=12.6, 7.8 Hz, 1H), 4.77 (dd, J=20.6, 12.4 Hz, 2H), 4.62-4.48 (m, 3H), 4.35 (dt, J=14.9, 5.3 Hz, 1H), 4.13 (d, J=11.3 Hz, 1H), 3.98 (d, J=12.5 Hz, 1H), 3.59 (dd, J=11.3, 3.3 Hz, 1H), 3.23 (dt, J=13.7, 6.9 Hz, 1H), 3.14 (dd, J=19.2, 12.6 Hz, 1H), 3.07-2.67 (m, 5H), 2.67-2.59 (m, 1H), 2.59-2.48 (m, 3H), 2.41-2.30 (m, 2H), 2.28-2.09 (m, 5H), 2.04-1.97 (m, 1H), 1.87-1.75 (m, 2H), 1.70-1.46 (m, 5H), 1.39-1.22 (m, 14H), 0.96-0.84 (m, 6H). HRMS (ESI) calcd for C$_{58}$H$_{77}$ClN$_9$O$_8$S$_2{}^+$ [M+H]$^+$: 1126.5020, found, 1126.6505.

Compound Example 145: Synthesis of (2S,4R)-1-((S)-2-(9-(4-(4-((5-chloro-4-((2-(isopropylsulfonyl)phenyl)amino)pyrimidin-2-yl)amino)-5-isopropoxy-2-methylphenyl)piperidin-1-yl)-9-oxononanamido)-3,3-dimethylbutanoyl)-4-hydroxy-N-(4-(4-methylthiazol-5-yl)benzyl)pyrrolidine-2-carboxamide. (SIAIS074024)

According to the procedures for the preparation of Compound Example 1, Ceritinib and intermediate LM (SIAIS074016) was used to prepare SIAIS074024 (white solid, 31.2 mg, 76%). $^1$H NMR (500 MHz, MeOD) δ 8.90 (t, J=2.2 Hz, 1H), 8.35 (d, J=7.5 Hz, 1H), 8.19 (s, 1H), 7.98 (dd, J=8.0, 1.4 Hz, 1H), 7.71 (t, J=7.5 Hz, 1H), 7.53-7.38 (m, 6H), 6.86 (d, J=1.7 Hz, 1H), 4.70 (d, J=12.8 Hz, 1H), 4.66-4.47 (m, 5H), 4.36 (d, J=15.5 Hz, 1H), 4.11 (d, J=13.5 Hz, 1H), 3.91 (d, J=11.0 Hz, 1H), 3.80 (dd, J=10.9, 3.8 Hz, 1H), 3.36 (td, J=13.3, 6.4 Hz, 2H), 3.23 (t, J=13.1 Hz, 1H), 3.03 (t, J=11.9 Hz, 1H), 2.72 (t, J=13.2 Hz, 1H), 2.51-2.39 (m, 5H), 2.35-2.16 (m, 7H), 2.12-1.99 (m, 2H), 1.84 (t, J=12.9 Hz, 1H), 1.78 (d, J=12.8 Hz, 1H), 1.69-1.49 (m, 7H), 1.32-1.21 (m, 14H), 1.02 (s, 9H). HRMS (ESI) calcd for C$_{59}$H$_{79}$ClN$_9$O$_8$S$_2{}^+$[M+H]$^+$: 1140.5176, found, 1140.5167.

Compound Example 146: Synthesis of (2S,4R)-1-((S)-2-(10-(4-(4-((5-chloro-4-((2-(isopropylsulfonyl)phenyl)amino)pyrimidin-2-yl)amino)-5-isopropoxy-2-methylphenyl)piperidin-1-yl)-10-oxodecanamido)-3,3-dimethylbutanoyl)-4-hydroxy-N-(4-(4-methylthiazol-5-yl)benzyl)pyrrolidine-2-carboxamide. (SIAIS074025)

According to the procedures for the preparation of Compound Example 1, Ceritinib and intermediate LM (SIAIS074019) was used to prepare SIAIS074025 (white solid, 31.5 mg, 76%). $^1$H NMR (500 MHz, MeOD) δ 8.90 (s, 1H), 8.37 (d, J=8.0 Hz, 1H), 8.18 (s, 1H), 7.97 (dd, J=8.0, 1.4 Hz, 1H), 7.70 (t, J=7.6 Hz, 1H), 7.50-7.40 (m, 6H), 6.85 (s, 1H), 4.70 (d, J=13.1 Hz, 1H), 4.66-4.44 (m, 6H), 4.38-4.33 (m, 1H), 4.11 (d, J=13.6 Hz, 1H), 3.90 (d, J=11.0 Hz, 1H), 3.80 (dd, J=10.9, 3.8 Hz, 1H), 3.39-3.32 (m, 2H), 3.23 (t, J=12.3 Hz, 1H), 3.03 (t, J=11.9 Hz, 1H), 2.72 (t, J=12.3 Hz, 1H), 2.50-2.41 (m, 5H), 2.34-2.20 (m, 4H), 2.19 (s, 3H), 2.14-1.97 (m, 2H), 1.81 (dd, J=28.9, 13.0 Hz, 3H), 1.67-1.50 (m, 7H), 1.28 (dd, J=6.0, 2.0 Hz, 8H), 1.25 (d, J=6.8 Hz, 6H), 1.02 (d, J=13.8 Hz, 9H). HRMS (ESI) calcd for C$_{60}$H$_{61}$ClN$_9$O$_8$S$_2{}^+$ [M+H]$^+$: 1154.5333, found, 1154.2914.

Compound Example 147: Synthesis of (2S,4R)-1-((S)-2-(11-(4-(4-((5-chloro-4-((2-(isopropylsulfonyl)phenyl)amino)pyrimidin-2-yl)amino)-5-isopropoxy-2-methylphenyl)piperidin-1-yl)-11-oxoundecanamido)-3,3-dimethylbutanoyl)-4-hydroxy-N-(4-(4-methylthiazol-5-yl)benzyl)pyrrolidine-2-carboxamide. (SIAIS074026)

According to the procedures for the preparation of Compound Example 1, Ceritinib and intermediate LM (SIAIS074020) was used to prepare SIAIS074026 (white solid, 32.0 mg, 76%). $^1$H NMR (500 MHz, MeOD) δ 8.89 (s, 1H), 8.39 (d, J=8.3 Hz, 1H), 8.17 (s, 1H), 7.96 (dd, J=8.0, 1.5 Hz, 1H), 7.70 (t, J=7.8 Hz, 1H), 7.56 (s, 1H), 7.51-7.37 (m, 5H), 6.84 (s, 1H), 4.71 (d, J=13.0 Hz, 1H), 4.67-4.46 (m, 5H), 4.35 (dd, J=15.3, 7.4 Hz, 1H), 4.11 (d, J=13.3 Hz, 1H), 3.90 (d, J=11.1 Hz, 1H), 3.80 (dd, J=10.9, 3.9 Hz, 1H), 3.39-3.32 (m, 2H), 3.23 (t, J=12.2 Hz, 1H), 3.02 (t, J=12.0 Hz, 1H), 2.72 (t, J=12.2 Hz, 1H), 2.50-2.40 (m, 5H), 2.34-2.15 (m, 6H), 2.12-2.00 (m, 2H), 1.83 (t, J=11.2 Hz, 1H), 1.78 (d, J=13.2 Hz, 1H), 1.67-1.51 (m, 6H), 1.36 (s, 3H), 1.29 (dd, J=6.0, 2.0 Hz, 8H), 1.25 (d, J=6.8 Hz, 6H), 1.02 (d, J=13.3 Hz, 9H). HRMS (ESI) calcd for C$_{61}$H$_{63}$ClN$_9$O$_8$S$_2{}^+$ [M+H]$^+$: 1168.5489, found, 1168.3009.

Compound Example 148: Synthesis of 4-((2-(3-(4-(4-(6-amino-5-((R)-1-(2,6-dichloro-3-fluorophenyl)ethoxy)pyridin-3-yl)-1H-pyrazol-1-yl)piperidin-1-yl)-3-oxopropoxy)ethyl)amino)-2-(2,6-dioxopiperidin-3-yl)isoindoline-1,3-dione. (SIAIS151049)

According to the procedures for the preparation of Compound Example 1, Crizotinib and intermediate LM (SIAIS151001) was used to prepare SIAIS151049 (yellow solid, 21.4 mg, 59%). $^1$H NMR (500 MHz, MeOD) δ 7.84 (dd, J=10.1, 6.3 Hz, 1H), 7.55-7.49 (m, 3H), 7.48-7.43 (m, 1H), 7.35-7.26 (m, 1H), 7.12-7.05 (m, 1H), 7.05-6.99 (m, 1H), 6.90 (dd, J=12.7, 6.8 Hz, 1H), 6.36-6.28 (m, 1H), 5.02-4.97 (m, 1H), 4.65 (d, J=13.5 Hz, 1H), 4.44-4.38 (m, 1H), 4.20 (d, J=13.3 Hz, 1H), 3.91-3.77 (m, 2H), 3.75-3.68 (m, 2H), 3.51-3.45 (m, 2H), 3.29-3.21 (m, 1H), 2.86-2.77 (m, 3H), 2.74-2.60 (m, 3H), 2.12 (d, J=11.7 Hz, 2H), 2.08-2.01 (m, 1H), 1.99-1.84 (m, 5H). HRMS (ESI) calcd for $C_{39}H_{40}Cl_2FN_8O_7^+$ [M+H]$^+$: 821.2376; found, 821.2334.

Compound Example 149: Synthesis of 4-((2-(2-(3-(4-(4-(6-amino-5-((R)-1-(2,6-dichloro-3-fluorophenyl) ethoxy)pyridin-3-yl)-1H-pyrazol-1-yl)piperidin-1-yl)-3-oxopropoxy)ethoxy)ethyl)amino)-2-(2,6-dioxopiperidin-3-yl)isoindoline-1,3-dione. (SIAIS151050)

According to the procedures for the preparation of Compound Example 1, Crizotinib and intermediate LM (SIAIS151004) was used to prepare SIAIS151050 (yellow solid, 31.8 mg, 83%). $^1$H NMR (500 MHz, MeOD) δ 7.88 (d, J=5.5 Hz, 1H), 7.61-7.56 (m, 1H), 7.55-7.49 (m, 2H), 7.48-7.41 (m, 1H), 7.31-7.27 (m, 1H), 7.08 (d, J=1.7 Hz, 1H), 6.98-6.90 (m, 2H), 6.32-6.27 (m, 1H), 5.06-4.99 (m, 1H), 4.64 (d, J=13.2 Hz, 1H), 4.44-4.36 (m, 1H), 4.15 (d, J=13.7 Hz, 1H), 3.85-3.71 (m, 2H), 3.70-3.61 (m, 6H), 3.40-3.34 (m, 2H), 3.25 (t, J=13.0 Hz, 1H), 2.90-2.66 (m, 5H), 2.60-2.52 (m, 1H), 2.14-2.05 (m, 3H), 2.01-1.83 (m, 5H). HRMS (ESI) calcd for $C_{41}H_{44}Cl_2FN_8O_8^+$ [M+H]$^+$: 865.2638; found, 865.2602.

Compound Example 150: Synthesis of 4-((2-(2-(2-(3-(4-(4-(6-amino-5-((R)-1-(2,6-dichloro-3-fluorophenyl) ethoxy)pyridin-3-yl)-1H-pyrazol-1-yl)piperidin-1-yl)-3-oxopropoxy)ethoxy)ethoxy)ethyl)amino)-2-(2,6-dioxopiperidin-3-yl)isoindoline-1,3-dione. (SIAIS151051)

According to the procedures for the preparation of Compound Example 1, Crizotinib and intermediate LM (SIAIS151005) was used to prepare SIAIS151051 (yellow solid, 36.7 mg, 91%). $^1$H NMR (500 MHz, MeOD) δ 7.91 (d, J=1.6 Hz, 1H), 7.60 (s, 1H), 7.56-7.54 (m, 1H), 7.52-7.46 (m, 2H), 7.31-7.27 (t, J=8.6 Hz, 1H), 7.12-7.08 (m, 1H), 7.01-6.92 (m, 2H), 6.33-6.27 (m, 1H), 5.07-5.01 (m, 1H), 4.63 (d, J=11.1 Hz, 1H), 4.45-4.39 (m, 1H), 4.16 (d, J=13.5 Hz, 1H), 3.80-3.70 (m, 2H), 3.66-3.59 (m, 10H), 3.45-3.34 (m, 2H), 3.29-3.24 (m, 1H), 2.87-2.64 (m, 5H), 2.61-2.52 (m, 1H), 2.19-2.06 (m, 3H), 2.03-1.83 (m, 5H). HRMS (ESI) calcd for $C_{43}H_{48}Cl_2FN_8O_9^+$ [M+H]$^+$: 909.2900; found, 909.3068.

Compound Example 151: Synthesis of 4-((15-(4-(4-(6-amino-5-((R)-1-(2,6-dichloro-3-fluorophenyl) ethoxy)pyridin-3-yl)-1H-pyrazol-1-yl)piperidin-1-yl)-15-oxo-3,6,9,12-tetraoxapentadecyl)amino)-2-(2,6-dioxopiperidin-3-yl)isoindoline-1,3-dione. (SIAIS151060)

According to the procedures for the preparation of Compound Example 1, Crizotinib and intermediate LM (SIAIS151006) was used to prepare SIAIS151060 (yellow solid, 27.7 mg, 65%). $^1$H NMR (500 MHz, MeOD) δ 7.92 (s, 1H), 7.59 (d, J=17.3 Hz, 2H), 7.52-7.42 (m, 2H), 7.29 (td, J=8.7, 1.8 Hz, 1H), 7.11 (d, J=1.6 Hz, 1H), 7.02-6.98 (m, 2H), 6.33-6.29 (m, 1H), 5.03 (dd, J=12.8, 5.5 Hz, 1H), 4.62 (d, J=13.2 Hz, 1H), 4.48-4.38 (m, 1H), 4.16 (d, J=13.4 Hz, 1H), 3.77-3.73 (m, 2H), 3.69-3.66 (m, 2H), 3.63-3.59 (m, 12H), 3.45-3.38 (m, 2H), 3.29-3.25 (m, 1H), 2.89-2.80 (m, 2H), 2.78-2.68 (m, 3H), 2.64-2.59 (m, 2H), 2.17-2.07 (m, 3H), 2.03-1.86 (m, 5H). HRMS (ESI) calcd for $C_{45}H_{52}Cl_2FN_8O_{10}^+$ [M+H]$^+$: 953.3162; found, 953.4072.

Compound Example 152: Synthesis of 4-((18-(4-(4-(6-amino-5-((R)-1-(2,6-dichloro-3-fluorophenyl) ethoxy)pyridin-3-yl)-1H-pyrazol-1-yl)piperidin-1-yl)-18-oxo-3,6,9,12,15-pentaoxaoctadecyl)amino)-2-(2,6-dioxopiperidin-3-yl)isoindoline-1,3-dione. (SIAIS151061)

According to the procedures for the preparation of Compound Example 1, Crizotinib and intermediate LM (SIAIS151007) was used to prepare SIAIS151061 (yellow solid, 27.0 mg, 61%). $^1$H NMR (500 MHz, MeOD) δ 7.93 (s, 1H), 7.60 (d, J=14.4 Hz, 2H), 7.53-7.47 (m, 2H), 7.29 (t, J=8.6 Hz, 1H), 7.11 (s, 1H), 7.02-6.99 (m, 2H), 6.34-6.28 (m, 1H), 5.03 (dd, J=12.8, 5.5 Hz, 1H), 4.63 (d, J=12.9 Hz, 1H), 4.48-4.38 (m, 1H), 4.15 (d, J=13.9 Hz, 1H), 3.77-3.73 (m, 2H), 3.72-3.66 (m, 2H), 3.63 (s, 3H), 3.62-3.55 (m, 13H), 3.44-3.41 (m, 2H), 3.29-3.25 (m, 1H), 2.87-2.59 (m, 6H), 2.20-2.06 (m, 3H), 2.01-1.84 (m, 5H). HRMS (ESI) calcd for $C_{47}H_{56}Cl_2FN_8O_{11}^+$ [M+H]$^+$: 997.3424; found, 997.4381.

Compound Example 153: Synthesis of 4-((2-(4-(4-(6-amino-5-((R)-1-(2,6-dichloro-3-fluorophenyl) ethoxy)pyridin-3-yl)-1H-pyrazol-1-yl)piperidin-1-yl)-2-oxoethyl)amino)-2-(2,6-dioxopiperidin-3-yl) isoindoline-1,3-dione. (SIAIS151083)

According to the procedures for the preparation of Compound Example 1, Crizotinib and intermediate LM (SIAIS151025) was used to prepare SIAIS151083 (yellow solid, 18.4 mg, 54%). $^1$H NMR (500 MHz, MeOD) δ 7.95 (s, 1H), 7.64 (s, 1H), 7.59 (d, J=1.4 Hz, 1H), 7.56-7.45 (m, 2H), 7.28 (t, J=8.5 Hz, 1H), 7.15 (s, 1H), 7.05 (d, J=7.1 Hz, 1H), 6.98 (dd, J=8.5, 2.5 Hz, 1H), 6.34 (q, J=6.6 Hz, 1H), 5.06 (dd, J=12.5, 5.4 Hz, 1H), 4.64 (d, J=13.5 Hz, 1H), 4.55-4.46 (m, 1H), 4.29-4.16 (m, 2H), 4.08 (d, J=13.3 Hz, 1H), 3.35-3.31 (m, 1H), 2.95 (t, J=12.6 Hz, 1H), 2.88-2.80 (m, 1H), 2.78-2.64 (m, 2H), 2.24-2.04 (m, 4H), 1.94 (d, J=6.6 Hz, 4H). HRMS (ESI) calcd for $C_{36}H_{34}Cl_2FN_8O_6$ [M+H]$^+$: 763.1957; found, 763.1696.

Compound Example 154: Synthesis of 4-((3-(4-(4-(6-amino-5-((R)-1-(2,6-dichloro-3-fluorophenyl) ethoxy)pyridin-3-yl)-1H-pyrazol-1-yl)piperidin-1-yl)-3-oxopropyl)amino)-2-(2,6-dioxopiperidin-3-yl) isoindoline-1,3-dione. (SIAIS151084)

According to the procedures for the preparation of Compound Example 1, Crizotinib and intermediate LM (SIAIS151026) was used to prepare SIAIS151084 (yellow solid, 22 mg, 64%). $^1$H NMR (500 MHz, MeOD) δ 7.85 (s, 1H), 7.65-7.54 (m, 3H), 7.51 (dd, J=8.9, 4.7 Hz, 1H), 7.29 (t, J=8.6 Hz, 1H), 7.16-7.11 (m, 2H), 7.05-7.01 (m, 1H), 6.35 (q, J=6.0 Hz, 1H), 5.06-4.97 (m, 1H), 4.65 (d, J=11.5 Hz, 1H), 4.45-4.39 (m, 1H), 4.12-4.06 (m, 1H), 3.75-3.63 (m, 2H), 3.26-3.22 (m, 1H), 2.89-2.78 (m, 3H), 2.74-2.61 (m, 3H), 2.10-2.00 (m, 3H), 1.95 (d, J=6.6 Hz, 3H), 1.82-1.70 (m, 2H). HRMS (ESI) calcd for $C_{37}H_{36}Cl_2FN_8O_6$ [M+H]$^+$: 777.2113; found, 777.1842.

Compound Example 155: Synthesis of 4-((4-(4-(4-(6-amino-5-((R)-1-(2,6-dichloro-3-fluorophenyl) ethoxy)pyridin-3-yl)-1H-pyrazol-1-yl)piperidin-1-yl)-4-oxobutyl)amino)-2-(2,6-dioxopiperidin-3-yl) isoindoline-1,3-dione. (SIAIS151081)

According to the procedures for the preparation of Compound Example 1, Crizotinib and intermediate LM (SIAIS151019) was used to prepare SIAIS151081 (yellow solid, 26.3 mg, 75%). $^1$H NMR (500 MHz, MeOD) δ 7.88 (d, J=2.8 Hz, 1H), 7.62 (s, 1H), 7.57 (d, J=1.4 Hz, 1H), 7.54-7.48 (m, 2H), 7.31-7.25 (m, 1H), 7.14 (d, J=1.3 Hz, 1H), 7.10 (d, J=8.6 Hz, 1H), 7.02-6.94 (m, 1H), 6.34 (q, J=6.6 Hz, 1H), 5.07-4.99 (m, 1H), 4.64 (d, J=13.5 Hz, 1H), 4.48-4.38 (m, 1H), 4.08 (d, J=13.5 Hz, 1H), 3.42 (t, J=6.7 Hz, 2H), 3.25 (t, J=13.0 Hz, 1H), 2.87-2.80 (m, 2H), 2.75-2.65 (m, 2H), 2.62-2.57 (d, J=7.1 Hz, 1H), 2.56-2.50 (m, 1H), 2.16-2.04 (m, 3H), 2.03-1.96 (m, 2H), 1.95 (d, J=6.6 Hz, 3H), 1.87-1.77 (m, 2H). HRMS (ESI) calcd for $C_{38}H_{38}C_{12}FN_8O_6$ [M+H]$^+$: 791.2270; found, 791.1991.

Compound Example 156: Synthesis of 4-((5-(4-(4-(6-amino-5-((R)-1-(2,6-dichloro-3-fluorophenyl) ethoxy)pyridin-3-yl)-1H-pyrazol-1-yl)piperidin-1-yl)-5-oxopentyl)amino)-2-(2,6-dioxopiperidin-3-yl) isoindoline-1,3-dione. (SIAIS151082)

According to the procedures for the preparation of Compound Example 1, Crizotinib and intermediate LM (SIAIS151020) was used to prepare SIAIS151082 (yellow solid, 25.0 mg, 70%). $^1$H NMR (500 MHz, MeOD) δ 7.91 (s, 1H), 7.64-7.62 (m, 2H), 7.59 (m, 1H), 7.55-7.49 (m, 2H), 7.28 (t, J=8.6 Hz, 1H), 7.15 (s, 1H), 7.06 (d, J=8.6 Hz, 1H), 7.01 (d, J=7.1 Hz, 1H), 6.37-6.32 (m, 1H), 5.06-4.95 (m, 1H), 4.63 (d, J=14.0 Hz, 1H), 4.48-4.42 (m, 1H), 4.08 (d, J=13.3 Hz, 1H), 3.41-3.35 (m, 2H), 3.30-3.24 (m, 1H), 2.88-2.76 (m, 2H), 2.75-2.62 (m, 2H), 2.55-2.48 (m, 2H), 2.17-2.03 (m, 3H), 1.95 (d, J=6.6 Hz, 3H), 1.91-1.78 (m, 2H), 1.77-1.68 (m, 4H). HRMS (ESI) calcd for $C_{39}H_{40}C_{12}FN_8O_6$[M+H]$^+$: 805.2426; found 805.2123.

Compound Example 157: Synthesis of 4-((6-(4-(4-(6-amino-5-((R)-1-(2,6-dichloro-3-fluorophenyl) ethoxy)pyridin-3-yl)-1H-pyrazol-1-yl)piperidin-1-yl)-6-oxohexyl)amino)-2-(2,6-dioxopiperidin-3-yl) isoindoline-1,3-dione. (SIAIS151085)

According to the procedures for the preparation of Compound Example 1, Crizotinib and intermediate LM (SIAIS151027) was used to prepare SIAIS151085 (yellow solid, 19.5 mg, 54%). $^1$H NMR (500 MHz, MeOD) δ 7.91 (s, 1H), 7.63 (s, 1H), 7.58 (d, J=1.5 Hz, 1H), 7.53-7.49 (m, 2H), 7.28 (t, J=8.6 Hz, 1H), 7.16-7.11 (m, 1H), 7.02 (t, J=7.5 Hz, 1H), 6.99 (dd, J=7.1, 1.8 Hz, 1H), 6.36-6.31 (m, 1H), 5.04-5.00 (m, 1H), 4.64 (d, J=13.5 Hz, 1H), 4.48-4.42 (m, 1H), 4.10 (d, J=13.7 Hz, 1H), 3.35 (t, J=6.8 Hz, 2H), 3.30-3.23 (m, 1H), 2.87-2.78 (m, 2H), 2.75-2.65 (m, 2H), 2.53-2.43 (m, 2H), 2.21-2.05 (m, 3H), 1.95 (d, J=6.7 Hz, 3H), 1.93-1.79 (m, 2H), 1.74-1.66 (m, 4H), 1.54-1.47 (m, 2H). HRMS (ESI) calcd for $C_{40}H_{42}C_{12}FN_8O_6$[M+H]$^+$: 819.2583; found 819.2583.

Compound Example 158: Synthesis of N-(1-(4-((5-chloro-4-((2-(dimethylphosphoryl)phenyl)amino) pyrimidin-2-yl)amino)-3-methoxyphenyl)piperidin-4-yl)-4-((2-(2,6-dioxopiperidin-3-yl)-1,3-dioxoisoindolin-4-yl)amino)-N-methylbutanamide. (SIAIS220030)

Scheme 16

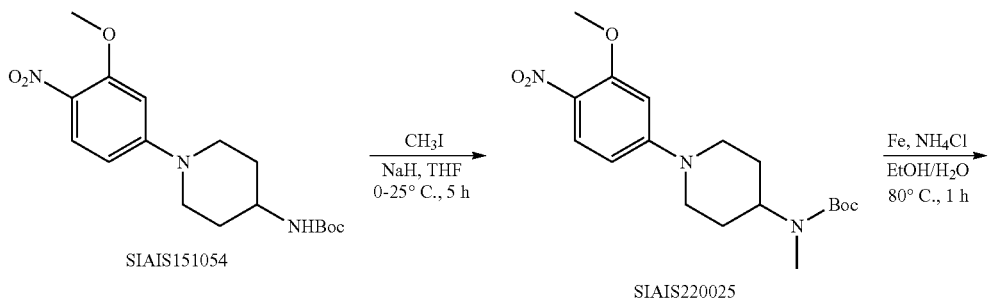

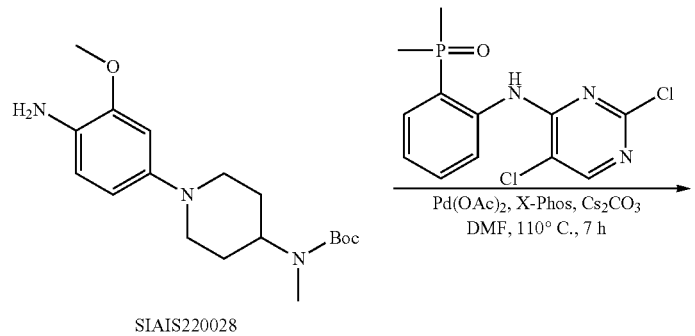

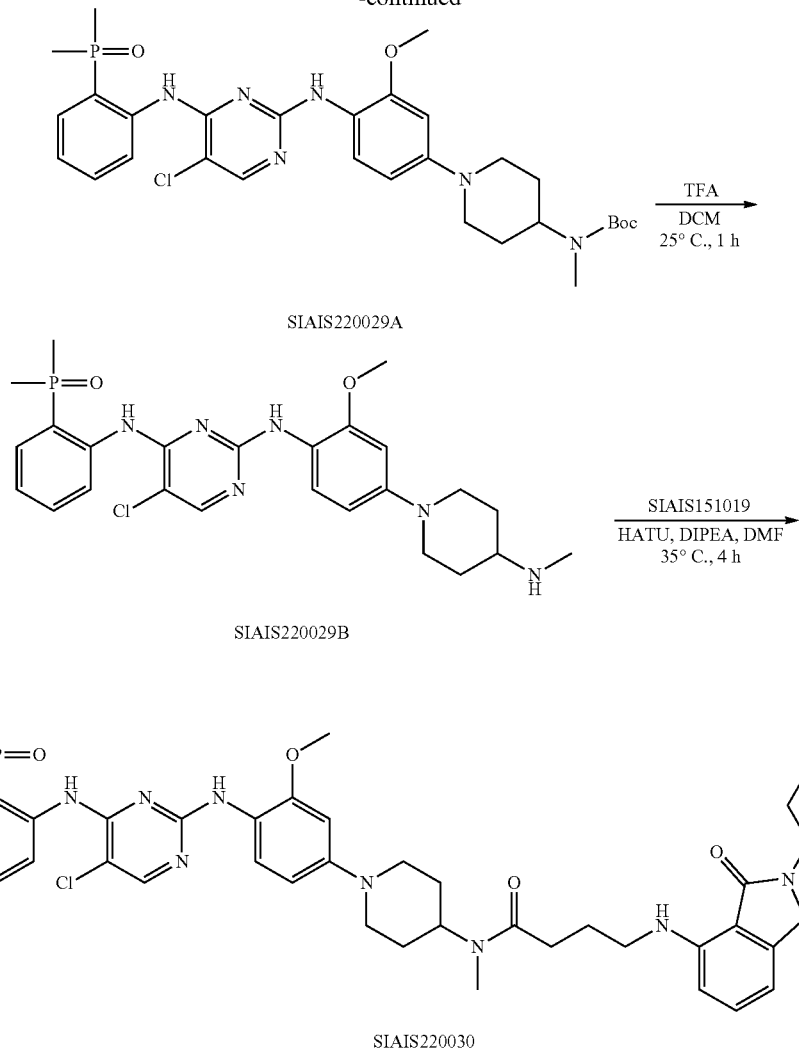

Step 1: Synthesis of tert-butyl (1-(3-methoxy-4-nitrophenyl)piperidin-4-yl)(methyl) carbamate (SIAIS220025) According to Scheme 16

SIAIS151054 (1 g, 2.85 mmol) and anhydrous tetrahydrofuran (15 mL) were added to a three-necked flask, the mixture was evacuated and replaced with nitrogen three times, then NaH (60% in oil, 342 mg, 8.55 mmol) was added in portions under ice-water bath, the resulting mixture was stirred under ice-water bath for 1 h, then methyl iodide (2 g, 8.55 mmol) was slowly added dropwise to the reaction system and the solution was stirred at room temperature for 5 h. When the reaction was complete, water was added slowly under ice-water bath to quench the reaction, the resulting solution was extracted with ethyl acetate, washed with water, brine and dried over anhydrous sodium sulfate, the solvent was evaporated under reduced pressure to give a yellow oil (SIAIS220025), the crude was used for the following reaction without further purification. (1000 mg, 96%) $^1$H NMR (500 MHz, CDCl$_3$) δ 7.99 (d, J=9.4 Hz, 1H), 6.42 (dd, J=9.4, 2.5 Hz, 1H), 6.31 (d, J=2.4 Hz, 1H), 4.38-4.20 (m, 1H), 3.98 (d, J=13.0 Hz, 2H), 3.94 (s, 3H), 3.01 (t, J=12.0 Hz, 2H), 2.72 (s, 3H), 1.80-1.72 (m, 4H), 1.47 (s, 9H). HRMS (ESI) calcd for C18H25N3O5$^+$ [M+H]$^+$, 366.2023; found, 366.2019.

Step 2: Synthesis of tert-butyl (1-(4-amino-3-methoxyphenyl)piperidin-4-yl)(methyl) carbamate (SIAIS220028) According to Scheme 16

SIAIS220025 (900 mg, 2.46 mmol), ethanol (15 mL) and water (15 mL) were added to a egg-shaped flask, followed by ammonium chloride (520 mg, 9.84 mmol) and iron powder (700 mg, 12.30 mmol), then the resulting mixture was slowly heated to reflux for 2 h. When the reaction was complete, the crude mixture was concentrated under reduced pressure, extracted with DCM (3×50 mL), the combined organic layer was washed with water and brine (20 mL), then dried over anhydrous Na$_2$SO$_4$ and concentrated in vacuum to afford SIAIS220028 in 85% yield (700 mg) as a white solid. The crude was used for the following reaction without further purification. 1H NMR (500 MHz, CDCl$_3$) δ 6.63 (d, J=8.3 Hz, 1H), 6.52 (d, J=2.4 Hz, 1H), 6.42 (dd, J=8.3, 2.4 Hz, 1H), 3.83 (s, 3H), 3.56-3.50 (m, 3H), 2.77 (s, 3H), 2.70 (t, J=11.5 Hz, 2H), 1.91-1.83 (m, 2H), 1.75-1.70 (m, 2H), 1.47 (s, 9H). HRMS (ESI) calcd for C$_{18}$H$_{30}$N$_3$O$_3$$^+$ [M+H]$^+$, 336.2282; found, 336.2286.

Step 3: Synthesis of tert-butyl (1-(4-((5-chloro-4-((2-(dimethylphosphoryl)phenyl)amino)pyrimidin-2-yl)amino)-3-methoxyphenyl)Piperidin-4-yl)(methyl)carbamate (SIAIS220029A) according to scheme 16

To a solution of 2,5-dichloro-N-(2-(dimethylphosphoryl)phenyl)pyrimidin-4-amine (405 mg, 1.28 mmol) in anhydrous DMF (10 mL) were added SIAIS220028 (410 mg, 1.22 mmol), Pd(OAc)$_2$ (29 mg, 0.13 mmol), Xantphos (64 mg, 0.13 mmol) and Cs$_2$CO$_3$(1.26 g, 3.84 mmol) in a 100 mL egg-shaped flask, the solution was purged and refilled with argon three times. Then the mixture was slowly heated to 110° C. and stirred for 7 h. After the starting material was consumed, the reaction mixture was filtered through a pad of silica gel, then extracted with ethyl acetate, washed with water and brine, dried over anhydrous Na$_2$SO$_4$. The solvent was evaporated under the reduced pressure and the residue was purified by silica gel chromatography (eluent: MeOH/DCM=3:97) to give the title compound (300 mg, 38%) as a brown solid. $^1$H NMR (500 MHz, CDCl$_3$) δ 10.80 (s, 1H), 8.62 (dd, J=8.4, 4.4 Hz, 1H), 8.09 (d, J=9.5 Hz, 2H), 7.49 (t, J=7.9 Hz, 1H), 7.31-7.27 (m, 1H), 7.12 (dd, J=10.4, 4.3 Hz, 1H), 6.56 (d, J=2.1 Hz, 1H), 6.50 (dd, J=8.8, 2.3 Hz, 1H), 4.30-4.10 (m, 1H), 3.88 (d, J=8.4 Hz, 3H), 3.65 (d, J=12.2 Hz, 2H), 2.78 (s, 3H), 2.84-2.72 (m, 2H), 1.93-1.86 (m, 2H), 1.85 (s, 3H), 1.82 (s, 3H), 1.79-1.73 (m, 2H), 1.48 (s, 9H). HRMS (ESI) calcd for C$_{30}$H$_{41}$ClN$_6$O$_4$P$^+$ [M+H]$^+$, 615.2610; found, 615.2606.

Step 4: Synthesis of SIAIS220029B according to scheme 16

To a solution of SIAIS220029A (250 mg, 0.40 mmol) in DCM (6 mL) was added TFA (2 mL) at room temperature, the resulting solution was stirred at room temperature for 1 h. When the reaction was complete detected by LC-MS, most of the solvent was removed under the reduced pressure, 10 mL 10% MeOH/DCM was added, the pH of the solution was adjusted to 8-9 with saturated NaHCO$_3$ solution, then extracted with DCM, dried over anhydrous Na$_2$SO$_4$. The solvent was evaporated under the reduced pressure to afford SIAIS220029B. The crude was used for the following reaction without further purification.

Step 5: Synthesis of N-(1-(4-((5-chloro-4-((2-(dimethylphosphoryl)phenyl)amino)pyrimidin-2-yl)amino)-3-methoxyphenyl)piperidin-4-yl)-4-((2-(2,6-dioxopiperidin-3-yl)-1,3-dioxoisoindolin-4-yl)amino)-N-methylbutanamide (SIAIS220030) According to Scheme 16

SIAIS220029B (15 mg, 0.029 mmol, 1 equiv), SIAIS151019 (10.4 mg, 0.029 mmol, 1 equiv)), HATU (22.1 mg, 0.058 mmol, 2 equiv), DIPEA (18.7 mg, 0.145 mmol, 5 equiv) and anhydrous DMF (2 mL) were added sequentially in a 25 mL flask at RT. The resulting reaction mixture was stirred at room temperature overnight. After the reaction was complete detected by LC-MS, the reaction solution was purified by preparative HPLC, eluent (v/v): acetonitrile/(water+0.5% HCl)=10%-100%, after concentration under reduced pressure and freeze-drying, the desired product SIAIS220030 was obtained as yellow solid (10.2 mg, 76%). $^1$H NMR (500 MHz, MeOD) δ 8.34 (s, 1H), 8.06 (s, 1H), 7.69-7.60 (m, 2H), 7.56 (dt, J=8.4, 6.5 Hz, 2H), 7.31 (dd, J=15.9, 8.0 Hz, 1H), 7.13 (d, J=8.6 Hz, 1H), 7.04 (dd, J=7.0, 4.4 Hz, 1H), 6.84-6.48 (m, 2H), 5.05 (dd, J=12.6, 5.5 Hz, 1H), 4.95 (dd, J=12.5, 5.5 Hz, 1H), 3.87 (s, 3H), 3.87-3.61 (m, 3H), 3.46-3.40 (m, 2H), 2.94 (s, 2H), 2.85-2.81 (m, 2H), 2.76-2.70 (m, 2H), 2.64-2.58 (m, 2H), 2.53 (t, J=6.9 Hz, 1H), 2.17-2.05 (m, 1H), 2.03-1.95 (m, 4H), 1.87 (d, J=2.5 Hz, 3H), 1.84 (d, J=2.5 Hz, 3H), 1.76-1.70 (m, 2H). HRMS (ESI) calcd for C$_{42}$H$_{48}$ClN$_9$O$_7$P$^+$ [M+H]$^+$, 856.3097; found, 856.3095.

Compound Example 159: Synthesis of 4-((4-((1-(4-((5-chloro-4-((2-(dimethylphosphoryl)phenyl)amino)pyrimidin-2-yl)amino)-3-methoxyphenyl)piperidin-4-yl)amino)butyl)amino)-2-(2,6-dioxopiperidin-3-yl)isoindoline-1,3-dione. (SIAIS220026)

Scheme 17

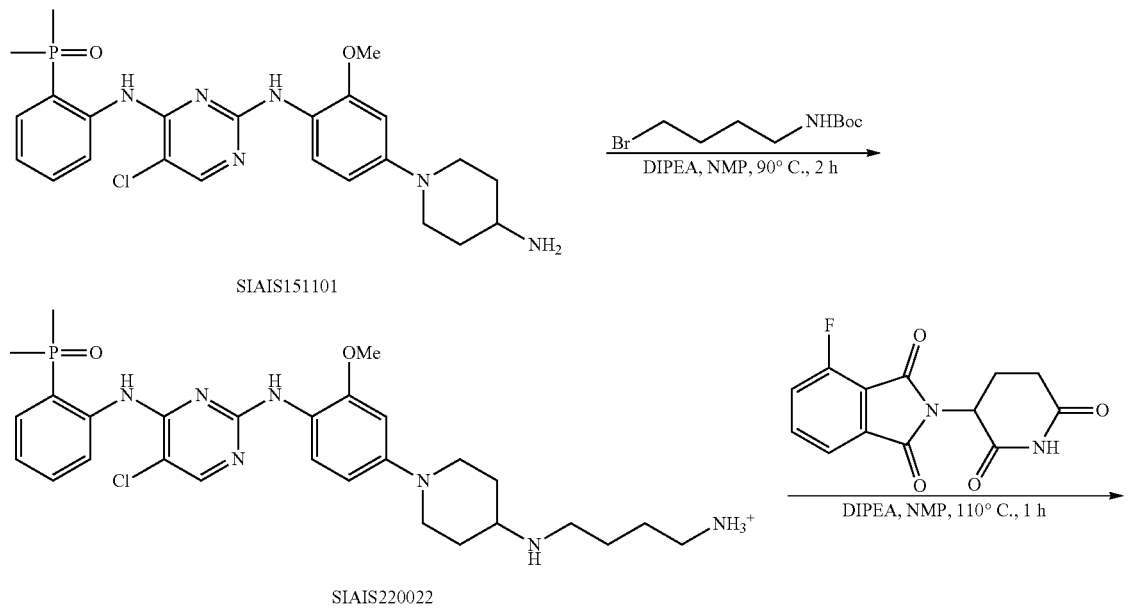

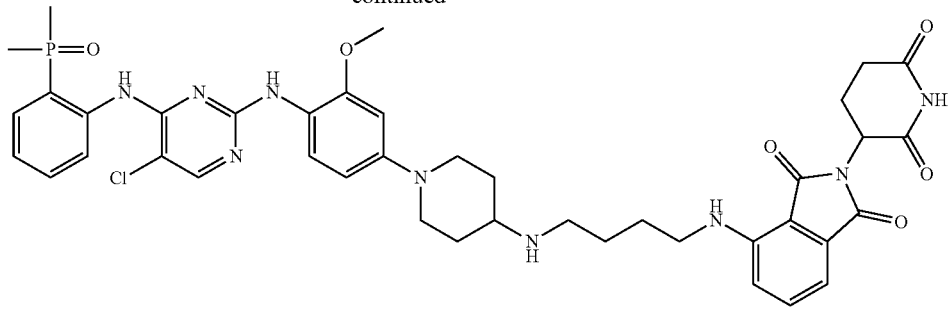

SIAIS220026

Step 1: Synthesis of (2-((2-((4-(4-((4-aminobutyl)amino)piperidin-1-yl)-2-methoxyphenyl)amino)-5-chloropyrimidine-4-yl)amino)phenyl)dimethylphosphine oxide (SIAIS220022) according to scheme 17

SIAIS151101 (100 mg, 0.20 mmol), tert-butyl (4-bromobutyl) carbamate (76 mg, 0.30 mmol), DIPEA (129 mg, 1.00 mmol) and NMP (3 mL) were added sequentially in a 50 mL egg-shaped flask at RT. The resulting reaction mixture was slowly heated to 90° C. under an atmosphere of nitrogen and then stirred for 2 h. After the reaction was complete detected by LC-MS, the reaction solution was purified by reverse phase chromatography, eluent (v/v): acetonitrile/(water+0.5% HCl)=10%-100%, after concentration under reduced pressure and freeze-drying, the desired product SIAIS220022 was obtained as a brown solid (30 mg, 22%). $^1$H NMR (500 MHz, MeOD) δ 8.32 (dd, J=8.0, 4.4 Hz, 1H), 8.03 (s, 1H), 7.68 (d, J=8.7 Hz, 1H), 7.62 (dd, J=14.0, 6.4 Hz, 1H), 7.52 (t, J=7.9 Hz, 1H), 7.27 (t, J=6.9 Hz, 1H), 6.67 (d, J=2.5 Hz, 1H), 6.45 (dd, J=8.8, 2.5 Hz, 1H), 3.85 (s, 3H), 3.75-3.72 (m, 2H), 3.22-3.11 (m, 1H), 3.05 (dd, J=17.3, 10.1 Hz, 2H), 2.99 (t, J=6.7 Hz, 2H), 2.78 (t, J=11.5 Hz, 2H), 2.20 (d, J=11.3 Hz, 2H), 1.85 (s, 3H), 1.82 (s, 3H), 1.82-1.71 (m, 6H). HRMS (ESI) calcd for $C_{28}H_{40}ClN_7O_2P^+$ [M+H]$^+$, 572.2664; found, 572.2660.

Step 2: Synthesis of 4-((4-((1-(4-((5-chloro-4-((2-(dimethylphosphoryl)phenyl)amino)pyrimidin-2-yl)amino)-3-methoxyphenyl)piperidin-4-yl)amino)butyl)amino)-2-(2,6-dioxopiperidin-3-yl) isoindolin-1,3-dione (SIAIS220026) According to Scheme 17

SIAIS220022 (25 mg, 0.04 mmol), 2-(2,6-dioxopiperidin-3-yl)-4-fluoroisoindolin-1,3-dione (11 mg, 0.04 mmol), DIPEA (26 mg, 0.20 mmol) and NMP (1 mL) were added sequentially in a 25 mL egg-shaped flask at RT. The resulting reaction mixture was slowly heated to 110° C. under an atmosphere of nitrogen and then stirred for 1 h. After the reaction was complete detected by LC-MS, the reaction solution was purified by reverse phase chromatography, eluent (v/v): acetonitrile/(water+0.5% HCl)=10%-100%, after concentration under reduced pressure and freeze-drying, the desired product SIAIS220026 was obtained as a yellow solid (2.3 mg, 17%). $^1$H NMR (500 MHz, MeOD) δ 8.35-8.33 (m, 1H), 8.06 (s, 1H), 7.88-8.86 (m, 1H), 7.74 (d, J=7.3 Hz, 1H), 7.66-7.63 (m, 2H), 7.57-7.45 (m, 2H), 7.28 (t, J=7.3 Hz, 1H), 6.68 (d, J=2.3 Hz, 1H), 6.47 (d, J=8.5 Hz, 1H), 5.14-5.12 (m, 1H), 3.86 (s, 3H), 3.75-3.72 (m, 3H), 3.19-2.99 (m, 3H), 2.90-2.85 (m, 1H), 2.79-2.73 (m, 2H), 2.53-2.45 (m, 2H), 2.30-2.13 (m, 6H), 1.87-1.76 (m, 10H). HRMS (ESI) calcd for $C_{41}H_{48}ClN_9O_6P^+$ [M+H]$^+$, 828.3148; found, 828.3143.

Compound Example 160: Synthesis of 4-((2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)ethyl)amino)-2-(2,6-dioxopiperidin-3-yl)isoindoline-1,3-dione. (SIAIS220027)

Synthesis of Brigatinib Analogue D (SIAIS220023)

Brigatinib Analogue D was synthesized according to scheme 1, using similar procedures for the preparation of Brigatinib Analogue A in Intermediate Example 1.

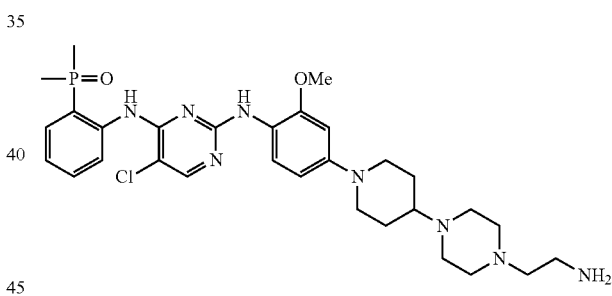

(2-((2-((4-(4-(4-(2-aminoethyl)piperazin-1-yl)piperidin-1-yl)-2-methoxyphenyl)amino)-5-chloropyrimidin-4-yl)amino)phenyl)dimethylphosphine oxide (SIAIS220023), yellow solid, 30 mg, 27% yield. $^1$H NMR (500 MHz, MeOD) δ 8.33 (dd, J=8.2, 4.5 Hz, 1H), 8.04 (s, 1H), 7.67 (d, J=8.7 Hz, 1H), 7.65-7.60 (m, 1H), 7.53 (t, J=7.9 Hz, 1H), 7.28 (t, J=6.9 Hz, 1H), 6.68 (d, J=2.4 Hz, 1H), 6.47 (dd, J=8.7, 2.4 Hz, 1H), 3.88-3.80 (m, 2H), 3.65 (s, 3H), 3.65-3.61 (m, 1H), 3.36-3.30 (m, 8H), 3.12-3.08 (m, 2H), 2.81 (t, J=11.7 Hz, 2H), 2.77-2.72 (m, 2H), 2.28 (d, J=12.4 Hz, 2H), 1.95-1.89 (m, 2H), 1.85 (s, 3H), 1.83 (s, 3H). HRMS (ESI) calcd for $C_{30}H_{43}ClN_8O_2P^+$ [M+H]$^+$: 613.2930, found 613.2925.

Synthesis of the Title Compound SIAIS220027

According to step 2 of the preparation of Compound Example 159, Brigatinib Analogue D (SIAIS220023) instead of SIAIS220022 was used to prepare SIAIS220027 (yellow solid, 3.1 mg, 23%). $^1$H NMR (500 MHz, MeOD) δ 8.33 (dd, J=8.3, 4.5 Hz, 1H), 8.04 (s, 1H), 7.69 (d, J=8.7

Hz, 1H), 7.64-7.56 (m, 2H), 7.53 (t, J=7.8 Hz, 1H), 7.27 (t, J=6.7 Hz, 1H), 7.08 (d, J=7.6 Hz, 2H), 6.69 (d, J=2.4 Hz, 1H), 6.46 (dd, J=8.7, 2.4 Hz, 1H), 5.34 (t, J=4.8 Hz, 1H), 5.07 (dd, J=12.6, 5.6 Hz, 1H), 4.60-4.56 (m, 4H), 3.86 (s, 3H), 3.79 (d, J=12.0 Hz, 2H), 3.64 (s, 1H), 2.88-2.86 (m, 1H), 2.77-2.75 (m, 2H), 2.21-2.17 (m, 4H), 2.16-2.10 (m, 1H), 1.85 (s, 3H), 1.82 (s, 3H), 1.63-1.57 (m, 2H), 1.40-1.36 (m, 2H). HRMS (ESI) calcd for $C_{43}H_{51}ClN_{10}O_6P^+$ [M+H]$^+$: 869.3414, found 869.3414.
Comparative Example 161: Synthesis of 4-((2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-2-oxoethyl)amino)-2-(1-methyl-2,6-dioxopiperidin-3-yl)isoindoline-1,3-dione (SIAIS1210003)
方案 18 Scheme 18
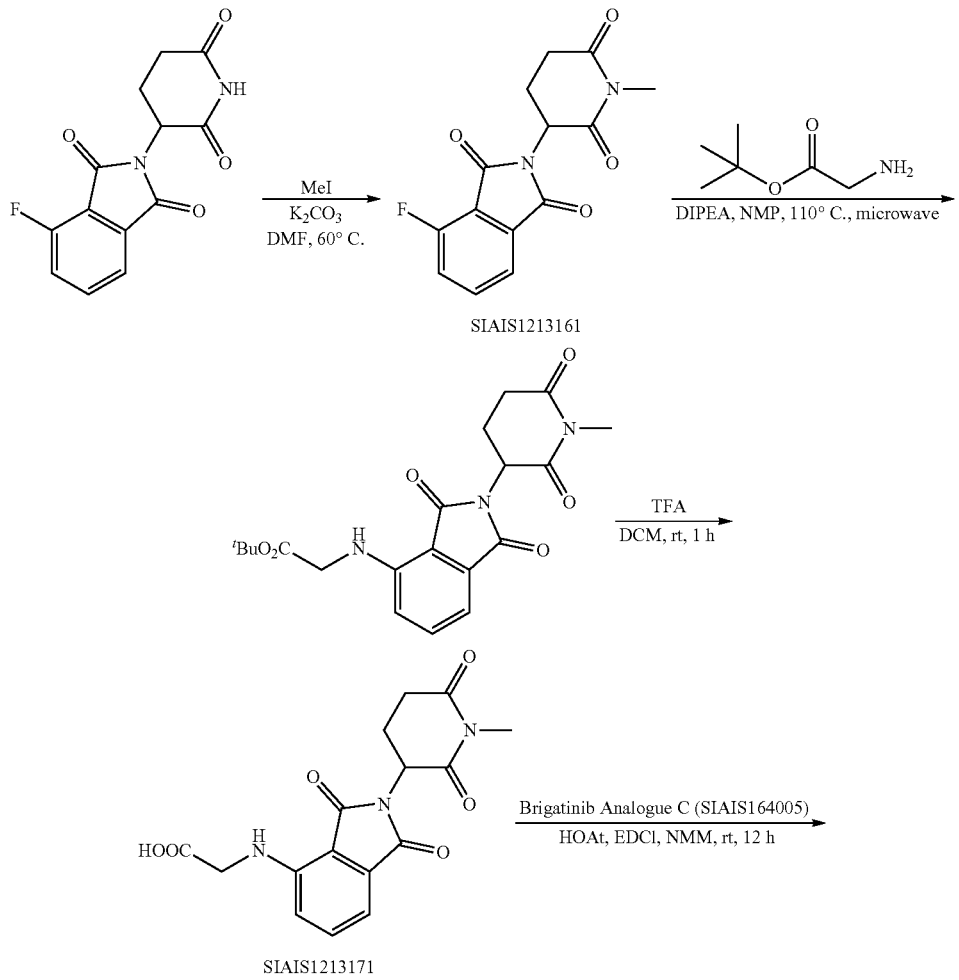
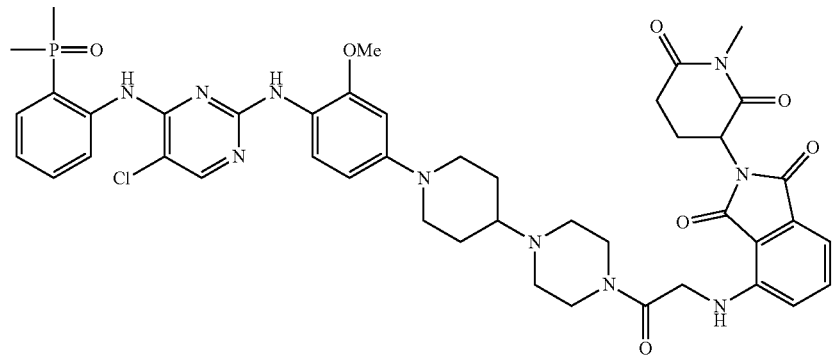
SIAIS1210003

Step 1: Synthesis of 4-fluoro-2-(1-methyl-2,6-dioxopiperidin-3-yl)isoindolin-1,3-dione (SIAIS1213161) According to Scheme 18

2-(2,6-dioxopiperidin-3-yl)-4-fluoroisoindolin-1,3-dione (2 g, 7.24 mmol), Potassium carbonate (2 g, 14.48 mmol) and DMF (8 mL) were added sequentially in a 50 mL egg-shaped flask at RT, then methyl iodide (2 g, 14.48 mmol) was slowly added dropwise to the reaction system under an atmosphere of nitrogen and the solution was slowly heated to 60° C. and stirred for 4 h. When the reaction was complete detected by LC-MS, the reaction solution was purified by reverse phase chromatography, eluent (v/v): acetonitrile/(water+0.5% HCl)=10%-100%, after concentration under reduced pressure and freeze-drying, the desired product SIAIS1213161 was obtained as a gray solid (736 mg, 35%). $^1$H NMR (500 MHz, DMSO) δ 7.97-7.93 (m, 1H), 7.79 (d, J=7.3 Hz, 1H), 7.74 (t, J=8.9 Hz, 1H), 5.22 (dd, J=13.1, 5.4 Hz, 1H), 3.02 (s, 3H), 2.99-2.92 (m, 1H), 2.80-2.75 (m, 1H), 2.58-2.52 (m, 1H), 2.11-2.05 (m, 1H). HRMS (ESI) calcd for $C_{14}H_{12}FN_2O_4^+$ [M+H]$^+$, 291.0776; found, 291.0771.

Step 2: Synthesis of (2-(1-methyl-2,6-dioxopiperidin-3-yl)-1,3-dioxoisoindololin-4-yl)aminoacetic acid (SIAIS1213171) According to Scheme 18

SIAIS1213161 (500 mg, 1.72 mmol), tert-butyl aminoacetate (339 mg, 2.59 mmol), DIPEA (668 mg, 5.17 mmol) and NMP (5 mL) were added sequentially in a 50 mL egg-shaped flask at RT. The resulting reaction mixture was slowly heated to 110° C. under an atmosphere of nitrogen and then stirred for 3 h. After the reaction was complete detected by LC-MS, the reaction solution was purified by reverse phase chromatography, eluent (v/v): acetonitrile/(water+0.5% HCl)=10%-100%, after concentration under reduced pressure and freeze-drying, the desired tert-butyl ester intermediate was obtained. This intermediate was added to a 25 mL flask, followed by DCM (5 mL) and TFA (2 mL), then stirred at room temperature for 1 h. After concentration under reduced pressure and freeze-drying, the desired product SIAIS1213171 was obtained as yellow solid (421 mg, 71% yield). $^1$H NMR (500 MHz, MeOD) δ 7.58 (dd, J=8.5, 7.2 Hz, 1H), 7.11 (d, J=7.0 Hz, 1H), 6.96 (d, J=8.5 Hz, 1H), 5.10 (dd, J=12.9, 5.5 Hz, 1H), 4.13 (s, 2H), 3.15 (s, 3H), 2.88 (d, J=4.0 Hz, 2H), 2.73-2.65 (m, 1H), 2.14-2.06 (m, 1H). HRMS (ESI) calcd for $C_{16}H_{16}N_3O_6^+$ [M+H]$^+$, 346.1034; found, 346.1030.

Step 3: Synthesis of 4-((2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-2-oxoethyl)amino)-2-(1-methyl-2,6-dioxopiperidin-3-yl)isoindoline-1,3-dione (SIAIS1210003) According to Scheme 18

Brigatinib Analogue C SIAIS164005 (15 mg, 0.026 mmol, 1 equiv), SIAIS1213171 (9 mg, 0.026 mmol, 1 equiv)), HOAT (7.1 mg, 0.052 mmol, 2 equiv), EDCI (10 mg, 0.052 mmol, 2 equiv) DMF (2 mL) and NMM (15.2 mg, 0.15 mmol, 5 equiv) were added sequentially in a reaction bottle at RT. The resulting reaction mixture was stirred at room temperature overnight. After the reaction was complete detected by LC-MS, the reaction solution was purified by preparative HPLC, eluent (v/v): acetonitrile/(water+0.5% HCl)=10%-100%, after concentration under reduced pressure and freeze-drying, the desired product SIAIS1210003 was obtained as yellow solid (8.8 mg, 43%). $^1$H NMR (500 MHz, MeOD) δ 8.41 (s, 1H), 8.09 (d, J=17.8 Hz, 1H), 7.69 (dd, J=14.1, 7.7 Hz, 1H), 7.65-7.55 (m, 2H), 7.39 (t, J=7.5 Hz, 1H), 7.36 (d, J=8.9 Hz, 1H), 7.12 (d, J=7.0 Hz, 1H), 7.02 (d, J=8.5 Hz, 1H), 6.78 (d, J=2.4 Hz, 1H), 6.61 (d, J=7.9 Hz, 1H), 5.11 (dd, J=12.5, 5.5 Hz, 1H), 4.28 (s, 2H), 3.99 (d, J=12.4 Hz, 2H), 3.88 (s, 3H), 3.71-3.34 (m, 9H), 3.16 (s, 3H), 2.99-2.82 (m, 3H), 2.79-2.70 (m, 2H), 2.29 (d, J=11.4 Hz, 2H), 2.19-2.08 (m, 1H), 2.03-1.94 (m, 2H), 1.89 (d, J=13.6 Hz, 6H). HRMS (ESI) calcd for $C_{44}H_{51}ClN_{10}O_7P^+$ [M+H]$^+$, 897.3363; found, 897.2919.

Bioactivity Assay

Biological Materials

Halt proteinase and phosphatase inhibitor (Thermo Fisher)
   Cell TITER BLUE detection kit (Promega)
   Cell TITER GLO detection kit (Promega)
   RPMI1640 and serum from (Gibico company)
   Cell Counting Kit-8 (CCK-8, WST) reagent (Dojindo)
   Fetal Bovine Serum (FBS) (Gibico)
   Penicillin-Streptomycin (Gibico)
   SuperSignal West Pico Chemiluminescent Substrate (Thermo Fisher)
   SuperSignal West Femto Maximum Sensitivity Substrate (Thermo Fisher)
   Cycloheximide (Sigma)
Antibodies: antibodies of ALK (#3633S) and p-ALK (#6962S), AKT (#4691S), p-AKT (#4060S), p-ERK (#4370) and ERK (#9107S) were purchased from Cell Signaling Technology, Tunulin and GAPDH antibody were purchased from Abcam.

Cell Culture

SR (NPM-ALK) and NCI-H2228 (EML4-ALK, V3) cells were purchased from ATCC. NCI-H3122 (EML4-ALK, V1) cells were from NCI (Bethesda, Md., see ref: Fujishita et al., 2003). PC9 (EGFR, exon 19 del) and PC9Brc1 (EGFR, exon 19 del+T790M) were got as previous and as a gift of Katerin Politi (Xiaoling Song et al., 2015). All Cells were cultured in RPMI1640 medium with 10% FBS and Penicillin-Streptomycin in 37° C. incubator with 5% $CO_2$. All cell lines were maintained in active growing state without reaching confluence, and all cell lines were STR identified and examined as mycoplasma free by regular check.

Western Blot

Cancer cells were seeded in 1 ml RPMI1640 medium in 24-well plate at the density of 3×10^5 or 1.5×10^5 cells/ml. The next day cells were treated with different concentration of drugs for 16 hours. Then cells were washed twice with PBS and lyzed in RIPA lysis buffer with Halt Proteinase and Phosphotase inhibitor. Equal amount of proteins were loaded to run SDS-PAGE gels after denature. The gels were blotted to PVDF membrane. After incubating with first and secondary antibodies, the images were developed using SuperSignal West Pico Chemiluminescent Substrate.

$DC_{50}$ (concentration required to degrade protein by half) were calculated based on the intensity from western blot, and data were analyzed via Prism GraphPad with non-linear regression.

Evaluation of compounds IC50s

Cells were seeded at specific density in 96 well plates one day before treatment. Cells were treated with a series concentration of different compounds and incubated for 72 hours. Viable cells were measured via CCK8 reagent and IC50s were calculated via Prism Graphad. Experiments were repeated at least three times.

Colony Formation Assay

Cell were digested to become single cell suspension. Cells were seeded in the intensity of 250 cells/well in 12 well plate. Treated cells at the concentration of 100, 250, 500 nM. Fixed cells 2-3 weeks after and stained cells with crystyl violate.

Results:

The PROTAD molecules developed in the present disclosure were based on ALK tyrosine kinase inhibitors, which can be chosen from Criztinib, Ceritinib, Alectinib, Brigatinib, TAE684, ASP3026, GSK1838795A, AZD3463, Entrectinib (RXDX-101) and Ensartinib (X-396) etc. Different ALK inhibitors-based ALK PROTAD molecules can inhibit ALK kinase activity, degrade ALK proteins, and the proliferation of ALK mutant positive cells. These ALK PROTAD molecules can be developed into new therapeutic ways to treat cancer patients.

I. Bioactivity Assay for Brigatinib-Based PROTAD Molecule

1. Effect of Brigatinib Based PROTAD Molecule on the Growth Inhibition on ALK Mutant Positive Cells We performed dose-dependent effect test for these compounds in SR cells, which contain NPM-ALK gene fusion and highly sensitive to ALK inhibitors. SR cells were treated with different concentration of PROTAD molecules (started from 10 uM, 3 or 5 folds dilution for 10 concentrations) for 72 hours, CCK8 reagent were then used to examinate cell number for detection for the IC50s. Experiments were repeated for more than 3 times, results were summarized in Table 3.

Results showed that Brigatinib based on PROTAD molecules can effectively inhibit the growth of SR cells. The IC50 of Brigatinib in SR cells was 2.8 nM. The compounds we developed kept about similar growth inhibition effect as Brigatinib. Some of the compounds of the present invention had significant lower IC50 in killing SR cells. For example, the IC50 of compound SIAIS1197055 in SR cells was about 1 nM.

Besides above, we also tested the dosage-dependent effects on the growth inhibition in H2228 cells. The compounds we developed also showed growth inhibition on H2228 cells. (Table 3).

TABLE 3

The IC50 of Brigatinib-based PROTAD molecules in ALCL and lung adenocarcinoma cell lines.

| Cell line | PROTAD compounds | Test reagent | $IC_{50}$ (nM) |
|---|---|---|---|
| SR | Brigatinib | WST | 2.8 ± 0.4 |
| SR | Brigatinib Analogue A(SIAIS1197135) | WST | 1.6 ± 1.0 |
| SR | SIAIS1197065 | WST | 20.7 ± 14.9 |
| SR | SIAIS1197067 | WST | 16.1 ± 6.1 |
| SR | SIAIS1197069 | WST | 22.3 ± 18.2 |
| SR | SIAIS1197073 | WST | 34.2 ± 23.9 |
| SR | SIAIS1197055 | WST | 1.0 ± 0.7 |
| SR | SIAIS1197057 | WST | 17.7 ± 9.6 |
| SR | SIAIS1197059 | WST | 10.7 ± 6.2 |
| SR | SIAIS1197061 | WST | 8.0 ± 4.4 |
| SR | SIAIS1197063 | WST | 14.1 ± 7.3 |
| SR | SIAIS1197077 | WST | 7.9 ± 4.9 |
| SR | SIAIS1197087 | WST | 10.6 ± 2.4 |
| SR | SIAIS197079 | WST | 15.9 ± 8.5 |
| SR | SIAIS1197081 | WST | 32.5 ± 19.8 |
| SR | SIAIS1197083 | WST | 49.9 ± 30.8 |
| SR | SIAIS1197085 | WST | 62.5 ± 39.2 |
| SR | SIAIS1197145 | WST | 8.5 ± 5.6 |
| SR | SIAIS1197147 | WST | 14.2 ± 8.2 |
| SR | SIAIS1197149 | WST | 8.2 ± 3.9 |

TABLE 3-continued

The IC50 of Brigatinib-based PROTAD molecules in ALCL and lung adenocarcinoma cell lines.

| Cell line | PROTAD compounds | Test reagent | $IC_{50}$ (nM) |
|---|---|---|---|
| SR | SIAIS1197151 | WST | 16.7 ± 7.3 |
| SR | SIAIS1197153 | WST | 4.6 ± 1.9 |
| SR | SIAIS1197155 | WST | 3.4 ± 0.5 |
| SR | SIAIS1197157 | WST | 3.1 ± 1.3 |
| SR | Brigatinib Analogue B(SIAIS151101) | WST | 1.7 ± 1.4 |
| SR | SIAIS151113 | WST | 7.5 ± 5.2 |
| SR | SIAIS151114 | WST | 10.9 ± 7.5 |
| SR | SIAIS151115 | WST | 8.0 ± 3.2 |
| SR | SIAIS151116 | WST | 15.3 ± 9.8 |
| SR | SIAIS151117 | WST | 30.9 ± 21.3 |
| SR | SIAIS151120 | WST | 11.4 ± 7.8 |
| SR | SIAIS151121 | WST | 20.4 ± 8.5 |
| SR | SIAIS151118 | WST | 0.9 ± 0.2 |
| SR | SIAIS151119 | WST | 1.6 ± 1.0 |
| SR | SIAIS151123 | WST | 1.9 ± 1.5 |
| SR | SIAIS219151 | WST | 102.3 ± 4.8 |
| SR | SIAIS219128 | WST | 6.67 ± 1 |
| SR | SIAIS219152 | WST | 3.78 ± 0.4 |
| SR | SIAIS219153 | WST | 3.12 ± 0.2 |
| SR | SIAIS219154 | WST | 3.8 ± 0.2 |
| SR | SIAIS219170 | WST | 10.8 ± 1.4 |
| SR | SIAIS220030 | WST | 5.8 |
| SR | SIAIS220026 | WST | 7.4 |
| SR | SIAIS164157 | WST | 15.7 ± 15.0 |
| SR | SIAIS151124 | WST | 76.9 ± 15.9 |
| SR | SIAIS151128 | WST | 6.3 ± 0.2 |
| SR | SIAIS151125 | WST | 61.9 ± 30.5 |
| SR | SIAIS151126 | WST | 31.9 ± 11.9 |
| SR | SIAIS151127 | WST | 36.4 ± 23.5 |
| SR | SIAIS164143 | WST | 11.7 ± 4.2 |
| SR | SIAIS164144 | WST | 13.6 ± 9.1 |
| SR | SIAIS164145 | WST | 10.3 ± 6.3 |
| SR | SIAIS164146 | WST | 3.6 ± 2.1 |
| SR | SIAIS164147 | WST | 2.0 ± 1.2 |
| SR | SIAIS164148 | WST | 1.5 ± 0.8 |
| SR | SIAIS164149 | WST | 2.3 ± 2.0 |
| SR | SIAIS1210117 | WST | 1.7 ± 1.0 |
| SR | Brigatinib Analogue C(SIAIS164005) | WST | 6.7 ± 3.1 |
| SR | SIAIS164007 | WST | 3.8 ± 1.9 |
| SR | SIAIS164008 | WST | 3.6 ± 2.1 |
| SR | SIAIS164009 | WST | 5.3 ± 1.7 |
| SR | SIAIS164016 | WST | 11.2 ± 6.8 |
| SR | SIAIS164017 | WST | 14.0 ± 8.6 |
| SR | SIAIS164018 | WST | 2.0 ± 1.4 |
| SR | SIAIS164019 | WST | 9.6 ± 8.0 |
| SR | SIAIS164020 | WST | 2.9 ± 1.5 |
| SR | SIAIS164021 | WST | 7.4 ± 5.0 |
| SR | SIAIS164022 | WST | 3.3 ± 2.2 |
| SR | SIAIS164023 | WST | 4.8 ± 2.7 |
| SR | SIAIS219073 | WST | 1.8 ± 1 |
| SR | SIAIS219155 | WST | 4.34 ± 0.4 |
| SR | SIAIS219156 | WST | 3.09 ± 0.2 |
| SR | SIAIS219157 | WST | 1.99 ± 0.2 |
| SR | SIAIS219124 | WST | 2.47 ± 0.6 |
| SR | SIAIS219158 | WST | 30.3 ± 3.8 |
| SR | SIAIS220027 | WST | 3.8 |
| SR | SIAIS164152 | WST | 7.9 ± 3.5 |
| SR | SIAIS164041 | WST | 42.7 ± 29.4 |
| SR | SIAIS164032 | WST | 54.5 ± 31.2 |
| SR | SIAIS164033 | WST | 50.1 ± 34.9 |
| SR | SIAIS164034 | WST | 88.6 ± 63.0 |
| SR | SIAIS164035 | WST | 41.8 ± 24.7 |
| SR | SIAIS164120 | WST | 19.2 ± 8.8 |
| SR | SIAIS164121 | WST | 21.6 ± 12.5 |
| SR | SIAIS164122 | WST | 12.1 ± 9.2 |
| SR | SIAIS164123 | WST | 11.4 ± 8.1 |
| SR | SIAIS164124 | WST | 9.5 ± 8.1 |
| SR | SIAIS164125 | WST | 9.0 ± 5.7 |
| SR | SIAIS164126 | WST | 8.0 ± 6.7 |
| SR | SIAIS164153 | WST | 55.9 ± 19.9 |
| H2228 | Brigatinib | WST | 45.2 |
| H2228 | SIAIS151118 | WST | 346.3 |
| H2228 | SIAIS1210117 | WST | 30.3 |
| H2228 | SIAIS164008 | WST | 74.0 |

TABLE 3-continued

The IC50 of Brigatinib-based PROTAD molecules in ALCL and lung adenocarcinoma cell lines.

| Cell line | PROTAD compounds | Test reagent | $IC_{50}$ (nM) |
|---|---|---|---|
| H2228 | SIAIS164018 | WST | 17.9 |
| H2228 | SIAIS164023 | WST | 15.5 |

1.2 Effect of Brigatinib Based ALK PROTADS on the Level of ALK Protein

The effect of Brigtinib based PROTAD molecules on the ALK protein total level were studied by western blot in ALCL SR (NPM-ALK) cell line and lung adenocarcinoma cell line H2228 and H3122 (EML4-ALK). The results were shown in FIGS. 1-6 and table 6. SR cells were treated with Brigatinib at different concentrations (0, 10, 50, 100, 500 nM) for 16 hours. Results indicated that Brigatinib did not degrade ALK proteins (FIG. 1).

Figure 2:
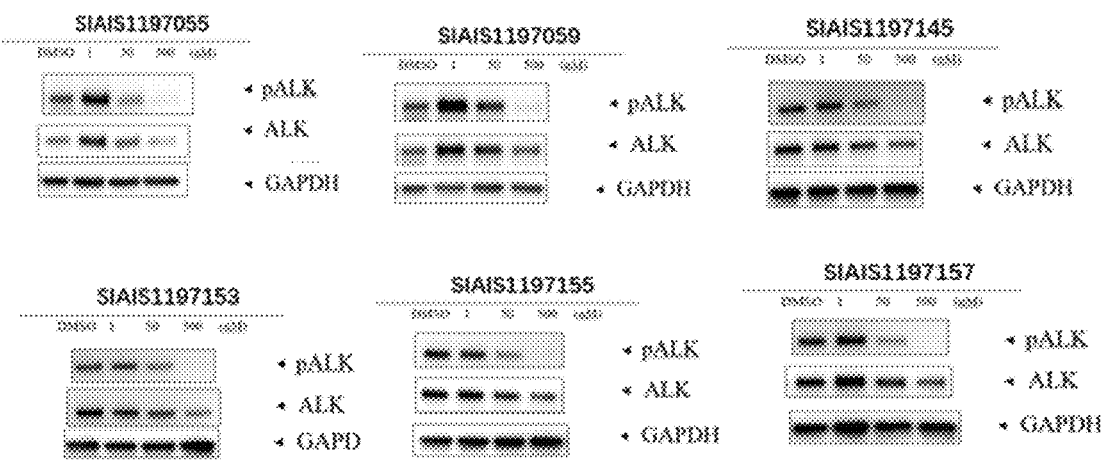
FIG. 2 shows ALK protein degradation activities for Brigatinib Analogue A-based PROTAD molecules according to the present invention in lung cancer cell line H3122.
Figure 3:
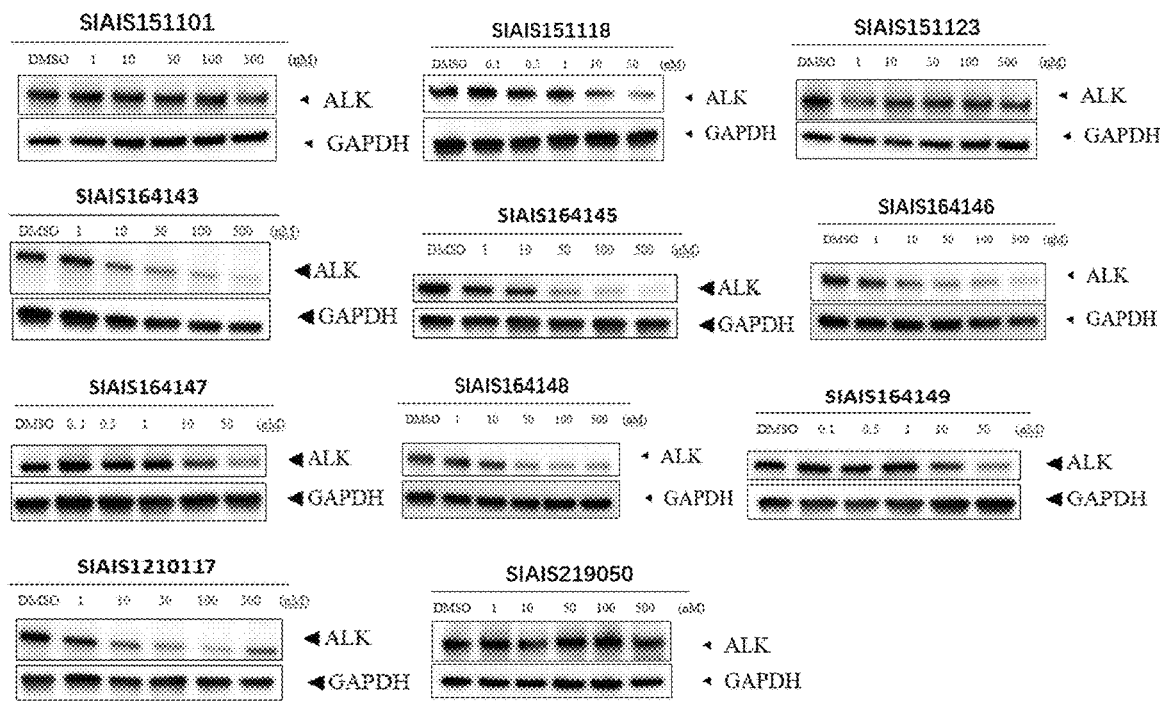
FIG. 3 shows ALK protein degradation activities for Brigatinib Analogue B-based PROTAD molecules according to the present invention in ALCL cell line SR.

The effects of Brigatinib Analogue A-based PROTAD compounds on ALK protein level were shown in FIGS. 1-2 and Table 6. With the increase of concentration, more ALK proteins were degraded in lung cancer H3122 cells. In the meanwhile, the phosphorylation of ALK protein was also significantly inhibited (FIG. 2).

Figure 4:
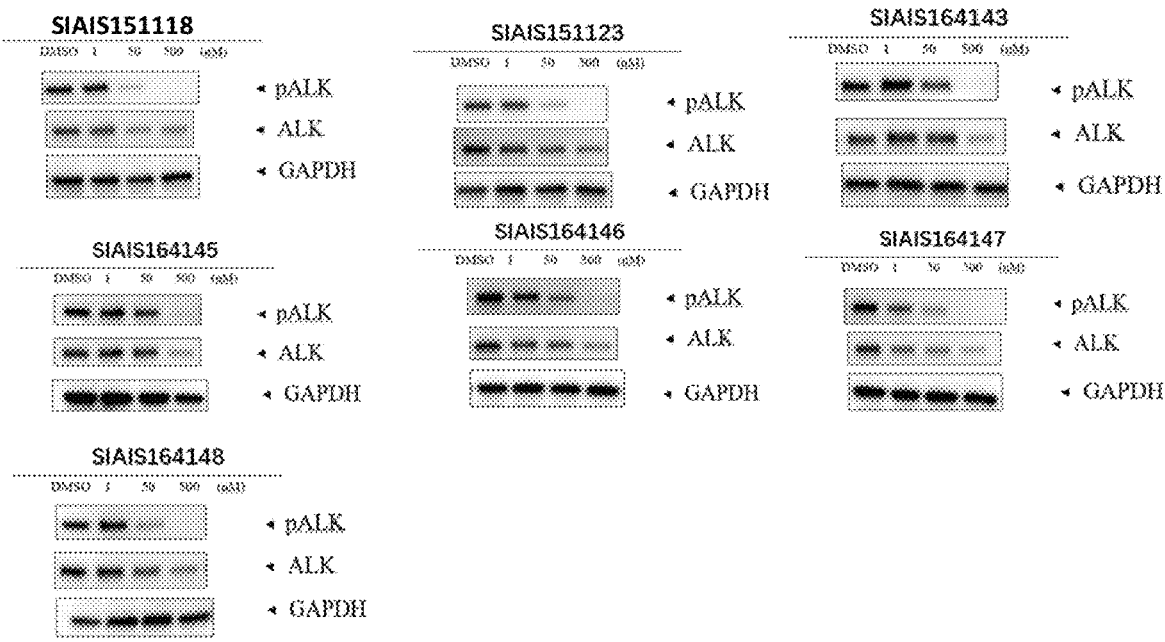
FIG. 4 shows ALK phosphorylation and protein degradation activities for Brigatinib Analogue B-based PROTAD molecules according to the present invention in lung cancer cell line H3122.
Figure 5:
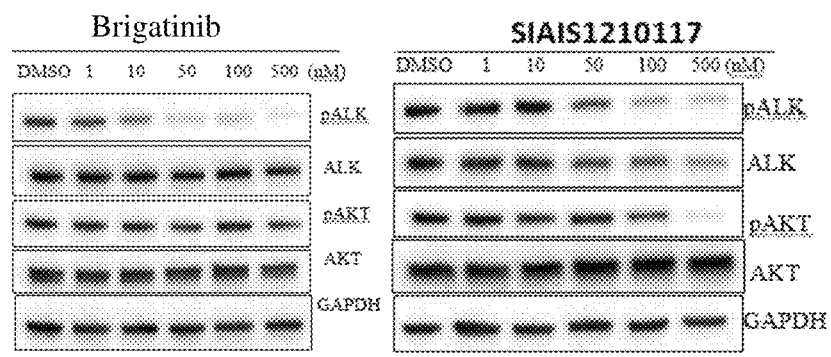
FIG. 5 shows ALK phoshorylation, protein degradation activities and inhibition of downstream signaling pathway for Brigatinib Analogue B-based PROTAD molecules according to the present invention in lung cancer cell line H2228.

Results showed Brigatinib Analogue B based PROTADs molecules not only significantly induced ALK protein degradation (FIGS. 3-4 and table 6), but also significantly reduced the phosphorylation of ALK protein (FIGS. 4-5). Besides that, the down-stream signaling pathway such as PI3K/AKT pathway was also significantly inhibited.

Figure 6:
FIG. 6 shows ALK protein degradation activities for Brigatinib Analogue C-based PROTAD molecules according to the present invention in ALCL cell line SR.
Figure 7:
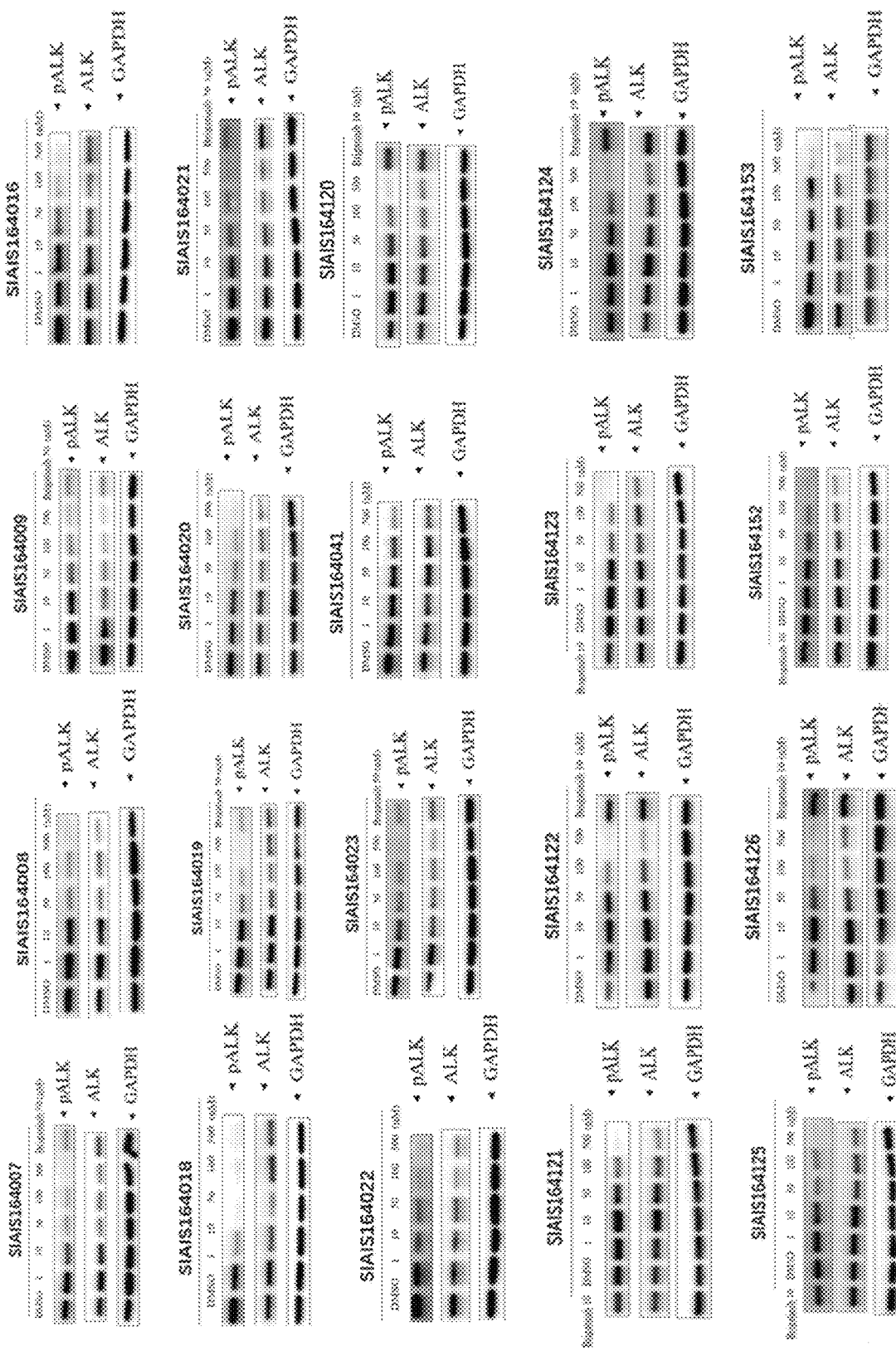
FIG. 7 shows ALK phosphorylation and protein degradation activities for Brigatinib Analogue C-based PROTAD molecules according to the present invention in lung cancer cell line H3122.
Figure 8:
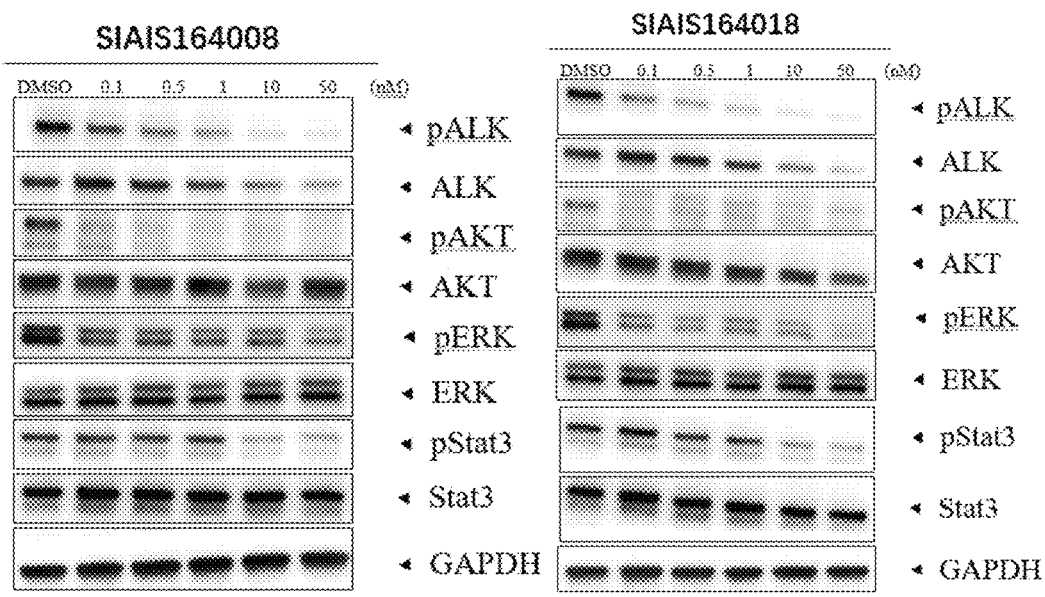
FIG. 8 shows ALK phoshorylation and protein degradation activities for Brigatinib Analogue C-based PROTAD molecules according to the present invention in lung cancer cell line H2228.
Figure 8:
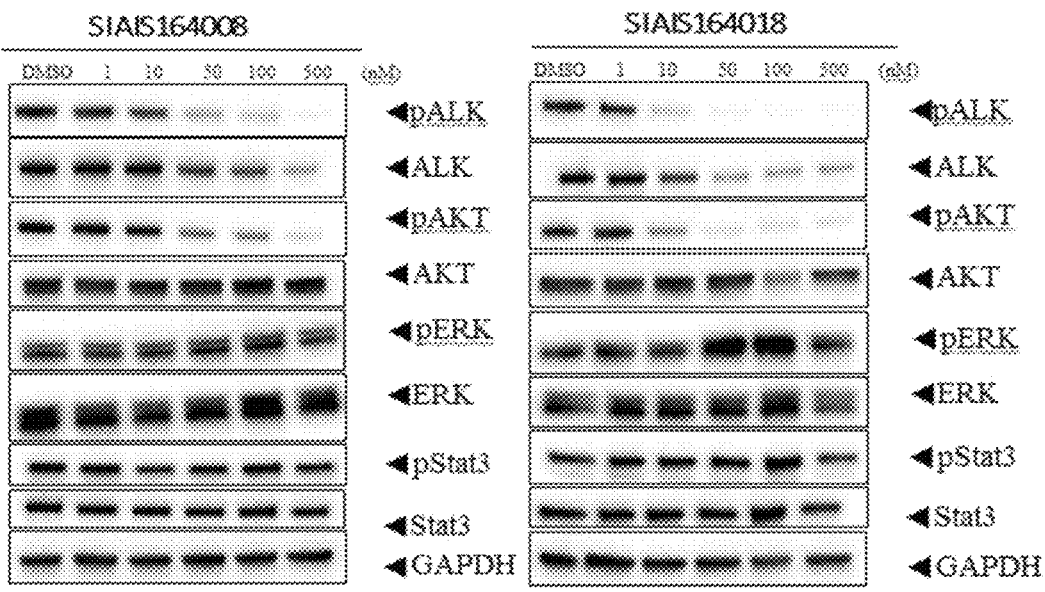

The results for the effect of Brigatinib Analogue C based PROTADs molecules on ALK protein degradations were shown in FIG. 6 and table 6. In SR cell line, parental drug Brigatinib Analogue C (SIAIS164005) did not degrade ALK protein even at the concentration of 500 n. However, Brigatinib Analogue C based PROTAD compounds effectively degrade ALK proteins. PROTAD compound SIAIS164018 degraded ALK proteins at the concentration less than 1 nM in SR cells, and a similar effects was observed in H3122 cells (FIG. 7 and table 6). Other compounds also showed the abilities to degrade ALK protein at the concentration lower than 10 nM. For example, compound SIAIS164009, SIAIS164021 and SIAIS164153 degraded ALK proteins at the concentration of 1 nM. These results indicated that the PROTADs molecules we developed had good protein degradation capabilities. Besides that, the compounds we developed also significantly inhibited the phosphorylation of ALK protein (FIG. 7).

The effects of compounds SIAIS164008 and SIAIS164018 of the present invention on the activation of ALK mediated signaling pathways were also studied in SR cells and H2228 cells. Both of these two compounds effectively degrade ALK proteins at nano mole concentration. In the meanwhile, both compounds inhibited the phophorylation of ALK proteins at the concentration of 0.1 nM and downstream signaling pathway such as PI3K/AKT, MEK/ERK and STAT3 pathway were all significantly inhibited. Both SIAIS164008 and SIAIS164018 also inhibited the phosphorylation of ALK protein and activation of PI3K/AKT pathway as well in lung cancer cell line H2228 cells although H2228 cells were less sensitive than SR cells. The overall effect of compound of SIAIS164018 was better than that of SIAIS164008.

In summary, we successfully developed Brigatinib based PROTAD compounds. These PROTAD compounds reduced ALK protein levels, blocked ALK down-stream signaling, inhibited the growth of cancer cells, and potentially could be used in cancer therapy.

II. Bioactivity Assay for Alectinib Based ALK PROTAD

Alectinib (Roche) was approve on Nov. 7, 2017 by FDA to treat ALK mutant positive metastic non-small cell lung cancer. Three different Alectinib derivatives were designed and generated, and these three different forms of Alectinib derivatives were used to develop ALK PROTADs compounds. The IC50s of these Alectinib based ALK PROTADs compounds were tested in SR cells and the results were listed in table 4. The IC50 of Alectinib in SR cells was 10.6 nM. Within these different Alectinib Analogue forms, the growth inhibition effect of Alectinib Analogue A is better than that of Alectinib, while the effect of Alectinib Analogue B and C were slightly weaker than that of Alectinib in inhibiting the growth of SR cells. Even with the addition of different E3 linkers, the developed ALK PROTAD compounds retained the growth inhibition in SR cells.

TABLE 4

The IC50s of Alectinib based ALK PROTAD compopunds

| Cell line | Compounds name | Testing reagents | $IC_{50}$ (nM) |
|---|---|---|---|
| SR | Alectinib | WST | 10.6 |
| SR | Alectinib Analogue A | WST | 2.4 |
| SR | SIAIS164012 | WST | 48.9 |
| SR | SIAIS164014 | WST | 81.0 |
| SR | SIAIS164028 | WST | 19.7 |
| SR | SIAIS164024 | WST | 35.8 |
| SR | SIAIS164026 | WST | 147.9 |
| SR | SIAIS164036 | WST | 131.9 |
| SR | SIAIS164094 | WST | 124.0 |
| SR | SIAIS164095 | WST | 71.3 |
| SR | SIAIS164096 | WST | 79.5 |
| SR | SIAIS164155 | WST | 103.7 |
| SR | SIAIS164029 | WST | 27.3 |
| SR | SIAIS164037 | WST | 152.8 |
| SR | Alectinib Analogue B(SIAIS184193) | WST | 14.7 |
| SR | SIAIS219023 | WST | 29.3 |
| SR | SIAIS219024 | WST | 73.1 |
| SR | SIAIS219001 | WST | 21.3 |
| SR | SIAIS219010 | WST | 31.1 |
| SR | SIAIS219011 | WST | 49.9 |
| SR | SIAIS219020 | WST | 30.3 |
| SR | SIAIS219021 | WST | 115 |
| SR | Alectinib Analogue C(SIAIS184192) | WST | 19.1 |
| SR | SIAIS219018 | WST | 13.3 |
| SR | SIAIS219019 | WST | 38.3 |
| SR | SIAIS184194 | WST | 24.2 |
| SR | SIAIS219003 | WST | 21.8 |
| SR | SIAIS219004 | WST | 36.8 |
| SR | SIAIS219015 | WST | 110.3 |
| SR | SIAIS219016 | WST | 80.8 |

Figure 9:
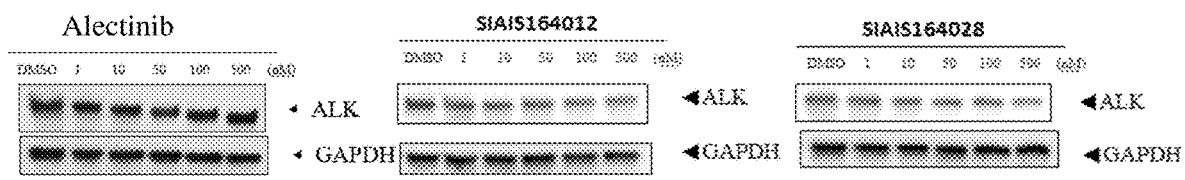
FIG. 9 shows ALK protein degradation activities for Alectinib Analogue A-based PROTAD molecules according to the present invention in ALCL cell line SR.
Figure 10:
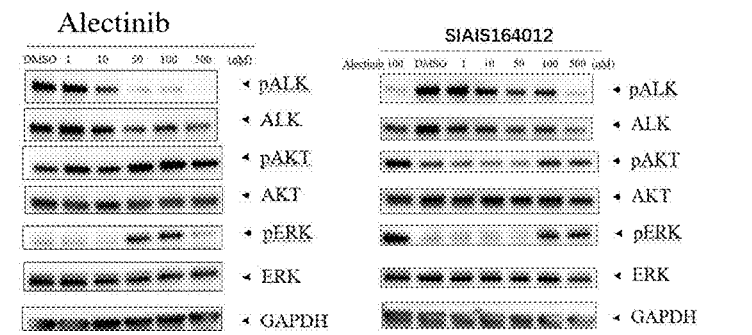
FIG. 10 shows ALK phosphorylation, protein degradation activities and downstream signaling pathway for Alectinib Analogue A-based PROTAD molecules according to the present invention in lung cancer cell line H3122.
Figure 10:
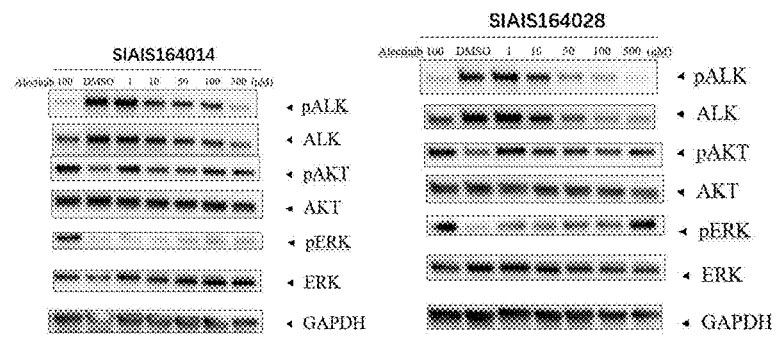
Figure 10:
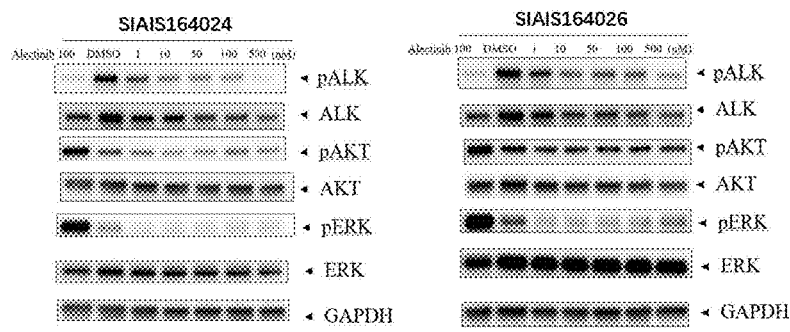

The effect of Alectinib-based ALK PROTAD compounds on ALK protein level and down-stream signaling pathway were studied in ALCL cell line SR and non-small cell lung cancer cell line H3122 (FIGS. 9 and 10). Alectinib did not degrade ALK proteins at the concentration of 1-500 nM in SR cell. However, Alectinib Analogue A-based ALK PROTAD compounds could degraded ALK proteins in these cells (FIG. 9 and table 6). In addition, Alectinib based ALK PROTAD compounds also could degrade ALK protein in H3122 lung cancer cells.

The phosphorylation of ALK protein is an indication of ALK activation. ALK phosphorylation were also studied after treated ALK mutant cells with Alectinib based compounds. In H3122 cell line, Alectinib inhibited the phosphorylation of ALK but not affected the total protein level of ALK (FIG. 10). In contrast, Alectinib based ALK PROTAD compounds exhibited different degradation capabilities of ALK protein (FIG. 10 and Table 6). These ALK PROTAD compounds also inhibited the phosphorylation of ALK signaling. These results indicated that Alectinib based-ALK PROTAD compounds not only retained the capabilities to inhibit ALK phosphorylation but also able to degraded ALK proteins, which fully showed the advantage of ALK PROTAD compounds comparing to ALK kinase inhibitors.

Accordingly, Alectinib based ALK PROTAD compounds also blocked the activation of ALK downstream signaling. Parental compound Alectinib did not affect much the phosphorylation of AKT protein and some at the ERK phosphorylation. Alectinib based ALK PROTAD compounds such as SIAIS164024 and SIAIS164026 not only reduced the protein level of ALK protein, but also inhibited the phosphorylation of AKT and ERK.

In summary, Alectinib based ALK PROTAD compounds not only effectively reduced ALK protein level, but also reduced the phosphorylation of AKT and ERK.

III. Bioactivities Assay of Ceritinib and Crizotinib Based ALK PROTAD Compounds

Our data indicated that Certinib-based ALK PROTAD compounds also not only degraded ALK protein, inhibited ALK kinase activities, but also inhibited the growth of ALK mutant positive cells. In the meanwhile, Crizotinib based ALK PROTAD compounds also could reduced the level of ALK protein.

Figure 11:
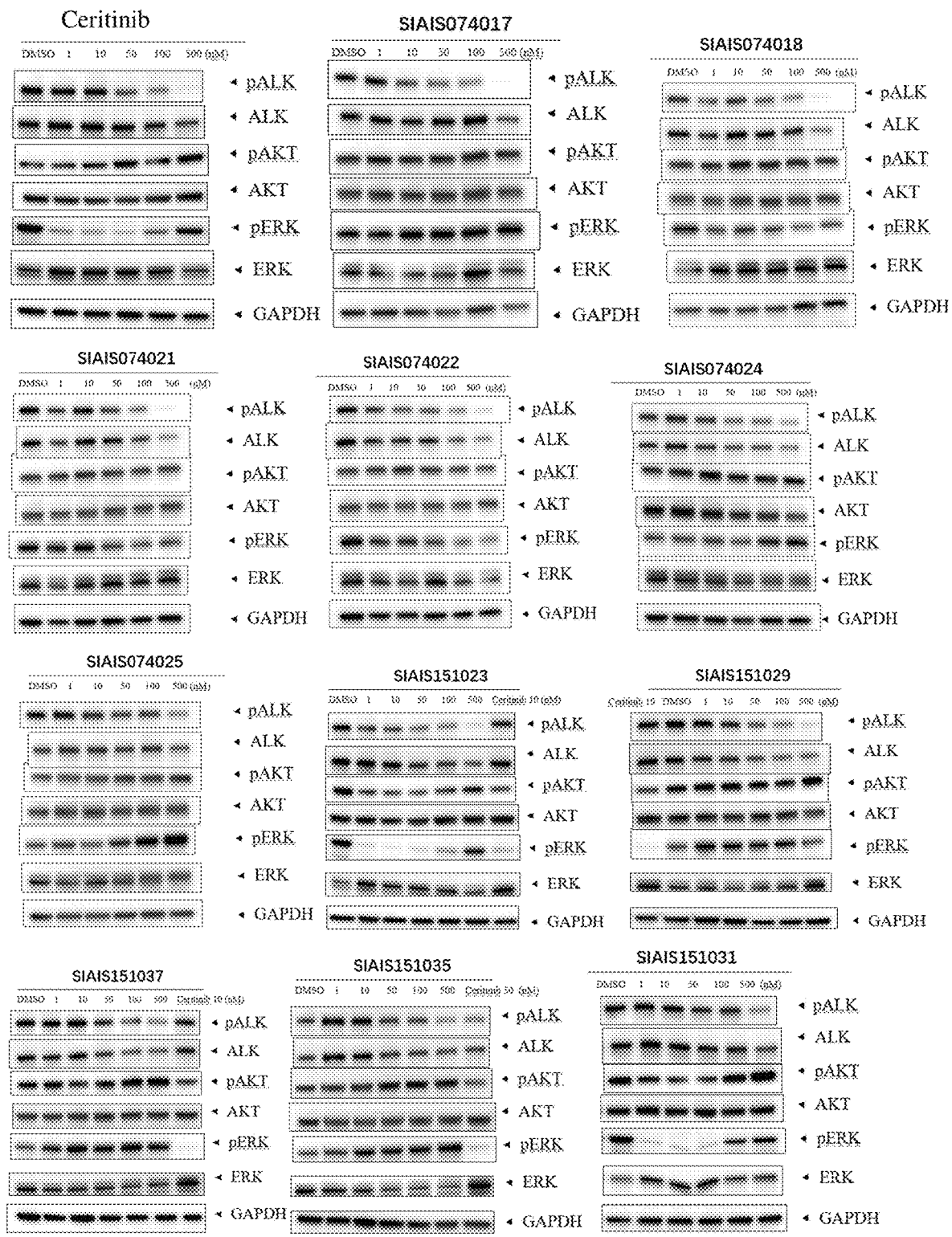
FIG. 11 shows ALK protein degradation activities for Ceritinib based PROTAD molecules according to the present invention in lung cancer cell line H3122.
Figure 12:
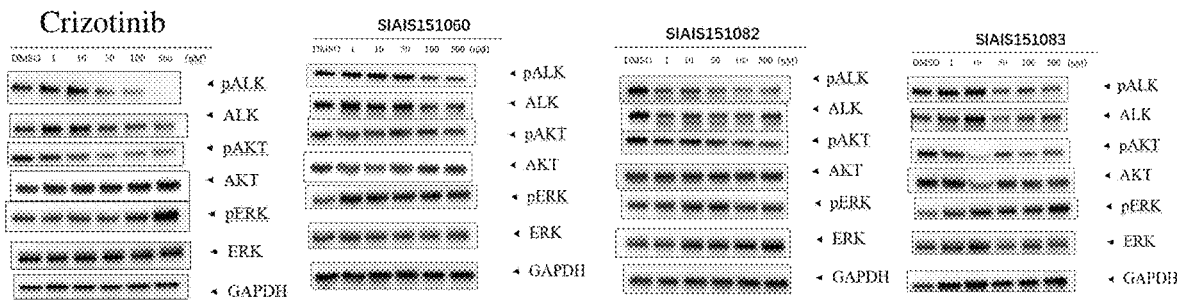
FIG. 12 shows ALK phosphorylation, protein degradation activities and downstream signaling pathway for Crizotinib based PROTAD molecules according to the present invention in lung cancer cell line H3122.

3.1 Both Ceritinib and Criztinib-Based ALK PROTAD Compounds Effectively Reduced ALK Protein Level Ceritnib did not affect ALK protein level in H3122 cells even at the concentration as high as 500 nM (FIG. 11). However, Ceritinib based-ALK PROTAD compounds could induced significant reduction of ALK protein level in the dose-dependent manner (FIG. 11 and Table 6). For example, ALK PROTAD compound SIAIS074024 reduced ALK protein level at the concentration as low as 50 nM.

Similarly, Crizotinib-based ALK PROTAD compound SIAIS151082 could also reduced ALK protein level at the concentration of about 50 nM.

3.2 the Effect on Cell Growth for Certinib-Based ALK PROTAD Compounds

The effect of Certinib-based ALK PROTAD compounds on ALK mutant positive cells were examined in H3122 cells and the results were summarized in Table 5. Certain ALK PROTAD compounds such as SIAIS074008 and SIAIS074032 had a very potent growth inhibition effect (IC50 at the nano mole range) in SR and H3122 cells (Table 5).

TABLE 5

The IC50s for Ceritinib based ALK PROTAD compounds

| Cell line | Compound name | Testing reagents | $IC_{50}$ (μM) |
|---|---|---|---|
| SR | Ceritinib | WST | 0.016 |
| SR | SIAIS151031 | WST | 0.085 |
| SR | SIAIS151028 | WST | 0.038 |
| SR | SIAIS074017 | WST | 0.116 |
| H3122 | Ceritinib | CTB | 0.014 |
| H3122 | SIAIS074017 | CTB | 0.045 |
| H3122 | SIAIS074018 | CTB | 0.209 |
| H3122 | SIAIS074021 | CTB | 0.125 |
| H3122 | SIAIS074022 | CTB | 0.269 |
| H3122 | SIAIS074008 | CTB | 0.428 |
| H3122 | SIAIS074024 | CTB | 0.721 |
| H3122 | SIAIS074025 | CTB | 1.241 |

TABLE 5-continued

The IC50s for Ceritinib based ALK PROTAD compounds

| Cell line | Compound name | Testing reagents | $IC_{50}$ (μM) |
|---|---|---|---|
| H3122 | SIAIS074026 | CTB | 2.560 |
| H3122 | SIAIS074036 | CTB | 3.900 |
| H3122 | SIAIS151023 | CTB | 0.015 |
| H3122 | SIAIS151028 | CTB | 0.006 |
| H3122 | SIAIS151029 | CTB | 0.023 |
| H3122 | SIAIS151031 | CTB | 0.007 |
| H3122 | SIAIS151034 | CTB | 0.014 |
| H3122 | SIAIS151035 | CTB | 0.033 |
| H3122 | SIAIS151036 | CTB | 0.031 |
| H3122 | SIAIS151037 | CTB | 0.151 |
| H3122 | SIAIS151038 | CTB | 0.393 |
| H3122 | SIAIS151039 | CTB | 0.441 |
| H3122 | SIAIS151040 | CTB | 0.141 |
| H3122 | SIAIS151041 | CTB | 0.332 |
| H3122 | SIAIS151042 | CTB | 0.153 |
| H3122 | SIAIS151043 | CTB | 0.156 |
| H3122 | Ceritinib | CTG | 0.044 |
| H3122 | SIAIS074017 | CTG | 0.041 |
| H3122 | SIAIS151023 | CTG | 0.076 |
| H3122 | SIAIS151028 | CTG | 0.080 |
| H3122 | SIAIS151029 | CTG | 0.095 |
| H3122 | SIAIS151031 | CTG | 0.081 |
| H3122 | DMSO | CTB | 17.19 |

CTB: Cell Titer Blue;
CTG: Cell Titer Glo.

Summary from above, the bioactivities of different ALK PROTAD compounds were evaluated in ALCL SR cell lines and non-small cell line H3122 cells. Resulted showed these ALK PROTAD compounds could effective reduced ALK protein level in SR and H3122 cell lines (Table 6). These compounds could inhibited ALK kinase activities, blocked ALK-dependent downstream signaling pathway, and finally inhibited the growth of ALK mutant positive cells.

TABLE 6

The DC50s of ALK PROTAD compounds in SR and H3122 cells

| ALK PROTAD Compounds | $DC_{50}$ (nM) in SR | $DC_{50}$ (nM)) in H3122 |
|---|---|---|
| Brigtinib | not degrade | nt |
| Brigatinib Analogue A | not degrade | nt |
| SIAIS1197053 |  |  |
| SIAIS1197065 | nt | 100-500 |
| SIAIS1197067 | nt | 100-500 |
| SIAIS1197069 | nt | 100-500 |
| SIAIS1197073 | nt | 100-500 |
| SIAIS1197055 | 1-10 | 1-50 |
| SIAIS1197057 | nt | 50-500 |
| SIAIS1197059 | nt | 1-50 |
| SIAIS1197061 | nt | 50-500 |
| SIAIS1197063 | nt | 50-500 |
| SIAIS1197077 | 0.1-0.5 | 50-500 |
| SIAIS164156 | nt | 50-500 |
| SIAIS1197087 | nt | 50-500 |
| SIAIS197079 | nt | 50-500 |
| SIAIS1197081 | nt | 50-500 |
| SIAIS1197083 | nt | 50-500 |
| SIAIS1197085 | nt | 20-100 |
| SIAIS1197145 | nt | 1-50 |
| SIAIS1197147 | nt | 20-100 |
| SIAIS1197149 | nt | 20-100 |
| SIAIS1197151 | nt | 20-100 |
| SIAIS1197153 | 1-50 | 1-50 |
| SIAIS1197155 | 1-10 | 1-50 |
| SIAIS1197157 | 1-10 | 1-50 |
| Brigatinib Analogue B | Not degrade | Not degrade |
| SIAIS151101 |  |  |
| SIAIS151113 | nt | 100-500 |
| SIAIS151114 | nt | 100-500 |
| SIAIS151115 | nt | 100-500 |

TABLE 6-continued

The DC50s of ALK PROTAD compounds in SR and H3122 cells

| ALK PROTAD Compounds | DC$_{50}$ (nM) in SR | DC$_{50}$ (nM) in H3122 |
| --- | --- | --- |
| SIAIS151116 | nt | 100-500 |
| SIAIS151120 | nt | 20-100 |
| SIAIS151121 | nt | 100-500 |
| SIAIS151118 | 1-10 | 1-50 |
| SIAIS151119 | nt | 100-500 |
| SIAIS151123 | 0.1-2 | 1-50 |
| SIAIS164157 | nt | 1-50 |
| SIAIS151124 | nt | 100-500 |
| SIAIS151128 | nt | 100-500 |
| SIAIS151125 | nt | 100-500 |
| SIAIS151126 | nt | 100-500 |
| SIAIS151127 | nt | 20-100 |
| SIAIS164143 | 1-10 | 50-100 |
| SIAIS164144 | 1-10 | 20-100 |
| SIAIS164145 | 1-10 | 50-100 |
| SIAIS164146 | 1-10 | 0.1-10 |
| SIAIS164147 | 1-10 | 0.02-1 |
| SIAIS164148 | 1-10 | 1-50 |
| SIAIS164149 | 1-10 | 0.02-20 |
| SIAIS1210117 | 0.5-10 | nt |
| Brigatinib Analogue C | Not degrade | Not degrade |
| SIAIS164005 | | |
| SIAIS164007 | 1-10 | 10-50 |
| SIAIS164008 | 1-10 | 10-50 |
| SIAIS164009 | 1-10 | 1-10 |
| SIAIS164016 | 1-10 | 1-10 |
| SIAIS164017 | 100-500 | 0.02-20 |
| SIAIS164018 | 0.5-1 | 1-10 |
| SIAIS164019 | 1-10 | 10-20 |
| SIAIS164020 | 0.5-10 | 1-50 |
| SIAIS164021 | 0.1-0.5 | 1-10 |
| SIAIS164022 | 1-10 | 1-10 |
| SIAIS164023 | 0.5-10 | 1-10 |
| SIAIS164152 | 0.5-10 | 10-50 |
| SIAIS164041 | 10-50 | 10-500 |
| SIAIS164032 | 100-500 | 20-100 |
| SIAIS164033 | 100-500 | 100-500 |
| SIAIS164034 | 100-500 | 100-500 |
| SIAIS164035 | 100-500 | 100-500 |
| SIAIS164120 | 1-10 | 10-100 |
| SIAIS164121 | 1-10 | 50-100 |
| SIAIS164122 | 1-50 | 50-100 |
| SIAIS164123 | 1-50 | 10-50 |
| SIAIS164124 | 1-10 | 100-500 |
| SIAIS164125 | 1-10 | 10-50 |
| SIAIS164126 | 1-10 | 10-50 |
| SIAIS164153 | 100-500 | 1-10 |
| Alectinib | Not degrade | >500 |
| Alectinib Analogue A | nt | nt |
| SIAIS164011 | nt | nt |
| SIAIS164012 | 1-50 | 1-50 |
| SIAIS164014 | nt | 100-500 |
| SIAIS164028 | 1-50 | 1-10 |
| SIAIS164029 | nt | nt |
| SIAIS164024 | nt | 1-10 |
| SIAIS164026 | nt | 1-10 |
| SIAIS164036 | nt | 20-100 |
| SIAIS164094 | nt | 20-100 |
| SIAIS164095 | nt | nt |
| SIAIS164096 | nt | nt |
| SIAIS164155 | nt | 10-50 |
| Ceritnib | nt | Not degrade |
| SIAIS074017 | nt | 100-500 |
| SIAIS074018 | nt | 100-500 |
| SIAIS074021 | nt | 50-100 |
| SIAIS074022 | nt | 20-100 |
| SIAIS074024 | nt | 10-50 |
| SIAIS074025 | nt | 100-500 |
| SIAIS151023 | nt | 10-100 |
| SIAIS151029 | nt | 10-50 |
| SIAIS151037 | nt | 50-100 |
| SIAIS151035 | nt | 50-100 |
| SIAIS151031 | nt | 100-500 |
| SIAIS151028 | nt | 20-100 |
| SIAIS151032 | nt | 20-100 |
| Crizotinib | nt | 100-500 |
| SIAIS151060 | nt | 100-500 |
| SIAIS151082 | nt | 1-10 |
| SIAIS151083 | nt | 10-50 | nt: not tested

IV. The Effect of ALK PROTAD Compounds on ALK Resistance Mutation

Drug resistance always occurs after treating ALK mutant positive lung cancer patients with ALK inhibitor drugs. The resistance mechanisms include acquiring resistance mutations in ALK protein such as gate keeper mutation L1196M and C1156Y. We tested the growth inhibition effect with Brigatinib-based ALK PROTAD compounds developed in this project in mutant ALK expressing Ba/F3 cells, and the results were summarized in table 7. Results showed that ALK PROTAD compounds not only inhibited the growth of EML4-ALK that was wild type in the ALK kinase domain, but also inhibited the growth of EML4-ALK that harbored L1196M and C1156Y mutant mutations in the kinase domain.

TABLE 7

The IC50s of Brigatinib based ALK PROTAD compounds against ALK resistant mutations

| Cell line | Compounds | IC$_{50}$ (nM) |
| --- | --- | --- |
| Ba/F3 (EML4-ALK/WT) | Crizotinib | 188.6 |
| | Brigatinib | 11 |
| | SIAIS164008 | 114.6 |
| | SIAIS164018 | 30.9 |
| | SIAIS164023 | 33.6 |
| | SIAIS164142 | 64.7 |
| | SIAIS1210117 | 123.4 |
| | SIAIS151118 | 92 |
| Ba/F3 (EML4-ALK/L1196M) | Crizotinib | 395 |
| | Brigatinib | 35.9 |
| | SIAIS164008 | 376.2 |
| | SIAIS164018 | 57.4 |
| | SIAIS164023 | 75.8 |
| | SIAIS164142 | 117 |
| | SIAIS1210117 | 170.4 |
| | SIAIS151118 | 145.8 |
| Ba/F3 (EML4-ALK/C1156Y) | Crizotinib | 366.8 |
| | Brigatinib | 36.8 |
| | SIAIS164008 | 242.5 |
| | SIAIS164018 | 42.7 |
| | SIAIS164023 | 47.5 |
| | SIAIS164142 | 92.1 |
| | SIAIS1210117 | 119.5 |
| | SIAIS151118 | 128.9 |

V. The Mechanisms Study for ALK PROTAD Compounds in Cells 5.1 ALK PROTAD Compounds Reduced the Stability of ALK Proteins The mechanism of PROTAD compound to degrade its target protein acts through recruiting E3 ubiquitining ligase to the proximity of its target protein, which leads to the target protein being highly ubiquitinzed and eventually being degraded. In order to see the mechanism of ALK PROTAD compounds we developed, we firstly examined the half-life of ALK protein. Because the total level of ALK protein was determined by both the translational activity and protein degradation, we used cyclohexmide to stop protein translation to examine the effect of ALK PROTAD compounds on ALK protein stabilities.

Figure 13:
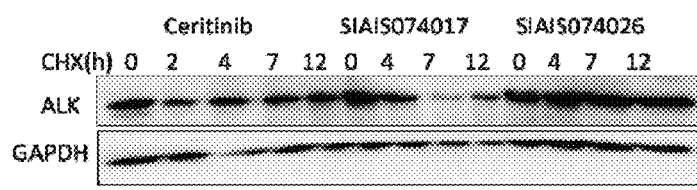
FIG. 13 shows that PROTAD molecules according to the present invention reduced ALK protein stability.

We listed data for Ceritinib-based ALK PROTAD compounds here as an example, and data for other ALK PROTAD compounds were tested in the same way and similar results were found. H3122 cells were firstly treated with 0.5 uM Ceritinib and Certinib based ALK PROTAD compounds for 24 hours, and 1 ug/ml cyhexmide was used to stop protein translation. The difference at the total ALK protein level will reflect the different influence of drugs on protein stability. Results showed ALK protein level did not show much difference 12 hours after Ceritinib treatment (FIGS. 11 & 13). However, ALK PROTAD compound SIAIS074017 significantly reduced ALK protein level even after 7 hours-treatment. This indicated that the ALK PROTAD compounds treatment promoted the degradation of ALK protein.

5.2 ALK PROTAD Compounds Act Through the Proteosome to have their Function

Figure 14:
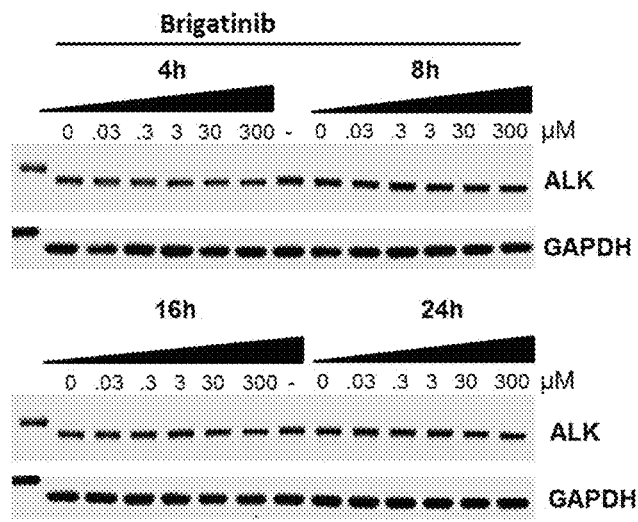
FIG. 14 shows time-dependent and concentration dependent effect of Brigatinib on ALK protein in SR cell lines.

In order to study the time- and dose-dependent effect of ALK PROTAD compounds to ALK proteins, we firstly examined the effect of Brigatinib on ALK protein level (FIG. 14). ALCL cell line SR was treated with Brigatinib at a serial concentration of Brigatinib from 30 nM to 300 uM for 4-24 hours. Western blot was used to examine the level of ALK protein. Results showed with different concentration of Brigatinib even high as 300 μM did not affect ALK protein levels. And with increase of the treatment time from 4 to 24 hours, Brigatinib did not affect ALK protein levels.

Figure 15:
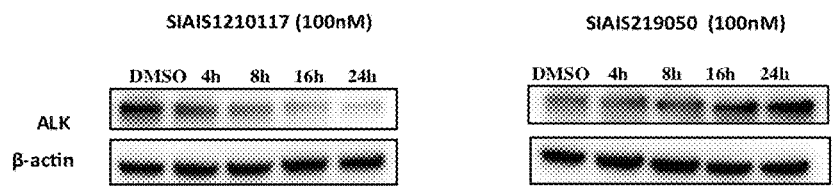
FIG. 15 shows that Brigatini-based PROTAD molecules according to the present invention degrade ALK protein in SR cell lines in the manner of time-dependent way.

We also tested the effects of an ALK PROTAD compound SIAIS1210117 on ALK protein levels within a time course. Results showed at the concentration of 100 nM, treating SR cells with SIAIS1210117 for 4 hours could lead to significant ALK protein degradation (FIG. 15). To further confirm the degradation act through E3 ubiqutinase, an inactive epimer of SIAIS1210117 were synthesized. This epimer, SIAIS219050, was similar to SIAIS1210117 in the structure except it lost the ability of recruiting E3-ligase. Results showed that this epimer did not induce degradation of ALK protein even after 24 hours treatment.

Figure 16:
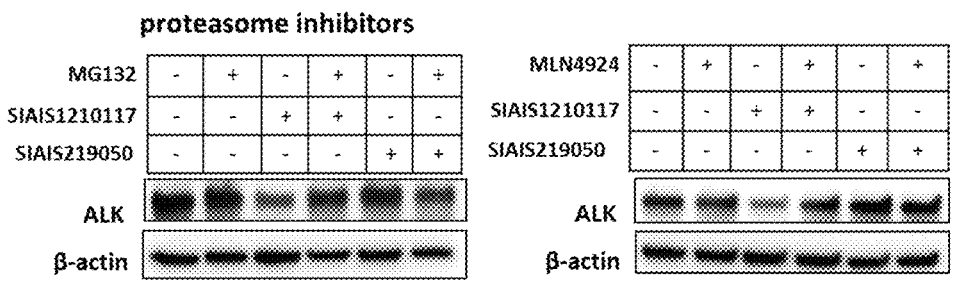
FIG. 16 shows that the PROTAD molecules according to the present invention act through proteosome-mediated proteolysis pathway (SR cell line)
Figure 16:
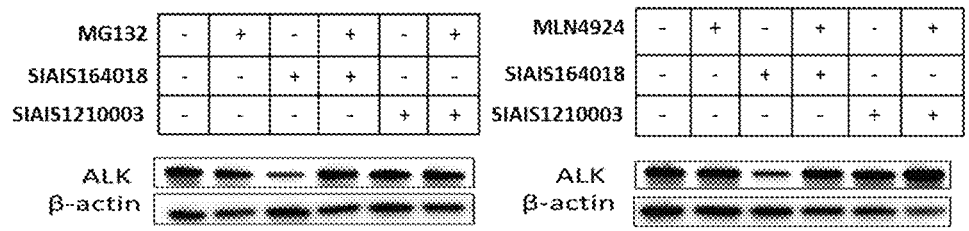

To further validate the degradation effect act through proteosome mediated pathway, we also treated cells with two different proteosome inhibitors MG132 and MLN4924 to block protein degradation (FIG. 16). Results showed that although SIAIS1210117 reduced ALK protein level in SR cells, and this effect was able to be blocked by proteosome inhibitor MG132 and MLN4924. Where as the control epimer SIAIS219050 did not have such effect. The same results were observed for ALK PROTAD compound SIAIS164018. The degradation of ALK protein by SIAIS164018 was able to be blocked by MK132 and MLN4924, and there was no such effect on the negative epimer SIAIS1210003 of SIAIS164018.

Figure 17:
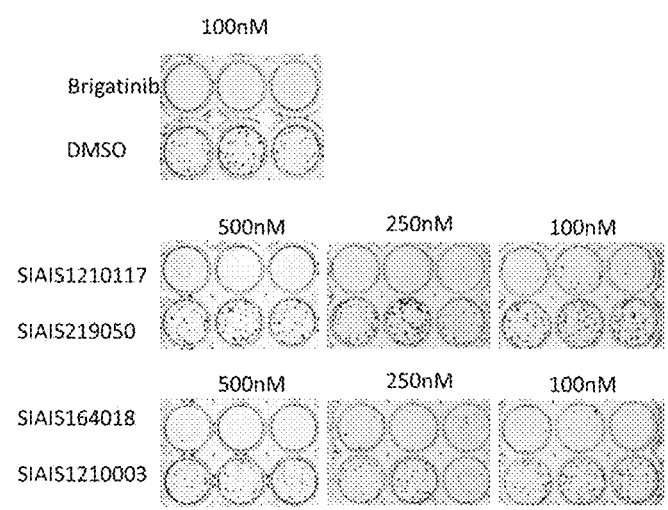
FIG. 17 shows the effect of PROTAD molecules according to the present invention on cell colony formation abilities in lung cancer cell lines H2228.

VI. The Effect of ALK PROTAD Compounds on the Colony Formation Ability of Cancer Cells In order to see the effect of ALK PROTAD compounds on the colony formation ability of cancer cells, EML4-ALK mutant lung cancer cells H2228 were firstly seeded in 12 well plate at the density of 200 cells per well. Cells were treated with different ALK PROTAD compounds at different concentration for about 2 weeks. ALK PROTAD compounds SIAIS1210117, SIAIS164018 and their epimers were used as an example, and results were shown in FIG. 17. Both negative control epimers could not inhibit the colony formation of H2228 cells, and two ALK PROTAD compounds SIAIS1210117 and SIAIS164018 dramatically inhibited the colony formation of H2228 cells.

VII. The Effect of ALK PROTAD Compounds on EGFR Mutant Cells 7.1 ALK PROTAD Compounds Inhibited the Growth of EGFR Mutant Cells Previous results showed that Brigatinib could inhibit the activity of EGFR. So we tested the effect of ALK PROTAD compounds on two different EGFR mutant lung cancer cell lines. PC9 cells contain EGFR exon19 deletion mutation and PC9Brc1 harbor exon 19 deletion and T790M point mutation. Results showed ALK PROTAD compounds also could inhibited the growth of EGFR mutant non-small cell lung cancer cells even for PC9Brc1 cells that carry with resistant mutations against EGFR TKIs (Tables 8-9).

TABLE 8

The IC50s of ALK PROTAD compounds in lung adenocarcinoma PC9 cells

| | Half Inhibitory Concentration (IC$_{50}$) | | |
|---|---|---|---|
| (n ≥ 3) | Mean (nM) | Standard Error | Testing Reagent |
| Brigatinib | 102 | 33 | CTB |
| SIAIS164007 | 358 | 35 | CTB |
| SIAIS164008 | 265 | 28 | CTB |
| SIAIS164018 | 150 | 36 | CTB |
| SIAIS164021 | 434 | 178 | CTB |
| SIAIS164022 | 233 | 91 | CTB |
| SIAIS164023 | 379 | 92 | CTB |
| SIAIS164147 | 321 | 74 | CTB |
| SIAIS164148 | 153 | 44 | CTB |
| SIAIS164149 | 187 | 26 | CTB |
| SIAIS1210117 | 106 | 26 | CTB |

TABLE 9

The IC50s of ALK PROTAD compounds in lung cancer cell line PC9Brc1

| | Half Inhibitory Concentration (IC$_{50}$) | | |
|---|---|---|---|
| (n ≥ 3) | Mean (nM) | Standard Error (SE) | Testing Reagent |
| Brigatinib | 246 | 31 | CTB |
| SIAIS164007 | 1606 | 194 | CTB |
| SIAIS164008 | 1834 | 430 | CTB |
| SIAIS164018 | 900 | 166 | CTB |
| SIAIS164021 | 2445 | 1062 | CTB |
| SIAIS164022 | 696 | 428 | CTB |
| SIAIS164023 | 870 | 289 | CTB |
| SIAIS164147 | 1285 | 158 | CTB |
| SIAIS164148 | 1340 | 139 | CTB |
| SIAIS164149 | 988 | 116 | CTB |
| SIAIS1210117 | 460 | 66 | CTB |

Figure 18:
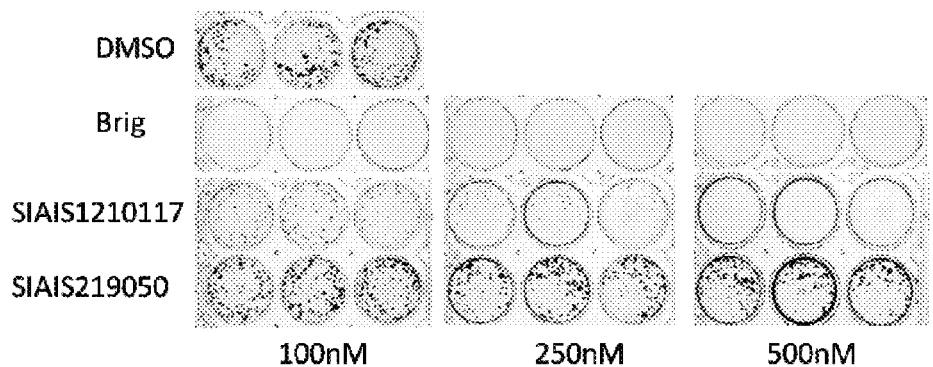
FIG. 18 shows the effect of PROTAD molecules according to the present invention on cell colony formation abilities in lung cancer cell lines PC9.
Figure 19:
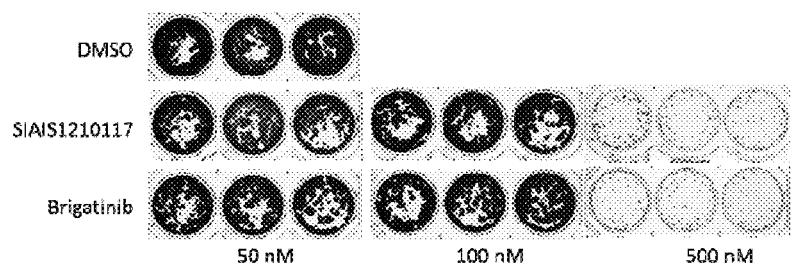
FIG. 19 shows the effect of PROTAD molecules according to the present invention on cell colony formation abilities in lung cancer cell lines PC9Brc1.

7.2. The Effect of ALK PROTAD Compounds on the Colny Formation of EGFR Mutant Cells ALK PROTOAD compounds we developed also could significantly inhibited the colony formation ability of EGFR mutant non-small cell lung cancer. Results were shown in FIG. 18 and FIG. 19. ALK PROTAD compound SIAIS1210117 and its negative control epimer SIAIS219050 were used. ALK PROTAD compound was able to inhibit the colony formation of PC9 and PC9 Brc1 cells, but its negative epimer could not.

7.3. The Growth Inhibition Effect of ALK PROTAD Compounds on EGFR Mutant Colorectal Cancer Cell Line SW48

Figure 20:
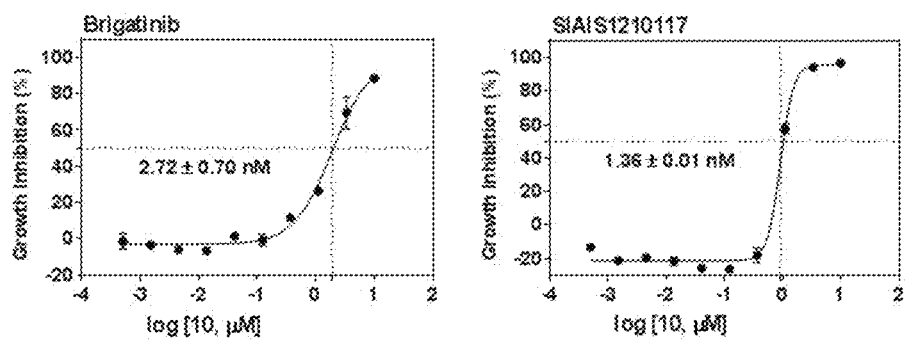
FIG. 20 shows the effect of PROTAD molecules according to the present invention on cell growth in colorectal cancer cell lines SW48.

Colorectal cancer cell line SW48 harbors an EGFR G719S mutation. We tested ALK PROTAD compounds we developed in this cell line, and we found our ALK PROTAD compounds had better growth inhibition effect than Brigatinib (see Table 10 and FIG. 20).

TABLE 10

The IC50s of ALK PROTAD compounds in SW48 cell line

| (n = 2) | Half Inhibitory Concentration ($IC_{50}$) | | |
|---|---|---|---|
| | Mean (μM) | Standard Error (SE) | Reagent |
| Crizotinib | 0.19 | 0.03 | CTG |
| Alectinib | 0.80 | 0.22 | CTG |
| Brigatinib | 2.72 | 0.70 | CTG |
| SIAIS164008 | 15.25 | 1.68 | CTG |
| SIAIS164018 | 2.76 | 0.12 | CTG |
| SIAIS219073 | >20 | Na | CTG |
| SIAIS1210117 | 1.36 | 0.01 | CTG |
| SIAIS151118 | 1.92 | 0.07 | CTG |

Na: not available

VIII. The Effect of ALK PROTAD Compounds on ROS1 Mutant Cells

Human glioblastoma cell line U118MG carries a FIG-ROS1 gene fusion. We have treated U118MG cells with ALK PROTAD compounds at a serial concentration for 72 hours and the IC50s were summarized in Table 11. Results showed that different ALK inhibitor drugs had different cell killing potency in this ROS1 mutant cell line, and ALK PROTAD compounds showed better activity than their parental compound Brigatinib in the ability to inhibit cell growth. The IC50 for Brigatinib in U118MG cells was about 6.8 μM, and Brigatinib based ALK PROTAD compound SIAIS164008 had the IC50 about 3.52M and SIAIS1210117 had an IC50 about 0.92 M (Table 11).

TABLE 11

The IC50s of ALK PROTAD compounds in glioblastoma cell line U118MG

| (n = 2) | Half Inhibitory Concentration ($IC_{50}$) | | |
|---|---|---|---|
| | Mean (μM) | Standard Error (SE) | Reagent |
| Crizotinib | 2.57 | 0.39 | CTG |
| Alectinib | 1.48 | 0.29 | CTG |
| Brigatinib | 6.80 | 2.00 | CTG |
| SIAIS164008 | 3.52 | 3.17 | CTG |
| SIAIS164018 | 16.88 | 14.38 | CTG |
| SIAIS219073 | >20 | na | CTG |
| SIAIS1210117 | 0.92 | 0.09 | CTG |
| SIAIS151118 | 4.26 | 0.25 | CTG | na: not available

VIIII. The Effect of ALK PROTAD Compounds on FLT3 Mutant Cancer Cells

We also tested the effect of ALK PROTAD compounds we developed in FLT3 mutant cell line. MOLM13 is an acute monocytic leukemia cell line with mutation of FLT3-ITD mutation. Parental drug Brigatinib inhibited MOLM13 cells with an IC50 about 152 nM (Table 12). Selected ALK PROTAD compound SIAIS164018 and SIAIS151118 both showed a better growth inhibition effect than Brigatinib with an IC50 value of 79 nM and 101 nM respectively.

TABLE 12

The IC50s of ALK PROTAD compoundS in AML cell line MOLM13

| (n = 2) | Half Inhibitory Concentration ($IC_{50}$) | | |
|---|---|---|---|
| | Mean (μM) | Standard Error (SE) | Reagent |
| Crizotinib | 291 | 69 | CTG |
| Alectinib | 255 | 35 | CTG |
| Brigatinib | 152 | 14 | CTG |
| SIAIS164008 | 392 | 10 | CTG |
| SIAIS164018 | 79 | 18 | CTG |
| SIAIS219073 | 373 | 68 | CTG |
| SIAIS1210117 | 345 | 10 | CTG |
| SIAIS151118 | 101 | 9 | CTG |

X. The Pharmacokinetics (PK) Study of ALK PROTAD Compounds

SD rat were used to study the PK of ALK PROTAD compounds. ALK PROTAD compounds SIAIS164008, SIAIS164018, SIAIS164023 and SIAIS151118 were administrated into SD rat via three different routes: IV (Intravenous Injection), IP (Intraperitoneal Injection) and PO (paricalcitol to oral). Blood samples at different sampling time points up to 24 hours post dosing were collected from each animal and analyzed with LC-MS/MS to calculate the PK for each chemical.

Results showed that, after single dose of SD rats with 2 mg/kg ALK PROTAD compounds (SIAIS164008, SIAIS164018, SIAIS164023 and SIAIS151118) via IV, testing drugs were quickly distributed in blood, with the maximal peak levels were reached about at 0.083-2 hours, and serum clearance half-life was about 0.85, 4.65, 7.71 and 4.73 hours, and the mean value of clearance rates were about 414.27, 22.63, 88.16 and 6.35 mL/min/kg. When administrated ALK PROTAD compounds via IP at the dose of 2 mg/kg, the time to maximal serum peak level (Tmax) were about 0.42, 2.67, 2.00 and 1.67 hours for these compounds respectively, and the serum half-life were 1.54, 3.65, 1.62 and 3.27 hours respectively, and the bioavailability were 92.96%, 157.49%, 122.13% 和 224.67% respectively. When administrated these ALK PROTAD compounds via PO at the dose of 10 mg/kg, the Tmax were 2.75, 2.00, 3.33 and 3.33 hours respectively, and the serum half-life were 3.98, 7.09, 2.13 and 4.66 hours, and the bioavailable were 14.89%, 18.38%, 34.43% and 35.99% respectively.

In summary, ALK PROTAD compounds we developed could promote degradation of ALK protein, inhibit ALK kinase activity in, block ALK-mediated signaling pathway, and inhibit cell growth and reduce the colony formation abilities in ALK mutant positive cancer cells. In the meanwhile, developed ALK PROTAD compounds also could inhibited the growth of cancer cells harboring EGFR activating mutations, FLT3 activating mutation and ROS1 gene rearrangement with a lower IC50 value comparing to parental drug. These developed ALK PROTAD compounds also had a good PK in rat. These compounds had serum long half-life, good oral bioavailabilities, and are suitable for therapeutic treatment of human cancer.

The basic principles, main features and advantages of the present disclosure are shown and described above. Those skilled in the art should understand that the present disclosure is not limited by the foregoing embodiments, and they can make various changes, substitutions and alterations herein without departing from the spirit and scope of the present disclosure. These changes, substitutions and alterations fall within the scope of the present disclosure. The claimed scope of the present disclosure is defined by the appended claims and their equivalents.

REFERENCES

Asao, T., Fujiwara, Y., Itahashi, K., Kitahara, S., Goto, Y., Horinouchi, H., Kanda, S., Nokihara, H., Yamamoto, N., Takahashi, K., et al. (2017). Sequential Use of Anaplastic Lymphoma Kinase Inhibitors in Japanese Patients With ALK-Rearranged Non-Small-Cell Lung Cancer: A Retrospective Analysis. Clin Lung Cancer 18, e251-e258.

Bordi, P., Tiseo, M., Rofi, E., Petrini, I., Restante, G., Danesi, R. and Del Re, M. (2017). Detection of ALK and KRAS Mutations in Circulating Tumor DNA of Patients With Advanced ALK-Positive NSCLC With Disease Progression During Crizotinib Treatment. Clinical lung cancer 18, 692-697.

Cha, Y. J., Kim, H. R. and Shim, H. S. (2016). Clinical outcomes in ALK-rearranged lung adenocarcinomas according to ALK fusion variants. Journal of translational medicine 14, 296.

Chan, K. I., Vong, H. T., Sin, L. F., Yip, Y. C., Zhong, X. Y. and Wen, J. M. (2017). Relationship between driver gene mutations, their relative protein expressions and survival in non-small cell lung carcinoma in Macao. The clinical respiratory journal.

Choi, Y. L., Takeuchi, K., Soda, M., Inamura, K., Togashi, Y., Hatano, S., Enomoto, M., Hamada, T., Haruta, H., Watanabe, H., et al. (2008). Identification of novel isoforms of the EML4-ALK transforming gene in non-small cell lung cancer. Cancer research 68, 4971-4976.

Dagogo-Jack, I. and Shaw, A. T. (2016). Crizotinib resistance: implications for therapeutic strategies. Annals of oncology: official journal of the European Society for Medical Oncology 27 Suppl 3, iii42-iii50.

Drizou, M., Kotteas, E. A. and Syrigos, N. (2017). Treating patients with ALK-rearranged non-small-cell lung cancer: mechanisms of resistance and strategies to overcome it. Clinical & translational oncology: official publication of the Federation of Spanish Oncology Societies and of the National Cancer Institute of Mexico 19, 658-666.

Fujishita, T., Loda, M., Turner, R. E., Gentler, M., Kashii, T., Breathnach, O. S. and Johnson, B. E. (2003). Sensitivity of non-small-cell lung cancer cell lines established from patients treated with prolonged infusions of Paclitaxel. Oncology 64, 399-406.

Ju, Y. S., Lee, W. C., Shin, J. Y., Lee, S., Bleazard, T., Won, J. K., Kim, Y. T., Kim, J. I., Kang, J. H. and Seo, J. S. (2012). A transforming KIF5B and RET gene fusion in lung adenocarcinoma revealed from whole-genome and transcriptome sequencing. Genome Res 22, 436-445.

Nishio, M., Kim, D. W., Wu, Y. L., Nakagawa, K., Solomon, B. J., Shaw, A. T., Hashigaki, S., Ohki, E., Usari, T., Paolini, J., et al. (2017). Crizotinib Versus Chemotherapy in Asian Patients with Advanced ALK-positive Non-small Cell Lung Cancer. Cancer research and treatment: official journal of Korean Cancer Association.

Shaw, A. T., Kim, T. M., Crino, L., Gridelli, C., Kiura, K., Liu, G., Novello, S., Bearz, A., Gautschi, O., Mok, T., et al. (2017). Ceritinib versus chemotherapy in patients with ALK-rearranged non-small-cell lung cancer previously given chemotherapy and crizotinib (ASCEND-5): a randomised, controlled, open-label, phase 3 trial. The Lancet. Oncology 18, 874-886.

Soda, M., Choi, Y. L., Enomoto, M., Takada, S., Yamashita, Y., Ishikawa, S., Fujiwara, S., Watanabe, H., Kurashina, K., Hatanaka, H., et al. (2007). Identification of the transforming EML4-ALK fusion gene in non-small-cell lung cancer. Nature 448, 561-566.

Takeuchi, K., Choi, Y. L., Togashi, Y., Soda, M., Hatano, S., Inamura, K., Takada, S., Ueno, T., Yamashita, Y., Satoh, Y., et al. (2009). KIF5B-ALK, a novel fusion oncokinase identified by an immunohistochemistry-based diagnostic system for ALK-positive lung cancer. Clinical cancer research: an official journal of the American Association for Cancer Research 15, 3143-3149.

Wellmann, A., Doseeva, V., Butscher, W., Raffeld, M., Fukushima, P., Stetler-Stevenson, M. and Gardner, K. (1997). The activated anaplastic lymphoma kinase increases cellular proliferation and oncogene up-regulation in rat 1a fibroblasts. FASEB journal: official publication of the Federation of American Societies for Experimental Biology 11, 965-972.

Zhang, S., Anjum, R., Squillace, R., Nadworny, S., Zhou, T., Keats, J., Ning, Y., Wardwell, S. D., Miller, D., Song, Y., et al. (2016). The Potent ALK Inhibitor Brigatinib (AP26113) Overcomes Mechanisms of Resistance to First- and Second-Generation ALK Inhibitors in Preclinical Models. Clinical cancer research: an official journal of the American Association for Cancer Research 22, 5527-5538.

Xiaoling Song, Pang-Dian Fan, Amlak Bantikassegn, Udayan Guha, David Threadgill, Harold Varmus and Katerina Politi. ERBB3-Independent Activation of the PI3K Pathway in EGFR-Mutant Lung Adenocarcinomas. Cancer Research. 2015 Epub January 16. DOI: 10.1158/0008-5472.

The invention claimed is:

1. A compound of formula (I)

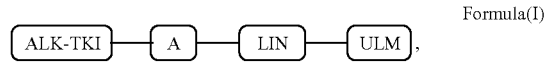

Formula(I)

or a salt, enantiomer, solvate, or polymorph thereof, in which:

ALK-TKI is covalently connected to LIN via group A, and ULM is covalently connected to LIN;

wherein ALK-TKI is an ALK tyrosine kinase inhibitor or an analogue thereof with the same function;

LIN is a linking group, which represents a linear or branched alkylene chain, a spiro-cycloalkylene, a 1,4-piperazinylene, or a 1,3-dialkynylene group, wherein the linear or branched alkylene chain is optionally interrupted one or more times by one or more selected from the group consisting of O, C(O)NH, NHC(O), NHC(O)NH, NH, S, sulfinyl, sulfonyl, aminosulfonylamino, alkynylene, alkenylene, cycloalkylene, arylene, heterocyclylene, or heteroarylene group, or any combination thereof, wherein the linear or branched alkylene chain is optionally substituted with one or more substituents;

ULM is a small molecule ligand of VHL or CRBN protease with ubiquitination function; and the group A is C(O) or absent;

wherein the ALK-TKI is the structure represented by the following general formula:

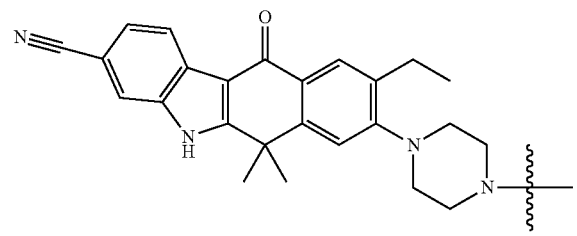
(Ic)
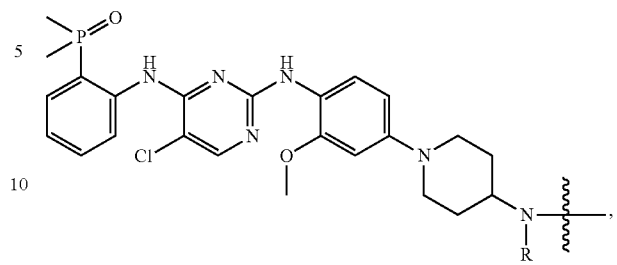
(Ig)
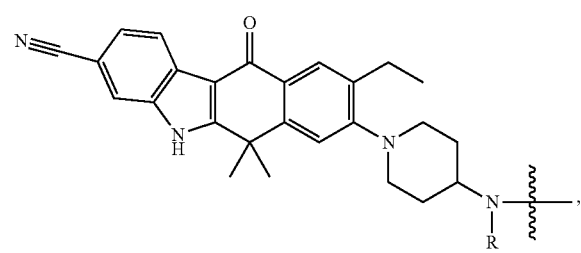
(Id)
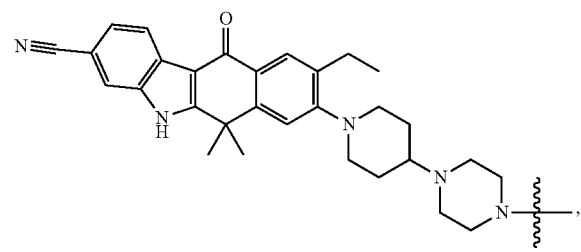
(Ie)
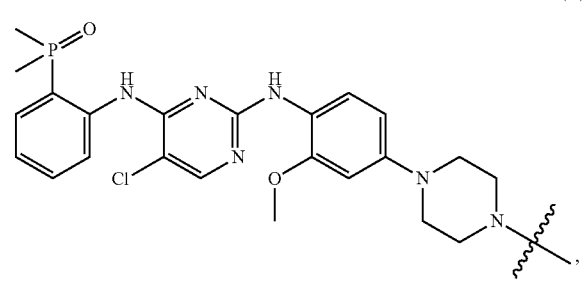
(If)
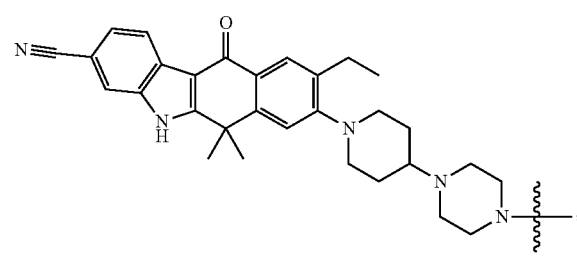
(Ie)
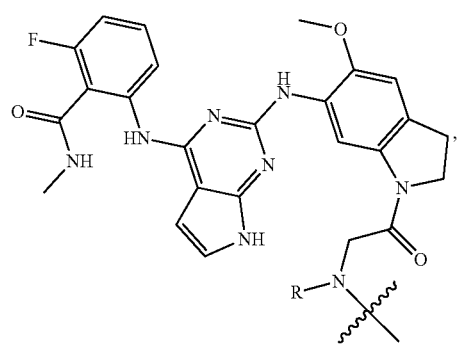
(Ih)
(Ii)
(Ij)
(Ik)

-continued (II)

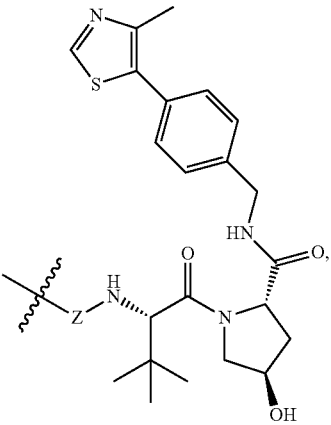

(Im)

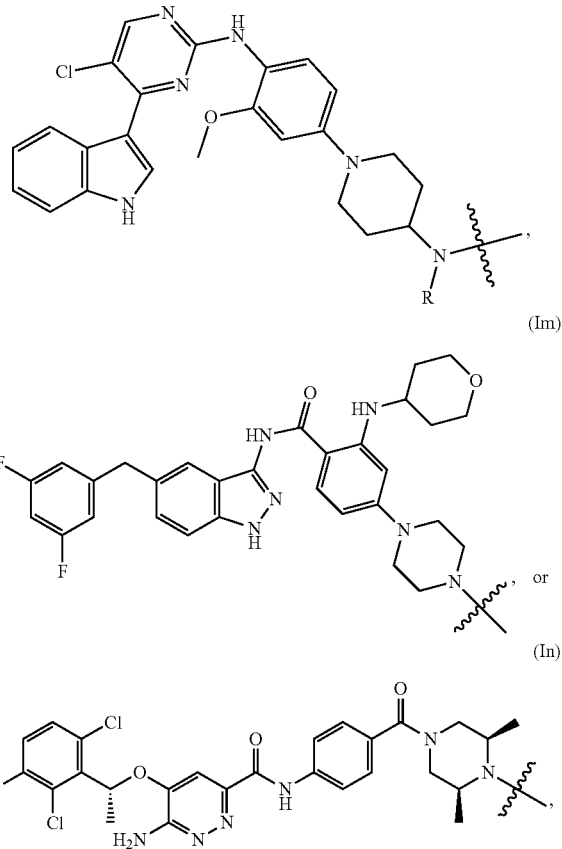

(In)

wherein R represents an alkyl group or H.

2. The compound of formula (I) or a salt, enantiomer, solvate, polymorph thereof according to claim 1, wherein R represents a linear or branched C1-10 alkyl group.

3. The compound of formula (I) or a salt, enantiomer, solvate, polymorph thereof according to claim 1, wherein the ULM represents the structure of the following formula (II):

Formula (II)

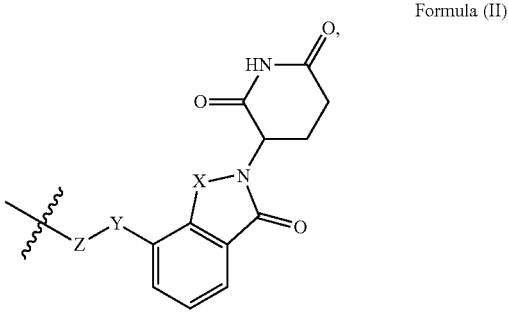

wherein X represents $CH_2$ or C(O), Y represents $CH_2$, NH or O, and Z represents a carbonyl group or is absent.

4. The compound of formula (I) or a salt, enantiomer, solvate, polymorph thereof according to claim 1, wherein the ULM represents the structure of the following formula (III):

Formula (III)

wherein Z represents a carbonyl group or is absent.

5. The compound of formula (I) or a salt, enantiomer, solvate, polymorph thereof according to claim 1, wherein the LIN represents: linear or branched $C_{1-20}$ alkylene chain; $-(CH_2)_{n1}-(O(CH_2)_{n2})_{m1}-$; $-(CH_2)_{n1}-(O(CH_2)_{n2})_{m1}-O-(CH_2)_{n3}-$; $-(CR_1R_2)_{n1}-(O(CR_1R_2)_{n2})_{m1}-O-(CR_1R_2)_{n3}-$; $-(CH_2)_{n1}-C(O)NH-(CH_2)_{n2})_{m1}-$; $-(CH_2)_{n1}-C(O)NH-(CH_2)_{n2})_{m1}-(CH_2)_{n3}-$; $-(CH_2)_{n1}-(O(CH_2)_{n2})_{m1}-O-(CH_2)_{n3}-C(O)NH-(CH_2)_{n4}-(O(CH_2)_{n5})_{m2}-O-(CH_2)_{n6}-$; $-(CR_1R_2)_{n1}-(O(CR_1R_2)_{n2})_{m1}-O-(CR_1R_2)_{n3}-C(O)NH-(CR_1R_2)_{n4}-(O(CR_1R_2)_{n5})_{m2}-O-(CR_1R_2)_{n6}-$; $-(CH_2)_{n1}-C(O)NH-(O(CR_1R_2)_{n2})_{m1}-$; linear or branched alkylene chain interrupted one or more times by one or more selected from the group consisting of NHC(O), NHC(O)NH, S, sulfinyl, sulfonyl, alkynylene, alkenylene, cycloalkylene, arylene, heterocyclylene, heteroarylene, or any combination thereof; or $-(CH_2)_{n1}-(O(CH_2)_{n2})_{m1}-$ in which carbon chain is interrupted one or more times by one or more selected from the group consisting of arylene, heterocyclylene, heteroarylene or any combination thereof;

wherein $R_1$ and $R_2$ each independently represent a linear or branched $C_{1-10}$ alkyl group or a cycloalkyl group; and n1, n2, n3, n4, n5, n6, m1, and m2 each independently represent an integer of 1, 2, 3, 4, 5, 6, 7, 8, 9, 10, 11, 12, 13, 14, 15, 16, 17, 18, 19, or 20.

6. The compound of formula (I) or a salt, enantiomer, solvate, polymorph thereof according to claim 5, wherein the LIN represents:
$-(CH_2)_2O(CH_2)_2OCH_2-$; $-CH_2O(CH_2)_2OCH_2-$; $-(CH_2)_3O(CH_2)_2-$; $-(CH_2)_3O(CH_2)_2O(CH_2)_2-$; $-(CH_2)_3O(CH_2)_3-$; $-(CH_2)_2O(CH_2)_2-$; $-(CH_2)_2O(CH_2)_2O(CH_2)_2-$; $-(CH_2)_2O(CH_2)_2O(CH_2)_2-$; $-(CH_2)_2O(CH_2)_2O(CH_2)_2O(CH_2)_2-$; $-(CH_2)_2O(CH_2)_2O(CH_2)_2O(CH_2)_3-$; $-(CH_2)_2O(CH_2)_2O(CH_2)_2O$ $(CH_2)_2$ $O(CH_2)_2O(CH_2)_2-$; $-(CH_2)_2O(CH_2)_2O(CH_2)_2O(CH_2)_2O(CH_2)_2O(CH_2)_2-$; $-(CH_2)_3O(CH_2)_2$ $O(CH_2)_2O(CH_2)_2O(CH_2)_2O(CH_2)_2-$; or $-(CH_2)_3O(CH_2)_2O(CH_2)_2O(CH_2)_2O(CH_2)_2O$ $(CH_2)_3-$.

7. The compound of formula (I) or a salt, enantiomer, solvate, polymorph thereof according to claim 5, wherein the LIN represents: $-CH_2-$; $-(CH_2)_2-$; $-(CH_2)_3-$; $-(CH_2)_4-$; $-(CH_2)_5-$; $-(CH_2)_6-$; $-(CH_2)_7-$; $-(CH_2)_8-$; $-(CH_2)_9-$; $-(CH_2)_{10}-$; $-(CH_2)_{11}-$;

—(CH$_2$)$_{12}$—; —(CH$_2$)$_{13}$—; —(CH$_2$)$_{14}$—; —(CH$_2$)$_{15}$—; —(CH$_2$)$_{16}$—; —(CH$_2$)$_{17}$—; —(CH$_2$)$_{18}$—; —(CH$_2$)$_{19}$—; or —(CH$_2$)$_{20}$—.

8. The compound of formula (I) or a salt, enantiomer, solvate, polymorph thereof according to claim 1, wherein the substituent for the linear or branched alkylene chain is selected from the group consisting of hydroxyl, amino, mercapto, halogen, or any combination thereof.

9. The compound of formula (I) or a salt, enantiomer, solvate, polymorph thereof according to claim 8, wherein the LIN represents a linear or branched C$_{1-20}$ alkylene chain substituted with one or more substituent groups selected from the group consisting of hydroxyl, amino, mercapto, halogen, or any combination thereof.

10. The compound of formula (I) or a salt, enantiomer, solvate, polymorph thereof according to claim 8, wherein the LIN represents —(CH$_2$)$_3$CH(OH)CH(OH)(CH$_2$)$_4$—.

11. The compound of formula (I) or a salt, enantiomer, solvate, polymorph thereof according to claim 1, wherein the LIN represents: —(CH$_2$)$_{n1}$-triazolylene-(CH$_2$)$_{n2}$—, —(CH$_2$)$_{n1}$—(O(CH$_2$)$_{n2}$)$_{m1}$—O—(CH$_2$)$_{n3}$-triazolylene-(CH$_2$)$_{n4}$—(O(CH$_2$)$_{n5}$)$_{m2}$—O—(CH$_2$)$_{n6}$—, —(CH$_2$)$_{n1}$-triazolylene-(CH$_2$)$_{n2}$—(O(CH$_2$)$_{n3}$)$_{m1}$—O—(CH$_2$)$_{n4}$—, or —(CH$_2$)$_{n1}$—(O(CH$_2$)$_{n2}$)$_{m1}$—O—(CH$_2$)$_{n3}$-triazolylene-(CH$_2$)$_{n4}$—; and n1, n2, n3, n4, n5, n6, m1, and m2 each independently represent an integer of 1, 2, 3, 4, 5, 6, 7, 8, 9, 10, 11, 12, 13, 14, 15, 16, 17, 18, 19, or 20.

12. The compound of formula (I) or a salt, enantiomer, solvate, polymorph thereof according to claim 11, wherein the LIN represents:

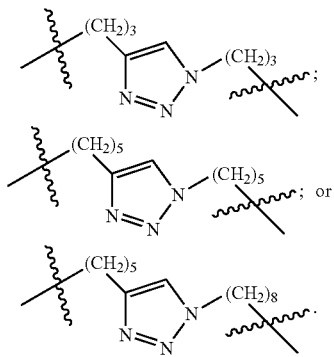

13. The compound of formula (I) or a salt, enantiomer, solvate, polymorph thereof according to claim 5, wherein the LIN represents:
—(CH$_2$)$_2$C(O)NH(CH$_2$)$_2$—; —(CH$_2$)$_3$C(O)NH(CH$_2$)$_3$—; —(CH$_2$)$_3$C(O)NH(CH$_2$)$_4$—; —(CH$_2$)$_6$C(O)NH(CH$_2$)$_7$—; or —(CH$_2$)$_8$C(O)NH(CH$_2$)$_8$—.

14. The compound of formula (I) or a salt, enantiomer, solvate, polymorph thereof according to claim 5, wherein the LIN is —(CH$_2$)$_{n1}$—NHC(O)—(CH$_2$)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

15. The compound of formula (I) or a salt, enantiomer, solvate, polymorph thereof according to claim 14, wherein the LIN is —(CH$_2$)$_3$NHC(O)(CH$_2$)$_3$—.

16. The compound of formula (I) or a salt, enantiomer, solvate, polymorph thereof according to claim 5, wherein the LIN is —(CH$_2$)$_{n1}$—NHC(O)NH—(CH$_2$)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

17. The compound of formula (I) or a salt, enantiomer, solvate, polymorph thereof according to claim 16, wherein the LIN is —(CH$_2$)$_4$NHC(O)NH(CH$_2$)$_4$—.

18. The compound of formula (I) or a salt, enantiomer, solvate, polymorph thereof according to claim 5, wherein the LIN is —(CH$_2$)$_{n1}$—S—(CH$_2$)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

19. The compound of formula (I) or a salt, enantiomer, solvate, polymorph thereof according to claim 18, wherein the LIN is —(CH$_2$)$_5$S(CH$_2$)$_5$— or —(CH$_2$)$_6$S(CH$_2$)$_5$—.

20. The compound of formula (I) or a salt, enantiomer, solvate, polymorph thereof according to claim 5, wherein the LIN is —(CH$_2$)$_{n1}$—S(O)—(CH$_2$)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

21. The compound of formula (I) or a salt, enantiomer, solvate, polymorph thereof according to claim 20, wherein the LIN is —(CH$_2$)$_5$S(O)(CH$_2$)$_5$— or —(CH$_2$)$_6$S(O)(CH$_2$)$_5$—.

22. The compound of formula (I) or a salt, enantiomer, solvate, polymorph thereof according to claim 5, wherein the LIN is —(CH$_2$)$_{n1}$—S(O)$_2$—(CH$_2$)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

23. The compound of formula (I) or a salt, enantiomer, solvate, polymorph thereof according to claim 22, wherein the LIN is —(CH$_2$)$_5$S(O)$_2$(CH$_2$)$_5$— or —(CH$_2$)$_6$S(O)$_2$(CH$_2$)$_5$—.

24. The compound of formula (I) or a salt, enantiomer, solvate, polymorph thereof according to claim 5, wherein the LIN is —(CH$_2$)$_{n1}$—CH=CH—(CH$_2$)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

25. The compound of formula (I) or a salt, enantiomer, solvate, polymorph thereof according to claim 24, wherein the LIN is —(CH$_2$)$_4$CH=CH(CH$_2$)$_3$—.

26. The compound of formula (I) or a salt, enantiomer, solvate, polymorph thereof according to claim 5, wherein the LIN is —(CH$_2$)$_{n1}$—C≡C—(CH$_2$)$_{n2}$— or —(CH$_2$)$_{n1}$—C≡C—C≡C—(CH$_2$)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

27. The compound of formula (I) or a salt, enantiomer, solvate, polymorph thereof according to claim 26, wherein the LIN is —(CH$_2$)$_2$C≡C(CH$_2$)$_2$— or —(CH$_2$)$_5$C≡C(CH$_2$)$_4$—.

28. The compound of formula (I) or a salt, enantiomer, solvate, polymorph thereof according to claim 5, wherein the LIN is a linear or branched alkylene chain interrupted one or more times by one or more selected from the group consisting of NHC(O), NHC(O)NH, S, sulfinyl, sulfonyl, alkynylene, alkenylene, spiro-cycloalkylene, arylene, heterocyclylene, heteroarylene group, or any combination thereof.

29. The compound of formula (I) or a salt, enantiomer, solvate, polymorph thereof according to claim 28, wherein the LIN is —(CH$_2$)$_{n1}$-piperazinylene-(CH$_2$)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

30. The compound of formula (I) or a salt, enantiomer, solvate, polymorph thereof according to claim 29, wherein the LIN is: —CH$_2$-piperazinylene-CH$_2$—, —(CH$_2$)$_2$-piperazinylene-(CH$_2$)$_2$—, —(CH$_2$)$_3$-piperazinylene-(CH$_2$)$_3$—, —(CH$_2$)$_2$-piperazinylene-(CH$_2$)$_3$—, —CH$_2$-piperazinylene-(CH$_2$)$_2$—, —CH$_2$-piperazinylene-(CH$_2$)$_3$—, or —(CH$_2$)$_2$-piperazinylene-(CH$_2$)$_3$—.

31. The compound of formula (I) or a salt, enantiomer, solvate, polymorph thereof according to claim 28, wherein the LIN is —(CH$_2$)$_{n1}$-phenylene-(CH$_2$)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

32. The compound of formula (I) or a salt, enantiomer, solvate, polymorph thereof according to claim 31, wherein the LIN is: —CH$_2$-phenylene-CH$_2$—, —(CH$_2$)$_2$-phenylene-(CH$_2$)$_2$—, —CH$_2$-phenylene-(CH$_2$)$_2$—, —(CH$_2$)$_2$-phenylene-CH$_2$—, —(CH$_2$)$_3$-phenylene-(CH$_2$)$_3$—, —CH$_2$-phenylene-(CH$_2$)$_3$—, —(CH$_2$)$_2$-phenylene-(CH$_2$)$_3$—, —(CH$_2$)$_3$-phenylene-(CH$_2$)$_2$—, or —(CH$_2$)$_3$-phenylene-CH$_2$—.

33. The compound of formula (I) or a salt, enantiomer, solvate, polymorph thereof according to claim 1, wherein the LIN represents 1,4-piperazinylene, spiro-cycloalkylene or 1,3-dialkynylene group.

34. The compound of formula (I) or a salt, enantiomer, solvate, polymorph thereof according to claim 33, wherein the LIN represents:

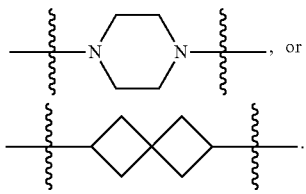, or

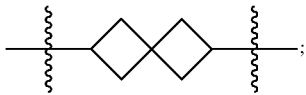 [SMILES: *C1CC2(C1)CC(*)C2].

35. The compound of formula (I) or a salt, enantiomer, solvate, polymorph thereof according to claim 34, wherein the LIN represents:

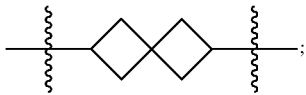 [SMILES: *C1CC2(C1)CC(*)C2];

and
the group A is C(O).

36. The compound of formula (I) or a salt, enantiomer, solvate, polymorph thereof according to claim 1, which is selected from the group consisting of:
4-((2-(3-(4-(4-((5-chloro-4-((2-(dimethylphosphoryl) phenyl)amino)pyrimidin-2-yl)amino)-3-methoxyphenyl)piperazin-1-yl)-3-oxopropoxy)ethyl)amino)-2-(2, 6-dioxopiperidin-3-yl)isoindoline-1,3-dione;
4-((2-(2-(3-(4-(4-((5-chloro-4-((2-(dimethylphosphoryl) phenyl)amino)pyrimidin-2-yl)amino)-3-methoxyphenyl)piperazin-1-yl)-3-oxopropoxy)ethoxy)ethyl) amino)-2-(2,6-dioxopiperidin-3-yl)isoindoline-1,3-dione;
3-(4-(2-(2-(3-(4-(4-((5-chloro-4-((2-(dimethylphosphoryl)phenyl)amino)pyrimidin-2-yl)amino)-3-methoxyphenyl)piperazin-1-yl)-3-oxopropoxy)ethoxy)ethoxy)-1-oxoisoindolin-2-yl)piperidine-2,6-dione;
4-((2-(2-(2-(3-(4-(4-((4-((2-(dimethylphosphoryl)phenyl) amino)-5-methylpyrimidin-2-yl)amino)-3-methoxyphenyl)piperazin-1-yl)-3-oxopropoxy)ethoxy)ethoxy) ethyl)amino)-2-(2,6-dioxopiperidin-3-yl)isoindoline-1, 3-dione;
4-((15-(4-(4-((5-chloro-4-((2-(dimethylphosphoryl)phenyl)amino)pyrimidin-2-yl)amino)-3-methoxyphenyl) piperazin-1-yl)-15-oxo-3,6,9,12-tetraoxapentadecyl) amino)-2-(2,6-dioxopiperidin-3-yl)isoindoline-1,3-dione;
4-((18-(4-(4-((5-chloro-4-((2-(dimethylphosphoryl)phenyl)amino)pyrimidin-2-yl)amino)-3-methoxyphenyl) piperazin-1-yl)-18-oxo-3,6,9,12,15-pentaoxaoctadecyl)amino)-2-(2,6-dioxopiperidin-3-yl)isoindoline-1,3-dione;
4-((18-(4-(4-((5-chloro-4-((2-(dimethylphosphoryl)phenyl)amino)pyrimidin-2-yl)amino)-3-methoxyphenyl) piperazin-1-yl)-3,6,9,12,15-pentaoxaoctadecyl) amino)-2-(2,6-dioxopiperidin-3-yl)isoindoline-1,3-dione;
3-(4-((18-(4-(4-((5-chloro-4-((2-(dimethylphosphoryl) phenyl)amino)pyrimidin-2-yl)amino)-3-methoxyphenyl)piperazin-1-yl)-3,6,9,12,15-pentaoxaoctadecyl) amino)-1-oxoisoindolin-2-yl)piperidine-2,6-dione;
3-(4-(19-(4-(4-((5-chloro-4-((2-(dimethylphosphoryl) phenyl)amino)pyrimidin-2-yl)amino)-3-methoxyphenyl)piperazin-1-yl)-4,7,10,13,16-pentaoxanonadecyl)-1-oxoisoindolin-2-yl)piperidine-2,6-dione;
4-((2-(4-(4-((5-chloro-4-((2-(dimethylphosphoryl)phenyl)amino)pyrimidin-2-yl)amino)-3-methoxyphenyl) piperazin-1-yl)-2-oxoethyl)amino)-2-(2,6-dioxopiperidin-3-yl)isoindoline-1,3-dione;
4-((3-(4-(4-((5-chloro-4-((2-(dimethylphosphoryl)phenyl)amino)pyrimidin-2-yl)amino)-3-methoxyphenyl) piperazin-1-yl)-3-oxopropyl)amino)-2-(2,6-dioxopiperidin-3-yl)isoindoline-1,3-dione;
4-((4-(4-(4-((5-chloro-4-((2-(dimethylphosphoryl)phenyl)amino)pyrimidin-2-yl)amino)-3-methoxyphenyl) piperazin-1-yl)-4-oxobutyl)amino)-2-(2,6-dioxopiperidin-3-yl)isoindoline-1,3-dione;
4-((5-(4-(4-((5-chloro-4-((2-(dimethylphosphoryl)phenyl)amino)pyrimidin-2-yl)amino)-3-methoxyphenyl) piperazin-1-yl)-5-oxopentyl)amino)-2-(2,6-dioxopiperidin-3-yl)isoindoline-1,3-dione;
4-((6-(4-(4-((5-chloro-4-((2-(dimethylphosphoryl)phenyl)amino)pyrimidin-2-yl)amino)-3-methoxyphenyl) piperazin-1-yl)-6-oxohexyl)amino)-2-(2,6-dioxopiperidin-3-yl)isoindoline-1,3-dione;
4-((7-(4-(4-((5-chloro-4-((2-(dimethylphosphoryl)phenyl)amino)pyrimidin-2-yl)amino)-3-methoxyphenyl) piperazin-1-yl)-7-oxoheptyl)amino)-2-(2,6-dioxopiperidin-3-yl)isoindoline-1,3-dione;
4-((7-(4-(4-((5-chloro-4-((2-(dimethylphosphoryl)phenyl)amino)pyrimidin-2-yl)amino)-3-methoxyphenyl) piperazin-1-yl)-7-oxoheptyl)oxy)-2-(2,6-dioxopiperidin-3-yl)isoindoline-1,3-dione;
7-(4-(4-((5-chloro-4-((2-(dimethylphosphoryl)phenyl) amino)pyrimidin-2-yl)amino)-3-methoxyphenyl)piperazin-1-yl)-N-(2-(2,6-dioxopiperidin-3-yl)-1,3-dioxoisoindolin-4-yl)-7-oxoheptanamide;
7-(4-(4-((5-chloro-4-((2-(dimethylphosphoryl)phenyl) amino)pyrimidin-2-yl)amino)-3-methoxyphenyl)piperazin-1-yl)-N-(2-(2,6-dioxopiperidin-3-yl)-1-oxoisoindolin-4-yl)-7-oxoheptanamide;
3-(4-(8-(4-(4-((5-chloro-4-((2-(dimethylphosphoryl)phenyl)amino)pyrimidin-2-yl)amino)-3-methoxyphenyl) piperazin-1-yl)-8-oxooctyl)-1-oxoisoindolin-2-yl)piperidine-2,6-dione;
4-((7-(4-(4-((5-chloro-4-((2-(dimethylphosphoryl)phenyl)amino)pyrimidin-2-yl)amino)-3-methoxyphenyl) piperazin-1-yl)heptyl)amino)-2-(2,6-dioxopiperidin-3-yl)isoindoline-1,3-dione;

3-(4-((7-(4-(4-((5-chloro-4-((2-(dimethylphosphoryl)phenyl)amino)pyrimidin-2-yl)amino)-3-methoxyphenyl)piperazin-1-yl)heptyl)amino)-1-oxoisoindolin-2-yl)piperidine-2,6-dione;

7-(4-(4-((5-chloro-4-((2-(dimethylphosphoryl)phenyl)amino)pyrimidin-2-yl)amino)-3-methoxyphenyl)piperazin-1-yl)-N-(2-(2,6-dioxopiperidin-3-yl)-1-oxoisoindolin-4-yl)heptanamide;

4-((8-(4-(6-(4-(4-((5-chloro-4-((2-(dimethylphosphoryl)phenyl)amino)pyrimidin-2-yl)amino)-3-methoxyphenyl)piperazin-1-yl)-6-oxohexyl)-1H-1,2,3-triazol-1-yl)octyl)amino)-2-(2,6-dioxopiperidin-3-yl)isoindoline-1,3-dione;

4-((5-((7-(4-(4-((5-chloro-4-((2-(dimethylphosphoryl)phenyl)amino)pyrimidin-2-yl)amino)-3-methoxyphenyl)piperazin-1-yl)-7-oxoheptyl)thio)pentyl)amino)-2-(2,6-dioxopiperidin-3-yl)isoindoline-1,3-dione;

4-((5-((7-(4-(4-((5-chloro-4-((2-(dimethylphosphoryl)phenyl)amino)pyrimidin-2-yl)amino)-3-methoxyphenyl)piperazin-1-yl)-7-oxoheptyl) sulfinyl)pentyl)amino)-2-(2,6-dioxopiperidin-3-yl)isoindoline-1,3-dione;

4-((5-((7-(4-(4-((5-chloro-4-((2-(dimethylphosphoryl)phenyl)amino)pyrimidin-2-yl)amino)-3-methoxyphenyl)piperazin-1-yl)-7-oxoheptyl) sulfonyl)pentyl)amino)-2-(2,6-dioxopiperidin-3-yl)isoindoline-1,3-dione;

4-((12-(4-(4-((5-chloro-4-((2-(dimethylphosphoryl)phenyl)amino)pyrimidin-2-yl)amino)-3-methoxyphenyl)piperazin-1-yl)-12-oxododec-5-yn-1-yl)amino)-2-(2,6-dioxopiperidin-3-yl)isoindoline-1,3-dione;

(2S,4R)-1-((S)-2-(2-(2-(2-(4-(4-((5-chloro-4-((2-(dimethylphosphoryl)phenyl)amino)pyrimidin-2-yl)amino)-3-methoxyphenyl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(3-(2-(3-(4-(4-((5-chloro-4-((2-(dimethylphosphoryl)phenyl)amino)pyrimidin-2-yl)amino)-3-methoxyphenyl)piperazin-1-yl)-3-oxopropoxy)ethoxy) propanamido)-3,3-dimethylbutanoyl)-4-hydroxy-N-(4-(4-methylthiazol-5-yl)benzyl)pyrrolidine-2-carboxamide;

(2S,4R)-1-((S)-2-(3-(2-(3-(4-(4-((5-chloro-4-((2-(dimethylphosphoryl)phenyl)amino)pyrimidin-2-yl)amino)-3-methoxyphenyl)piperazin-1-yl)propoxy)ethoxy)propanamido)-3,3-dimethylbutanoyl)-4-hydroxy-N-(4-(4-methylthiazol-5-yl)benzyl)pyrrolidine-2-carboxamide;

(2S,4R)-1-((S)-2-(tert-butyl)-16-(4-(4-((5-chloro-4-((2-(dimethylphosphoryl)phenyl)amino)pyrimidin-2-yl)amino)-3-methoxyphenyl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide;

(2S,4R)-1-((S)-2-(tert-butyl)-19-(4-(4-((5-chloro-4-((2-(dimethylphosphoryl)phenyl)amino)pyrimidin-2-yl)amino)-3-methoxyphenyl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide;

(2S,4R)-1-((S)-2-(tert-butyl)-22-(4-(4-((5-chloro-4-((2-(dimethylphosphoryl)phenyl)amino)pyrimidin-2-yl)amino)-3-methoxyphenyl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide;

(2S,4R)-1-((S)-2-(4-(4-((5-chloro-4-((2-(dimethylphosphoryl)phenyl)amino)pyrimidin-2-yl)amino)-3-methoxyphenyl)piperazin-1-yl)-4-oxobutanamido)-3,3-dimethylbutanoyl)-4-hydroxy-N-(4-(4-methylthiazol-5-yl)benzyl)pyrrolidine-2-carboxamide;

(2S,4R)-1-((S)-2-(5-(4-(4-((5-chloro-4-((2-(dimethylphosphoryl)phenyl)amino)pyrimidin-2-yl)amino)-3-methoxyphenyl)piperazin-1-yl)-5-oxopentanamido)-3,3-dimethylbutanoyl)-4-hydroxy-N-(4-(4-methylthiazol-5-yl)benzyl)pyrrolidine-2-carboxamide;

(2S,4R)-1-((S)-2-(6-(4-(4-((5-chloro-4-((2-(dimethylphosphoryl)phenyl)amino)pyrimidin-2-yl)amino)-3-methoxyphenyl)piperazin-1-yl)-6-oxohexanamido)-3,3-dimethylbutanoyl)-4-hydroxy-N-(4-(4-methylthiazol-5-yl)benzyl)pyrrolidine-2-carboxamide;

(2S,4R)-1-((S)-2-(7-(4-(4-((5-chloro-4-((2-(dimethylphosphoryl)phenyl)amino)pyrimidin-2-yl)amino)-3-methoxyphenyl)piperazin-1-yl)-7-oxoheptanamido)-3,3-dimethylbutanoyl)-4-hydroxy-N-(4-(4-methylthiazol-5-yl)benzyl)pyrrolidine-2-carboxamide;

(2S,4R)-1-((S)-2-(7-(4-(4-((5-chloro-4-((2-(dimethylphosphoryl)phenyl)amino)pyrimidin-2-yl)amino)-3-methoxyphenyl)piperazin-1-yl)heptanamido)-3,3-dimethylbutanoyl)-4-hydroxy-N-(4-(4-methylthiazol-5-yl)benzyl)pyrrolidine-2-carboxamide;

(2S,4R)-1-((S)-2-(8-(4-(4-((5-chloro-4-((2-(dimethylphosphoryl)phenyl)amino)pyrimidin-2-yl)amino)-3-methoxyphenyl)piperazin-1-yl)-8-oxooctanamido)-3,3-dimethylbutanoyl)-4-hydroxy-N-(4-(4-methylthiazol-5-yl)benzyl)pyrrolidine-2-carboxamide;

(2S,4R)-1-((S)-2-(9-(4-(4-((5-chloro-4-((2-(dimethylphosphoryl)phenyl)amino)pyrimidin-2-yl)amino)-3-methoxyphenyl)piperazin-1-yl)-9-oxononanamido)-3,3-dimethylbutanoyl)-4-hydroxy-N-(4-(4-methylthiazol-5-yl)benzyl)pyrrolidine-2-carboxamide;

(2S,4R)-1-((S)-2-(10-(4-(4-((5-chloro-4-((2-(dimethylphosphoryl)phenyl)amino)pyrimidin-2-yl)amino)-3-methoxyphenyl)piperazin-1-yl)-10-oxodecanamido)-3,3-dimethylbutanoyl)-4-hydroxy-N-(4-(4-methylthiazol-5-yl)benzyl)pyrrolidine-2-carboxamide;

N1-(4-(4-(4-((5-chloro-4-((2-(dimethylphosphoryl)phenyl)amino)pyrimidin-2-yl)amino)-3-methoxyphenyl)piperazin-1-yl)-4-oxobutyl)-N5-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl) glutaramide;

N-(1-(4-((5-chloro-4-((2-(dimethylphosphoryl)phenyl)amino)pyrimidin-2-yl)amino)-3-methoxyphenyl)piperidin-4-yl)-3-(2-((2-(2,6-dioxopiperidin-3-yl)-1,3-dioxoisoindolin-4-yl)amino)ethoxy)propanamide;

N-(1-(4-((5-chloro-4-((2-(dimethylphosphoryl)phenyl)amino)pyrimidin-2-yl)amino)-3-methoxyphenyl)piperidin-4-yl)-3-(2-(2-((2-(2,6-dioxopiperidin-3-yl)-1,3-dioxoisoindolin-4-yl)amino)ethoxy)ethoxy)propanamide;

N-(1-(4-((5-chloro-4-((2-(dimethylphosphoryl)phenyl)amino)pyrimidin-2-yl)amino)-3-methoxyphenyl)piperidin-4-yl)-3-(2-(2-(2-((2-(2,6-dioxopiperidin-3-yl)-1,3-dioxoisoindolin-4-yl)amino)ethoxy)ethoxy)ethoxy)propanamide;

N-(1-(4-((5-chloro-4-((2-(dimethylphosphoryl)phenyl)amino)pyrimidin-2-yl)amino)-3-methoxyphenyl)piperidin-4-yl)-3-(2-(2-(2-((2-(2,6-dioxopiperidin-3-yl)-1,3-dioxoisoindolin-4-yl)oxy)ethoxy)ethoxy)ethoxy)propanamide;

N-(1-(4-((5-chloro-4-((2-(dimethylphosphoryl)phenyl)amino)pyrimidin-2-yl)amino)-3-methoxyphenyl)piperidin-4-yl)-3-(2-(2-(2-((2-(2,6-dioxopiperidin-3-yl)-1-oxoisoindolin-4-yl)oxy)ethoxy)ethoxy)ethoxy)propanamide;

4-((2-(2-(2-(3-((1-(4-((5-chloro-4-((2-(dimethylphosphoryl)phenyl)amino)pyrimidin-2-yl)amino)-3-methoxyphenyl)piperidin-4-yl)amino)propoxy)ethoxy)ethoxy)ethyl)amino)-2-(2,6-dioxopiperidin-3-yl)isoindoline-1,3-dione;

3-(4-((2-(2-(2-(3-((1-(4-((5-chloro-4-((2-(dimethylphosphoryl)phenyl)amino)pyrimidin-2-yl)amino)-3-methoxyphenyl)piperidin-4-yl)amino)propoxy)ethoxy)ethoxy)ethyl)amino)-1-oxoisoindolin-2-yl)piperidine-2,6-dione;

N-(1-(4-((5-chloro-4-((2-(dimethylphosphoryl)phenyl)amino)pyrimidin-2-yl)amino)-3-methoxyphenyl)piperidin-4-yl)-3-(2-(2-(3-(2-(2,6-dioxopiperidin-3-yl)-1-oxoisoindolin-4-yl)propoxy)ethoxy)ethoxy)propanamide;

N-(1-(4-((5-chloro-4-((2-(dimethylphosphoryl)phenyl)amino)pyrimidin-2-yl)amino)-3-methoxyphenyl)piperidin-4-yl)-1-((2-(2,6-dioxopiperidin-3-yl)-1,3-dioxoisoindolin-4-yl)amino)-3,6,9,12-tetraoxapentadecan-15-amide;

N-(1-(4-((5-chloro-4-((2-(dimethylphosphoryl)phenyl)amino)pyrimidin-2-yl)amino)-3-methoxyphenyl)piperidin-4-yl)-1-((2-(2,6-dioxopiperidin-3-yl)-1,3-dioxoisoindolin-4-yl)amino)-3,6,9,12,15-pentaoxaoctadecan-18-amide;

N-(1-(4-((5-chloro-4-((2-(dimethylphosphoryl)phenyl)amino)pyrimidin-2-yl)amino)-3-methoxyphenyl)piperidin-4-yl)-2-((2-(2,6-dioxopiperidin-3-yl)-1,3-dioxoisoindolin-4-yl)amino)acetamide;

N-(1-(4-((5-chloro-4-((2-(dimethylphosphoryl)phenyl)amino)pyrimidin-2-yl)amino)-3-methoxyphenyl)piperidin-4-yl)-3-((2-(2,6-dioxopiperidin-3-yl)-1,3-dioxoisoindolin-4-yl)amino)propanamide;

N-(1-(4-((5-chloro-4-((2-(dimethylphosphoryl)phenyl)amino)pyrimidin-2-yl)amino)-3-methoxyphenyl)piperidin-4-yl)-4-((2-(2,6-dioxopiperidin-3-yl)-1,3-dioxoisoindolin-4-yl)amino)butanamide;

N-(1-(4-((5-chloro-4-((2-(dimethylphosphoryl)phenyl)amino)pyrimidin-2-yl)amino)-3-methoxyphenyl)piperidin-4-yl)-5-((2-(2,6-dioxopiperidin-3-yl)-1,3-dioxoisoindolin-4-yl)amino)pentanamide;

N-(1-(4-((5-chloro-4-((2-(dimethylphosphoryl)phenyl)amino)pyrimidin-2-yl)amino)-3-methoxyphenyl)piperidin-4-yl)-6-((2-(2,6-dioxopiperidin-3-yl)-1,3-dioxoisoindolin-4-yl)amino)hexanamide;

N-(1-(4-((5-chloro-4-((2-(dimethylphosphoryl)phenyl)amino)pyrimidin-2-yl)amino)-3-methoxyphenyl)piperidin-4-yl)-7-((2-(2,6-dioxopiperidin-3-yl)-1,3-dioxoisoindolin-4-yl)amino)heptanamide;

N-(1-(4-((5-chloro-4-((2-(dimethylphosphoryl)phenyl)amino)pyrimidin-2-yl)amino)-3-methoxyphenyl)piperidin-4-yl)-7-((2-(2,6-dioxopiperidin-3-yl)-1,3-dioxoisoindolin-4-yl)oxy)heptanamide;

N-(1-(4-((5-chloro-4-((2-(dimethylphosphoryl)phenyl)amino)pyrimidin-2-yl)amino)-3-methoxyphenyl)piperidin-4-yl)-7-((2-(2,6-dioxopiperidin-3-yl)-1-oxoisoindolin-4-yl)oxy)heptanamide;

4-((7-((1-(4-((5-chloro-4-((2-(dimethylphosphoryl)phenyl)amino)pyrimidin-2-yl)amino)-3-methoxyphenyl)piperidin-4-yl)amino)heptyl)amino)-2-(2,6-dioxopiperidin-3-yl)isoindoline-1,3-dione;

N-(1-(4-((5-chloro-4-((2-(dimethylphosphoryl)phenyl)amino)pyrimidin-2-yl)amino)-3-methoxyphenyl)piperidin-4-yl)-7-((2-(2,6-dioxopiperidin-3-yl)-1-oxoisoindolin-4-yl)amino)heptanamide;

N1-(1-(4-((5-chloro-4-((2-(dimethylphosphoryl)phenyl)amino)pyrimidin-2-yl)amino)-3-methoxyphenyl)piperidin-4-yl)-N7-(2-(2,6-dioxopiperidin-3-yl)-1,3-dioxoisoindolin-4-yl)heptanediamide;

(2S,4R)-1-((S)-2-(2-(2-(2-((1-(4-((5-chloro-4-((2-(dimethylphosphoryl)phenyl)amino)pyrimidin-2-yl)amino)-3-methoxyphenyl)piperidin-4-yl)amino)-2-oxoethoxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(3-(2-(3-((1-(4-((5-chloro-4-((2-(dimethylphosphoryl)phenyl)amino)pyrimidin-2-yl)amino)-3-methoxyphenyl)piperidin-4-yl)amino)-3-oxopropoxy)ethoxy)propanamido)-3,3-dimethylbutanoyl)-4-hydroxy-N-(4-(4-methylthiazol-5-yl)benzyl)pyrrolidine-2-carboxamide;

(2S,4R)-1-((S)-2-(tert-butyl)-16-((1-(4-((5-chloro-4-((2-(dimethylphosphoryl)phenyl)amino)pyrimidin-2-yl)amino)-3-methoxyphenyl)piperidin-4-yl)amino)-4,16-dioxo-7,10,13-trioxa-3-azahexadecanoyl)-4-hydroxy-N-(4-(4-methylthiazol-5-yl)benzyl)pyrrolidine-2-carboxamide;

N1-(1-(4-((5-chloro-4-((2-(dimethylphosphoryl)phenyl)amino)pyrimidin-2-yl)amino)-3-methoxyphenyl)piperidin-4-yl)-N16-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13-tetraoxahexadecanediamide;

N1-(1-(4-((5-chloro-4-((2-(dimethylphosphoryl)phenyl)amino)pyrimidin-2-yl)amino)-3-methoxyphenyl)piperidin-4-yl)-N19-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13,16-pentaoxanonadecanediamide;

N1-(1-(4-((5-chloro-4-((2-(dimethylphosphoryl)phenyl)amino)pyrimidin-2-yl)amino)-3-methoxyphenyl)piperidin-4-yl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide;

N1-(1-(4-((5-chloro-4-((2-(dimethylphosphoryl)phenyl)amino)pyrimidin-2-yl)amino)-3-methoxyphenyl)piperidin-4-yl)-N5-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide;

N1-(1-(4-((5-chloro-4-((2-(dimethylphosphoryl)phenyl)amino)pyrimidin-2-yl)amino)-3-methoxyphenyl)piperidin-4-yl)-N6-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)adipamide;

N1-(1-(4-((5-chloro-4-((2-(dimethylphosphoryl)phenyl)amino)pyrimidin-2-yl)amino)-3-methoxyphenyl)piperidin-4-yl)-N7-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)heptanediamide;

N1-(1-(4-((5-chloro-4-((2-(dimethylphosphoryl)phenyl)amino)pyrimidin-2-yl)amino)-3-methoxyphenyl)piperidin-4-yl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide;

N1-(1-(4-((5-chloro-4-((2-(dimethylphosphoryl)phenyl)amino)pyrimidin-2-yl)amino)-3-methoxyphenyl)piperidin-4-yl)-N9-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)nonanediamide;

N1-(1-(4-((5-chloro-4-((2-(dimethylphosphoryl)phenyl)
amino)pyrimidin-2-yl)amino)-3-methoxyphenyl)piperidin-4-yl)-N10-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide;

N1-(1-(4-((5-chloro-4-((2-(dimethylphosphoryl)phenyl)
amino)pyrimidin-2-yl)amino)-3-methoxyphenyl)piperidin-4-yl)-N4-(2-((2-(2,6-dioxopiperidin-3-yl)-1,3-dioxoisoindolin-4-yl)amino)ethyl)succinamide;

4-((2-(3-(4-(1-(4-((5-chloro-4-((2-(dimethylphosphoryl)
phenyl)amino)pyrimidin-2-yl)amino)-3-methoxyphenyl)piperidin-4-yl)piperazin-1-yl)-3-oxopropoxy)
ethyl)amino)-2-(2,6-dioxopiperidin-3-yl)isoindoline-1,3-dione;

4-((2-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)
ethoxy)ethyl)amino)-2-(2,6-dioxopiperidin-3-yl)
isoindoline-1,3-dione;

4-(2-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)
ethoxy)ethoxy)-2-(2,6-dioxopiperidin-3-yl)
isoindoline-1,3-dione;

3-(4-(2-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethoxy)ethoxy)-1-oxoisoindolin-2-yl)
piperidine-2,6-dione;

4-((2-(2-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethoxy)ethoxy)ethyl)amino)-2-(2,6-dioxopiperidin-3-yl)isoindoline-1,3-dione;

4-((15-(4-(1-(4-((5-chloro-4-((2-(dimethylphosphoryl)
phenyl)amino)pyrimidin-2-yl)amino)-3-methoxyphenyl)piperidin-4-yl)piperazin-1-yl)-15-oxo-3,6,9,12-tetraoxapentadecyl)amino)-2-(2,6-dioxopiperidin-3-yl)
isoindoline-1,3-dione;

4-((18-(4-(1-(4-((5-chloro-4-((2-(dimethylphosphoryl)
phenyl)amino)pyrimidin-2-yl)amino)-3-methoxyphenyl)piperidin-4-yl)piperazin-1-yl)-18-oxo-3,6,9,12,15-pentaoxaoctadecyl)amino)-2-(2,6-dioxopiperidin-3-yl)
isoindoline-1,3-dione;

4-((2-(4-(1-(4-((5-chloro-4-((2-(dimethylphosphoryl)
phenyl)amino)pyrimidin-2-yl)amino)-3-methoxyphenyl)piperidin-4-yl)piperazin-1-yl)-2-oxoethyl)amino)-2-(2,6-dioxopiperidin-3-yl)isoindoline-1,3-dione;

4-((3-(4-(1-(4-((5-chloro-4-((2-(dimethylphosphoryl)
phenyl)amino)pyrimidin-2-yl)amino)-3-methoxyphenyl)piperidin-4-yl)piperazin-1-yl)-3-oxopropyl)
amino)-2-(2,6-dioxopiperidin-3-yl)isoindoline-1,3-dione;

4-((4-(4-(1-(4-((5-chloro-4-((2-(dimethylphosphoryl)
phenyl)amino)pyrimidin-2-yl)amino)-3-methoxyphenyl)piperidin-4-yl)piperazin-1-yl)-4-oxobutyl)amino)-2-(2,6-dioxopiperidin-3-yl)isoindoline-1,3-dione;

4-(4-(4-(1-(4-((5-chloro-4-((2-(dimethylphosphoryl)phenyl)amino)pyrimidin-2-yl)amino)-3-methoxyphenyl)
piperidin-4-yl)piperazin-1-yl)-4-oxobutoxy)-2-(2,6-dioxopiperidin-3-yl)isoindoline-1,3-dione;

3-(4-(4-(4-(1-(4-((5-chloro-4-((2-(dimethylphosphoryl)
phenyl)amino)pyrimidin-2-yl)amino)-3-methoxyphenyl)piperidin-4-yl)piperazin-1-yl)-4-oxobutoxy)-1-oxoisoindolin-2-yl)piperidine-2,6-dione;

4-(5-(4-(1-(4-((5-chloro-4-((2-(dimethylphosphoryl)phenyl)amino)pyrimidin-2-yl)amino)-3-methoxyphenyl)
piperidin-4-yl)piperazin-1-yl)-5-oxopentyl)-2-(2,6-dioxopiperidin-3-yl)isoindoline-1,3-dione;

3-(4-((4-(4-(1-(4-((5-chloro-4-((2-(dimethylphosphoryl)
phenyl)amino)pyrimidin-2-yl)amino)-3-methoxyphenyl)piperidin-4-yl)piperazin-1-yl)-4-oxobutyl)amino)-1-oxoisoindolin-2-yl)piperidine-2,6-dione;

4-((4-(4-(1-(4-((5-chloro-4-((2-(dimethylphosphoryl)
phenyl)amino)pyrimidin-2-yl)amino)-3-methoxyphenyl)piperidin-4-yl)piperazin-1-yl)butyl)amino)-2-(2,6-dioxopiperidin-3-yl)isoindoline-1,3-dione;

4-((5-(4-(1-(4-((5-chloro-4-((2-(dimethylphosphoryl)
phenyl)amino)pyrimidin-2-yl)amino)-3-methoxyphenyl)piperidin-4-yl)piperazin-1-yl)-5-oxopentyl)
amino)-2-(2,6-dioxopiperidin-3-yl)isoindoline-1,3-dione;

4-((6-(4-(1-(4-((5-chloro-4-((2-(dimethylphosphoryl)
phenyl)amino)pyrimidin-2-yl)amino)-3-methoxyphenyl)piperidin-4-yl)piperazin-1-yl)-6-oxohexyl)amino)-2-(2,6-dioxopiperidin-3-yl)isoindoline-1,3-dione;

4-((7-(4-(1-(4-((5-chloro-4-((2-(dimethylphosphoryl)
phenyl)amino)pyrimidin-2-yl)amino)-3-methoxyphenyl)piperidin-4-yl)piperazin-1-yl)-7-oxoheptyl)
amino)-2-(2,6-dioxopiperidin-3-yl)isoindoline-1,3-dione;

(2S,4R)-1-((S)-2-(2-(2-(2-(4-(1-(4-((5-chloro-4-((2-(dimethylphosphoryl)phenyl)amino)pyrimidin-2-yl)
amino)-3-methoxyphenyl)piperidin-4-yl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(3-(2-(3-(4-(1-(4-((5-chloro-4-((2-(dimethylphosphoryl)phenyl)amino)pyrimidin-2-yl)
amino)-3-methoxyphenyl)piperidin-4-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide;

(2S,4R)-1-((S)-2-(3-(2-(3-(4-(1-(4-((5-chloro-4-((2-(dimethylphosphoryl)phenyl)amino)pyrimidin-2-yl)
amino)-3-methoxyphenyl)piperidin-4-yl)piperazin-1-yl)propoxy)ethoxy)propanamido)-3,3-dimethylbutanoyl)-4-hydroxy-N-(4-(4-methylthiazol-5-yl)benzyl)pyrrolidine-2-carboxamide;

(2S,4R)-1-((S)-2-(tert-butyl)-16-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4,16-dioxo-7,10,13-trioxa-3-azahexadecanoyl)-4-hydroxy-N-(4-(4-methylthiazol-5-yl)benzyl)
pyrrolidine-2-carboxamide;

(2S,4R)-1-((S)-2-(tert-butyl)-19-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide;

(2S,4R)-1-((S)-2-(tert-butyl)-22-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide;

(2S,4R)-1-((S)-2-(4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide;

(2S,4R)-1-((S)-2-(5-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide;

(2S,4R)-1-((S)-2-(6-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide;

(2S,4R)-1-((S)-2-(7-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-7-oxoheptanamido)-3,3-dimethylbutanoyl)-4-hydroxy-N-(4-(4-methylthiazol-5-yl)benzyl)pyrrolidine-2-carboxamide;

(2S,4R)-1-((S)-2-(7-(4-(1-(4-((5-chloro-4-((2-(dimethylphosphoryl)phenyl)amino)pyrimidin-2-yl)amino)-3-methoxyphenyl)piperidin-4-yl)piperazin-1-yl)heptanamido)-3,3-dimethylbutanoyl)-4-hydroxy-N-(4-(4-methylthiazol-5-yl)benzyl)pyrrolidine-2-carboxamide;

(2S,4R)-1-((S)-2-(8-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide;

(2S,4R)-1-((S)-2-(9-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-9-oxononanamido)-3,3-dimethylbutanoyl)-4-hydroxy-N-(4-(4-methylthiazol-5-yl)benzyl)pyrrolidine-2-carboxamide;

(2S,4R)-1-((S)-2-(10-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide;

4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-N-(2-((2-(2,6-dioxopiperidin-3-yl)-1,3-dioxoisoindolin-4-yl)amino)ethyl)-4-oxobutanamide;

(2S,4R)-1-((S)-2-(4-(4-(4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4-oxobutyl)-1H-1,2,3-triazol-1-yl)butanamido)-3,3-dimethylbutanoyl)-4-hydroxy-N-(4-(4-methylthiazol-5-yl)benzyl)pyrrolidine-2-carboxamide;

8-(4-(3-(2-((2-(2,6-dioxopiperidin-3-yl)-1,3-dioxoisoindolin-4-yl)amino)ethoxy)propanoyl)piperazin-1-yl)-9-ethyl-6,6-dimethyl-11-oxo-6,11-dihydro-5H-benzo[b]carbazole-3-carbonitrile;

8-(4-(3-(2-(2-((2-(2,6-dioxopiperidin-3-yl)-1,3-dioxoisoindolin-4-yl)amino)ethoxy)ethoxy)propanoyl)piperazin-1-yl)-9-ethyl-6,6-dimethyl-11-oxo-6,11-dihydro-5H-benzo[b]carbazole-3-carbonitrile;

N-(1-(3-cyano-9-ethyl-6,6-dimethyl-11-oxo-6,11-dihydro-5H-benzo[b]carbazol-8-yl)piperidin-4-yl)-3-(2-(2-((2-(2,6-dioxopiperidin-3-yl)-1,3-dioxoisoindolin-4-yl)amino)ethoxy)ethoxy)propanamide;

8-(4-(4-(3-(2-(2-((2-(2,6-dioxopiperidin-3-yl)-1,3-dioxoisoindolin-4-yl)amino)ethoxy)ethoxy)propanoyl)piperazin-1-yl)piperidin-1-yl)-9-ethyl-6,6-dimethyl-11-oxo-6,11-dihydro-5H-benzo[b]carbazole-3-carbonitrile;

8-(4-(4-(3-(2-(2-((2-(2,6-dioxopiperidin-3-yl)-1-oxoisoindolin-4-yl)amino)ethoxy)ethoxy)propanoyl)piperazin-1-yl)piperidin-1-yl)-9-ethyl-6,6-dimethyl-11-oxo-6,11-dihydro-5H-benzo[b]carbazole-3-carbonitrile;

8-(4-(4-(3-(2-(2-((2-(2,6-dioxopiperidin-3-yl)-1,3-dioxoisoindolin-4-yl)oxy)ethoxy)ethoxy)propanoyl)piperazin-1-yl)piperidin-1-yl)-9-ethyl-6,6-dimethyl-11-oxo-6,11-dihydro-5H-benzo[b]carbazole-3-carbonitrile;

8-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)-9-ethyl-6,6-dimethyl-11-oxo-6,11-dihydro-5H-benzo[b]carbazole-3-carbonitrile;

8-(4-(1-((2-(2,6-dioxopiperidin-3-yl)-1,3-dioxoisoindolin-4-yl)amino)-3,6,9,12-tetraoxapentadecan-15-oyl)piperazin-1-yl)-9-ethyl-6,6-dimethyl-11-oxo-6,11-dihydro-5H-benzo[b]carbazole-3-carbonitrile;

8-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)-9-ethyl-6,6-dimethyl-11-oxo-6,11-dihydro-5H-benzo[b]carbazole-3-carbonitrile;

8-(4-((2-(2,6-dioxopiperidin-3-yl)-1,3-dioxoisoindolin-4-yl)glycyl)piperazin-1-yl)-9-ethyl-6,6-dimethyl-11-oxo-6,11-dihydro-5H-benzo[b]carbazole-3-carbonitrile  8-(4-(3-((2-(2,6-dioxopiperidin-3-yl)-1,3-dioxoisoindolin-4-yl)amino)propanoyl)piperazin-1-yl)-9-ethyl-6,6-dimethyl-11-oxo-6,11-dihydro-5H-benzo[b]carbazole-3-carbonitrile;

8-(4-(4-((2-(2,6-dioxopiperidin-3-yl)-1,3-dioxoisoindolin-4-yl)amino)butanoyl)piperazin-1-yl)-9-ethyl-6,6-dimethyl-11-oxo-6,11-dihydro-5H-benzo[b]carbazole-3-carbonitrile;

8-(4-(5-((2-(2,6-dioxopiperidin-3-yl)-1,3-dioxoisoindolin-4-yl)amino)pentanoyl)piperazin-1-yl)-9-ethyl-6,6-dimethyl-11-oxo-6,11-dihydro-5H-benzo[b]carbazole-3-carbonitrile;

8-(4-(6-((2-(2,6-dioxopiperidin-3-yl)-1,3-dioxoisoindolin-4-yl)amino)hexanoyl)piperazin-1-yl)-9-ethyl-6,6-dimethyl-11-oxo-6,11-dihydro-5H-benzo[b]carbazole-3-carbonitrile;

8-(4-(6-((2-(2,6-dioxopiperidin-3-yl)-1-oxoisoindolin-4-yl)amino)hexanoyl)piperazin-1-yl)-9-ethyl-6,6-dimethyl-11-oxo-6,11-dihydro-5H-benzo[b]carbazole-3-carbonitrile;

N-(1-(3-cyano-9-ethyl-6,6-dimethyl-11-oxo-6,11-dihydro-5H-benzo[b]carbazol-8-yl)piperidin-4-yl)-6-((2-(2,6-dioxopiperidin-3-yl)-1,3-dioxoisoindolin-4-yl)amino)hexanamide;

N-(1-(3-cyano-9-ethyl-6,6-dimethyl-11-oxo-6,11-dihydro-5H-benzo[b]carbazol-8-yl)piperidin-4-yl)-6-((2-(2,6-dioxopiperidin-3-yl)-1-oxoisoindolin-4-yl)amino)hexanamide;

8-(4-(4-(6-((2-(2,6-dioxopiperidin-3-yl)-1,3-dioxoisoindolin-4-yl)amino)hexanoyl)piperazin-1-yl)piperidin-1-yl)-9-ethyl-6,6-dimethyl-11-oxo-6,11-dihydro-5H-benzo[b]carbazole-3-carbonitrile;

8-(4-(4-(7-(2-(2,6-dioxopiperidin-3-yl)-1,3-dioxoisoindolin-4-yl)heptanoyl)piperazin-1-yl)piperidin-1-yl)-9-ethyl-6,6-dimethyl-11-oxo-6,11-dihydro-5H-benzo[b]carbazole-3-carbonitrile;

8-(4-(4-(6-((2-(2,6-dioxopiperidin-3-yl)-1,3-dioxoisoindolin-4-yl)oxy)hexanoyl)piperazin-1-yl)piperidin-1-yl)-9-ethyl-6,6-dimethyl-11-oxo-6,11-dihydro-5H-benzo[b]carbazole-3-carbonitrile;

8-(4-(4-(6-((2-(2,6-dioxopiperidin-3-yl)-1-oxoisoindolin-4-yl)amino)hexanoyl)piperazin-1-yl)piperidin-1-yl)-9-ethyl-6,6-dimethyl-11-oxo-6,11-dihydro-5H-benzo[b]carbazole-3-carbonitrile;

8-(4-(4-(6-((2-(2,6-dioxopiperidin-3-yl)-1-oxoisoindolin-4-yl)amino)hexyl)piperazin-1-yl)piperidin-1-yl)-9-ethyl-6,6-dimethyl-11-oxo-6,11-dihydro-5H-benzo[b]carbazole-3-carbonitrile;

8-(4-(7-((2-(2,6-dioxopiperidin-3-yl)-1,3-dioxoisoindolin-4-yl)amino)heptanoyl)piperazin-1-yl)-9-ethyl-6,6-dimethyl-11-oxo-6,11-dihydro-5H-benzo[b]carbazole-3-carbonitrile;

(2S,4R)-1-((S)-2-(2-(2-(2-(4-(3-cyano-9-ethyl-6,6-dimethyl-11-oxo-6,11-dihydro-5H-benzo[b]carbazol-8-yl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(3-(2-(3-(4-(3-cyano-9-ethyl-6,6-dimethyl-11-oxo-6,11-dihydro-5H-benzo[b]carbazol-8-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide;

(2S,4R)-1-((S)-2-(tert-butyl)-16-(4-(3-cyano-9-ethyl-6,6-dimethyl-11-oxo-6,11-dihydro-5H-benzo[b]carbazol-8-yl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide;

(2S,4R)-1-((S)-2-(tert-butyl)-16-((1-(3-cyano-9-ethyl-6,6-dimethyl-11-oxo-6,11-dihydro-5H-benzo[b]carbazol-8-yl)piperidin-4-yl)amino)-4,16-dioxo-7,10,13-trioxa-3-azahexadecanoyl)-4-hydroxy-N-(4-(4-methylthiazol-5-yl)benzyl)pyrrolidine-2-carboxamide;

(2S,4R)-1-((S)-2-(tert-butyl)-16-(4-(1-(3-cyano-9-ethyl-6,6-dimethyl-11-oxo-6,11-dihydro-5H-benzo[b]carbazol-8-yl)piperidin-4-yl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide;

(2S,4R)-1-((S)-2-(tert-butyl)-19-(4-(3-cyano-9-ethyl-6,6-dimethyl-11-oxo-6,11-dihydro-5H-benzo[b]carbazol-8-yl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide;

(2S,4R)-1-((S)-2-(tert-butyl)-22-(4-(3-cyano-9-ethyl-6,6-dimethyl-11-oxo-6,11-dihydro-5H-benzo[b]carbazol-8-yl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide;

(2S,4R)-1-((S)-2-(4-(4-(3-cyano-9-ethyl-6,6-dimethyl-11-oxo-6,11-dihydro-5H-benzo[b]carbazol-8-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide;

(2S,4R)-1-((S)-2-(5-(4-(3-cyano-9-ethyl-6,6-dimethyl-11-oxo-6,11-dihydro-5H-benzo[b]carbazol-8-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide;

(2S,4R)-1-((S)-2-(6-(4-(3-cyano-9-ethyl-6,6-dimethyl-11-oxo-6,11-dihydro-5H-benzo[b]carbazol-8-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide;

(2S,4R)-1-((S)-2-(7-(4-(3-cyano-9-ethyl-6,6-dimethyl-11-oxo-6,11-dihydro-5H-benzo[b]carbazol-8-yl)piperazin-1-yl)-7-oxoheptanamido)-3,3-dimethylbutanoyl)-4-hydroxy-N-(4-(4-methylthiazol-5-yl)benzyl)pyrrolidine-2-carboxamide;

(2S,4R)-1-((S)-2-(8-(4-(3-cyano-9-ethyl-6,6-dimethyl-11-oxo-6,11-dihydro-5H-benzo[b]carbazol-8-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide;

(2S,4R)-1-((S)-2-(9-(4-(3-cyano-9-ethyl-6,6-dimethyl-11-oxo-6,11-dihydro-5H-benzo[b]carbazol-8-yl)piperazin-1-yl)-9-oxononanamido)-3,3-dimethylbutanoyl)-4-hydroxy-N-(4-(4-methylthiazol-5-yl)benzyl)pyrrolidine-2-carboxamide;

N1-(1-(3-cyano-9-ethyl-6,6-dimethyl-11-oxo-6,11-dihydro-5H-benzo[b]carbazol-8-yl)piperidin-4-yl)-N9-((S)-1-(((2S,4R)-4-hydroxy-2-((4-(4-methylthiazol-5-yl)benzyl)carbamoyl)pyrrolidin-1-yl)-3,3-dimethyl-1-oxobutan-2-yl)nonanediamide;

(2S,4R)-1-((S)-2-(9-(4-(1-(3-cyano-9-ethyl-6,6-dimethyl-11-oxo-6,11-dihydro-5H-benzo[b]carbazol-8-yl)piperidin-4-yl)piperazin-1-yl)-9-oxononanamido)-3,3-dimethylbutanoyl)-4-hydroxy-N-(4-(4-methylthiazol-5-yl)benzyl)pyrrolidine-2-carboxamide;

(2S,4R)-1-((S)-2-(10-(4-(3-cyano-9-ethyl-6,6-dimethyl-11-oxo-6,11-dihydro-5H-benzo[b]carbazol-8-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide;

4-(4-(3-cyano-9-ethyl-6,6-dimethyl-11-oxo-6,11-dihydro-5H-benzo[b]carbazol-8-yl)piperazin-1-yl)-N-(2-((2-(2,6-dioxopiperidin-3-yl)-1,3-dioxoisoindolin-4-yl)amino)ethyl)-4-oxobutanamide;

(2S,4R)-1-((S)-2-(4-(4-(4-(4-(3-cyano-9-ethyl-6,6-dimethyl-11-oxo-6,11-dihydro-5H-benzo[b]carbazol-8-yl)piperazin-1-yl)-4-oxobutyl)-1H-1,2,3-triazol-1-yl)butanamido)-3,3-dimethylbutanoyl)-4-hydroxy-N-(4-(4-methylthiazol-5-yl)benzyl)pyrrolidine-2-carboxamide;

(2S,4R)-1-((S)-2-(4-(4-(4-((1-(3-cyano-9-ethyl-6,6-dimethyl-11-oxo-6,11-dihydro-5H-benzo[b]carbazol-8-yl)piperidin-4-yl)amino)-4-oxobutyl)-1H-1,2,3-triazol-1-yl)butanamido)-3,3-dimethylbutanoyl)-4-hydroxy-N-(4-(4-methylthiazol-5-yl)benzyl)pyrrolidine-2-carboxamide;

(2S,4R)-1-((S)-2-(4-(4-(4-(1-(3-cyano-9-ethyl-6,6-dimethyl-11-oxo-6,11-dihydro-5H-benzo[b]carbazol-8-yl)piperidin-4-yl)piperazin-1-yl)-4-oxobutyl)-1H-1,2,3-triazol-1-yl)butanamido)-3,3-dimethylbutanoyl)-4-hydroxy-N-(4-(4-methylthiazol-5-yl)benzyl)pyrrolidine-2-carboxamide;

(2S,4R)-1-((S)-2-(6-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide;

(2S,4R)-1-((S)-2-(6-(4-(1-(4-((5-chloro-4-((2-(isopropylsulfonyl)phenyl)amino)pyrimidin-2-yl)amino)-3-methoxyphenyl)piperidin-4-yl)piperazin-1-yl)hexanamido)-3,3-dimethylbutanoyl)-4-hydroxy-N-(4-(4-methylthiazol-5-yl)benzyl)pyrrolidine-2-carboxamide;

(2S,4R)-1-((S)-2-(tert-butyl)-16-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide;

4-((8-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-8-oxooctyl)amino)-2-(2,6-dioxopiperidin-3-yl)isoindoline-1,3-dione;

3-(4-((8-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-8-oxooctyl)amino)-1-oxoisoindolin-2-yl)piperidine-2,6-dione;

4-((2-(2-(2-(3-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-3-oxopropoxy)ethoxy)ethyl)amino)-2-(2,6-dioxopiperidin-3-yl)isoindoline-1,3-dione;

(2S,4R)-4-hydroxy-1-((S)-2-(13-(4-(1-(5-isopropoxy-4-((4-((2-(isopropylsulfonyl)phenyl)amino)-1,3,5-triazin-2-yl)amino)-2-methylphenyl)piperidin-4-yl)piperazin-1-yl)-13-oxotridecanamido)-3,3-dimethylbutanoyl)-N-(4-(4-methylthiazol-5-yl)benzyl)pyrrolidine-2-carboxamide;

(2S,4R)-1-((S)-2-(tert-butyl)-16-(4-(1-(4-((4-((2-(isopropylsulfonyl)phenyl)amino)-1,3,5-triazin-2-yl)amino)-3-methoxyphenyl)piperidin-4-yl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide;

(2S,4R)-1-((S)-2-(tert-butyl)-16-(4-(1-(4-((4-((2-(isopropylsulfonyl)phenyl)amino)-1,3,5-triazin-2-yl)amino)-3-methoxyphenyl)piperidin-4-yl)piperazin-1-yl)-4-oxo-7,10,13-trioxa-3-azahexadecanoyl)-4-hydroxy-N-(4-(4-methylthiazol-5-yl)benzyl)pyrrolidine-2-carboxamide;

2-(2,6-dioxopiperidin-3-yl)-4-((12-(4-(1-(4-((4-((2-(isopropylsulfonyl)phenyl)amino)-1,3,5-triazin-2-yl)amino)-3-methoxyphenyl)piperidin-4-yl)piperazin-1-yl)-12-oxododecyl)amino)isoindoline-1,3-dione;

3-(4-((12-(4-(1-(4-((4-((2-(isopropylsulfonyl)phenyl)amino)-1,3,5-triazin-2-yl)amino)-3-methoxyphenyl)piperidin-4-yl)piperazin-1-yl)-12-oxododecyl)amino)-1-oxoisoindolin-2-yl)piperidine-2,6-dione;

N-(2-(2,6-dioxopiperidin-3-yl)-1-oxoisoindolin-4-yl)-12-(4-(1-(4-((4-((2-(isopropylsulfonyl)phenyl)amino)-1,3,5-triazin-2-yl)amino)-3-methoxyphenyl)piperidin-4-yl)piperazin-1-yl)-12-oxododecanamide;

2-(2,6-dioxopiperidin-3-yl)-4-((2-(2-(2-(3-(4-(1-(4-((4-((2-(isopropylsulfonyl)phenyl)amino)-1,3,5-triazin-2-yl)amino)-3-methoxyphenyl)piperidin-4-yl)piperazin-1-yl)-3-oxopropoxy)ethoxy)ethyl)amino)isoindoline-1,3-dione;

N1-(2-(6-(((4-((3-fluoro-2-(methylcarbamoyl)phenyl)amino)-7H-pyrrolo[2,3-d]pyrimidin-2-yl)amino)-5-methoxyindolin-1-yl)-2-oxoethyl)-N13-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyltridecanediamide;

(2S,4R)-1-((S)-2-(tert-butyl)-19-(6-(((4-((3-fluoro-2-(methylcarbamoyl)phenyl)amino)-7H-pyrrolo[2,3-d]pyrimidin-2-yl)amino)-5-methoxyindolin-1-yl)-17-methyl-4,16,19-trioxo-7,10,13-trioxa-3,17-diazanonadecanoyl)-4-hydroxy-N-(4-(4-methylthiazol-5-yl)benzyl)pyrrolidine-2-carboxamide;

2-((2-((1-(N-(8-((2-(2,6-dioxopiperidin-3-yl)-1,3-dioxoisoindolin-4-yl)amino)octanoyl)-N-methylglycyl)-5-methoxyindolin-6-yl)amino)-7H-pyrrolo[2,3-d]pyrimidin-4-yl)amino)-6-fluoro-N-methylbenzamide;

2-((2-((1-(N-(8-((2-(2,6-dioxopiperidin-3-yl)-1-oxoisoindolin-4-yl)amino)octanoyl)-N-methylglycyl)-5-methoxyindolin-6-yl)amino)-7H-pyrrolo[2,3-d]pyrimidin-4-yl)amino)-6-fluoro-N-methylbenzamide;

N1-(2-(2,6-dioxopiperidin-3-yl)-1-oxoisoindolin-4-yl)-N8-(2-(6-(((4-((3-fluoro-2-(methylcarbamoyl)phenyl)amino)-7H-pyrrolo[2,3-d]pyrimidin-2-yl)amino)-5-methoxyindolin-1-yl)-2-oxoethyl)-N8-methyloctanediamide;

2-((2-((1-(1-((2-(2,6-dioxopiperidin-3-yl)-1,3-dioxoisoindolin-4-yl)amino)-13-methyl-12-oxo-3,6,9-trioxa-13-azapentadecan-15-oyl)-5-methoxyindolin-6-yl)amino)-7H-pyrrolo[2,3-d]pyrimidin-4-yl)amino)-6-fluoro-N-methylbenzamide;

N1-(1-(4-((5-chloro-4-(1H-indol-3-yl)pyrimidin-2-yl)amino)-3-methoxyphenyl)piperidin-4-yl)-N6-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyladipamide;

(2S,4R)-1-((S)-2-(6-((1-(4-((5-chloro-4-(1H-indol-3-yl)pyrimidin-2-yl)amino)-3-methoxyphenyl)piperidin-4-yl)(methyl)amino)hexanamido)-3,3-dimethylbutanoyl)-4-hydroxy-N-(4-(4-methylthiazol-5-yl)benzyl)pyrrolidine-2-carboxamide;

(2S,4R)-1-((S)-17-(tert-butyl)-2-(1-(4-((5-chloro-4-(1H-indol-3-yl)pyrimidin-2-yl)amino)-3-methoxyphenyl)piperidin-4-yl)-3,15-dioxo-6,9,12-trioxa-2,16-diazaoctadecan-18-oyl)-4-hydroxy-N-(4-(4-methylthiazol-5-yl)benzyl)pyrrolidine-2-carboxamide;

N-(1-(4-((5-chloro-4-(1H-indol-3-yl)pyrimidin-2-yl)amino)-3-methoxyphenyl)piperidin-4-yl)-12-((2-(2,6-dioxopiperidin-3-yl)-1,3-dioxoisoindolin-4-yl)amino)-N-methyldodecanamide;

N-(1-(4-((5-chloro-4-(1H-indol-3-yl)pyrimidin-2-yl)amino)-3-methoxyphenyl)piperidin-4-yl)-12-((2-(2,6-dioxopiperidin-3-yl)-1-oxoisoindolin-4-yl)amino)-N-methyldodecanamide;

N1-(1-(4-((5-chloro-4-(1H-indol-3-yl)pyrimidin-2-yl)amino)-3-methoxyphenyl)piperidin-4-yl)-N12-(2-(2,6-dioxopiperidin-3-yl)-1-oxoisoindolin-4-yl)-N1-methyldodecanediamide;

N-(1-(4-((5-chloro-4-(1H-indol-3-yl)pyrimidin-2-yl)amino)-3-methoxyphenyl)piperidin-4-yl)-3-(2-(2-((2-(2,6-dioxopiperidin-3-yl)-1,3-dioxoisoindolin-4-yl)amino)ethoxy)ethoxy)ethoxy)-N-methylpropanamide;

(2S,4R)-1-((S)-2-(13-(4-(4-((5-(3,5-difluorobenzyl)-1H-indazol-3-yl)carbamoyl)-3-((tetrahydro-2H-pyran-4-yl)amino)phenyl)piperazin-1-yl)-13-oxotridecanamido)-3,3-dimethylbutanoyl)-4-hydroxy-N-(4-(4-methylthiazol-5-yl)benzyl)pyrrolidine-2-carboxamide;

(2S,4R)-1-((S)-2-(13-(4-(4-((5-(3,5-difluorobenzyl)-1H-indazol-3-yl)carbamoyl)-3-((tetrahydro-2H-pyran-4-yl)amino)phenyl)piperazin-1-yl)tridecanamido)-3,3-dimethylbutanoyl)-4-hydroxy-N-(4-(4-methylthiazol-5-yl)benzyl)pyrrolidine-2-carboxamide;

(2S,4R)-1-((S)-2-(tert-butyl)-16-(4-(4-((5-(3,5-difluorobenzyl)-1H-indazol-3-yl)carbamoyl)-3-((tetrahydro-2H-pyran-4-yl)amino)phenyl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide;

N-(5-(3,5-difluorobenzyl)-1H-indazol-3-yl)-4-(4-(12-((2-(2,6-dioxopiperidin-3-yl)-1,3-dioxoisoindolin-4-yl)amino)dodecanoyl)piperazin-1-yl)-2-((tetrahydro-2H-pyran-4-yl)amino)benzamide;

N-(5-(3,5-difluorobenzyl)-1H-indazol-3-yl)-4-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)-2-((tetrahydro-2H-pyran-4-yl)amino)benzamide;

N-(5-(3,5-difluorobenzyl)-1H-indazol-3-yl)-4-(4-(3-(2-(2-((2-(2,6-dioxopiperidin-3-yl)-1-oxoisoindolin-4- yl)amino)ethoxy)ethoxy)ethoxy)propanoyl)piperazin-1-yl)-2-((tetrahydro-2H-pyran-4-yl)amino)benzamide;

N-(5-(3,5-difluorobenzyl)-1H-indazol-3-yl)-4-(4-(3-(2-(2-(3-(2-(2,6-dioxopiperidin-3-yl)-1,3-dioxoisoindolin-4-yl)propoxy)ethoxy)ethoxy)propanoyl)piperazin-1-yl)-2-((tetrahydro-2H-pyran-4-yl)amino)benzamide;

6-amino-5-((R)-1-(2,6-dichloro-3-fluorophenyl)ethoxy)-N-(4-((3R,5S)-4-(13-(((S)-1-((2S,4R)-4-hydroxy-24 (4-(4-methylthiazol-5-yl)benzyl)carbamoyl)pyrrolidin-1-yl)-3,3-dimethyl-1-oxobutan-2-yl)amino)-13-oxotridecyl)-3,5-dimethylpiperazine-1-carbonyl)phenyl)pyridazine-3-carboxamide 6-amino-5-((R)-1-(2,6-dichloro-3-fluorophenyl)ethoxy)-N-(4-((3R,5S)-4-((S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecyl)-3,5-dimethylpiperazine-1-carbonyl)phenyl)pyridazine-3-carboxamide 6-amino-5-((R)-1-(2,6-dichloro-3-fluorophenyl)ethoxy)-N-(4-((3R,5S)-4-(13-(((S)-1-((2S,4R)-4-hydroxy-24 (4-(4-methylthiazol-5-yl)benzyl)carbamoyl)pyrrolidin-1-yl)-3,3-dimethyl-1-oxobutan-2-yl)amino)-13-oxotridecanoyl)-3,5-dimethylpiperazine-1-carbonyl)phenyl)pyridazine-3-carboxamide 6-amino-5-((R)-1-(2,6-dichloro-3-fluorophenyl)ethoxy)-N-(4-((3R,5S)-4-((S)-3-((2S,4R)-4-hydroxy-2-((4-(4-methylthiazol-5-yl)benzyl)carbamoyl)pyrrolidine-1-carbonyl)-2,2-dimethyl-5-oxo-7,11,14-trioxa-4-azaheptadecan-17-oyl)-3,5-dimethylpiperazine-1-carbonyl)phenyl)pyridazine-3-carboxamide 6-amino-5-((R)-1-(2,6-dichloro-3-fluorophenyl)ethoxy)-N-(4-((3S,5R)-4-(10-((2-(2,6-dioxopiperidin-3-yl)-1,3-dioxoisoindolin-4-yl)amino)decanoyl)-3,5-dimethylpiperazine-1-carbonyl)phenyl)pyridazine-3-carboxamide;

6-amino-5-((R)-1-(2,6-dichloro-3-fluorophenyl)ethoxy)-N-(4-((3S,5R)-4-(10-((2-(2,6-dioxopiperidin-3-yl)-1-oxoisoindolin-4-yl)amino)decanoyl)-3,5-dimethylpiperazine-1-carbonyl)phenyl)pyridazine-3-carboxamide;

6-amino-5-((R)-1-(2,6-dichloro-3-fluorophenyl)ethoxy)-N-(4-((3S,5R)-4-(10-((2-(2,6-dioxopiperidin-3-yl)-1-oxoisoindolin-4-yl)amino)decyl)-3,5-dimethylpiperazine-1-carbonyl)phenyl)pyridazine-3-carboxamide;

6-amino-5-((R)-1-(2,6-dichloro-3-fluorophenyl)ethoxy)-N-(4-((3S,5R)-4-(11-(2-(2,6-dioxopiperidin-3-yl)-1,3-dioxoisoindolin-4-yl)undecanoyl)-3,5-dimethylpiperazine-1-carbonyl)phenyl)pyridazine-3-carboxamide; and 6-amino-5-((R)-1-(2,6-dichloro-3-fluorophenyl)ethoxy)-N-(4-((3S,5R)-4-(3-(2-(2-(2-((2-(2,6-dioxopiperidin-3-yl)-1,3-dioxoisoindolin-4-yl)amino)ethoxy)ethoxy)ethoxy)propanoyl)-3,5-dimethylpiperazine-1-carbonyl)phenyl)pyridazine-3-carboxamide.

37. The compound of formula (I) or a salt, enantiomer, solvate, polymorph thereof according to claim 1, which is selected from the group consisting of:

3-(4-((2-(3-(4-(4-((5-chloro-4-((2-(dimethylphosphoryl)phenyl)amino)pyrimidin-2-yl)amino)-3-methoxyphenyl)piperazin-1-yl)-3-oxopropoxy)ethyl)amino)-1-oxoisoindolin-2-yl)piperidine-2,6-dione;

3-(4-((2-(2-(3-(4-(4-((5-chloro-4-((2-(dimethylphosphoryl)phenyl)amino)pyrimidin-2-yl)amino)-3-methoxyphenyl)piperazin-1-yl)-3-oxopropoxy)ethoxy)ethyl)amino)-1-oxoisoindolin-2-yl)piperidine-2,6-dione;

3-(4-((2-(2-(2-(3-(4-(4-((2-(dimethylphosphoryl)phenyl)amino)-5-methylpyrimidin-2-yl)amino)-3-methoxyphenyl)piperazin-1-yl)-3-oxopropoxy)ethoxy)ethoxy)ethyl)amino)-1-oxoisoindolin-2-yl)piperidine-2,6-dione;

3-(4-((15-(4-(4-((5-chloro-4-((2-(dimethylphosphoryl)phenyl)amino)pyrimidin-2-yl)amino)-3-methoxyphenyl)piperazin-1-yl)-15-oxo-3,6,9,12-tetraoxapentadecyl)amino)-1-oxoisoindolin-2-yl)piperidine-2,6-dione;

3-(4-((18-(4-(4-((5-chloro-4-((2-(dimethylphosphoryl)phenyl)amino)pyrimidin-2-yl)amino)-3-methoxyphenyl)piperazin-1-yl)-18-oxo-3,6,9,12,15-pentaoxaoctadecyl)amino)-1-oxoisoindolin-2-yl)piperidine-2,6-dione;

4-((2-(2-(3-(4-(4-((5-chloro-4-((2-(dimethylphosphoryl)phenyl)amino)pyrimidin-2-yl)amino)-3-methoxyphenyl)piperazin-1-yl)propoxy)ethoxy)ethyl)amino)-2-(2,6-dioxopiperidin-3-yl)isoindoline-1,3-dione;

4-(2-(2-(3-(4-(4-((5-chloro-4-((2-(dimethylphosphoryl)phenyl)amino)pyrimidin-2-yl)amino)-3-methoxyphenyl)piperazin-1-yl)-3-oxopropoxy)ethoxy)-2-(2,6-dioxopiperidin-3-yl)isoindoline-1,3-dione;

3-(4-((2-(4-(4-((5-chloro-4-((2-(dimethylphosphoryl)phenyl)amino)pyrimidin-2-yl)amino)-3-methoxyphenyl)piperazin-1-yl)-2-oxoethyl)amino)-1-oxoisoindolin-2-yl)piperidine-2,6-dione;

3-(4-((3-(4-(4-((5-chloro-4-((2-(dimethylphosphoryl)phenyl)amino)pyrimidin-2-yl)amino)-3-methoxyphenyl)piperazin-1-yl)-3-oxopropyl)amino)-1-oxoisoindolin-2-yl)piperidine-2,6-dione;

3-(4-((4-(4-(4-((5-chloro-4-((2-(dimethylphosphoryl)phenyl)amino)pyrimidin-2-yl)amino)-3-methoxyphenyl)piperazin-1-yl)-4-oxobutyl)amino)-1-oxoisoindolin-2-yl)piperidine-2,6-dione;

3-(4-((5-(4-(4-((5-chloro-4-((2-(dimethylphosphoryl)phenyl)amino)pyrimidin-2-yl)amino)-3-methoxyphenyl)piperazin-1-yl)-5-oxopentyl)amino)-1-oxoisoindolin-2-yl)piperidine-2,6-dione;

3-(4-((6-(4-(4-((5-chloro-4-((2-(dimethylphosphoryl)phenyl)amino)pyrimidin-2-yl)amino)-3-methoxyphenyl)piperazin-1-yl)-6-oxohexyl)amino)-1-oxoisoindolin-2-yl)piperidine-2,6-dione;

3-(4-((7-(4-(4-((5-chloro-4-((2-(dimethylphosphoryl)phenyl)amino)pyrimidin-2-yl)amino)-3-methoxyphenyl)piperazin-1-yl)-7-oxoheptyl)amino)-1-oxoisoindolin-2-yl)piperidine-2,6-dione;

4-((2-(4-(4-((5-chloro-4-((2-(dimethylphosphoryl)phenyl)amino)pyrimidin-2-yl)amino)-3-methoxyphenyl)piperazin-1-yl)ethyl)amino)-2-(2,6-dioxopiperidin-3-yl)isoindoline-1,3-dione;

3-(4-((2-(4-(4-((5-chloro-4-((2-(dimethylphosphoryl)phenyl)amino)pyrimidin-2-yl)amino)-3-methoxyphenyl)piperazin-1-yl)ethyl)amino)-1-oxoisoindolin-2-yl)piperidine-2,6-dione;

3-(4-((7-(4-(4-((5-chloro-4-((2-(dimethylphosphoryl)phenyl)amino)pyrimidin-2-yl)amino)-3-methoxyphenyl)piperazin-1-yl)-7-oxoheptyl)oxy)-1-oxoisoindolin-2-yl)piperidine-2,6-dione;

4-(3-(4-(4-((5-chloro-4-((2-(dimethylphosphoryl)phenyl)amino)pyrimidin-2-yl)amino)-3-methoxyphenyl)piperazin-1-yl)-3-oxopropyl)-2-(2,6-dioxopiperidin-3-yl)isoindoline-1,3-dione;

3-(4-(3-(4-(4-((5-chloro-4-((2-(dimethylphosphoryl)phenyl)amino)pyrimidin-2-yl)amino)-3-methoxyphenyl)piperazin-1-yl)-3-oxopropyl)-1-oxoisoindolin-2-yl)piperidine-2,6-dione;

N-(1-(4-((5-chloro-4-((2-(dimethylphosphoryl)phenyl)amino)pyrimidin-2-yl)amino)-3-methoxyphenyl)piperidin-4-yl)-3-(2-((2-(2,6-dioxopiperidin-3-yl)-1-oxoisoindolin-4-yl)amino)ethoxy)propanamide;

N-(1-(4-((5-chloro-4-((2-(dimethylphosphoryl)phenyl)amino)pyrimidin-2-yl)amino)-3-methoxyphenyl)piperidin-4-yl)-3-(2-(2-((2-(2,6-dioxopiperidin-3-yl)-1-oxoisoindolin-4-yl)amino)ethoxy)ethoxy)propanamide;

N-(1-(4-((5-chloro-4-((2-(dimethylphosphoryl)phenyl)amino)pyrimidin-2-yl)amino)-3-methoxyphenyl)piperidin-4-yl)-3-(2-(2-(2-((2-(2,6-dioxopiperidin-3-yl)-1-oxoisoindolin-4-yl)amino)ethoxy)ethoxy)ethoxy)propanamide;

N-(1-(4-((5-chloro-4-((2-(dimethylphosphoryl)phenyl)amino)pyrimidin-2-yl)amino)-3-methoxyphenyl)piperidin-4-yl)-1-((2-(2,6-dioxopiperidin-3-yl)-1-oxoisoindolin-4-yl)amino)-3,6,9,12-tetraoxapentadecan-15-amide;

N-(1-(4-((5-chloro-4-((2-(dimethylphosphoryl)phenyl)amino)pyrimidin-2-yl)amino)-3-methoxyphenyl)piperidin-4-yl)-1-((2-(2,6-dioxopiperidin-3-yl)-1-oxoisoindolin-4-yl)amino)-3,6,9,12,15-pentaoxaoctadecan-18-amide;

N-(1-(4-((5-chloro-4-((2-(dimethylphosphoryl)phenyl)amino)pyrimidin-2-yl)amino)-3-methoxyphenyl)piperidin-4-yl)-2-((2-(2,6-dioxopiperidin-3-yl)-1-oxoisoindolin-4-yl)amino)acetamide;

N-(1-(4-((5-chloro-4-((2-(dimethylphosphoryl)phenyl)amino)pyrimidin-2-yl)amino)-3-methoxyphenyl)piperidin-4-yl)-3-((2-(2,6-dioxopiperidin-3-yl)-1-oxoisoindolin-4-yl)amino)propanamide;

N-(1-(4-((5-chloro-4-((2-(dimethylphosphoryl)phenyl)amino)pyrimidin-2-yl)amino)-3-methoxyphenyl)piperidin-4-yl)-4-((2-(2,6-dioxopiperidin-3-yl)-1-oxoisoindolin-4-yl)amino)butanamide;

N-(1-(4-((5-chloro-4-((2-(dimethylphosphoryl)phenyl)amino)pyrimidin-2-yl)amino)-3-methoxyphenyl)piperidin-4-yl)-5-((2-(2,6-dioxopiperidin-3-yl)-1-oxoisoindolin-4-yl)amino)pentanamide;

N-(1-(4-((5-chloro-4-((2-(dimethylphosphoryl)phenyl)amino)pyrimidin-2-yl)amino)-3-methoxyphenyl)piperidin-4-yl)-6-((2-(2,6-dioxopiperidin-3-yl)-1-oxoisoindolin-4-yl)amino)hexanamide;

N-(1-(4-((5-chloro-4-((2-(dimethylphosphoryl)phenyl)amino)pyrimidin-2-yl)amino)-3-methoxyphenyl)piperidin-4-yl)-4-((2-(2,6-dioxopiperidin-3-yl)-1,3-dioxoisoindolin-4-yl)amino)-N-methylbutanamide;

N-(1-(4-((5-chloro-4-((2-(dimethylphosphoryl)phenyl)amino)pyrimidin-2-yl)amino)-3-methoxyphenyl)piperidin-4-yl)-4-((2-(2,6-dioxopiperidin-3-yl)-1-oxoisoindolin-4-yl)amino)-N-methylbutanamide;

4-((4-((1-(4-((5-chloro-4-((2-(dimethylphosphoryl)phenyl)amino)pyrimidin-2-yl)amino)-3-methoxyphenyl)piperidin-4-yl)amino)butyl)amino)-2-(2,6-dioxopiperidin-3-yl)isoindoline-1,3-dione;

3-(4-((4-((1-(4-((5-chloro-4-((2-(dimethylphosphoryl)phenyl)amino)pyrimidin-2-yl)amino)-3-methoxyphenyl)piperidin-4-yl)amino)butyl)amino)-1-oxoisoindolin-2-yl)piperidine-2,6-dione;

4-((1-(4-((5-chloro-4-((2-(dimethylphosphoryl)phenyl)amino)pyrimidin-2-yl)amino)-3-methoxyphenyl)piperidin-4-yl)(methyl)amino)butyl)amino)-2-(2,6-dioxopiperidin-3-yl)isoindoline-1,3-dione;

N-(1-(4-((5-chloro-4-((2-(dimethylphosphoryl)phenyl)amino)pyrimidin-2-yl)amino)-3-methoxyphenyl)piperidin-4-yl)-3-(2-(2,6-dioxopiperidin-3-yl)-1,3-dioxoisoindolin-4-yl)propanamide;

N-(1-(4-((5-chloro-4-((2-(dimethylphosphoryl)phenyl)amino)pyrimidin-2-yl)amino)-3-methoxyphenyl)piperidin-4-yl)-3-(2-(2,6-dioxopiperidin-3-yl)-1-oxoisoindolin-4-yl)propanamide;

N1-(1-(4-((5-chloro-4-((2-(dimethylphosphoryl)phenyl)amino)pyrimidin-2-yl)amino)-3-methoxyphenyl)piperidin-4-yl)-N11-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)undecanediamide;

(2S,4R)-1-((S)-2-(8-((1-(4-((5-chloro-4-((2-(dimethylphosphoryl)phenyl)amino)pyrimidin-2-yl)amino)-3-methoxyphenyl)piperidin-4-yl)amino)octanamido)-3,3-dimethylbutanoyl)-4-hydroxy-N-(4-(4-methylthiazol-5-yl)benzyl)pyrrolidine-2-carboxamide;

(2S,4R)-1-((S)-2-((8-((1-(4-((5-chloro-4-((2-(dimethylphosphoryl)phenyl)amino)pyrimidin-2-yl)amino)-3-methoxyphenyl)piperidin-4-yl)amino)octyl)amino)-3,3-dimethylbutanoyl)-4-hydroxy-N-(4-(4-methylthiazol-5-yl)benzyl)pyrrolidine-2-carboxamide;

(2S,4R)-1-((S)-2-(11-((1-(4-((5-chloro-4-((2-(dimethylphosphoryl)phenyl)amino)pyrimidin-2-yl)amino)-3-methoxyphenyl)piperidin-4-yl)amino)undecanamido)-3,3-dimethylbutanoyl)-4-hydroxy-N-(4-(4-methylthiazol-5-yl)benzyl)pyrrolidine-2-carboxamide;

(2S,4R)-1-((S)-2-((11-((1-(4-((5-chloro-4-((2-(dimethylphosphoryl)phenyl)amino)pyrimidin-2-yl)amino)-3-methoxyphenyl)piperidin-4-yl)amino)-11-oxoundecyl)amino)-3,3-dimethylbutanoyl)-4-hydroxy-N-(4-(4-methylthiazol-5-yl)benzyl)pyrrolidine-2-carboxamide;

(2S,4R)-1-((S)-2-((11-((1-(4-((5-chloro-4-((2-(dimethylphosphoryl)phenyl)amino)pyrimidin-2-yl)amino)-3-methoxyphenyl)piperidin-4-yl)amino)undecyl)amino)-3,3-dimethylbutanoyl)-4-hydroxy-N-(4-(4-methylthiazol-5-yl)benzyl)pyrrolidine-2-carboxamide;

(2S,4R)-1-((S)-2-(3-(4-(3-((1-(4-((5-chloro-4-((2-(dimethylphosphoryl)phenyl)amino)pyrimidin-2-yl)amino)-3-methoxyphenyl)piperidin-4-yl)amino)-3-oxopropyl)piperazin-1-yl)propanamido)-3,3-dimethylbutanoyl)-4-hydroxy-N-(4-(4-methylthiazol-5-yl)benzyl)pyrrolidine-2-carboxamide;

(2S,4R)-1-((S)-2-(3-(4-(3-((1-(4-((5-chloro-4-((2-(dimethylphosphoryl)phenyl)amino)pyrimidin-2-yl)amino)-3-methoxyphenyl)piperidin-4-yl)amino)-3-oxopropyl)phenyl)propanamido)-3,3-dimethylbutanoyl)-4-hydroxy-N-(4-(4-methylthiazol-5-yl)benzyl)pyrrolidine-2-carboxamide;

3-(4-((2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethyl)amino)-1-oxoisoindolin-2-yl)piperidine-2,6-dione;

3-(4-((2-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethoxy)ethyl)amino)-1-oxoisoindolin-2-yl)piperidine-2,6-dione;

3-(4-((2-(2-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)ethoxy)ethoxy)ethyl)amino)-1-oxoisoindolin-2-yl)piperidine-2,6-dione;

3-(4-((15-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-15-oxo-3,6,9,12-tetraoxapentadecyl)amino)-1-oxoisoindolin-2-yl)piperidine-2,6-dione;

3-(4-((18-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-18-oxo-3,6,9,12,15-pentaoxaoctadecyl)amino)-1-oxoisoindolin-2-yl)piperidine-2,6-dione;

4-((2-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)propoxy)ethoxy)ethyl)amino)-2-(2,6-dioxopiperidin-3-yl)isoindoline-1,3-dione;

3-(4-((2-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)propoxy)ethoxy)ethyl)amino)-1-oxoisoindolin-2-yl)piperidine-2,6-dione;

4-(3-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)propoxy)ethoxy)propyl)-2-(2,6-dioxopiperidin-3-yl)isoindoline-1,3-dione;

3-(4-(3-(2-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)propoxy)ethoxy)propyl)-1-oxoisoindolin-2-yl)piperidine-2,6-dione;

3-(4-((2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-2-oxoethyl)amino)-1-oxoisoindolin-2-yl)piperidine-2,6-dione;

3-(4-((3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)amino)-1-oxoisoindolin-2-yl)piperidine-2,6-dione;

3-(4-((5-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-5-oxopentyl)amino)-1-oxoisoindolin-2-yl)piperidine-2,6-dione;

3-(4-((6-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-6-oxohexyl)amino)-1-oxoisoindolin-2-yl)piperidine-2,6-dione;

3-(4-((7-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-7-oxoheptyl)amino)-1-oxoisoindolin-2-yl)piperidine-2,6-dione;

4-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)-2-(2,6-dioxopiperidin-3-yl)isoindoline-1,3-dione;

3-(4-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)-1-oxoisoindolin-2-yl)piperidine-2,6-dione;

4-((2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)ethyl)amino)-2-(2,6-dioxopiperidin-3-yl)isoindoline-1,3-dione;

3-(4-((2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)ethyl)amino)-1-oxoisoindolin-2-yl)piperidine-2,6-dione;

(2S,4R)-1-((S)-2-(3-(4-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)propanamido)-3,3-dimethylbutanoyl)-4-hydroxy-N-(4-(4-methylthiazol-5-yl)benzyl)pyrrolidine-2-carboxamide;

(2S,4R)-1-((S)-2-(3-(4-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)phenyl)propanamido)-3,3-dimethylbutanoyl)-4-hydroxy-N-(4-(4-methylthiazol-5-yl)benzyl)pyrrolidine-2-carboxamide;

3-(4-((2-(4-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)piperazin-1-yl)ethyl)amino)-1-oxoisoindolin-2-yl)piperidine-2,6-dione;

3-(4-((4-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)phenethyl)amino)-1-oxoisoindolin-2-yl)piperidine-2,6-dione;

8-(4-((2-(2,6-dioxopiperidin-3-yl)-1-oxoisoindolin-4-yl)glycyl)piperazin-1-yl)-9-ethyl-6,6-dimethyl-11-oxo-6,11-dihydro-5H-benzo[b]carbazole-3-carbonitrile;

8-(4-(2-((2-(2,6-dioxopiperidin-3-yl)-1,3-dioxoisoindolin-4-yl)amino)ethyl)piperazin-1-yl)-9-ethyl-6,6-dimethyl-11-oxo-6,11-dihydro-5H-benzo[b]carbazole-3-carbonitrile;

8-(4-(2-((2-(2,6-dioxopiperidin-3-yl)-1-oxoisoindolin-4-yl)amino)ethyl)piperazin-1-yl)-9-ethyl-6,6-dimethyl-11-oxo-6,11-dihydro-5H-benzo[b]carbazole-3-carbonitrile;

(2S,4R)-1-((S)-2-(8-(4-(3-cyano-9-ethyl-6,6-dimethyl-11-oxo-6,11-dihydro-5H-benzo[b]carbazol-8-yl)piperazin-1-yl)octanamido)-3,3-dimethylbutanoyl)-4-hydroxy-N-(4-(4-methylthiazol-5-yl)benzyl)pyrrolidine-2-carboxamide;

N-(1-(3-cyano-9-ethyl-6,6-dimethyl-11-oxo-6,11-dihydro-5H-benzo[b]carbazol-8-yl)piperidin-4-yl)-3-(24(2-(2,6-dioxopiperidin-3-yl)-1,3-dioxoisoindolin-4-yl)amino)ethoxy)propanamide;

N-(1-(3-cyano-9-ethyl-6,6-dimethyl-11-oxo-6,11-dihydro-5H-benzo[b]carbazol-8-yl)piperidin-4-yl)-3-(2-(2-(24(2-(2,6-dioxopiperidin-3-yl)-1,3-dioxoisoindolin-4-yl)amino)ethoxy)ethoxy)ethoxy)propanamide;

N-(1-(3-cyano-9-ethyl-6,6-dimethyl-11-oxo-6,11-dihydro-5H-benzo[b]carbazol-8-yl)piperidin-4-yl)-1-((2-(2,6-dioxopiperidin-3-yl)-1,3-dioxoisoindolin-4-yl)amino)-3,6,9,12-tetraoxapentadecan-15-amide;

N-(1-(3-cyano-9-ethyl-6,6-dimethyl-11-oxo-6,11-dihydro-5H-benzo[b]carbazol-8-yl)piperidin-4-yl)-1-((2-(2,6-dioxopiperidin-3-yl)-1,3-dioxoisoindolin-4-yl)amino)-3,6,9,12,15-pentaoxaoctadecan-18-amide;

N-(1-(3-cyano-9-ethyl-6,6-dimethyl-11-oxo-6,11-dihydro-5H-benzo[b]carbazol-8-yl)piperidin-4-yl)-2-((2-(2,6-dioxopiperidin-3-yl)-1,3-dioxoisoindolin-4-yl)amino)acetamide;

N-(1-(3-cyano-9-ethyl-6,6-dimethyl-11-oxo-6,11-dihydro-5H-benzo[b]carbazol-8-yl)piperidin-4-yl)-3-((2-(2,6-dioxopiperidin-3-yl)-1,3-dioxoisoindolin-4-yl)amino)propanamide;

N-(1-(3-cyano-9-ethyl-6,6-dimethyl-11-oxo-6,11-dihydro-5H-benzo[b]carbazol-8-yl)piperidin-4-yl)-3-((2-(2,6-dioxopiperidin-3-yl)-1,3-dioxoisoindolin-4-yl)amino)propanamide;

N-(1-(3-cyano-9-ethyl-6,6-dimethyl-11-oxo-6,11-dihydro-5H-benzo[b]carbazol-8-yl)piperidin-4-yl)-5-((2-(2,6-dioxopiperidin-3-yl)-1,3-dioxoisoindolin-4-yl)amino)pentanamide;

N-(1-(3-cyano-9-ethyl-6,6-dimethyl-11-oxo-6,11-dihydro-5H-benzo[b]carbazol-8-yl)piperidin-4-yl)-2-((2-(2,6-dioxopiperidin-3-yl)-1-oxoisoindolin-4-yl)amino)acetamide;

N-(1-(3-cyano-9-ethyl-6,6-dimethyl-11-oxo-6,11-dihydro-5H-benzo[b]carbazol-8-yl)piperidin-4-yl)-4-((2-(2,6-dioxopiperidin-3-yl)-1-oxoisoindolin-4-yl)amino)butanamide;

(2S,4R)-1-((S)-2-(2-(2-(2-((1-(3-cyano-9-ethyl-6,6-dimethyl-11-oxo-6,11-dihydro-5H-benzo[b]carbazol-8-yl)piperidin-4-yl)amino)-2-oxoethoxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(3-(2-(3-((1-(3-cyano-9-ethyl-6,6-dimethyl-11-oxo-6,11-dihydro-5H-benzo[b]carbazol-8-yl)piperidin-4-yl)amino)-3-oxopropoxy)ethoxy)propanamido)-3,3-dimethylbutanoyl)-4-hydroxy-N-(4-(4-methylthiazol-5-yl)benzyl)pyrrolidine-2-carboxamide;

N1-(1-(3-cyano-9-ethyl-6,6-dimethyl-11-oxo-6,11-dihydro-5H-benzo[b]carbazol-8-yl)piperidin-4-yl)-N16-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13-tetraoxahexadecanediamide;

N1-(1-(3-cyano-9-ethyl-6,6-dimethyl-11-oxo-6,11-dihydro-5H-benzo[b]carbazol-8-yl)piperidin-4-yl)-N19-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13,16-pentaoxanonadecanediamide;

N1-(1-(3-cyano-9-ethyl-6,6-dimethyl-11-oxo-6,11-dihydro-5H-benzo[b]carbazol-8-yl)piperidin-4-yl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide;

N1-(1-(3-cyano-9-ethyl-6,6-dimethyl-11-oxo-6,11-dihydro-5H-benzo[b]carbazol-8-yl)piperidin-4-yl)-N5-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide;

N1-(1-(3-cyano-9-ethyl-6,6-dimethyl-11-oxo-6,11-dihydro-5H-benzo[b]carbazol-8-yl)piperidin-4-yl)-N6-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)adipamide;

N1-(1-(3-cyano-9-ethyl-6,6-dimethyl-11-oxo-6,11-dihydro-5H-benzo[b]carbazol-8-yl)piperidin-4-yl)-N7-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)heptanediamide;

N1-(1-(3-cyano-9-ethyl-6,6-dimethyl-11-oxo-6,11-dihydro-5H-benzo[b]carbazol-8-yl)piperidin-4-yl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide;

N1-(1-(3-cyano-9-ethyl-6,6-dimethyl-11-oxo-6,11-dihydro-5H-benzo[b]carbazol-8-yl)piperidin-4-yl)-N10-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide;

8-(4-(4-(3-(2-((2-(2,6-dioxopiperidin-3-yl)-1,3-dioxoisoindolin-4-yl)amino)ethoxy)propanoyl)piperazin-1-yl)piperidin-1-yl)-9-ethyl-6,6-dimethyl-11-oxo-6,11-dihydro-5H-benzo[b]carbazole-3-carbonitrile;

8-(4-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)piperidin-1-yl)-9-ethyl-6,6-dimethyl-11-oxo-6,11-dihydro-5H-benzo[b]carbazole-3-carbonitrile;

8-(4-(4-(1-((2-(2,6-dioxopiperidin-3-yl)-1,3-dioxoisoindolin-4-yl)amino)-3,6,9,12-tetraoxapentadecan-15-oyl)piperazin-1-yl)piperidin-1-yl)-9-ethyl-6,6-dimethyl-11-oxo-6,11-dihydro-5H-benzo[b]carbazole-3-carbonitrile;

8-(4-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)piperidin-1-yl)-9-ethyl-6,6-dimethyl-11-oxo-6,11-dihydro-5H-benzo[b]carbazole-3-carbonitrile;

8-(4-(4-((2-(2,6-dioxopiperidin-3-yl)-1,3-dioxoisoindolin-4-yl)glycyl)piperazin-1-yl)piperidin-1-yl)-9-ethyl-6,6-dimethyl-11-oxo-6,11-dihydro-5H-benzo[b]carbazole-3-carbonitrile;

8-(4-(4-(3-((2-(2,6-dioxopiperidin-3-yl)-1,3-dioxoisoindolin-4-yl)amino)propanoyl)piperazin-1-yl)piperidin-1-yl)-9-ethyl-6,6-dimethyl-11-oxo-6,11-dihydro-5H-benzo[b]carbazole-3-carbonitrile;

8-(4-(4-(4-((2-(2,6-dioxopiperidin-3-yl)-1,3-dioxoisoindolin-4-yl)amino)butanoyl)piperazin-1-yl)piperidin-1-yl)-9-ethyl-6,6-dimethyl-11-oxo-6,11-dihydro-5H-benzo[b]carbazole-3-carbonitrile;

8-(4-(4-(5-((2-(2,6-dioxopiperidin-3-yl)-1,3-dioxoisoindolin-4-yl)amino)pentanoyl)piperazin-1-yl)piperidin-1-yl)-9-ethyl-6,6-dimethyl-11-oxo-6,11-dihydro-5H-benzo[b]carbazole-3-carbonitrile;

8-(4-(4-(7-((2-(2,6-dioxopiperidin-3-yl)-1,3-dioxoisoindolin-4-yl)amino)heptanoyl)piperazin-1-yl)piperidin-1-yl)-9-ethyl-6,6-dimethyl-11-oxo-6,11-dihydro-5H-benzo[b]carbazole-3-carbonitrile;

8-(4-(4-(2-((2-(2,6-dioxopiperidin-3-yl)-1,3-dioxoisoindolin-4-yl)amino)ethyl)piperazin-1-yl)piperidin-1-yl)-9-ethyl-6,6-dimethyl-11-oxo-6,11-dihydro-5H-benzo[b]carbazole-3-carbonitrile;

(2S,4R)-1-((S)-2-(2-(2-(2-(4-(1-(3-cyano-9-ethyl-6,6-dimethyl-11-oxo-6,11-dihydro-5H-benzo[b]carbazol-8-yl)piperidin-4-yl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(3-(2-(3-(4-(1-(3-cyano-9-ethyl-6,6-dimethyl-11-oxo-6,11-dihydro-5H-benzo[b]carbazol-8-yl)piperidin-4-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide;

(2S,4R)-1-((S)-2-(tert-butyl)-19-(4-(1-(3-cyano-9-ethyl-6,6-dimethyl-11-oxo-6,11-dihydro-5H-benzo[b]carbazol-8-yl)piperidin-4-yl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide;

(2S,4R)-1-((S)-2-(tert-butyl)-22-(4-(1-(3-cyano-9-ethyl-6,6-dimethyl-11-oxo-6,11-dihydro-5H-benzo[b]carbazol-8-yl)piperidin-4-yl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide;

(2S,4R)-1-((S)-2-(4-(4-(1-(3-cyano-9-ethyl-6,6-dimethyl-11-oxo-6,11-dihydro-5H-benzo[b]carbazol-8-yl)piperidin-4-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide;

(2S,4R)-1-((S)-2-(5-(4-(1-(3-cyano-9-ethyl-6,6-dimethyl-11-oxo-6,11-dihydro-5H-benzo[b]carbazol-8-yl)

piperidin-4-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide;

(2S,4R)-1-((S)-2-(6-(4-(1-(3-cyano-9-ethyl-6,6-dimethyl-11-oxo-6,11-dihydro-5H-benzo[b]carbazol-8-yl)piperidin-4-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide;

(2S,4R)-1-((S)-2-(7-(4-(1-(3-cyano-9-ethyl-6,6-dimethyl-11-oxo-6,11-dihydro-5H-benzo[b]carbazol-8-yl)piperidin-4-yl)piperazin-1-yl)-7-oxoheptanamido)-3,3-dimethylbutanoyl)-4-hydroxy-N-(4-(4-methylthiazol-5-yl)benzyl)pyrrolidine-2-carboxamide;

(2S,4R)-1-((S)-2-(8-(4-(1-(3-cyano-9-ethyl-6,6-dimethyl-11-oxo-6,11-dihydro-5H-benzo[b]carbazol-8-yl)piperidin-4-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide;

(2S,4R)-1-((S)-2-(10-(4-(1-(3-cyano-9-ethyl-6,6-dimethyl-11-oxo-6,11-dihydro-5H-benzo[b]carbazol-8-yl)piperidin-4-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide;

4-((2-(3-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-3-oxopropoxy)ethyl)amino)-2-(2,6-dioxopiperidin-3-yl)isoindoline-1,3-dione;

4-((2-(2-(3-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-3-oxopropoxy)ethoxy)ethyl)amino)-2-(2,6-dioxopiperidin-3-yl)isoindoline-1,3-dione;

4-((18-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-18-oxo-3,6,9,12,15-pentaoxaoctadecyl)amino)-2-(2,6-dioxopiperidin-3-yl)isoindoline-1,3-dione;

4-((2-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-2-oxoethyl)amino)-2-(2,6-dioxopiperidin-3-yl)isoindoline-1,3-dione;

4-((3-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-3-oxopropyl)amino)-2-(2,6-dioxopiperidin-3-yl)isoindoline-1,3-dione;

4-((4-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-4-oxobutyl)amino)-2-(2,6-dioxopiperidin-3-yl)isoindoline-1,3-dione;

4-((5-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-5-oxopentyl)amino)-2-(2,6-dioxopiperidin-3-yl)isoindoline-1,3-dione;

4-((6-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-6-oxohexyl)amino)-2-(2,6-dioxopiperidin-3-yl)isoindoline-1,3-dione;

4-((7-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-7-oxoheptyl)amino)-2-(2,6-dioxopiperidin-3-yl)isoindoline-1,3-dione;

3-(4-((2-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-2-oxoethyl)amino)-1-oxoisoindolin-2-yl)piperidine-2,6-dione;

(2S,4R)-1-((S)-2-(2-(2-(2-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(3-(2-(3-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide;

(2S,4R)-1-((S)-2-(tert-butyl)-19-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide;

(2S,4R)-1-((S)-2-(tert-butyl)-22-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide;

(2S,4R)-1-((S)-2-(4-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide;

(2S,4R)-1-((S)-2-(5-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide;

(2S,4R)-1-((S)-2-(7-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-7-oxoheptanamido)-3,3-dimethylbutanoyl)-4-hydroxy-N-(4-(4-methylthiazol-5-yl)benzyl)pyrrolidine-2-carboxamide;

(2S,4R)-1-((S)-2-(8-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide;

(2S,4R)-1-((S)-2-(9-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-9-oxononanamido)-3,3-dimethylbutanoyl)-4-hydroxy-N-(4-(4-methylthiazol-5-yl)benzyl)pyrrolidine-2-carboxamide;

(2S,4R)-1-((S)-2-(10-(4-(1-(4-((5-chloro-4-((2-(isopropylsulfonyl)phenyl)amino)pyrimidin-2-yl)amino)-3-methoxyphenyl)piperidin-4-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide;

2-(2,6-dioxopiperidin-3-yl)-4-((2-(3-(4-(1-(4-((4-((2-(isopropylsulfonyl)phenyl)amino)-1,3,5-triazin-2-yl)amino)-3-methoxyphenyl)piperidin-4-yl)piperazin-1-yl)-3-oxopropoxy)ethyl)amino)isoindoline-1,3-dione;

2-(2,6-dioxopiperidin-3-yl)-4-((2-(2-(3-(4-(1-(4-((4-((2-(isopropylsulfonyl)phenyl)amino)-1,3,5-triazin-2-yl)

amino)-3-methoxyphenyl)piperidin-4-yl)piperazin-1-yl)-3-oxopropoxy)ethoxy)ethyl)amino)isoindoline-1,3-dione;

2-(2,6-dioxopiperidin-3-yl)-4-((15-(4-(1-(4-((4-((2-(isopropylsulfonyl)phenyl)amino)-1,3,5-triazin-2-yl)amino)-3-methoxyphenyl)piperidin-4-yl)piperazin-1-yl)-15-oxo-3,6,9,12-tetraoxapentadecyl)amino)isoindoline-1,3-dione;

2-(2,6-dioxopiperidin-3-yl)-4-((18-(4-(1-(4-((4-((2-(isopropylsulfonyl)phenyl)amino)-1,3,5-triazin-2-yl)amino)-3-methoxyphenyl)piperidin-4-yl)piperazin-1-yl)-18-oxo-3,6,9,12,15-pentaoxaoctadecyl)amino)isoindoline-1,3-dione;

2-(2,6-dioxopiperidin-3-yl)-4-((2-(4-(1-(4-((4-((2-(isopropylsulfonyl)phenyl)amino)-1,3,5-triazin-2-yl)amino)-3-methoxyphenyl)piperidin-4-yl)piperazin-1-yl)-2-oxoethyl)amino)isoindoline-1,3-dione;

2-(2,6-dioxopiperidin-3-yl)-4-((3-(4-(1-(4-((4-((2-(isopropylsulfonyl)phenyl)amino)-1,3,5-triazin-2-yl)amino)-3-methoxyphenyl)piperidin-4-yl)piperazin-1-yl)-3-oxopropyl)amino)isoindoline-1,3-dione;

2-(2,6-dioxopiperidin-3-yl)-4-((4-(4-(1-(4-((4-((2-(isopropylsulfonyl)phenyl)amino)-1,3,5-triazin-2-yl)amino)-3-methoxyphenyl)piperidin-4-yl)piperazin-1-yl)-4-oxobutyl)amino)isoindoline-1,3-dione;

2-(2,6-dioxopiperidin-3-yl)-4-((5-(4-(1-(4-((4-((2-(isopropylsulfonyl)phenyl)amino)-1,3,5-triazin-2-yl)amino)-3-methoxyphenyl)piperidin-4-yl)piperazin-1-yl)-5-oxopentyl)amino)isoindoline-1,3-dione;

2-(2,6-dioxopiperidin-3-yl)-4-((6-(4-(1-(4-((4-((2-(isopropylsulfonyl)phenyl)amino)-1,3,5-triazin-2-yl)amino)-3-methoxyphenyl)piperidin-4-yl)piperazin-1-yl)-6-oxohexyl)amino)isoindoline-1,3-dione;

2-(2,6-dioxopiperidin-3-yl)-4-((7-(4-(1-(4-((4-((2-(isopropylsulfonyl)phenyl)amino)-1,3,5-triazin-2-yl)amino)-3-methoxyphenyl)piperidin-4-yl)piperazin-1-yl)-'7-oxoheptyl)amino)isoindoline-1,3-dione;

3-(4-((2-(4-(1-(4-((4-((2-(isopropylsulfonyl)phenyl)amino)-1,3,5-triazin-2-yl)amino)-3-methoxyphenyl)piperidin-4-yl)piperazin-1-yl)-2-oxoethyl)amino)-1-oxoisoindolin-2-yl)piperidine-2,6-dione;

(2S,4R)-4-hydroxy-1-((S)-2-(2-(2-(2-(4-(1-(4-((4-((2-(isopropylsulfonyl)phenyl)amino)-1,3,5-triazin-2-yl)amino)-3-methoxyphenyl)piperidin-4-yl)piperazin-1-yl)-2-oxoethoxy)ethoxy)acetamido)-3,3-dimethylbutanoyl)-N-(4-(4-methylthiazol-5-yl)benzyl)pyrrolidine-2-carboxamide;

(2S,4R)-4-hydroxy-1-((S)-2-(3-(2-(3-(4-(1-(4-((4-((2-(isopropylsulfonyl)phenyl)amino)-1,3,5-triazin-2-yl)amino)-3-methoxyphenyl)piperidin-4-yl)piperazin-1-yl)-3-oxopropoxy)ethoxy)propanamido)-3,3-dimethylbutanoyl)-N-(4-(4-methylthiazol-5-yl)benzyl)pyrrolidine-2-carboxamide;

(2S,4R)-1-((S)-2-(tert-butyl)-19-(4-(1-(4-((4-((2-(isopropylsulfonyl)phenyl)amino)-1,3,5-triazin-2-yl)amino)-3-methoxyphenyl)piperidin-4-yl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide;

(2S,4R)-1-((S)-2-(tert-butyl)-22-(4-(1-(4-((4-((2-(isopropylsulfonyl)phenyl)amino)-1,3,5-triazin-2-yl)amino)-5-methoxy-2-methylphenyl)piperidin-4-yl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide;

(2S,4R)-4-hydroxy-1-((S)-2-(4-(4-(1-(4-((4-((2-(isopropylsulfonyl)phenyl)amino)-1,3,5-triazin-2-yl)amino)-3-methoxyphenyl)piperidin-4-yl)piperazin-1-yl)-4-oxobutanamido)-3,3-dimethylbutanoyl)-N-(4-(4-methylthiazol-5-yl)benzyl)pyrrolidine-2-carboxamide;

(2S,4R)-4-hydroxy-1-((S)-2-(5-(4-(1-(4-((4-((2-(isopropylsulfonyl)phenyl)amino)-1,3,5-triazin-2-yl)amino)-5-methoxy-2-methylphenyl)piperidin-4-yl)piperazin-1-yl)-5-oxopentanamido)-3,3-dimethylbutanoyl)-N-(4-(4-methylthiazol-5-yl)benzyl)pyrrolidine-2-carboxamide;

(2S,4R)-4-hydroxy-1-((S)-2-(6-(4-(1-(5-isopropoxy-4-((4-((2-(isopropylsulfonyl)phenyl)amino)-1,3,5-triazin-2-yl)amino)-2-methylphenyl)piperidin-4-yl)piperazin-1-yl)-6-oxohexanamido)-3,3-dimethylbutanoyl)-N-(4-(4-methylthiazol-5-yl)benzyl)pyrrolidine-2-carboxamide;

(2S,4R)-4-hydroxy-1-((S)-2-(7-(4-(1-(4-((4-((2-(isopropylsulfonyl)phenyl)amino)-1,3,5-triazin-2-yl)amino)-3-methoxyphenyl)piperidin-4-yl)piperazin-1-yl)-7-oxoheptanamido)-3,3-dimethylbutanoyl)-N-(4-(4-methylthiazol-5-yl)benzyl)pyrrolidine-2-carboxamide;

(2S,4R)-4-hydroxy-1-((S)-2-(8-(4-(1-(4-((4-((2-(isopropylsulfonyl)phenyl)amino)-1,3,5-triazin-2-yl)amino)-5-methoxy-2-methylphenyl)piperidin-4-yl)piperazin-1-yl)-8-oxooctanamido)-3,3-dimethylbutanoyl)-N-(4-(4-methylthiazol-5-yl)benzyl)pyrrolidine-2-carboxamide;

(2S,4R)-4-hydroxy-1-((S)-2-(9-(4-(1-(5-isopropoxy-4-((4-((2-(isopropylsulfonyl)phenyl)amino)-1,3,5-triazin-2-yl)amino)-2-methylphenyl)piperidin-4-yl)piperazin-1-yl)-9-oxononanamido)-3,3-dimethylbutanoyl)-N-(4-(4-methylthiazol-5-yl)benzyl)pyrrolidine-2-carboxamide;

(2S,4R)-4-hydroxy-1-((S)-2-(10-(4-(1-(5-isopropoxy-4-((4-((2-(isopropylsulfonyl)phenyl)amino)-1,3,5-triazin-2-yl)amino)-2-methylphenyl)piperidin-4-yl)piperazin-1-yl)-10-oxodecanamido)-3,3-dimethylbutanoyl)-N-(4-(4-methylthiazol-5-yl)benzyl)pyrrolidine-2-carboxamide;

2-((2-((1-(N-(3-(2-((2-(2,6-dioxopiperidin-3-yl)-1,3-dioxoisoindolin-4-yl)amino)ethoxy)propanoyl)-N-methylglycyl)-5-methoxyindolin-6-yl)amino)-7H-pyrrolo[2,3-d]pyrimidin-4-yl)amino)-6-fluoro-N-methylbenzamide;

2-((2-((1-(N-(3-(2-(2-((2-(2,6-dioxopiperidin-3-yl)-1,3-dioxoisoindolin-4-yl)amino)ethoxy)ethoxy)propanoyl)-N-methylglycyl)-5-methoxyindolin-6-yl)amino)-7H-pyrrolo[2,3-d]pyrimidin-4-yl)amino)-6-fluoro-N-methylbenzamide;

1-((2-(2,6-dioxopiperidin-3-yl)-1,3-dioxoisoindolin-4-yl)amino)-N-(2-(6-((4-((3-fluoro-2-(methylcarbamoyl)phenyl)amino)-7H-pyrrolo[2,3-d]pyrimidin-2-yl)amino)-5-methoxyindolin-1-yl)-2-oxoethyl)-N-methyl-3,6,9,12-tetraoxapentadecan-15-amide 1-((2-(2,6-dioxopiperidin-3-yl)-1,3-dioxoisoindolin-4-yl)amino)-N-(2-(6-((4-((3-fluoro-2-(methylcarbamoyl)phenyl)amino)-7H-pyrrolo[2,3-d]pyrimidin-2-yl)amino)-5-methoxyindolin-1-yl)-2-oxoethyl)-N-methyl-3,6,9,12,15-pentaoxaoctadecan-18-amide;

2-((2-((1-(N-((2-(2,6-dioxopiperidin-3-yl)-1,3-dioxoisoindolin-4-yl)glycyl)-N-methylglycyl)-5-methoxyindolin-6-yl)amino)-7H-pyrrolo[2,3-d]pyrimidin-4-yl)amino)-6-fluoro-N-methylbenzamide;

2-((2-((1-(N-(3-((2-(2,6-dioxopiperidin-3-yl)-1,3-dioxoisoindolin-4-yl)amino)propanoyl)-N-methylglycyl)-5-methoxyindolin-6-yl)amino)-7H-pyrrolo[2,3-d]pyrimidin-4-yl)amino)-6-fluoro-N-methylbenzamide;

2-((2-((1-(N-(4-((2-(2,6-dioxopiperidin-3-yl)-1,3-dioxoisoindolin-4-yl)amino)butanoyl)-N-methylglycyl)-5-methoxyindolin-6-yl)amino)-7H-pyrrolo[2,3-d]pyrimidin-4-yl)amino)-6-fluoro-N-methylbenzamide;

2-((2-((1-(N-(5-((2-(2,6-dioxopiperidin-3-yl)-1,3-dioxoisoindolin-4-yl)amino)pentanoyl)-N-methylglycyl)-5-methoxyindolin-6-yl)amino)-7H-pyrrolo[2,3-d]pyrimidin-4-yl)amino)-6-fluoro-N-methylbenzamide;

2-((2-((1-(N-(6-((2-(2,6-dioxopiperidin-3-yl)-1,3-dioxoisoindolin-4-yl)amino)hexanoyl)-N-methylglycyl)-5-methoxyindolin-6-yl)amino)-7H-pyrrolo[2,3-d]pyrimidin-4-yl)amino)-6-fluoro-N-methylbenzamide;

2-((2-((1-(N-(7-((2-(2,6-dioxopiperidin-3-yl)-1,3-dioxoisoindolin-4-yl)amino)heptanoyl)-N-methylglycyl)-5-methoxyindolin-6-yl)amino)-7H-pyrrolo[2,3-d]pyrimidin-4-yl)amino)-6-fluoro-N-methylbenzamide;

(2S,4R)-1-((S)-2-(tert-butyl)-14-(6-((4-((3-fluoro-2-(methylcarbamoyl)phenyl)amino)-7H-pyrrolo[2,3-d]pyrimidin-2-yl)amino)-5-methoxyindolin-1-yl)-12-methyl-4,11,14-trioxo-6,9-dioxa-3,12-diazatetradecanoyl)-4-hydroxy-N-(4-(4-methylthiazol-5-yl)benzyl)pyrrolidine-2-carboxamide;

(2S,4R)-1-((S)-2-(tert-butyl)-16-(6-((4-((3-fluoro-2-(methylcarbamoyl)phenyl)amino)-7H-pyrrolo[2,3-d]pyrimidin-2-yl)amino)-5-methoxyindolin-1-yl)-14-methyl-4,13,16-trioxo-7,10-dioxa-3,14-diazahexadecanoyl)-4-hydroxy-N-(4-(4-methylthiazol-5-yl)benzyl)pyrrolidine-2-carboxamide;

N1-(2-(6-((4-((3-fluoro-2-(methylcarbamoyl)phenyl)amino)-7H-pyrrolo[2,3-d]pyrimidin-2-yl)amino)-5-methoxyindolin-1-yl)-2-oxoethyl)-N16-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyl-4,7,10,13-tetraoxahexadecanediamide;

N1-(2-(6-((4-((3-fluoro-2-(methylcarbamoyl)phenyl)amino)-7H-pyrrolo[2,3-d]pyrimidin-2-yl)amino)-5-methoxyindolin-1-yl)-2-oxoethyl)-N19-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyl-4,7,10,13,16-pentaoxanonadecanediamide;

N1-(2-(6-((4-((3-fluoro-2-(methylcarbamoyl)phenyl)amino)-7H-pyrrolo[2,3-d]pyrimidin-2-yl)amino)-5-methoxyindolin-1-yl)-2-oxoethyl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methylsuccinamide;

N1-(2-(6-((4-((3-fluoro-2-(methylcarbamoyl)phenyl)amino)-7H-pyrrolo[2,3-d]pyrimidin-2-yl)amino)-5-methoxyindolin-1-yl)-2-oxoethyl)-N5-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methylglutaramide;

N1-(2-(6-((4-((3-fluoro-2-(methylcarbamoyl)phenyl)amino)-7H-pyrrolo[2,3-d]pyrimidin-2-yl)amino)-5-methoxyindolin-1-yl)-2-oxoethyl)-N6-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyladipamide;

N1-(2-(6-((4-((3-fluoro-2-(methylcarbamoyl)phenyl)amino)-7H-pyrrolo[2,3-d]pyrimidin-2-yl)amino)-5-methoxyindolin-1-yl)-2-oxoethyl)-N7-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methylheptanediamide;

N1-(2-(6-((4-((3-fluoro-2-(methylcarbamoyl)phenyl)amino)-7H-pyrrolo[2,3-d]pyrimidin-2-yl)amino)-5-methoxyindolin-1-yl)-2-oxoethyl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloctanediamide;

N1-(2-(6-((4-((3-fluoro-2-(methylcarbamoyl)phenyl)amino)-7H-pyrrolo[2,3-d]pyrimidin-2-yl)amino)-5-methoxyindolin-1-yl)-2-oxoethyl)-N9-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methylnonanediamide;

N1-(2-(6-((4-((3-fluoro-2-(methylcarbamoyl)phenyl)amino)-7H-pyrrolo[2,3-d]pyrimidin-2-yl)amino)-5-methoxyindolin-1-yl)-2-oxoethyl)-N10-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyldecanediamide;

N-(1-(4-((5-chloro-4-(1H-indol-3-yl)pyrimidin-2-yl)amino)-3-methoxyphenyl)piperidin-4-yl)-3-(2-((2-(2,6-dioxopiperidin-3-yl)-1,3-dioxoisoindolin-4-yl)amino)ethoxy)-N-methylpropanamide;

N-(1-(4-((5-chloro-4-(1H-indol-3-yl)pyrimidin-2-yl)amino)-3-methoxyphenyl)piperidin-4-yl)-3-(2-(2-((2-(2,6-dioxopiperidin-3-yl)-1,3-dioxoisoindolin-4-yl)amino)ethoxy)ethoxy)-N-methylpropanamide;

N-(1-(4-((5-chloro-4-(1H-indol-3-yl)pyrimidin-2-yl)amino)-3-methoxyphenyl)piperidin-4-yl)-1-((2-(2,6-dioxopiperidin-3-yl)-1,3-dioxoisoindolin-4-yl)amino)-N-methyl-3,6,9,12-tetraoxapentadecan-15-amide;

N-(1-(4-((5-chloro-4-(1H-indol-3-yl)pyrimidin-2-yl)amino)-3-methoxyphenyl)piperidin-4-yl)-1-((2-(2,6-dioxopiperidin-3-yl)-1,3-dioxoisoindolin-4-yl)amino)-N-methyl-3,6,9,12,15-pentaoxaoctadecan-18-amide;

N-(1-(4-((5-chloro-4-(1H-indol-3-yl)pyrimidin-2-yl)amino)-3-methoxyphenyl)piperidin-4-yl)-2-((2-(2,6-dioxopiperidin-3-yl)-1,3-dioxoisoindolin-4-yl)amino)-N-methylacetamide;

N-(1-(4-((5-chloro-4-(1H-indol-3-yl)pyrimidin-2-yl)amino)-3-methoxyphenyl)piperidin-4-yl)-3-((2-(2,6-dioxopiperidin-3-yl)-1,3-dioxoisoindolin-4-yl)amino)-N-methylpropanamide;

N-(1-(4-((5-chloro-4-(1H-indol-3-yl)pyrimidin-2-yl)amino)-3-methoxyphenyl)piperidin-4-yl)-4-((2-(2,6-dioxopiperidin-3-yl)-1,3-dioxoisoindolin-4-yl)amino)-N-methylbutanamide;

N-(1-(4-((5-chloro-4-(1H-indol-3-yl)pyrimidin-2-yl)amino)-3-methoxyphenyl)piperidin-4-yl)-5-((2-(2,6-dioxopiperidin-3-yl)-1,3-dioxoisoindolin-4-yl)amino)-N-methylpentanamide;

N-(1-(4-((5-chloro-4-(1H-indol-3-yl)pyrimidin-2-yl)amino)-3-methoxyphenyl)piperidin-4-yl)-6-((2-(2,6-dioxopiperidin-3-yl)-1,3-dioxoisoindolin-4-yl)amino)-N-methylhexanamide;

N-(1-(4-((5-chloro-4-(1H-indol-3-yl)pyrimidin-2-yl)amino)-3-methoxyphenyl)piperidin-4-yl)-7-((2-(2,6-dioxopiperidin-3-yl)-1,3-dioxoisoindolin-4-yl)amino)-N-methylheptanamide;

(2S,4R)-1-((S)-12-(tert-butyl)-2-(1-(4-((5-chloro-4-(1H-indol-3-yl)pyrimidin-2-yl)amino)-3-methoxyphenyl)piperidin-4-yl)-3,10-dioxo-5,8-dioxa-2,11-diazatridecan-13-oyl)-4-hydroxy-N-(4-(4-methylthiazol-5-yl)benzyl)pyrrolidine-2-carboxamide;

N1-(1-(4-((5-chloro-4-(1H-indol-3-yl)pyrimidin-2-yl)amino)-3-methoxyphenyl)piperidin-4-yl)-N19-((S)-1-((2S,4R)-4-hydroxy-2-((4-(4-methylthiazol-5-yl)benzyl)carbamoyl)pyrrolidin-1-yl)-3,3-dimethyl-1- oxobutan-2-yl)-N1-methyl-4,7,10,13,16-pentaoxanonadecanediamide;

N1-(1-(4-((5-chloro-4-(1H-indol-3-yl)pyrimidin-2-yl)amino)-3-methoxyphenyl)piperidin-4-yl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methylsuccinamide;

N1-(1-(4-((5-chloro-4-(1H-indol-3-yl)pyrimidin-2-yl)amino)-3-methoxyphenyl)piperidin-4-yl)-N8-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyloctanediamide;

N1-(1-(4-((5-chloro-4-(1H-indol-3-yl)pyrimidin-2-yl)amino)-3-methoxyphenyl)piperidin-4-yl)-N10-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N1-methyldecanediamide;

N-(5-(3,5-difluorobenzyl)-1H-indazol-3-yl)-4-(4-(3-(2-((2-(2,6-dioxopiperidin-3-yl)-1,3-dioxoisoindolin-4-yl)amino)ethoxy)propanoyl)piperazin-1-yl)-2-((tetrahydro-2H-pyran-4-yl)amino)benzamide;

N-(5-(3,5-difluorobenzyl)-1H-indazol-3-yl)-4-(4-(3-(2-(2-((2-(2,6-dioxopiperidin-3-yl)-1,3-dioxoisoindolin-4-yl)amino)ethoxy)ethoxy)propanoyl)piperazin-1-yl)-2-((tetrahydro-2H-pyran-4-yl)amino)benzamide;

N-(5-(3,5-difluorobenzyl)-1H-indazol-3-yl)-4-(4-(1-((2-(2,6-dioxopiperidin-3-yl)-1,3-dioxoisoindolin-4-yl)amino)-3,6,9,12-tetraoxapentadecan-15-oyl)piperazin-1-yl)-2-((tetrahydro-2H-pyran-4-yl)amino)benzamide;

N-(5-(3,5-difluorobenzyl)-1H-indazol-3-yl)-4-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)-2-((tetrahydro-2H-pyran-4-yl)amino)benzamide;

N-(5-(3,5-difluorobenzyl)-1H-indazol-3-yl)-4-(4-((2-(2,6-dioxopiperidin-3-yl)-1,3-dioxoisoindolin-4-yl)glycyl)piperazin-1-yl)-2-((tetrahydro-2H-pyran-4-yl)amino)benzamide;

N-(5-(3,5-difluorobenzyl)-1H-indazol-3-yl)-4-(4-(3-((2-(2,6-dioxopiperidin-3-yl)-1,3-dioxoisoindolin-4-yl)amino)propanoyl)piperazin-1-yl)-2-((tetrahydro-2H-pyran-4-yl)amino)benzamide;

N-(5-(3,5-difluorobenzyl)-1H-indazol-3-yl)-4-(4-(4-((2-(2,6-dioxopiperidin-3-yl)-1,3-dioxoisoindolin-4-yl)amino)butanoyl)piperazin-1-yl)-2-((tetrahydro-2H-pyran-4-yl)amino)benzamide;

N-(5-(3,5-difluorobenzyl)-1H-indazol-3-yl)-4-(4-(5-((2-(2,6-dioxopiperidin-3-yl)-1,3-dioxoisoindolin-4-yl)amino)pentanoyl)piperazin-1-yl)-2-((tetrahydro-2H-pyran-4-yl)amino)benzamide;

N-(5-(3,5-difluorobenzyl)-1H-indazol-3-yl)-4-(4-(6-((2-(2,6-dioxopiperidin-3-yl)-1,3-dioxoisoindolin-4-yl)amino)hexanoyl)piperazin-1-yl)-2-((tetrahydro-2H-pyran-4-yl)amino)benzamide;

N-(5-(3,5-difluorobenzyl)-1H-indazol-3-yl)-4-(4-(7-((2-(2,6-dioxopiperidin-3-yl)-1,3-dioxoisoindolin-4-yl)amino)heptanoyl)piperazin-1-yl)-2-((tetrahydro-2H-pyran-4-yl)amino)benzamide;

(2S,4R)-1-((S)-2-(2-(2-(2-(4-(4-((5-(3,5-difluorobenzyl)-1H-indazol-3-yl)carbamoyl)-3-((tetrahydro-2H-pyran-4-yl)amino)phenyl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(tert-butyl)-22-(4-(4-((5-(3,5-difluorobenzyl)-1H-indazol-3-yl)carbamoyl)-3-((tetrahydro-2H-pyran-4-yl)amino)phenyl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide;

(2S,4R)-1-((S)-2-(4-(4-(4-((5-(3,5-difluorobenzyl)-1H-indazol-3-yl)carbamoyl)-3-((tetrahydro-2H-pyran-4-yl)amino)phenyl)piperazin-1-yl)-4-oxobutanamido)-3,3-dimethylbutanoyl)-4-hydroxy-N-(4-(4-methylthiazol-5-yl)benzyl)pyrrolidine-2-carboxamide;

(2S,4R)-1-((S)-2-(6-(4-(4-((5-(3,5-difluorobenzyl)-1H-indazol-3-yl)carbamoyl)-3-((tetrahydro-2H-pyran-4-yl)amino)phenyl)piperazin-1-yl)-6-oxohexanamido)-3,3-dimethylbutanoyl)-4-hydroxy-N-(4-(4-methylthiazol-5-yl)benzyl)pyrrolidine-2-carboxamide;

(2S,4R)-1-((S)-2-(8-(4-(4-((5-(3,5-difluorobenzyl)-1H-indazol-3-yl)carbamoyl)-3-((tetrahydro-2H-pyran-4-yl)amino)phenyl)piperazin-1-yl)-8-oxooctanamido)-3,3-dimethylbutanoyl)-4-hydroxy-N-(4-(4-methylthiazol-5-yl)benzyl)pyrrolidine-2-carboxamide;

(2S,4R)-1-((S)-2-(10-(4-(4-((5-(3,5-difluorobenzyl)-1H-indazol-3-yl)carbamoyl)-3-((tetrahydro-2H-pyran-4-yl)amino)phenyl)piperazin-1-yl)-10-oxodecanamido)-3,3-dimethylbutanoyl)-4-hydroxy-N-(4-(4-methylthiazol-5-yl)benzyl)pyrrolidine-2-carboxamide;

6-amino-5-((R)-1-(2,6-dichloro-3-fluorophenyl)ethoxy)-N-(4-((3S,5R)-4-(3-(2-((2-(2,6-dioxopiperidin-3-yl)-1,3-dioxoisoindolin-4-yl)amino)ethoxy)propanoyl)-3,5-dimethylpiperazine-1-carbonyl)phenyl)pyridazine-3-carboxamide;

6-amino-5-((R)-1-(2,6-dichloro-3-fluorophenyl)ethoxy)-N-(4-((3S,5R)-4-(3-(2-(2-((2-(2,6-dioxopiperidin-3-yl)-1,3-dioxoisoindolin-4-yl)amino)ethoxy)ethoxy)propanoyl)-3,5-dimethylpiperazine-1-carbonyl)phenyl)pyridazine-3-carboxamide;

6-amino-5-((R)-1-(2,6-dichloro-3-fluorophenyl)ethoxy)-N-(4-((3S,5R)-4-(1-((2-(2,6-dioxopiperidin-3-yl)-1,3-dioxoisoindolin-4-yl)amino)-3,6,9,12-tetraoxapentadecan-15-oyl)-3,5-dimethylpiperazine-1-carbonyl)phenyl)pyridazine-3-carboxamide;

6-amino-5-((R)-1-(2,6-dichloro-3-fluorophenyl)ethoxy)-N-(4-((3S,5R)-4-(1-((2-(2,6-dioxopiperidin-3-yl)-1,3-dioxoisoindolin-4-yl)amino)-3,6,9,12,15-pentaoxaoctadecan-18-oyl)-3,5-dimethylpiperazine-1-carbonyl)phenyl)pyridazine-3-carboxamide;

6-amino-5-((R)-1-(2,6-dichloro-3-fluorophenyl)ethoxy)-N-(4-((3S,5R)-4-((2-(2,6-dioxopiperidin-3-yl)-1,3-dioxoisoindolin-4-yl)glycyl)-3,5-dimethylpiperazine-1-carbonyl)phenyl)pyridazine-3-carboxamide;

6-amino-5-((R)-1-(2,6-dichloro-3-fluorophenyl)ethoxy)-N-(4-((3S,5R)-4-(3-((2-(2,6-dioxopiperidin-3-yl)-1,3-dioxoisoindolin-4-yl)amino)propanoyl)-3,5-dimethylpiperazine-1-carbonyl)phenyl)pyridazine-3-carboxamide;

6-amino-5-((R)-1-(2,6-dichloro-3-fluorophenyl)ethoxy)-N-(4-((3S,5R)-4-(4-((2-(2,6-dioxopiperidin-3-yl)-1,3-dioxoisoindolin-4-yl)amino)butanoyl)-3,5-dimethylpiperazine-1-carbonyl)phenyl)pyridazine-3-carboxamide;

6-amino-5-((R)-1-(2,6-dichloro-3-fluorophenyl)ethoxy)-N-(4-((3S,5R)-4-(5-((2-(2,6-dioxopiperidin-3-yl)-1,3-dioxoisoindolin-4-yl)amino)pentanoyl)-3,5-dimethylpiperazine-1-carbonyl)phenyl)pyridazine-3-carboxamide;

6-amino-5-((R)-1-(2,6-dichloro-3-fluorophenyl)ethoxy)-N-(4-((3S,5R)-4-(6-((2-(2,6-dioxopiperidin-3-yl)-1,3-dioxoisoindolin-4-yl)amino)hexanoyl)-3,5-dimethylpiperazine-1-carbonyl)phenyl)pyridazine-3-carboxamide;

6-amino-5-((R)-1-(2,6-dichloro-3-fluorophenyl)ethoxy)-N-(4-((3S,5R)-4-(7-((2-(2,6-dioxopiperidin-3-yl)-1,3-dioxoisoindolin-4-yl)amino)heptanoyl)-3,5-dimethylpiperazine-1-carbonyl)phenyl)pyridazine-3-carboxamide 6-amino-5-((R)-1-(2,6-dichloro-3-fluorophenyl)ethoxy)-N-(4-((3S,5R)-4-(2-(2-(2-(((S)-1-((2S,4R)-4-hydroxy-24(4-(4-methylthiazol-5-yl)benzyl)carbamoyl)pyrrolidin-1-yl)-3,3-dimethyl-1-oxobutan-2-yl)amino)-2-oxoethoxy)ethoxy)acetyl)-3,5-dimethylpiperazine-1-carbonyl)phenyl)pyridazine-3-carboxamide;

6-amino-5-((R)-1-(2,6-dichloro-3-fluorophenyl)ethoxy)-N-(4-((3S,5R)-4-((S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecanoyl)-3,5-dimethylpiperazine-1-carbonyl)phenyl)pyridazine-3-carboxamide;

6-amino-5-((R)-1-(2,6-dichloro-3-fluorophenyl)ethoxy)-N-(4-((3S,5R)-4-((S)-21-((2S,4R)-4-hydroxy-2-((4-(4-methylthiazol-5-yl)benzyl)carbamoyl)pyrrolidine-1-carbonyl)-22,22-dimethyl-19-oxo-4,7,10,13,16-pentaoxa-20-azatricosanoyl)-3,5-dimethylpiperazine-1-carbonyl)phenyl)pyridazine-3-carboxamide;

6-amino-5-((R)-1-(2,6-dichloro-3-fluorophenyl)ethoxy)-N-(4-((3S,5R)-4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoyl)-3,5-dimethylpiperazine-1-carbonyl)phenyl)pyridazine-3-carboxamide;

6-amino-5-((R)-1-(2,6-dichloro-3-fluorophenyl)ethoxy)-N-(4-((3S,5R)-4-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoyl)-3,5-dimethylpiperazine-1-carbonyl)phenyl)pyridazine-3-carboxamide;

6-amino-5-((R)-1-(2,6-dichloro-3-fluorophenyl)ethoxy)-N-(4-((3S,5R)-4-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoyl)-3,5-dimethylpiperazine-1-carbonyl)phenyl)pyridazine-3-carboxamide; and 6-amino-5-((R)-1-(2,6-dichloro-3-fluorophenyl)ethoxy)-N-(4-((3S,5R)-4-(10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoyl)-3,5-dimethylpiperazine-1-carbonyl)phenyl)pyridazine-3-carboxamide.

38. A pharmaceutical composition comprising the compound of formula (I) according to claim 1 or a pharmaceutically acceptable salt thereof, and at least one pharmaceutically acceptable carrier.

39. The pharmaceutical composition according to claim 38, further comprising at least one additional agent for treating cancer.

40. A method for treating cancer in a subject, comprising administering to the subject a therapeutically effective amount of the compound of formula (I) according to claim 1, or a pharmaceutically acceptable salt thereof.

41. The method according to claim 40, wherein the cancer is selected from the group consisting of lung cancer, lymphoma, inflammatory myofibroblastic tumor (IMT), colorectal cancer, brain tumor, acute myeloid leukemia, and ovarian cancer.

42. The method according to claim 40, wherein the cancer is selected from the group consisting of: small cell lung cancer, non-small cell lung cancer, anaplastic lymphoma kinase (ALK) mutation-positive non-small cell lung cancer (NSCLC), ROS1-mutation positive non-small cell lung cancer, MET mutated or amplified lung cancer, EGFR-mutated non-small cell lung cancer, diffuse large B-cell lymphoma, anaplastic lymphoma, anaplastic large cell lymphoma, glioma, and glioblastoma.

43. The method according to claim 41, wherein the lung cancer is a lung adenocarcinoma.

44. The method according to claim 40, wherein the compound of formula (I) according to claim 1, or a pharmaceutically acceptable salt thereof is administered to the subject by at least one mode of administration selected from the group consisting of oral administration, oral mucosal administration, subcutaneous administration, transdermal administration, and intravenous administration.

* * * * *